US012054738B2

(12) United States Patent
Prentice et al.

(10) Patent No.: US 12,054,738 B2
(45) Date of Patent: Aug. 6, 2024

(54) STABLE CELL LINES FOR INDUCIBLE PRODUCTION OF rAAV VIRIONS

(71) Applicant: Shape Therapeutics Inc., Seattle, WA (US)

(72) Inventors: Kenneth Prentice, Seattle, WA (US); Sandhya Pande, Kent, WA (US)

(73) Assignee: Shape Therapeutics Inc., Seattle, WA (US)

( * ) Notice: Subject to any disclaimer, the term of this patent is extended or adjusted under 35 U.S.C. 154(b) by 109 days.

(21) Appl. No.: 17/390,777

(22) Filed: Jul. 30, 2021

(65) Prior Publication Data

US 2022/0145328 A1 May 12, 2022

Related U.S. Application Data

(60) Provisional application No. 63/216,615, filed on Jun. 30, 2021, provisional application No. 63/156,207, filed on Mar. 3, 2021, provisional application No. 63/156,239, filed on Mar. 3, 2021, provisional application No. 63/156,230, filed on Mar. 3, 2021, provisional application No. 63/058,894, filed on Jul. 30, 2020, provisional application No. 63/058,900, filed on Jul. 30, 2020, provisional application No. 63/058,887, filed on Jul. 30, 2020.

(51) Int. Cl.
*C07K 14/005* (2006.01)
*C12N 15/864* (2006.01)

(52) U.S. Cl.
CPC ........ *C12N 15/8645* (2013.01); *C07K 14/005* (2013.01); *C12N 2750/14143* (2013.01); *C12N 2750/14152* (2013.01)

(58) Field of Classification Search
CPC ...... C12N 15/8645; C12N 2750/14143; C12N 2750/14152; C07K 14/005
See application file for complete search history.

(56) References Cited

U.S. PATENT DOCUMENTS

| | | | |
|---|---|---|---|
| 5,837,484 | A | 11/1998 | Trempe et al. |
| 6,274,354 | B1 | 8/2001 | Wilson et al. |
| 6,953,690 | B1 | 10/2005 | Gao et al. |
| 7,125,705 | B2 | 10/2006 | Colosi |
| 7,282,199 | B2 | 10/2007 | Gao et al. |
| 7,790,449 | B2 | 9/2010 | Gao et al. |
| 8,999,678 | B2 | 4/2015 | Vandenberghe et al. |
| 10,780,182 | B2 | 9/2020 | Wilson et al. |
| 10,815,497 | B2 | 10/2020 | Kyostio-More et al. |
| 10,858,631 | B2 | 12/2020 | Vink |
| 11,078,464 | B2 | 8/2021 | Zhao et al. |
| 11,299,713 | B2 | 4/2022 | Han |
| 11,332,719 | B2 | 5/2022 | Zhang et al. |
| 2003/0190746 | A1 | 10/2003 | Xiao |
| 2018/0127470 | A1 | 5/2018 | Cawood |
| 2019/0078099 | A1 | 3/2019 | Zhou et al. |
| 2020/0002682 | A1 | 1/2020 | Feary et al. |
| 2020/0032221 | A1 | 1/2020 | Tiernan et al. |
| 2020/0048641 | A1 | 2/2020 | Jing et al. |
| 2020/0199627 | A1 | 6/2020 | Gu et al. |
| 2020/0208121 | A1 | 7/2020 | Hewitt et al. |
| 2020/0239909 | A1 | 7/2020 | Cawood et al. |
| 2020/0277628 | A1 | 9/2020 | Hein et al. |
| 2020/0325455 | A1 | 10/2020 | Tiernan et al. |
| 2020/0377895 | A1 | 12/2020 | Faust et al. |
| 2020/0407753 | A1 | 12/2020 | Agbandje-Mckenna et al. |
| 2021/0032657 | A1 | 2/2021 | Perry, III et al. |
| 2021/0275614 | A1 | 9/2021 | Choi et al. |
| 2021/0388343 | A1 | 12/2021 | Lisowski et al. |
| 2022/0025396 | A1 | 1/2022 | Qu et al. |
| 2022/0098556 | A1 | 3/2022 | Dobrowsky et al. |
| 2022/0135954 | A1 | 5/2022 | Goepfert et al. |
| 2022/0177854 | A1* | 6/2022 | Chanas .................. C12N 15/86 |

FOREIGN PATENT DOCUMENTS

| | | |
|---|---|---|
| EP | 2771455 | 5/2013 |
| EP | 3697917 | 7/2019 |
| WO | WO1998/10086 | 3/1998 |
| WO | WO1998/027207 | 6/1998 |
| WO | WO2018/160582 A1 | 9/2019 |
| WO | WO2020/033842 A1 | 2/2020 |
| WO | WO2020/078953 A1 | 4/2020 |
| WO | WO2020/161484 | 8/2020 |
| WO | WO2020/193698 | 10/2020 |
| WO | WO2020/235543 | 11/2020 |
| WO | WO2021/041485 | 3/2021 |
| WO | WO2021/076634 | 4/2021 |
| WO | WO2021/127432 | 6/2021 |
| WO | WO2021/146591 | 7/2021 |
| WO | WO2021/188740 | 9/2021 |
| WO | WO2021/195491 | 9/2021 |
| WO | WO2021/198508 | 10/2021 |
| WO | WO2021/231884 | 11/2021 |
| WO | WO2022/020712 | 1/2022 |
| WO | WO2022/037710 | 2/2022 |
| WO | WO2022/038368 | 2/2022 |
| WO | WO2022/038369 | 2/2022 |

OTHER PUBLICATIONS

Qiao C, Wang B, Zhu X, Li J, Xiao X. A novel gene expression control system and its use in stable, high-titer 293 cell-based adeno-associated virus packaging cell lines. J Virol. Dec. 2002;76(24):13015-27. (Year: 2002).*
Rohan RM, Ketner G. A comprehensive collection of point mutations in the internal promoter of the adenoviral VAI gene. J Biol Chem. Jun. 25, 1987;262(18):8500-7. (Year: 1987).*
Anton M, Graham FL. Site-specific recombination mediated by an adenovirus vector expressing the Cre recombinase protein: a molecular switch for control of gene expression. J Virol. Aug. 1995;69(8):4600-6. (Year: 1996).*

(Continued)

*Primary Examiner* — Nicole Kinsey White
*Assistant Examiner* — Ruixue Wang
(74) *Attorney, Agent, or Firm* — Edward J. Baba; Shweta Chandra; Bozicevic, Field & Francis LLP

(57) ABSTRACT

Described herein are polynucleotide constructs and stable cell lines for inducible production of rAAV virions within which are packaged a payload polynucleotide.

32 Claims, 46 Drawing Sheets

Specification includes a Sequence Listing.

(56) References Cited

OTHER PUBLICATIONS

Cannon et al., (2015) "Functions of and interactions between the A and B blovks in adenovirus type 2-specific VARNA1 gene" Proceedings of the National Academy of Sciences of the United States of America, 83: 185-1289.
Economides et al., (2013) "Conditionals by inversion provide a universal method for the generation of conditional alleles" PNAS, E3179-E3188.
Fowlkes et al., (1980) "Transcriptional control regions of the adenovirus VAI RNA gene" Cell, 22 (2): 405-413.
Jillette et al., (2019) "Split selectable markers" Nature Communications, 10: 4986.
Matsushita et al., (1998) "Adeno-associated virus vectors can be efficiently produced without helper virus" Gene Therapy, 5: 938-945.
Mlynarova et al., (2003) "A self-excising Cre recombinase allows efficient recombination of multiple ectopic heterospecific lox sites in transgenic tobacco" Transgenic Research, 12: 45-57.
Qiao et al., (2002) "A Novel Gene Expression Control System and Its Use in Stable High-Titer 293 Cell-Based Adeno-Associated Virus Packaging Cell Lines" Journal of Virology, 76 (24): 13015-13027.
Wu et al., (1994) "Transcription Function of Each Base Pair in the Control Region of the Adenovirus VARNA1 Gene" Virology, 200 (1): 105-113.
Yu et al., (2006) "Reproducible and Inducible Knockdown of Gene Expression in Mice" Genesis, 44: 252-261.
Chu et al., "SV40 DNA Transfection of Cells in Suspension: Analysis of the Efficiency of Transcription and Translation of T-antigen", 1981, Gene 13: 197-202.
De et al., "High Levels of Persistent Expression of Alpha1-Antitrypsin Mediated by the Nonhuman Primate Serotype Rh.10 Adeno-Associated Virus Despite Preexisting Immunity to Common Human Adeno-Associated Viruses" Molecular Therapy, 2006, 13:1 67-76.
Deal et al., "Vectored Antibody Gene Delivery for the Prevention or Treatment of HIV Infection" Current Opinion HIV and AIDS, 2015, 10:3 190-197.
Gao et al., "Clades of Adeno-associated Viruses Are Widely Disseminated In Human Tissues" Journal of Virology, 2004, 78: 6381-6388.
GenBank Accession No. AF085716.
GenBank Accession No. AX753246.
GenBank Accession No. AX753249.
GenBank Accession No. NC_001401.
GenBank Accession No. NC_ 001829.
GenBank Accession No. NC_001862.
GenBank Accession No. NC_002077.
Graham et al., "A new technique for the assay of infectivity of human adenovirus 5 DNA" Virology, 1973, 52:2 456-467.
Mori et al., "Two Novel Adeno-Associated Viruses From Cynomolgus Monkey: Pseudotyping Characterization of Capsid Protein" Journal of Virology, 2004, 330:2 375-383.
Satoh et al., "Site-Specific Integration of an Adeno-Associated Virus Vector Plasmid Mediated by Regulated Expression of Rep Based on Cre-loxP Recombination" Journal of Virology, 2000, 74(22): 10631-10638.
Srivastava et al., "Nucleotide Sequence and Organization of the Adeno-Associated Virus 2 Genome" Journal of Virology, 1983, 45: 555-564.
Clark, (2002) "Recent advances in recombinant adeno-associated virus vector production", Kidney International, 61 (1): S9-S15.
Daya et al., (2008) "Gene Therapy Using Adeno-Associated Virus Vectors", Clinical Microbiology Reviews, 21 (4): 583-593.
Liu et al., (2000) "Selective Rep-Cap Gene Amplification as a Mechanism for High-Titer Recombinant AAV Production from Stable Cell Lines", Molecular Therapy, 2 (4): 394-403.
Naso et al., (2017) "Adeno-Associated Virus (AAV) as a Vector for Gene Therapy", BioDrugs, 31: 317-334.
Kamel, et al., The Adenovirus VA RNA-Derived miRNAs are not Essential for Lytic Virus Growth in Tissue Culture Cells, Nucleic Acids Research, 41(9): 4802-4812, Mar. 21, 2013 (Mar. 21, 2013).

* cited by examiner construct 2 option

An optional segment in construct 2 for expression of VA RNA

A Cre inducible U6 promoter drives the expression of transcriptionally dead mutant of VA RNA1 (VA RNA).

The Stuffer sequence is flanked by Lox sites.

| Plasmids | pHelper | STXC0002 | STXC0016 |
|---|---|---|---|
| STX295 | + | + | + |
| pRC2 | + | + | + |
| pHelper | + | | |
| STXC0002 | | + | |
| STXC0016 | | | + |

| Plasmids | Description |
|---|---|
| STXC0032 | STXC0002 with WTVA |
| STXC0033 | STXC0002 with 6nt deleted in B box ofVA |
| STXC0034 | STXC0002 with nt substitutions in B box of VA |
| STXC0035 | STXC0002 with G16A, T45C mutant VA |
| STXC0036 | STXC0002 with G60A mutant VA |
| STXC0037 | STXC0002 with G16A, G60A mutant VA |

| Plasmids | Description |
|---|---|
| STXC0032 | STXC0002 with WTVA |
| STXC0033 | STXC0002 with 6nt deleted in B box of VA |
| STXC0035 | STXC0002 with G16A ,T45C mutant VA |
| STXC0037 | STXC0002 with G16A,G60A mutant VA |
| STXC0041 | STXC0033 with U6 driven VA |
| STXC0042 | STXC0035 with U6 driven VA |
| STXC0043 | STXC0037 with U6 driven VA |

Rescue of Select Mutants with Inducible Promoter

Where((Sample = T42-, T42+, T59-, T59+, T60-, T60+, T61-, T61+) and (Nuclease = +)) Each error bar is constructed using the minimum and maximum of the data.

Each error bar is constructed using the minimum and maximum of the data.

Where(Sample Name= (AAV, Bal, CDM4HEK, Cyt1, Cyt2, Cyt9, Cyt10, Cyt13, Expi, Fuji, HE300, HE400, LVMax, NX, TS1) & more)
Each error bar is constructed using the minimum and maximum of the data.

Where(Cell Line = 1D1, 1D3, 2C2, 3A1, T42)
Each error bar is constructed using the minimum and maximum of the data.

SEQUENCE LISTING

```
<160> NUMBER OF SEQ ID NOS: 39

<210> SEQ ID NO 1
<211> LENGTH: 353
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1

gtgagtttgg ggacccttga ttgttctttc tttttcgcta ttgtaaaatt catgttatat      60

ggagggggca aagttttcag ggtgttgttt agaatgggaa gatgtccctt gtatcaccat     120

ggaccctcat gataattttg tttctttcac tttctactct gttgacaacc attgtctcct     180

cttattttct tttcattttc tgtaactttt tcgttaaact ttagcttgca tttgtaacga     240

atttttaaat tcacttttgt ttatttgtca gattgtaagt actttctcta atcacttttt     300

tttcaaggca atcagggtat attatattgt acttcagcac agttttagag aac            353


<210> SEQ ID NO 2
<211> LENGTH: 1356
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 2

ataacttcgt ataatgtatg ctatacgaag ttatcgggcc cctctgctaa ccatgttcat      60

gccttcttct ttttcctaca gatggtgagc aagggcgagg agctgttcac cggggtggtg     120

cccatcctgg tcgagctgga cggcgacgta aacggccaca agttcagcgt gtccggcgag     180

ggcgagggcg atgccaccta cggcaagctg accctgaagt tcatctgcac caccggcaag     240

ctgcccgtgc cctggcccac cctcgtgacc accctgacct acggcgtgca gtgcttcagc     300

cgctaccccg accacatgaa gcagcacgac ttcttcaagt ccgccatgcc cgaaggctac     360

gtccaggagc gcaccatctt cttcaaggac gacggcaact acaagacccg cgccgaggtg     420

aagttcgagg gcgacaccct ggtgaaccgc atcgagctga agggcatcga cttcaaggag     480

gacggcaaca tcctggggca caagctggag tacaactaca acagccacaa cgtctatatc     540

atggccgaca agcagaagaa cggcatcaag gtgaacttca agatccgcca caacatcgag     600

gacggcagcg tgcagctcgc cgaccactac cagcagaaca cccccatcgg cgacggcccc     660

gtgctgctgc ccgacaacca ctacctgagc acccagtccg ccctgagcaa agaccccaac     720

gagaagcgcg atcacatggt cctgctggag ttcgtgaccg ccgccgggat cactctcggc     780

atggacgagc tgtacaagta acctcaggtg caggctgcct atcagaaggt ggtggctggt     840

gtggccaatg ccctggctca caaataccac tgagatcttt ttccctctgc caaaaattat     900
```

ggggacatca tgaagcccct tgagcatctg acttctggct aataaaggaa atttattttc 960
attgcaatag tgtgttggaa tttttgtgt ctctcactcg gaaggacata tgggagggca 1020
aatcatttaa aacatcagaa tgagtatttg gtttagagtt tggcaacata tgcccatatg 1080
ctggctgcca tgaacaaagg ttggctataa agaggtcatc agtatatgaa acagccccct 1140
gctgtccatt ccttattcca tagaaaagcc ttgacttgag gttagatttt ttttatattt 1200
tgttttgtgt tattttttc tttaacatcc ctaaaatttt ccttacatgt tttactagcc 1260
agatttttcc tcctctcctg actactccca gtcatagctg tccctcttct cttatggaga 1320
tcataacttc gtataatgta tgctatacga agttat 1356

<210> SEQ ID NO 3
<211> LENGTH: 220
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 3
aattgttata attaaatgat aaggtagaat atttctgcat ataaattctg gctggcgtgg 60
aaatattctt attggtagaa acaactacac cctggtcatc atcctgcctt tctctttatg 120
gttacaatga tatacactgt ttgagatgag gataaaatac tctgagtcca aaccgggccc 180
ctctgctaac catgttcatg ccttcttctt tttcctacag 220

<210> SEQ ID NO 4
<211> LENGTH: 534
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 4
atgagagggt cagatccggc agcgttgaag cgggctagga acactgaggc agcaaggcgc 60
tctcgagcaa ggaagttgca acggatgaaa caattggaag acaaagttga agagctgctt 120
tcaaaaaact accaccttga aaatgaagtc gcgaggctga agaaattggt cggatctgct 180
ggcagcgcag cggggagcgg tgagtttatg gtcagacctc tcaactgtat tgtcgctgtc 240
tcacagaaca tgggtatcgg aaagaacggt gacttgccgt ggccgccact gcggaatgag 300
ttcaaatact ttcagcgcat gacgaccacc agcagtgtgg agggtaagca aaatcttgtc 360
ataatgggtc gcaagacttg gttttctatt ccagagaaaa acagaccgct taaagatagg 420
attaacatcg tgttgagccg ggaactgaaa gagccaccaa ggggagcaca ttttttggct 480
aagtccttgg atgacgccct gcgactgata gagcaaccag aacttgctta gtaa 534

<210> SEQ ID NO 5
<211> LENGTH: 453
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 5

-continued atgcgcggtt ccgacccagc agctttgaaa cgagcacgaa acacggaagc agcccgcagg 60
agtcgagcga gaaaacttca gcggatgaag cagcttgaag ataaagtcga ggaattgctt 120
agcaagaatt atcacctcga gaatgaagtg gcgcgactga aaaaacttgt aggttctgct 180
gggagcgcag ccggaagcgg cgagttctca aaagttgaca tggtgtggat cgtgggtgga 240
agttctgtct atcaagaggc gatgaatcag cctggccacc tcagactgtt tgttacaagg 300
atcatgcagg agttcgagtc tgacacgttt tttccagaga tcgacctggg gaaatataaa 360
ctcctcccag agtacccagg agtgcttagt gaggtccaag aagagaaggg aatcaaatat 420
aaatttgaag tttacgaaaa gaaggattag taa 453

<210> SEQ ID NO 6
<211> LENGTH: 9837
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 6
ggaggggtgg agtcgtgacg tgaattacgt catagggtta gggaggtcct gtattagagg 60
tcacgtgagt gttttgcgac attttgcgac accatgtggt cacgctgggt atttaagccc 120
gagtgagcac gcagggtctc cattttgaag cgggaggttt gaacgcgcag ccgccatgcc 180
ggggttttac gagattgtga ttaaggtccc cagcgacctt gacgagcatc tgcccggcat 240
ttctgacagc tttgtgaact gggtggccga gaaggaatgg gagttgccgc cagattctga 300
catggatctg aatctgattg agcaggcacc cctgaccgtg gccgagaagc tgcagcgcga 360
ctttctgacg gaatggcgcc gtgtgagtaa ggccccggag gcccttttct ttgtgcaatt 420
tgagaaggga gagagctact tccacatgca cgtgctcgtg gaaaccaccg gggtgaaatc 480
catggttttg ggacgtttcc tgagtcagat tcgcgaaaaa ctgattcaga gaatttaccg 540
cgggatcgag ccgactttgc caaactggtt cgcggtcaca aagaccagaa atggcgccgg 600
aggcgggaac aaggtggtgg atgagtgcta catccccaat tacttgctcc ccaaaaccca 660
gcctgagctc cagtgggcgt ggactaatat ggaacagtat ttaagcgcct gtttgaatct 720
cacggagcgt aaacggttgg tggcgcagca tctgacgcac gtgtcgcaga cgcaggagca 780
gaacaaagag aatcagaatc ccaattctga tgcgccggtg atcagatcaa aaacttcagc 840
caggtacatg gagctggtcg ggtggctcgt ggacaaggtg agtttgggga cccttgattg 900
ttctttcttt ttcgctattg taaaattcat gttatatgga gggggcaaag ttttcagggt 960
gttgtttaga atgggaagat gtcccttgta tcaccatgga ccctcatgat aattttgttt 1020
ctttcacttt ctactctgtt gacaaccatt gtctcctctt attttctttt cattttctgt 1080
aactttttcg ttaaacttta gcttgcattt gtaacgaatt tttaaattca cttttgttta 1140
tttgtcagat tgtaagtact ttctctaatc actttttttt caaggcaatc agggtatatt 1200
atattgtact tcagcacagt tttagagaac ataacttcgt ataatgtatg ctatacgaag 1260
ttatcgggcc cctctgctaa ccatgttcat gccttcttct ttttcctaca gatggtgagc 1320
aagggcgagg agctgttcac cggggtggtg cccatcctgg tcgagctgga cggcgacgta 1380
aacggccaca agttcagcgt gtccggcgag ggcgagggcg atgccaccta cggcaagctg 1440
accctgaagt tcatctgcac caccggcaag ctgcccgtgc cctggcccac cctcgtgacc 1500
accctgacct acggcgtgca gtgcttcagc cgctaccccg accacatgaa gcagcacgac 1560

-continued

```
ttcttcaagt ccgccatgcc cgaaggctac gtccaggagc gcaccatctt cttcaaggac   1620
gacggcaact acaagacccg cgccgaggtg aagttcgagg gcgacaccct ggtgaaccgc   1680
atcgagctga agggcatcga cttcaaggag gacggcaaca tcctggggca caagctggag   1740
tacaactaca acagccacaa cgtctatatc atggccgaca agcagaagaa cggcatcaag   1800
gtgaacttca agatccgcca caacatcgag gacggcagcg tgcagctcgc cgaccactac   1860
cagcagaaca cccccatcgg cgacggcccc gtgctgctgc ccgacaacca ctacctgagc   1920
acccagtccg ccctgagcaa agaccccaac gagaagcgcg atcacatggt cctgctggag   1980
ttcgtgaccg ccgccgggat cactctcggc atggacgagc tgtacaagta acctcaggtg   2040
caggctgcct atcagaaggt ggtggctggt gtggccaatg ccctggctca caaataccac   2100
tgagatcttt ttccctctgc caaaaattat ggggacatca tgaagcccct tgagcatctg   2160
acttctggct aataaaggaa atttattttc attgcaatag tgtgttggaa ttttttgtgt   2220
ctctcactcg gaaggacata tgggagggca aatcatttaa aacatcagaa tgagtatttg   2280
gtttagagtt tggcaacata tgcccatatg ctggctgcca tgaacaaagg ttggctataa   2340
agaggtcatc agtatatgaa acagccccct gctgtccatt ccttattcca tagaaaagcc   2400
ttgacttgag gttagatttt ttttatattt tgttttgtgt tatttttttc tttaacatcc   2460
ctaaaatttt ccttacatgt tttactagcc agatttttcc tcctctcctg actactccca   2520
gtcatagctg tccctcttct cttatggaga tcataacttc gtataatgta tgctatacga   2580
agttataatt gttataatta aatgataagg tagaatattt ctgcatataa attctggctg   2640
gcgtggaaat attcttattg gtagaaacaa ctacaccctg gtcatcatcc tgcctttctc   2700
tttatggtta caatgatata cactgtttga gatgaggata aaatactctg agtccaaacc   2760
gggcccctct gctaaccatg ttcatgcctt cttctttttc ctacagggga ttacctcgga   2820
gaagcagtgg atccaggagg accaggcctc atacatctcc ttcaatgcgg cctccaactc   2880
gcggtcccaa atcaaggctg ccttggacaa tgcgggaaag attatgagcc tgactaaaac   2940
cgcccccgac tacctggtgg gccagcagcc cgtggaggac atttccagca atcggattta   3000
taaaattttg gaactaaacg ggtacgatcc ccaatatgcg gcttccgtct ttctgggatg   3060
ggccacgaaa aagttcggca agaggaacac catctggctg tttgggcctg caactaccgg   3120
gaagaccaac atcgcggagg ccatagccca cactgtgccc ttctacgggt gcgtaaactg   3180
gaccaatgag aactttccct tcaacgactg tgtcgacaag atggtgatct ggtgggagga   3240
ggggaagatg accgccaagg tcgtggagtc ggccaaagcc attctcggag gaagcaaggt   3300
gcgcgtggac cagaaatgca agtcctcggc ccagatagac ccgactcccg tgatcgtcac   3360
ctccaacacc aacatgtgcg ccgtgattga cgggaactca acgaccttcg aacaccagca   3420
gccgttgcaa gaccggatgt tcaaatttga actcacccgc cgtctggatc atgactttgg   3480
gaaggtcacc aagcaggaag tcaaagactt tttccggtgg gcaaaggatc acgtggttga   3540
ggtggagcat gaattctacg tcaaaaaggg tggagccaag aaaagacccg cccccagtga   3600
cgcagatata agtgagccca aacgggtgcg cgagtcagtt gcgcagccat cgacgtcaga   3660
cgcggaagct tcgatcaact acgcagacag gtaccaaaac aaatgttctc gtcacgtggg   3720
catgaatctg atgctgtttc cctgcagaca atgcgagaga atgaatcaga attcaaatat   3780
ctgcttcact cacggacaga aagactgttt agagtgcttt cccgtgtcag aatctcaacc   3840
cgtttctgtc gtcaaaaagg cgtatcagaa actgtgctac attcatcata tcatgggaaa   3900
```

-continued

```
ggtgccagac gcttgcactg cctgcgatct ggtcaatgtg gatttggatg actgcatctt   3960
tgaacaataa atgatttaaa tcaggtatgg ctgccgatgg ttatcttcca gattggctcg   4020
aggacactct ctctgaagga ataagacagt ggtggaagct caaacctggc ccaccaccac   4080
caaagcccgc agagcggcat aaggacgaca gcaggggtct tgtgcttcct gggtacaagt   4140
acctcggacc cttcaacgga ctcgacaagg gagagccggt caacgaggca gacgccgcgg   4200
ccctcgagca cgacaaagcc tacgaccggc agctcgacag cggagacaac ccgtacctca   4260
agtacaacca cgccgacgcg gagtttcagg agcgccttaa agaagatacg tcttttgggg   4320
gcaacctcgg acgagcagtc ttccaggcga aaaagagggt tcttgaacct ctgggcctgg   4380
ttgaggaacc tgttaagacg gctccgggaa aaaagaggcc ggtagagcac tctcctgtgg   4440
agccagactc ctcctcggga accggaaagg cgggccagca gcctgcaaga aaaagattga   4500
attttggtca gactggagac gcagactcag tacctgaccc ccagcctctc ggacagccac   4560
cagcagcccc ctctggtctg ggaactaata cgatggctac aggcagtggc gcaccaatgg   4620
cagacaataa cgagggcgcc gacggagtgg gtaattcctc gggaaattgg cattgcgatt   4680
ccacatggat gggcgacaga gtcatcacca ccagcacccg aacctgggcc ctgcccacct   4740
acaacaacca cctctacaaa caaatttcca gccaatcagg agcctcgaac gacaatcact   4800
actttggcta cagcacccct tgggggtatt ttgacttcaa cagattccac tgccactttt   4860
caccacgtga ctggcaaaga ctcatcaaca acaactgggg attccgaccc aagagactca   4920
acttcaagct ctttaacatt caagtcaaag aggtcacgca gaatgacggt acgacgacga   4980
ttgccaataa ccttaccagc acggttcagg tgtttactga ctcggagtac cagctcccgt   5040
acgtcctcgg ctcggcgcat caaggatgcc tcccgccgtt cccagcagac gtcttcatgg   5100
tgccacagta tggatacctc accctgaaca acgggagtca ggcagtagga cgctcttcat   5160
tttactgcct ggagtacttt ccttctcaga tgctgcgtac cggaaacaac tttaccttca   5220
gctacacttt tgaggacgtt cctttccaca gcagctacgc tcacagccag agtctggacc   5280
gtctcatgaa tcctctcatc gaccagtacc tgtattactt gagcagaaca aacactccaa   5340
gtggaaccac cacgcagtca aggcttcagt tttctcaggc cggagcgagt gacattcggg   5400
accagtctag gaactggctt cctggaccct gttaccgcca gcagcgagta tcaaagacat   5460
ctgcggataa caacaacagt gaatactcgt ggactggagc taccaagtac cacctcaatg   5520
gcagagactc tctggtgaat ccgggcccgg ccatggcaag ccacaaggac gatgaagaaa   5580
agtttttttcc tcagagcggg gttctcatct ttgggaagca aggctcagag aaaacaaatg   5640
tggacattga aaaggtcatg attacagacg aagaggaaat caggacaacc aatcccgtgg   5700
ctacggagca gtatggttct gtatctacca acctccagag aggcaacaga caagcagcta   5760
ccgcagatgt caacacacaa ggcgttcttc caggcatggt ctggcaggac agagatgtgt   5820
accttcaggg gcccatctgg gcaaagattc cacacacgga cggacatttt cacccctctc   5880
ccctcatggg tggattcgga cttaaacacc ctcctccaca gattctcatc aagaacaccc   5940
cggtacctgc gaatccttcg accaccttca gtgcggcaaa gtttgcttcc ttcatcacac   6000
agtactccac gggacaggtc agcgtggaga tcgagtggga gctgcagaag gaaaacagca   6060
aacgctggaa tcccgaaatt cagtacactt ccaactacaa caagtctgtt aatgtggact   6120
ttactgtgga cactaatggc gtgtattcag agcctcgccc cattggcacc agatacctga   6180
ctcgtaatct gtaattgctt gttaatcaat aaaccgttta attcgtttca gttgaacttt   6240
ggtctctgcg tatttctttc ttatctagtt tccatggcta cgtagataag tagcatggcg   6300
```

-continued ggttaatcat taactacata agggcgaatt ctgcagatat ccatcacact ggcggccgct 6360
cgagcatgca tctagagggc ccaattcgcc ctatagtgag tcgtattaca attcactggc 6420
cgtcgtttta caacgtcgtg actgggaaaa ccctggcgtt acccaactta atcgccttgc 6480
agcacatccc cctttcgcca gctggcgtaa tagcgaagag gcccgcaccg atcgcccttc 6540
ccaacagttg cgcagcctat acgtacggca gtttaaggtt tacacctata aaagagagag 6600
ccgttatcgt ctgtttgtgg atgtacagag tgatattatt gacacgccgg ggcgacggat 6660
ggtgatcccc ctggccagtg cacgtctgct gtcagataaa gtctcccgtg aactttaccc 6720
ggtggtgcat atcggggatg aaagctggcg catgatgacc accgatatgg ccagtgtgcc 6780
ggtctccgtt atcggggaag aagtggctga tctcagccac cgcgaaaatg acatcaaaaa 6840
cgccattaac ctgatgttct ggggaatata aatgtcaggc atgagattat caaaaaggat 6900
cttcacctag atccttttca cgtagaaagc cagtccgcag aaacggtgct gaccccggat 6960
gaatgtcagc tactgggcta tctggacaag ggaaaacgca agcgcaaaga gaaagcaggt 7020
agcttgcagt gggcttacat ggcgatagct agactgggcg gttttatgga cagcaagcga 7080
accggaattg ccagctgggg cgccctctgg taaggttggg aagccctgca aagtaaactg 7140
gatggctttc tcgccgccaa ggatctgatg gcgcagggga tcaagctctg atcaagagac 7200
aggatgagga tcgtttcgca tgattgaaca agatggattg cacgcaggtt ctccggccgc 7260
ttgggtggag aggctattcg gctatgactg ggcacaacag acaatcggct gctctgatgc 7320
cgccgtgttc cggctgtcag cgcaggggcg cccggttctt tttgtcaaga ccgacctgtc 7380
cggtgccctg aatgaactgc aagacgaggc agcgcggcta tcgtggctgg ccacgacggg 7440
cgttccttgc gcagctgtgc tcgacgttgt cactgaagcg ggaagggact ggctgctatt 7500
gggcgaagtg ccggggcagg atctcctgtc atctcacctt gctcctgccg agaaagtatc 7560
catcatggct gatgcaatgc ggcggctgca tacgcttgat ccggctacct gcccattcga 7620
ccaccaagcg aaacatcgca tcgagcgagc acgtactcgg atggaagccg gtcttgtcga 7680
tcaggatgat ctggacgaag agcatcaggg gctcgcgcca gccgaactgt tcgccaggct 7740
caaggcgagc atgcccgacg gcgaggatct cgtcgtgacc catggcgatg cctgcttgcc 7800
gaatatcatg gtggaaaatg gccgcttttc tggattcatc gactgtggcc ggctgggtgt 7860
ggcggaccgc tatcaggaca tagcgttggc tacccgtgat attgctgaag agcttggcgg 7920
cgaatgggct gaccgcttcc tcgtgcttta cggtatcgcc gctcccgatt cgcagcgcat 7980
cgccttctat cgccttcttg acgagttctt ctgaattatt aacgcttaca atttcctgat 8040
gcggtatttt ctccttacgc atctgtgcgg tatttcacac cgcatacagg tggcactttt 8100
cggggaaatg tgcgcggaac ccctatttgt ttatttttct aaatacattc aaatatgtat 8160
ccgctcatga gacaataacc ctgataaatg cttcaataat agcacgtgag gagggccacc 8220
atggccaagt tgaccagtgc cgttccggtg ctcaccgcgc gcgacgtcgc cggagcggtc 8280
gagttctgga ccgaccggct cgggttctcc cgggacttcg tggaggacga cttcgccggt 8340
gtggtccggg acgacgtgac cctgttcatc agcgcggtcc aggaccaggt ggtgccggac 8400
aacaccctgg cctgggtgtg ggtgcgcggc ctggacgagc tgtacgccga gtggtcggag 8460
gtcgtgtcca cgaacttccg ggacgcctcc gggccggcca tgaccgagat cggcgagcag 8520
ccgtgggggc gggagttcgc cctgcgcgac ccggccggca actgcgtgca cttcgtggcc 8580
gaggagcagg actgacacgt gctaaaactt catttttaat ttaaaaggat ctaggtgaag 8640 atccttttg ataatctcat gaccaaaatc ccttaacgtg agttttcgtt ccactgagcg 8700
tcagaccccg tagaaaagat caaaggatct tcttgagatc cttttttct gcgcgtaatc 8760 tgctgcttgc aaacaaaaaa accaccgcta ccagcggtgg tttgtttgcc ggatcaagag 8820
ctaccaactc tttttccgaa ggtaactggc ttcagcagag cgcagatacc aaatactgtc 8880
cttctagtgt agccgtagtt aggccaccac ttcaagaact ctgtagcacc gcctacatac 8940
ctcgctctgc taatcctgtt accagtggct gctgccagtg gcgataagtc gtgtcttacc 9000
gggttggact caagacgata gttaccggat aaggcgcagc ggtcgggctg aacgggggt 9060 tcgtgcacac agcccagctt ggagcgaacg acctacaccg aactgagata cctacagcgt 9120
gagctatgag aaagcgccac gcttcccgaa gggagaaagg cggacaggta tccggtaagc 9180
ggcagggtcg gaacaggaga gcgcacgagg gagcttccag ggggaaacgc ctggtatctt 9240
tatagtcctg tcgggtttcg ccacctctga cttgagcgtc gatttttgtg atgctcgtca 9300 gggggcgga gcctatggaa aaacgccagc aacgcggcct ttttacggtt cctgggcttt 9360
tgctggcctt ttgctcacat gttctttcct gcgttatccc ctgattctgt ggataaccgt 9420
attaccgcct ttgagtgagc tgataccgct cgccgcagcc gaacgaccga gcgcagcgag 9480
tcagtgagcg aggaagcgga agagcgccca atacgcaaac cgcctctccc cgcgcgttgg 9540
ccgattcatt aatgcagctg gcacgacagg tttcccgact ggaaagcggg cagtgagcgc 9600
aacgcaatta atgtgagtta gctcactcat taggcacccc aggctttaca ctttatgctt 9660
ccggctcgta tgttgtgtgg aattgtgagc ggataacaat ttcacacagg aaacagctat 9720
gaccatgatt acgccaagct atttaggtga cactatagaa tactcaagct atgcatcaag 9780
cttggtaccg agctcggatc cactagtaac ggccgccagt gtgctggaat tcgccct 9837

<210> SEQ ID NO 7
<211> LENGTH: 6367
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 7
ggcctccacg gccactagta acggccgcca gtgtgctgga attcgccctg gaggggtgga 60
gtcgtgacgt gaattacgtc atagggttag ggaggtcctg tattagaggt cacgtgagtg 120
ttttgcgaca ttttgcgaca ccatgtggtc acgctgggta tttaagcccg agtgagcacg 180
cagggtctcc attttgaagc gggaggtttg aacgcgcagc cgccatgccg gggttttacg 240
agattgtgat taaggtcccc agcgaccttg acgagcatct gcccggcatt tctgacagct 300
ttgtgaactg ggtggccgag aaggaatggg agttgccgcc agattctgac atggatctga 360
atctgattga gcaggcaccc ctgaccgtgg ccgagaagct gcagcgcgac tttctgacgg 420
aatggcgccg tgtgagtaag gccccggagg cccttttctt tgtgcaattt gagaagggag 480
agagctactt ccacatgcac gtgctcgtgg aaaccaccgg ggtgaaatcc atggttttgg 540
gacgtttcct gagtcagatt cgcgaaaaac tgattcagag aatttaccgc gggatcgagc 600
cgactttgcc aaactggttc gcggtcacaa agaccagaaa tggcgccgga ggcgggaaca 660
aggtggtgga tgagtgctac atccccaatt acttgctccc caaaacccag cctgagctcc 720
agtgggcgtg gactaatatg gaacagtatt taagcgcctg tttgaatctc acggagcgta 780
aacggttggt ggcgcagcat ctgacgcacg tgtcgcagac gcaggagcag aacaaagaga 840
atcagaatcc caattctgat gcgccggtga tcagatcaaa aacttcagcc aggtacatgg 900
agctggtcgg gtggctcgtg gacaaggtga gtttggggac ccttgattgt tctttctttt 960
tcgctattgt aaaattcatg ttatatggag ggggcaaagt tttcagggtg ttgtttagaa 1020
tgggaagatg tcccttgtat caccatggac cctcatgata attttgtttc tttcactttc 1080
tactctgttg acaaccattg tctcctctta ttttcttttc attttctgta actttttcgt 1140
taaactttag cttgcatttg taacgaattt ttaaattcac ttttgtttat ttgtcagatt 1200
gtaagtactt tctctaatca cttttttttc aaggcaatca gggtatatta tattgtactt 1260
cagcacagtt ttagagaaca taacttcgta taatgtatgc tatacgaagt tatcgggccc 1320
ctctgctaac catgttcatg ccttcttctt tttcctacag atggtgagca agggcgagga 1380
gctgttcacc ggggtggtgc ccatcctggt cgagctggac ggcgacgtaa acggccacaa 1440
gttcagcgtg tccggcgagg gcgagggcga tgccacctac ggcaagctga ccctgaagtt 1500
catctgcacc accggcaagc tgcccgtgcc ctggcccacc ctcgtgacca ccctgaccta 1560
cggcgtgcag tgcttcagcc gctaccccga ccacatgaag cagcacgact tcttcaagtc 1620
cgccatgccc gaaggctacg tccaggagcg caccatcttc ttcaaggacg acggcaacta 1680
caagacccgc gccgaggtga agttcgaggg cgacaccctg gtgaaccgca tcgagctgaa 1740
gggcatcgac ttcaaggagg acggcaacat cctggggcac aagctggagt acaactacaa 1800
cagccacaac gtctatatca tggccgacaa gcagaagaac ggcatcaagg tgaacttcaa 1860
gatccgccac aacatcgagg acggcagcgt gcagctcgcc gaccactacc agcagaacac 1920
ccccatcggc gacggccccg tgctgctgcc cgacaaccac tacctgagca cccagtccgc 1980
cctgagcaaa gaccccaacg agaagcgcga tcacatggtc ctgctggagt tcgtgaccgc 2040
cgccgggatc actctcggca tggacgagct gtacaagtaa cctcaggtgc aggctgccta 2100
tcagaaggtg gtggctggtg tggccaatgc cctggctcac aaataccact gagatctttt 2160
tccctctgcc aaaaattatg gggacatcat gaagcccctt gagcatctga cttctggcta 2220
ataaaggaaa tttattttca ttgcaatagt gtgttggaat tttttgtgtc tctcactcgg 2280
aaggacatat gggagggcaa atcatttaaa acatcagaat gagtatttgg tttagagttt 2340
ggcaacatat gcccatatgc tggctgccat gaacaaaggt tggctataaa gaggtcatca 2400
gtatatgaaa cagccccctg ctgtccattc cttattccat agaaaagcct tgacttgagg 2460
ttagattttt tttatatttt gttttgtgtt atttttttct ttaacatccc taaaattttc 2520
cttacatgtt ttactagcca gatttttcct cctctcctga ctactcccag tcatagctgt 2580
ccctcttctc ttatggagat cataacttcg tataatgtat gctatacgaa gttataattg 2640
ttataattaa atgataaggt agaatatttc tgcatataaa ttctggctgg cgtggaaata 2700
ttcttattgg tagaaacaac tacaccctgg tcatcatcct gcctttctct ttatggttac 2760
aatgatatac actgtttgag atgaggataa aatactctga gtccaaaccg ggcccctctg 2820
ctaaccatgt tcatgccttc ttctttttcc tacaggggat tacctcggag aagcagtgga 2880
tccaggagga ccaggcctca tacatctcct tcaatgcggc ctccaactcg cggtcccaaa 2940
tcaaggctgc cttggacaat gcgggaaaga ttatgagcct gactaaaacc gcccccgact 3000
acctggtggg ccagcagccc gtggaggaca tttccagcaa tcggatttat aaaattttgg 3060
aactaaacgg gtacgatccc caatatgcgg cttccgtctt tctgggatgg gccacgaaaa 3120
agttcggcaa gaggaacacc atctggctgt ttgggcctgc aactaccggg aagaccaaca 3180

```
tcgcggaggc catagcccac actgtgccct tctacgggtg cgtaaactgg accaatgaga   3240
actttccctt caacgactgt gtcgacaaga tggtgatctg gtgggaggag gggaagatga   3300
ccgccaaggt cgtggagtcg gccaaagcca ttctcggagg aagcaaggtg cgcgtggacc   3360
agaaatgcaa gtcctcggcc cagatagacc cgactcccgt gatcgtcacc tccaacacca   3420
acatgtgcgc cgtgattgac gggaactcaa cgaccttcga acaccagcag ccgttgcaag   3480
accggatgtt caaatttgaa ctcacccgcc gtctggatca tgactttggg aaggtcacca   3540
agcaggaagt caaagacttt ttccggtggg caaaggatca cgtggttgag gtggagcatg   3600
aattctacgt caaaaagggt ggagccaaga aaagacccgc ccccagtgac gcagatataa   3660
gtgagcccaa acgggtgcgc gagtcagttg cgcagccatc gacgtcagac gcggaagctt   3720
cgatcaacta cgcagacagg taccaaaaca aatgttctcg tcacgtgggc atgaatctga   3780
tgctgtttcc ctgcagacaa tgcgagagaa tgaatcagaa ttcaaatatc tgcttcactc   3840
acggacagaa agactgttta gagtgctttc ccgtgtcaga atctcaaccc gtttctgtcg   3900
tcaaaaaggc gtatcagaaa ctgtgctaca ttcatcatat catgggaaag gtgccagacg   3960
cttgcactgc ctgcgatctg gtcaatgtgg atttggatga ctgcatcttt gaacaataaa   4020
tgatttaaat caggtatggc tgccgatggt tatcttccag attggctcga ggacactctc   4080
tctgaaggaa taagacagtg gtggaagctc aaacctggcc caccaccacc aaagcccgca   4140
gagcggcata aggacgacag caggggtctt gtgcttcctg ggtacaagta cctcggaccc   4200
ttcaacggac tcgacaaggg agagccggtc aacgaggcag acgccgcggc cctcgagcac   4260
gacaaagcct acgaccggca gctcgacagc ggagacaacc cgtacctcaa gtacaaccac   4320
gccgacgcgg agtttcagga gcgccttaaa gaagatacgt cttttggggg caacctcgga   4380
cgagcagtct tccaggcgaa aaagagggtt cttgaacctc tgggcctggt tgaggaacct   4440
gttaagacgg ctccgggaaa aaagaggccg gtagagcact ctcctgtgga gccagactcc   4500
tcctcgggaa ccggaaaggc gggccagcag cctgcaagaa aaagattgaa ttttggtcag   4560
actggagacg cagactcagt acctgacccc cagcctctcg gacagccacc agcagccccc   4620
tctggtctgg gaactaatac gatggctaca ggcagtggcg caccaatggc agacaataac   4680
gagggcgccg acggagtggg taattcctcg ggaaattggc attgcgattc cacatggatg   4740
ggcgacagag tcatcaccac cagcacccga acctgggccc tgcccaccta caacaaccac   4800
ctctacaaac aaatttccag ccaatcagga gcctcgaacg acaatcacta ctttggctac   4860
agcacccctt gggggtattt tgacttcaac agattccact gccacttttc accacgtgac   4920
tggcaaagac tcatcaacaa caactgggga ttccgaccca agagactcaa cttcaagctc   4980
tttaacattc aagtcaaaga ggtcacgcag aatgacggta cgacgacgat tgccaataac   5040
cttaccagca cggttcaggt gtttactgac tcggagtacc agctcccgta cgtcctcggc   5100
tcggcgcatc aaggatgcct cccgccgttc ccagcagacg tcttcatggt gccacagtat   5160
ggatacctca ccctgaacaa cgggagtcag gcagtaggac gctcttcatt ttactgcctg   5220
gagtactttc cttctcagat gctgcgtacc ggaaacaact ttaccttcag ctacactttt   5280
gaggacgttc ctttccacag cagctacgct cacagccaga gtctggaccg tctcatgaat   5340
cctctcatcg accagtacct gtattacttg agcagaacaa acactccaag tggaaccacc   5400
acgcagtcaa ggcttcagtt ttctcaggcc ggagcgagtg acattcggga ccagtctagg   5460
aactggcttc ctggaccctg ttaccgccag cagcgagtat caaagacatc tgcggataac   5520
aacaacagtg aatactcgtg gactggagct accaagtacc acctcaatgg cagagactct   5580
```

```
ctggtgaatc cgggcccggc catggcaagc cacaaggacg atgaagaaaa gtttttttcct   5640

cagagcgggg ttctcatctt tgggaagcaa ggctcagaga aaacaaatgt ggacattgaa   5700

aaggtcatga ttacagacga agaggaaatc aggacaacca atcccgtggc tacggagcag   5760

tatggttctg tatctaccaa cctccagaga ggcaacagac aagcagctac cgcagatgtc   5820

aacacacaag gcgttcttcc aggcatggtc tggcaggaca gagatgtgta ccttcagggg   5880

cccatctggg caaagattcc acacacggac ggacattttc acccctctcc cctcatgggt   5940

ggattcggac ttaaacaccc tcctccacag attctcatca agaacacccc ggtacctgcg   6000

aatccttcga ccaccttcag tgcggcaaag tttgcttcct tcatcacaca gtactccacg   6060

ggacaggtca gcgtggagat cgagtgggag ctgcagaagg aaaacagcaa acgctggaat   6120

cccgaaattc agtacacttc caactacaac aagtctgtta atgtggactt tactgtggac   6180

actaatggcg tgtattcaga gcctcgcccc attggcacca gatacctgac tcgtaatctg   6240

taattgcttg ttaatcaata aaccgtttaa ttcgtttcag ttgaactttg gtctctgcgt   6300

atttctttct tatctagttt ccatggctac gtagataagt agcatggcgg gttaatcatt   6360

aactaca                                                             6367
```

<210> SEQ ID NO 8
<211> LENGTH: 12385
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 8

```
actcttcctt tttcaatatt attgaagcat ttatcagggt tattgtctca tgagcggata     60

catatttgaa tgtatttaga aaaataaaca aataggggtt ccgcgcacat ttccccgaaa    120

agtgccacct aaattgtaag cgttaatatt ttgttaaaat tcgcgttaaa tttttgttaa    180

atcagctcat tttttaacca ataggccgaa atcggcaaaa tcccttataa atcaaaagaa    240

tagaccgaga tagggttgag tgttgttcca gtttggaaca agagtccact attaaagaac    300

gtggactcca acgtcaaagg gcgaaaaacc gtctatcagg gcgatggccc actacgtgaa    360

ccatcaccct aatcaagttt tttggggtcg aggtgccgta aagcactaaa tcggaaccct    420

aaagggagcc cccgatttag agcttgacgg ggaaagccgg cgaacgtggc gagaaaggaa    480

gggaagaaag cgaaaggagc gggcgctagg gcgctggcaa gtgtagcggt cacgctgcgc    540

gtaaccacca cacccgccgc gcttaatgcg ccgctacagg gcgcgtccca ttcgccattc    600

aggctgcgca actgttggga agggcgatcg gtgcgggcct cttcgctatt acgccagctg    660

gcgaaagggg gatgtgctgc aaggcgatta agttgggtaa cgccagggtt ttcccagtca    720

cgacgttgta aaacgacggc cagtgagcgc gcctcgttca ttcacgtttt tgaacccgtg    780

gaggacgggc agactcgcgg tgcaaatgtg ttttacagcg tgatggagca gatgaagatg    840

ctcgacacgc tgcagaacac gcagctagat taaccctaga aagataatca tattgtgacg    900

tacgttaaag ataatcatgt gtaaaattga cgcatgtgtt ttatcggtct gtatatcgag    960

gtttatttat taatttgaat agatattaag ttttattata tttacactta catactaata   1020

ataaattcaa caaacaattt atttatgttt atttatttat taaaaaaaac aaaaactcaa   1080

aatttcttct ataaagtaac aaaactttta tgagggacag cccccccccca aagcccccag   1140
```

```
ggatgtaatt acgtccctcc cccgctaggg ggcagcagcg agccgcccgg ggctccgctc   1200
cggtccggcg ctcccccgc atccccgagc cggcagcgtg cggggacagc ccgggcacgg   1260
ggaaggtggc acgggatcgc tttcctctga acgcttctcg ctgctctttg agcctgcaga   1320
cacctggggg gatacgggga aaaggcctcc acggccacta gtaacggccg ccagtgtgct   1380
ggaattcgcc ctggaggggt ggagtcgtga cgtgaattac gtcatagggt tagggaggtc   1440
ctgtattaga ggtcacgtga gtgttttgcg acattttgcg acaccatgtg gtcacgctgg   1500
gtatttaagc ccgagtgagc acgcagggtc tccattttga agcgggaggt ttgaacgcgc   1560
agccgccatg ccggggtttt acgagattgt gattaaggtc cccagcgacc ttgacgagca   1620
tctgcccggc atttctgaca gctttgtgaa ctgggtggcc gagaaggaat gggagttgcc   1680
gccagattct gacatggatc tgaatctgat tgagcaggca cccctgaccg tggccgagaa   1740
gctgcagcgc gactttctga cggaatggcg ccgtgtgagt aaggccccgg aggccctttt   1800
ctttgtgcaa tttgagaagg gagagagcta cttccacatg cacgtgctcg tggaaaccac   1860
cggggtgaaa tccatggttt tgggacgttt cctgagtcag attcgcgaaa aactgattca   1920
gagaatttac cgcgggatcg agccgacttt gccaaactgg ttcgcggtca caaagaccag   1980
aaatggcgcc ggaggcggga acaaggtggt ggatgagtgc tacatcccca attacttgct   2040
ccccaaaacc cagcctgagc tccagtgggc gtggactaat atggaacagt atttaagcgc   2100
ctgtttgaat ctcacggagc gtaaacggtt ggtggcgcag catctgacgc acgtgtcgca   2160
gacgcaggag cagaacaaag agaatcagaa tcccaattct gatgcgccgg tgatcagatc   2220
aaaaacttca gccaggtaca tggagctggt cgggtggctc gtggacaagg tgagtttggg   2280
gacccttgat tgttctttct ttttcgctat tgtaaaattc atgttatatg gagggggcaa   2340
agttttcagg gtgttgttta gaatgggaag atgtcccttg tatcaccatg gaccctcatg   2400
ataattttgt ttctttcact ttctactctg ttgacaacca ttgtctcctc ttattttctt   2460
ttcattttct gtaacttttt cgttaaactt tagcttgcat ttgtaacgaa tttttaaatt   2520
cacttttgtt tatttgtcag attgtaagta ctttctctaa tcactttttt ttcaaggcaa   2580
tcagggtata ttatattgta cttcagcaca gttttagaga acataacttc gtataatgta   2640
tgctatacga agttatcggg cccctctgct aaccatgttc atgccttctt ctttttccta   2700
cagatggtga gcaagggcga ggagctgttc accggggtgg tgcccatcct ggtcgagctg   2760
gacggcgacg taaacggcca caagttcagc gtgtccggcg agggcgaggg cgatgccacc   2820
tacggcaagc tgaccctgaa gttcatctgc accaccggca agctgcccgt gccctggccc   2880
accctcgtga ccaccctgac ctacggcgtg cagtgcttca gccgctaccc cgaccacatg   2940
aagcagcacg acttcttcaa gtccgccatg cccgaaggct acgtccagga gcgcaccatc   3000
ttcttcaagg acgacggcaa ctacaagacc cgcgccgagg tgaagttcga gggcgacacc   3060
ctggtgaacc gcatcgagct gaagggcatc gacttcaagg aggacggcaa catcctgggg   3120
cacaagctgg agtacaacta caacagccac aacgtctata tcatggccga caagcagaag   3180
aacggcatca aggtgaactt caagatccgc cacaacatcg aggacggcag cgtgcagctc   3240
gccgaccact accagcagaa cacccccatc ggcgacggcc ccgtgctgct gcccgacaac   3300
cactacctga gcacccagtc cgccctgagc aaagacccca acgagaagcg cgatcacatg   3360
gtcctgctgg agttcgtgac cgccgccggg atcactctcg gcatggacga gctgtacaag   3420
taacctcagg tgcaggctgc ctatcagaag gtggtggctg gtgtggccaa tgccctggct   3480
cacaaatacc actgagatct tttccctct gccaaaaatt atggggacat catgaagccc   3540
```

-continued

```
cttgagcatc tgacttctgg ctaataaagg aaatttattt tcattgcaat agtgtgttgg   3600
aattttttgt gtctctcact cggaaggaca tatgggaggg caaatcattt aaaacatcag   3660
aatgagtatt tggtttagag tttggcaaca tatgcccata tgctggctgc catgaacaaa   3720
ggttggctat aaagaggtca tcagtatatg aaacagcccc ctgctgtcca ttccttattc   3780
catagaaaag ccttgacttg aggttagatt tttttatat tttgttttgt gttatttttt   3840
tctttaacat ccctaaaatt ttccttacat gttttactag ccagattttt cctcctctcc   3900
tgactactcc cagtcatagc tgtccctctt ctcttatgga gatcataact tcgtataatg   3960
tatgctatac gaagttataa ttgttataat taaatgataa ggtagaatat ttctgcatat   4020
aaattctggc tggcgtggaa atattcttat tggtagaaac aactacaccc tggtcatcat   4080
cctgcctttc tctttatggt tacaatgata tacactgttt gagatgagga taaaatactc   4140
tgagtccaaa ccgggcccct ctgctaacca tgttcatgcc ttcttctttt tcctacaggg   4200
gattacctcg gagaagcagt ggatccagga ggaccaggcc tcatacatct ccttcaatgc   4260
ggcctccaac tcgcggtccc aaatcaaggc tgccttggac aatgcgggaa agattatgag   4320
cctgactaaa accgcccccg actacctggt gggccagcag cccgtggagg acatttccag   4380
caatcggatt tataaaattt tggaactaaa cgggtacgat ccccaatatg cggcttccgt   4440
ctttctggga tgggccacga aaaagttcgg caagaggaac accatctggc tgtttgggcc   4500
tgcaactacc gggaagacca acatcgcgga ggccatagcc cacactgtgc ccttctacgg   4560
gtgcgtaaac tggaccaatg agaactttcc cttcaacgac tgtgtcgaca agatggtgat   4620
ctggtgggag gaggggaaga tgaccgccaa ggtcgtggag tcggccaaag ccattctcgg   4680
aggaagcaag gtgcgcgtgg accagaaatg caagtcctcg gcccagatag acccgactcc   4740
cgtgatcgtc acctccaaca ccaacatgtg cgccgtgatt gacgggaact caacgacctt   4800
cgaacaccag cagccgttgc aagaccggat gttcaaattt gaactcaccc gccgtctgga   4860
tcatgacttt gggaaggtca ccaagcagga agtcaaagac tttttccggt gggcaaagga   4920
tcacgtggtt gaggtggagc atgaattcta cgtcaaaaag ggtggagcca agaaaagacc   4980
cgcccccagt gacgcagata taagtgagcc caaacgggtg cgcgagtcag ttgcgcagcc   5040
atcgacgtca gacgcggaag cttcgatcaa ctacgcagac aggtaccaaa acaaatgttc   5100
tcgtcacgtg ggcatgaatc tgatgctgtt tccctgcaga caatgcgaga gaatgaatca   5160
gaattcaaat atctgcttca ctcacggaca gaaagactgt ttagagtgct ttcccgtgtc   5220
agaatctcaa cccgtttctg tcgtcaaaaa ggcgtatcag aaactgtgct acattcatca   5280
tatcatggga aaggtgccag acgcttgcac tgcctgcgat ctggtcaatg tggatttgga   5340
tgactgcatc tttgaacaat aaatgattta aatcaggtat ggctgccgat ggttatcttc   5400
cagattggct cgaggacact ctctctgaag gaataagaca gtggtggaag ctcaaacctg   5460
gcccaccacc accaaagccc gcagagcggc ataaggacga cagcaggggt cttgtgcttc   5520
ctgggtacaa gtacctcgga cccttcaacg gactcgacaa gggagagccg gtcaacgagg   5580
cagacgccgc ggccctcgag cacgacaaag cctacgaccg gcagctcgac agcggagaca   5640
acccgtacct caagtacaac cacgccgacg cggagtttca ggagcgcctt aaagaagata   5700
cgtcttttgg gggcaacctc ggacgagcag tcttccaggc gaaaaagagg gttcttgaac   5760
ctctgggcct ggttgaggaa cctgttaaga cggctccggg aaaaaagagg ccggtagagc   5820
actctcctgt ggagccagac tcctcctcgg gaaccggaaa ggcgggccag cagcctgcaa   5880
```

-continued

```
gaaaaagatt gaattttggt cagactggag acgcagactc agtacctgac ccccagcctc   5940
tcggacagcc accagcagcc ccctctggtc tgggaactaa tacgatggct acaggcagtg   6000
gcgcaccaat ggcagacaat aacgagggcg ccgacggagt gggtaattcc tcgggaaatt   6060
ggcattgcga ttccacatgg atgggcgaca gagtcatcac caccagcacc cgaacctggg   6120
ccctgcccac ctacaacaac cacctctaca aacaaatttc cagccaatca ggagcctcga   6180
acgacaatca ctactttggc tacagcaccc cttgggggta ttttgacttc aacagattcc   6240
actgccactt ttcaccacgt gactggcaaa gactcatcaa caacaactgg ggattccgac   6300
ccaagagact caacttcaag ctctttaaca ttcaagtcaa agaggtcacg cagaatgacg   6360
gtacgacgac gattgccaat aaccttacca gcacggttca ggtgtttact gactcggagt   6420
accagctccc gtacgtcctc ggctcggcgc atcaaggatg cctcccgccg ttcccagcag   6480
acgtcttcat ggtgccacag tatggatacc tcaccctgaa caacgggagt caggcagtag   6540
gacgctcttc attttactgc ctggagtact ttccttctca gatgctgcgt accggaaaca   6600
actttacctt cagctacact tttgaggacg ttcctttcca cagcagctac gctcacagcc   6660
agagtctgga ccgtctcatg aatcctctca tcgaccagta cctgtattac ttgagcagaa   6720
caaacactcc aagtggaacc accacgcagt caaggcttca gttttctcag gccggagcga   6780
gtgacattcg ggaccagtct aggaactggc ttcctggacc ctgttaccgc cagcagcgag   6840
tatcaaagac atctgcggat aacaacaaca gtgaatactc gtggactgga gctaccaagt   6900
accacctcaa tggcagagac tctctggtga atccgggccc ggccatggca agccacaagg   6960
acgatgaaga aaagtttttt cctcagagcg gggttctcat ctttgggaag caaggctcag   7020
agaaaacaaa tgtggacatt gaaaaggtca tgattacaga cgaagaggaa atcaggacaa   7080
ccaatcccgt ggctacggag cagtatggtt ctgtatctac caacctccag agaggcaaca   7140
gacaagcagc taccgcagat gtcaacacac aaggcgttct tccaggcatg gtctggcagg   7200
acagagatgt gtaccttcag gggcccatct gggcaaagat tccacacacg gacggacatt   7260
ttcacccctc tcccctcatg ggtggattcg gacttaaaca ccctcctcca cagattctca   7320
tcaagaacac cccggtacct gcgaatcctt cgaccacctt cagtgcggca aagtttgctt   7380
ccttcatcac acagtactcc acgggacagg tcagcgtgga gatcgagtgg gagctgcaga   7440
aggaaaacag caaacgctgg aatcccgaaa ttcagtacac ttccaactac aacaagtctg   7500
ttaatgtgga ctttactgtg gacactaatg gcgtgtattc agagcctcgc cccattggca   7560
ccagatacct gactcgtaat ctgtaattgc ttgttaatca ataaaccgtt taattcgttt   7620
cagttgaact ttggtctctg cgtatttctt tcttatctag tttccatggc tacgtagata   7680
agtagcatgg cgggttaatc attaactaca taagggcgaa ttctgcagat atccatcaca   7740
ctggcggccg ctcgagcatg catctagagc tagcgaattc gaatttaaat cggatccgcg   7800
gccgcaagga tctgcgatcg ctccggtgcc cgtcagtggg cagagcgcac atcgcccaca   7860
gtccccgaga agttgggggg aggggtcggc aattgaacgg gtgcctagag aaggtggcgc   7920
ggggtaaact gggaaagtga tgtcgtgtac tggctccgcc tttttcccga gggtggggga   7980
gaaccgtata taagtgcagt agtcgccgtg aacgttcttt ttcgcaacgg gtttgccgcc   8040
agaacacagc tgaagcttcg aggggctcgc atctctcctt cacgcgcccg ccgccctacc   8100
tgaggccgcc atccacgccg gttgagtcgc gttctgccgc ctcccgcctg tggtgcctcc   8160
tgaactgcgt ccgccgtcta ggtaagttta aagctcaggt cgagaccggg cctttgtccg   8220
gcgctccctt ggagcctacc tagactcagc cggctctcca cgctttgcct gaccctgctt   8280
```

gctcaactct acgtctttgt ttcgttttct gttctgcgcc gttacagatc caagctgtga 8340
ccggcgccta cgatatcgcc accatgaaaa catttaacat ttctcaacag gatctagaat 8400
tagtagaagt agcgacagag aagattacaa tgctttatga ggataataaa catcatgtgg 8460
gagcggcaat tcgtacgaaa acaggagaaa tcatttcggc agtacatatt gaagcgtata 8520
taggacgagt aactgtttgt gcagaagcca ttgcgattgg tagtgcagtt tcgaatggac 8580
aaaaggattt tgacacgatt gtagctgtta gacaccctta ttctgacgaa gtagatagaa 8640
gtattcgagt ggtaagtcct tgtggtatgt gtagggagtt gatttcagac tatgcaccag 8700
attgttttgt gttaatagaa atgaatggca agttagtcaa aactacgatt gaagaactca 8760
ttccactcaa atatacccga aattaaggta cctcgacaac cttccaaact gagtgcatga 8820
cccgcaagcc cggtgcctga aatcaacctc tggattacaa aatttgtgaa agattgactg 8880
gtattcttaa ctatgttgct ccttttacgc tatgtggata cgctgcttta atgcctttgt 8940
atcatgcgtt aactaaactt gtttattgca gcttataatg gttacaaata aagcaatagc 9000
atcacaaatt tcacaaataa agcatttttt tcactgcatt ctagttgtgg tttgtccaaa 9060
ctcatcaatg tatcttatca tgtctggaat tgactcaaat gatgtcaatt agtctatcag 9120
aagctatctg gtctcccttc cgggggacaa gacatccctg tttaatattt aaacagcagt 9180
gttcccaaac tgggttctta tatcccttgc tctggtcaac caggttgcag ggtttcctgt 9240
cctcacagga acgaagtccc taaagaaaca gtggcagcca ggtttagccc cggaattgac 9300
tggattcctt ttttagggcc cattggtatg gctttttccc cgtatccccc caggtgtctg 9360
caggctcaaa gagcagcgag aagcgttcag aggaaagcga tcccgtgcca ccttccccgt 9420
gcccgggctg tccccgcacg ctgccggctc ggggatgcgg ggggagcgcc ggaccggagc 9480
ggagccccgg gcggctcgct gctgccccct agcgggggag ggacgtaatt acatccctgg 9540
gggctttggg ggggggctgt ccctgatatc tataacaaga aaatatatat ataataagtt 9600
atcacgtaag tagaacatga aataacaata taattatcgt atgagttaaa tcttaaaagt 9660
cacgtaaaag ataatcatgc gtcattttga ctcacgcggt cgttatagtt caaaatcagt 9720
gacacttacc gcattgacaa gcacgcctca cgggagctcc aagcggcgac tgagatgtcc 9780
taaatgcaca gcgacggatt cgcgctattt agaaagagag agcaatattt caagaatgca 9840
tgcgtcaatt ttacgcagac tatctttcta gggttaatct agctgcatca ggatcatatc 9900
gtcgggtctt ttttccggct cagtcatcgc ccaagctggc gctatctggg catcggggag 9960
gaagaagccc gtgccttttc ccgcgaggtt gaagcggcat ggaaagagtt tgccgaggat 10020
gactgctgct gcattgacgt tgagcgaaaa cgcacgttta ccatgatgat tcgggaaggt 10080
gtggccatgc acgcctttaa cggtgaactg ttcgttcagg ccacctggga taccagttcg 10140
tcgcggcttt tccggacaca gttccggatg gtcagcccga agcgcatcag caacccgaac 10200
aataccggcg acagccggaa ctgccgtgcc ggtgtgcaga ttaatgacag cggtgcggcg 10260
ctgggatatt acgtcagcga ggacgggtat cctggctgga tgccgcagaa atggacatgg 10320
ataccccgtg agttacccgg cgggcgcgct tggcgtaatc atggtcatag ctgtttcctg 10380
tgtgaaattg ttatccgctc acaattccac acaacatacg agccggaagc ataaagtgta 10440
aagcctgggg tgcctaatga gtgagctaac tcacattaat tgcgttgcgc tcactgcccg 10500
ctttccagtc gggaaacctg tcgtgccagc tgcattaatg aatcggccaa cgcgcgggga 10560
gaggcggttt gcgtattggg cgctcttccg cttcctcgct cactgactcg ctgcgctcgg 10620

```
tcgttcggct gcggcgagcg gtatcagctc actcaaaggc ggtaatacgg ttatccacag  10680

aatcagggga taacgcagga aagaacatgt gagcaaaagg ccagcaaaag gccaggaacc  10740

gtaaaaaggc cgcgttgctg gcgtttttcc ataggctccg cccccctgac gagcatcaca  10800

aaaatcgacg ctcaagtcag aggtggcgaa acccgacagg actataaaga taccaggcgt  10860

ttccccctgg aagctccctc gtgcgctctc ctgttccgac cctgccgctt accggatacc  10920

tgtccgcctt tctcccttcg ggaagcgtgg cgctttctca tagctcacgc tgtaggtatc  10980

tcagttcggt gtaggtcgtt cgctccaagc tgggctgtgt gcacgaaccc cccgttcagc  11040

ccgaccgctg cgccttatcc ggtaactatc gtcttgagtc caacccggta agacacgact  11100

tatcgccact ggcagcagcc actggtaaca ggattagcag agcgaggtat gtaggcggtg  11160

ctacagagtt cttgaagtgg tggcctaact acggctacac tagaaggaca gtatttggta  11220

tctgcgctct gctgaagcca gttaccttcg gaaaaagagt tggtagctct tgatccggca  11280

aacaaaccac cgctggtagc ggtggttttt ttgtttgcaa gcagcagatt acgcgcagaa  11340

aaaaaggatc tcaagaagat cctttgatct tttctacggg gtctgacgct cagtggaacg  11400

aaaactcacg ttaagggatt ttggtcatga gattatcaaa aaggatcttc acctagatcc  11460

ttttaaatta aaaatgaagt tttaaatcaa tctaaagtat atatgagtaa acttggtctg  11520

acagttacca atgcttaatc agtgaggcac ctatctcagc gatctgtcta tttcgttcat  11580

ccatagttgc ctgactcccc gtcgtgtaga taactacgat acgggagggc ttaccatctg  11640

gccccagtgc tgcaatgata ccgcgagacc cacgctcacc ggctccagat ttatcagcaa  11700

taaaccagcc agccggaagg gccgagcgca gaagtggtcc tgcaacttta tccgcctcca  11760

tccagtctat taattgttgc cgggaagcta gagtaagtag ttcgccagtt aatagtttgc  11820

gcaacgttgt tgccattgct acaggcatcg tggtgtcacg ctcgtcgttt ggtatggctt  11880

cattcagctc cggttcccaa cgatcaaggc gagttacatg atcccccatg ttgtgcaaaa  11940

aagcggttag ctccttcggt cctccgatcg ttgtcagaag taagttggcc gcagtgttat  12000

cactcatggt tatggcagca ctgcataatt ctcttactgt catgccatcc gtaagatgct  12060

tttctgtgac tggtgagtac tcaaccaagt cattctgaga atagtgtatg cggcgaccga  12120

gttgctcttg cccggcgtca atacgggata ataccgcgcc acatagcaga actttaaaag  12180

tgctcatcat tggaaaacgt tcttcggggc gaaaactctc aaggatctta ccgctgttga  12240

gatccagttc gatgtaaccc actcgtgcac ccaactgatc ttcagcatct tttactttca  12300

ccagcgtttc tgggtgagca aaaacaggaa ggcaaaatgc cgcaaaaaag ggaataaggg  12360

cgacacggaa atgttgaata ctcat                                        12385
```

```
<210> SEQ ID NO 9
<211> LENGTH: 14766
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 9
```

```
actcttcctt tttcaatatt attgaagcat ttatcagggt tattgtctca tgagcggata     60

catatttgaa tgtatttaga aaaataaaca aataggggtt ccgcgcacat ttccccgaaa    120

agtgccacct aaattgtaag cgttaatatt ttgttaaaat tcgcgttaaa tttttgttaa    180

atcagctcat tttttaacca ataggccgaa atcggcaaaa tcccttataa atcaaaagaa    240
```

```
tagaccgaga tagggttgag tgttgttcca gtttggaaca agagtccact attaaagaac    300
gtggactcca acgtcaaagg gcgaaaaacc gtctatcagg gcgatggccc actacgtgaa    360
ccatcaccct aatcaagttt tttggggtcg aggtgccgta aagcactaaa tcggaaccct    420
aaagggagcc cccgatttag agcttgacgg ggaaagccgg cgaacgtggc gagaaaggaa    480
gggaagaaag cgaaaggagc gggcgctagg gcgctggcaa gtgtagcggt cacgctgcgc    540
gtaaccacca cacccgccgc gcttaatgcg ccgctacagg gcgcgtccca ttcgccattc    600
aggctgcgca actgttggga agggcgatcg gtgcgggcct cttcgctatt acgccagctg    660
gcgaaagggg gatgtgctgc aaggcgatta agttgggtaa cgccagggtt ttcccagtca    720
cgacgttgta aaacgacggc cagtgagcgc gcctcgttca ttcacgtttt tgaacccgtg    780
gaggacgggc agactcgcgg tgcaaatgtg ttttacagcg tgatggagca gatgaagatg    840
ctcgacacgc tgcagaacac gcagctagat taaccctaga aagataatca tattgtgacg    900
tacgttaaag ataatcatgt gtaaaattga cgcatgtgtt ttatcggtct gtatatcgag    960
gtttatttat taatttgaat agatattaag ttttattata tttacactta catactaata   1020
ataaattcaa caaacaattt atttatgttt atttatttat taaaaaaaac aaaaactcaa   1080
aatttcttct ataaagtaac aaaactttta tgagggacag cccccccccca aagcccccag   1140
ggatgtaatt acgtccctcc cccgctaggg ggcagcagcg agccgcccgg ggctccgctc   1200
cggtccggcg ctccccccgc atccccgagc cggcagcgtg cggggacagc ccgggcacgg   1260
ggaaggtggc acgggatcgc tttcctctga acgcttctcg ctgctctttg agcctgcaga   1320
cacctggggg gatacgggga aaaggcctcc acggccacta gtccatagag cccaccgcat   1380
ccccagcatg cctgctattg tcttcccaat cctcccccctt gctgtcctgc cccaccccac   1440
cccctagaat agaatgacac ctactcagac aatgcgatgc aatttcctca ttttattagg   1500
aaaggacagt gggagtggca ccttccaggg tcaaggaagg cacgggggag ggcaaacaa   1560
cagatggctg gcaactagaa ggcacagcta catgggggta gagtcataat cgtgcatcag   1620
gatagggcgg tggtgctgca gcagcgcgcg aataaactgc tgccgccgcc gctccgtcct   1680
gcaggaatac aacatggcag tggtctcctc agcgatgatt cgcaccgccc gcagcatgag   1740
acgccttgtc ctccgggcac agcagcgcac cctgatctca cttaaatcag cacagtaact   1800
gcagcacagc accacaatat tgttcaaaat cccacagtgc aaggcgctgt atccaaagct   1860
catggcgggg accacagaac ccacgtggcc atcataccac aagcgcaggt agattaagtg   1920
gcgacccctc ataaacacgc tggacataaa cattacctct tttggcatgt tgtaattcac   1980
cacctcccgg taccatataa acctctgatt aaacatggcg ccatccacca ccatcctaaa   2040
ccagctggcc aaaacctgcc cgccggctat gcactgcagg gaaccgggac tggaacaatg   2100
acagtggaga gcccaggact cgtaaccatg gatcatcatg ctcgtcatga tatcaatgtt   2160
ggcacaacac aggcacacgt gcatacactt cctcaggatt acaagctcct cccgcgtcag   2220
aaccatatcc cagggaacaa cccattcctg aatcagcgta aatcccacac tgcagggaag   2280
acctcgcacg taactcacgt tgtgcattgt caaagtgtta cattcgggca gcagcggatg   2340
atcctccagt atggtagcgc gggtctctgt ctcaaaagga ggtaggcgat ccctactgta   2400
cggagtgcgc cgagacaacc gagatcgtgt tggtcgtagt gtcatgccaa atggaacgcc   2460
ggacgtagtc atggttgtgg ccatattatc atcgtgtttt tcaaaggaaa accacgtccc   2520
cgtggttcgg ggggcctaga cgttttttta acctcgacta aacacatgta aagcatgtgc   2580
```

-continued

```
accgaggccc cagatcagat cccatacaat ggggtacctt ctgggcatcc ttcagcccct   2640
tgttgaatac gcttgaggag agccatttga ctctttccac aactatccaa ctcacaacgt   2700
ggcactgggg ttgtgccgcc tttgcaggtg tatcttatac acgtggcttt tggccgcaga   2760
ggcacctgtc gccaggtggg gggttccgct gcctgcaaag ggtcgctaca gacgttgttt   2820
gtcttcaaga agcttccaga ggaactgctt ccttcacgac attcaacaga ccttgcattc   2880
ctttggcgag aggggaaaga cccctaggaa tgctcgtcaa gaagacaggg ccaggtttcc   2940
gggccctcac attgccaaaa gacggcaata tggtggaaaa taacatatag acaaacgcac   3000
accggcctta ttccaagcgg cttcggccag taacgttagg ggggggggag ggagaggggc   3060
ttaaaaatca aaggggttct gccgcgcatc actatgcgcc actggcaggg acacgttgcg   3120
atactggtgt ttagtgctcc acttaaactc aggcacaacc atccgcggca gctcggtgaa   3180
gttttcactc cacaggctgc gcaccatcac caacgcgttt agcaggtcgg gcgccgatat   3240
cttgaagtcg cagttggggc ctccgccctg cgcgcgcgag ttgcgataca cagggttgca   3300
gcactggaac actatcagcg ccgggtggtg cacgctggcc agcacgctct tgtcggagat   3360
cagatccgcg tccaggtcct ccgcgttgct cagggcgaac ggagtcaact ttggtagctg   3420
ccttcccaaa aagggtgcat gcccaggctt tgagttgcac tcgcaccgta gtggcatcag   3480
aaggtgaccg tgcccggtct gggcgttagg atacagcgcc tgcatgaaag ccttgatctg   3540
cttaaaagcc acctgagcct ttgcgccttc agagaagaac atgccgcaag acttgccgga   3600
aaactgattg gccggacagg ccgcgtcatg cacgcagcac cttgcgtcgg tgttggagat   3660
ctgcaccaca tttcggcccc accggttctt cacgatcttg gccttgctag actgctcctt   3720
cagcgcgcgc tgcccgtttt cgctcgtcac atccatttca atcacgtgct ccttatttat   3780
cataatgctc ccgtgtagac acttaagctc gccttcgatc tcagcgcagc ggtgcagcca   3840
caacgcgcag cccgtgggct cgtggtgctt gtaggttacc tctgcaaacg actgcaggta   3900
cgcctgcagg aatcgcccca tcatcgtcac aaaggtcttg ttgctggtga aggtcagctg   3960
caacccgcgg tgctcctcgt ttagccaggt cttgcatacg gccgccagag cttccacttg   4020
gtcaggcagt agcttgaagt ttgcctttag atcgttatcc acgtggtact tgtccatcaa   4080
cgcgcgcgca gcctccatgc ccttctccca cgcagacacg atcggcaggc tcagcgggtt   4140
tatcaccgtg ctttcacttt ccgcttcact ggactcttcc ttttcctctt gcgtccgcat   4200
accccgcgcc actgggtcgt cttcattcag ccgccgcacc gtgcgcttac ctcccttgcc   4260
gtgcttgatt agcaccggtg ggttgctgaa acccaccatt tgtagcgcca catcttctct   4320
ttcttcctcg ctgtccacga tcacctctgg ggatggcggg cgctcgggct tgggagaggg   4380
gcgcttcttt ttcttttttgg acgcaatggc caaatccgcc gtcgaggtcg atggccgcgg   4440
gctgggtgtg cgcggcacca gcgcatcttg tgacgagtct tcttcgtcct cggactcgag   4500
acgccgcctc agccgctttt ttgggggcgc gcgcttgtcg tcatcgtctt tgtagtcggg   4560
aggcggcggc gacggcgacg gggacgacac gtcctccatg gttggtggac gtcgcgccgc   4620
accgcgtccg cgctcggggg tggtttcgcg ctgctcctct tcccgactgg ccatggtggc   4680
cgaggataac ttcgtatatg gtttcttata cgaagttatg atccagacat gataagatac   4740
attgatgagt ttggacaaac cacaactaga atgcagtgaa aaaaatgctt tatttgtgaa   4800
atttgtgatg ctattgcttt atttgtaacc attataagct gcaataaaca agttaacaac   4860
aacaattgca ttcattttat gtttcaggtt cagggggagg tgtgggaggt tttttaaagc   4920
aagtaaaacc tctacaaatg tggtatggct gattatgatc ctctagagtc gcagatctgc   4980
```

-continued

```
tacgtatcaa gctgtggcag ggaaaccctc tgcctccccc gtgatgtaat acttttgcaa   5040
ggaatgcgat gaagtagagc ccgcagtggc caagtggctt tggtccgtct cctccacgga   5100
tgcccctcca cggctagtgg gcgcatgtag gcggtgggcg tccgccgcct ccagcagcag   5160
gtcatagagg ggcaccacgt tcttgcactt catgctgtac agatgctcca tgcctttgtt   5220
actcatgtgt cggatgtggg agaggatgag gaggagctgg gccagccgct ggtgctgctg   5280
ctgcagggtc aggcctgcct tggccatcag gtggatcaaa gtgtctgtga tcttgtccag   5340
gactcggtgg atatggtcct tctcttccag agacttcagg gtgctggaca gaaatgtgta   5400
cactccagaa ttaagcaaaa taatagattt gaggcacaca aactcctctc cctgcagatt   5460
catcatgcgg aaccgagatg atgtagccag cagcatgtcg aagatctcca ccatgccctc   5520
tacacatttt ccctggttcc tgtccaagag caagttagga gcaaacagta gcttcactgg   5580
gtgctccatg gagcgccaga cgagaccaat catcaggatc tctagccagg cacattctag   5640
aaggtggacc tgatcatgga gggtcaaatc cacaaagcct ggcaccctct tcgcccagtt   5700
gatcatgtga accagctccc tgtctgccag gttggtcagt aagcccatca tcgaagcttc   5760
actgaagggt ctggtaggat catactcgga atagagtatg gggggctcag catccaacaa   5820
ggcactgacc atctggtcgg ccgtcaggga caaggccagg ctgttcttct tagagcgttt   5880
gatcatgagc gggcttggcc aaaggttggc agctctcatg tctccagcag atggctcgag   5940
atcgccatct tccagcaggc gcaccattgc ccctgtttca ctatccaggt tacggatata   6000
gttcatgaca atatttacat tggtccagcc accagcttgc atgatctccg gtattgaaac   6060
tccagcgcgg gccatatctc gcgcggctcc gacacgggca ctgtgtccag accaggccag   6120
gtatctctga ccagagtcat cctaaaatac acaaacaatt agaatcagta gtttaacaca   6180
ttatacactt aaaaatttta tatttacctt agcgccgtaa atcaatcgat gagttgcttc   6240
aaaaatccct tccagggcgc gagttgatag ctggctggtg gcagatggcg cggcaacacc   6300
atttttctg acccggcaaa acaggtagtt attcggatca tcagctacac cagagacgga   6360
aatccatcgc tcgaccagtt tagtgactcc caggctaagt gccttctcta cacctgcggt   6420
gctaaccagc gttttcgttc tgccaatatg gattaacatt ctcccaccgt cagtacgtga   6480
gatatcttta accctgatcc tggcaatttc ggctatacgt aacagggtgt tataagcaat   6540
ccccagaaat gccagattac gtatatcctg gcagcgatcg ctattttcca tgagtgaacg   6600
gacttggtcg aaatcagtgc gttcgaacgc tagagcctgt tttgcacgtt caccggcatc   6660
aacgttttct tttcggatcc gccgcataac cagtgaaaca gcattgctgt cacttggtcg   6720
tggcagcccg gaccgacgat gaagcatgtt tagctggccc aaatgttgct ggatagtttt   6780
tactgccaga ccgcgcgctt gaagatatag aagataatcg cgaacatctt caggttctgc   6840
gggaaaccat ttccggttat tcaacttgca ccatgccgcc cacgaccggc aaacggacag   6900
aagcatttc caggtatgct cagaaaacgc ctggcgatcc ctgaacatgt ccatcaggtt   6960
cttgcgaacc tcatcactcg ttgcatcgac cggtaatgca ggcaaatttt ggtgtacggt   7020
cagtaaattg gacatggtgg ctacgtaata acttcgtata tggtttctta tacgaagtta   7080
tgcggccgct ttacgagggt aggaagtggt acggaaagtt ggtataagac aaaagtgttg   7140
tggaattgct ccaggcgatc tgacggttca ctaaacgagc tctgctttta taggcgccca   7200
ccgtacacgc ctaaagctta tacgttctct atcactgata gggagtaaac tggatatacg   7260
ttctctatca ctgataggga gtaaactgta gatacgttct ctatcactga tagggagtaa   7320
```

-continued

```
actggtcata cgttctctat cactgatagg gagtaaactc cttatacgtt ctctatcact   7380
gatagggagt aaagtctgca tacgttctct atcactgata gggagtaaac tcttcatacg   7440
ttctctatca ctgataggga gtaaactcgc ggccgcagag aaatgttctg gcacctgcac   7500
ttgcactggg gacagcctat tttgctagtt tgttttgttt cgttttgttt tgatggagag   7560
cgtatgttag tactatcgat tcacacaaaa aaccaacaca cagatgtaat gaaaataaag   7620
atattttatt ggatctgcga tcgctccggt gcccgtcagt gggcagagcg cacatcgccc   7680
acagtccccg agaagttggg gggaggggtc ggcaattgaa cgggtgccta gagaaggtgg   7740
cgcggggtaa actgggaaag tgatgtcgtg tactggctcc gcctttttcc cgagggtggg   7800
ggagaaccgt atgtaagtgc agtagtcgcc gtgaacgttc tttttcgcaa cgggtttgcc   7860
gccagaacac agctgaagct tcgaggggct cgcatctctc cttcacgcgc ccgccgccct   7920
acctgaggcc gccatccacg ccggttgagt cgcgttctgc cgcctcccgc ctgtggtgcc   7980
tcctgaactg cgtccgccgt ctaggtaagt ttaaagctca ggtcgagacc gggcctttgt   8040
ccggcgctcc cttggagcct acctagactc agccggctct ccacgctttg cctgaccctg   8100
cttgctcaac tctacgtctt tgtttcgttt tctgttctgc gccgttacag atccaagctg   8160
tgaccggcgc ctacgctagc ggatccgccg ccaccatgtc tagactggac aagagcaaag   8220
tcataaactc tgctctggaa ttactcaatg gagtcggtat cgaaggcctg acgacaagga   8280
aactcgctca aaagctggga gttgagcagc ctaccctgta ctggcacgtg aagaacaagc   8340
gggccctgct cgatgccctg ccaatcgaga tgctggacag gcatcatacc cactcctgcc   8400
ccctggaagg cgagtcatgg caagactttc tgcggaacaa cgccaagtca taccgctgtg   8460
ctcttctctc acatcgcgac ggggctaaag tgcatctcgg cacccgccca acagagaaac   8520
agtacgaaac cctggaaaat cagctcgcgt tcctgtgtca gcaaggcttc tccctggaga   8580
acgcactgta cgctctgtcc gccgtgggcc actttacact gggctgcgta ttggaggaac   8640
aggagcatca agtagcaaaa gaggaaagag agacacctac caccgattct atgcccccac   8700
ttctgaaaca agcaattgag ctgttcgacc ggcagggagc cgaacctgcc ttccttttcg   8760
gcctggaact aatcatatgt ggcctggaga aacagctaaa gtgcgaaagc ggcgggccga   8820
ccgacgccct tgacgatttt gacttagaca tgctcccagc cgatgccctt gacgactttg   8880
accttgatat gctgcctgct gacgctcttg acgattttga ccttgacatg ctccccgggt   8940
gaaccggtcg ctgatcagcc tcgactgtgc cttctagttg ccagccatct gttgtttgcc   9000
cctcccccgt gccttccttg accctggaag gtgccactcc cactgtcctt tcctaataaa   9060
atgaggaaat tgcatcgcat tgtctgagta ggtgtcattc tattctgggg ggtggggtgg   9120
ggcaggacag caagggggag gattgggaag acaatagcag gcatgctggg gatgcggtgg   9180
gctctatggc ttctgaggcg gaaagaacca gctggggctc gactagagct tgcggaaccc   9240
ttagagggcc tatttcccat gattccttca tatttgcata tacgatacaa ggctgttaga   9300
gagataatta gaattaattt gactgtaaac acaaagatat tagtacaaaa taataacttc   9360
gtataatgta tgctatacga agttatcaga catgataaga tacattgatg agtttggaca   9420
aaccacaact agaatgcagt gaaaaaaatg ctttatttgt gaaatttgtg atgctattgc   9480
tttatttgta accattataa gctgcaataa acaaggtacc tcaagcgccg ggttttcgcg   9540
tcatgcacca cgtccgtggg ccctcgggta cttcaacgtc agcagtaact gtaaatccga   9600
gccgttcata gaagggcaaa ttccttggcg ctgacgtttc aagaaaggct ggcactccgg   9660
ctcgttctgc ggcttctact ccgggcaata ccaccgcgga accaaggccc tttccctgat   9720
```

-continued gatcggggct aacgcccaca gtagcgagga accaagctgg ttctttaggg cggtgagggg 9780
cgaggagtcc ttccatttgt tgctgagccg cgagacgaga gccactaagc tcagccattc 9840
ggggaccaat ttctgcaaat acagccccgg cctcaacgct ctccggagtc gtccacactg 9900
ccactgcagc cccgtcgtcg gcgacccaaa ctttaccgat gtccaatcct accctggtca 9960
aaaaaagttc ttgcaattct gtaacccgtt caatatgtct atcaggatca actgtgtggc 10020
gtgtagcggg ataatccgcg aaagcggcag ccaatgttct cacggcccta gggacgtcgt 10080
ctcgagttgc cagtctgaca gtaggtttat attctgtcat aggtccaggg ttctcctcca 10140
cgtctccagc ctgcttcagc aggctgaagt tagtagctcc ggatccttta cctccatcac 10200
cagcgccacc agtagagtat ctggccacag ccacctcgtg ctgctcgacg taggtctcat 10260
cgtcggcctc cttgattctt tccagtctgt ggtccacgtt gtagacgccg ggcatcttga 10320
ggttcgtagc gggtttcttg gatctgtatg tggtctcaag gttgcagatc aggtggcccc 10380
cgcccacgag cttcagggcc atgtcacatg cgccttccag gccgccgtca gcggggtaca 10440
tcgtctcggt ggaggcctcc cagccgagtg ttttcttctg catcacaggg ccgttggctg 10500
ggaagttcac ccctctaacc ttgacgttgt agatgaggca gccgtcctgg aggctggtgt 10560
cctgggtagc ggtcagcacg cccccgtctt cgtatgtggt gactctctcc catgtgaagc 10620
cctcagggaa ggactgctta aagaagtcgg ggatgcccgg agggtgcttg atgaaggttc 10680
tgctgccgta catgaagctg gtagccagga tgtcgaaggc gaaggggaga gggccgccct 10740
cgacgacctt gattctcatg gtctgggtgc cctcgtaggg cttgccttcg ccctcggatg 10800
tgcacttgaa gtggtggttg ttcacggtgc cctccatgta cagcttcatg ggcatgttct 10860
ccttaatcag ctcgctcacg gtggcggcga attccgaaag gcccggagat gaggaagagg 10920
agaacagcgc ggcagacgtg cgcttttgaa gcgtgcagaa tgccgggcct ccggaggacc 10980
ttcgggcgcc cgccccgccc ctgagcccgc ccctgagccc gcccccggac ccaccccttc 11040
ccagcctctg agcccagaaa gcgaaggagc aaagctgcta ttggccgctg ccccaaaggc 11100
ctacccgctt ccattgctca gcggtgctgt ccatctgcac gagactagtg agacgtgcta 11160
cttccatttg tcacgtcctg cacgacgcga gctgcggggc ggggggggaac ttcctgacta 11220
ggggaggagt agaaggtggc gcgaaggggc caccaaagaa cggagccggt tggcgcctac 11280
cggtggatgt ggaatgtgtg cgaggccaga ggccacttgt gtagcgccaa gtgcccagcg 11340
gggctgctaa agcgcatgct ccagactgcc ttgggaaaag cgctccccta cccataactt 11400
cgtataatgt atgctatacg aagttatttt gcagttttaa aattatgttt taaaatggac 11460
tatcatatgc ttaccgtaac ttgaaagtat ttcgatttct tggctttata tatcttgtgg 11520
aaaggacgaa acaccgggca ctcttccgtg atctggtgga taaattcgca agggtatcat 11580
ggcggacgac cgggattcga accccggatc cggccgtccg ccgtgatcca tgcggttacc 11640
gcccgcgtgt cgaacccagg tgtgcgacgt cagacaacgg gggagcgctc ctttttgggc 11700
ccattggtat ggctttttcc ccgtatcccc ccaggtgtct gcaggctcaa agagcagcga 11760
gaagcgttca gaggaaagcg atcccgtgcc accttccccg tgcccgggct gtccccgcac 11820
gctgccggct cggggatgcg gggggagcgc cggaccggag cggagccccg ggcggctcgc 11880
tgctgccccc tagcggggga gggacgtaat tacatccctg gggggctttgg gggggggctg 11940
tccctgatat ctataacaag aaaatatata tataataagt tatcacgtaa gtagaacatg 12000
aaataacaat ataattatcg tatgagttaa atcttaaaag tcacgtaaaa gataatcatg 12060

-continued cgtcattttg actcacgcgg tcgttatagt tcaaaatcag tgacacttac cgcattgaca 12120
agcacgcctc acgggagctc caagcggcga ctgagatgtc ctaaatgcac agcgacggat 12180
tcgcgctatt tagaaagaga gagcaatatt tcaagaatgc atgcgtcaat tttacgcaga 12240
ctatctttct agggttaatc tagctgcatc aggatcatat cgtcgggtct tttttccggc 12300
tcagtcatcg cccaagctgg cgctatctgg gcatcgggga ggaagaagcc cgtgcctttt 12360
cccgcgaggt tgaagcggca tggaaagagt ttgccgagga tgactgctgc tgcattgacg 12420
ttgagcgaaa acgcacgttt accatgatga ttcgggaagg tgtggccatg cacgccttta 12480
acggtgaact gttcgttcag gccacctggg ataccagttc gtcgcggctt ttccggacac 12540
agttccggat ggtcagcccg aagcgcatca gcaacccgaa caataccggc gacagccgga 12600
actgccgtgc cggtgtgcag attaatgaca gcggtgcggc gctgggatat tacgtcagcg 12660
aggacgggta tcctggctgg atgccgcaga aatggacatg gataccccgt gagttacccg 12720
gcgggcgcgc ttggcgtaat catggtcata gctgtttcct gtgtgaaatt gttatccgct 12780
cacaattcca cacaacatac gagccggaag cataaagtgt aaagcctggg gtgcctaatg 12840
agtgagctaa ctcacattaa ttgcgttgcg ctcactgccc gctttccagt cgggaaacct 12900
gtcgtgccag ctgcattaat gaatcggcca acgcgcgggg agaggcggtt tgcgtattgg 12960
gcgctcttcc gcttcctcgc tcactgactc gctgcgctcg gtcgttcggc tgcggcgagc 13020
ggtatcagct cactcaaagg cggtaatacg gttatccaca gaatcagggg ataacgcagg 13080
aaagaacatg tgagcaaaag gccagcaaaa ggccaggaac cgtaaaaagg ccgcgttgct 13140
ggcgtttttc cataggctcc gcccccctga cgagcatcac aaaaatcgac gctcaagtca 13200
gaggtggcga aacccgacag gactataaag ataccaggcg tttccccctg gaagctccct 13260
cgtgcgctct cctgttccga ccctgccgct taccggatac ctgtccgcct ttctcccttc 13320
gggaagcgtg gcgctttctc atagctcacg ctgtaggtat ctcagttcgg tgtaggtcgt 13380
tcgctccaag ctgggctgtg tgcacgaacc ccccgttcag cccgaccgct gcgccttatc 13440
cggtaactat cgtcttgagt ccaacccggt aagacacgac ttatcgccac tggcagcagc 13500
cactggtaac aggattagca gagcgaggta tgtaggcggt gctacagagt tcttgaagtg 13560
gtggcctaac tacggctaca ctagaaggac agtatttggt atctgcgctc tgctgaagcc 13620
agttaccttc ggaaaaagag ttggtagctc ttgatccggc aaacaaacca ccgctggtag 13680
cggtggtttt tttgtttgca agcagcagat tacgcgcaga aaaaaaggat ctcaagaaga 13740
tcctttgatc ttttctacgg ggtctgacgc tcagtggaac gaaaactcac gttaagggat 13800
tttggtcatg agattatcaa aaaggatctt cacctagatc cttttaaatt aaaaatgaag 13860
ttttaaatca atctaaagta tatatgagta aacttggtct gacagttacc aatgcttaat 13920
cagtgaggca cctatctcag cgatctgtct atttcgttca tccatagttg cctgactccc 13980
cgtcgtgtag ataactacga tacgggaggg cttaccatct ggccccagtg ctgcaatgat 14040
accgcgagac ccacgctcac cggctccaga tttatcagca ataaaccagc cagccggaag 14100
ggccgagcgc agaagtggtc ctgcaacttt atccgcctcc atccagtcta ttaattgttg 14160
ccgggaagct agagtaagta gttcgccagt taatagtttg cgcaacgttg ttgccattgc 14220
tacaggcatc gtggtgtcac gctcgtcgtt tggtatggct tcattcagct ccggttccca 14280
acgatcaagg cgagttacat gatcccccat gttgtgcaaa aaagcggtta gctccttcgg 14340
tcctccgatc gttgtcagaa gtaagttggc cgcagtgtta tcactcatgg ttatggcagc 14400
actgcataat tctcttactg tcatgccatc cgtaagatgc ttttctgtga ctggtgagta 14460
ctcaaccaag tcattctgag aatagtgtat gcggcgaccg agttgctctt gcccggcgtc 14520
aatacgggat aataccgcgc cacatagcag aactttaaaa gtgctcatca ttggaaaacg 14580
ttcttcgggg cgaaaactct caaggatctt accgctgttg agatccagtt cgatgtaacc 14640
cactcgtgca cccaactgat cttcagcatc ttttactttc accagcgttt ctgggtgagc 14700
aaaaacagga aggcaaaatg ccgcaaaaaa gggaataagg gcgacacgga aatgttgaat 14760
actcat 14766

<210> SEQ ID NO 10
<211> LENGTH: 13743
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 10
actcttcctt tttcaatatt attgaagcat ttatcagggt tattgtctca tgagcggata 60
catatttgaa tgtatttaga aaaataaaca aataggggtt ccgcgcacat ttccccgaaa 120
agtgccacct aaattgtaag cgttaatatt ttgttaaaat tcgcgttaaa tttttgttaa 180
atcagctcat tttttaacca ataggccgaa atcggcaaaa tcccttataa atcaaaagaa 240
tagaccgaga tagggttgag tgttgttcca gtttggaaca agagtccact attaaagaac 300
gtggactcca acgtcaaagg gcgaaaaacc gtctatcagg gcgatggccc actacgtgaa 360
ccatcaccct aatcaagttt tttggggtcg aggtgccgta aagcactaaa tcggaaccct 420
aaagggagcc cccgatttag agcttgacgg ggaaagccgg cgaacgtggc gagaaaggaa 480
gggaagaaag cgaaaggagc gggcgctagg gcgctggcaa gtgtagcggt cacgctgcgc 540
gtaaccacca cacccgccgc gcttaatgcg ccgctacagg gcgcgtccca ttcgccattc 600
aggctgcgca actgttggga agggcgatcg gtgcgggcct cttcgctatt acgccagctg 660
gcgaaagggg gatgtgctgc aaggcgatta agttgggtaa cgccagggtt ttcccagtca 720
cgacgttgta aaacgacggc cagtgagcgc gcctcgttca ttcacgtttt tgaacccgtg 780
gaggacgggc agactcgcgg tgcaaatgtg ttttacagcg tgatggagca gatgaagatg 840
ctcgacacgc tgcagaacac gcagctagat taaccctaga aagataatca tattgtgacg 900
tacgttaaag ataatcatgt gtaaaattga cgcatgtgtt ttatcggtct gtatatcgag 960
gtttatttat taatttgaat agatattaag ttttattata tttacactta catactaata 1020
ataaattcaa caaacaattt atttatgttt atttatttat taaaaaaaac aaaaactcaa 1080
aatttcttct ataaagtaac aaaactttta tgagggacag cccccccccc aagcccccag 1140
ggatgtaatt acgtccctcc cccgctaggg ggcagcagcg agccgcccgg ggctccgctc 1200
cggtccggcg ctccccccgc atccccgagc cggcagcgtg cggggacagc ccgggcacgg 1260
ggaaggtggc acgggatcgc tttcctctga acgcttctcg ctgctctttg agcctgcaga 1320
cacctggggg gatacgggga aaaggcctcc acggccacta gtccatagag cccaccgcat 1380
ccccagcatg cctgctattg tcttcccaat cctcccccctt gctgtcctgc cccaccccac 1440
cccctagaat agaatgacac ctactcagac aatgcgatgc aatttcctca ttttattagg 1500
aaaggacagt gggagtggca ccttccaggg tcaaggaagg cacgggggag gggcaaacaa 1560
cagatggctg gcaactagaa ggcacagcta catgggggta gagtcataat cgtgcatcag 1620

-continued gatagggcgg tggtgctgca gcagcgcgcg aataaactgc tgccgccgcc gctccgtcct 1680
gcaggaatac aacatggcag tggtctcctc agcgatgatt cgcaccgccc gcagcatgag 1740
acgccttgtc ctccgggcac agcagcgcac cctgatctca cttaaatcag cacagtaact 1800
gcagcacagc accacaatat tgttcaaaat cccacagtgc aaggcgctgt atccaaagct 1860
catggcgggg accacagaac ccacgtggcc atcataccac aagcgcaggt agattaagtg 1920
gcgacccctc ataaacacgc tggacataaa cattacctct tttggcatgt tgtaattcac 1980
cacctcccgg taccatataa acctctgatt aaacatggcg ccatccacca ccatcctaaa 2040
ccagctggcc aaaacctgcc cgccggctat gcactgcagg gaaccgggac tggaacaatg 2100
acagtggaga gcccaggact cgtaaccatg gatcatcatg ctcgtcatga tatcaatgtt 2160
ggcacaacac aggcacacgt gcatacactt cctcaggatt acaagctcct cccgcgtcag 2220
aaccatatcc cagggaacaa cccattcctg aatcagcgta aatcccacac tgcagggaag 2280
acctcgcacg taactcacgt tgtgcattgt caaagtgtta cattcgggca gcagcggatg 2340
atcctccagt atggtagcgc gggtctctgt ctcaaaagga ggtaggcgat ccctactgta 2400
cggagtgcgc cgagacaacc gagatcgtgt tggtcgtagt gtcatgccaa atggaacgcc 2460
ggacgtagtc atggttgtgg ccatattatc atcgtgtttt tcaaaggaaa accacgtccc 2520
cgtggttcgg ggggcctaga cgttttttta acctcgacta aacacatgta aagcatgtgc 2580
accgaggccc cagatcagat cccatacaat ggggtacctt ctgggcatcc ttcagcccct 2640
tgttgaatac gcttgaggag agccatttga ctctttccac aactatccaa ctcacaacgt 2700
ggcactgggg ttgtgccgcc tttgcaggtg tatcttatac acgtggcttt tggccgcaga 2760
ggcacctgtc gccaggtggg gggttccgct gcctgcaaag ggtcgctaca gacgttgttt 2820
gtcttcaaga agcttccaga ggaactgctt ccttcacgac attcaacaga ccttgcattc 2880
ctttggcgag aggggaaaga cccctaggaa tgctcgtcaa gaagacaggg ccaggtttcc 2940
gggccctcac attgccaaaa gacggcaata tggtggaaaa taacatatag acaaacgcac 3000
accggcctta ttccaagcgg cttcggccag taacgttagg ggggggggag ggagaggggc 3060
ttaaaaatca aaggggttct gccgcgcatc actatgcgcc actggcaggg acacgttgcg 3120
atactggtgt ttagtgctcc acttaaactc aggcacaacc atccgcggca gctcggtgaa 3180
gttttcactc cacaggctgc gcaccatcac caacgcgttt agcaggtcgg gcgccgatat 3240
cttgaagtcg cagttggggc ctccgccctg cgcgcgcgag ttgcgataca cagggttgca 3300
gcactggaac actatcagcg ccgggtggtg cacgctggcc agcacgctct tgtcggagat 3360
cagatccgcg tccaggtcct ccgcgttgct cagggcgaac ggagtcaact ttggtagctg 3420
ccttcccaaa aagggtgcat gcccaggctt tgagttgcac tcgcaccgta gtggcatcag 3480
aaggtgaccg tgcccggtct gggcgttagg atacagcgcc tgcatgaaag ccttgatctg 3540
cttaaaagcc acctgagcct ttgcgccttc agagaagaac atgccgcaag acttgccgga 3600
aaactgattg gccggacagg ccgcgtcatg cacgcagcac cttgcgtcgg tgttggagat 3660
ctgcaccaca tttcggcccc accggttctt cacgatcttg gccttgctag actgctcctt 3720
cagcgcgcgc tgcccgtttt cgctcgtcac atccatttca atcacgtgct ccttatttat 3780
cataatgctc ccgtgtagac acttaagctc gccttcgatc tcagcgcagc ggtgcagcca 3840
caacgcgcag cccgtgggct cgtggtgctt gtaggttacc tctgcaaacg actgcaggta 3900
cgcctgcagg aatcgcccca tcatcgtcac aaaggtcttg ttgctggtga aggtcagctg 3960
caacccgcgg tgctcctcgt ttagccaggt cttgcatacg gccgccagag cttccacttg 4020

```
gtcaggcagt agcttgaagt ttgcctttag atcgttatcc acgtggtact tgtccatcaa   4080
cgcgcgcgca gcctccatgc ccttctccca cgcagacacg atcggcaggc tcagcgggtt   4140
tatcaccgtg ctttcacttt ccgcttcact ggactcttcc ttttcctctt gcgtccgcat   4200
accccgcgcc actgggtcgt cttcattcag ccgccgcacc gtgcgcttac ctcccttgcc   4260
gtgcttgatt agcaccggtg ggttgctgaa acccaccatt tgtagcgcca catcttctct   4320
ttcttcctcg ctgtccacga tcacctctgg ggatggcggg cgctcgggct tgggagaggg   4380
gcgcttcttt ttctttttgg acgcaatggc caaatccgcc gtcgaggtcg atggccgcgg   4440
gctgggtgtg cgcggcacca gcgcatcttg tgacgagtct tcttcgtcct cggactcgag   4500
acgccgcctc agccgctttt ttgggggcgc gcgcttgtcg tcatcgtctt tgtagtcggg   4560
aggcggcggc gacggcgacg gggacgacac gtcctccatg gttggtggac gtcgcgccgc   4620
accgcgtccg cgctcggggg tggtttcgcg ctgctcctct tcccgactgg ccatggtggc   4680
cgaggataac ttcgtatatg gtttcttata cgaagttatg atccagacat gataagatac   4740
attgatgagt ttggacaaac cacaactaga atgcagtgaa aaaaatgctt tatttgtgaa   4800
atttgtgatg ctattgcttt atttgtaacc attataagct gcaataaaca agttaacaac   4860
aacaattgca ttcattttat gtttcaggtt cagggggagg tgtgggaggt tttttaaagc   4920
aagtaaaacc tctacaaatg tggtatggct gattatgatc ctctagagtc gcagatctgc   4980
tacgtatcaa gctgtggcag ggaaaccctc tgcctccccc gtgatgtaat acttttgcaa   5040
ggaatgcgat gaagtagagc ccgcagtggc caagtggctt tggtccgtct cctccacgga   5100
tgcccctcca cggctagtgg gcgcatgtag gcggtgggcg tccgccgcct ccagcagcag   5160
gtcatagagg ggcaccacgt tcttgcactt catgctgtac agatgctcca tgcctttgtt   5220
actcatgtgt cggatgtggg agaggatgag gaggagctgg gccagccgct ggtgctgctg   5280
ctgcagggtc aggcctgcct tggccatcag gtggatcaaa gtgtctgtga tcttgtccag   5340
gactcggtgg atatggtcct tctcttccag agacttcagg gtgctggaca gaaatgtgta   5400
cactccagaa ttaagcaaaa taatagattt gaggcacaca aactcctctc cctgcagatt   5460
catcatgcgg aaccgagatg atgtagccag cagcatgtcg aagatctcca ccatgccctc   5520
tacacatttt ccctggttcc tgtccaagag caagttagga gcaaacagta gcttcactgg   5580
gtgctccatg gagcgccaga cgagaccaat catcaggatc tctagccagg cacattctag   5640
aaggtggacc tgatcatgga gggtcaaatc cacaaagcct ggcaccctct tcgcccagtt   5700
gatcatgtga accagctccc tgtctgccag gttggtcagt aagcccatca tcgaagcttc   5760
actgaagggt ctggtaggat catactcgga atagagtatg gggggctcag catccaacaa   5820
ggcactgacc atctggtcgg ccgtcaggga caaggccagg ctgttcttct tagagcgttt   5880
gatcatgagc gggcttggcc aaaggttggc agctctcatg tctccagcag atggctcgag   5940
atcgccatct tccagcaggc gcaccattgc ccctgtttca ctatccaggt tacggatata   6000
gttcatgaca atatttacat tggtccagcc accagcttgc atgatctccg gtattgaaac   6060
tccagcgcgg gccatatctc gcgcggctcc gacacgggca ctgtgtccag accaggccag   6120
gtatctctga ccagagtcat cctaaaatac acaaacaatt agaatcagta gtttaacaca   6180
ttatacactt aaaaatttta tatttacctt agcgccgtaa atcaatcgat gagttgcttc   6240
aaaaatccct tccagggcgc gagttgatag ctggctggtg gcagatggcg cggcaacacc   6300
attttttctg acccggcaaa acaggtagtt attcggatca tcagctacac cagagacgga   6360
```

-continued

```
aatccatcgc tcgaccagtt tagtgactcc caggctaagt gccttctcta cacctgcggt   6420
gctaaccagc gttttcgttc tgccaatatg gattaacatt ctcccaccgt cagtacgtga   6480
gatatcttta accctgatcc tggcaatttc ggctatacgt aacagggtgt tataagcaat   6540
ccccagaaat gccagattac gtatatcctg gcagcgatcg ctattttcca tgagtgaacg   6600
gacttggtcg aaatcagtgc gttcgaacgc tagagcctgt tttgcacgtt caccggcatc   6660
aacgttttct tttcggatcc gccgcataac cagtgaaaca gcattgctgt cacttggtcg   6720
tggcagcccg gaccgacgat gaagcatgtt tagctggccc aaatgttgct ggatagtttt   6780
tactgccaga ccgcgcgctt gaagatatag aagataatcg cgaacatctt caggttctgc   6840
gggaaaccat ttccggttat tcaacttgca ccatgccgcc cacgaccggc aaacggacag   6900
aagcatttc caggtatgct cagaaaacgc ctggcgatcc ctgaacatgt ccatcaggtt   6960
cttgcgaacc tcatcactcg ttgcatcgac cggtaatgca ggcaaatttt ggtgtacggt   7020
cagtaaattg gacatggtgg ctacgtaata acttcgtata tggtttctta tacgaagtta   7080
tgcggccgct ttacgagggt aggaagtggt acggaaagtt ggtataagac aaaagtgttg   7140
tggaattgct ccaggcgatc tgacggttca ctaaacgagc tctgctttta taggcgccca   7200
ccgtacacgc ctaaagctta tacgttctct atcactgata gggagtaaac tggatatacg   7260
ttctctatca ctgataggga gtaaactgta gatacgttct ctatcactga tagggagtaa   7320
actggtcata cgttctctat cactgatagg gagtaaactc cttatacgtt ctctatcact   7380
gatagggagt aaagtctgca tacgttctct atcactgata gggagtaaac tcttcatacg   7440
ttctctatca ctgataggga gtaaactcgc ggccgcagag aaatgttctg gcacctgcac   7500
ttgcactggg gacagcctat tttgctagtt tgttttgttt cgttttgttt tgatggagag   7560
cgtatgttag tactatcgat tcacacaaaa aaccaacaca cagatgtaat gaaaataaag   7620
atattttatt ggatctgcga tcgctccggt gcccgtcagt gggcagagcg cacatcgccc   7680
acagtccccg agaagttggg gggaggggtc ggcaattgaa cgggtgccta gagaaggtgg   7740
cgcggggtaa actgggaaag tgatgtcgtg tactggctcc gcctttttcc cgagggtggg   7800
ggagaaccgt atgtaagtgc agtagtcgcc gtgaacgttc tttttcgcaa cgggtttgcc   7860
gccagaacac agctgaagct tcgaggggct cgcatctctc cttcacgcgc ccgccgccct   7920
acctgaggcc gccatccacg ccggttgagt cgcgttctgc cgcctcccgc ctgtggtgcc   7980
tcctgaactg cgtccgccgt ctaggtaagt ttaaagctca ggtcgagacc gggcctttgt   8040
ccggcgctcc cttggagcct acctagactc agccggctct ccacgctttg cctgaccctg   8100
cttgctcaac tctacgtctt tgtttcgttt tctgttctgc gccgttacag atccaagctg   8160
tgaccggcgc ctacgctagc ggatccgccg ccaccatgtc tagactggac aagagcaaag   8220
tcataaactc tgctctggaa ttactcaatg gagtcggtat cgaaggcctg acgacaagga   8280
aactcgctca aaagctggga gttgagcagc ctaccctgta ctggcacgtg aagaacaagc   8340
gggccctgct cgatgccctg ccaatcgaga tgctggacag gcatcatacc cactcctgcc   8400
ccctggaagg cgagtcatgg caagactttc tgcggaacaa cgccaagtca taccgctgtg   8460
ctcttctctc acatcgcgac ggggctaaag tgcatctcgg cacccgccca acagagaaac   8520
agtacgaaac cctggaaaat cagctcgcgt tcctgtgtca gcaaggcttc tccctggaga   8580
acgcactgta cgctctgtcc gccgtgggcc actttacact gggctgcgta ttggaggaac   8640
aggagcatca agtagcaaaa gaggaaagag agacacctac caccgattct atgcccccac   8700
ttctgaaaca agcaattgag ctgttcgacc ggcagggagc cgaacctgcc ttccttttcg   8760
```

-continued

```
gcctggaact aatcatatgt ggcctggaga aacagctaaa gtgcgaaagc ggcgggccga   8820
ccgacgccct tgacgatttt gacttagaca tgctcccagc cgatgccctt gacgactttg   8880
accttgatat gctgcctgct gacgctcttg acgattttga ccttgacatg ctccccgggg   8940
gatccggagc tactaacttc agcctgctga agcaggctgg agacgtggag gagaaccctg   9000
gacctatgac agaatataaa cctactgtca gactggcaac tcgagacgac gtccctaggg   9060
ccgtgagaac attggctgcc gctttcgcgg attatcccgc tacacgccac acagttgatc   9120
ctgatagaca tattgaacgg gttacagaat tgcaagaact ttttttgacc agggtaggat   9180
tggacatcgg taaagtttgg gtcgccgacg acggggctgc agtggcagtg tggacgactc   9240
cggagagcgt tgaggccggg gctgtatttg cagaaattgg tccccgaatg gctgagctta   9300
gtggctctcg tctcgcggct cagcaacaaa tggaaggact cctcgcccct caccgcccta   9360
aagaaccagc ttggttcctc gctactgtgg gcgttagccc cgatcatcag ggaaagggcc   9420
ttggttccgc ggtggtattg cccggagtag aagccgcaga acgagccgga gtgccagcct   9480
ttcttgaaac gtcagcgcca aggaatttgc ccttctatga acggctcgga tttacagtta   9540
ctgctgacgt tgaagtaccc gagggcccac ggacgtggtg catgacgcga aaacccggcg   9600
cttgagttta aaccgctgat cagcctcgac tgtgccttct agttgccagc catctgttgt   9660
ttgcccctcc cccgtgcctt ccttgaccct ggaaggtgcc actcccactg tcctttccta   9720
ataaaatgag gaaattgcat cgcattgtct gagtaggtgt cattctattc tggggggtgg   9780
ggtggggcag gacagcaagg gggaggattg ggaagacaat agcaggcatg ctggggatgc   9840
ggtgggctct atggcttctg aggcggaaag aaccagctgg ggctcgacta gagcttgcgg   9900
aacccttagt ttaaacgggc ccttaattaa tcgatgtagg atgttgcccc tcctgacgcg   9960
gtaggagaag ggagggtgc cctgcatgtc tgccgctgct cttgctcttg ccgctgctga  10020
ggaggggggc gcatctgccg cagcaccgga tgcatctggg aaaagcaaaa aaggggctcg  10080
tccctgtttc cggaggaatt tgcaagcggg gtcttgcatg acggggaggc aaaccccccgt  10140
tcgccgcagt ccggccggcc cgagactcga accgggggtc ctgcgactca acccttggaa  10200
aataaccctc cggctacagg gagcgagcca cttaatgctt tcgctttcca gcctaaccgc  10260
ttacgccgcg cgcggccagt ggccaaaaaa gctagcgcag cagccgccgc gcctggaagg  10320
aagccaaaag gagcgctccc ccgttgtctg acgtcgcaca cctgggttcg acacgcgggc  10380
ggtaaccgca tggatcacgg cggacggccg gatccggggt tcgaaccccg gtcgtccgcc  10440
atgataccct tgcgaattta tccaccagac cacggaagag tgcccgctta caggctctcc  10500
ttttgcacgg tctagagcgt caacgactgc gcacgcctca ccggccagag cgtcccgacc  10560
atggagcact ttttgccgct gcgcaacatc tggaaccgcg tccgcgactt tccgcgcgcc  10620
tccaccaccg ccgccggcat cacctggatg tccaggtaca tctacggatt acggggccca  10680
ttggtatggc tttttccccg tatcccccca ggtgtctgca ggctcaaaga gcagcgagaa  10740
gcgttcagag gaaagcgatc ccgtgccacc ttccccgtgc ccgggctgtc cccgcacgct  10800
gccggctcgg ggatgcgggg ggagcgccgg accggagcgg agccccgggc ggctcgctgc  10860
tgccccctag cgggggaggg acgtaattac atccctgggg gctttggggg ggggctgtcc  10920
ctgatatcta taacaagaaa atatatatat aataagttat cacgtaagta gaacatgaaa  10980
taacaatata attatcgtat gagttaaatc ttaaaagtca cgtaaaagat aatcatgcgt  11040
cattttgact cacgcggtcg ttatagttca aaatcagtga cacttaccgc attgacaagc  11100
```

acgcctcacg ggagctccaa gcggcgactg agatgtccta aatgcacagc gacggattcg 11160
cgctatttag aaagagagag caatatttca agaatgcatg cgtcaatttt acgcagacta 11220
tctttctagg gttaatctag ctgcatcagg atcatatcgt cgggtctttt ttccggctca 11280
gtcatcgccc aagctggcgc tatctgggca tcggggagga agaagcccgt gccttttccc 11340
gcgaggttga agcggcatgg aaagagtttg ccgaggatga ctgctgctgc attgacgttg 11400
agcgaaaacg cacgtttacc atgatgattc gggaaggtgt ggccatgcac gcctttaacg 11460
gtgaactgtt cgttcaggcc acctgggata ccagttcgtc gcggcttttc cggacacagt 11520
tccggatggt cagcccgaag cgcatcagca acccgaacaa taccggcgac agccggaact 11580
gccgtgccgg tgtgcagatt aatgacagcg gtgcggcgct gggatattac gtcagcgagg 11640
acgggtatcc tggctggatg ccgcagaaat ggacatggat accccgtgag ttacccggcg 11700
ggcgcgcttg gcgtaatcat ggtcatagct gtttcctgtg tgaaattgtt atccgctcac 11760
aattccacac aacatacgag ccggaagcat aaagtgtaaa gcctggggtg cctaatgagt 11820
gagctaactc acattaattg cgttgcgctc actgcccgct ttccagtcgg gaaacctgtc 11880
gtgccagctg cattaatgaa tcggccaacg cgcggggaga ggcggtttgc gtattgggcg 11940
ctcttccgct tcctcgctca ctgactcgct gcgctcggtc gttcggctgc ggcgagcggt 12000
atcagctcac tcaaaggcgg taatacggtt atccacagaa tcaggggata acgcaggaaa 12060
gaacatgtga gcaaaaggcc agcaaaaggc caggaaccgt aaaaaggccg cgttgctggc 12120
gtttttccat aggctccgcc cccctgacga gcatcacaaa aatcgacgct caagtcagag 12180
gtggcgaaac ccgacaggac tataaagata ccaggcgttt ccccctggaa gctccctcgt 12240
gcgctctcct gttccgaccc tgccgcttac cggatacctg tccgcctttc tcccttcggg 12300
aagcgtggcg ctttctcata gctcacgctg taggtatctc agttcggtgt aggtcgttcg 12360
ctccaagctg ggctgtgtgc acgaaccccc cgttcagccc gaccgctgcg ccttatccgg 12420
taactatcgt cttgagtcca acccggtaag acacgactta tcgccactgg cagcagccac 12480
tggtaacagg attagcagag cgaggtatgt aggcggtgct acagagttct tgaagtggtg 12540
gcctaactac ggctacacta gaaggacagt atttggtatc tgcgctctgc tgaagccagt 12600
taccttcgga aaaagagttg gtagctcttg atccggcaaa caaaccaccg ctggtagcgg 12660
tggttttttt gtttgcaagc agcagattac gcgcagaaaa aaaggatctc aagaagatcc 12720
tttgatcttt tctacggggt ctgacgctca gtggaacgaa aactcacgtt aagggatttt 12780
ggtcatgaga ttatcaaaaa ggatcttcac ctagatcctt ttaaattaaa aatgaagttt 12840
taaatcaatc taaagtatat atgagtaaac ttggtctgac agttaccaat gcttaatcag 12900
tgaggcacct atctcagcga tctgtctatt tcgttcatcc atagttgcct gactccccgt 12960
cgtgtagata actacgatac gggagggctt accatctggc cccagtgctg caatgatacc 13020
gcgagaccca cgctcaccgg ctccagattt atcagcaata aaccagccag ccggaagggc 13080
cgagcgcaga agtggtcctg caactttatc cgcctccatc cagtctatta attgttgccg 13140
ggaagctaga gtaagtagtt cgccagttaa tagtttgcgc aacgttgttg ccattgctac 13200
aggcatcgtg gtgtcacgct cgtcgtttgg tatggcttca ttcagctccg gttcccaacg 13260
atcaaggcga gttacatgat cccccatgtt gtgcaaaaaa gcggttagct ccttcggtcc 13320
tccgatcgtt gtcagaagta agttggccgc agtgttatca ctcatggtta tggcagcact 13380
gcataattct cttactgtca tgccatccgt aagatgcttt tctgtgactg gtgagtactc 13440
aaccaagtca ttctgagaat agtgtatgcg gcgaccgagt tgctcttgcc cggcgtcaat 13500
acgggataat accgcgccac atagcagaac tttaaaagtg ctcatcattg gaaaacgttc 13560
ttcggggcga aaactctcaa ggatcttacc gctgttgaga tccagttcga tgtaacccac 13620
tcgtgcaccc aactgatctt cagcatcttt tactttcacc agcgtttctg ggtgagcaaa 13680
aacaggaagg caaaatgccg caaaaaaggg aataagggcg acacggaaat gttgaatact 13740
cat 13743

<210> SEQ ID NO 11
<211> LENGTH: 10347
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 11
gcctccacgg ccactagtcc atagagccca ccgcatcccc agcatgcctg ctattgtctt 60
cccaatcctc cccttgctg tcctgcccca ccccaccccc tagaatagaa tgacacctac 120
tcagacaatg cgatgcaatt tcctcatttt attaggaaag gacagtggga gtggcacctt 180
ccagggtcaa ggaaggcacg gggggagggc aaacaacaga tggctggcaa ctagaaggca 240
cagctacatg gggtagagt cataatcgtg catcaggata gggcggtggt gctgcagcag 300
cgcgcgaata aactgctgcc gccgccgctc cgtcctgcag gaatacaaca tggcagtggt 360
ctcctcagcg atgattcgca ccgcccgcag catgagacgc cttgtcctcc gggcacagca 420
gcgcaccctg atctcactta aatcagcaca gtaactgcag cacagcacca caatattgtt 480
caaaatccca cagtgcaagg cgctgtatcc aaagctcatg gcggggacca cagaacccac 540
gtggccatca taccacaagc gcaggtagat taagtggcga cccctcataa acacgctgga 600
cataaacatt acctcttttg gcatgttgta attcaccacc tcccggtacc atataaacct 660
ctgattaaac atggcgccat ccaccaccat cctaaaccag ctggccaaaa cctgcccgcc 720
ggctatgcac tgcagggaac cgggactgga acaatgacag tggagagccc aggactcgta 780
accatggatc atcatgctcg tcatgatatc aatgttggca caacacaggc acacgtgcat 840
acacttcctc aggattacaa gctcctcccg cgtcagaacc atatcccagg gaacaaccca 900
ttcctgaatc agcgtaaatc ccacactgca gggaagacct cgcacgtaac tcacgttgtg 960
cattgtcaaa gtgttacatt cgggcagcag cggatgatcc tccagtatgg tagcgcgggt 1020
ctctgtctca aaggaggta ggcgatccct actgtacgga gtgcgccgag acaaccgaga 1080
tcgtgttggt cgtagtgtca tgccaaatgg aacgccggac gtagtcatgg ttgtggccat 1140
attatcatcg tgtttttcaa aggaaaacca cgtccccgtg gttcgggggg cctagacgtt 1200
tttttaacct cgactaaaca catgtaaagc atgtgcaccg aggccccaga tcagatccca 1260
tacaatgggg taccttctgg gcatccttca gccccttgtt gaatacgctt gaggagagcc 1320
atttgactct ttccacaact atccaactca caacgtggca ctggggttgt gccgcctttg 1380
caggtgtatc ttatacacgt ggcttttggc cgcagaggca cctgtcgcca ggtgggggt 1440 tccgctgcct gcaaagggtc gctacagacg ttgtttgtct tcaagaagct tccagaggaa 1500
ctgcttcctt cacgacattc aacagacctt gcattccttt ggcgagaggg gaaagacccc 1560
taggaatgct cgtcaagaag acagggccag gtttccgggc cctcacattg ccaaaagacg 1620
gcaatatggt ggaaaataac atatagacaa acgcacaccg gccttattcc aagcggcttc 1680

-continued ggccagtaac gttagggggg ggggagggag aggggcttaa aaatcaaagg ggttctgccg 1740
cgcatcacta tgcgccactg gcagggacac gttgcgatac tggtgtttag tgctccactt 1800
aaactcaggc acaaccatcc gcggcagctc ggtgaagttt tcactccaca ggctgcgcac 1860
catcaccaac gcgtttagca ggtcgggcgc cgatatcttg aagtcgcagt tggggcctcc 1920
gccctgcgcg cgcgagttgc gatacacagg gttgcagcac tggaacacta tcagcgccgg 1980
gtggtgcacg ctggccagca cgctcttgtc ggagatcaga tccgcgtcca ggtcctccgc 2040
gttgctcagg gcgaacggag tcaactttgg tagctgcctt cccaaaaagg gtgcatgccc 2100
aggctttgag ttgcactcgc accgtagtgg catcagaagg tgaccgtgcc cggtctgggc 2160
gttaggatac agcgcctgca tgaaagcctt gatctgctta aaagccacct gagcctttgc 2220
gccttcagag aagaacatgc cgcaagactt gccggaaaac tgattggccg gacaggccgc 2280
gtcatgcacg cagcaccttg cgtcggtgtt ggagatctgc accacatttc ggccccaccg 2340
gttcttcacg atcttggcct tgctagactg ctccttcagc gcgcgctgcc cgttttcgct 2400
cgtcacatcc atttcaatca cgtgctcctt atttatcata atgctcccgt gtagacactt 2460
aagctcgcct tcgatctcag cgcagcggtg cagccacaac gcgcagcccg tgggctcgtg 2520
gtgcttgtag gttacctctg caaacgactg caggtacgcc tgcaggaatc gccccatcat 2580
cgtcacaaag gtcttgttgc tggtgaaggt cagctgcaac ccgcggtgct cctcgtttag 2640
ccaggtcttg catacggccg ccagagcttc cacttggtca ggcagtagct tgaagtttgc 2700
ctttagatcg ttatccacgt ggtacttgtc catcaacgcg cgcgcagcct ccatgccctt 2760
ctcccacgca gacacgatcg gcaggctcag cgggtttatc accgtgcttt cactttccgc 2820
ttcactggac tcttcctttt cctcttgcgt ccgcataccc cgcgccactg ggtcgtcttc 2880
attcagccgc cgcaccgtgc gcttacctcc cttgccgtgc ttgattagca ccggtgggtt 2940
gctgaaaccc accatttgta gcgccacatc ttctctttct tcctcgctgt ccacgatcac 3000
ctctggggat ggcgggcgct cgggcttggg agaggggcgc ttctttttct ttttggacgc 3060
aatggccaaa tccgccgtcg aggtcgatgg ccgcgggctg ggtgtgcgcg gcaccagcgc 3120
atcttgtgac gagtcttctt cgtcctcgga ctcgagacgc cgcctcagcc gcttttttgg 3180
gggcgcgcgc ttgtcgtcat cgtctttgta gtcgggaggc ggcggcgacg gcgacgggga 3240
cgacacgtcc tccatggttg gtggacgtcg cgccgcaccg cgtccgcgct cgggggtggt 3300
ttcgcgctgc tcctcttccc gactggccat ggtggccgag gataacttcg tatatggttt 3360
cttatacgaa gttatgatcc agacatgata agatacattg atgagtttgg acaaaccaca 3420
actagaatgc agtgaaaaaa atgctttatt tgtgaaattt gtgatgctat tgctttattt 3480
gtaaccatta taagctgcaa taaacaagtt aacaacaaca attgcattca ttttatgttt 3540
caggttcagg gggaggtgtg ggaggttttt taaagcaagt aaaacctcta caaatgtggt 3600
atggctgatt atgatcctct agagtcgcag atctgctacg tatcaagctg tggcagggaa 3660
accctctgcc tcccccgtga tgtaatactt ttgcaaggaa tgcgatgaag tagagcccgc 3720
agtggccaag tggctttggt ccgtctcctc cacggatgcc cctccacggc tagtgggcgc 3780
atgtaggcgg tgggcgtccg ccgcctccag cagcaggtca tagaggggca ccacgttctt 3840
gcacttcatg ctgtacagat gctccatgcc tttgttactc atgtgtcgga tgtgggagag 3900
gatgaggagg agctgggcca gccgctggtg ctgctgctgc agggtcaggc ctgccttggc 3960
catcaggtgg atcaaagtgt ctgtgatctt gtccaggact cggtggatat ggtccttctc 4020
ttccagagac ttcagggtgc tggacagaaa tgtgtacact ccagaattaa gcaaaataat 4080

-continued

```
agatttgagg cacacaaact cctctccctg cagattcatc atgcggaacc gagatgatgt   4140
agccagcagc atgtcgaaga tctccaccat gccctctaca cattttccct ggttcctgtc   4200
caagagcaag ttaggagcaa acagtagctt cactgggtgc tccatggagc gccagacgag   4260
accaatcatc aggatctcta gccaggcaca ttctagaagg tggacctgat catggagggt   4320
caaatccaca aagcctggca ccctcttcgc ccagttgatc atgtgaacca gctccctgtc   4380
tgccaggttg gtcagtaagc ccatcatcga agcttcactg aagggtctgg taggatcata   4440
ctcggaatag agtatggggg gctcagcatc caacaaggca ctgaccatct ggtcggccgt   4500
cagggacaag gccaggctgt tcttcttaga gcgtttgatc atgagcgggc ttggccaaag   4560
gttggcagct ctcatgtctc cagcagatgg ctcgagatcg ccatcttcca gcaggcgcac   4620
cattgcccct gtttcactat ccaggttacg gatatagttc atgacaatat ttacattggt   4680
ccagccacca gcttgcatga tctccggtat tgaaactcca gcgcgggcca tatctcgcgc   4740
ggctccgaca cgggcactgt gtccagacca ggccaggtat ctctgaccag agtcatccta   4800
aaatacacaa acaattagaa tcagtagttt aacacattat acacttaaaa attttatatt   4860
taccttagcg ccgtaaatca atcgatgagt tgcttcaaaa atcccttcca gggcgcgagt   4920
tgatagctgg ctggtggcag atggcgcggc aacaccattt tttctgaccc ggcaaaacag   4980
gtagttattc ggatcatcag ctacaccaga gacggaaatc catcgctcga ccagtttagt   5040
gactcccagg ctaagtgcct tctctacacc tgcggtgcta accagcgttt tcgttctgcc   5100
aatatggatt aacattctcc caccgtcagt acgtgagata tctttaaccc tgatcctggc   5160
aatttcggct atacgtaaca gggtgttata agcaatcccc agaaatgcca gattacgtat   5220
atcctggcag cgatcgctat ttccatgag tgaacggact tggtcgaaat cagtgcgttc   5280
gaacgctaga gcctgttttg cacgttcacc ggcatcaacg ttttcttttc ggatccgccg   5340
cataaccagt gaaacagcat tgctgtcact tggtcgtggc agcccggacc gacgatgaag   5400
catgtttagc tggcccaaat gttgctggat agtttttact gccagaccgc gcgcttgaag   5460
atatagaaga taatcgcgaa catcttcagg ttctgcggga aaccatttcc ggttattcaa   5520
cttgcaccat gccgcccacg accggcaaac ggacagaagc attttccagg tatgctcaga   5580
aaacgcctgg cgatccctga acatgtccat caggttcttg cgaacctcat cactcgttgc   5640
atcgaccggt aatgcaggca aattttggtg tacggtcagt aaattggaca tggtggctac   5700
gtaataactt cgtatatggt ttcttatacg aagttatgcg gccgctttac gagggtagga   5760
agtggtacgg aaagttggta taagacaaaa gtgttgtgga attgctccag gcgatctgac   5820
ggttcactaa acgagctctg cttttatagg cgcccaccgt acacgcctaa agcttatacg   5880
ttctctatca ctgataggga gtaaactgga tatacgttct ctatcactga tagggagtaa   5940
actgtagata cgttctctat cactgatagg gagtaaactg gtcatacgtt ctctatcact   6000
gatagggagt aaactcctta tacgttctct atcactgata gggagtaaag tctgcatacg   6060
ttctctatca ctgataggga gtaaactctt catacgttct ctatcactga tagggagtaa   6120
actcgcggcc gcagagaaat gttctggcac ctgcacttgc actggggaca gcctattttg   6180
ctagtttgtt ttgtttcgtt ttgttttgat ggagagcgta tgttagtact atcgattcac   6240
acaaaaaacc aacacacaga tgtaatgaaa ataaagatat tttattggat ctgcgatcgc   6300
tccggtgccc gtcagtgggc agagcgcaca tcgcccacag tccccgagaa gttgggggga   6360
ggggtcggca attgaacggg tgcctagaga aggtggcgcg gggtaaactg ggaaagtgat   6420
```

-continued

```
gtcgtgtact ggctccgcct ttttcccgag ggtgggggag aaccgtatgt aagtgcagta   6480
gtcgccgtga acgttctttt tcgcaacggg tttgccgcca gaacacagct gaagcttcga   6540
ggggctcgca tctctccttc acgcgcccgc cgccctacct gaggccgcca tccacgccgg   6600
ttgagtcgcg ttctgccgcc tcccgcctgt ggtgcctcct gaactgcgtc cgccgtctag   6660
gtaagtttaa agctcaggtc gagaccgggc ctttgtccgg cgctcccttg gagcctacct   6720
agactcagcc ggctctccac gctttgcctg accctgcttg ctcaactcta cgtctttgtt   6780
tcgttttctg ttctgcgccg ttacagatcc aagctgtgac cggcgcctac gctagcggat   6840
ccgccgccac catgtctaga ctggacaaga gcaaagtcat aaactctgct ctggaattac   6900
tcaatggagt cggtatcgaa ggcctgacga caaggaaact cgctcaaaag ctgggagttg   6960
agcagcctac cctgtactgg cacgtgaaga acaagcgggc cctgctcgat gccctgccaa   7020
tcgagatgct ggacaggcat catacccact cctgcccccct ggaaggcgag tcatggcaag   7080
actttctgcg gaacaacgcc aagtcatacc gctgtgctct tctctcacat cgcgacgggg   7140
ctaaagtgca tctcggcacc cgcccaacag agaaacagta cgaaaccctg gaaaatcagc   7200
tcgcgttcct gtgtcagcaa ggcttctccc tggagaacgc actgtacgct ctgtccgccg   7260
tgggccactt tacactgggc tgcgtattgg aggaacagga gcatcaagta gcaaaagagg   7320
aaagagagac acctaccacc gattctatgc ccccacttct gaaacaagca attgagctgt   7380
tcgaccggca gggagccgaa cctgccttcc ttttcggcct ggaactaatc atatgtggcc   7440
tggagaaaca gctaaagtgc gaaagcggcg ggccgaccga cgcccttgac gattttgact   7500
tagacatgct cccagccgat gcccttgacg actttgacct tgatatgctg cctgctgacg   7560
ctcttgacga ttttgacctt gacatgctcc ccgggtgaac cggtcgctga tcagcctcga   7620
ctgtgccttc tagttgccag ccatctgttg tttgcccctc ccccgtgcct tccttgaccc   7680
tggaaggtgc cactcccact gtcctttcct aataaaatga ggaaattgca tcgcattgtc   7740
tgagtaggtg tcattctatt ctggggggtg gggtggggca ggacagcaag ggggaggatt   7800
gggaagacaa tagcaggcat gctggggatg cggtgggctc tatggcttct gaggcggaaa   7860
gaaccagctg gggctcgact agagcttgcg gaacccttag agggcctatt tcccatgatt   7920
ccttcatatt tgcatatacg atacaaggct gttagagaga taattagaat taatttgact   7980
gtaaacacaa agatattagt acaaaataat aacttcgtat aatgtatgct atacgaagtt   8040
atcagacatg ataagataca ttgatgagtt tggacaaacc acaactagaa tgcagtgaaa   8100
aaaatgcttt atttgtgaaa tttgtgatgc tattgcttta tttgtaacca ttataagctg   8160
caataaacaa ggtacctcaa gcgccgggtt ttcgcgtcat gcaccacgtc cgtgggccct   8220
cgggtacttc aacgtcagca gtaactgtaa atccgagccg ttcatagaag ggcaaattcc   8280
ttggcgctga cgtttcaaga aaggctggca ctccggctcg ttctgcggct tctactccgg   8340
gcaataccac cgcggaacca aggccctttc cctgatgatc ggggctaacg cccacagtag   8400
cgaggaacca agctggttct ttagggcggt gaggggcgag gagtccttcc atttgttgct   8460
gagccgcgag acgagagcca ctaagctcag ccattcgggg accaatttct gcaaatacag   8520
ccccggcctc aacgctctcc ggagtcgtcc acactgccac tgcagccccg tcgtcggcga   8580
cccaaacttt accgatgtcc aatcctaccc tggtcaaaaa aagttcttgc aattctgtaa   8640
cccgttcaat atgtctatca ggatcaactg tgtggcgtgt agcgggataa tccgcgaaag   8700
cggcagccaa tgttctcacg gccctaggga cgtcgtctcg agttgccagt ctgacagtag   8760
gtttatattc tgtcataggt ccagggttct cctccacgtc tccagcctgc ttcagcaggc   8820
```

```
tgaagttagt agctccggat cctttacctc catcaccagc gccaccagta gagtatctgg   8880

ccacagccac ctcgtgctgc tcgacgtagg tctcatcgtc ggcctccttg attctttcca   8940

gtctgtggtc cacgttgtag acgccgggca tcttgaggtt cgtagcgggt ttcttggatc   9000

tgtatgtggt ctcaaggttg cagatcaggt ggcccccgcc cacgagcttc agggccatgt   9060

cacatgcgcc ttccaggccg ccgtcagcgg ggtacatcgt ctcggtggag gcctcccagc   9120

cgagtgtttt cttctgcatc acagggccgt tggctgggaa gttcacccct ctaaccttga   9180

cgttgtagat gaggcagccg tcctggaggc tggtgtcctg ggtagcggtc agcacgcccc   9240

cgtcttcgta tgtggtgact ctctcccatg tgaagccctc agggaaggac tgcttaaaga   9300

agtcggggat gcccggaggg tgcttgatga aggttctgct gccgtacatg aagctggtag   9360

ccaggatgtc gaaggcgaag gggagagggc cgccctcgac gaccttgatt ctcatggtct   9420

gggtgccctc gtagggcttg ccttcgccct cggatgtgca cttgaagtgg tggttgttca   9480

cggtgccctc catgtacagc ttcatgggca tgttctcctt aatcagctcg ctcacggtgg   9540

cggcgaattc cgaaaggccc ggagatgagg aagaggagaa cagcgcggca gacgtgcgct   9600

tttgaagcgt gcagaatgcc gggcctccgg aggaccttcg ggcgcccgcc ccgcccctga   9660

gcccgcccct gagcccgccc ccggacccac cccttcccag cctctgagcc cagaaagcga   9720

aggagcaaag ctgctattgg ccgctgcccc aaaggcctac ccgcttccat tgctcagcgg   9780

tgctgtccat ctgcacgaga ctagtgagac gtgctacttc catttgtcac gtcctgcacg   9840

acgcgagctg cggggcgggg gggaacttcc tgactagggg aggagtagaa ggtggcgcga   9900

aggggccacc aaagaacgga gccggttggc gcctaccggt ggatgtggaa tgtgtgcgag   9960

gccagaggcc acttgtgtag cgccaagtgc ccagcggggc tgctaaagcg catgctccag  10020

actgccttgg gaaaagcgct cccctaccca taacttcgta taatgtatgc tatacgaagt  10080

tattttgcag ttttaaaatt atgttttaaa atggactatc atatgcttac cgtaacttga  10140

aagtatttcg atttcttggc tttatatatc ttgtggaaag gacgaaacac cgggcactct  10200

tccgtgatct ggtggataaa ttcgcaaggg tatcatggcg gacgaccggg attcgaaccc  10260

cggatccggc cgtccgccgt gatccatgcg gttaccgccc gcgtgtcgaa cccaggtgtg  10320

cgacgtcaga caacggggga gcgctcc                                      10347
```

```
<210> SEQ ID NO 12
<211> LENGTH: 9344
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 12

gcctccacgg ccactagtcc atagagccca ccgcatcccc agcatgcctg ctattgtctt     60

cccaatcctc ccccttgctg tcctgcccca ccccaccccc tagaatagaa tgacacctac    120

tcagacaatg cgatgcaatt tcctcatttt attaggaaag gacagtggga gtggcacctt    180

ccagggtcaa ggaaggcacg ggggagggggc aaacaacaga tggctggcaa ctagaaggca   240

cagctacatg gggtagagt cataatcgtg catcaggata gggcggtggt gctgcagcag    300

cgcgcgaata aactgctgcc gccgccgctc cgtcctgcag gaatacaaca tggcagtggt    360

ctcctcagcg atgattcgca ccgcccgcag catgagacgc cttgtcctcc gggcacagca    420
```

gcgcaccctg atctcactta aatcagcaca gtaactgcag cacagcacca caatattgtt 480
caaaatccca cagtgcaagg cgctgtatcc aaagctcatg gcggggacca cagaacccac 540
gtggccatca taccacaagc gcaggtagat taagtggcga cccctcataa acacgctgga 600
cataaacatt acctcttttg gcatgttgta attcaccacc tcccggtacc atataaacct 660
ctgattaaac atggcgccat ccaccaccat cctaaaccag ctggccaaaa cctgcccgcc 720
ggctatgcac tgcagggaac cgggactgga acaatgacag tggagagccc aggactcgta 780
accatggatc atcatgctcg tcatgatatc aatgttggca caacacaggc acacgtgcat 840
acacttcctc aggattacaa gctcctcccg cgtcagaacc atatcccagg gaacaaccca 900
ttcctgaatc agcgtaaatc ccacactgca gggaagacct cgcacgtaac tcacgttgtg 960
cattgtcaaa gtgttacatt cgggcagcag cggatgatcc tccagtatgg tagcgcgggt 1020
ctctgtctca aaaggaggta ggcgatccct actgtacgga gtgcgccgag acaaccgaga 1080
tcgtgttggt cgtagtgtca tgccaaatgg aacgccggac gtagtcatgg ttgtggccat 1140
attatcatcg tgtttttcaa aggaaaacca cgtccccgtg gttcgggggg cctagacgtt 1200
tttttaacct cgactaaaca catgtaaagc atgtgcaccg aggccccaga tcagatccca 1260
tacaatgggg taccttctgg gcatccttca gccccttgtt gaatacgctt gaggagagcc 1320
atttgactct ttccacaact atccaactca caacgtggca ctggggttgt gccgcctttg 1380
caggtgtatc ttatacacgt ggcttttggc cgcagaggca cctgtcgcca ggtgggggt 1440
tccgctgcct gcaaagggtc gctacagacg ttgtttgtct tcaagaagct tccagaggaa 1500
ctgcttcctt cacgacattc aacagacctt gcattccttt ggcgagaggg gaaagacccc 1560
taggaatgct cgtcaagaag acagggccag gtttccgggc cctcacattg ccaaaagacg 1620
gcaatatggt ggaaaataac atatagacaa acgcacaccg gccttattcc aagcggcttc 1680
ggccagtaac gttagggggg ggggagggag aggggcttaa aaatcaaagg ggttctgccg 1740
cgcatcacta tgcgccactg gcagggacac gttgcgatac tggtgtttag tgctccactt 1800
aaactcaggc acaaccatcc gcggcagctc ggtgaagttt tcactccaca ggctgcgcac 1860
catcaccaac gcgtttagca ggtcgggcgc cgatatcttg aagtcgcagt tggggcctcc 1920
gccctgcgcg cgcgagttgc gatacacagg gttgcagcac tggaacacta tcagcgccgg 1980
gtggtgcacg ctggccagca cgctcttgtc ggagatcaga tccgcgtcca ggtcctccgc 2040
gttgctcagg gcgaacggag tcaactttgg tagctgcctt cccaaaaagg gtgcatgccc 2100
aggctttgag ttgcactcgc accgtagtgg catcagaagg tgaccgtgcc cggtctgggc 2160
gttaggatac agcgcctgca tgaaagcctt gatctgctta aaagccacct gagcctttgc 2220
gccttcagag aagaacatgc cgcaagactt gccggaaaac tgattggccg gacaggccgc 2280
gtcatgcacg cagcaccttg cgtcggtgtt ggagatctgc accacatttc ggccccaccg 2340
gttcttcacg atcttggcct tgctagactg ctccttcagc gcgcgctgcc cgttttcgct 2400
cgtcacatcc atttcaatca cgtgctcctt atttatcata atgctcccgt gtagacactt 2460
aagctcgcct tcgatctcag cgcagcggtg cagccacaac gcgcagcccg tgggctcgtg 2520
gtgcttgtag gttacctctg caaacgactg caggtacgcc tgcaggaatc gccccatcat 2580
cgtcacaaag gtcttgttgc tggtgaaggt cagctgcaac ccgcggtgct cctcgtttag 2640
ccaggtcttg catacggccg ccagagcttc cacttggtca ggcagtagct tgaagtttgc 2700
ctttagatcg ttatccacgt ggtacttgtc catcaacgcg cgcgcagcct ccatgccctt 2760
ctcccacgca gacacgatcg gcaggctcag cgggtttatc accgtgcttt cactttccgc 2820

-continued

```
ttcactggac tcttcctttt cctcttgcgt ccgcataccc cgcgccactg ggtcgtcttc   2880
attcagccgc cgcaccgtgc gcttacctcc cttgccgtgc ttgattagca ccggtgggtt   2940
gctgaaaccc accatttgta gcgccacatc ttctctttct tcctcgctgt ccacgatcac   3000
ctctggggat ggcgggcgct cgggcttggg agaggggcgc ttcttttct ttttggacgc   3060
aatggccaaa tccgccgtcg aggtcgatgg ccgcgggctg ggtgtgcgcg gcaccagcgc   3120
atcttgtgac gagtcttctt cgtcctcgga ctcgagacgc cgcctcagcc gcttttttgg   3180
gggcgcgcgc ttgtcgtcat cgtctttgta gtcgggaggc ggcggcgacg gcgacgggga   3240
cgacacgtcc tccatggttg gtggacgtcg cgccgcaccg cgtccgcgct cgggggtggt   3300
ttcgcgctgc tcctcttccc gactggccat ggtggccgag gataacttcg tatatggttt   3360
cttatacgaa gttatgatcc agacatgata agatacattg atgagtttgg acaaaccaca   3420
actagaatgc agtgaaaaaa atgctttatt tgtgaaattt gtgatgctat tgctttattt   3480
gtaaccatta taagctgcaa taaacaagtt aacaacaaca attgcattca ttttatgttt   3540
caggttcagg gggaggtgtg ggaggttttt taaagcaagt aaaacctcta caaatgtggt   3600
atggctgatt atgatcctct agagtcgcag atctgctacg tatcaagctg tggcagggaa   3660
accctctgcc tcccccgtga tgtaatactt ttgcaaggaa tgcgatgaag tagagcccgc   3720
agtggccaag tggctttggt ccgtctcctc cacggatgcc cctccacggc tagtgggcgc   3780
atgtaggcgg tgggcgtccg ccgcctccag cagcaggtca tagaggggca ccacgttctt   3840
gcacttcatg ctgtacagat gctccatgcc tttgttactc atgtgtcgga tgtgggagag   3900
gatgaggagg agctgggcca gccgctggtg ctgctgctgc agggtcaggc ctgccttggc   3960
catcaggtgg atcaaagtgt ctgtgatctt gtccaggact cggtggatat ggtccttctc   4020
ttccagagac ttcagggtgc tggacagaaa tgtgtacact ccagaattaa gcaaaataat   4080
agatttgagg cacacaaact cctctccctg cagattcatc atgcggaacc gagatgatgt   4140
agccagcagc atgtcgaaga tctccaccat gccctctaca cattttccct ggttcctgtc   4200
caagagcaag ttaggagcaa acagtagctt cactgggtgc tccatggagc gccagacgag   4260
accaatcatc aggatctcta gccaggcaca ttctagaagg tggacctgat catggagggt   4320
caaatccaca aagcctggca ccctcttcgc ccagttgatc atgtgaacca gctccctgtc   4380
tgccaggttg gtcagtaagc ccatcatcga agcttcactg aagggtctgg taggatcata   4440
ctcggaatag agtatggggg gctcagcatc caacaaggca ctgaccatct ggtcggccgt   4500
cagggacaag gccaggctgt tcttcttaga gcgtttgatc atgagcgggc ttggccaaag   4560
gttggcagct ctcatgtctc cagcagatgg ctcgagatcg ccatcttcca gcaggcgcac   4620
cattgcccct gtttcactat ccaggttacg gatatagttc atgacaatat ttacattggt   4680
ccagccacca gcttgcatga tctccggtat tgaaactcca gcgcgggcca tatctcgcgc   4740
ggctccgaca cgggcactgt gtccagacca ggccaggtat ctctgaccag agtcatccta   4800
aaatacacaa acaattagaa tcagtagttt aacacattat acacttaaaa attttatatt   4860
taccttagcg ccgtaaatca atcgatgagt tgcttcaaaa atcccttcca gggcgcgagt   4920
tgatagctgg ctggtggcag atggcgcggc aacaccattt tttctgaccc ggcaaaacag   4980
gtagttattc ggatcatcag ctacaccaga gacggaaatc catcgctcga ccagtttagt   5040
gactcccagg ctaagtgcct tctctacacc tgcggtgcta accagcgttt tcgttctgcc   5100
aatatggatt aacattctcc caccgtcagt acgtgagata tctttaaccc tgatcctggc   5160
```

-continued

```
aatttcggct atacgtaaca gggtgttata agcaatcccc agaaatgcca gattacgtat   5220
atcctggcag cgatcgctat tttccatgag tgaacggact tggtcgaaat cagtgcgttc   5280
gaacgctaga gcctgttttg cacgttcacc ggcatcaacg ttttcttttc ggatccgccg   5340
cataaccagt gaaacagcat tgctgtcact tggtcgtggc agcccggacc gacgatgaag   5400
catgtttagc tggcccaaat gttgctggat agtttttact gccagaccgc gcgcttgaag   5460
atatagaaga taatcgcgaa catcttcagg ttctgcggga aaccatttcc ggttattcaa   5520
cttgcaccat gccgcccacg accggcaaac ggacagaagc attttccagg tatgctcaga   5580
aaacgcctgg cgatccctga acatgtccat caggttcttg cgaacctcat cactcgttgc   5640
atcgaccggt aatgcaggca aattttggtg tacggtcagt aaattggaca tggtggctac   5700
gtaataactt cgtatatggt ttcttatacg aagttatgcg gccgctttac gagggtagga   5760
agtggtacgg aaagttggta taagacaaaa gtgttgtgga attgctccag gcgatctgac   5820
ggttcactaa acgagctctg cttttatagg cgcccaccgt acacgcctaa agcttatacg   5880
ttctctatca ctgataggga gtaaactgga tatacgttct ctatcactga tagggagtaa   5940
actgtagata cgttctctat cactgatagg gagtaaactg gtcatacgtt ctctatcact   6000
gatagggagt aaactcctta tacgttctct atcactgata gggagtaaag tctgcatacg   6060
ttctctatca ctgataggga gtaaactctt catacgttct ctatcactga tagggagtaa   6120
actcgcggcc gcagagaaat gttctggcac ctgcacttgc actggggaca gcctattttg   6180
ctagtttgtt ttgtttcgtt ttgttttgat ggagagcgta tgttagtact atcgattcac   6240
acaaaaaacc aacacacaga tgtaatgaaa ataaagatat tttattggat ctgcgatcgc   6300
tccggtgccc gtcagtgggc agagcgcaca tcgcccacag tccccgagaa gttgggggga   6360
ggggtcggca attgaacggg tgcctagaga aggtggcgcg gggtaaactg ggaaagtgat   6420
gtcgtgtact ggctccgcct ttttcccgag ggtgggggag aaccgtatgt aagtgcagta   6480
gtcgccgtga acgttctttt tcgcaacggg tttgccgcca gaacacagct gaagcttcga   6540
ggggctcgca tctctccttc acgcgcccgc cgccctacct gaggccgcca tccacgccgg   6600
ttgagtcgcg ttctgccgcc tcccgcctgt ggtgcctcct gaactgcgtc cgccgtctag   6660
gtaagtttaa agctcaggtc gagaccgggc ctttgtccgg cgctcccttg gagcctacct   6720
agactcagcc ggctctccac gctttgcctg accctgcttg ctcaactcta cgtctttgtt   6780
tcgttttctg ttctgcgccg ttacagatcc aagctgtgac cggcgcctac gctagcggat   6840
ccgccgccac catgtctaga ctggacaaga gcaaagtcat aaactctgct ctggaattac   6900
tcaatggagt cggtatcgaa ggcctgacga caaggaaact cgctcaaaag ctgggagttg   6960
agcagcctac cctgtactgg cacgtgaaga acaagcgggc cctgctcgat gccctgccaa   7020
tcgagatgct ggacaggcat catacccact cctgcccccct ggaaggcgag tcatggcaag   7080
actttctgcg gaacaacgcc aagtcatacc gctgtgctct tctctcacat cgcgacgggg   7140
ctaaagtgca tctcggcacc cgcccaacag agaaacagta cgaaaccctg gaaaatcagc   7200
tcgcgttcct gtgtcagcaa ggcttctccc tggagaacgc actgtacgct ctgtccgccg   7260
tgggccactt tacactgggc tgcgtattgg aggaacagga gcatcaagta gcaaaagagg   7320
aaagagagac acctaccacc gattctatgc ccccacttct gaaacaagca attgagctgt   7380
tcgaccggca gggagccgaa cctgccttcc ttttcggcct ggaactaatc atatgtggcc   7440
tggagaaaca gctaaagtgc gaaagcggcg ggccgaccga cgcccttgac gattttgact   7500
tagacatgct cccagccgat gcccttgacg actttgacct tgatatgctg cctgctgacg   7560
```

```
ctcttgacga ttttgacctt gacatgctcc ccgggggatc cggagctact aacttcagcc   7620

tgctgaagca ggctggagac gtggaggaga accctggacc tatgacagaa tataaaccta   7680

ctgtcagact ggcaactcga gacgacgtcc ctagggccgt gagaacattg gctgccgctt   7740

tcgcggatta tcccgctaca cgccacacag ttgatcctga tagacatatt gaacgggtta   7800

cagaattgca agaacttttt ttgaccaggg taggattgga catcggtaaa gtttgggtcg   7860

ccgacgacgg ggctgcagtg gcagtgtgga cgactccgga gagcgttgag gccggggctg   7920

tatttgcaga aattggtccc cgaatggctg agcttagtgg ctctcgtctc gcggctcagc   7980

aacaaatgga aggactcctc gcccctcacc gccctaaaga accagcttgg ttcctcgcta   8040

ctgtgggcgt tagccccgat catcagggaa agggccttgg ttccgcggtg gtattgcccg   8100

gagtagaagc cgcagaacga gccggagtgc cagcctttct tgaaacgtca gcgccaagga   8160

atttgccctt ctatgaacgg ctcggattta cagttactgc tgacgttgaa gtacccgagg   8220

gcccacggac gtggtgcatg acgcgaaaac ccggcgcttg agtttaaacc gctgatcagc   8280

ctcgactgtg ccttctagtt gccagccatc tgttgtttgc ccctcccccg tgccttcctt   8340

gaccctggaa ggtgccactc ccactgtcct ttcctaataa aatgaggaaa ttgcatcgca   8400

ttgtctgagt aggtgtcatt ctattctggg gggtggggtg gggcaggaca gcaaggggga   8460

ggattgggaa gacaatagca ggcatgctgg ggatgcggtg ggctctatgg cttctgaggc   8520

ggaaagaacc agctggggct cgactagagc ttgcggaacc cttagtttaa acggcccctt   8580

aattaatcga tgtaggatgt tgcccctcct gacgcggtag gagaagggga gggtgccctg   8640

catgtctgcc gctgctcttg ctcttgccgc tgctgaggag gggggcgcat ctgccgcagc   8700

accggatgca tctgggaaaa gcaaaaaagg ggctcgtccc tgtttccgga ggaatttgca   8760

agcggggtct tgcatgacgg ggaggcaaac cccgttcgc cgcagtccgg ccggcccgag   8820

actcgaaccg gggtcctgc gactcaaccc ttggaaaata accctccggc tacagggagc   8880

gagccactta atgctttcgc tttccagcct aaccgcttac gccgcgcgcg gccagtggcc   8940

aaaaaagcta gcgcagcagc cgccgcgcct ggaaggaagc caaaaggagc gctcccccgt   9000

tgtctgacgt cgcacacctg ggttcgacac gcgggcggta accgcatgga tcacggcgga   9060

cggccggatc cggggttcga accccggtcg tccgccatga tacccttgcg aatttatcca   9120

ccagaccacg gaagagtgcc cgcttacagg ctctcctttt gcacggtcta gagcgtcaac   9180

gactgcgcac gcctcaccgg ccagagcgtc ccgaccatgg agcacttttt gccgctgcgc   9240

aacatctgga accgcgtccg cgactttccg cgcgcctcca ccaccgccgc cggcatcacc   9300

tggatgtcca ggtacatcta cggattacgg ggcccattgg tatg                    9344
```

<210> SEQ ID NO 13
<211> LENGTH: 161
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 13

```
gggcactctt ccgtggtctg gtggataaat tcgcaagggt atcatggcgg acgaccgggg     60

ttcgaacccc ggatccggcc gtccgccgtg atccatgcgg ttaccgcccg cgtgtcgaac    120

ccaggtgtgc gacgtcagac aacgggggag cgctcctttt t                        161
```

<210> SEQ ID NO 14
<211> LENGTH: 151
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 14
gggcactctt ccgtggtctg gtggataaat tcgcaagggt atcatggcgg acgaccggcc 60
ggatccggcc gtccgccgtg atccatgcgg ttaccgcccg cgtgtcgaac ccaggtgtgc 120
gacgtcagac aacgggggag cgctcctttt t 151

<210> SEQ ID NO 15
<211> LENGTH: 161
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 15
gggcactctt ccgtgatctg gtggataaat tcgcaagggt atcatggcgg acgaccgggg 60
ttcgaacccc ggatccggcc gtccgccgtg atccatgcgg ttaccgcccg cgtgtcgaac 120
ccaggtgtgc gacgtcagac aacgggggag cgctcctttt t 161

<210> SEQ ID NO 16
<211> LENGTH: 161
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 16
gggcactctt ccgtgatctg gtggataaat tcgcaagggt atcatggcgg acgaccggga 60
ttcgaacccc ggatccggcc gtccgccgtg atccatgcgg ttaccgcccg cgtgtcgaac 120
ccaggtgtgc gacgtcagac aacgggggag cgctcctttt t 161

<210> SEQ ID NO 17
<211> LENGTH: 393
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 17
cgatggaggg cctatttccc atgattcctt catatttgca tatacgatac aaggctgtta 60
gagagataat tagaattaat ttgactgtaa acacaaagat attagtacaa aataataact 120
tcgtataatg tatgctatac gaagttattt tgcagtttta aaattatgtt ttaaaatgga 180
ctatcatatg cttaccgtaa cttgaaagta tttcgatttc ttggctttat atatcttgtg 240
gaaaggacga aacaccgggc actcttccgt ggtctggtgg ataaattcgc aagggtatca 300
tggcggacga ccggccggat ccggccgtcc gccgtgatcc atgcggttac cgcccgcgtg 360
tcgaacccag gtgtgcgacg tcagacaacg ggg 393

<210> SEQ ID NO 18
<211> LENGTH: 417
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 18
cgatggaggg cctatttccc atgattcctt catatttgca tatacgatac aaggctgtta 60
gagagataat tagaattaat ttgactgtaa acacaaagat attagtacaa aataataact 120
tcgtataatg tatgctatac gaagttattt tgcagtttta aaattatgtt ttaaaatgga 180
ctatcatatg cttaccgtaa cttgaaagta tttcgatttc ttggctttat atatcttgtg 240
gaaaggacga aacaccgggc actcttccgt gatctggtgg ataaattcgc aagggtatca 300
tggcggacga ccggggttcg aaccccggat ccggccgtcc gccgtgatcc atgcggttac 360
cgcccgcgtg tcgaacccag gtgtgcgacg tcagacaacg ggggagcgct ccttttt 417

<210> SEQ ID NO 19
<211> LENGTH: 428
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 19
ttcactagaa tcgatggagg gcctatttcc catgattcct tcatatttgc atatacgata 60
caaggctgtt agagagataa ttagaattaa tttgactgta aacacaaaga tattagtaca 120
aaataataac ttcgtataat gtatgctata cgaagttatt ttgcagtttt aaaattatgt 180
tttaaaatgg actatcatat gcttaccgta acttgaaagt atttcgattt cttggcttta 240
tatatcttgt ggaaaggacg aaacaccggg cactcttccg tgatctggtg gataaattcg 300
caagggtatc atggcggacg accgggattc gaaccccgga tccggccgtc cgccgtgatc 360
catgcggtta ccgcccgcgt gtcgaaccca ggtgtgcgac gtcagacaac gggggagcgc 420
tcctttt 428

<210> SEQ ID NO 20
<211> LENGTH: 544
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 20
ggatctgcga tcgctccggt gcccgtcagt gggcagagcg cacatcgccc acagtccccg 60
agaagttggg gggaggggtc ggcaattgaa cgggtgccta gagaaggtgg cgcggggtaa 120
actgggaaag tgatgtcgtg tactggctcc gcctttttcc cgagggtggg ggagaaccgt 180
atgtaagtgc agtagtcgcc gtgaacgttc tttttcgcaa cgggtttgcc gccagaacac 240
agctgaagct tcgaggggct cgcatctctc cttcacgcgc ccgccgccct acctgaggcc 300
gccatccacg ccggttgagt cgcgttctgc cgcctcccgc ctgtggtgcc tcctgaactg 360
cgtccgccgt ctaggtaagt ttaaagctca ggtcgagacc gggcctttgt ccggcgctcc 420
cttggagcct acctagactc agccggctct ccacgctttg cctgaccctg cttgctcaac 480
tctacgtctt tgtttcgttt tctgttctgc gccgttacag atccaagctg tgaccggcgc 540
ctac 544

<210> SEQ ID NO 21
<211> LENGTH: 744
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 21
atgtctagac tggacaagag caaagtcata aactctgctc tggaattact caatggagtc 60
ggtatcgaag gcctgacgac aaggaaactc gctcaaaagc tgggagttga gcagcctacc 120
ctgtactggc acgtgaagaa caagcgggcc ctgctcgatg ccctgccaat cgagatgctg 180
gacaggcatc atacccactc ctgcccccctg gaaggcgagt catggcaaga ctttctgcgg 240
aacaacgcca agtcataccg ctgtgctctt ctctcacatc gcgacggggc taaagtgcat 300
ctcggcaccc gcccaacaga gaaacagtac gaaaccctgg aaaatcagct cgcgttcctg 360
tgtcagcaag gcttctccct ggagaacgca ctgtacgctc tgtccgccgt gggccacttt 420
acactgggct gcgtattgga ggaacaggag catcaagtag caaaagagga aagagagaca 480
cctaccaccg attctatgcc cccacttctg aaacaagcaa ttgagctgtt cgaccggcag 540
ggagccgaac ctgccttcct tttcggcctg gaactaatca tatgtggcct ggagaaacag 600
ctaaagtgcg aaagcggcgg gccgaccgac gcccttgacg attttgactt agacatgctc 660
ccagccgatg cccttgacga ctttgacctt gatatgctgc ctgctgacgc tcttgacgat 720
tttgaccttg acatgctccc cggg 744

<210> SEQ ID NO 22
<211> LENGTH: 379
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 22
gagtttactc cctatcagtg atagagaacg tatgaagagt ttactcccta tcagtgatag 60
agaacgtatg cagactttac tccctatcag tgatagagaa cgtataagga gtttactccc 120
tatcagtgat agagaacgta tgaccagttt actccctatc agtgatagag aacgtatcta 180
cagtttactc cctatcagtg atagagaacg tatatccagt ttactcccta tcagtgatag 240
agaacgtata agctttaggc gtgtacggtg ggcgcctata aaagcagagc tcgtttagtg 300
aaccgtcaga tcgcctggag caattccaca acacttttgt cttataccaa ctttccgtac 360
cacttcctac cctcgtaaa 379

<210> SEQ ID NO 23
<211> LENGTH: 11051
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 23
ggtacccaac tccatgctta acagtcccca ggtacagccc accctgcgtc gcaaccagga 60
acagctctac agcttcctgg agcgccactc gccctacttc cgcagccaca gtgcgcagat 120
taggagcgcc acttcttttt gtcacttgaa aaacatgtaa aataatgta ctaggagaca 180 ctttcaataa aggcaaatgt ttttatttgt acactctcgg gtgattattt accccccacc 240
cttgccgtct gcgccgttta aaaatcaaag gggttctgcc gcgcatcgct atgcgccact 300
ggcagggaca cgttgcgata ctggtgttta gtgctccact taaactcagg cacaaccatc 360
cgcggcagct cggtgaagtt ttcactccac aggctgcgca ccatcaccaa cgcgtttagc 420
aggtcgggcg ccgatatctt gaagtcgcag ttggggcctc cgccctgcgc gcgcgagttg 480
cgatacacag ggttgcagca ctggaacact atcagcgccg ggtggtgcac gctggccagc 540
acgctcttgt cggagatcag atccgcgtcc aggtcctccg cgttgctcag ggcgaacgga 600
gtcaactttg gtagctgcct tcccaaaaag ggtgcatgcc caggctttga gttgcactcg 660
caccgtagtg gcatcagaag gtgaccgtgc ccggtctggg cgttaggata cagcgcctgc 720
atgaaagcct tgatctgctt aaaagccacc tgagcctttg cgccttcaga gaagaacatg 780
ccgcaagact tgccggaaaa ctgattggcc ggacaggccg cgtcatgcac gcagcacctt 840
gcgtcggtgt tggagatctg caccacattt cggccccacc ggttcttcac gatcttggcc 900
ttgctagact gctccttcag cgcgcgctgc ccgttttcgc tcgtcacatc catttcaatc 960
acgtgctcct tatttatcat aatgctcccg tgtagacact taagctcgcc ttcgatctca 1020
gcgcagcggt gcagccacaa cgcgcagccc gtgggctcgt ggtgcttgta ggttacctct 1080
gcaaacgact gcaggtacgc ctgcaggaat cgccccatca tcgtcacaaa ggtcttgttg 1140
ctggtgaagg tcagctgcaa cccgcggtgc tcctcgttta gccaggtctt gcatacggcc 1200
gccagagctt ccacttggtc aggcagtagc ttgaagtttg cctttagatc gttatccacg 1260
tggtacttgt ccatcaacgc gcgcgcagcc tccatgccct tctcccacgc agacacgatc 1320
ggcaggctca gcgggtttat caccgtgctt tcactttccg cttcactgga ctcttccttt 1380
tcctcttgcg tccgcatacc ccgcgccact gggtcgtctt cattcagccg ccgcaccgtg 1440
cgcttacctc ccttgccgtg cttgattagc accggtgggt tgctgaaacc caccatttgt 1500
agcgccacat cttctctttc ttcctcgctg tccacgatca cctctgggga tggcgggcgc 1560
tcgggcttgg gagaggggcg cttctttttc tttttggacg caatggccaa atccgccgtc 1620
gaggtcgatg gccgcgggct gggtgtgcgc ggcaccagcg catcttgtga cgagtcttct 1680
tcgtcctcgg actcgagacg ccgcctcagc cgcttttttg ggggcgcgcg gggaggcggc 1740
ggcgacggcg acggggacga cacgtcctcc atggttggtg gacgtcgcgc cgcaccgcgt 1800
ccgcgctcgg gggtggtttc gcgctgctcc tcttcccgac tggccatttc cttctcctat 1860
aggcagaaaa agatcatgga gtcagtcgag aaggaggaca gcctaaccgc cccctttgag 1920
ttcgccacca ccgcctccac cgatgccgcc aacgcgccta ccaccttccc cgtcgaggca 1980
cccccgcttg aggaggagga agtgattatc gagcaggacc caggttttgt aagcgaagac 2040
gacgaggatc gctcagtacc aacagaggat aaaaagcaag accaggacga cgcagaggca 2100
aacgaggaac aagtcgggcg gggggaccaa aggcatggcg actacctaga tgtgggagac 2160
gacgtgctgt tgaagcatct gcagcgccag tgcgccatta tctgcgacgc gttgcaagag 2220

-continued

```
cgcagcgatg tgcccctcgc catagcggat gtcagccttg cctacgaacg ccacctgttc   2280
tcaccgcgcg taccccccaa acgccaagaa aacggcacat gcgagcccaa cccgcgcctc   2340
aacttctacc ccgtatttgc cgtgccagag gtgcttgcca cctatcacat ctttttccaa   2400
aactgcaaga taccccctatc ctgccgtgcc aaccgcagcc gagcggacaa gcagctggcc   2460
ttgcggcagg gcgctgtcat acctgatatc gcctcgctcg acgaagtgcc aaaaatcttt   2520
gagggtcttg gacgcgacga gaaacgcgcg gcaaacgctc tgcaacaaga aaacagcgaa   2580
aatgaaagtc actgtggagt gctggtggaa cttgagggtg acaacgcgcg cctagccgtg   2640
ctgaaacgca gcatcgaggt cacccacttt gcctacccgg cacttaacct accccccaag   2700
gttatgagca cagtcatgag cgagctgatc gtgcgccgtg cacgacccct ggagagggat   2760
gcaaacttgc aagaacaaac cgaggagggc ctacccgcag ttggcgatga gcagctggcg   2820
cgctggcttg agacgcgcga gcctgccgac ttggaggagc gacgcaagct aatgatggcc   2880
gcagtgcttg ttaccgtgga gcttgagtgc atgcagcggt tctttgctga cccggagatg   2940
cagcgcaagc tagaggaaac gttgcactac acctttcgcc agggctacgt gcgccaggcc   3000
tgcaaaattt ccaacgtgga gctctgcaac ctggtctcct accttggaat tttgcacgaa   3060
aaccgcctcg ggcaaaacgt gcttcattcc acgctcaagg gcgaggcgcg ccgcgactac   3120
gtccgcgact gcgtttactt atttctgtgc tacacctggc aaacggccat gggcgtgtgg   3180
cagcaatgcc tggaggagcg caacctaaag gagctgcaga agctgctaaa gcaaaacttg   3240
aaggacctat ggacggcctt caacgagcgc tccgtggccg cgcacctggc ggacattatc   3300
ttccccgaac gcctgcttaa aaccctgcaa cagggtctgc cagacttcac cagtcaaagc   3360
atgttgcaaa actttaggaa ctttatccta gagcgttcag gaattctgcc cgccacctgc   3420
tgtgcgcttc ctagcgactt tgtgcccatt aagtaccgtg aatgccctcc gccgctttgg   3480
ggtcactgct accttctgca gctagccaac taccttgcct accactccga catcatggaa   3540
gacgtgagcg gtgacggcct actggagtgt cactgtcgct gcaacctatg caccccgcac   3600
cgctccctgg tctgcaattc gcaactgctt agcgaaagtc aaattatcgg tacctttgag   3660
ctgcagggtc cctcgcctga cgaaaagtcc gcggctccgg ggttgaaact cactccgggg   3720
ctgtggacgt cggcttacct tcgcaaattt gtacctgagg actaccacgc ccacgagatt   3780
aggttctacg aagaccaatc ccgcccgcca aatgcggagc ttaccgcctg cgtcattacc   3840
cagggccaca tccttggcca attgcaagcc atcaacaaag cccgccaaga gtttctgcta   3900
cgaaagggac ggggggttta cctggacccc cagtccggcg aggagctcaa cccaatcccc   3960
ccgccgccgc agccctatca gcagccgcgg gcccttgctt cccaggatgg cacccaaaaa   4020
gaagctgcag ctgccgccgc cgccacccac ggacgaggag gaatactggg acagtcaggc   4080
agaggaggtt ttggacgagg aggaggagat gatggaagac tgggacagcc tagacgaagc   4140
ttccgaggcc gaagaggtgt cagacgaaac accgtcaccc tcggtcgcat tcccctcgcc   4200
ggcgccccag aaattggcaa ccgttcccag catcgctaca acctccgctc ctcaggcgcc   4260
gccggcactg cctgttcgcc gacccaaccg tagatgggac accactggaa ccagggccgg   4320
taagtctaag cagccgccgc cgttagccca agagcaacaa cagcgccaag gctaccgctc   4380
gtggcgcggg cacaagaacg ccatagttgc ttgcttgcaa gactgtgggg gcaacatctc   4440
cttcgcccgc cgctttcttc tctaccatca cggcgtggcc ttcccccgta acatcctgca   4500
ttactaccgt catctctaca gcccctactg caccggcggc agcggcagcg gcagcaacag   4560
cagcggtcac acagaagcaa aggcgaccgg atagcaagac tctgacaaag cccaagaaat   4620
```

```
ccacagcggc ggcagcagca ggaggaggag cgctgcgtct ggcgcccaac gaacccgtat   4680
cgacccgcga gcttagaaat aggatttttc ccactctgta tgctatattt caacaaagca   4740
ggggccaaga acaagagctg aaaataaaaa acaggtctct gcgctccctc acccgcagct   4800
gcctgtatca caaaagcgaa gatcagcttc ggcgcacgct ggaagacgcg gaggctctct   4860
tcagcaaata ctgcgcgctg actcttaagg actagtttcg cgccctttct caaatttaag   4920
cgcgaaaact acgtcatctc cagcggccac acccggcgcc agcacctgtc gtcagcgcca   4980
ttatgagcaa ggaaattccc acgccctaca tgtggagtta ccagccacaa atgggacttg   5040
cggctggagc tgcccaagac tactcaaccc gaataaacta catgagcgcg ggaccccaca   5100
tgatatcccg ggtcaacgga atccgcgccc accgaaaccg aattctcctc gaacaggcgg   5160
ctattaccac cacacctcgt aataacctta atccccgtag ttggcccgct gccctggtgt   5220
accaggaaag tcccgctccc accactgtgg tacttcccag agacgcccag gccgaagttc   5280
agatgactaa ctcaggggcg cagcttgcgg gcggctttcg tcacagggtg cggtcgcccg   5340
ggcgttttag ggcggagtaa cttgcatgta ttgggaattg tagttttttt aaaatgggaa   5400
gtgacgtatc gtgggaaaac ggaagtgaag atttgaggaa gttgtgggtt ttttggcttt   5460
cgtttctggg cgtaggttcg cgtgcggttt tctgggtgtt ttttgtggac tttaaccgtt   5520
acgtcatttt ttagtcctat atatactcgc tctgtacttg gcccttttta cactgtgact   5580
gattgagctg gtgccgtgtc gagtggtgtt ttttaatagg tttttttact ggtaaggctg   5640
actgttatgg ctgccgctgt ggaagcgctg tatgttgttc tggagcggga gggtgctatt   5700
ttgcctaggc aggagggttt ttcaggtgtt tatgtgtttt tctctcctat taattttgtt   5760
atacctccta tgggggctgt aatgttgtct ctacgcctgc gggtatgtat tcccccgggc   5820
tatttcggtc gctttttagc actgaccgat gttaaccaac ctgatgtgtt taccgagtct   5880
tacattatga ctccggacat gaccgaggaa ctgtcggtgg tgctttttaa tcacggtgac   5940
cagttttttt acggtcacgc cggcatggcc gtagtccgtc ttatgcttat aagggttgtt   6000
tttcctgttg taagacaggc ttctaatgtt taaatgtttt tttttttgtt attttatttt   6060
gtgtttaatg caggaacccg cagacatgtt tgagagaaaa atggtgtctt tttctgtggt   6120
ggttccggaa cttacctgcc tttatctgca tgagcatgac tacgatgtgc ttgctttttt   6180
gcgcgaggct ttgcctgatt ttttgagcag caccttgcat tttatatcgc cgcccatgca   6240
acaagcttac ataggggcta cgctggttag catagctccg agtatgcgtg tcataatcag   6300
tgtgggttct tttgtcatgg ttcctggcgg ggaagtggcc gcgctggtcc gtgcagacct   6360
gcacgattat gttcagctgg ccctgcgaag ggacctacgg gatcgcggta tttttgttaa   6420
tgttccgctt ttgaatctta tacaggtctg tgaggaacct gaatttttgc aatcatgatt   6480
cgctgcttga ggctgaaggt ggagggcgct ctggagcaga tttttacaat ggccggactt   6540
aatattcggg atttgcttag agacatattg ataaggtggc gagatgaaaa ttatttgggc   6600
atggttgaag gtgctggaat gtttatagag gagattcacc ctgaagggtt tagcctttac   6660
gtccacttgg acgtgagggc agtttgcctt ttggaagcca ttgtgcaaca tcttacaaat   6720
gccattatct gttctttggc tgtagagttt gaccacgcca ccggagggga gcgcgttcac   6780
ttaatagatc ttcattttga ggttttggat aatcttttgg aataaaaaaa aaaaaacatg   6840
gttcttccag ctcttcccgc tcctcccgtg tgtgactcgc agaacgaatg tgtaggttgg   6900
ctgggtgtgg cttattctgc ggtggtggat gttatcaggg cagcggcgca tgaaggagtt   6960
```

-continued

```
tacatagaac ccgaagccag ggggcgcctg gatgctttga gagagtggat atactacaac   7020
tactacacag agcgagctaa gcgacgagac cggagacgca gatctgtttg tcacgcccgc   7080
acctggtttt gcttcaggaa atatgactac gtccggcgtt ccatttggca tgacactacg   7140
accaacacga tctcggttgt ctcggcgcac tccgtacagt agggatcgcc tacctccttt   7200
tgagacagag acccgcgcta ccatactgga ggatcatccg ctgctgcccg aatgtaacac   7260
tttgacaatg cacaacgtga gttacgtgcg aggtcttccc tgcagtgtgg gatttacgct   7320
gattcaggaa tgggttgttc cctgggatat ggttctgacg cgggaggagc ttgtaatcct   7380
gaggaagtgt atgcacgtgt gcctgtgttg tgccaacatt gatatcatga cgagcatgat   7440
gatccatggt tacgagtcct gggctctcca ctgtcattgt tccagtcccg gttccctgca   7500
gtgcatagcc ggcgggcagg ttttggccag ctggtttagg atggtggtgg atggcgccat   7560
gtttaatcag aggtttatat ggtaccggga ggtggtgaat tacaacatgc caaaagaggt   7620
aatgtttatg tccagcgtgt ttatgagggg tcgccactta atctacctgc gcttgtggta   7680
tgatggccac gtgggttctg tggtccccgc catgagcttt ggatacagcg ccttgcactg   7740
tgggattttg aacaatattg tggtgctgtg ctgcagttac tgtgctgatt taagtgagat   7800
cagggtgcgc tgctgtgccc ggaggacaag gcgtctcatg ctgcgggcgg tgcgaatcat   7860
cgctgaggag accactgcca tgttgtattc ctgcaggacg gagcggcggc ggcagcagtt   7920
tattcgcgcg ctgctgcagc accaccgccc tatcctgatg cacgattatg actctacccc   7980
catgtaggcg tggacttccc cttcgccgcc cgttgagcaa ccgcaagttg gacagcagcc   8040
tgtggctcag cagctggaca gcgacatgaa cttaagcgag ctgcccgggg agtttattaa   8100
tatcactgat gagcgtttgg ctcgacagga aaccgtgtgg aatataacac ctaagaatat   8160
gtctgttacc catgatatga tgctttttaa ggccagccgg ggagaaagga ctgtgtactc   8220
tgtgtgttgg gagggaggtg gcaggttgaa tactagggtt ctgtgagttt gattaaggta   8280
cggtgatcaa tataagctat gtggtggtgg ggctatacta ctgaatgaaa aatgacttga   8340
aattttctgc aattgaaaaa taaacacgtt gaaacataac atgcaacagg ttcacgattc   8400
tttattcctg ggcaatgtag gagaaggtgt aagagttggt agcaaaagtt tcagtggtgt   8460
attttccact ttcccaggac catgtaaaag acatagagta agtgcttacc tcgctagttt   8520
ctgtggattc actagaatcg atgtcgacgg gcactcttcc gtggtctggt ggataaattc   8580
gcaagggtat catggcggac gaaccggtac cgaaccccgg atccggccgt ccgccgtgat   8640
ccatgcggtt accgcccgcg tgtcgaaccc aggtgtgcga cgtcagacaa cgggggagcg   8700
ctccttttc atatgatcag ctcactcaaa ggcggtaata cggttatcca cagaatcagg   8760
ggataacgca ggaaagaaca tgtgagcaaa aggccagcaa aaggccagga accgtaaaaa   8820
ggccgcgttg ctggcgtttt tccataggct ccgcccccct gacgagcatc acaaaaatcg   8880
acgctcaagt cagaggtggc gaaacccgac aggactataa agataccagg cgtttccccc   8940
tggaagctcc ctcgtgcgct ctcctgttcc gaccctgccg cttaccggat acctgtccgc   9000
ctttctccct tcgggaagcg tggcgctttc tcatagctca cgctgtaggt atctcagttc   9060
ggtgtaggtc gttcgctcca agctgggctg tgtgcacgaa ccccccgttc agcccgaccg   9120
ctgcgcctta tccggtaact atcgtcttga gtccaacccg gtaagacacg acttatcgcc   9180
actggcagca gccactggta acaggattag cagagcgagg tatgtaggcg gtgctacaga   9240
gttcttgaag tggtggccta actacggcta cactagaaga acagtatttg gtatctgcgc   9300
tctgctgaag ccagttacct tcggaaaaag agttggtagc tcttgatccg gcaaacaaac   9360
```

caccgctggt agcggtggtt tttttgtttg caagcagcag attacgcgca gaaaaaaagg 9420
atctcaagaa gatcctttga tcttttctac ggggtctgac gctcagtgga acgaaaactc 9480
acgttaaggg attttggtca tgagattatc aaaaaggatc ttcacctaga tccttttaaa 9540
ttaaaaatga agttttaaat caatctaaag tatatatgag taaacttggt ctgacagtta 9600
ccaatgctta atcagtgagg cacctatctc agcgatctgt ctatttcgtt catccatagt 9660
tgcctgactc cccgtcgtgt agataactac gatacgggag ggcttaccat ctggccccag 9720
tgctgcaatg ataccgcgag acccacgctc accggctcca gatttatcag caataaacca 9780
gccagccgga agggccgagc gcagaagtgg tcctgcaact ttatccgcct ccatccagtc 9840
tattaattgt tgccgggaag ctagagtaag tagttcgcca gttaatagtt tgcgcaacgt 9900
tgttgccatt gctacaggca tcgtggtgtc acgctcgtcg tttggtatgg cttcattcag 9960
ctccggttcc caacgatcaa ggcgagttac atgatccccc atgttgtgca aaaaagcggt 10020
tagctccttc ggtcctccga tcgttgtcag aagtaagttg gccgcagtgt tatcactcat 10080
ggttatggca gcactgcata attctcttac tgtcatgcca tccgtaagat gcttttctgt 10140
gactggtgag tactcaacca agtcattctg agaatagtgt atgcggcgac cgagttgctc 10200
ttgcccggcg tcaatacggg ataataccgc gccacatagc agaactttaa aagtgctcat 10260
cattggaaaa cgttcttcgg ggcgaaaact ctcaaggatc ttaccgctgt tgagatccag 10320
ttcgatgtaa cccactcgtg cacccaactg atcttcagca tcttttactt tcaccagcgt 10380
ttctgggtga gcaaaaacag gaaggcaaaa tgccgcaaaa aagggaataa gggcgacacg 10440
gaaatgttga atactcatac tcttcctttt tcaatattat tgaagcattt atcagggtta 10500
ttgtctcatg agcggataca tatttgaatg tatttagaaa aataaacaaa taggggttcc 10560
gcgcacattt ccccgaaaag tgccacctaa attgtaagcg ttaatatttt gttaaaattc 10620
gcgttaaatt tttgttaaat cagctcattt tttaaccaat aggccgaaat cggcaaaatc 10680
ccttataaat caaaagaata gaccgagata gggttgagtg ttgttccagt ttggaacaag 10740
agtccactat taaagaacgt ggactccaac gtcaaagggc gaaaaaccgt ctatcagggc 10800
gatggcccac tacgtgaacc atcaccctaa tcaagttttt tggggtcgag gtgccgtaaa 10860
gcactaaatc ggaaccctaa agggagcccc cgatttagag cttgacgggg aaagccggcg 10920
aacgtggcga gaaaggaagg gaagaaagcg aaaggagcgg gcgctagggc gctggcaagt 10980
gtagcggtca cgctgcgcgt aaccaccaca cccgccgcgc ttaatgcgcc gctacagggc 11040
gcgatggatc c 11051

<210> SEQ ID NO 24
<211> LENGTH: 11051
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 24
ggtacccaac tccatgctta acagtcccca ggtacagccc accctgcgtc gcaaccagga 60
acagctctac agcttcctgg agcgccactc gccctacttc cgcagccaca gtgcgcagat 120
taggagcgcc acttcttttt gtcacttgaa aaacatgtaa aaataatgta ctaggagaca 180
ctttcaataa aggcaaatgt tttatttgt acactctcgg gtgattattt accccccacc 240

-continued

```
cttgccgtct gcgccgttta aaaatcaaag gggttctgcc gcgcatcgct atgcgccact    300
ggcagggaca cgttgcgata ctggtgttta gtgctccact taaactcagg cacaaccatc    360
cgcggcagct cggtgaagtt ttcactccac aggctgcgca ccatcaccaa cgcgtttagc    420
aggtcgggcg ccgatatctt gaagtcgcag ttggggcctc cgccctgcgc gcgcgagttg    480
cgatacacag ggttgcagca ctggaacact atcagcgccg ggtggtgcac gctggccagc    540
acgctcttgt cggagatcag atccgcgtcc aggtcctccg cgttgctcag ggcgaacgga    600
gtcaactttg gtagctgcct tcccaaaaag ggtgcatgcc caggctttga gttgcactcg    660
caccgtagtg gcatcagaag gtgaccgtgc ccggtctggg cgttaggata cagcgcctgc    720
atgaaagcct tgatctgctt aaaagccacc tgagcctttg cgccttcaga gaagaacatg    780
ccgcaagact tgccggaaaa ctgattggcc ggacaggccg cgtcatgcac gcagcacctt    840
gcgtcggtgt tggagatctg caccacattt cggccccacc ggttcttcac gatcttggcc    900
ttgctagact gctccttcag cgcgcgctgc ccgttttcgc tcgtcacatc catttcaatc    960
acgtgctcct tatttatcat aatgctcccg tgtagacact taagctcgcc ttcgatctca   1020
gcgcagcggt gcagccacaa cgcgcagccc gtgggctcgt ggtgcttgta ggttacctct   1080
gcaaacgact gcaggtacgc ctgcaggaat cgccccatca tcgtcacaaa ggtcttgttg   1140
ctggtgaagg tcagctgcaa cccgcggtgc tcctcgttta gccaggtctt gcatacggcc   1200
gccagagctt ccacttggtc aggcagtagc ttgaagtttg cctttagatc gttatccacg   1260
tggtacttgt ccatcaacgc gcgcgcagcc tccatgccct tctcccacgc agacacgatc   1320
ggcaggctca gcgggtttat caccgtgctt tcactttccg cttcactgga ctcttccttt   1380
tcctcttgcg tccgcatacc ccgcgccact gggtcgtctt cattcagccg ccgcaccgtg   1440
cgcttacctc ccttgccgtg cttgattagc accggtgggt tgctgaaacc caccatttgt   1500
agcgccacat cttctctttc ttcctcgctg tccacgatca cctctgggga tggcgggcgc   1560
tcgggcttgg gagaggggcg cttctttttc tttttggacg caatggccaa atccgccgtc   1620
gaggtcgatg gccgcgggct gggtgtgcgc ggcaccagcg catcttgtga cgagtcttct   1680
tcgtcctcgg actcgagacg ccgcctcagc cgcttttttg ggggcgcgcg gggaggcggc   1740
ggcgacggcg acggggacga cacgtcctcc atggttggtg gacgtcgcgc cgcaccgcgt   1800
ccgcgctcgg gggtggtttc gcgctgctcc tcttcccgac tggccatttc cttctcctat   1860
aggcagaaaa agatcatgga gtcagtcgag aaggaggaca gcctaaccgc cccctttgag   1920
ttcgccacca ccgcctccac cgatgccgcc aacgcgccta ccaccttccc cgtcgaggca   1980
cccccgcttg aggaggagga agtgattatc gagcaggacc caggttttgt aagcgaagac   2040
gacgaggatc gctcagtacc aacagaggat aaaaagcaag accaggacga cgcagaggca   2100
aacgaggaac aagtcgggcg gggggaccaa aggcatggcg actacctaga tgtgggagac   2160
gacgtgctgt tgaagcatct gcagcgccag tgcgccatta tctgcgacgc gttgcaagag   2220
cgcagcgatg tgcccctcgc catagcggat gtcagccttg cctacgaacg ccacctgttc   2280
tcaccgcgcg taccccccaa acgccaagaa aacggcacat gcgagcccaa cccgcgcctc   2340
aacttctacc ccgtatttgc cgtgccagag gtgcttgcca cctatcacat ctttttccaa   2400
aactgcaaga taccccctatc ctgccgtgcc aaccgcagcc gagcggacaa gcagctggcc   2460
ttgcggcagg gcgctgtcat acctgatatc gcctcgctcg acgaagtgcc aaaaatcttt   2520
gagggtcttg gacgcgacga gaaacgcgcg gcaaacgctc tgcaacaaga aaacagcgaa   2580
aatgaaagtc actgtggagt gctggtggaa cttgagggtg acaacgcgcg cctagccgtg   2640
```

```
ctgaaacgca gcatcgaggt cacccacttt gcctacccgg cacttaacct accccccaag   2700
gttatgagca cagtcatgag cgagctgatc gtgcgccgtg cacgacccct ggagagggat   2760
gcaaacttgc aagaacaaac cgaggagggc ctacccgcag ttggcgatga gcagctggcg   2820
cgctggcttg agacgcgcga gcctgccgac ttggaggagc gacgcaagct aatgatggcc   2880
gcagtgcttg ttaccgtgga gcttgagtgc atgcagcggt tctttgctga cccggagatg   2940
cagcgcaagc tagaggaaac gttgcactac acctttcgcc agggctacgt gcgccaggcc   3000
tgcaaaattt ccaacgtgga gctctgcaac ctggtctcct accttggaat tttgcacgaa   3060
aaccgcctcg ggcaaaacgt gcttcattcc acgctcaagg gcgaggcgcg ccgcgactac   3120
gtccgcgact gcgtttactt atttctgtgc tacacctggc aaacggccat gggcgtgtgg   3180
cagcaatgcc tggaggagcg caacctaaag gagctgcaga agctgctaaa gcaaaacttg   3240
aaggacctat ggacggcctt caacgagcgc tccgtggccg cgcacctggc ggacattatc   3300
ttccccgaac gcctgcttaa aaccctgcaa cagggtctgc cagacttcac cagtcaaagc   3360
atgttgcaaa actttaggaa ctttatccta gagcgttcag gaattctgcc cgccacctgc   3420
tgtgcgcttc ctagcgactt tgtgcccatt aagtaccgtg aatgccctcc gccgctttgg   3480
ggtcactgct accttctgca gctagccaac taccttgcct accactccga catcatggaa   3540
gacgtgagcg gtgacggcct actggagtgt cactgtcgct gcaacctatg caccccgcac   3600
cgctccctgg tctgcaattc gcaactgctt agcgaaagtc aaattatcgg tacctttgag   3660
ctgcagggtc cctcgcctga cgaaaagtcc gcggctccgg ggttgaaact cactccgggg   3720
ctgtggacgt cggcttacct tcgcaaattt gtacctgagg actaccacgc ccacgagatt   3780
aggttctacg aagaccaatc ccgcccgcca aatgcggagc ttaccgcctg cgtcattacc   3840
cagggccaca tccttggcca attgcaagcc atcaacaaag cccgccaaga gtttctgcta   3900
cgaaagggac gggggtttta cctggacccc cagtccggcg aggagctcaa cccaatcccc   3960
ccgccgccgc agccctatca gcagccgcgg gcccttgctt cccaggatgg cacccaaaaa   4020
gaagctgcag ctgccgccgc cgccacccac ggacgaggag gaatactggg acagtcaggc   4080
agaggaggtt ttggacgagg aggaggagat gatggaagac tgggacagcc tagacgaagc   4140
ttccgaggcc gaagaggtgt cagacgaaac accgtcaccc tcggtcgcat tcccctcgcc   4200
ggcgccccag aaattggcaa ccgttcccag catcgctaca acctccgctc ctcaggcgcc   4260
gccggcactg cctgttcgcc gacccaaccg tagatgggac accactggaa ccagggccgg   4320
taagtctaag cagccgccgc cgttagccca agagcaacaa cagcgccaag gctaccgctc   4380
gtggcgcggg cacaagaacg ccatagttgc ttgcttgcaa gactgtgggg gcaacatctc   4440
cttcgcccgc cgctttcttc tctaccatca cggcgtggcc ttcccccgta acatcctgca   4500
ttactaccgt catctctaca gcccctactg caccggcggc agcggcagcg gcagcaacag   4560
cagcggtcac acagaagcaa aggcgaccgg atagcaagac tctgacaaag cccaagaaat   4620
ccacagcggc ggcagcagca ggaggaggag cgctgcgtct ggcgcccaac gaacccgtat   4680
cgacccgcga gcttagaaat aggatttttc ccactctgta tgctatattt caacaaagca   4740
ggggccaaga acaagagctg aaaataaaaa acaggtctct gcgctccctc acccgcagct   4800
gcctgtatca caaaagcgaa gatcagcttc ggcgcacgct ggaagacgcg gaggctctct   4860
tcagcaaata ctgcgcgctg actcttaagg actagtttcg cgccctttct caaatttaag   4920
cgcgaaaact acgtcatctc cagcggccac acccggcgcc agcacctgtc gtcagcgcca   4980
```

```
ttatgagcaa ggaaattccc acgccctaca tgtggagtta ccagccacaa atgggacttg   5040
cggctggagc tgcccaagac tactcaaccc gaataaacta catgagcgcg ggaccccaca   5100
tgatatcccg ggtcaacgga atccgcgccc accgaaaccg aattctcctc gaacaggcgg   5160
ctattaccac cacacctcgt aataacctta atccccgtag ttggcccgct gccctggtgt   5220
accaggaaag tcccgctccc accactgtgg tacttcccag agacgcccag gccgaagttc   5280
agatgactaa ctcaggggcg cagcttgcgg gcggctttcg tcacagggtg cggtcgcccg   5340
ggcgttttag ggcggagtaa cttgcatgta ttgggaattg tagttttttt aaaatgggaa   5400
gtgacgtatc gtgggaaaac ggaagtgaag atttgaggaa gttgtgggtt ttttggcttt   5460
cgtttctggg cgtaggttcg cgtgcggttt tctgggtgtt ttttgtggac tttaaccgtt   5520
acgtcatttt ttagtcctat atatactcgc tctgtacttg gcccttttta cactgtgact   5580
gattgagctg gtgccgtgtc gagtggtgtt ttttaatagg tttttttact ggtaaggctg   5640
actgttatgg ctgccgctgt ggaagcgctg tatgttgttc tggagcggga gggtgctatt   5700
ttgcctaggc aggagggttt ttcaggtgtt tatgtgtttt tctctcctat taattttgtt   5760
atacctccta tgggggctgt aatgttgtct ctacgcctgc gggtatgtat tcccccgggc   5820
tatttcggtc gctttttagc actgaccgat gttaaccaac ctgatgtgtt taccgagtct   5880
tacattatga ctccggacat gaccgaggaa ctgtcggtgg tgctttttaa tcacggtgac   5940
cagttttttt acggtcacgc cggcatggcc gtagtccgtc ttatgcttat aagggttgtt   6000
tttcctgttg taagacaggc ttctaatgtt taaatgtttt tttttttgtt attttatttt   6060
gtgtttaatg caggaacccg cagacatgtt tgagagaaaa atggtgtctt tttctgtggt   6120
ggttccggaa cttacctgcc tttatctgca tgagcatgac tacgatgtgc ttgctttttt   6180
gcgcgaggct ttgcctgatt ttttgagcag caccttgcat tttatatcgc cgcccatgca   6240
acaagcttac ataggggcta cgctggttag catagctccg agtatgcgtg tcataatcag   6300
tgtgggttct tttgtcatgg ttcctggcgg ggaagtggcc gcgctggtcc gtgcagacct   6360
gcacgattat gttcagctgg ccctgcgaag ggacctacgg gatcgcggta tttttgttaa   6420
tgttccgctt ttgaatctta tacaggtctg tgaggaacct gaatttttgc aatcatgatt   6480
cgctgcttga ggctgaaggt ggagggcgct ctggagcaga tttttacaat ggccggactt   6540
aatattcggg atttgcttag agacatattg ataaggtggc gagatgaaaa ttatttgggc   6600
atggttgaag gtgctggaat gtttatagag gagattcacc ctgaagggtt tagcctttac   6660
gtccacttgg acgtgagggc agtttgcctt ttggaagcca ttgtgcaaca tcttacaaat   6720
gccattatct gttctttggc tgtagagttt gaccacgcca ccggagggga gcgcgttcac   6780
ttaatagatc ttcattttga ggttttggat aatcttttgg aataaaaaaa aaaaaacatg   6840
gttcttccag ctcttcccgc tcctcccgtg tgtgactcgc agaacgaatg tgtaggttgg   6900
ctgggtgtgg cttattctgc ggtggtggat gttatcaggg cagcggcgca tgaaggagtt   6960
tacatagaac ccgaagccag gggcgcctg gatgctttga gagagtggat atactacaac    7020
tactacacag agcgagctaa gcgacgagac cggagacgca gatctgtttg tcacgcccgc   7080
acctggtttt gcttcaggaa atatgactac gtccggcgtt ccatttggca tgacactacg   7140
accaacacga tctcggttgt ctcggcgcac tccgtacagt agggatcgcc tacctccttt   7200
tgagacagag acccgcgcta ccatactgga ggatcatccg ctgctgcccg aatgtaacac   7260
tttgacaatg cacaacgtga gttacgtgcg aggtcttccc tgcagtgtgg gatttacgct   7320
gattcaggaa tgggttgttc cctgggatat ggttctgacg cgggaggagc ttgtaatcct   7380
```

-continued

```
gaggaagtgt atgcacgtgt gcctgtgttg tgccaacatt gatatcatga cgagcatgat   7440
gatccatggt tacgagtcct gggctctcca ctgtcattgt tccagtcccg gttccctgca   7500
gtgcatagcc ggcgggcagg ttttggccag ctggtttagg atggtggtgg atggcgccat   7560
gtttaatcag aggtttatat ggtaccggga ggtggtgaat tacaacatgc caaaagaggt   7620
aatgtttatg tccagcgtgt ttatgagggg tcgccactta atctacctgc gcttgtggta   7680
tgatggccac gtgggttctg tggtccccgc catgagcttt ggatacagcg ccttgcactg   7740
tgggattttg aacaatattg tggtgctgtg ctgcagttac tgtgctgatt taagtgagat   7800
cagggtgcgc tgctgtgccc ggaggacaag gcgtctcatg ctgcgggcgg tgcgaatcat   7860
cgctgaggag accactgcca tgttgtattc ctgcaggacg gagcggcggc ggcagcagtt   7920
tattcgcgcg ctgctgcagc accaccgccc tatcctgatg cacgattatg actctacccc   7980
catgtaggcg tggacttccc cttcgccgcc cgttgagcaa ccgcaagttg gacagcagcc   8040
tgtggctcag cagctggaca gcgacatgaa cttaagcgag ctgcccgggg agtttattaa   8100
tatcactgat gagcgtttgg ctcgacagga aaccgtgtgg aatataacac ctaagaatat   8160
gtctgttacc catgatatga tgctttttaa ggccagccgg ggagaaagga ctgtgtactc   8220
tgtgtgttgg gagggaggtg gcaggttgaa tactagggtt ctgtgagttt gattaaggta   8280
cggtgatcaa tataagctat gtggtggtgg ggctatacta ctgaatgaaa aatgacttga   8340
aattttctgc aattgaaaaa taaacacgtt gaaacataac atgcaacagg ttcacgattc   8400
tttattcctg ggcaatgtag gagaaggtgt aagagttggt agcaaaagtt tcagtggtgt   8460
attttccact ttcccaggac catgtaaaag acatagagta agtgcttacc tcgctagttt   8520
ctgtggattc actagaatcg atgtcgacgg gcactcttcc gtggtctggt ggataaattc   8580
gcaagggtat catggcggac gaccgggatt cgaaccccgg atccggccgt ccgccgtgat   8640
ccatgcggtt accgcccgcg tgtcgaaccc aggtgtgcga cgtcagacaa cgggggagcg   8700
ctcctttttc atatgatcag ctcactcaaa ggcggtaata cggttatcca cagaatcagg   8760
ggataacgca ggaaagaaca tgtgagcaaa aggccagcaa aaggccagga accgtaaaaa   8820
ggccgcgttg ctggcgtttt tccataggct ccgcccccct gacgagcatc acaaaaatcg   8880
acgctcaagt cagaggtggc gaaacccgac aggactataa agataccagg cgtttccccc   8940
tggaagctcc ctcgtgcgct ctcctgttcc gaccctgccg cttaccggat acctgtccgc   9000
ctttctccct tcgggaagcg tggcgctttc tcatagctca cgctgtaggt atctcagttc   9060
ggtgtaggtc gttcgctcca agctgggctg tgtgcacgaa ccccccgttc agcccgaccg   9120
ctgcgcctta tccggtaact atcgtcttga gtccaacccg gtaagacacg acttatcgcc   9180
actggcagca gccactggta acaggattag cagagcgagg tatgtaggcg gtgctacaga   9240
gttcttgaag tggtggccta actacggcta cactagaaga acagtatttg gtatctgcgc   9300
tctgctgaag ccagttacct tcggaaaaag agttggtagc tcttgatccg gcaaacaaac   9360
caccgctggt agcggtggtt tttttgtttg caagcagcag attacgcgca gaaaaaaagg   9420
atctcaagaa gatcctttga tcttttctac ggggtctgac gctcagtgga acgaaaactc   9480
acgttaaggg attttggtca tgagattatc aaaaaggatc ttcacctaga tccttttaaa   9540
ttaaaaatga agttttaaat caatctaaag tatatatgag taaacttggt ctgacagtta   9600
ccaatgctta atcagtgagg cacctatctc agcgatctgt ctatttcgtt catccatagt   9660
tgcctgactc cccgtcgtgt agataactac gatacgggag ggcttaccat ctggccccag   9720
```

tgctgcaatg ataccgcgag acccacgctc accggctcca gatttatcag caataaacca 9780
gccagccgga agggccgagc gcagaagtgg tcctgcaact ttatccgcct ccatccagtc 9840
tattaattgt tgccgggaag ctagagtaag tagttcgcca gttaatagtt tgcgcaacgt 9900
tgttgccatt gctacaggca tcgtggtgtc acgctcgtcg tttggtatgg cttcattcag 9960
ctccggttcc caacgatcaa ggcgagttac atgatccccc atgttgtgca aaaaagcggt 10020
tagctccttc ggtcctccga tcgttgtcag aagtaagttg gccgcagtgt tatcactcat 10080
ggttatggca gcactgcata attctcttac tgtcatgcca tccgtaagat gcttttctgt 10140
gactggtgag tactcaacca agtcattctg agaatagtgt atgcggcgac cgagttgctc 10200
ttgcccggcg tcaatacggg ataataccgc gccacatagc agaactttaa aagtgctcat 10260
cattggaaaa cgttcttcgg ggcgaaaact ctcaaggatc ttaccgctgt tgagatccag 10320
ttcgatgtaa cccactcgtg cacccaactg atcttcagca tcttttactt tcaccagcgt 10380
ttctgggtga gcaaaaacag gaaggcaaaa tgccgcaaaa aagggaataa gggcgacacg 10440
gaaatgttga atactcatac tcttcctttt tcaatattat tgaagcattt atcagggtta 10500
ttgtctcatg agcggataca tatttgaatg tatttagaaa aataaacaaa taggggttcc 10560
gcgcacattt ccccgaaaag tgccacctaa attgtaagcg ttaatatttt gttaaaattc 10620
gcgttaaatt tttgttaaat cagctcattt tttaaccaat aggccgaaat cggcaaaatc 10680
ccttataaat caaaagaata gaccgagata gggttgagtg ttgttccagt ttggaacaag 10740
agtccactat taaagaacgt ggactccaac gtcaaagggc gaaaaaccgt ctatcagggc 10800
gatggcccac tacgtgaacc atcaccctaa tcaagttttt tggggtcgag gtgccgtaaa 10860
gcactaaatc ggaaccctaa agggagcccc cgatttagag cttgacgggg aaagccggcg 10920
aacgtggcga gaaaggaagg gaagaaagcg aaaggagcgg gcgctagggc gctggcaagt 10980
gtagcggtca cgctgcgcgt aaccaccaca cccgccgcgc ttaatgcgcc gctacagggc 11040
gcgatggatc c 11051

<210> SEQ ID NO 25
<211> LENGTH: 6770
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 25
ccgcggccgc caactttgta tagaaaagtt gtagttatta atagtaatca attacggggt 60
cattagttca tagcccatat atggagttcc gcgttacata acttacggta aatggcccgc 120
ctggctgacc gcccaacgac ccccgcccat tgacgtcaat aatgacgtat gttcccatag 180
taacgccaat agggactttc cattgacgtc aatgggtgga gtatttacgg taaactgccc 240
acttggcagt acatcaagtg tatcatatgc caagtacgcc ccctattgac gtcaatgacg 300
gtaaatggcc cgcctggcat tatgcccagt acatgacctt atgggacttt cctacttggc 360
agtacatcta cgtattagtc atcgctatta ccatggtgat gcggttttgg cagtacatca 420
atgggcgtgg atagcggttt gactcacggg gatttccaag tctccacccc attgacgtca 480
atgggagttt gttttggcac caaaatcaac gggactttcc aaaatgtcgt aacaactccg 540
ccccattgac gcaaatgggc ggtaggcgtg tacggtggga ggtctatata agcagagctg 600
gtttagtgaa ccgtcagatc caagtttgta caaaaaagca ggctgccacc atggccagtc 660

-continued

```
gggaagagga gcagcgcgaa accacccccg agcgcggacg cggtgcggcg cgacgtccac    720
caaccatgga ggacgtgtcg tccccgtcgc cgtcgccgcc gcctccccgc gcgcccccaa    780
aaaagcggct gaggcggcgt ctcgagtccg aggacgaaga agactcgtca caagatgcgc    840
tggtgccgcg cacacccagc ccgcggccat cgacctcgac ggcggatttg gccattgcgt    900
ccaaaaagaa aaagaagcgc ccctctccca agcccgagcg cccgccatcc ccagaggtga    960
tcgtggacag cgaggaagaa agagaagatg tggcgctaca aatggtgggt ttcagcaacc   1020
caccggtgct aatcaagcac ggcaagggag gtaagcgcac ggtgcggcgg ctgaatgaag   1080
acgacccagt ggcgcggggt atgcggacgc aagaggaaaa ggaagagtcc agtgaagcgg   1140
aaagtgaaag cacggtgata aacccgctga gcctgccgat cgtgtctgcg tgggagaagg   1200
gcatggaggc tgcgcgcgcg ttgatggaca agtaccacgt ggataacgat ctaaaggcaa   1260
acttcaagct actgcctgac caagtggaag ctctggcggc cgtatgcaag acctggctaa   1320
acgaggagca ccgcgggttg cagctgacct tcaccagcaa caagaccttt gtgacgatga   1380
tggggcgatt cctgcaggcg tacctgcagt cgtttgcaga ggtaacctac aagcaccacg   1440
agcccacggg ctgcgcgttg tggctgcacc gctgcgctga gatcgaaggc gagcttaagt   1500
gtctacacgg gagcattatg ataaataagg agcacgtgat tgaaatggat gtgacgagcg   1560
aaaacgggca gcgcgcgctg aaggagcagt ctagcaaggc caagatcgtg aagaaccggt   1620
ggggccgaaa tgtggtgcag atctccaaca ccgacgcaag gtgctgcgtg catgacgcgg   1680
cctgtccggc caatcagttt tccggcaagt cttgcggcat gttcttctct gaaggcgcaa   1740
aggctcaggt ggcttttaag cagatcaagg ctttcatgca ggcgctgtat cctaacgccc   1800
agaccgggca cggtcacctt ctgatgccac tacggtgcga gtgcaactca aagcctgggc   1860
atgcaccctt tttgggaagg cagctaccaa agttgactcc gttcgccctg agcaacgcgg   1920
aggacctgga cgcggatctg atctccgaca agagcgtgct ggccagcgtg caccacccgg   1980
cgctgatagt gttccagtgc tgcaaccctg tgtatcgcaa ctcgcgcgcg cagggcggag   2040
gccccaactg cgacttcaag atatcggcgc ccgacctgct aaacgcgttg gtgatggtgc   2100
gcagcctgtg gagtgaaaac ttcaccgagc tgccgcggat ggttgtgcct gagtttaagt   2160
ggagcactaa acaccagtat cgcaacgtgt ccctgccagt ggcgcatagc gatgcgcggc   2220
agaacccctt tgatttttaa acccagcttt cttgtacaaa gtgggcccct ctccctcccc   2280
ccccccctaac gttactggcc gaagccgctt ggaataaggc cggtgtgcgt ttgtctatat   2340
gttattttcc accatattgc cgtcttttgg caatgtgagg gcccggaaac ctggccctgt   2400
cttcttgacg agcattccta ggggtctttc ccctctcgcc aaaggaatgc aaggtctgtt   2460
gaatgtcgtg aaggaagcag ttcctctgga agcttcttga agacaaacaa cgtctgtagc   2520
gaccctttgc aggcagcgga accccccacc tggcgacagg tgcctctgcg gccaaaagcc   2580
acgtgtataa gatacacctg caaaggcggc acaaccccag tgccacgttg tgagttggat   2640
agttgtggaa agagtcaaat ggctctcctc aagcgtattc aacaaggggc tgaaggatgc   2700
ccagaaggta ccccattgta tgggatctga tctggggcct cggtgcacat gctttacatg   2760
tgtttagtcg aggttaaaaa aacgtctagg ccccccgaac cacggggacg tggttttcct   2820
ttgaaaaaca cgatgataat atggccacaa ccatgactac gtccggcgtt ccatttggca   2880
tgacactacg accaacacga tctcggttgt ctcggcgcac tccgtacagt agggatcgcc   2940
tacctccttt tgagacagag acccgcgcta ccatactgga ggatcatccg ctgctgcccg   3000
```

-continued aatgtaacac tttgacaatg cacaacgtga gttacgtgcg aggtcttccc tgcagtgtgg 3060
gatttacgct gattcaggaa tgggttgttc cctgggatat ggttctgacg cgggaggagc 3120
ttgtaatcct gaggaagtgt atgcacgtgt gcctgtgttg tgccaacatt gatatcatga 3180
cgagcatgat gatccatggt tacgagtcct gggctctcca ctgtcattgt tccagtcccg 3240
gttccctgca gtgcatagcc ggcgggcagg ttttggccag ctggtttagg atggtggtgg 3300
atggcgccat gtttaatcag aggtttatat ggtaccggga ggtggtgaat tacaacatgc 3360
caaaagaggt aatgtttatg tccagcgtgt ttatgagggg tcgccactta atctacctgc 3420
gcttgtggta tgatggccac gtgggttctg tggtccccgc catgagcttt ggatacagcg 3480
ccttgcactg tgggattttg aacaatattg tggtgctgtg ctgcagttac tgtgctgatt 3540
taagtgagat cagggtgcgc tgctgtgccc ggaggacaag gcgtctcatg ctgcgggcgg 3600
tgcgaatcat cgctgaggag accactgcca tgttgtattc ctgcaggacg gagcggcggc 3660
ggcagcagtt tattcgcgcg ctgctgcagc accaccgccc tatcctgatg cacgattatg 3720
actctacccc catgtagcaa ctttattata catagttgat ggccggccgc ttcgagcaga 3780
catgataaga tacattgatg agtttggaca aaccacaact agaatgcagt gaaaaaaatg 3840
ctttatttgt gaaatttgtg atgctattgc tttatttgta accattataa gctgcaataa 3900
acaagttaac aacaacaatt gcattcattt tatgtttcag gttcaggggg aggtgtggga 3960
ggttttttaa agcaagtaaa acctctacaa atgtggtagc ggccgcggcg ctcttccgct 4020
tcctcgctca ctgactcgct gcgctcggtc gttcggctgc ggcgagcggt atcagctcac 4080
tcaaaggcgg taatacggtt atccacagaa tcaggggata acgcaggaaa gaacatgtga 4140
gcaaaaggcc agcaaaaggc caggaaccgt aaaaaggccg cgttgctggc gtttttccat 4200
aggctccgcc cccctgacga gcatcacaaa aatcgacgct caagtcagag gtggcgaaac 4260
ccgacaggac tataaagata ccaggcgttt ccccctggaa gctccctcgt gcgctctcct 4320
gttccgaccc tgccgcttac cggatacctg tccgcctttc tcccttcggg aagcgtggcg 4380
ctttctcata gctcacgctg taggtatctc agttcggtgt aggtcgttcg ctccaagctg 4440
ggctgtgtgc acgaaccccc cgttcagccc gaccgctgcg ccttatccgg taactatcgt 4500
cttgagtcca acccggtaag acacgactta tcgccactgg cagcagccac tggtaacagg 4560
attagcagag cgaggtatgt aggcggtgct acagagttct tgaagtggtg gcctaactac 4620
ggctacacta gaagaacagt atttggtatc tgcgctctgc tgaagccagt taccttcgga 4680
aaaagagttg gtagctcttg atccggcaaa caaaccaccg ctggtagcgg tggttttttt 4740
gtttgcaagc agcagattac gcgcagaaaa aaaggatctc aagaagatcc tttgatcttt 4800
tctacggggt ctgacgctca gtggaacgaa aactcacgtt aagggatttt ggtcatgaga 4860
ttatcaaaaa ggatcttcac ctagatcctt ttaaattaaa aatgaagttt taaatcaatc 4920
taaagtatat atgagtaaac ttggtctgac agttaccaat gcttaatcag tgaggcacct 4980
atctcagcga tctgtctatt tcgttcatcc atagttgcct gactccccgt cgtgtagata 5040
actacgatac gggagggctt accatctggc cccagtgctg caatgatacc gcgagaccca 5100
cgctcaccgg ctccagattt atcagcaata aaccagccag ccggaagggc cgagcgcaga 5160
agtggtcctg caactttatc cgcctccatc cagtctatta attgttgccg ggaagctaga 5220
gtaagtagtt cgccagttaa tagtttgcgc aacgttgttg ccattgctac aggcatcgtg 5280
gtgtcacgct cgtcgtttgg tatggcttca ttcagctccg gttcccaacg atcaaggcga 5340
gttacatgat cccccatgtt gtgcaaaaaa gcggttagct ccttcggtcc tccgatcgtt 5400

```
gtcagaagta agttggccgc agtgttatca ctcatggtta tggcagcact gcataattct   5460

cttactgtca tgccatccgt aagatgcttt tctgtgactg gtgagtactc aaccaagtca   5520

ttctgagaat agtgtatgcg gcgaccgagt tgctcttgcc cggcgtcaat acgggataat   5580

accgcgccac atagcagaac tttaaaagtg ctcatcattg gaaaacgttc ttcggggcga   5640

aaactctcaa ggatcttacc gctgttgaga tccagttcga tgtaacccac tcgtgcaccc   5700

aactgatctt cagcatcttt tactttcacc agcgtttctg ggtgagcaaa aacaggaagg   5760

caaaatgccg caaaaaaggg aataagggcg acacggaaat gttgaatact catactcttc   5820

ctttttcaat attattgaag catttatcag ggttattgtc tcatgagcgg atacatattt   5880

gaatgtattt agaaaaataa acaaataggg gttccgcgca catttccccg aaaagtgcca   5940

cctgacgtct aagaaaccat tattatcatg acattaacct ataaaaatag gcgtatcacg   6000

aggccctttc gtcggcgcgc ctcgatgtag gatgttgccc ctcctgacgc ggtaggagaa   6060

ggggagggtg ccctgcatgt ctgccgctgc tcttgctctt gccgctgctg aggagggggg   6120

cgcatctgcc gcagcaccgg atgcatctgg gaaaagcaaa aaaggggctc gtccctgttt   6180

ccggaggaat ttgcaagcgg ggtcttgcat gacggggagg caaacccccg ttcgccgcag   6240

tccggccggc ccgagactcg aaccgggggt cctgcgactc aacccttgga aaataaccct   6300

ccggctacag ggagcgagcc acttaatgct ttcgctttcc agcctaaccg cttacgccgc   6360

gcgcggccag tggccaaaaa agctagcgca gcagccgccg cgcctggaag gaagccaaaa   6420

ggagcgctcc cccgttgtct gacgtcgcac acctgggttc gacacgcggg cggtaaccgc   6480

atggatcacg gcggacggcc ggatccgggg ttcgaacccc ggtcgtccgc catgataccc   6540

ttgcgaattt atccaccaga ccacggaaga gtgcccgctt acaggctctc cttttgcacg   6600

gtctagagcg tcaacgactg cgcacgcctc accggccaga gcgtcccgac catggagcac   6660

tttttgccgc tgcgcaacat ctggaaccgc gtccgcgact ttccgcgcgc ctccaccacc   6720

gccgccggca tcacctggat gtccaggtac atctacggat tacgggcgcg              6770
```

```
<210> SEQ ID NO 26
<211> LENGTH: 6770
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 26
```

```
ccgcggccgc caactttgta tagaaaagtt gtagttatta atagtaatca attacggggt     60

cattagttca tagcccatat atggagttcc gcgttacata acttacggta aatggcccgc    120

ctggctgacc gcccaacgac ccccgcccat tgacgtcaat aatgacgtat gttcccatag    180

taacgccaat agggactttc cattgacgtc aatgggtgga gtatttacgg taaactgccc    240

acttggcagt acatcaagtg tatcatatgc caagtacgcc ccctattgac gtcaatgacg    300

gtaaatggcc cgcctggcat tatgcccagt acatgacctt atgggacttt cctacttggc    360

agtacatcta cgtattagtc atcgctatta ccatggtgat gcggttttgg cagtacatca    420

atgggcgtgg atagcggttt gactcacggg gatttccaag tctccacccc attgacgtca    480

atgggagttt gttttggcac caaaatcaac gggactttcc aaaatgtcgt aacaactccg    540

ccccattgac gcaaatgggc ggtaggcgtg tacggtggga ggtctatata agcagagctg    600
```

```
gtttagtgaa ccgtcagatc caagtttgta caaaaaagca ggctgccacc atgactacgt    660
ccggcgttcc atttggcatg acactacgac caacacgatc tcggttgtct cggcgcactc    720
cgtacagtag ggatcgccta cctccttttg agacagagac ccgcgctacc atactggagg    780
atcatccgct gctgcccgaa tgtaacactt tgacaatgca caacgtgagt tacgtgcgag    840
gtcttccctg cagtgtggga tttacgctga ttcaggaatg ggttgttccc tgggatatgg    900
ttctgacgcg ggaggagctt gtaatcctga ggaagtgtat gcacgtgtgc ctgtgttgtg    960
ccaacattga tatcatgacg agcatgatga tccatggtta cgagtcctgg gctctccact   1020
gtcattgttc cagtcccggt tccctgcagt gcatagccgg cgggcaggtt ttggccagct   1080
ggtttaggat ggtggtggat ggcgccatgt ttaatcagag gtttatatgg taccgggagg   1140
tggtgaatta caacatgcca aaagaggtaa tgtttatgtc cagcgtgttt atgaggggtc   1200
gccacttaat ctacctgcgc ttgtggtatg atggccacgt gggttctgtg gtccccgcca   1260
tgagctttgg atacagcgcc ttgcactgtg ggattttgaa caatattgtg gtgctgtgct   1320
gcagttactg tgctgattta agtgagatca gggtgcgctg ctgtgcccgg aggacaaggc   1380
gtctcatgct gcgggcggtg cgaatcatcg ctgaggagac cactgccatg ttgtattcct   1440
gcaggacgga gcggcggcgg cagcagttta ttcgcgcgct gctgcagcac caccgcccta   1500
tcctgatgca cgattatgac tctaccccca tgtagaccca gctttcttgt acaaagtggg   1560
cccctctccc tccccccccc ctaacgttac tggccgaagc cgcttggaat aaggccggtg   1620
tgcgtttgtc tatatgttat tttccaccat attgccgtct tttggcaatg tgagggcccg   1680
gaaacctggc cctgtcttct tgacgagcat tcctaggggt ctttcccctc tcgccaaagg   1740
aatgcaaggt ctgttgaatg tcgtgaagga agcagttcct ctggaagctt cttgaagaca   1800
aacaacgtct gtagcgaccc tttgcaggca gcggaacccc ccacctggcg acaggtgcct   1860
ctgcggccaa aagccacgtg tataagatac acctgcaaag gcggcacaac cccagtgcca   1920
cgttgtgagt tggatagttg tggaaagagt caaatggctc tcctcaagcg tattcaacaa   1980
ggggctgaag gatgcccaga aggtacccca ttgtatggga tctgatctgg ggcctcggtg   2040
cacatgcttt acatgtgttt agtcgaggtt aaaaaaacgt ctaggccccc cgaaccacgg   2100
ggacgtggtt ttcctttgaa aaacacgatg ataatatggc cacaaccatg gccagtcggg   2160
aagaggagca gcgcgaaacc acccccgagc gcggacgcgg tgcggcgcga cgtccaccaa   2220
ccatggagga cgtgtcgtcc ccgtcgccgt cgccgccgcc tccccgcgcg cccccaaaaa   2280
agcggctgag gcggcgtctc gagtccgagg acgaagaaga ctcgtcacaa gatgcgctgg   2340
tgccgcgcac acccagcccg cggccatcga cctcgacggc ggatttggcc attgcgtcca   2400
aaaagaaaaa gaagcgcccc tctcccaagc ccgagcgccc gccatcccca gaggtgatcg   2460
tggacagcga ggaagaaaga gaagatgtgg cgctacaaat ggtgggtttc agcaacccac   2520
cggtgctaat caagcacggc aagggaggta agcgcacggt gcggcggctg aatgaagacg   2580
acccagtggc gcggggtatg cggacgcaag aggaaaagga agagtccagt gaagcggaaa   2640
gtgaaagcac ggtgataaac ccgctgagcc tgccgatcgt gtctgcgtgg gagaagggca   2700
tggaggctgc gcgcgcgttg atggacaagt accacgtgga taacgatcta aaggcaaact   2760
tcaagctact gcctgaccaa gtggaagctc tggcggccgt atgcaagacc tggctaaacg   2820
aggagcaccg cgggttgcag ctgaccttca ccagcaacaa gacctttgtg acgatgatgg   2880
ggcgattcct gcaggcgtac ctgcagtcgt ttgcagaggt aacctacaag caccacgagc   2940
ccacgggctg cgcgttgtgg ctgcaccgct gcgctgagat cgaaggcgag cttaagtgtc   3000
```

-continued

```
tacacgggag cattatgata aataaggagc acgtgattga aatggatgtg acgagcgaaa   3060
acgggcagcg cgcgctgaag gagcagtcta gcaaggccaa gatcgtgaag aaccggtggg   3120
gccgaaatgt ggtgcagatc tccaacaccg acgcaaggtg ctgcgtgcat gacgcggcct   3180
gtccggccaa tcagttttcc ggcaagtctt gcggcatgtt cttctctgaa ggcgcaaagg   3240
ctcaggtggc ttttaagcag atcaaggctt tcatgcaggc gctgtatcct aacgcccaga   3300
ccgggcacgg tcaccttctg atgccactac ggtgcgagtg caactcaaag cctgggcatg   3360
cacccttttt gggaaggcag ctaccaaagt tgactccgtt cgccctgagc aacgcggagg   3420
acctggacgc ggatctgatc tccgacaaga gcgtgctggc cagcgtgcac cacccggcgc   3480
tgatagtgtt ccagtgctgc aaccctgtgt atcgcaactc gcgcgcgcag ggcggaggcc   3540
ccaactgcga cttcaagata tcggcgcccg acctgctaaa cgcgttggtg atggtgcgca   3600
gcctgtggag tgaaaacttc accgagctgc cgcggatggt tgtgcctgag tttaagtgga   3660
gcactaaaca ccagtatcgc aacgtgtccc tgccagtggc gcatagcgat gcgcggcaga   3720
acccctttga tttttaacaa ctttattata catagttgat ggccggccgc ttcgagcaga   3780
catgataaga tacattgatg agtttggaca aaccacaact agaatgcagt gaaaaaaatg   3840
ctttatttgt gaaatttgtg atgctattgc tttatttgta accattataa gctgcaataa   3900
acaagttaac aacaacaatt gcattcattt tatgtttcag gttcaggggg aggtgtggga   3960
ggtttttttaa agcaagtaaa acctctacaa atgtggtagc ggccgcggcg ctcttccgct   4020
tcctcgctca ctgactcgct gcgctcggtc gttcggctgc ggcgagcggt atcagctcac   4080
tcaaaggcgg taatacggtt atccacagaa tcaggggata acgcaggaaa gaacatgtga   4140
gcaaaaggcc agcaaaaggc caggaaccgt aaaaaggccg cgttgctggc gtttttccat   4200
aggctccgcc cccctgacga gcatcacaaa aatcgacgct caagtcagag gtggcgaaac   4260
ccgacaggac tataaagata ccaggcgttt ccccctggaa gctccctcgt gcgctctcct   4320
gttccgaccc tgccgcttac cggatacctg tccgcctttc tcccttcggg aagcgtggcg   4380
ctttctcata gctcacgctg taggtatctc agttcggtgt aggtcgttcg ctccaagctg   4440
ggctgtgtgc acgaaccccc cgttcagccc gaccgctgcg ccttatccgg taactatcgt   4500
cttgagtcca acccggtaag acacgactta tcgccactgg cagcagccac tggtaacagg   4560
attagcagag cgaggtatgt aggcggtgct acagagttct tgaagtggtg gcctaactac   4620
ggctacacta gaagaacagt atttggtatc tgcgctctgc tgaagccagt taccttcgga   4680
aaaagagttg gtagctcttg atccggcaaa caaaccaccg ctggtagcgg tggttttttt   4740
gtttgcaagc agcagattac gcgcagaaaa aaaggatctc aagaagatcc tttgatcttt   4800
tctacggggt ctgacgctca gtggaacgaa aactcacgtt aagggatttt ggtcatgaga   4860
ttatcaaaaa ggatcttcac ctagatcctt ttaaattaaa aatgaagttt taaatcaatc   4920
taaagtatat atgagtaaac ttggtctgac agttaccaat gcttaatcag tgaggcacct   4980
atctcagcga tctgtctatt tcgttcatcc atagttgcct gactccccgt cgtgtagata   5040
actacgatac gggagggctt accatctggc cccagtgctg caatgatacc gcgagaccca   5100
cgctcaccgg ctccagattt atcagcaata aaccagccag ccggaagggc cgagcgcaga   5160
agtggtcctg caactttatc cgcctccatc cagtctatta attgttgccg ggaagctaga   5220
gtaagtagtt cgccagttaa tagtttgcgc aacgttgttg ccattgctac aggcatcgtg   5280
gtgtcacgct cgtcgtttgg tatggcttca ttcagctccg gttcccaacg atcaaggcga   5340
```

gttacatgat cccccatgtt gtgcaaaaaa gcggttagct ccttcggtcc tccgatcgtt 5400
gtcagaagta agttggccgc agtgttatca ctcatggtta tggcagcact gcataattct 5460
cttactgtca tgccatccgt aagatgcttt tctgtgactg gtgagtactc aaccaagtca 5520
ttctgagaat agtgtatgcg gcgaccgagt tgctcttgcc cggcgtcaat acgggataat 5580
accgcgccac atagcagaac tttaaaagtg ctcatcattg gaaaacgttc ttcggggcga 5640
aaactctcaa ggatcttacc gctgttgaga tccagttcga tgtaacccac tcgtgcaccc 5700
aactgatctt cagcatcttt tactttcacc agcgtttctg ggtgagcaaa aacaggaagg 5760
caaaatgccg caaaaaaggg aataagggcg acacggaaat gttgaatact catactcttc 5820
ctttttcaat attattgaag catttatcag ggttattgtc tcatgagcgg atacatattt 5880
gaatgtattt agaaaaataa acaaataggg gttccgcgca catttccccg aaaagtgcca 5940
cctgacgtct aagaaaccat tattatcatg acattaacct ataaaaatag gcgtatcacg 6000
aggccctttc gtcggcgcgc ctcgatgtag gatgttgccc ctcctgacgc ggtaggagaa 6060
ggggagggtg ccctgcatgt ctgccgctgc tcttgctctt gccgctgctg aggagggggg 6120
cgcatctgcc gcagcaccgg atgcatctgg gaaaagcaaa aaaggggctc gtccctgttt 6180
ccggaggaat ttgcaagcgg ggtcttgcat gacggggagg caaacccccg ttcgccgcag 6240
tccggccggc ccgagactcg aaccgggggt cctgcgactc aacccttgga aaataaccct 6300
ccggctacag ggagcgagcc acttaatgct ttcgctttcc agcctaaccg cttacgccgc 6360
gcgcggccag tggccaaaaa agctagcgca gcagccgccg cgcctggaag gaagccaaaa 6420
ggagcgctcc cccgttgtct gacgtcgcac acctgggttc gacacgcggg cggtaaccgc 6480
atggatcacg gcggacggcc ggatccgggg ttcgaacccc ggtcgtccgc catgataccc 6540
ttgcgaattt atccaccaga ccacggaaga gtgcccgctt acaggctctc cttttgcacg 6600
gtctagagcg tcaacgactg cgcacgcctc accggccaga gcgtcccgac catggagcac 6660
tttttgccgc tgcgcaacat ctggaaccgc gtccgcgact ttccgcgcgc ctccaccacc 6720
gccgccggca tcacctggat gtccaggtac atctacggat tacgggcgcg 6770

<210> SEQ ID NO 27
<211> LENGTH: 14227
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 27
tggtatggct ttttccccgt atccccccag gtgtctgcag gctcaaagag cagcgagaag 60
cgttcagagg aaagcgatcc cgtgccacct tccccgtgcc cgggctgtcc ccgcacgctg 120
ccggctcggg gatgcggggg gagcgccgga ccggagcgga gccccgggcg gctcgctgct 180
gccccctagc gggggaggga cgtaattaca tccctggggg ctttgggggg gggctgtccc 240
tgatatctat aacaagaaaa tatatatata ataagttatc acgtaagtag aacatgaaat 300
aacaatataa ttatcgtatg agttaaatct taaaagtcac gtaaaagata atcatgcgtc 360
attttgactc acgcggtcgt tatagttcaa aatcagtgac acttaccgca ttgacaagca 420
cgcctcacgg gagctccaag cggcgactga gatgtcctaa atgcacagcg acggattcgc 480
gctatttaga aagagagagc aatatttcaa gaatgcatgc gtcaatttta cgcagactat 540
ctttctaggg ttaatctagc tgcatcagga tcatatcgtc gggtcttttt tccggctcag 600

-continued tcatcgccca agctggcgct atctgggcat cggggaggaa gaagcccgtg ccttttcccg 660
cgaggttgaa gcggcatgga aagagtttgc cgaggatgac tgctgctgca ttgacgttga 720
gcgaaaacgc acgtttacca tgatgattcg ggaaggtgtg gccatgcacg cctttaacgg 780
tgaactgttc gttcaggcca cctgggatac cagttcgtcg cggcttttcc ggacacagtt 840
ccggatggtc agcccgaagc gcatcagcaa cccgaacaat accggcgaca gccggaactg 900
ccgtgccggt gtgcagatta atgacagcgg tgcggcgctg ggatattacg tcagcgagga 960
cgggtatcct ggctggatgc cgcagaaatg gacatggata ccccgtgagt tacccggcgg 1020
gcgcgcttgg cgtaatcatg gtcatagctg tttcctgtgt gaaattgtta tccgctcaca 1080
attccacaca acatacgagc cggaagcata aagtgtaaag cctggggtgc ctaatgagtg 1140
agctaactca cattaattgc gttgcgctca ctgcccgctt tccagtcggg aaacctgtcg 1200
tgccagctgc attaatgaat cggccaacgc gcggggagag gcggtttgcg tattgggcgc 1260
tcttccgctt cctcgctcac tgactcgctg cgctcggtcg ttcggctgcg gcgagcggta 1320
tcagctcact caaaggcggt aatacggtta tccacagaat caggggataa cgcaggaaag 1380
aacatgtgag caaaaggcca gcaaaaggcc aggaaccgta aaaaggccgc gttgctggcg 1440
tttttccata ggctccgccc ccctgacgag catcacaaaa atcgacgctc aagtcagagg 1500
tggcgaaacc cgacaggact ataaagatac caggcgtttc cccctggaag ctccctcgtg 1560
cgctctcctg ttccgaccct gccgcttacc ggatacctgt ccgcctttct cccttcggga 1620
agcgtggcgc tttctcatag ctcacgctgt aggtatctca gttcggtgta ggtcgttcgc 1680
tccaagctgg gctgtgtgca cgaacccccc gttcagcccg accgctgcgc cttatccggt 1740
aactatcgtc ttgagtccaa cccggtaaga cacgacttat cgccactggc agcagccact 1800
ggtaacagga ttagcagagc gaggtatgta ggcggtgcta cagagttctt gaagtggtgg 1860
cctaactacg gctacactag aaggacagta tttggtatct gcgctctgct gaagccagtt 1920
accttcggaa aaagagttgg tagctcttga tccggcaaac aaaccaccgc tggtagcggt 1980
ggtttttttg tttgcaagca gcagattacg cgcagaaaaa aaggatctca agaagatcct 2040
ttgatctttt ctacggggtc tgacgctcag tggaacgaaa actcacgtta agggattttg 2100
gtcatgagat tatcaaaaag gatcttcacc tagatccttt taaattaaaa atgaagtttt 2160
aaatcaatct aaagtatata tgagtaaact tggtctgaca gttaccaatg cttaatcagt 2220
gaggcaccta tctcagcgat ctgtctattt cgttcatcca tagttgcctg actccccgtc 2280
gtgtagataa ctacgatacg ggagggctta ccatctggcc ccagtgctgc aatgataccg 2340
cgagacccac gctcaccggc tccagattta tcagcaataa accagccagc cggaagggcc 2400
gagcgcagaa gtggtcctgc aactttatcc gcctccatcc agtctattaa ttgttgccgg 2460
gaagctagag taagtagttc gccagttaat agtttgcgca acgttgttgc cattgctaca 2520
ggcatcgtgg tgtcacgctc gtcgtttggt atggcttcat tcagctccgg ttcccaacga 2580
tcaaggcgag ttacatgatc ccccatgttg tgcaaaaaag cggttagctc cttcggtcct 2640
ccgatcgttg tcagaagtaa gttggccgca gtgttatcac tcatggttat ggcagcactg 2700
cataattctc ttactgtcat gccatccgta agatgctttt ctgtgactgg tgagtactca 2760
accaagtcat tctgagaata gtgtatgcgg cgaccgagtt gctcttgccc ggcgtcaata 2820
cgggataata ccgcgccaca tagcagaact ttaaaagtgc tcatcattgg aaaacgttct 2880
tcggggcgaa aactctcaag gatcttaccg ctgttgagat ccagttcgat gtaacccact 2940

-continued

```
cgtgcaccca actgatcttc agcatctttt actttcacca gcgtttctgg gtgagcaaaa   3000
acaggaaggc aaaatgccgc aaaaaaggga ataagggcga cacggaaatg ttgaatactc   3060
atactcttcc tttttcaata ttattgaagc atttatcagg gttattgtct catgagcgga   3120
tacatatttg aatgtattta gaaaaataaa caaatagggg ttccgcgcac atttccccga   3180
aaagtgccac ctaaattgta agcgttaata ttttgttaaa attcgcgtta aatttttgtt   3240
aaatcagctc attttttaac caataggccg aaatcggcaa aatcccttat aaatcaaaag   3300
aatagaccga gatagggttg agtgttgttc cagtttggaa caagagtcca ctattaaaga   3360
acgtggactc caacgtcaaa gggcgaaaaa ccgtctatca gggcgatggc ccactacgtg   3420
aaccatcacc ctaatcaagt tttttggggt cgaggtgccg taaagcacta aatcggaacc   3480
ctaaagggag cccccgattt agagcttgac ggggaaagcc ggcgaacgtg gcgagaaagg   3540
aagggaagaa agcgaaagga gcgggcgcta gggcgctggc aagtgtagcg gtcacgctgc   3600
gcgtaaccac cacacccgcc gcgcttaatg cgccgctaca gggcgcgtcc cattcgccat   3660
tcaggctgcg caactgttgg gaagggcgat cggtgcgggc ctcttcgcta ttacgccagc   3720
tggcgaaagg gggatgtgct gcaaggcgat taagttgggt aacgccaggg ttttcccagt   3780
cacgacgttg taaaacgacg gccagtgagc gcgcctcgtt cattcacgtt tttgaacccg   3840
tggaggacgg gcagactcgc ggtgcaaatg tgttttacag cgtgatggag cagatgaaga   3900
tgctcgacac gctgcagaac acgcagctag attaacccta gaaagataat catattgtga   3960
cgtacgttaa agataatcat gtgtaaaatt gacgcatgtg ttttatcggt ctgtatatcg   4020
aggtttattt attaatttga atagatatta agttttatta tatttacact tacatactaa   4080
taataaattc aacaaacaat ttatttatgt ttatttattt attaaaaaaa acaaaaactc   4140
aaaatttctt ctataaagta acaaaacttt tatgagggac agcccccccc caaagccccc   4200
agggatgtaa ttacgtccct cccccgctag ggggcagcag cgagccgccc ggggctccgc   4260
tccggtccgg cgctcccccc gcatccccga gccggcagcg tgcggggaca gcccgggcac   4320
ggggaaggtg gcacgggatc gctttcctct gaacgcttct cgctgctctt tgagcctgca   4380
gacacctggg gggatacggg gaaaaggcct ccacggccac tagtccatag agcccaccgc   4440
atccccagca tgcctgctat tgtcttccca atcctccccc ttgctgtcct gccccacccc   4500
accccctaga atagaatgac acctactcag acaatgcgat gcaatttcct cattttatta   4560
ggaaaggaca gtgggagtgg caccttccag ggtcaaggaa ggcacggggg aggggcaaac   4620
aacagatggc tggcaactag aaggcacagc tacatggggg tagagtcata atcgtgcatc   4680
aggatagggc ggtggtgctg cagcagcgcg cgaataaact gctgccgccg ccgctccgtc   4740
ctgcaggaat acaacatggc agtggtctcc tcagcgatga ttcgcaccgc ccgcagcatg   4800
agacgccttg tcctccgggc acagcagcgc accctgatct cacttaaatc agcacagtaa   4860
ctgcagcaca gcaccacaat attgttcaaa atcccacagt gcaaggcgct gtatccaaag   4920
ctcatggcgg ggaccacaga acccacgtgg ccatcatacc acaagcgcag gtagattaag   4980
tggcgacccc tcataaacac gctggacata aacattacct cttttggcat gttgtaattc   5040
accacctccc ggtaccatat aaacctctga ttaaacatgg cgccatccac caccatccta   5100
aaccagctgg ccaaaacctg cccgccggct atgcactgca gggaaccggg actggaacaa   5160
tgacagtgga gagcccagga ctcgtaacca tggatcatca tgctcgtcat gatatcaatg   5220
ttggcacaac acaggcacac gtgcatacac ttcctcagga ttacaagctc ctcccgcgtc   5280
agaaccatat cccagggaac aacccattcc tgaatcagcg taaatcccac actgcaggga   5340
```

```
agacctcgca cgtaactcac gttgtgcatt gtcaaagtgt tacattcggg cagcagcgga   5400
tgatcctcca gtatggtagc gcgggtctct gtctcaaaag gaggtaggcg atccctactg   5460
tacggagtgc gccgagacaa ccgagatcgt gttggtcgta gtgtcatgcc aaatggaacg   5520
ccggacgtag tcatggttgt ggccatatta tcatcgtgtt tttcaaagga aaaccacgtc   5580
cccgtggttc ggggggccta gacgtttttt taacctcgac taaacacatg taaagcatgt   5640
gcaccgaggc cccagatcag atcccataca atggggtacc ttctgggcat ccttcagccc   5700
cttgttgaat acgcttgagg agagccattt gactctttcc acaactatcc aactcacaac   5760
gtggcactgg ggttgtgccg cctttgcagg tgtatcttat acacgtggct tttggccgca   5820
gaggcacctg tcgccaggtg gggggttccg ctgcctgcaa agggtcgcta cagacgttgt   5880
ttgtcttcaa gaagcttcca gaggaactgc ttccttcacg acattcaaca gaccttgcat   5940
tcctttggcg agaggggaaa gacccctagg aatgctcgtc aagaagacag ggccaggttt   6000
ccgggccctc acattgccaa aagacggcaa tatggtggaa aataacatat agacaaacgc   6060
acaccggcct tattccaagc ggcttcggcc agtaacgtta gggggggggg agggagaggg   6120
gcttaaaaat caaaggggtt ctgccgcgca tcactatgcg ccactggcag ggacacgttg   6180
cgatactggt gtttagtgct ccacttaaac tcaggcacaa ccatccgcgg cagctcggtg   6240
aagttttcac tccacaggct gcgcaccatc accaacgcgt ttagcaggtc gggcgccgat   6300
atcttgaagt cgcagttggg gcctccgccc tgcgcgcgcg agttgcgata cacagggttg   6360
cagcactgga acactatcag cgccgggtgg tgcacgctgg ccagcacgct cttgtcggag   6420
atcagatccg cgtccaggtc ctccgcgttg ctcagggcga acggagtcaa ctttggtagc   6480
tgccttccca aaaagggtgc atgcccaggc tttgagttgc actcgcaccg tagtggcatc   6540
agaaggtgac cgtgcccggt ctgggcgtta ggatacagcg cctgcatgaa agccttgatc   6600
tgcttaaaag ccacctgagc ctttgcgcct tcagagaaga acatgccgca agacttgccg   6660
gaaaactgat tggccggaca ggccgcgtca tgcacgcagc accttgcgtc ggtgttggag   6720
atctgcacca catttcggcc ccaccggttc ttcacgatct tggccttgct agactgctcc   6780
ttcagcgcgc gctgcccgtt ttcgctcgtc acatccattt caatcacgtg ctccttattt   6840
atcataatgc tcccgtgtag acacttaagc tcgccttcga tctcagcgca gcggtgcagc   6900
cacaacgcgc agcccgtggg ctcgtggtgc ttgtaggtta cctctgcaaa cgactgcagg   6960
tacgcctgca ggaatcgccc catcatcgtc acaaaggtct tgttgctggt gaaggtcagc   7020
tgcaacccgc ggtgctcctc gtttagccag gtcttgcata cggccgccag agcttccact   7080
tggtcaggca gtagcttgaa gtttgccttt agatcgttat ccacgtggta cttgtccatc   7140
aacgcgcgcg cagcctccat gcccttctcc cacgcagaca cgatcggcag gctcagcggg   7200
tttatcaccg tgctttcact ttccgcttca ctggactctt ccttttcctc ttgcgtccgc   7260
ataccccgcg ccactgggtc gtcttcattc agccgccgca ccgtgcgctt acctcccttg   7320
ccgtgcttga ttagcaccgg tgggttgctg aaacccacca tttgtagcgc cacatcttct   7380
ctttcttcct cgctgtccac gatcacctct ggggatggcg ggcgctcggg cttgggagag   7440
gggcgcttct ttttcttttt ggacgcaatg gccaaatccg ccgtcgaggt cgatggccgc   7500
gggctgggtg tgcgcggcac cagcgcatct tgtgacgagt cttcttcgtc ctcggactcg   7560
agacgccgcc tcagccgctt ttttgggggc gcgcgcttgt cgtcatcgtc tttgtagtcg   7620
ggaggcggcg gcgacggcga cggggacgac acgtcctcca tggttggtgg acgtcgcgcc   7680
```

-continued

```
gcaccgcgtc cgcgctcggg ggtggtttcg cgctgctcct cttcccgact ggccatggtg   7740
gccgaggata acttcgtata tggtttctta tacgaagtta tgatccagac atgataagat   7800
acattgatga gtttggacaa accacaacta gaatgcagtg aaaaaaatgc tttatttgtg   7860
aaatttgtga tgctattgct ttatttgtaa ccattataag ctgcaataaa caagttaaca   7920
acaacaattg cattcatttt atgtttcagg ttcaggggga ggtgtgggag gtttttttaaa   7980
gcaagtaaaa cctctacaaa tgtggtatgg ctgattatga tcctctagag tcgcagatct   8040
gctacgtatc aagctgtggc agggaaaccc tctgcctccc ccgtgatgta atacttttgc   8100
aaggaatgcg atgaagtaga gcccgcagtg gccaagtggc tttggtccgt ctcctccacg   8160
gatgcccctc cacggctagt gggcgcatgt aggcggtggg cgtccgccgc ctccagcagc   8220
aggtcataga ggggcaccac gttcttgcac ttcatgctgt acagatgctc catgcctttg   8280
ttactcatgt gtcggatgtg ggagaggatg aggaggagct gggccagccg ctggtgctgc   8340
tgctgcaggg tcaggcctgc cttggccatc aggtggatca aagtgtctgt gatcttgtcc   8400
aggactcggt ggatatggtc cttctcttcc agagacttca gggtgctgga cagaaatgtg   8460
tacactccag aattaagcaa aataatagat ttgaggcaca caaactcctc tccctgcaga   8520
ttcatcatgc ggaaccgaga tgatgtagcc agcagcatgt cgaagatctc caccatgccc   8580
tctacacatt ttccctggtt cctgtccaag agcaagttag gagcaaacag tagcttcact   8640
gggtgctcca tggagcgcca gacgagacca atcatcagga tctctagcca ggcacattct   8700
agaaggtgga cctgatcatg gagggtcaaa tccacaaagc ctggcaccct cttcgcccag   8760
ttgatcatgt gaaccagctc cctgtctgcc aggttggtca gtaagcccat catcgaagct   8820
tcactgaagg gtctggtagg atcatactcg gaatagagta tgggggctc agcatccaac   8880
aaggcactga ccatctggtc ggccgtcagg gacaaggcca ggctgttctt cttagagcgt   8940
ttgatcatga gcgggcttgg ccaaaggttg gcagctctca tgtctccagc agatggctcg   9000
agatcgccat cttccagcag gcgcaccatt gcccctgttt cactatccag gttacggata   9060
tagttcatga caatatttac attggtccag ccaccagctt gcatgatctc cggtattgaa   9120
actccagcgc gggccatatc tcgcgcggct ccgacacggg cactgtgtcc agaccaggcc   9180
aggtatctct gaccagagtc atcctaaaat acacaaacaa ttagaatcag tagtttaaca   9240
cattatacac ttaaaaattt tatatttacc ttagcgccgt aaatcaatcg atgagttgct   9300
tcaaaaatcc cttccagggc gcgagttgat agctggctgg tggcagatgg cgcggcaaca   9360
ccatttttc tgacccggca aaacaggtag ttattcggat catcagctac accagagacg   9420
gaaatccatc gctcgaccag tttagtgact cccaggctaa gtgccttctc tacacctgcg   9480
gtgctaacca gcgttttcgt tctgccaata tggattaaca ttctcccacc gtcagtacgt   9540
gagatatctt taaccctgat cctggcaatt tcggctatac gtaacagggt gttataagca   9600
atccccagaa atgccagatt acgtatatcc tggcagcgat cgctattttc catgagtgaa   9660
cggacttggt cgaaatcagt gcgttcgaac gctagagcct gttttgcacg ttcaccggca   9720
tcaacgtttt cttttcggat ccgccgcata accagtgaaa cagcattgct gtcacttggt   9780
cgtggcagcc cggaccgacg atgaagcatg tttagctggc ccaaatgttg ctggatagtt   9840
tttactgcca gaccgcgcgc ttgaagatat agaagataat cgcgaacatc ttcaggttct   9900
gcgggaaacc atttccggtt attcaacttg caccatgccg cccacgaccg gcaaacggac   9960
agaagcattt tccaggtatg ctcagaaaac gcctggcgat ccctgaacat gtccatcagg  10020
ttcttgcgaa cctcatcact cgttgcatcg accggtaatg caggcaaatt ttggtgtacg  10080
```

```
gtcagtaaat tggacatggt ggctacgtaa taacttcgta tatggtttct tatacgaagt  10140
tatgcggccg ctttacgagg gtaggaagtg gtacggaaag ttggtataag acaaaagtgt  10200
tgtggaattg ctccaggcga tctgacggtt cactaaacga gctctgcttt tataggcgcc  10260
caccgtacac gcctaaagct tatacgttct ctatcactga tagggagtaa actggatata  10320
cgttctctat cactgatagg gagtaaactg tagatacgtt ctctatcact gatagggagt  10380
aaactggtca tacgttctct atcactgata gggagtaaac tccttatacg ttctctatca  10440
ctgataggga gtaaagtctg catacgttct ctatcactga tagggagtaa actcttcata  10500
cgttctctat cactgatagg gagtaaactc gcggccgcag agaaatgttc tggcacctgc  10560
acttgcactg gggacagcct attttgctag tttgttttgt ttcgttttgt tttgatggag  10620
agcgtatgtt agtactatcg attcacacaa aaaaccaaca cacagatgta atgaaaataa  10680
agatatttta ttggatctgc gatcgctccg gtgcccgtca gtgggcagag cgcacatcgc  10740
ccacagtccc cgagaagttg gggggagggg tcggcaattg aacgggtgcc tagagaaggt  10800
ggcgcggggt aaactgggaa agtgatgtcg tgtactggct ccgccttttt cccgagggtg  10860
ggggagaacc gtatgtaagt gcagtagtcg ccgtgaacgt tctttttcgc aacgggtttg  10920
ccgccagaac acagctgaag cttcgagggg ctcgcatctc tccttcacgc gcccgccgcc  10980
ctacctgagg ccgccatcca cgccggttga gtcgcgttct gccgcctccc gcctgtggtg  11040
cctcctgaac tgcgtccgcc gtctaggtaa gtttaaagct caggtcgaga ccgggccttt  11100
gtccggcgct cccttggagc ctacctagac tcagccggct ctccacgctt tgcctgaccc  11160
tgcttgctca actctacgtc tttgtttcgt tttctgttct gcgccgttac agatccaagc  11220
tgtgaccggc gcctacgcta gcggatccgc cgccaccatg tctagactgg acaagagcaa  11280
agtcataaac tctgctctgg aattactcaa tggagtcggt atcgaaggcc tgacgacaag  11340
gaaactcgct caaaagctgg gagttgagca gcctaccctg tactggcacg tgaagaacaa  11400
gcgggccctg ctcgatgccc tgccaatcga gatgctggac aggcatcata cccactcctg  11460
ccccctggaa ggcgagtcat ggcaagactt tctgcggaac aacgccaagt cataccgctg  11520
tgctcttctc tcacatcgcg acggggctaa agtgcatctc ggcacccgcc caacagagaa  11580
acagtacgaa accctggaaa atcagctcgc gttcctgtgt cagcaaggct tctccctgga  11640
gaacgcactg tacgctctgt ccgccgtggg ccactttaca ctgggctgcg tattggagga  11700
acaggagcat caagtagcaa aagaggaaag agagacacct accaccgatt ctatgccccc  11760
acttctgaaa caagcaattg agctgttcga ccggcaggga gccgaacctg ccttcctttt  11820
cggcctggaa ctaatcatat gtggcctgga gaaacagcta aagtgcgaaa gcggcgggcc  11880
gaccgacgcc cttgacgatt ttgacttaga catgctccca gccgatgccc ttgacgactt  11940
tgaccttgat atgctgcctg ctgacgctct tgacgatttt gaccttgaca tgctccccgg  12000
gtgaaccggt cgctgatcag cctcgactgt gccttctagt tgccagccat ctgttgtttg  12060
cccctccccc gtgccttcct tgaccctgga aggtgccact cccactgtcc tttcctaata  12120
aaatgaggaa attgcatcgc attgtctgag taggtgtcat tctattctgg ggggtggggt  12180
ggggcaggac agcaaggggg aggattggga agacaatagc aggcatgctg gggatgcggt  12240
gggctctatg gcttctgagg cggaaagaac cagctggggc tcgactagag cttgcggaac  12300
ccttagaggg cctatttccc atgattcctt catatttgca tatacgatac aaggctgtta  12360
gagagataat tagaattaat ttgactgtaa acacaaagat attagtacaa aataataact  12420
```

```
tcgtataatg tatgctatac gaagttatca gacatgataa gatacattga tgagtttgga  12480
caaaccacaa ctagaatgca gtgaaaaaaa tgctttattt gtgaaatttg tgatgctatt  12540
gctttatttg taaccattat aagctgcaat aaacaaggta cctcaagcgc cgggttttcg  12600
cgtcatgcac cacgtccgtg gtagaactag tattatgccc agtacatgac cttatgggac  12660
tttcctactt ggcagtacat ctacgtatta gtcatcgcta ttaccatggt gatgcggttt  12720
tggcagtaca tcaatgggcg tggatagcgg tttgactcac ggggatttcc aagtctccac  12780
cccattgacg tcaatgggag tttgttttgg caccaaaatc aacgggactt tccaaaatgt  12840
cgtaacaact ccgccccatt gacgcaaatg ggcggtaggc gtgtacggtg ggaggtttat  12900
ataagcagag ctcgtttagt gaaccgtcag atcgcctgga gacgccatcc acgctgtttt  12960
gacctccata gaagagaatt cgccgccacc atgacagaat ataaacctac tgtcagactg  13020
gcaactcgag acgacgtccc tagggccgtg agaacattgg ctgccgcttt cgcggattat  13080
cccgctacac gccacacagt tgatcctgat agacatattg aacgggttac agaattgcaa  13140
gaactttttt tgaccagggt aggattggac atcggtaaag tttgggtcgc cgacgacggg  13200
gctgcagtgg cagtgtggac gactccggag agcgttgagg ccggggctgt atttgcagaa  13260
attggtcccc gaatggctga gcttagtggc tctcgtctcg cggctcagca acaaatggaa  13320
ggactcctcg cccctcaccg ccctaaagaa ccagcttggt tcctcgctac tgtgggcgtt  13380
agccccgatc atcagggaaa gggccttggt tccgcggtgg tattgcccgg agtagaagcc  13440
gcagaacgag ccggagtgcc agcctttctt gaaacgtcag cgccaaggaa tttgcccttc  13500
tatgaacggc tcggatttac agttactgct gacgttgaag tacccgaggg cccacggacg  13560
tggtgcatga cgcgaaaacc cggcgcttga accggtcgct gatcagcctc gactgtgcct  13620
tctagttgcc agccatctgt tgtttgcccc tcccccgtgc cttccttgac cctggaaggt  13680
gccactccca ctgtcctttc ctaataaaat gaggaaattg catcgcattg tctgagtagg  13740
tgtcattcta ttctgggggg tggggtgggg caggacagca agggggagga ttgggaagac  13800
aatagcaggc atgctgggga tgcggtgggc tctatggctt ctgaggcgga aagaaccagc  13860
tggggctcga ctagagcttg cggaaccctt aggttgggaa aagcgctccc ctacccataa  13920
cttcgtataa tgtatgctat acgaagttat tttgcagttt taaaattatg ttttaaaatg  13980
gactatcata tgcttaccgt aacttgaaag tatttcgatt tcttggcttt atatatcttg  14040
tggaaaggac gaaacaccgg gcactcttcc gtgatctggt ggataaattc gcaagggtat  14100
catggcggac gaccgggatt cgaaccccgg atccggccgt ccgccgtgat ccatgcggtt  14160
accgcccgcg tgtcgaaccc aggtgtgcga cgtcagacaa cgggggagcg ctccttttg   14220
ggcccat                                                            14227
```

<210> SEQ ID NO 28
<211> LENGTH: 14058
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 28

```
tggtatggct ttttccccgt atccccccag gtgtctgcag gctcaaagag cagcgagaag     60
cgttcagagg aaagcgatcc cgtgccacct tccccgtgcc cgggctgtcc ccgcacgctg    120
ccggctcggg gatgcggggg gagcgccgga ccggagcgga gccccgggcg gctcgctgct    180
```

```
gcccccctagc gggggaggga cgtaattaca tccctggggg ctttgggggg gggctgtccc    240
tgatatctat aacaagaaaa tatatatata ataagttatc acgtaagtag aacatgaaat    300
aacaatataa ttatcgtatg agttaaatct taaaagtcac gtaaaagata atcatgcgtc    360
attttgactc acgcggtcgt tatagttcaa aatcagtgac acttaccgca ttgacaagca    420
cgcctcacgg gagctccaag cggcgactga gatgtcctaa atgcacagcg acggattcgc    480
gctatttaga aagagagagc aatatttcaa gaatgcatgc gtcaatttta cgcagactat    540
ctttctaggg ttaatctagc tgcatcagga tcatatcgtc gggtcttttt tccggctcag    600
tcatcgccca agctggcgct atctgggcat cggggaggaa gaagcccgtg ccttttcccg    660
cgaggttgaa gcggcatgga aagagtttgc cgaggatgac tgctgctgca ttgacgttga    720
gcgaaaacgc acgtttacca tgatgattcg ggaaggtgtg gccatgcacg cctttaacgg    780
tgaactgttc gttcaggcca cctgggatac cagttcgtcg cggcttttcc ggacacagtt    840
ccggatggtc agcccgaagc gcatcagcaa cccgaacaat accggcgaca gccggaactg    900
ccgtgccggt gtgcagatta atgacagcgg tgcggcgctg ggatattacg tcagcgagga    960
cgggtatcct ggctggatgc cgcagaaatg gacatggata ccccgtgagt tacccggcgg   1020
gcgcgcttgg cgtaatcatg gtcatagctg tttcctgtgt gaaattgtta tccgctcaca   1080
attccacaca acatacgagc cggaagcata aagtgtaaag cctggggtgc ctaatgagtg   1140
agctaactca cattaattgc gttgcgctca ctgcccgctt tccagtcggg aaacctgtcg   1200
tgccagctgc attaatgaat cggccaacgc gcggggagag gcggtttgcg tattgggcgc   1260
tcttccgctt cctcgctcac tgactcgctg cgctcggtcg ttcggctgcg gcgagcggta   1320
tcagctcact caaaggcggt aatacggtta tccacagaat caggggataa cgcaggaaag   1380
aacatgtgag caaaaggcca gcaaaaggcc aggaaccgta aaaaggccgc gttgctggcg   1440
tttttccata ggctccgccc ccctgacgag catcacaaaa atcgacgctc aagtcagagg   1500
tggcgaaacc cgacaggact ataaagatac caggcgtttc cccctggaag ctccctcgtg   1560
cgctctcctg ttccgaccct gccgcttacc ggatacctgt ccgcctttct cccttcggga   1620
agcgtggcgc tttctcatag ctcacgctgt aggtatctca gttcggtgta ggtcgttcgc   1680
tccaagctgg gctgtgtgca cgaacccccc gttcagcccg accgctgcgc cttatccggt   1740
aactatcgtc ttgagtccaa cccggtaaga cacgacttat cgccactggc agcagccact   1800
ggtaacagga ttagcagagc gaggtatgta ggcggtgcta cagagttctt gaagtggtgg   1860
cctaactacg gctacactag aaggacagta tttggtatct gcgctctgct gaagccagtt   1920
accttcggaa aaagagttgg tagctcttga tccggcaaac aaaccaccgc tggtagcggt   1980
ggtttttttg tttgcaagca gcagattacg cgcagaaaaa aaggatctca agaagatcct   2040
ttgatctttt ctacggggtc tgacgctcag tggaacgaaa actcacgtta agggattttg   2100
gtcatgagat tatcaaaaag gatcttcacc tagatccttt taaattaaaa atgaagtttt   2160
aaatcaatct aaagtatata tgagtaaact tggtctgaca gttaccaatg cttaatcagt   2220
gaggcaccta tctcagcgat ctgtctattt cgttcatcca tagttgcctg actccccgtc   2280
gtgtagataa ctacgatacg ggagggctta ccatctggcc ccagtgctgc aatgataccg   2340
cgagacccac gctcaccggc tccagattta tcagcaataa accagccagc cggaagggcc   2400
gagcgcagaa gtggtcctgc aactttatcc gcctccatcc agtctattaa ttgttgccgg   2460
gaagctagag taagtagttc gccagttaat agtttgcgca acgttgttgc cattgctaca   2520
```

```
ggcatcgtgg tgtcacgctc gtcgtttggt atggcttcat tcagctccgg ttcccaacga   2580
tcaaggcgag ttacatgatc ccccatgttg tgcaaaaaag cggttagctc cttcggtcct   2640
ccgatcgttg tcagaagtaa gttggccgca gtgttatcac tcatggttat ggcagcactg   2700
cataattctc ttactgtcat gccatccgta agatgctttt ctgtgactgg tgagtactca   2760
accaagtcat tctgagaata gtgtatgcgg cgaccgagtt gctcttgccc ggcgtcaata   2820
cgggataata ccgcgccaca tagcagaact ttaaaagtgc tcatcattgg aaaacgttct   2880
tcggggcgaa aactctcaag gatcttaccg ctgttgagat ccagttcgat gtaacccact   2940
cgtgcaccca actgatcttc agcatctttt actttcacca gcgtttctgg gtgagcaaaa   3000
acaggaaggc aaaatgccgc aaaaaaggga ataagggcga cacggaaatg ttgaatactc   3060
atactcttcc tttttcaata ttattgaagc atttatcagg gttattgtct catgagcgga   3120
tacatatttg aatgtattta gaaaaataaa caaatagggg ttccgcgcac atttccccga   3180
aaagtgccac ctaaattgta agcgttaata ttttgttaaa attcgcgtta aatttttgtt   3240
aaatcagctc attttttaac caataggccg aaatcggcaa aatcccttat aaatcaaaag   3300
aatagaccga gatagggttg agtgttgttc cagtttggaa caagagtcca ctattaaaga   3360
acgtggactc caacgtcaaa gggcgaaaaa ccgtctatca gggcgatggc ccactacgtg   3420
aaccatcacc ctaatcaagt tttttggggt cgaggtgccg taaagcacta aatcggaacc   3480
ctaaagggag cccccgattt agagcttgac ggggaaagcc ggcgaacgtg gcgagaaagg   3540
aagggaagaa agcgaaagga gcgggcgcta gggcgctggc aagtgtagcg gtcacgctgc   3600
gcgtaaccac cacacccgcc gcgcttaatg cgccgctaca gggcgcgtcc cattcgccat   3660
tcaggctgcg caactgttgg gaagggcgat cggtgcgggc ctcttcgcta ttacgccagc   3720
tggcgaaagg gggatgtgct gcaaggcgat taagttgggt aacgccaggg ttttcccagt   3780
cacgacgttg taaaacgacg gccagtgagc gcgcctcgtt cattcacgtt tttgaacccg   3840
tggaggacgg gcagactcgc ggtgcaaatg tgttttacag cgtgatggag cagatgaaga   3900
tgctcgacac gctgcagaac acgcagctag attaacccta gaaagataat catattgtga   3960
cgtacgttaa agataatcat gtgtaaaatt gacgcatgtg ttttatcggt ctgtatatcg   4020
aggtttattt attaatttga atagatatta agttttatta tatttacact tacatactaa   4080
taataaattc aacaaacaat ttatttatgt ttatttattt attaaaaaaa acaaaaaactc  4140
aaaatttctt ctataaagta acaaaacttt tatgagggac agcccccccc caaagccccc   4200
agggatgtaa ttacgtccct cccccgctag ggggcagcag cgagccgccc ggggctccgc   4260
tccggtccgg cgctcccccc gcatccccga gccggcagcg tgcggggaca gcccgggcac   4320
ggggaaggtg gcacgggatc gctttcctct gaacgcttct cgctgctctt tgagcctgca   4380
gacacctggg gggatacggg gaaaaggcct ccacggccac tagtccatag agcccaccgc   4440
atccccagca tgcctgctat tgtcttccca atcctccccc ttgctgtcct gccccacccc   4500
acccccctaga atagaatgac acctactcag acaatgcgat gcaatttcct cattttatta  4560
ggaaaggaca gtgggagtgg caccttccag ggtcaaggaa ggcacggggg aggggcaaac   4620
aacagatggc tggcaactag aaggcacagc tacatggggg tagagtcata atcgtgcatc   4680
aggatagggc ggtggtgctg cagcagcgcg cgaataaact gctgccgccg ccgctccgtc   4740
ctgcaggaat acaacatggc agtggtctcc tcagcgatga ttcgcaccgc ccgcagcatg   4800
agacgccttg tcctccgggc acagcagcgc accctgatct cacttaaatc agcacagtaa   4860
ctgcagcaca gcaccacaat attgttcaaa atcccacagt gcaaggcgct gtatccaaag   4920
```

```
ctcatggcgg ggaccacaga acccacgtgg ccatcatacc acaagcgcag gtagattaag   4980
tggcgacccc tcataaacac gctggacata aacattacct cttttggcat gttgtaattc   5040
accacctccc ggtaccatat aaacctctga ttaaacatgg cgccatccac caccatccta   5100
aaccagctgg ccaaaacctg cccgccggct atgcactgca gggaaccggg actggaacaa   5160
tgacagtgga gagcccagga ctcgtaacca tggatcatca tgctcgtcat gatatcaatg   5220
ttggcacaac acaggcacac gtgcatacac ttcctcagga ttacaagctc ctcccgcgtc   5280
agaaccatat cccagggaac aacccattcc tgaatcagcg taaatcccac actgcaggga   5340
agacctcgca cgtaactcac gttgtgcatt gtcaaagtgt tacattcggg cagcagcgga   5400
tgatcctcca gtatggtagc gcgggtctct gtctcaaaag gaggtaggcg atccctactg   5460
tacggagtgc gccgagacaa ccgagatcgt gttggtcgta gtgtcatgcc aaatggaacg   5520
ccggacgtag tcatggttgt ggccatatta tcatcgtgtt tttcaaagga aaaccacgtc   5580
cccgtggttc ggggggccta gacgtttttt taacctcgac taaacacatg taaagcatgt   5640
gcaccgaggc cccagatcag atcccataca atggggtacc ttctgggcat ccttcagccc   5700
cttgttgaat acgcttgagg agagccattt gactctttcc acaactatcc aactcacaac   5760
gtggcactgg ggttgtgccg cctttgcagg tgtatcttat acacgtggct tttggccgca   5820
gaggcacctg tcgccaggtg gggggttccg ctgcctgcaa agggtcgcta cagacgttgt   5880
ttgtcttcaa gaagcttcca gaggaactgc ttccttcacg acattcaaca gaccttgcat   5940
tcctttggcg agaggggaaa gacccctagg aatgctcgtc aagaagacag ggccaggttt   6000
ccgggccctc acattgccaa aagacggcaa tatggtggaa aataacatat agacaaacgc   6060
acaccggcct tattccaagc ggcttcggcc agtaacgtta gggggggggg agggagaggg   6120
gcttaaaaat caaaggggtt ctgccgcgca tcactatgcg ccactggcag ggacacgttg   6180
cgatactggt gtttagtgct ccacttaaac tcaggcacaa ccatccgcgg cagctcggtg   6240
aagttttcac tccacaggct gcgcaccatc accaacgcgt ttagcaggtc gggcgccgat   6300
atcttgaagt cgcagttggg gcctccgccc tgcgcgcgcg agttgcgata cacagggttg   6360
cagcactgga acactatcag cgccgggtgg tgcacgctgg ccagcacgct cttgtcggag   6420
atcagatccg cgtccaggtc ctccgcgttg ctcagggcga acggagtcaa ctttggtagc   6480
tgccttccca aaaagggtgc atgcccaggc tttgagttgc actcgcaccg tagtggcatc   6540
agaaggtgac cgtgcccggt ctgggcgtta ggatacagcg cctgcatgaa agccttgatc   6600
tgcttaaaag ccacctgagc ctttgcgcct tcagagaaga acatgccgca agacttgccg   6660
gaaaactgat tggccggaca ggccgcgtca tgcacgcagc accttgcgtc ggtgttggag   6720
atctgcacca catttcggcc ccaccggttc ttcacgatct tggccttgct agactgctcc   6780
ttcagcgcgc gctgcccgtt ttcgctcgtc acatccattt caatcacgtg ctccttattt   6840
atcataatgc tcccgtgtag acacttaagc tcgccttcga tctcagcgca gcggtgcagc   6900
cacaacgcgc agcccgtggg ctcgtggtgc ttgtaggtta cctctgcaaa cgactgcagg   6960
tacgcctgca ggaatcgccc catcatcgtc acaaaggtct tgttgctggt gaaggtcagc   7020
tgcaacccgc ggtgctcctc gtttagccag gtcttgcata cggccgccag agcttccact   7080
tggtcaggca gtagcttgaa gtttgccttt agatcgttat ccacgtggta cttgtccatc   7140
aacgcgcgcg cagcctccat gcccttctcc cacgcagaca cgatcggcag gctcagcggg   7200
tttatcaccg tgctttcact ttccgcttca ctggactctt ccttttcctc ttgcgtccgc   7260
```

-continued

```
ataccccgcg ccactgggtc gtcttcattc agccgccgca ccgtgcgctt acctcccttg   7320
ccgtgcttga ttagcaccgg tgggttgctg aaacccacca tttgtagcgc cacatcttct   7380
ctttcttcct cgctgtccac gatcacctct ggggatggcg ggcgctcggg cttgggagag   7440
gggcgcttct ttttcttttt ggacgcaatg gccaaatccg ccgtcgaggt cgatggccgc   7500
gggctgggtg tgcgcggcac cagcgcatct tgtgacgagt cttcttcgtc ctcggactcg   7560
agacgccgcc tcagccgctt ttttgggggc gcgcgcttgt cgtcatcgtc tttgtagtcg   7620
ggaggcggcg gcgacggcga cggggacgac acgtcctcca tggttggtgg acgtcgcgcc   7680
gcaccgcgtc cgcgctcggg ggtggtttcg cgctgctcct cttcccgact ggccatggtg   7740
gccgaggata acttcgtata tggtttctta tacgaagtta tgatccagac atgataagat   7800
acattgatga gtttggacaa accacaacta gaatgcagtg aaaaaaatgc tttatttgtg   7860
aaatttgtga tgctattgct ttatttgtaa ccattataag ctgcaataaa caagttaaca   7920
acaacaattg cattcatttt atgtttcagg ttcaggggga ggtgtgggag gtttttttaaa  7980
gcaagtaaaa cctctacaaa tgtggtatgg ctgattatga tcctctagag tcgcagatct   8040
gctacgtatc aagctgtggc agggaaaccc tctgcctccc ccgtgatgta atacttttgc   8100
aaggaatgcg atgaagtaga gcccgcagtg gccaagtggc tttggtccgt ctcctccacg   8160
gatgcccctc cacggctagt gggcgcatgt aggcggtggg cgtccgccgc ctccagcagc   8220
aggtcataga ggggcaccac gttcttgcac ttcatgctgt acagatgctc catgcctttg   8280
ttactcatgt gtcggatgtg ggagaggatg aggaggagct gggccagccg ctggtgctgc   8340
tgctgcaggg tcaggcctgc cttggccatc aggtggatca aagtgtctgt gatcttgtcc   8400
aggactcggt ggatatggtc cttctcttcc agagacttca gggtgctgga cagaaatgtg   8460
tacactccag aattaagcaa aataatagat ttgaggcaca caaactcctc tccctgcaga   8520
ttcatcatgc ggaaccgaga tgatgtagcc agcagcatgt cgaagatctc caccatgccc   8580
tctacacatt ttccctggtt cctgtccaag agcaagttag gagcaaacag tagcttcact   8640
gggtgctcca tggagcgcca gacgagacca atcatcagga tctctagcca ggcacattct   8700
agaaggtgga cctgatcatg gagggtcaaa tccacaaagc ctggcaccct cttcgcccag   8760
ttgatcatgt gaaccagctc cctgtctgcc aggttggtca gtaagcccat catcgaagct   8820
tcactgaagg gtctggtagg atcatactcg gaatagagta tggggggctc agcatccaac   8880
aaggcactga ccatctggtc ggccgtcagg gacaaggcca ggctgttctt cttagagcgt   8940
ttgatcatga gcgggcttgg ccaaaggttg gcagctctca tgtctccagc agatggctcg   9000
agatcgccat cttccagcag gcgcaccatt gcccctgttt cactatccag gttacggata   9060
tagttcatga caatatttac attggtccag ccaccagctt gcatgatctc cggtattgaa   9120
actccagcgc gggccatatc tcgcgcggct ccgacacggg cactgtgtcc agaccaggcc   9180
aggtatctct gaccagagtc atcctaaaat acacaaacaa ttagaatcag tagtttaaca   9240
cattatacac ttaaaaattt tatatttacc ttagcgccgt aaatcaatcg atgagttgct   9300
tcaaaaatcc cttccagggc gcgagttgat agctggctgg tggcagatgg cgcggcaaca   9360
ccattttttc tgacccggca aaacaggtag ttattcggat catcagctac accagagacg   9420
gaaatccatc gctcgaccag tttagtgact cccaggctaa gtgccttctc tacacctgcg   9480
gtgctaacca gcgttttcgt tctgccaata tggattaaca ttctcccacc gtcagtacgt   9540
gagatatctt taaccctgat cctggcaatt tcggctatac gtaacagggt gttataagca   9600
atccccagaa atgccagatt acgtatatcc tggcagcgat cgctattttc catgagtgaa   9660
```

cggacttggt cgaaatcagt gcgttcgaac gctagagcct gttttgcacg ttcaccggca 9720
tcaacgtttt cttttcggat ccgccgcata accagtgaaa cagcattgct gtcacttggt 9780
cgtggcagcc cggaccgacg atgaagcatg tttagctggc ccaaatgttg ctggatagtt 9840
tttactgcca gaccgcgcgc ttgaagatat agaagataat cgcgaacatc ttcaggttct 9900
gcgggaaacc atttccggtt attcaacttg caccatgccg cccacgaccg gcaaacggac 9960
agaagcattt tccaggtatg ctcagaaaac gcctggcgat ccctgaacat gtccatcagg 10020
ttcttgcgaa cctcatcact cgttgcatcg accggtaatg caggcaaatt ttggtgtacg 10080
gtcagtaaat tggacatggt ggctacgtaa taacttcgta tatggtttct tatacgaagt 10140
tatgcggccg ctttacgagg gtaggaagtg gtacggaaag ttggtataag acaaaagtgt 10200
tgtggaattg ctccaggcga tctgacggtt cactaaacga gctctgcttt tataggcgcc 10260
caccgtacac gcctaaagct tatacgttct ctatcactga tagggagtaa actggatata 10320
cgttctctat cactgatagg gagtaaactg tagatacgtt ctctatcact gatagggagt 10380
aaactggtca tacgttctct atcactgata gggagtaaac tccttatacg ttctctatca 10440
ctgataggga gtaaagtctg catacgttct ctatcactga tagggagtaa actcttcata 10500
cgttctctat cactgatagg gagtaaactc gcggccgcag agaaatgttc tggcacctgc 10560
acttgcactg gggacagcct attttgctag tttgttttgt ttcgttttgt tttgatggag 10620
agcgtatgtt agtactatcg attcacacaa aaaaccaaca cacagatgta atgaaaataa 10680
agatatttta ttggatctgc gatcgctccg gtgcccgtca gtgggcagag cgcacatcgc 10740
ccacagtccc cgagaagttg gggggagggg tcggcaattg aacgggtgcc tagagaaggt 10800
ggcgcggggt aaactgggaa agtgatgtcg tgtactggct ccgccttttt cccgagggtg 10860
ggggagaacc gtatgtaagt gcagtagtcg ccgtgaacgt tctttttcgc aacgggtttg 10920
ccgccagaac acagctgaag cttcgagggg ctcgcatctc tccttcacgc gcccgccgcc 10980
ctacctgagg ccgccatcca cgccggttga gtcgcgttct gccgcctccc gcctgtggtg 11040
cctcctgaac tgcgtccgcc gtctaggtaa gtttaaagct caggtcgaga ccgggccttt 11100
gtccggcgct cccttggagc ctacctagac tcagccggct ctccacgctt tgcctgaccc 11160
tgcttgctca actctacgtc tttgtttcgt tttctgttct gcgccgttac agatccaagc 11220
tgtgaccggc gcctacgcta gcggatccgc cgccaccatg tctagactgg acaagagcaa 11280
agtcataaac tctgctctgg aattactcaa tggagtcggt atcgaaggcc tgacgacaag 11340
gaaactcgct caaaagctgg gagttgagca gcctaccctg tactggcacg tgaagaacaa 11400
gcgggccctg ctcgatgccc tgccaatcga gatgctggac aggcatcata cccactcctg 11460
ccccctggaa ggcgagtcat ggcaagactt tctgcggaac aacgccaagt cataccgctg 11520
tgctcttctc tcacatcgcg acggggctaa agtgcatctc ggcacccgcc caacagagaa 11580
acagtacgaa accctggaaa atcagctcgc gttcctgtgt cagcaaggct tctccctgga 11640
gaacgcactg tacgctctgt ccgccgtggg ccactttaca ctgggctgcg tattggagga 11700
acaggagcat caagtagcaa aagaggaaag agagacacct accaccgatt ctatgccccc 11760
acttctgaaa caagcaattg agctgttcga ccggcaggga gccgaacctg ccttcctttt 11820
cggcctggaa ctaatcatat gtggcctgga gaaacagcta aagtgcgaaa gcggcgggcc 11880
gaccgacgcc cttgacgatt ttgacttaga catgctccca gccgatgccc ttgacgactt 11940
tgaccttgat atgctgcctg ctgacgctct tgacgatttt gaccttgaca tgctccccgg 12000

-continued

```
gtgaaccggt cgctgatcag cctcgactgt gccttctagt tgccagccat ctgttgtttg  12060
cccctccccc gtgccttcct tgaccctgga aggtgccact cccactgtcc tttcctaata  12120
aaatgaggaa attgcatcgc attgtctgag taggtgtcat tctattctgg ggggtggggt  12180
ggggcaggac agcaaggggg aggattggga agacaatagc aggcatgctg gggatgcggt  12240
gggctctatg gcttctgagg cggaaagaac cagctggggc tcgactagag cttgcggaac  12300
ccttagaggg cctatttccc atgattcctt catatttgca tatacgatac aaggctgtta  12360
gagagataat tagaattaat ttgactgtaa acacaaagat attagtacaa aataataact  12420
tcgtataatg tatgctatac gaagttatca gacatgataa gatacattga tgagtttgga  12480
caaaccacaa ctagaatgca gtgaaaaaaa tgctttattt gtgaaatttg tgatgctatt  12540
gctttatttg taaccattat aagctgcaat aaacaaggta cctcaagcgc cgggttttcg  12600
cgtcatgcac cacgtccgtg gtcaaccctc ccacacgtaa ccagatggga gaagctctcg  12660
tattccaaca gctgtaggtt gaccgtctga atccttcact atggccttta tacctggatg  12720
cagatccaac aggacttgtc tacatctacc acaaggtgac aagatcccgc gattctcgtt  12780
accaatagca acgatacaag tcagattccc tgcggcggcg gcagcggcgg ttcccagtac  12840
tacgagttct gcgcaggggc cacccgtaaa atgatacaca tttaccccag taaaaatccg  12900
cccatcggat gacaaggctg cactagccac ggaatagtcg tcagatatag gtatggaatt  12960
gattgtggcg gtagccctct ctatcagcgt ggactcctcc tgagagaggg gttttgccat  13020
ggtggcggct taagggttcg atcctctaga gtccggaggc tggatcggtc ccggtgtctt  13080
ctatggaggt caaaacagcg tggatggcgt ctccaggcga tctgacggtt cactaaacga  13140
gctctgctta tatagacctc ccaccgtaca cgcctaccgc ccatttgcgt caatggggcg  13200
gagttgttac gacattttgg aaagtcccgt tgattttggt gccaaaacaa actcccattg  13260
acgtcaatgg ggtggagact tggaaatccc cgtgagtcaa accgctatcc acgcccattg  13320
atgtactgcc aaaaccgcat caccatggta atagcgatga ctaatacgta gatgtactgc  13380
caagtaggaa agtcccataa ggtcatgtac tgggcataat gccaggcggg ccatttaccg  13440
tcattgacgt caataggggg cgtacttggc atatgataca cttgatgtac tgccaagtgg  13500
gcagtttacc gtaaatactc cacccattga cgtcaatgga aagtccctat tggcgttact  13560
atgggaacat acgtcattat tgacgtcaat gggcgggggt cgttgggcgg tcagccaggc  13620
gggccattta ccgtaagtta tgtaacgcgg aactccatat atgggctatg aactaatgac  13680
cccgtaattg attactatta ataactagtc aataatcaat gtcattggga aaagcgctcc  13740
cctacccata acttcgtata atgtatgcta tacgaagtta ttttgcagtt ttaaaattat  13800
gttttaaaat ggactatcat atgcttaccg taacttgaaa gtatttcgat ttcttggctt  13860
tatatatctt gtggaaagga cgaaacaccg ggcactcttc cgtgatctgg tggataaatt  13920
cgcaagggta tcatggcgga cgaccgggat tcgaaccccg gatccggccg tccgccgtga  13980
tccatgcggt taccgcccgc gtgtcgaacc caggtgtgcg acgtcagaca acgggggagc  14040
gctccttttt gggcccat                                                14058
```

<210> SEQ ID NO 29
<211> LENGTH: 14067
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 29
tggtatggct ttttccccgt atccccccag gtgtctgcag gctcaaagag cagcgagaag 60
cgttcagagg aaagcgatcc cgtgccacct tccccgtgcc cggctgtcc ccgcacgctg 120
ccggctcggg gatgcggggg gagcgccgga ccggagcgga gccccgggcg gctcgctgct 180
gccccctagc gggggaggga cgtaattaca tccctggggg ctttgggggg gggctgtccc 240
tgatatctat aacaagaaaa tatatatata ataagttatc acgtaagtag aacatgaaat 300
aacaatataa ttatcgtatg agttaaatct taaaagtcac gtaaaagata atcatgcgtc 360
attttgactc acgcggtcgt tatagttcaa aatcagtgac acttaccgca ttgacaagca 420
cgcctcacgg gagctccaag cggcgactga gatgtcctaa atgcacagcg acggattcgc 480
gctatttaga aagagagagc aatatttcaa gaatgcatgc gtcaatttta cgcagactat 540
ctttctaggg ttaatctagc tgcatcagga tcatatcgtc gggtcttttt tccggctcag 600
tcatcgccca agctggcgct atctgggcat cggggaggaa gaagcccgtg ccttttcccg 660
cgaggttgaa gcggcatgga aagagtttgc cgaggatgac tgctgctgca ttgacgttga 720
gcgaaaacgc acgtttacca tgatgattcg ggaaggtgtg gccatgcacg cctttaacgg 780
tgaactgttc gttcaggcca cctgggatac cagttcgtcg cggcttttcc ggacacagtt 840
ccggatggtc agcccgaagc gcatcagcaa cccgaacaat accggcgaca gccggaactg 900
ccgtgccggt gtgcagatta atgacagcgg tgcggcgctg ggatattacg tcagcgagga 960
cgggtatcct ggctggatgc cgcagaaatg gacatggata ccccgtgagt tacccggcgg 1020
gcgcgcttgg cgtaatcatg gtcatagctg tttcctgtgt gaaattgtta tccgctcaca 1080
attccacaca acatacgagc cggaagcata aagtgtaaag cctggggtgc ctaatgagtg 1140
agctaactca cattaattgc gttgcgctca ctgcccgctt tccagtcggg aaacctgtcg 1200
tgccagctgc attaatgaat cggccaacgc gcggggagag gcggtttgcg tattgggcgc 1260
tcttccgctt cctcgctcac tgactcgctg cgctcggtcg ttcggctgcg gcgagcggta 1320
tcagctcact caaaggcggt aatacggtta tccacagaat caggggataa cgcaggaaag 1380
aacatgtgag caaaaggcca gcaaaaggcc aggaaccgta aaaaggccgc gttgctggcg 1440
tttttccata ggctccgccc ccctgacgag catcacaaaa atcgacgctc aagtcagagg 1500
tggcgaaacc cgacaggact ataaagatac caggcgtttc cccctggaag ctccctcgtg 1560
cgctctcctg ttccgaccct gccgcttacc ggatacctgt ccgcctttct cccttcggga 1620
agcgtggcgc tttctcatag ctcacgctgt aggtatctca gttcggtgta ggtcgttcgc 1680
tccaagctgg gctgtgtgca cgaacccccc gttcagcccg accgctgcgc cttatccggt 1740
aactatcgtc ttgagtccaa cccggtaaga cacgacttat cgccactggc agcagccact 1800
ggtaacagga ttagcagagc gaggtatgta ggcggtgcta cagagttctt gaagtggtgg 1860
cctaactacg gctacactag aaggacagta tttggtatct gcgctctgct gaagccagtt 1920
accttcggaa aaagagttgg tagctcttga tccggcaaac aaaccaccgc tggtagcggt 1980
ggtttttttg tttgcaagca gcagattacg cgcagaaaaa aaggatctca agaagatcct 2040
ttgatctttt ctacggggtc tgacgctcag tggaacgaaa actcacgtta agggattttg 2100
gtcatgagat tatcaaaaag gatcttcacc tagatccttt taaattaaaa atgaagtttt 2160
aaatcaatct aaagtatata tgagtaaact tggtctgaca gttaccaatg cttaatcagt 2220
gaggcaccta tctcagcgat ctgtctattt cgttcatcca tagttgcctg actccccgtc 2280

```
gtgtagataa ctacgatacg ggagggctta ccatctggcc ccagtgctgc aatgataccg   2340
cgagacccac gctcaccggc tccagattta tcagcaataa accagccagc cggaagggcc   2400
gagcgcagaa gtggtcctgc aactttatcc gcctccatcc agtctattaa ttgttgccgg   2460
gaagctagag taagtagttc gccagttaat agtttgcgca acgttgttgc cattgctaca   2520
ggcatcgtgg tgtcacgctc gtcgtttggt atggcttcat tcagctccgg ttcccaacga   2580
tcaaggcgag ttacatgatc ccccatgttg tgcaaaaaag cggttagctc cttcggtcct   2640
ccgatcgttg tcagaagtaa gttggccgca gtgttatcac tcatggttat ggcagcactg   2700
cataattctc ttactgtcat gccatccgta agatgctttt ctgtgactgg tgagtactca   2760
accaagtcat tctgagaata gtgtatgcgg cgaccgagtt gctcttgccc ggcgtcaata   2820
cgggataata ccgcgccaca tagcagaact ttaaaagtgc tcatcattgg aaaacgttct   2880
tcggggcgaa aactctcaag gatcttaccg ctgttgagat ccagttcgat gtaacccact   2940
cgtgcaccca actgatcttc agcatctttt actttcacca gcgtttctgg gtgagcaaaa   3000
acaggaaggc aaaatgccgc aaaaaaggga ataagggcga cacggaaatg ttgaatactc   3060
atactcttcc tttttcaata ttattgaagc atttatcagg gttattgtct catgagcgga   3120
tacatatttg aatgtattta gaaaaataaa caaatagggg ttccgcgcac atttccccga   3180
aaagtgccac ctaaattgta agcgttaata ttttgttaaa attcgcgtta aatttttgtt   3240
aaatcagctc attttttaac caataggccg aaatcggcaa aatcccttat aaatcaaaag   3300
aatagaccga gatagggttg agtgttgttc cagtttggaa caagagtcca ctattaaaga   3360
acgtggactc caacgtcaaa gggcgaaaaa ccgtctatca gggcgatggc ccactacgtg   3420
aaccatcacc ctaatcaagt tttttggggt cgaggtgccg taaagcacta aatcggaacc   3480
ctaaagggag cccccgattt agagcttgac ggggaaagcc ggcgaacgtg gcgagaaagg   3540
aagggaagaa agcgaaagga gcgggcgcta gggcgctggc aagtgtagcg gtcacgctgc   3600
gcgtaaccac cacacccgcc gcgcttaatg cgccgctaca gggcgcgtcc cattcgccat   3660
tcaggctgcg caactgttgg gaagggcgat cggtgcgggc ctcttcgcta ttacgccagc   3720
tggcgaaagg gggatgtgct gcaaggcgat taagttgggt aacgccaggg ttttcccagt   3780
cacgacgttg taaaacgacg gccagtgagc gcgcctcgtt cattcacgtt tttgaacccg   3840
tggaggacgg gcagactcgc ggtgcaaatg tgttttacag cgtgatggag cagatgaaga   3900
tgctcgacac gctgcagaac acgcagctag attaacccta gaaagataat catattgtga   3960
cgtacgttaa agataatcat gtgtaaaatt gacgcatgtg ttttatcggt ctgtatatcg   4020
aggtttattt attaatttga atagatatta agttttatta tatttacact tacatactaa   4080
taataaattc aacaaacaat ttatttatgt ttatttattt attaaaaaaa acaaaaactc   4140
aaaatttctt ctataaagta acaaaacttt tatgagggac agcccccccc caaagccccc   4200
agggatgtaa ttacgtccct cccccgctag ggggcagcag cgagccgccc ggggctccgc   4260
tccggtccgg cgctcccccc gcatccccga gccggcagcg tgcggggaca gcccgggcac   4320
ggggaaggtg gcacgggatc gctttcctct gaacgcttct cgctgctctt tgagcctgca   4380
gacacctggg gggatacggg gaaaaggcct ccacggccac tagtccatag agcccaccgc   4440
atccccagca tgcctgctat tgtcttccca atcctccccc ttgctgtcct gccccacccc   4500
accccctaga atagaatgac acctactcag acaatgcgat gcaatttcct cattttatta   4560
ggaaaggaca gtgggagtgg caccttccag ggtcaaggaa ggcacggggg aggggcaaac   4620
aacagatggc tggcaactag aaggcacagc tacatggggg tagagtcata atcgtgcatc   4680
```

aggatagggc ggtggtgctg cagcagcgcg cgaataaact gctgccgccg ccgctccgtc 4740
ctgcaggaat acaacatggc agtggtctcc tcagcgatga ttcgcaccgc ccgcagcatg 4800
agacgccttg tcctccgggc acagcagcgc accctgatct cacttaaatc agcacagtaa 4860
ctgcagcaca gcaccacaat attgttcaaa atcccacagt gcaaggcgct gtatccaaag 4920
ctcatggcgg ggaccacaga acccacgtgg ccatcatacc acaagcgcag gtagattaag 4980
tggcgacccc tcataaacac gctggacata aacattacct cttttggcat gttgtaattc 5040
accacctccc ggtaccatat aaacctctga ttaaacatgg cgccatccac caccatccta 5100
aaccagctgg ccaaaacctg cccgccggct atgcactgca gggaaccggg actggaacaa 5160
tgacagtgga gagcccagga ctcgtaacca tggatcatca tgctcgtcat gatatcaatg 5220
ttggcacaac acaggcacac gtgcatacac ttcctcagga ttacaagctc ctcccgcgtc 5280
agaaccatat cccagggaac aacccattcc tgaatcagcg taaatcccac actgcaggga 5340
agacctcgca cgtaactcac gttgtgcatt gtcaaagtgt tacattcggg cagcagcgga 5400
tgatcctcca gtatggtagc gcgggtctct gtctcaaaag gaggtaggcg atccctactg 5460
tacggagtgc gccgagacaa ccgagatcgt gttggtcgta gtgtcatgcc aaatggaacg 5520
ccggacgtag tcatggttgt ggccatatta tcatcgtgtt tttcaaagga aaaccacgtc 5580
cccgtggttc ggggggccta gacgtttttt taacctcgac taaacacatg taaagcatgt 5640
gcaccgaggc cccagatcag atcccataca atggggtacc ttctgggcat ccttcagccc 5700
cttgttgaat acgcttgagg agagccattt gactctttcc acaactatcc aactcacaac 5760
gtggcactgg ggttgtgccg cctttgcagg tgtatcttat acacgtggct tttggccgca 5820
gaggcacctg tcgccaggtg gggggttccg ctgcctgcaa agggtcgcta cagacgttgt 5880
ttgtcttcaa gaagcttcca gaggaactgc ttccttcacg acattcaaca gaccttgcat 5940
tcctttggcg agaggggaaa gacccctagg aatgctcgtc aagaagacag ggccaggttt 6000
ccgggccctc acattgccaa aagacggcaa tatggtggaa aataacatat agacaaacgc 6060
acaccggcct tattccaagc ggcttcggcc agtaacgtta gggggggggg agggagaggg 6120
gcttaaaaat caaaggggtt ctgccgcgca tcactatgcg ccactggcag ggacacgttg 6180
cgatactggt gtttagtgct ccacttaaac tcaggcacaa ccatccgcgg cagctcggtg 6240
aagttttcac tccacaggct gcgcaccatc accaacgcgt ttagcaggtc gggcgccgat 6300
atcttgaagt cgcagttggg gcctccgccc tgcgcgcgcg agttgcgata cacagggttg 6360
cagcactgga acactatcag cgccgggtgg tgcacgctgg ccagcacgct cttgtcggag 6420
atcagatccg cgtccaggtc ctccgcgttg ctcagggcga acggagtcaa ctttggtagc 6480
tgccttccca aaaagggtgc atgcccaggc tttgagttgc actcgcaccg tagtggcatc 6540
agaaggtgac cgtgcccggt ctgggcgtta ggatacagcg cctgcatgaa agccttgatc 6600
tgcttaaaag ccacctgagc ctttgcgcct tcagagaaga acatgccgca agacttgccg 6660
gaaaactgat tggccggaca ggccgcgtca tgcacgcagc accttgcgtc ggtgttggag 6720
atctgcacca catttcggcc ccaccggttc ttcacgatct tggccttgct agactgctcc 6780
ttcagcgcgc gctgcccgtt ttcgctcgtc acatccattt caatcacgtg ctccttattt 6840
atcataatgc tcccgtgtag acacttaagc tcgccttcga tctcagcgca gcggtgcagc 6900
cacaacgcgc agcccgtggg ctcgtggtgc ttgtaggtta cctctgcaaa cgactgcagg 6960
tacgcctgca ggaatcgccc catcatcgtc acaaaggtct tgttgctggt gaaggtcagc 7020

-continued

```
tgcaacccgc ggtgctcctc gtttagccag gtcttgcata cggccgccag agcttccact   7080
tggtcaggca gtagcttgaa gtttgccttt agatcgttat ccacgtggta cttgtccatc   7140
aacgcgcgcg cagcctccat gcccttctcc cacgcagaca cgatcggcag gctcagcggg   7200
tttatcaccg tgctttcact ttccgcttca ctggactctt ccttttcctc ttgcgtccgc   7260
ataccccgcg ccactgggtc gtcttcattc agccgccgca ccgtgcgctt acctcccttg   7320
ccgtgcttga ttagcaccgg tgggttgctg aaacccacca tttgtagcgc cacatcttct   7380
ctttcttcct cgctgtccac gatcacctct ggggatggcg ggcgctcggg cttgggagag   7440
gggcgcttct ttttcttttt ggacgcaatg gccaaatccg ccgtcgaggt cgatggccgc   7500
gggctgggtg tgcgcggcac cagcgcatct tgtgacgagt cttcttcgtc ctcggactcg   7560
agacgccgcc tcagccgctt ttttgggggc gcgcgcttgt cgtcatcgtc tttgtagtcg   7620
ggaggcggcg gcgacggcga cggggacgac acgtcctcca tggttggtgg acgtcgcgcc   7680
gcaccgcgtc cgcgctcggg ggtggtttcg cgctgctcct cttcccgact ggccatggtg   7740
gccgaggata acttcgtata tggtttctta tacgaagtta tgatccagac atgataagat   7800
acattgatga gtttggacaa accacaacta gaatgcagtg aaaaaaatgc tttatttgtg   7860
aaatttgtga tgctattgct ttatttgtaa ccattataag ctgcaataaa caagttaaca   7920
acaacaattg cattcatttt atgtttcagg ttcaggggga ggtgtgggag gtttttaaa    7980
gcaagtaaaa cctctacaaa tgtggtatgg ctgattatga tcctctagag tcgcagatct   8040
gctacgtatc aagctgtggc agggaaaccc tctgcctccc ccgtgatgta atacttttgc   8100
aaggaatgcg atgaagtaga gcccgcagtg gccaagtggc tttggtccgt ctcctccacg   8160
gatgcccctc cacggctagt gggcgcatgt aggcggtggg cgtccgccgc ctccagcagc   8220
aggtcataga ggggcaccac gttcttgcac ttcatgctgt acagatgctc catgcctttg   8280
ttactcatgt gtcggatgtg ggagaggatg aggaggagct gggccagccg ctggtgctgc   8340
tgctgcaggg tcaggcctgc cttggccatc aggtggatca aagtgtctgt gatcttgtcc   8400
aggactcggt ggatatggtc cttctcttcc agagacttca gggtgctgga cagaaatgtg   8460
tacactccag aattaagcaa aataatagat ttgaggcaca caaactcctc tccctgcaga   8520
ttcatcatgc ggaaccgaga tgatgtagcc agcagcatgt cgaagatctc caccatgccc   8580
tctacacatt ttccctggtt cctgtccaag agcaagttag gagcaaacag tagcttcact   8640
gggtgctcca tggagcgcca gacgagacca atcatcagga tctctagcca ggcacattct   8700
agaaggtgga cctgatcatg gagggtcaaa tccacaaagc ctggcaccct cttcgcccag   8760
ttgatcatgt gaaccagctc cctgtctgcc aggttggtca gtaagcccat catcgaagct   8820
tcactgaagg gtctggtagg atcatactcg gaatagagta tgggggctc agcatccaac    8880
aaggcactga ccatctggtc ggccgtcagg gacaaggcca ggctgttctt cttagagcgt   8940
ttgatcatga gcgggcttgg ccaaaggttg gcagctctca tgtctccagc agatggctcg   9000
agatcgccat cttccagcag gcgcaccatt gcccctgttt cactatccag gttacggata   9060
tagttcatga caatatttac attggtccag ccaccagctt gcatgatctc cggtattgaa   9120
actccagcgc gggccatatc tcgcgcggct ccgacacggg cactgtgtcc agaccaggcc   9180
aggtatctct gaccagagtc atcctaaaat acacaaacaa ttagaatcag tagtttaaca   9240
cattatacac ttaaaaattt tatatttacc ttagcgccgt aaatcaatcg atgagttgct   9300
tcaaaaatcc cttccagggc gcgagttgat agctggctgg tggcagatgg cgcggcaaca   9360
ccatttttc tgacccggca aaacaggtag ttattcggat catcagctac accagagacg    9420
```

gaaatccatc gctcgaccag tttagtgact cccaggctaa gtgccttctc tacacctgcg 9480
gtgctaacca gcgttttcgt tctgccaata tggattaaca ttctcccacc gtcagtacgt 9540
gagatatctt taaccctgat cctggcaatt tcggctatac gtaacagggt gttataagca 9600
atccccagaa atgccagatt acgtatatcc tggcagcgat cgctattttc catgagtgaa 9660
cggacttggt cgaaatcagt gcgttcgaac gctagagcct gttttgcacg ttcaccggca 9720
tcaacgtttt cttttcggat ccgccgcata accagtgaaa cagcattgct gtcacttggt 9780
cgtggcagcc cggaccgacg atgaagcatg tttagctggc ccaaatgttg ctggatagtt 9840
tttactgcca gaccgcgcgc ttgaagatat agaagataat cgcgaacatc ttcaggttct 9900
gcgggaaacc atttccggtt attcaacttg caccatgccg cccacgaccg gcaaacggac 9960
agaagcattt tccaggtatg ctcagaaaac gcctggcgat ccctgaacat gtccatcagg 10020
ttcttgcgaa cctcatcact cgttgcatcg accggtaatg caggcaaatt ttggtgtacg 10080
gtcagtaaat tggacatggt ggctacgtaa taacttcgta tatggtttct tatacgaagt 10140
tatgcggccg ctttacgagg gtaggaagtg gtacggaaag ttggtataag acaaaagtgt 10200
tgtggaattg ctccaggcga tctgacggtt cactaaacga gctctgcttt tataggcgcc 10260
caccgtacac gcctaaagct tatacgttct ctatcactga tagggagtaa actggatata 10320
cgttctctat cactgatagg gagtaaactg tagatacgtt ctctatcact gatagggagt 10380
aaactggtca tacgttctct atcactgata gggagtaaac tccttatacg ttctctatca 10440
ctgataggga gtaaagtctg catacgttct ctatcactga tagggagtaa actcttcata 10500
cgttctctat cactgatagg gagtaaactc gcggccgcag agaaatgttc tggcacctgc 10560
acttgcactg gggacagcct attttgctag tttgttttgt ttcgttttgt tttgatggag 10620
agcgtatgtt agtactatcg attcacacaa aaaaccaaca cacagatgta atgaaaataa 10680
agatatttta ttggatctgc gatcgctccg gtgcccgtca gtgggcagag cgcacatcgc 10740
ccacagtccc cgagaagttg gggggagggg tcggcaattg aacgggtgcc tagagaaggt 10800
ggcgcggggt aaactgggaa agtgatgtcg tgtactggct ccgccttttt cccgagggtg 10860
ggggagaacc gtatgtaagt gcagtagtcg ccgtgaacgt tctttttcgc aacgggtttg 10920
ccgccagaac acagctgaag cttcgagggg ctcgcatctc tccttcacgc gcccgccgcc 10980
ctacctgagg ccgccatcca cgccggttga gtcgcgttct gccgcctccc gcctgtggtg 11040
cctcctgaac tgcgtccgcc gtctaggtaa gtttaaagct caggtcgaga ccgggccttt 11100
gtccggcgct cccttggagc ctacctagac tcagccggct ctccacgctt tgcctgaccc 11160
tgcttgctca actctacgtc tttgtttcgt tttctgttct gcgccgttac agatccaagc 11220
tgtgaccggc gcctacgcta gcggatccgc cgccaccatg tctagactgg acaagagcaa 11280
agtcataaac tctgctctgg aattactcaa tggagtcggt atcgaaggcc tgacgacaag 11340
gaaactcgct caaaagctgg gagttgagca gcctaccctg tactggcacg tgaagaacaa 11400
gcgggccctg ctcgatgccc tgccaatcga gatgctggac aggcatcata cccactcctg 11460
ccccctggaa ggcgagtcat ggcaagactt tctgcggaac aacgccaagt cataccgctg 11520
tgctcttctc tcacatcgcg acggggctaa agtgcatctc ggcacccgcc caacagagaa 11580
acagtacgaa accctggaaa atcagctcgc gttcctgtgt cagcaaggct tctccctgga 11640
gaacgcactg tacgctctgt ccgccgtggg ccactttaca ctgggctgcg tattggagga 11700
acaggagcat caagtagcaa aagaggaaag agagacacct accaccgatt ctatgccccc 11760
acttctgaaa caagcaattg agctgttcga ccggcaggga gccgaacctg ccttcctttt 11820
cggcctggaa ctaatcatat gtggcctgga gaaacagcta aagtgcgaaa gcggcgggcc 11880
gaccgacgcc cttgacgatt ttgacttaga catgctccca gccgatgccc ttgacgactt 11940
tgaccttgat atgctgcctg ctgacgctct tgacgatttt gaccttgaca tgctccccgg 12000
gtgaaccggt cgctgatcag cctcgactgt gccttctagt tgccagccat ctgttgtttg 12060
cccctccccc gtgccttcct tgaccctgga aggtgccact cccactgtcc tttcctaata 12120
aaatgaggaa attgcatcgc attgtctgag taggtgtcat tctattctgg ggggtggggt 12180
ggggcaggac agcaaggggg aggattggga agacaatagc aggcatgctg gggatgcggt 12240
gggctctatg gcttctgagg cggaaagaac cagctggggc tcgactagag cttgcggaac 12300
ccttagaggg cctatttccc atgattcctt catatttgca tatacgatac aaggctgtta 12360
gagagataat tagaattaat ttgactgtaa acacaaagat attagtacaa aataataact 12420
tcgtataatg tatgctatac gaagttatca gacatgataa gatacattga tgagtttgga 12480
caaaccacaa ctagaatgca gtgaaaaaaa tgctttattt gtgaaatttg tgatgctatt 12540
gctttatttg taaccattat aagctgcaat aaacaaggta cctcaagcgc cgggttttcg 12600
cgtcatgcac cacgtccgtg gtctagaact agtattatgc ccagtacatg accttatggg 12660
actttcctac ttggcagtac atctacgtat tagtcatcgc tattaccatg gtgatgcggt 12720
tttggcagta catcaatggg cgtggatagc ggtttgactc acggggattt ccaagtctcc 12780
accccattga cgtcaatggg agtttgtttt ggcaccaaaa tcaacgggac tttccaaaat 12840
gtcgtaacaa ctccgcccca ttgacgcaaa tgggcggtag gcgtgtacgg tgggaggttt 12900
atataagcag agctcgttta gtgaaccgtc agatcgcctg gagacgccat ccacgctgtt 12960
ttgacctcca tagaagagaa ttcgccgcca ccatgaaaac atttaacatt tctcaacagg 13020
atctagaatt agtagaagta gcgacagaga agattacaat gctttatgag gataataaac 13080
atcatgtggg agcggcaatt cgtacgaaaa caggagaaat catttcggca gtacatattg 13140
aagcgtatat aggacgagta actgtttgtg cagaagccat tgcgattggt agtgcagttt 13200
cgaatggaca aaaggatttt gacacgattg tagctgttag acacccttat tctgacgaag 13260
tagatagaag tattcgagtg gtaagtcctt gtggtatgtg tagggagttg atttcagact 13320
atgcaccaga ttgttttgtg ttaatagaaa tgaatggcaa gttagtcaaa actacgattg 13380
aagaactcat tccactcaaa tatacccgaa attaaaccgg tcgctgatca gcctcgactg 13440
tgccttctag ttgccagcca tctgttgttt gcccctcccc cgtgccttcc ttgaccctgg 13500
aaggtgccac tcccactgtc ctttcctaat aaaatgagga aattgcatcg cattgtctga 13560
gtaggtgtca ttctattctg gggggtgggg tggggcagga cagcaagggg gaggattggg 13620
aagacaatag caggcatgct ggggatgcgg tgggctctat ggcttctgag gcggaaagaa 13680
ccagctgggg ctcgactaga gcttgcggaa cccttagggc ccattggtat ggcttgggaa 13740
aagcgctccc ctacccataa cttcgtataa tgtatgctat acgaagttat tttgcagttt 13800
taaaattatg ttttaaaatg gactatcata tgcttaccgt aacttgaaag tatttcgatt 13860
tcttggcttt atatatcttg tggaaaggac gaaacaccgg gcactcttcc gtgatctggt 13920
ggataaattc gcaagggtat catggcggac gaccgggatt cgaaccccgg atccggccgt 13980
ccgccgtgat ccatgcggtt accgcccgcg tgtcgaaccc aggtgtgcga cgtcagacaa 14040
cgggggagcg ctccttttg ggcccat 14067

<210> SEQ ID NO 30
<211> LENGTH: 13923
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 30
tggtatggct ttttccccgt atccccccag gtgtctgcag gctcaaagag cagcgagaag 60
cgttcagagg aaagcgatcc cgtgccacct tccccgtgcc cgggctgtcc ccgcacgctg 120
ccggctcggg gatgcggggg gagcgccgga ccggagcgga gccccgggcg gctcgctgct 180
gccccctagc gggggaggga cgtaattaca tccctggggg ctttgggggg gggctgtccc 240
tgatatctat aacaagaaaa tatatatata ataagttatc acgtaagtag aacatgaaat 300
aacaatataa ttatcgtatg agttaaatct taaaagtcac gtaaaagata atcatgcgtc 360
attttgactc acgcggtcgt tatagttcaa aatcagtgac acttaccgca ttgacaagca 420
cgcctcacgg gagctccaag cggcgactga gatgtcctaa atgcacagcg acggattcgc 480
gctatttaga aagagagagc aatatttcaa gaatgcatgc gtcaatttta cgcagactat 540
ctttctaggg ttaatctagc tgcatcagga tcatatcgtc gggtcttttt tccggctcag 600
tcatcgccca agctggcgct atctgggcat cggggaggaa gaagcccgtg ccttttcccg 660
cgaggttgaa gcggcatgga aagagtttgc cgaggatgac tgctgctgca ttgacgttga 720
gcgaaaacgc acgtttacca tgatgattcg ggaaggtgtg gccatgcacg cctttaacgg 780
tgaactgttc gttcaggcca cctgggatac cagttcgtcg cggcttttcc ggacacagtt 840
ccggatggtc agcccgaagc gcatcagcaa cccgaacaat accggcgaca gccggaactg 900
ccgtgccggt gtgcagatta atgacagcgg tgcggcgctg ggatattacg tcagcgagga 960
cgggtatcct ggctggatgc cgcagaaatg gacatggata ccccgtgagt tacccggcgg 1020
gcgcgcttgg cgtaatcatg gtcatagctg tttcctgtgt gaaattgtta tccgctcaca 1080
attccacaca acatacgagc cggaagcata aagtgtaaag cctggggtgc ctaatgagtg 1140
agctaactca cattaattgc gttgcgctca ctgcccgctt tccagtcggg aaacctgtcg 1200
tgccagctgc attaatgaat cggccaacgc gcggggagag gcggtttgcg tattgggcgc 1260
tcttccgctt cctcgctcac tgactcgctg cgctcggtcg ttcggctgcg gcgagcggta 1320
tcagctcact caaaggcggt aatacggtta tccacagaat caggggataa cgcaggaaag 1380
aacatgtgag caaaaggcca gcaaaaggcc aggaaccgta aaaaggccgc gttgctggcg 1440
tttttccata ggctccgccc ccctgacgag catcacaaaa atcgacgctc aagtcagagg 1500
tggcgaaacc cgacaggact ataaagatac caggcgtttc cccctggaag ctccctcgtg 1560
cgctctcctg ttccgaccct gccgcttacc ggatacctgt ccgcctttct cccttcggga 1620
agcgtggcgc tttctcatag ctcacgctgt aggtatctca gttcggtgta ggtcgttcgc 1680
tccaagctgg gctgtgtgca cgaacccccc gttcagcccg accgctgcgc cttatccggt 1740
aactatcgtc ttgagtccaa cccggtaaga cacgacttat cgccactggc agcagccact 1800
ggtaacagga ttagcagagc gaggtatgta ggcggtgcta cagagttctt gaagtggtgg 1860
cctaactacg gctacactag aaggacagta tttggtatct gcgctctgct gaagccagtt 1920
accttcggaa aaagagttgg tagctcttga tccggcaaac aaaccaccgc tggtagcggt 1980
ggtttttttg tttgcaagca gcagattacg cgcagaaaaa aaggatctca agaagatcct 2040

-continued ttgatctttt ctacggggtc tgacgctcag tggaacgaaa actcacgtta agggattttg 2100
gtcatgagat tatcaaaaag gatcttcacc tagatccttt taaattaaaa atgaagtttt 2160
aaatcaatct aaagtatata tgagtaaact tggtctgaca gttaccaatg cttaatcagt 2220
gaggcaccta tctcagcgat ctgtctattt cgttcatcca tagttgcctg actccccgtc 2280
gtgtagataa ctacgatacg ggagggctta ccatctggcc ccagtgctgc aatgataccg 2340
cgagacccac gctcaccggc tccagattta tcagcaataa accagccagc cggaagggcc 2400
gagcgcagaa gtggtcctgc aactttatcc gcctccatcc agtctattaa ttgttgccgg 2460
gaagctagag taagtagttc gccagttaat agtttgcgca acgttgttgc cattgctaca 2520
ggcatcgtgg tgtcacgctc gtcgtttggt atggcttcat tcagctccgg ttcccaacga 2580
tcaaggcgag ttacatgatc ccccatgttg tgcaaaaaag cggttagctc cttcggtcct 2640
ccgatcgttg tcagaagtaa gttggccgca gtgttatcac tcatggttat ggcagcactg 2700
cataattctc ttactgtcat gccatccgta agatgctttt ctgtgactgg tgagtactca 2760
accaagtcat tctgagaata gtgtatgcgg cgaccgagtt gctcttgccc ggcgtcaata 2820
cgggataata ccgcgccaca tagcagaact ttaaaagtgc tcatcattgg aaaacgttct 2880
tcggggcgaa aactctcaag gatcttaccg ctgttgagat ccagttcgat gtaacccact 2940
cgtgcaccca actgatcttc agcatctttt actttcacca gcgtttctgg gtgagcaaaa 3000
acaggaaggc aaaatgccgc aaaaaaggga ataagggcga cacggaaatg ttgaatactc 3060
atactcttcc tttttcaata ttattgaagc atttatcagg gttattgtct catgagcgga 3120
tacatatttg aatgtattta gaaaaataaa caaatagggg ttccgcgcac atttccccga 3180
aaagtgccac ctaaattgta agcgttaata ttttgttaaa attcgcgtta aatttttgtt 3240
aaatcagctc attttttaac caataggccg aaatcggcaa aatcccttat aaatcaaaag 3300
aatagaccga gatagggttg agtgttgttc cagtttggaa caagagtcca ctattaaaga 3360
acgtggactc caacgtcaaa gggcgaaaaa ccgtctatca gggcgatggc ccactacgtg 3420
aaccatcacc ctaatcaagt tttttggggt cgaggtgccg taaagcacta aatcggaacc 3480
ctaaagggag cccccgattt agagcttgac ggggaaagcc ggcgaacgtg gcgagaaagg 3540
aagggaagaa agcgaaagga gcgggcgcta gggcgctggc aagtgtagcg gtcacgctgc 3600
gcgtaaccac cacacccgcc gcgcttaatg cgccgctaca gggcgcgtcc cattcgccat 3660
tcaggctgcg caactgttgg gaagggcgat cggtgcgggc ctcttcgcta ttacgccagc 3720
tggcgaaagg gggatgtgct gcaaggcgat taagttgggt aacgccaggg ttttcccagt 3780
cacgacgttg taaaacgacg gccagtgagc gcgcctcgtt cattcacgtt tttgaacccg 3840
tggaggacgg gcagactcgc ggtgcaaatg tgttttacag cgtgatggag cagatgaaga 3900
tgctcgacac gctgcagaac acgcagctag attaacccta gaaagataat catattgtga 3960
cgtacgttaa agataatcat gtgtaaaatt gacgcatgtg ttttatcggt ctgtatatcg 4020
aggtttattt attaatttga atagatatta agttttatta tatttacact tacatactaa 4080
taataaattc aacaaacaat ttatttatgt ttatttattt attaaaaaaa acaaaaactc 4140
aaaatttctt ctataaagta acaaaacttt tatgagggac agcccccccc caaagccccc 4200
agggatgtaa ttacgtccct cccccgctag ggggcagcag cgagccgccc ggggctccgc 4260
tccggtccgg cgctcccccc gcatccccga gccggcagcg tgcggggaca gcccgggcac 4320
ggggaaggtg gcacgggatc gctttcctct gaacgcttct cgctgctctt tgagcctgca 4380
gacacctggg gggatacggg gaaaaggcct ccacggccac tagtccatag agcccaccgc 4440

-continued

```
atccccagca tgcctgctat tgtcttccca atcctccccc ttgctgtcct gccccacccc   4500

acccccctaga atagaatgac acctactcag acaatgcgat gcaatttcct cattttatta   4560

ggaaaggaca gtgggagtgg caccttccag ggtcaaggaa ggcacggggg aggggcaaac   4620

aacagatggc tggcaactag aaggcacagc tacatggggg tagagtcata atcgtgcatc   4680

aggatagggc ggtggtgctg cagcagcgcg cgaataaact gctgccgccg ccgctccgtc   4740

ctgcaggaat acaacatggc agtggtctcc tcagcgatga ttcgcaccgc ccgcagcatg   4800

agacgccttg tcctccgggc acagcagcgc accctgatct cacttaaatc agcacagtaa   4860

ctgcagcaca gcaccacaat attgttcaaa atcccacagt gcaaggcgct gtatccaaag   4920

ctcatggcgg ggaccacaga acccacgtgg ccatcatacc acaagcgcag gtagattaag   4980

tggcgacccc tcataaacac gctggacata aacattacct cttttggcat gttgtaattc   5040

accacctccc ggtaccatat aaacctctga ttaaacatgg cgccatccac caccatccta   5100

aaccagctgg ccaaaacctg cccgccggct atgcactgca gggaaccggg actggaacaa   5160

tgacagtgga gagcccagga ctcgtaacca tggatcatca tgctcgtcat gatatcaatg   5220

ttggcacaac acaggcacac gtgcatacac ttcctcagga ttacaagctc ctcccgcgtc   5280

agaaccatat cccagggaac aacccattcc tgaatcagcg taaatcccac actgcaggga   5340

agacctcgca cgtaactcac gttgtgcatt gtcaaagtgt tacattcggg cagcagcgga   5400

tgatcctcca gtatggtagc gcgggtctct gtctcaaaag gaggtaggcg atccctactg   5460

tacggagtgc gccgagacaa ccgagatcgt gttggtcgta gtgtcatgcc aaatggaacg   5520

ccggacgtag tcatggttgt ggccatatta tcatcgtgtt tttcaaagga aaaccacgtc   5580

cccgtggttc ggggggccta gacgtttttt taacctcgac taaacacatg taaagcatgt   5640

gcaccgaggc cccagatcag atcccataca atggggtacc ttctgggcat ccttcagccc   5700

cttgttgaat acgcttgagg agagccattt gactctttcc acaactatcc aactcacaac   5760

gtggcactgg ggttgtgccg cctttgcagg tgtatcttat acacgtggct tttggccgca   5820

gaggcacctg tcgccaggtg gggggttccg ctgcctgcaa agggtcgcta cagacgttgt   5880

ttgtcttcaa gaagcttcca gaggaactgc ttccttcacg acattcaaca gaccttgcat   5940

tcctttggcg agaggggaaa gacccctagg aatgctcgtc aagaagacag ggccaggttt   6000

ccgggccctc acattgccaa aagacggcaa tatggtggaa aataacatat agacaaacgc   6060

acaccggcct tattccaagc ggcttcggcc agtaacgtta gggggggggg agggagaggg   6120

gcttaaaaat caaaggggtt ctgccgcgca tcactatgcg ccactggcag ggacacgttg   6180

cgatactggt gtttagtgct ccacttaaac tcaggcacaa ccatccgcgg cagctcggtg   6240

aagttttcac tccacaggct gcgcaccatc accaacgcgt ttagcaggtc gggcgccgat   6300

atcttgaagt cgcagttggg gcctccgccc tgcgcgcgcg agttgcgata cacagggttg   6360

cagcactgga acactatcag cgccgggtgg tgcacgctgg ccagcacgct cttgtcggag   6420

atcagatccg cgtccaggtc ctccgcgttg ctcagggcga acggagtcaa ctttggtagc   6480

tgccttccca aaaagggtgc atgcccaggc tttgagttgc actcgcaccg tagtggcatc   6540

agaaggtgac cgtgcccggt ctgggcgtta ggatacagcg cctgcatgaa agccttgatc   6600

tgcttaaaag ccacctgagc ctttgcgcct tcagagaaga acatgccgca agacttgccg   6660

gaaaactgat tggccggaca ggccgcgtca tgcacgcagc accttgcgtc ggtgttggag   6720

atctgcacca catttcggcc ccaccggttc ttcacgatct tggccttgct agactgctcc   6780
```

-continued

```
ttcagcgcgc gctgcccgtt ttcgctcgtc acatccattt caatcacgtg ctccttattt   6840
atcataatgc tcccgtgtag acacttaagc tcgccttcga tctcagcgca gcggtgcagc   6900
cacaacgcgc agcccgtggg ctcgtggtgc ttgtaggtta cctctgcaaa cgactgcagg   6960
tacgcctgca ggaatcgccc catcatcgtc acaaaggtct tgttgctggt gaaggtcagc   7020
tgcaacccgc ggtgctcctc gtttagccag gtcttgcata cggccgccag agcttccact   7080
tggtcaggca gtagcttgaa gtttgccttt agatcgttat ccacgtggta cttgtccatc   7140
aacgcgcgcg cagcctccat gcccttctcc cacgcagaca cgatcggcag gctcagcggg   7200
tttatcaccg tgctttcact ttccgcttca ctggactctt ccttttcctc ttgcgtccgc   7260
ataccccgcg ccactgggtc gtcttcattc agccgccgca ccgtgcgctt acctcccttg   7320
ccgtgcttga ttagcaccgg tgggttgctg aaacccacca tttgtagcgc cacatcttct   7380
ctttcttcct cgctgtccac gatcacctct ggggatggcg ggcgctcggg cttgggagag   7440
gggcgcttct ttttcttttt ggacgcaatg gccaaatccg ccgtcgaggt cgatggccgc   7500
gggctgggtg tgcgcggcac cagcgcatct tgtgacgagt cttcttcgtc ctcggactcg   7560
agacgccgcc tcagccgctt ttttgggggc gcgcgcttgt cgtcatcgtc tttgtagtcg   7620
ggaggcggcg gcgacggcga cggggacgac acgtcctcca tggttggtgg acgtcgcgcc   7680
gcaccgcgtc cgcgctcggg ggtggtttcg cgctgctcct cttcccgact ggccatggtg   7740
gccgaggata acttcgtata tggtttctta tacgaagtta tgatccagac atgataagat   7800
acattgatga gtttggacaa accacaacta gaatgcagtg aaaaaaatgc tttatttgtg   7860
aaatttgtga tgctattgct ttatttgtaa ccattataag ctgcaataaa caagttaaca   7920
acaacaattg cattcatttt atgtttcagg ttcaggggga ggtgtgggag gtttttaaa   7980
gcaagtaaaa cctctacaaa tgtggtatgg ctgattatga tcctctagag tcgcagatct   8040
gctacgtatc aagctgtggc agggaaaccc tctgcctccc ccgtgatgta atacttttgc   8100
aaggaatgcg atgaagtaga gcccgcagtg gccaagtggc tttggtccgt ctcctccacg   8160
gatgcccctc cacggctagt gggcgcatgt aggcggtggg cgtccgccgc ctccagcagc   8220
aggtcataga ggggcaccac gttcttgcac ttcatgctgt acagatgctc catgcctttg   8280
ttactcatgt gtcggatgtg ggagaggatg aggaggagct gggccagccg ctggtgctgc   8340
tgctgcaggg tcaggcctgc cttggccatc aggtggatca aagtgtctgt gatcttgtcc   8400
aggactcggt ggatatggtc cttctcttcc agagacttca gggtgctgga cagaaatgtg   8460
tacactccag aattaagcaa aataatagat ttgaggcaca caaactcctc tccctgcaga   8520
ttcatcatgc ggaaccgaga tgatgtagcc agcagcatgt cgaagatctc caccatgccc   8580
tctacacatt ttccctggtt cctgtccaag agcaagttag gagcaaacag tagcttcact   8640
gggtgctcca tggagcgcca gacgagacca atcatcagga tctctagcca ggcacattct   8700
agaaggtgga cctgatcatg gagggtcaaa tccacaaagc ctggcaccct cttcgcccag   8760
ttgatcatgt gaaccagctc cctgtctgcc aggttggtca gtaagcccat catcgaagct   8820
tcactgaagg gtctggtagg atcatactcg gaatagagta tgggggggctc agcatccaac   8880
aaggcactga ccatctggtc ggccgtcagg gacaaggcca ggctgttctt cttagagcgt   8940
ttgatcatga gcgggcttgg ccaaaggttg gcagctctca tgtctccagc agatggctcg   9000
agatcgccat cttccagcag gcgcaccatt gcccctgttt cactatccag gttacggata   9060
tagttcatga caatatttac attggtccag ccaccagctt gcatgatctc cggtattgaa   9120
actccagcgc gggccatatc tcgcgcggct ccgacacggg cactgtgtcc agaccaggcc   9180
```

```
aggtatctct gaccagagtc atcctaaaat acacaaacaa ttagaatcag tagtttaaca   9240
cattatacac ttaaaaattt tatatttacc ttagcgccgt aaatcaatcg atgagttgct   9300
tcaaaaatcc cttccagggc gcgagttgat agctggctgg tggcagatgg cgcggcaaca   9360
ccatttttc tgacccggca aaacaggtag ttattcggat catcagctac accagagacg   9420
gaaatccatc gctcgaccag tttagtgact cccaggctaa gtgccttctc tacacctgcg   9480
gtgctaacca gcgttttcgt tctgccaata tggattaaca ttctcccacc gtcagtacgt   9540
gagatatctt taaccctgat cctggcaatt tcggctatac gtaacagggt gttataagca   9600
atccccagaa atgccagatt acgtatatcc tggcagcgat cgctattttc catgagtgaa   9660
cggacttggt cgaaatcagt gcgttcgaac gctagagcct gttttgcacg ttcaccggca   9720
tcaacgtttt cttttcggat ccgccgcata accagtgaaa cagcattgct gtcacttggt   9780
cgtggcagcc cggaccgacg atgaagcatg tttagctggc ccaaatgttg ctggatagtt   9840
tttactgcca gaccgcgcgc ttgaagatat agaagataat cgcgaacatc ttcaggttct   9900
gcgggaaacc atttccggtt attcaacttg caccatgccg cccacgaccg gcaaacggac   9960
agaagcattt tccaggtatg ctcagaaaac gcctggcgat ccctgaacat gtccatcagg  10020
ttcttgcgaa cctcatcact cgttgcatcg accggtaatg caggcaaatt ttggtgtacg  10080
gtcagtaaat tggacatggt ggctacgtaa taacttcgta tatggtttct tatacgaagt  10140
tatgcggccg ctttacgagg gtaggaagtg gtacggaaag ttggtataag acaaaagtgt  10200
tgtggaattg ctccaggcga tctgacggtt cactaaacga gctctgcttt tataggcgcc  10260
caccgtacac gcctaaagct tatacgttct ctatcactga tagggagtaa actggatata  10320
cgttctctat cactgatagg gagtaaactg tagatacgtt ctctatcact gatagggagt  10380
aaactggtca tacgttctct atcactgata gggagtaaac tccttatacg ttctctatca  10440
ctgataggga gtaaagtctg catacgttct ctatcactga tagggagtaa actcttcata  10500
cgttctctat cactgatagg gagtaaactc gcggccgcag agaaatgttc tggcacctgc  10560
acttgcactg gggacagcct attttgctag tttgttttgt ttcgttttgt tttgatggag  10620
agcgtatgtt agtactatcg attcacacaa aaaaccaaca cacagatgta atgaaaataa  10680
agatatttta ttggatctgc gatcgctccg gtgcccgtca gtgggcagag cgcacatcgc  10740
ccacagtccc cgagaagttg gggggagggg tcggcaattg aacgggtgcc tagagaaggt  10800
ggcgcggggt aaactgggaa agtgatgtcg tgtactggct ccgccttttt cccgagggtg  10860
ggggagaacc gtatgtaagt gcagtagtcg ccgtgaacgt tctttttcgc aacgggtttg  10920
ccgccagaac acagctgaag cttcgagggg ctcgcatctc tccttcacgc gcccgccgcc  10980
ctacctgagg ccgccatcca cgccggttga gtcgcgttct gccgcctccc gcctgtggtg  11040
cctcctgaac tgcgtccgcc gtctaggtaa gtttaaagct caggtcgaga ccgggccttt  11100
gtccggcgct cccttggagc ctacctagac tcagccggct ctccacgctt tgcctgaccc  11160
tgcttgctca actctacgtc tttgtttcgt tttctgttct gcgccgttac agatccaagc  11220
tgtgaccggc gcctacgcta gcggatccgc cgccaccatg tctagactgg acaagagcaa  11280
agtcataaac tctgctctgg aattactcaa tggagtcggt atcgaaggcc tgacgacaag  11340
gaaactcgct caaaagctgg gagttgagca gcctaccctg tactggcacg tgaagaacaa  11400
gcgggccctg ctcgatgccc tgccaatcga gatgctggac aggcatcata cccactcctg  11460
ccccctggaa ggcgagtcat ggcaagactt tctgcggaac aacgccaagt cataccgctg  11520
```

-continued

```
tgctcttctc tcacatcgcg acggggctaa agtgcatctc ggcacccgcc caacagagaa  11580
acagtacgaa accctggaaa atcagctcgc gttcctgtgt cagcaaggct tctccctgga  11640
gaacgcactg tacgctctgt ccgccgtggg ccactttaca ctgggctgcg tattggagga  11700
acaggagcat caagtagcaa aagaggaaag agagacacct accaccgatt ctatgccccc  11760
acttctgaaa caagcaattg agctgttcga ccggcaggga gccgaacctg ccttcctttt  11820
cggcctggaa ctaatcatat gtggcctgga gaaacagcta aagtgcgaaa gcggcgggcc  11880
gaccgacgcc cttgacgatt ttgacttaga catgctccca gccgatgccc ttgacgactt  11940
tgaccttgat atgctgcctg ctgacgctct tgacgatttt gaccttgaca tgctccccgg  12000
gtgaaccggt cgctgatcag cctcgactgt gccttctagt tgccagccat ctgttgtttg  12060
cccctccccc gtgccttcct tgaccctgga aggtgccact cccactgtcc tttcctaata  12120
aaatgaggaa attgcatcgc attgtctgag taggtgtcat tctattctgg ggggtggggt  12180
ggggcaggac agcaaggggg aggattggga agacaatagc aggcatgctg gggatgcggt  12240
gggctctatg gcttctgagg cggaaagaac cagctggggc tcgactagag cttgcggaac  12300
ccttagaggg cctatttccc atgattcctt catatttgca tatacgatac aaggctgtta  12360
gagagataat tagaattaat ttgactgtaa acacaaagat attagtacaa aataataact  12420
tcgtataatg tatgctatac gaagttatca gacatgataa gatacattga tgagtttgga  12480
caaaccacaa ctagaatgca gtgaaaaaaa tgctttattt gtgaaatttg tgatgctatt  12540
gctttatttg taaccattat aagctgcaat aaacaaggta cctcaagcgc cgggttttcg  12600
cgtcatgcac cacgtccgtg gttcaagcgc cgggttttcg cgtcatgcac cacgtccgtg  12660
ggccctcggg tacttcaacg tcagcagtaa ctgtaaatcc gagccgttca tagaagggca  12720
aattccttgg cgctgacgtt tcaagaaagg ctggcactcc ggctcgttct gcggcttcta  12780
ctccgggcaa taccaccgcg gaaccaaggc cctttccctg atgatcgggg ctaacgccca  12840
cagtagcgag gaaccaagct ggttctttag ggcggtgagg ggcgaggagt ccttccattt  12900
gttgctgagc cgcgagacga gagccactaa gctcagccat tcggggacca atttctgcaa  12960
atacagcccc ggcctcaacg ctctccggag tcgtccacac tgccactgca gccccgtcgt  13020
cggcgaccca aactttaccg atgtccaatc ctaccctggt caaaaaaagt tcttgcaatt  13080
ctgtaacccg ttcaatatgt ctatcaggat caactgtgtg gcgtgtagcg ggataatccg  13140
cgaaagcggc agccaatgtt ctcacggccc tagggacgtc gtctcgagtt gccagtctga  13200
cagtaggttt atattctgtc atggtggcgg cgaattctct tctatggagg tcaaaacagc  13260
gtggatggcg tctccaggcg atctgacggt tcactaaacg agctctgctt atataaacct  13320
cccaccgtac acgcctaccg cccatttgcg tcaatggggc ggagttgtta cgacattttg  13380
gaaagtcccg ttgattttgg tgccaaaaca aactcccatt gacgtcaatg gggtggagac  13440
ttggaaatcc ccgtgagtca aaccgctatc cacgcccatt gatgtactgc caaaaccgca  13500
tcaccatggt aatagcgatg actaatacgt agatgtactg ccaagtagga aagtcccata  13560
aggtcatgta ctgggcataa tactagttct tgggaaaagc gctcccctac ccataacttc  13620
gtataatgta tgctatacga agttattttg cagttttaaa attatgtttt aaaatggact  13680
atcatatgct taccgtaact tgaaagtatt tcgatttctt ggctttatat atcttgtgga  13740
aaggacgaaa caccgggcac tcttccgtga tctggtggat aaattcgcaa gggtatcatg  13800
gcggacgacc gggattcgaa ccccggatcc ggccgtccgc cgtgatccat gcggttaccg  13860
cccgcgtgtc gaacccaggt gtgcgacgtc agacaacggg ggagcgctcc tttttgggcc  13920
```

cat 13923

<210> SEQ ID NO 31
<211> LENGTH: 14372
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 31
actcttcctt tttcaatatt attgaagcat ttatcagggt tattgtctca tgagcggata 60
catatttgaa tgtatttaga aaaataaaca aataggggtt ccgcgcacat ttccccgaaa 120
agtgccacct aaattgtaag cgttaatatt ttgttaaaat tcgcgttaaa tttttgttaa 180
atcagctcat tttttaacca ataggccgaa atcggcaaaa tcccttataa atcaaaagaa 240
tagaccgaga tagggttgag tgttgttcca gtttggaaca agagtccact attaaagaac 300
gtggactcca acgtcaaagg gcgaaaaacc gtctatcagg gcgatggccc actacgtgaa 360
ccatcaccct aatcaagttt tttggggtcg aggtgccgta aagcactaaa tcggaaccct 420
aaagggagcc cccgatttag agcttgacgg ggaaagccgg cgaacgtggc gagaaaggaa 480
gggaagaaag cgaaaggagc gggcgctagg gcgctggcaa gtgtagcggt cacgctgcgc 540
gtaaccacca cacccgccgc gcttaatgcg ccgctacagg gcgcgtccca ttcgccattc 600
aggctgcgca actgttggga agggcgatcg gtgcgggcct cttcgctatt acgccagctg 660
gcgaaagggg gatgtgctgc aaggcgatta agttgggtaa cgccagggtt ttcccagtca 720
cgacgttgta aaacgacggc cagtgagcgc gcctcgttca ttcacgtttt tgaacccgtg 780
gaggacgggc agactcgcgg tgcaaatgtg ttttacagcg tgatggagca gatgaagatg 840
ctcgacacgc tgcagaacac gcagctagat taaccctaga aagataatca tattgtgacg 900
tacgttaaag ataatcatgt gtaaaattga cgcatgtgtt ttatcggtct gtatatcgag 960
gtttatttat taatttgaat agatattaag ttttattata tttacactta catactaata 1020
ataaattcaa caaacaattt atttatgttt atttatttat taaaaaaaac aaaaactcaa 1080
aatttcttct ataaagtaac aaaactttta tgagggacag ccccccccca aagcccccag 1140
ggatgtaatt acgtccctcc cccgctaggg ggcagcagcg agccgcccgg ggctccgctc 1200
cggtccggcg ctccccccgc atccccgagc cggcagcgtg cggggacagc ccgggcacgg 1260
ggaaggtggc acgggatcgc tttcctctga acgcttctcg ctgctctttg agcctgcaga 1320
cacctggggg gatacgggga aaaggcctcc acggccacta gtccatagag cccaccgcat 1380
ccccagcatg cctgctattg tcttcccaat cctcccctt gctgtcctgc cccaccccac 1440
cccctagaat agaatgacac ctactcagac aatgcgatgc aatttcctca ttttattagg 1500
aaaggacagt gggagtggca ccttccaggg tcaaggaagg cacgggggag gggcaaacaa 1560
cagatggctg gcaactagaa ggcacagcta catgggggta gagtcataat cgtgcatcag 1620
gatagggcgg tggtgctgca gcagcgcgcg aataaactgc tgccgccgcc gctccgtcct 1680
gcaggaatac aacatggcag tggtctcctc agcgatgatt cgcaccgccc gcagcatgag 1740
acgccttgtc ctccgggcac agcagcgcac cctgatctca cttaaatcag cacagtaact 1800
gcagcacagc accacaatat tgttcaaaat cccacagtgc aaggcgctgt atccaaagct 1860
catggcgggg accacagaac ccacgtggcc atcataccac aagcgcaggt agattaagtg 1920

-continued

```
gcgacccctc ataaacacgc tggacataaa cattacctct tttggcatgt tgtaattcac   1980
cacctcccgg taccatataa acctctgatt aaacatggcg ccatccacca ccatcctaaa   2040
ccagctggcc aaaacctgcc cgccggctat gcactgcagg gaaccgggac tggaacaatg   2100
acagtggaga gcccaggact cgtaaccatg gatcatcatg ctcgtcatga tatcaatgtt   2160
ggcacaacac aggcacacgt gcatacactt cctcaggatt acaagctcct cccgcgtcag   2220
aaccatatcc cagggaacaa cccattcctg aatcagcgta aatcccacac tgcagggaag   2280
acctcgcacg taactcacgt tgtgcattgt caaagtgtta cattcgggca gcagcggatg   2340
atcctccagt atggtagcgc gggtctctgt ctcaaaagga ggtaggcgat ccctactgta   2400
cggagtgcgc cgagacaacc gagatcgtgt tggtcgtagt gtcatgccaa atggaacgcc   2460
ggacgtagtc atggttgtgg ccatattatc atcgtgtttt tcaaaggaaa accacgtccc   2520
cgtggttcgg ggggcctaga cgttttttta acctcgacta aacacatgta aagcatgtgc   2580
accgaggccc cagatcagat cccatacaat ggggtacctt ctgggcatcc ttcagcccct   2640
tgttgaatac gcttgaggag agccatttga ctctttccac aactatccaa ctcacaacgt   2700
ggcactgggg ttgtgccgcc tttgcaggtg tatcttatac acgtggcttt tggccgcaga   2760
ggcacctgtc gccaggtggg gggttccgct gcctgcaaag ggtcgctaca gacgttgttt   2820
gtcttcaaga agcttccaga ggaactgctt ccttcacgac attcaacaga ccttgcattc   2880
ctttggcgag aggggaaaga cccctaggaa tgctcgtcaa gaagacaggg ccaggtttcc   2940
gggccctcac attgccaaaa gacggcaata tggtggaaaa taacatatag acaaacgcac   3000
accggcctta ttccaagcgg cttcggccag taacgttagg ggggggggag ggagaggggc   3060
ttaaaaatca aaggggttct gccgcgcatc actatgcgcc actggcaggg acacgttgcg   3120
atactggtgt ttagtgctcc acttaaactc aggcacaacc atccgcggca gctcggtgaa   3180
gttttcactc cacaggctgc gcaccatcac caacgcgttt agcaggtcgg gcgccgatat   3240
cttgaagtcg cagttggggc ctccgccctg cgcgcgcgag ttgcgataca cagggttgca   3300
gcactggaac actatcagcg ccgggtggtg cacgctggcc agcacgctct tgtcggagat   3360
cagatccgcg tccaggtcct ccgcgttgct cagggcgaac ggagtcaact ttggtagctg   3420
ccttcccaaa aagggtgcat gcccaggctt tgagttgcac tcgcaccgta gtggcatcag   3480
aaggtgaccg tgcccggtct gggcgttagg atacagcgcc tgcatgaaag ccttgatctg   3540
cttaaaagcc acctgagcct ttgcgccttc agagaagaac atgccgcaag acttgccgga   3600
aaactgattg gccggacagg ccgcgtcatg cacgcagcac cttgcgtcgg tgttggagat   3660
ctgcaccaca tttcggcccc accggttctt cacgatcttg gccttgctag actgctcctt   3720
cagcgcgcgc tgcccgtttt cgctcgtcac atccatttca atcacgtgct ccttatttat   3780
cataatgctc ccgtgtagac acttaagctc gccttcgatc tcagcgcagc ggtgcagcca   3840
caacgcgcag cccgtgggct cgtggtgctt gtaggttacc tctgcaaacg actgcaggta   3900
cgcctgcagg aatcgcccca tcatcgtcac aaaggtcttg ttgctggtga aggtcagctg   3960
caacccgcgg tgctcctcgt ttagccaggt cttgcatacg gccgccagag cttccacttg   4020
gtcaggcagt agcttgaagt ttgcctttag atcgttatcc acgtggtact tgtccatcaa   4080
cgcgcgcgca gcctccatgc ccttctccca cgcagacacg atcggcaggc tcagcgggtt   4140
tatcaccgtg ctttcacttt ccgcttcact ggactcttcc ttttcctctt gcgtccgcat   4200
accccgcgcc actgggtcgt cttcattcag ccgccgcacc gtgcgcttac ctcccttgcc   4260
gtgcttgatt agcaccggtg ggttgctgaa acccaccatt tgtagcgcca catcttctct   4320
```

```
ttcttcctcg ctgtccacga tcacctctgg ggatggcggg cgctcgggct tgggagaggg   4380
gcgcttcttt ttctttttgg acgcaatggc caaatccgcc gtcgaggtcg atggccgcgg   4440
gctgggtgtg cgcggcacca gcgcatcttg tgacgagtct tcttcgtcct cggactcgag   4500
acgccgcctc agccgctttt ttgggggcgc gcgcttgtcg tcatcgtctt tgtagtcggg   4560
aggcggcggc gacggcgacg gggacgacac gtcctccatg gttggtggac gtcgcgccgc   4620
accgcgtccg cgctcggggg tggtttcgcg ctgctcctct tcccgactgg ccatggtggc   4680
cgaggataac ttcgtatatg gtttcttata cgaagttatg atccagacat gataagatac   4740
attgatgagt ttggacaaac cacaactaga atgcagtgaa aaaaatgctt tatttgtgaa   4800
atttgtgatg ctattgcttt atttgtaacc attataagct gcaataaaca agttaacaac   4860
aacaattgca ttcattttat gtttcaggtt caggggagg tgtgggaggt tttttaaagc   4920
aagtaaaacc tctacaaatg tggtatggct gattatgatc ctctagagtc gcagatctgc   4980
tacgtatcaa gctgtggcag ggaaaccctc tgcctccccc gtgatgtaat acttttgcaa   5040
ggaatgcgat gaagtagagc ccgcagtggc caagtggctt tggtccgtct cctccacgga   5100
tgcccctcca cggctagtgg gcgcatgtag gcggtgggcg tccgccgcct ccagcagcag   5160
gtcatagagg ggcaccacgt tcttgcactt catgctgtac agatgctcca tgcctttgtt   5220
actcatgtgt cggatgtggg agaggatgag gaggagctgg gccagccgct ggtgctgctg   5280
ctgcagggtc aggcctgcct tggccatcag gtggatcaaa gtgtctgtga tcttgtccag   5340
gactcggtgg atatggtcct tctcttccag agacttcagg gtgctggaca gaaatgtgta   5400
cactccagaa ttaagcaaaa taatagattt gaggcacaca aactcctctc cctgcagatt   5460
catcatgcgg aaccgagatg atgtagccag cagcatgtcg aagatctcca ccatgccctc   5520
tacacatttt ccctggttcc tgtccaagag caagttagga gcaaacagta gcttcactgg   5580
gtgctccatg gagcgccaga cgagaccaat catcaggatc tctagccagg cacattctag   5640
aaggtggacc tgatcatgga gggtcaaatc cacaaagcct ggcaccctct tcgcccagtt   5700
gatcatgtga accagctccc tgtctgccag gttggtcagt aagcccatca tcgaagcttc   5760
actgaagggt ctggtaggat catactcgga atagagtatg gggggctcag catccaacaa   5820
ggcactgacc atctggtcgg ccgtcaggga caaggccagg ctgttcttct tagagcgttt   5880
gatcatgagc gggcttggcc aaaggttggc agctctcatg tctccagcag atggctcgag   5940
atcgccatct tccagcaggc gcaccattgc ccctgtttca ctatccaggt tacggatata   6000
gttcatgaca atatttacat tggtccagcc accagcttgc atgatctccg gtattgaaac   6060
tccagcgcgg gccatatctc gcgcggctcc gacacgggca ctgtgtccag accaggccag   6120
gtatctctga ccagagtcat cctaaaatac acaaacaatt agaatcagta gtttaacaca   6180
ttatacactt aaaaatttta tatttacctt agcgccgtaa atcaatcgat gagttgcttc   6240
aaaaatccct tccagggcgc gagttgatag ctggctggtg gcagatggcg cggcaacacc   6300
attttttctg acccggcaaa acaggtagtt attcggatca tcagctacac cagagacgga   6360
aatccatcgc tcgaccagtt tagtgactcc caggctaagt gccttctcta cacctgcggt   6420
gctaaccagc gttttcgttc tgccaatatg gattaacatt ctcccaccgt cagtacgtga   6480
gatatcttta accctgatcc tggcaatttc ggctatacgt aacagggtgt tataagcaat   6540
ccccagaaat gccagattac gtatatcctg gcagcgatcg ctattttcca tgagtgaacg   6600
gacttggtcg aaatcagtgc gttcgaacgc tagagcctgt tttgcacgtt caccggcatc   6660
```

```
aacgttttct tttcggatcc gccgcataac cagtgaaaca gcattgctgt cacttggtcg   6720
tggcagcccg gaccgacgat gaagcatgtt tagctggccc aaatgttgct ggatagtttt   6780
tactgccaga ccgcgcgctt gaagatatag aagataatcg cgaacatctt caggttctgc   6840
gggaaaccat ttccggttat tcaacttgca ccatgccgcc cacgaccggc aaacggacag   6900
aagcatttc caggtatgct cagaaaacgc ctggcgatcc ctgaacatgt ccatcaggtt   6960
cttgcgaacc tcatcactcg ttgcatcgac cggtaatgca ggcaaatttt ggtgtacggt   7020
cagtaaattg gacatggtgg ctacgtaata acttcgtata tggtttctta tacgaagtta   7080
tgcggccgct ttacgagggt aggaagtggt acggaaagtt ggtataagac aaaagtgttg   7140
tggaattgct ccaggcgatc tgacggttca ctaaacgagc tctgctttta taggcgccca   7200
ccgtacacgc ctaaagctta tacgttctct atcactgata gggagtaaac tggatatacg   7260
ttctctatca ctgataggga gtaaactgta gatacgttct ctatcactga tagggagtaa   7320
actggtcata cgttctctat cactgatagg gagtaaactc cttatacgtt ctctatcact   7380
gatagggagt aaagtctgca tacgttctct atcactgata gggagtaaac tcttcatacg   7440
ttctctatca ctgataggga gtaaactcgc ggccgcagag aaatgttctg gcacctgcac   7500
ttgcactggg gacagcctat tttgctagtt tgttttgttt cgttttgttt tgatggagag   7560
cgtatgttag tactatcgat tcacacaaaa aaccaacaca cagatgtaat gaaaataaag   7620
atattttatt ggatctgcga tcgctccggt gcccgtcagt gggcagagcg cacatcgccc   7680
acagtccccg agaagttggg gggaggggtc ggcaattgaa cgggtgccta gagaaggtgg   7740
cgcggggtaa actgggaaag tgatgtcgtg tactggctcc gcctttttcc cgagggtggg   7800
ggagaaccgt atgtaagtgc agtagtcgcc gtgaacgttc tttttcgcaa cgggtttgcc   7860
gccagaacac agctgaagct tcgaggggct cgcatctctc cttcacgcgc ccgccgccct   7920
acctgaggcc gccatccacg ccggttgagt cgcgttctgc cgcctcccgc ctgtggtgcc   7980
tcctgaactg cgtccgccgt ctaggtaagt ttaaagctca ggtcgagacc gggcctttgt   8040
ccggcgctcc cttggagcct acctagactc agccggctct ccacgctttg cctgaccctg   8100
cttgctcaac tctacgtctt tgtttcgttt tctgttctgc gccgttacag atccaagctg   8160
tgaccggcgc ctacgctagc ggatccgccg ccaccatgtc tagactggac aagagcaaag   8220
tcataaactc tgctctggaa ttactcaatg gagtcggtat cgaaggcctg acgacaagga   8280
aactcgctca aaagctggga gttgagcagc ctaccctgta ctggcacgtg aagaacaagc   8340
gggccctgct cgatgccctg ccaatcgaga tgctggacag gcatcatacc cactcctgcc   8400
ccctggaagg cgagtcatgg caagactttc tgcggaacaa cgccaagtca taccgctgtg   8460
ctcttctctc acatcgcgac ggggctaaag tgcatctcgg cacccgccca acagagaaac   8520
agtacgaaac cctggaaaat cagctcgcgt tcctgtgtca gcaaggcttc tccctggaga   8580
acgcactgta cgctctgtcc gccgtgggcc actttacact gggctgcgta ttggaggaac   8640
aggagcatca agtagcaaaa gaggaaagag agacacctac caccgattct atgcccccac   8700
ttctgaaaca agcaattgag ctgttcgacc ggcagggagc cgaacctgcc ttccttttcg   8760
gcctggaact aatcatatgt ggcctggaga aacagctaaa gtgcgaaagc ggcgggccga   8820
ccgacgccct tgacgatttt gacttagaca tgctcccagc cgatgccctt gacgactttg   8880
accttgatat gctgcctgct gacgctcttg acgattttga ccttgacatg ctccccgggt   8940
gaaccggtcg ctgatcagcc tcgactgtgc cttctagttg ccagccatct gttgtttgcc   9000
cctcccccgt gccttccttg accctggaag gtgccactcc cactgtcctt tcctaataaa   9060
```

atgaggaaat tgcatcgcat tgtctgagta ggtgtcattc tattctgggg ggtggggtgg 9120
ggcaggacag caagggggag gattgggaag acaatagcag gcatgctggg gatgcggtgg 9180
gctctatggc ttctgaggcg gaaagaacca gctggggctc gactagagct tgcggaaccc 9240
ttagagggcc tatttcccat ggtggtagaa ctagtattat gcccagtaca tgaccttatg 9300
ggactttcct acttggcagt acatctacgt attagtcatc gctattacca tggtgatgcg 9360
gttttggcag tacatcaatg ggcgtggata gcggtttgac tcacggggat ttccaagtct 9420
ccaccccatt gacgtcaatg ggagtttgtt ttggcaccaa aatcaacggg actttccaaa 9480
atgtcgtaac aactccgccc cattgacgca aatgggcggt aggcgtgtac ggtgggaggt 9540
ttatataagc agagctcgtt tagtgaaccg tcagatcgcc tggagacgcc atccacgctg 9600
ttttgacctc catagaagag aattcgccgc caccatgaca gaatataaac ctactgtcag 9660
actggcaact cgagacgacg tccctagggc cgtgagaaca ttggctgccg ctttcgcgga 9720
ttatcccgct acacgccaca cagttgatcc tgatagacat attgaacggg ttacagaatt 9780
gcaagaactt tttttgacca gggtaggatt ggacatcggt aaagtttggg tcgccgacga 9840
cggggctgca gtggcagtgt ggacgactcc ggagagcgtt gaggccgggg ctgtatttgc 9900
agaaattggt ccccgaatgg ctgagcttag tggctctcgt ctcgcggctc agcaacaaat 9960
ggaaggactc ctcgcccctc accgccctaa agaaccagct tggttcctcg ctactgtggg 10020
cgttagcccc gatcatcagg gaaagggcct tggttccgcg gtggtattgc ccggagtaga 10080
agccgcagaa cgagccggag tgccagcctt tcttgaaacg tcagcgccaa ggaatttgcc 10140
cttctatgaa cggctcggat ttacagttac tgctgacgtt gaagtacccg agggcccacg 10200
gacgtggtgc atgacgcgaa aacccggcgc ttgagtttaa accgctgatc agcctcgact 10260
gtgccttcta gttgccagcc atctgttgtt tgcccctccc ccgtgccttc cttgaccctg 10320
gaaggtgcca ctcccactgt cctttcctaa taaaatgagg aaattgcatc gcattgtctg 10380
agtaggtgtc attctattct ggggggtggg gtggggcagg acagcaaggg ggaggattgg 10440
gaagacaata gcaggcatgc tggggatgcg gtgggctcta tggcttctga ggcggaaaga 10500
accagctggg gctcgactag agcttgcgga acccttagtt taaacgggcc cttaattaat 10560
cgatgtagga tgttgcccct cctgacgcgg taggagaagg ggagggtgcc ctgcatgtct 10620
gccgctgctc ttgctcttgc cgctgctgag gaggggggcg catctgccgc agcaccggat 10680
gcatctggga aaagcaaaaa aggggctcgt ccctgtttcc ggaggaattt gcaagcgggg 10740
tcttgcatga cggggaggca aacccccgtt cgccgcagtc cggccggccc gagactcgaa 10800
ccgggggtcc tgcgactcaa cccttggaaa ataaccctcc ggctacaggg agcgagccac 10860
ttaatgcttt cgctttccag cctaaccgct tacgccgcgc gcggccagtg gccaaaaaag 10920
ctagcgcagc agccgccgcg cctggaagga agccaaaagg agcgctcccc cgttgtctga 10980
cgtcgcacac ctgggttcga cacgcgggcg gtaaccgcat ggatcacggc ggacggccgg 11040
atccggggtt cgaaccccgg tcgtccgcca tgataccctt gcgaatttat ccaccagacc 11100
acggaagagt gcccgcttac aggctctcct tttgcacggt ctagagcgtc aacgactgcg 11160
cacgcctcac cggccagagc gtcccgacca tggagcactt tttgccgctg cgcaacatct 11220
ggaaccgcgt ccgcgacttt ccgcgcgcct ccaccaccgc cgccggcatc acctggatgt 11280
ccaggtacat ctacggatta cggggcccat tggtatggct tttccccgt atccccccag 11340
gtgtctgcag gctcaaagag cagcgagaag cgttcagagg aaagcgatcc cgtgccacct 11400

-continued

```
tccccgtgcc cgggctgtcc ccgcacgctg ccggctcggg gatgcggggg gagcgccgga  11460
ccggagcgga gccccgggcg gctcgctgct gccccctagc gggggaggga cgtaattaca  11520
tccctggggg ctttgggggg gggctgtccc tgatatctat aacaagaaaa tatatatata  11580
ataagttatc acgtaagtag aacatgaaat aacaatataa ttatcgtatg agttaaatct  11640
taaaagtcac gtaaaagata atcatgcgtc attttgactc acgcggtcgt tatagttcaa  11700
aatcagtgac acttaccgca ttgacaagca cgcctcacgg gagctccaag cggcgactga  11760
gatgtcctaa atgcacagcg acggattcgc gctatttaga aagagagagc aatatttcaa  11820
gaatgcatgc gtcaatttta cgcagactat ctttctaggg ttaatctagc tgcatcagga  11880
tcatatcgtc gggtcttttt tccggctcag tcatcgccca agctggcgct atctgggcat  11940
cggggaggaa gaagcccgtg ccttttcccg cgaggttgaa gcggcatgga aagagtttgc  12000
cgaggatgac tgctgctgca ttgacgttga gcgaaaacgc acgtttacca tgatgattcg  12060
ggaaggtgtg gccatgcacg cctttaacgg tgaactgttc gttcaggcca cctgggatac  12120
cagttcgtcg cggcttttcc ggacacagtt ccggatggtc agcccgaagc gcatcagcaa  12180
cccgaacaat accggcgaca gccggaactg ccgtgccggt gtgcagatta atgacagcgg  12240
tgcggcgctg ggatattacg tcagcgagga cgggtatcct ggctggatgc cgcagaaatg  12300
gacatggata ccccgtgagt tacccggcgg gcgcgcttgg cgtaatcatg gtcatagctg  12360
tttcctgtgt gaaattgtta tccgctcaca attccacaca acatacgagc cggaagcata  12420
aagtgtaaag cctggggtgc ctaatgagtg agctaactca cattaattgc gttgcgctca  12480
ctgcccgctt tccagtcggg aaacctgtcg tgccagctgc attaatgaat cggccaacgc  12540
gcggggagag gcggtttgcg tattgggcgc tcttccgctt cctcgctcac tgactcgctg  12600
cgctcggtcg ttcggctgcg gcgagcggta tcagctcact caaaggcggt aatacggtta  12660
tccacagaat caggggataa cgcaggaaag aacatgtgag caaaaggcca gcaaaaggcc  12720
aggaaccgta aaaaggccgc gttgctggcg tttttccata ggctccgccc ccctgacgag  12780
catcacaaaa atcgacgctc aagtcagagg tggcgaaacc cgacaggact ataaagatac  12840
caggcgtttc cccctggaag ctccctcgtg cgctctcctg ttccgaccct gccgcttacc  12900
ggatacctgt ccgcctttct cccttcggga agcgtggcgc tttctcatag ctcacgctgt  12960
aggtatctca gttcggtgta ggtcgttcgc tccaagctgg gctgtgtgca cgaacccccc  13020
gttcagcccg accgctgcgc cttatccggt aactatcgtc ttgagtccaa cccggtaaga  13080
cacgacttat cgccactggc agcagccact ggtaacagga ttagcagagc gaggtatgta  13140
ggcggtgcta cagagttctt gaagtggtgg cctaactacg gctacactag aaggacagta  13200
tttggtatct gcgctctgct gaagccagtt accttcggaa aaagagttgg tagctcttga  13260
tccggcaaac aaaccaccgc tggtagcggt ggtttttttg tttgcaagca gcagattacg  13320
cgcagaaaaa aaggatctca agaagatcct ttgatctttt ctacggggtc tgacgctcag  13380
tggaacgaaa actcacgtta agggattttg gtcatgagat tatcaaaaag gatcttcacc  13440
tagatccttt taaattaaaa atgaagtttt aaatcaatct aaagtatata tgagtaaact  13500
tggtctgaca gttaccaatg cttaatcagt gaggcaccta tctcagcgat ctgtctattt  13560
cgttcatcca tagttgcctg actccccgtc gtgtagataa ctacgatacg ggagggctta  13620
ccatctggcc ccagtgctgc aatgataccg cgagacccac gctcaccggc tccagattta  13680
tcagcaataa accagccagc cggaagggcc gagcgcagaa gtggtcctgc aactttatcc  13740
gcctccatcc agtctattaa ttgttgccgg gaagctagag taagtagttc gccagttaat  13800
```

```
agtttgcgca acgttgttgc cattgctaca ggcatcgtgg tgtcacgctc gtcgtttggt  13860

atggcttcat tcagctccgg ttcccaacga tcaaggcgag ttacatgatc ccccatgttg  13920

tgcaaaaaag cggttagctc cttcggtcct ccgatcgttg tcagaagtaa gttggccgca  13980

gtgttatcac tcatggttat ggcagcactg cataattctc ttactgtcat gccatccgta  14040

agatgctttt ctgtgactgg tgagtactca accaagtcat tctgagaata gtgtatgcgg  14100

cgaccgagtt gctcttgccc ggcgtcaata cgggataata ccgcgccaca tagcagaact  14160

ttaaaagtgc tcatcattgg aaaacgttct tcggggcgaa aactctcaag gatcttaccg  14220

ctgttgagat ccagttcgat gtaacccact cgtgcaccca actgatcttc agcatctttt  14280

actttcacca gcgtttctgg gtgagcaaaa acaggaaggc aaaatgccgc aaaaaaggga  14340

ataagggcga cacggaaatg ttgaatactc at                                14372


<210> SEQ ID NO 32
<211> LENGTH: 11646
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 32

actcttcctt tttcaatatt attgaagcat ttatcagggt tattgtctca tgagcggata     60

catatttgaa tgtatttaga aaaataaaca aataggggtt ccgcgcacat ttccccgaaa    120

agtgccacct aaattgtaag cgttaatatt ttgttaaaat tcgcgttaaa tttttgttaa    180

atcagctcat tttttaacca ataggccgaa atcggcaaaa tcccttataa atcaaaagaa    240

tagaccgaga tagggttgag tgttgttcca gtttggaaca agagtccact attaaagaac    300

gtggactcca acgtcaaagg gcgaaaaacc gtctatcagg gcgatggccc actacgtgaa    360

ccatcaccct aatcaagttt tttggggtcg aggtgccgta aagcactaaa tcggaaccct    420

aaagggagcc cccgatttag agcttgacgg ggaaagccgg cgaacgtggc gagaaaggaa    480

gggaagaaag cgaaaggagc gggcgctagg gcgctggcaa gtgtagcggt cacgctgcgc    540

gtaaccacca cacccgccgc gcttaatgcg ccgctacagg gcgcgtccca ttcgccattc    600

aggctgcgca actgttggga agggcgatcg gtgcgggcct cttcgctatt acgccagctg    660

gcgaaagggg gatgtgctgc aaggcgatta agttgggtaa cgccagggtt ttcccagtca    720

cgacgttgta aaacgacggc cagtgagcgc gcctcgttca ttcacgtttt tgaacccgtg    780

gaggacgggc agactcgcgg tgcaaatgtg ttttacagcg tgatggagca gatgaagatg    840

ctcgacacgc tgcagaacac gcagctagat taaccctaga aagataatca tattgtgacg    900

tacgttaaag ataatcatgt gtaaaattga cgcatgtgtt ttatcggtct gtatatcgag    960

gtttatttat taatttgaat agatattaag ttttattata tttacactta catactaata   1020

ataaattcaa caaacaattt atttatgttt atttatttat taaaaaaaac aaaaactcaa   1080

aatttcttct ataaagtaac aaaactttta tggagggggtg gagtcgtgac gtgaattacg  1140

tcatagggtt agggaggtcc tgtattagag gtcacgtgag tgttttgcga cattttgcga   1200

caccatgtgg tcacgctggg tatttaagcc cgagtgagca cgcagggtct ccattttgaa   1260

gcgggaggtt tgaacgcgca gccgccatgc cggggtttta cgagattgtg attaaggtcc   1320

ccagcgacct tgacgagcat ctgcccggca tttctgacag ctttgtgaac tgggtggccg   1380
```

```
agaaggaatg ggagttgccg ccagattctg acatggatct gaatctgatt gagcaggcac   1440
ccctgaccgt ggccgagaag ctgcagcgcg actttctgac ggaatggcgc cgtgtgagta   1500
aggccccgga ggccctttc tttgtgcaat ttgagaaggg agagagctac ttccacatgc   1560
acgtgctcgt ggaaaccacc ggggtgaaat ccatggtttt gggacgtttc ctgagtcaga   1620
ttcgcgaaaa actgattcag agaatttacc gcgggatcga gccgactttg ccaaactggt   1680
tcgcggtcac aaagaccaga aatggcgccg gaggcgggaa caaggtggtg gatgagtgct   1740
acatccccaa ttacttgctc cccaaaaccc agcctgagct ccagtgggcg tggactaata   1800
tggaacagta tttaagcgcc tgtttgaatc tcacggagcg taaacggttg gtggcgcagc   1860
atctgacgca cgtgtcgcag acgcaggagc agaacaaaga gaatcagaat cccaattctg   1920
atgcgccggt gatcagatca aaaacttcag ccaggtacat ggagctggtc gggtggctcg   1980
tggacaaggt gagtttgggg acccttgatt gttctttctt tttcgctatt gtaaaattca   2040
tgttatatgg agggggcaaa gttttcaggg tgttgtttag aatgggaaga tgtcccttgt   2100
atcaccatgg accctcatga taattttgtt tctttcactt tctactctgt tgacaaccgt   2160
tgtctcctct tattttcttt tcattttctg taactttttc gttaaacttt agcttgcatt   2220
tgtaacgaat ttttaaattc acttttgttt atttgtcaga ttgtaagtac tttctctaat   2280
cacttttttt tcaaggcaat cagggtatat tatattgtac ttcagcacag ttttagagaa   2340
cataacttcg tataaagtat actatacgaa gttatcgggc ccctctgcta accatgttca   2400
tgccttcttc tttttcctac agatgtcaga actcattaaa gagaatatgc acatgaagct   2460
gtatatggaa ggtactgtag acaaccacca tttcaaatgc acgtccgaag gtgaggggaa   2520
gccatacgag ggtacccaaa ctatgcgcat caaagtggtt gagggtggcc ccctgccatt   2580
cgcattcgac atcctggcaa ctagctttct ttacggttcc aagacattca taaatcatac   2640
ccagggtatt cccgatttct tcaaacaatc cttcccggaa gggtttactt gggagcgggt   2700
cacgacatat gaagacgggg gtgttcttac agccacacag gatacgagtt tgcaagacgg   2760
ttgtcttatc tataacgtga agattcgggg tgtgaatttc acatccaatg gcccggtgat   2820
gcagaaaaaa acactgggct gggaagcatt tacggagacg ttgtatcccg ccgatggagg   2880
tctcgagggc cgaaacgata tggccctcaa gttggtaggt ggttctcacc ttatagcaaa   2940
cattaagacc acgtatcgat caaaaaaacc cgctaagaat ctgaaaatgc caggcgtgta   3000
ttatgttgat tacagactgg agcgaataaa agaggctaac aatgagacct acgtcgaaca   3060
gcatgaagtc gctgtagcta gatattgcga cctcccgtca aagttgggcc ataaattgaa   3120
ttaacctcag gtgcaggctg cctatcagaa ggtggtggct ggtgtggcca atgccctggc   3180
tcacaaatac cactgagatc tttttccctc tgccaaaaat tatggggaca tcatgaagcc   3240
ccttgagcat ctgacttctg gctaataaag gaaatttatt ttcattgcaa tagtgtgttg   3300
gaattttttg tgtctctcac tcggaaggac atatgggagg gcaaatcatt taaaacatca   3360
gaatgagtat ttggtttaga gtttggcaac atatgcccat atgctggctg ccatgaacaa   3420
aggttggcta taaagaggtc atcagtatat gaaacagccc cctgctgtcc attccttatt   3480
ccatagaaaa gccttgactt gaggttagat ttttttttata ttttgttttg tgttattttt   3540
ttctttaaca tccctaaaat tttccttaca tgttttacta gccagatttt tcctcctctc   3600
ctgactactc ccagtcatag ctgtccctct tctcttatgg agatcataac ttcgtataaa   3660
gtatactata cgaagttata attgttataa ttaaatgata aggtagaata tttctgcata   3720
taaattctgg ctggcgtgga aatattctta ttggtagaaa caactacacc ctggtcatca   3780
```

```
tcctgccttt ctctttatgg ttacaatgat atacactgtt tgagatgagg ataaaatact   3840
ctgagtccaa accgggcccc tctgctaacc atgttcatgc cttcttcttt ttcctacagg   3900
ggattacctc ggagaagcag tggatccagg aggaccaggc ctcatacatc tccttcaatg   3960
cggcctccaa ctcgcggtcc caaatcaagg ctgccttgga caatgcggga aagattatga   4020
gcctgactaa aaccgccccc gactacctgg tgggccagca gcccgtggag gacatttcca   4080
gcaatcggat ttataaaatt ttggaactaa acgggtacga tccccaatat gcggcttccg   4140
tctttctggg atgggccacg aaaaagttcg gcaagaggaa caccatctgg ctgtttgggc   4200
ctgcaactac cgggaagacc aacatcgcgg aggccatagc ccacactgtg cccttctacg   4260
ggtgcgtaaa ctggaccaat gagaactttc ccttcaacga ctgtgtcgac aagatggtga   4320
tctggtggga ggaggggaag atgaccgcca aggtcgtgga gtcggccaaa gccattctcg   4380
gaggaagcaa ggtgcgcgtg gaccagaaat gcaagtcctc ggcccagata gacccgactc   4440
ccgtgatcgt cacctccaac accaacatgt gcgccgtgat tgacgggaac tcaacgacct   4500
tcgaacacca gcagccgttg caagaccgga tgttcaaatt tgaactcacc cgccgtctgg   4560
atcatgactt tgggaaggtc accaagcagg aagtcaaaga ctttttccgg tgggcaaagg   4620
atcacgtggt tgaggtggag catgaattct acgtcaaaaa gggtggagcc aagaaaagac   4680
ccgcccccag tgacgcagat ataagtgagc ccaaacgggt gcgcgagtca gttgcgcagc   4740
catcgacgtc agacgcggaa gcttcgatca actacgcaga caggtaccaa aacaaatgtt   4800
ctcgtcacgt gggcatgaat ctgatgctgt ttccctgcag acaatgcgag agaatgaatc   4860
agaattcaaa tatctgcttc actcacggac agaaagactg tttagagtgc tttcccgtgt   4920
cagaatctca acccgtttct gtcgtcaaaa aggcgtatca gaaactgtgc tacattcatc   4980
atatcatggg aaaggtgcca gacgcttgca ctgcctgcga tctggtcaat gtggatttgg   5040
atgactgcat ctttgaacaa taaatgattt gtaaataaat ttagtagtca tgtcttttgt   5100
tgatcaccct ccagattggt tggaagaagt tggtgaaggt cttcgcgagt tttgggcct    5160
tgaagcgggc ccaccgaaac caaaacccaa tcagcagcat caagatcaag cccgtggtct   5220
tgtgctgcct ggttataact atctcggacc cggaaacggt ctcgatcgag gagagcctgt   5280
caacagggca gacgaggtcg cgcgagagca cgacatctcg tacaacgagc agcttgaggc   5340
gggagacaac ccctacctca agtacaacca cgcggacgcc gagtttcagg agaagctcgc   5400
cgacgacaca tccttcgggg gaaacctcgg aaaggcagtc tttcaggcca agaaaagggt   5460
tctcgaacct tttggcctgg ttgaagaggg tgctaagacg gcccctaccg gaaagcggat   5520
agacgaccac tttccaaaaa gaaagaaggc tcggaccgaa gaggactcca agccttccac   5580
ctcgtcagac gccgaagctg gacccagcgg atcccagcag ctgcaaatcc cagcccaacc   5640
agcctcaagt ttgggagctg atacaatgtc tgcgggaggt ggcggcccat tgggcgacaa   5700
taaccaaggt gccgatggag tgggcaatgc ctcgggagat tggcattgcg attccacgtg   5760
gatgggggac agagtcgtca ccaagtccac ccgaacctgg gtgctgccca gctacaacaa   5820
ccaccagtac cgagagatca aaagcggctc cgtcgacgga agcaacgcca acgcctactt   5880
tggatacagc accccctggg ggtactttga ctttaaccgc ttccacagcc actggagccc   5940
ccgagactgg caaagactca tcaacaacta ctggggcttc agaccccggt ccctcagagt   6000
caaaatcttc aacattcaag tcaaagaggt cacggtgcag gactccacca ccaccatcgc   6060
caacaacctc acctccaccg tccaagtgtt tacggacgac gactaccagc tgccctacgt   6120
```

-continued

```
cgtcggcaac gggaccgagg gatgcctgcc ggccttccct ccgcaggtct ttacgctgcc   6180
gcagtacggt tacgcgacgc tgaaccgcga caacacagaa aatcccaccg agaggagcag   6240
cttcttctgc ctagagtact ttcccagcaa gatgctgaga acgggcaaca actttgagtt   6300
tacctacaac tttgaggagg tgcccttcca ctccagcttc gctcccagtc agaacctgtt   6360
caagctggcc aacccgctgg tggaccagta cttgtaccgc ttcgtgagca caaataacac   6420
tggcggagtc cagttcaaca agaacctggc cgggagatac gccaacacct acaaaaactg   6480
gttcccgggg cccatgggcc gaacccaggg ctggaacctg ggctccgggg tcaaccgcgc   6540
cagtgtcagc gccttcgcca cgaccaatag gatggagctc gagggcgcga gttaccaggt   6600
gcccccgcag ccgaacggca tgaccaacaa cctccagggc agcaacacct atgccctgga   6660
gaacactatg atcttcaaca gccagccggc gaacccgggc accaccgcca cgtacctcga   6720
gggcaacatg ctcatcacca gcgagagcga gacgcagccg gtgaaccgcg tggcgtacaa   6780
cgtcggcggg cagatggcca ccaacaacca gagctccacc actgcccccg cgaccggcac   6840
gtacaacctc caggaaatcg tgcccggcag cgtgtggatg gagagggacg tgtacctcca   6900
aggacccatc tgggccaaga tcccagagac gggggcgcac tttcacccct ctccggccat   6960
gggcggattc ggactcaaac acccaccgcc catgatgctc atcaagaaca cgcctgtgcc   7020
cggaaatatc accagcttct cggacgtgcc cgtcagcagc ttcatcaccc agtacagcac   7080
cgggcaggtc accgtggaga tggagtggga gctcaagaag gaaaactcca agaggtggaa   7140
cccagagatc cagtacacaa acaactacaa cgacccccag tttgtggact ttgccccgga   7200
cagcaccggg gaatacagaa ccaccagacc tatcggaacc cgatacctta cccgacccct   7260
ttaattgctt gttaatcaat aaaccgttta attcgtttca gttgaacttt ggtctctgcg   7320
tatttctttc ttatctagtt tccatggcta cgtagataag tagcatggcg ggttaatcat   7380
taactacagc ccgggcgttt aaacagcggg cggagggggtg gagtcgtgac gtgaattacg   7440
tcatagggtt agggaggtcc tgtattagag gtcacgtgag tgttttgcga cattttgcga   7500
caccatgtgg tccgcggccg caaggatctg cgatcgctcc ggtgcccgtc agtgggcaga   7560
gcgcacatcg cccacagtcc ccgagaagtt ggggggaggg gtcggcaatt gaacgggtgc   7620
ctagagaagg tggcgcgggg taaactggga aagtgatgtc gtgtactggc tccgcctttt   7680
tcccgagggt gggggagaac cgtatataag tgcagtagtc gccgtgaacg ttcttttttcg   7740
caacgggttt gccgccagaa cacagctgaa gcttcgaggg gctcgcatct ctccttcacg   7800
cgcccgccgc cctacctgag gccgccatcc acgccggttg agtcgcgttc tgccgcctcc   7860
cgcctgtggt gcctcctgaa ctgcgtccgc cgtctaggta agtttaaagc tcaggtcgag   7920
accgggcctt tgtccggcgc tcccttggag cctacctaga ctcagccggc tctccacgct   7980
ttgcctgacc ctgcttgctc aactctacgt ctttgtttcg ttttctgttc tgcgccgtta   8040
cagatccaag ctgtgaccgg cgcctacgat atcgccacca tgattaagat cgctacgcgg   8100
aagtacctgg ggaaacagaa cgtctacgac ataggtgtgg agcgcgatca caactttgct   8160
ctgaaaaatg gatttatcgc cagcaactgt agggagttga tttcagacta tgcaccagat   8220
tgttttgtgt taatagaaat gaatggcaag ttagtcaaaa ctacgattga agaactcatt   8280
ccactcaaat atacccgaaa ttaagtgcat gacccgcaag cccggtgcct gaaatcaacc   8340
tctggattac aaaatttgtg aaagattgac tggtattctt aactatgttg ctccttttac   8400
gctatgtgga tacgctgctt taatgccttt gtatcatgcg ttaactaaac ttgtttattg   8460
cagcttataa tggttacaaa taaagcaata gcatcacaaa tttcacaaat aaagcatttt   8520
```

```
tttcactgca ttctagttgt ggtttgtcca aactcatcaa tgtatcttat catgtctgga   8580
attgactcaa atgatgtcaa ttagtctatc agaagctcat ctggtctccc ttccggggga   8640
caagacatcc ctgtttaata tttaaacagc agtgttccca aactgggttc ttatatccct   8700
tgctctggtc aaccaggttg cagggtttcc tgtcctcaca ggaacgaagt ccctaaagaa   8760
acagtggcag ccaggtttag ccccggaatt gactggattc ctttttaggg gcccattggt   8820
atggcgatat ctataacaag aaaatatata tataataagt tatcacgtaa gtagaacatg   8880
aaataacaat ataattatcg tatgagttaa atcttaaaag tcacgtaaaa gataatcatg   8940
cgtcattttg actcacgcgg tcgttatagt tcaaaatcag tgacacttac cgcattgaca   9000
agcacgcctc acgggagctc caagcggcga ctgagatgtc ctaaatgcac agcgacggat   9060
tcgcgctatt tagaaagaga gagcaatatt tcaagaatgc atgcgtcaat tttacgcaga   9120
ctatctttct agggttaatc tagctgcatc aggatcatat cgtcgggtct tttttccggc   9180
tcagtcatcg cccaagctgg cgctatctgg gcatcgggga ggaagaagcc cgtgcctttt   9240
cccgcgaggt tgaagcggca tggaaagagt ttgccgagga tgactgctgc tgcattgacg   9300
ttgagcgaaa acgcacgttt accatgatga ttcgggaagg tgtggccatg cacgccttta   9360
acggtgaact gttcgttcag gccacctggg ataccagttc gtcgcggctt ttccggacac   9420
agttccggat ggtcagcccg aagcgcatca gcaacccgaa caataccggc gacagccgga   9480
actgccgtgc cggtgtgcag attaatgaca gcggtgcggc gctgggatat tacgtcagcg   9540
aggacgggta tcctggctgg atgccgcaga aatggacatg gataccccgt gagttacccg   9600
gcgggcgcgc ttggcgtaat catggtcata gctgtttcct gtgtgaaatt gttatccgct   9660
cacaattcca cacaacatac gagccggaag cataaagtgt aaagcctggg gtgcctaatg   9720
agtgagctaa ctcacattaa ttgcgttgcg ctcactgccc gctttccagt cgggaaacct   9780
gtcgtgccag ctgcattaat gaatcggcca acgcgcgggg agaggcggtt tgcgtattgg   9840
gcgctcttcc gcttcctcgc tcactgactc gctgcgctcg gtcgttcggc tgcggcgagc   9900
ggtatcagct cactcaaagg cggtaatacg gttatccaca gaatcagggg ataacgcagg   9960
aaagaacatg tgagcaaaag gccagcaaaa ggccaggaac cgtaaaaagg ccgcgttgct  10020
ggcgtttttc cataggctcc gcccccctga cgagcatcac aaaaatcgac gctcaagtca  10080
gaggtggcga aacccgacag gactataaag ataccaggcg tttccccctg gaagctccct  10140
cgtgcgctct cctgttccga ccctgccgct taccggatac ctgtccgcct ttctcccttc  10200
gggaagcgtg gcgctttctc atagctcacg ctgtaggtat ctcagttcgg tgtaggtcgt  10260
tcgctccaag ctgggctgtg tgcacgaacc ccccgttcag cccgaccgct gcgccttatc  10320
cggtaactat cgtcttgagt ccaacccggt aagacacgac ttatcgccac tggcagcagc  10380
cactggtaac aggattagca gagcgaggta tgtaggcggt gctacagagt tcttgaagtg  10440
gtggcctaac tacggctaca ctagaaggac agtatttggt atctgcgctc tgctgaagcc  10500
agttaccttc ggaaaaagag ttggtagctc ttgatccggc aaacaaacca ccgctggtag  10560
cggtggtttt tttgtttgca agcagcagat tacgcgcaga aaaaaaggat ctcaagaaga  10620
tcctttgatc ttttctacgg ggtctgacgc tcagtggaac gaaaactcac gttaagggat  10680
tttggtcatg agattatcaa aaaggatctt cacctagatc cttttaaatt aaaaatgaag  10740
ttttaaatca atctaaagta tatatgagta aacttggtct gacagttacc aatgcttaat  10800
cagtgaggca cctatctcag cgatctgtct atttcgttca tccatagttg cctgactccc  10860
```

cgtcgtgtag ataactacga tacgggaggg cttaccatct ggccccagtg ctgcaatgat 10920
accgcgagac ccacgctcac cggctccaga tttatcagca ataaaccagc cagccggaag 10980
ggccgagcgc agaagtggtc ctgcaacttt atccgcctcc atccagtcta ttaattgttg 11040
ccgggaagct agagtaagta gttcgccagt taatagtttg cgcaacgttg ttgccattgc 11100
tacaggcatc gtggtgtcac gctcgtcgtt tggtatggct tcattcagct ccggttccca 11160
acgatcaagg cgagttacat gatcccccat gttgtgcaaa aaagcggtta gctccttcgg 11220
tcctccgatc gttgtcagaa gtaagttggc cgcagtgtta tcactcatgg ttatggcagc 11280
actgcataat tctcttactg tcatgccatc cgtaagatgc ttttctgtga ctggtgagta 11340
ctcaaccaag tcattctgag aatagtgtat gcggcgaccg agttgctctt gcccggcgtc 11400
aatacgggat aataccgcgc cacatagcag aactttaaaa gtgctcatca ttggaaaacg 11460
ttcttcgggg cgaaaactct caaggatctt accgctgttg agatccagtt cgatgtaacc 11520
cactcgtgca cccaactgat cttcagcatc ttttactttc accagcgttt ctgggtgagc 11580
aaaaacagga aggcaaaatg ccgcaaaaaa gggaataagg gcgacacgga aatgttgaat 11640
actcat 11646

<210> SEQ ID NO 33
<211> LENGTH: 8190
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 33
actcttcctt tttcaatatt attgaagcat ttatcagggt tattgtctca tgagcggata 60
catatttgaa tgtatttaga aaaataaaca aataggggtt ccgcgcacat ttccccgaaa 120
agtgccacct aaattgtaag cgttaatatt ttgttaaaat tcgcgttaaa tttttgttaa 180
atcagctcat tttttaacca ataggccgaa atcggcaaaa tcccttataa atcaaaagaa 240
tagaccgaga tagggttgag tgttgttcca gtttggaaca agagtccact attaaagaac 300
gtggactcca acgtcaaagg gcgaaaaacc gtctatcagg gcgatggccc actacgtgaa 360
ccatcaccct aatcaagttt tttggggtcg aggtgccgta aagcactaaa tcggaaccct 420
aaagggagcc cccgatttag agcttgacgg ggaaagccgg cgaacgtggc gagaaaggaa 480
gggaagaaag cgaaaggagc gggcgctagg gcgctggcaa gtgtagcggt cacgctgcgc 540
gtaaccacca cacccgccgc gcttaatgcg ccgctacagg gcgcgtccca ttcgccattc 600
aggctgcgca actgttggga agggcgatcg gtgcgggcct cttcgctatt acgccagctg 660
gcgaaagggg gatgtgctgc aaggcgatta agttgggtaa cgccagggtt ttcccagtca 720
cgacgttgta aaacgacggc cagtgagcgc gcctcgttca ttcacgtttt tgaacccgtg 780
gaggacgggc agactcgcgg tgcaaatgtg ttttacagcg tgatggagca gatgaagatg 840
ctcgacacgc tgcagaacac gcagctagat taaccctaga aagataatca tattgtgacg 900
tacgttaaag ataatcatgt gtaaaattga cgcatgtgtt ttatcggtct gtatatcgag 960
gtttatttat taatttgaat agatattaag ttttattata tttacactta catactaata 1020
ataaattcaa caaacaattt atttatgttt atttatttat taaaaaaaac aaaaactcaa 1080
aatttcttct ataaagtaac aaaactttta tttctttcct gcgttatccc ctgattctgt 1140
ggataaccgt attaccgcct ttgagtgagc tgataccgct cgccgcagcc gaacgaccga 1200

-continued

```
gcgcagcgag tcagtgagcg aggaagcgga agagcgccca atacgcaaac cgcctctccc   1260
cgcgcgttgg ccgattcatt aatgcagctg gcacgacagg tttcccgact ggaaagcggg   1320
cagtgagcgc aacgcaatta atgtgagtta gctcactcat taggcacccc aggctttaca   1380
ctttatgctt ccggctcgta tgttgtgtgg aattgtgagc ggataacaat ttcacacagg   1440
aaacagctat gaccatgatt acgccaagct tttggccact ccctctctgc gcgctcgctc   1500
gctcactgag gccgggcgac caaaggtcgc ccgacgcccg ggctttgccc gggcggcctc   1560
agtgagcgag cgagcgcgca gagagggagt ggccaactcc atcactaggg gttcctctgc   1620
agccgcgacc ggccaaggtt taatgatagg ctgcaacggg atgttgggaa tatgttgcac   1680
tggtccgtga gggtaccaac ttgtttattg cagcttataa tggttacaaa taaagcaata   1740
gcatcacaaa tttcacaaat aaagcatttt tttcactgca ttctagttgt ggtttgtcca   1800
aactcatcaa tgtatcttat catgtctgac cggttcactt gagctcgaga tctgagtact   1860
tgtacagctc gtccatgccg agagtgatcc cggcggcggt cacgaactcc agcaggacca   1920
tgtgatcgcg cttctcgttg gggtctttgc tcagggcgga ctgggtgctc aggtagtggt   1980
tgtcgggcag cagcacgggg ccgtcgccga tgggggtgtt ctgctggtag tggtcggcga   2040
gctgcacgct gccgtcctcg atgttgtggc ggatcttgaa gttcaccttg atgccgttct   2100
tctgcttgtc ggccatgata tagacgttgt ggctgttgta gttgtactcc agcttgtgcc   2160
ccaggatgtt gccgtcctcc ttgaagtcga tgcccttcag ctcgatgcgg ttcaccaggg   2220
tgtcgccctc gaacttcacc tcggcgcggg tcttgtagtt gccgtcgtcc ttgaagaaga   2280
tggtgcgctc ctggacgtag ccttcgggca tggcggactt gaagaagtcg tgctgcttca   2340
tgtggtcggg gtagcggctg aagcactgca cgccgtaggt cagggtggtc acgagggtgg   2400
gccagggcac gggcagcttg ccggtggtgc agatgaactt cagggtcagc ttgccgtagg   2460
tggcatcgcc ctcgccctcg ccggacacgc tgaacttgtg gccgtttacg tcgccgtcca   2520
gctcgaccag gatgggcacc accccggtga acagctcctc gcccttgctc accatggtgg   2580
cggcttaagg gttcgatcct ctagagtccg gaggctggat cggtcccggt gtctactatg   2640
gaggtcaaaa cagcgtggat ggcgtctcca ggcgatctga cggttcacta aacgagctct   2700
gcttatatag acctcccacc gtacacgcct accgcccatt tgcgtcaatg gggcggagtt   2760
gttacgacat tttggaaagt cccgttgatt ttggtgccaa aacaaactcc cattgacgtc   2820
aatggggtgg agacttggaa atccccgtga gtcaaaccgc tatccacgcc cattgatgta   2880
ctgccaaaac cgcatcacca tggtaatagc gatgactaat acgtagatgt actgccaagt   2940
aggaaagtcc cataaggtca tgtactgggc ataatgccag gcgggccatt taccgtcatt   3000
gacgtcaata gggggcgtac ttggcatatg atacacttga tgtactgcca agtgggcagt   3060
ttaccgtaaa tactccaccc attgacgtca atggaaagtc cctattggcg ttactatggg   3120
aacatacgtc attattgacg tcaatgggcg ggggtcgttg ggcggtcagc caggcgggcc   3180
atttaccgta agttatgtaa cgcggaactc catatatggg ctatgaacta atgaccccgt   3240
aattgattac tattaataac tagtcaataa tcaatgtcaa cgcgtatggt acctgcggag   3300
gatgccgagg ataaccttgt tactagcctc cgcctggccg ttggactgtg gataatatgg   3360
cgtagaggat cctctgcgcg ctcgctcgct cactgaggcc gcccgggcaa agcccgggcg   3420
tcgggcgacc tttggtcgcc cggcctcagt gagcgagcga gcgcgcagag aattcactgg   3480
ccgtcgtttt acaacgtcgt gactgggaaa accctggcgt tacccaactt aatcgccttg   3540
```

```
cagcacatcc ccctttcgcc agctggcgta atagcgaaga ggcccgcacc gatcgccctt   3600
cccaacagtt gcgcagcctg aatggcgaat ggtctagagc tagcgaattc gaatttaaat   3660
cggatccgcg gccgcaagga tctgcgatcg ctccggtgcc cgtcagtggg cagagcgcac   3720
atcgcccaca gtccccgaga agttgggggg aggggtcggc aattgaacgg gtgcctagag   3780
aaggtggcgc ggggtaaact gggaaagtga tgtcgtgtac tggctccgcc tttttcccga   3840
gggtggggga gaaccgtata taagtgcagt agtcgccgtg aacgttcttt ttcgcaacgg   3900
gtttgccgcc agaacacagc tgaagcttcg aggggctcgc atctctcctt cacgcgcccg   3960
ccgccctacc tgaggccgcc atccacgccg gttgagtcgc gttctgccgc ctcccgcctg   4020
tggtgcctcc tgaactgcgt ccgccgtcta ggtaagttta aagctcaggt cgagaccggg   4080
cctttgtccg gcgctccctt ggagcctacc tagactcagc cggctctcca cgctttgcct   4140
gaccctgctt gctcaactct acgtctttgt ttcgttttct gttctgcgcc gttacagatc   4200
caagctgtga ccggcgccta cgatatcgcc accatgaaaa catttaacat ttctcaacag   4260
gatctagaat tagtagaagt agcgacagag aagattacaa tgctttatga ggataataaa   4320
catcatgtgg gagcggcaat tcgtacgaaa acaggagaaa tcatttcggc agtacatatt   4380
gaagcgtata taggacgagt aactgtttgt gcagaagcca ttgcgattgg tagtgcagtt   4440
tcgaatggac aaaaggattt tgacacgatt gtagctgtta gacaccctta ttctgacgaa   4500
gtagatagaa gtattcgagt ggtaagtcct tgtggtatgt gcctttcata cgagaccgag   4560
atcctgactg tcgagtacgg attgcttcct atcggcaaaa tcgtggagaa gaggattgaa   4620
tgtaccgtct attcagtcga taataatggg aacatctaca cacagcccgt ggctcaatgg   4680
cacgacagag gagagcagga agtttttgaa tactgtctcg aggacggatc cctcatccgc   4740
gctactaaag atcataagtt tatgaccgtg gacggccaga tgctgccaat tgacgaaatt   4800
tttgaacgag agctggatct gatgagagtc gacaaccttc caaactgagt gcatgacccg   4860
caagcccggt gcctgaaatc aacctctgga ttacaaaatt tgtgaaagat tgactggtat   4920
tcttaactat gttgctcctt ttacgctatg tggatacgct gctttaatgc ctttgtatca   4980
tgcgttaact aaacttgttt attgcagctt ataatggtta caaataaagc aatagcatca   5040
caaatttcac aaataaagca tttttttcac tgcattctag ttgtggtttg tccaaactca   5100
tcaatgtatc ttatcatgtc tggaattgac tcaaatgatg tcaattagtc tatcagaagc   5160
tatctggtct cccttccggg ggacaagaca tccctgttta atatttaaac agcagtgttc   5220
ccaaactggg ttcttatatc ccttgctctg gtcaaccagg ttgcagggtt tcctgtcctc   5280
acaggaacga agtccctaaa gaaacagtgg cagccaggtt tagccccgga attgactgga   5340
ttcctttttt agggcccatt ggtatggctg atatctataa caagaaaata tatatataat   5400
aagttatcac gtaagtagaa catgaaataa caatataatt atcgtatgag ttaaatctta   5460
aaagtcacgt aaaagataat catgcgtcat tttgactcac gcggtcgtta tagttcaaaa   5520
tcagtgacac ttaccgcatt gacaagcacg cctcacggga gctccaagcg gcgactgaga   5580
tgtcctaaat gcacagcgac ggattcgcgc tatttagaaa gagagagcaa tatttcaaga   5640
atgcatgcgt caattttacg cagactatct ttctagggtt aatctagctg catcaggatc   5700
atatcgtcgg gtcttttttc cggctcagtc atcgcccaag ctggcgctat ctgggcatcg   5760
gggaggaaga agcccgtgcc ttttcccgcg aggttgaagc ggcatggaaa gagtttgccg   5820
aggatgactg ctgctgcatt gacgttgagc gaaaacgcac gtttaccatg atgattcggg   5880
aaggtgtggc catgcacgcc tttaacggtg aactgttcgt tcaggccacc tgggatacca   5940
```

gttcgtcgcg gcttttccgg acacagttcc ggatggtcag cccgaagcgc atcagcaacc 6000
cgaacaatac cggcgacagc cggaactgcc gtgccggtgt gcagattaat gacagcggtg 6060
cggcgctggg atattacgtc agcgaggacg ggtatcctgg ctggatgccg cagaaatgga 6120
catggatacc ccgtgagtta cccggcgggc gcgcttggcg taatcatggt catagctgtt 6180
tcctgtgtga aattgttatc cgctcacaat tccacacaac atacgagccg gaagcataaa 6240
gtgtaaagcc tggggtgcct aatgagtgag ctaactcaca ttaattgcgt tgcgctcact 6300
gcccgctttc cagtcgggaa acctgtcgtg ccagctgcat taatgaatcg gccaacgcgc 6360
ggggagaggc ggtttgcgta ttgggcgctc ttccgcttcc tcgctcactg actcgctgcg 6420
ctcggtcgtt cggctgcggc gagcggtatc agctcactca aaggcggtaa tacggttatc 6480
cacagaatca ggggataacg caggaaagaa catgtgagca aaaggccagc aaaaggccag 6540
gaaccgtaaa aaggccgcgt tgctggcgtt tttccatagg ctccgccccc ctgacgagca 6600
tcacaaaaat cgacgctcaa gtcagaggtg gcgaaacccg acaggactat aaagatacca 6660
ggcgtttccc cctggaagct ccctcgtgcg ctctcctgtt ccgaccctgc cgcttaccgg 6720
atacctgtcc gcctttctcc cttcgggaag cgtggcgctt tctcatagct cacgctgtag 6780
gtatctcagt tcggtgtagg tcgttcgctc caagctgggc tgtgtgcacg aaccccccgt 6840
tcagcccgac cgctgcgcct tatccggtaa ctatcgtctt gagtccaacc cggtaagaca 6900
cgacttatcg ccactggcag cagccactgg taacaggatt agcagagcga ggtatgtagg 6960
cggtgctaca gagttcttga agtggtggcc taactacggc tacactagaa ggacagtatt 7020
tggtatctgc gctctgctga agccagttac cttcggaaaa agagttggta gctcttgatc 7080
cggcaaacaa accaccgctg gtagcggtgg tttttttgtt tgcaagcagc agattacgcg 7140
cagaaaaaaa ggatctcaag aagatccttt gatcttttct acggggtctg acgctcagtg 7200
gaacgaaaac tcacgttaag ggattttggt catgagatta tcaaaaagga tcttcaccta 7260
gatcctttta aattaaaaat gaagttttaa atcaatctaa agtatatatg agtaaacttg 7320
gtctgacagt taccaatgct taatcagtga ggcacctatc tcagcgatct gtctatttcg 7380
ttcatccata gttgcctgac tccccgtcgt gtagataact acgatacggg agggcttacc 7440
atctggcccc agtgctgcaa tgataccgcg agacccacgc tcaccggctc cagatttatc 7500
agcaataaac cagccagccg gaagggccga gcgcagaagt ggtcctgcaa ctttatccgc 7560
ctccatccag tctattaatt gttgccggga agctagagta agtagttcgc cagttaatag 7620
tttgcgcaac gttgttgcca ttgctacagg catcgtggtg tcacgctcgt cgtttggtat 7680
ggcttcattc agctccggtt cccaacgatc aaggcgagtt acatgatccc ccatgttgtg 7740
caaaaaagcg gttagctcct tcggtcctcc gatcgttgtc agaagtaagt tggccgcagt 7800
gttatcactc atggttatgg cagcactgca taattctctt actgtcatgc catccgtaag 7860
atgcttttct gtgactggtg agtactcaac caagtcattc tgagaatagt gtatgcggcg 7920
accgagttgc tcttgcccgg cgtcaatacg ggataatacc gcgccacata gcagaacttt 7980
aaaagtgctc atcattggaa aacgttcttc ggggcgaaaa ctctcaagga tcttaccgct 8040
gttgagatcc agttcgatgt aacccactcg tgcacccaac tgatcttcag catcttttac 8100
tttcaccagc gtttctgggt gagcaaaaac aggaaggcaa aatgccgcaa aaaagggaat 8160
aagggcgaca cggaaatgtt gaatactcat 8190

<210> SEQ ID NO 34

<211> LENGTH: 4639
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 34

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt ctctgcgcgc tcgctcgctc    420
actgaggccg ggcgaccaaa ggtcgcccga cgcccgggct ttgcccgggc ggcctcagtg    480
agcgagcgag cgcgcagagg atcctctacg ccatattatc cacagtccaa cggccaggcg    540
gaggctagta acaaggttat cctcggcatc ctccgcaggt accatacgcg ttgacattga    600
ttattgacta gttattaata gtaatcaatt acggggtcat tagttcatag cccatatatg    660
gagttccgcg ttacataact tacggtaaat ggcccgcctg gctgaccgcc caacgacccc    720
cgcccattga cgtcaataat gacgtatgtt cccatagtaa cgccaatagg gactttccat    780
tgacgtcaat gggtggagta tttacggtaa actgcccact tggcagtaca tcaagtgtat    840
catatgccaa gtacgccccc tattgacgtc aatgacggta aatggcccgc ctggcattat    900
gcccagtaca tgaccttatg ggactttcct acttggcagt acatctacgt attagtcatc    960
gctattacca tggtgatgcg gttttggcag tacatcaatg ggcgtggata gcggtttgac   1020
tcacggggat ttccaagtct ccaccccatt gacgtcaatg ggagtttgtt ttggcaccaa   1080
aatcaacggg actttccaaa atgtcgtaac aactccgccc cattgacgca aatgggcggt   1140
aggcgtgtac ggtgggaggt ctatataagc agagctcgtt tagtgaaccg tcagatcgcc   1200
tggagacgcc atccacgctg ttttgacctc catagtagac accgggaccg atccagcctc   1260
cggactctag aggatcgaac ccttaagccg ccaccatggt gagcaagggc gaggagctgt   1320
tcaccggggt ggtgcccatc ctggtcgagc tggacggcga cgtaaacggc cacaagttca   1380
gcgtgtccgg cgagggcgag ggcgatgcca cctacggcaa gctgaccctg aagttcatct   1440
gcaccaccgg caagctgccc gtgccctggc ccaccctcgt gaccaccctg acctacggcg   1500
tgcagtgctt cagccgctac cccgaccaca tgaagcagca cgacttcttc aagtccgcca   1560
tgcccgaagg ctacgtccag gagcgcacca tcttcttcaa ggacgacggc aactacaaga   1620
cccgcgccga ggtgaagttc gagggcgaca ccctggtgaa ccgcatcgag ctgaagggca   1680
tcgacttcaa ggaggacggc aacatcctgg ggcacaagct ggagtacaac tacaacagcc   1740
acaacgtcta tatcatggcc gacaagcaga agaacggcat caaggtgaac ttcaagatcc   1800
gccacaacat cgaggacggc agcgtgcagc tcgccgacca ctaccagcag aacaccccca   1860
tcggcgacgg ccccgtgctg ctgcccgaca accactacct gagcacccag tccgccctga   1920
gcaaagaccc caacgagaag cgcgatcaca tggtcctgct ggagttcgtg accgccgccg   1980
ggatcactct cggcatggac gagctgtaca agtactcaga tctcgagctc aagtgaaccg   2040
gtcagacatg ataagataca ttgatgagtt tggacaaacc acaactagaa tgcagtgaaa   2100
```

```
aaaatgcttt atttgtgaaa tttgtgatgc tattgcttta tttgtaacca ttataagctg   2160
caataaacaa gttggtaccc tcacggacca gtgcaacata ttcccaacat cccgttgcag   2220
cctatcatta aaccttggcc ggtcgcggct gcagaggaac ccctagtgat ggagttggcc   2280
actccctctc tgcgcgctcg ctcgctcact gaggccgccc gggcaaagcc cgggcgtcgg   2340
gcgacctttg gtcgcccggc ctcagtgagc gagcgagcgc gcagagaggg agtggccaaa   2400
agcttggcgt aatcatggtc atagctgttt cctgtgtgaa attgttatcc gctcacaatt   2460
ccacacaaca tacgagccgg aagcataaag tgtaaagcct ggggtgccta atgagtgagc   2520
taactcacat taattgcgtt gcgctcactg cccgctttcc agtcgggaaa cctgtcgtgc   2580
cagctgcatt aatgaatcgg ccaacgcgcg gggagaggcg gtttgcgtat tgggcgctct   2640
tccgcttcct cgctcactga ctcgctgcgc tcggtcgttc ggctgcggcg agcggtatca   2700
gctcactcaa aggcggtaat acggttatcc acagaatcag gggataacgc aggaaagaac   2760
atgtgagcaa aaggccagca aaaggccagg aaccgtaaaa aggccgcgtt gctggcgttt   2820
ttccataggc tccgcccccc tgacgagcat cacaaaaatc gacgctcaag tcagaggtgg   2880
cgaaacccga caggactata aagataccag gcgtttcccc ctggaagctc cctcgtgcgc   2940
tctcctgttc cgaccctgcc gcttaccgga tacctgtccg cctttctccc ttcgggaagc   3000
gtggcgcttt ctcatagctc acgctgtagg tatctcagtt cggtgtaggt cgttcgctcc   3060
aagctgggct gtgtgcacga accccccgtt cagcccgacc gctgcgcctt atccggtaac   3120
tatcgtcttg agtccaaccc ggtaagacac gacttatcgc cactggcagc agccactggt   3180
aacaggatta gcagagcgag gtatgtaggc ggtgctacag agttcttgaa gtggtggcct   3240
aactacggct acactagaag aacagtattt ggtatctgcg ctctgctgaa gccagttacc   3300
ttcggaaaaa gagttggtag ctcttgatcc ggcaaacaaa ccaccgctgg tagcggtggt   3360
tttttgttt gcaagcagca gattacgcgc agaaaaaaag gatctcaaga agatcctttg   3420
atcttttcta cggggtctga cgctcagtgg aacgaaaact cacgttaagg gattttggtc   3480
atgagattat caaaaaggat cttcacctag atccttttaa attaaaaatg aagttttaaa   3540
tcaatctaaa gtatatatga gtaaacttgg tctgacagtt accaatgctt aatcagtgag   3600
gcacctatct cagcgatctg tctatttcgt tcatccatag ttgcctgact ccccgtcgtg   3660
tagataacta cgatacggga gggcttacca tctggcccca gtgctgcaat gataccgcga   3720
gacccacgct caccggctcc agatttatca gcaataaacc agccagccgg aagggccgag   3780
cgcagaagtg gtcctgcaac tttatccgcc tccatccagt ctattaattg ttgccgggaa   3840
gctagagtaa gtagttcgcc agttaatagt ttgcgcaacg ttgttgccat tgctacaggc   3900
atcgtggtgt cacgctcgtc gtttggtatg gcttcattca gctccggttc ccaacgatca   3960
aggcgagtta catgatcccc catgttgtgc aaaaaagcgg ttagctcctt cggtcctccg   4020
atcgttgtca gaagtaagtt ggccgcagtg ttatcactca tggttatggc agcactgcat   4080
aattctctta ctgtcatgcc atccgtaaga tgcttttctg tgactggtga gtactcaacc   4140
aagtcattct gagaatagtg tatgcggcga ccgagttgct cttgcccggc gtcaatacgg   4200
gataataccg cgccacatag cagaacttta aaagtgctca tcattggaaa acgttcttcg   4260
gggcgaaaac tctcaaggat cttaccgctg ttgagatcca gttcgatgta acccactcgt   4320
gcacccaact gatcttcagc atcttttact ttcaccagcg tttctgggtg agcaaaaaca   4380
ggaaggcaaa atgccgcaaa aaagggaata agggcgacac ggaaatgttg aatactcata   4440
```

ctcttccttt ttcaatatta ttgaagcatt tatcagggtt attgtctcat gagcggatac 4500
atatttgaat gtatttagaa aaataaacaa ataggggttc cgcgcacatt tccccgaaaa 4560
gtgccacctg acgtctaaga aaccattatt atcatgacat taacctataa aaataggcgt 4620
atcacgaggc cctttcgtc 4639

<210> SEQ ID NO 35
<211> LENGTH: 10898
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 35
ggtacccaac tccatgctta acagtcccca ggtacagccc accctgcgtc gcaaccagga 60
acagctctac agcttcctgg agcgccactc gccctacttc cgcagccaca gtgcgcagat 120
taggagcgcc acttcttttt gtcacttgaa aaacatgtaa aaataatgta ctaggagaca 180
ctttcaataa aggcaaatgt ttttatttgt acactctcgg gtgattattt accccccacc 240
cttgccgtct gcgccgttta aaaatcaaag ggttctgcc gcgcatcgct atgcgccact 300
ggcagggaca cgttgcgata ctggtgttta gtgctccact taaactcagg cacaaccatc 360
cgcggcagct cggtgaagtt ttcactccac aggctgcgca ccatcaccaa cgcgtttagc 420
aggtcgggcg ccgatatctt gaagtcgcag ttggggcctc cgccctgcgc gcgcgagttg 480
cgatacacag ggttgcagca ctggaacact atcagcgccg ggtggtgcac gctggccagc 540
acgctcttgt cggagatcag atccgcgtcc aggtcctccg cgttgctcag ggcgaacgga 600
gtcaactttg gtagctgcct tcccaaaaag ggtgcatgcc caggctttga gttgcactcg 660
caccgtagtg gcatcagaag gtgaccgtgc ccggtctggg cgttaggata cagcgcctgc 720
atgaaagcct tgatctgctt aaaagccacc tgagcctttg cgccttcaga gaagaacatg 780
ccgcaagact tgccggaaaa ctgattggcc ggacaggccg cgtcatgcac gcagcacctt 840
gcgtcggtgt tggagatctg caccacattt cggccccacc ggttcttcac gatcttggcc 900
ttgctagact gctccttcag cgcgcgctgc ccgttttcgc tcgtcacatc catttcaatc 960
acgtgctcct tatttatcat aatgctcccg tgtagacact taagctcgcc ttcgatctca 1020
gcgcagcggt gcagccacaa cgcgcagccc gtgggctcgt ggtgcttgta ggttacctct 1080
gcaaacgact gcaggtacgc ctgcaggaat cgccccatca tcgtcacaaa ggtcttgttg 1140
ctggtgaagg tcagctgcaa cccgcggtgc tcctcgttta gccaggtctt gcatacggcc 1200
gccagagctt ccacttggtc aggcagtagc ttgaagtttg cctttagatc gttatccacg 1260
tggtacttgt ccatcaacgc gcgcgcagcc tccatgccct tctcccacgc agacacgatc 1320
ggcaggctca gcgggtttat caccgtgctt tcactttccg cttcactgga ctcttccttt 1380
tcctcttgcg tccgcatacc ccgcgccact gggtcgtctt cattcagccg ccgcaccgtg 1440
cgcttacctc ccttgccgtg cttgattagc accggtgggt tgctgaaacc caccatttgt 1500
agcgccacat cttctctttc ttcctcgctg tccacgatca cctctgggga tggcgggcgc 1560
tcgggcttgg gagaggggcg cttctttttc tttttggacg caatggccaa atccgccgtc 1620
gaggtcgatg gccgcgggct gggtgtgcgc ggcaccagcg catcttgtga cgagtcttct 1680
tcgtcctcgg actcgagacg ccgcctcagc cgcttttttg ggggcgcgcg gggaggcggc 1740
ggcgacggcg acggggacga cacgtcctcc atggttggtg gacgtcgcgc cgcaccgcgt 1800

-continued

```
ccgcgctcgg gggtggtttc gcgctgctcc tcttcccgac tggccatttc cttctcctat   1860
aggcagaaaa agatcatgga gtcagtcgag aaggaggaca gcctaaccgc cccctttgag   1920
ttcgccacca ccgcctccac cgatgccgcc aacgcgccta ccaccttccc cgtcgaggca   1980
cccccgcttg aggaggagga agtgattatc gagcaggacc caggttttgt aagcgaagac   2040
gacgaggatc gctcagtacc aacagaggat aaaaagcaag accaggacga cgcagaggca   2100
aacgaggaac aagtcgggcg gggggaccaa aggcatggcg actacctaga tgtgggagac   2160
gacgtgctgt tgaagcatct gcagcgccag tgcgccatta tctgcgacgc gttgcaagag   2220
cgcagcgatg tgcccctcgc catagcggat gtcagccttg cctacgaacg ccacctgttc   2280
tcaccgcgcg taccccccaa acgccaagaa aacggcacat gcgagcccaa cccgcgcctc   2340
aacttctacc ccgtatttgc cgtgccagag gtgcttgcca cctatcacat ctttttccaa   2400
aactgcaaga taccccctatc ctgccgtgcc aaccgcagcc gagcggacaa gcagctggcc   2460
ttgcggcagg gcgctgtcat acctgatatc gcctcgctcg acgaagtgcc aaaaatcttt   2520
gagggtcttg gacgcgacga gaaacgcgcg gcaaacgctc tgcaacaaga aaacagcgaa   2580
aatgaaagtc actgtggagt gctggtggaa cttgagggtg acaacgcgcg cctagccgtg   2640
ctgaaacgca gcatcgaggt cacccacttt gcctacccgg cacttaacct accccccaag   2700
gttatgagca cagtcatgag cgagctgatc gtgcgccgtg cacgacccct ggagagggat   2760
gcaaacttgc aagaacaaac cgaggagggc ctacccgcag ttggcgatga gcagctggcg   2820
cgctggcttg agacgcgcga gcctgccgac ttggaggagc gacgcaagct aatgatggcc   2880
gcagtgcttg ttaccgtgga gcttgagtgc atgcagcggt tctttgctga cccggagatg   2940
cagcgcaagc tagaggaaac gttgcactac acctttcgcc agggctacgt gcgccaggcc   3000
tgcaaaattt ccaacgtgga gctctgcaac ctggtctcct accttggaat tttgcacgaa   3060
aaccgcctcg ggcaaaacgt gcttcattcc acgctcaagg gcgaggcgcg ccgcgactac   3120
gtccgcgact gcgtttactt atttctgtgc tacacctggc aaacggccat gggcgtgtgg   3180
cagcaatgcc tggaggagcg caacctaaag gagctgcaga agctgctaaa gcaaaacttg   3240
aaggacctat ggacggcctt caacgagcgc tccgtggccg cgcacctggc ggacattatc   3300
ttccccgaac gcctgcttaa aaccctgcaa cagggtctgc cagacttcac cagtcaaagc   3360
atgttgcaaa actttaggaa ctttatccta gagcgttcag gaattctgcc cgccacctgc   3420
tgtgcgcttc ctagcgactt tgtgcccatt aagtaccgtg aatgccctcc gccgctttgg   3480
ggtcactgct accttctgca gctagccaac taccttgcct accactccga catcatggaa   3540
gacgtgagcg gtgacggcct actggagtgt cactgtcgct gcaacctatg caccccgcac   3600
cgctccctgg tctgcaattc gcaactgctt agcgaaagtc aaattatcgg tacctttgag   3660
ctgcagggtc cctcgcctga cgaaaagtcc gcggctccgg ggttgaaact cactccgggg   3720
ctgtggacgt cggcttacct tcgcaaattt gtacctgagg actaccacgc ccacgagatt   3780
aggttctacg aagaccaatc ccgcccgcca aatgcggagc ttaccgcctg cgtcattacc   3840
cagggccaca tccttggcca attgcaagcc atcaacaaag cccgccaaga gtttctgcta   3900
cgaaagggac ggggggttta cctggacccc cagtccggcg aggagctcaa cccaatcccc   3960
ccgccgccgc agccctatca gcagccgcgg gcccttgctt cccaggatgg cacccaaaaa   4020
gaagctgcag ctgccgccgc cgccacccac ggacgaggag gaatactggg acagtcaggc   4080
agaggaggtt ttggacgagg aggaggagat gatggaagac tgggacagcc tagacgaagc   4140
```

-continued

```
ttccgaggcc gaagaggtgt cagacgaaac accgtcaccc tcggtcgcat tcccctcgcc   4200
ggcgccccag aaattggcaa ccgttcccag catcgctaca acctccgctc ctcaggcgcc   4260
gccggcactg cctgttcgcc gacccaaccg tagatgggac accactggaa ccagggccgg   4320
taagtctaag cagccgccgc cgttagccca agagcaacaa cagcgccaag gctaccgctc   4380
gtggcgcggg cacaagaacg ccatagttgc ttgcttgcaa gactgtgggg gcaacatctc   4440
cttcgcccgc cgctttcttc tctaccatca cggcgtggcc ttcccccgta acatcctgca   4500
ttactaccgt catctctaca gcccctactg caccggcggc agcggcagcg gcagcaacag   4560
cagcggtcac acagaagcaa aggcgaccgg atagcaagac tctgacaaag cccaagaaat   4620
ccacagcggc ggcagcagca ggaggaggag cgctgcgtct ggcgcccaac gaacccgtat   4680
cgacccgcga gcttagaaat aggatttttc ccactctgta tgctatattt caacaaagca   4740
ggggccaaga acaagagctg aaaataaaaa acaggtctct gcgctccctc acccgcagct   4800
gcctgtatca caaaagcgaa gatcagcttc ggcgcacgct ggaagacgcg gaggctctct   4860
tcagcaaata ctgcgcgctg actcttaagg actagtttcg cgccctttct caaatttaag   4920
cgcgaaaact acgtcatctc cagcggccac acccggcgcc agcacctgtc gtcagcgcca   4980
ttatgagcaa ggaaattccc acgccctaca tgtggagtta ccagccacaa atgggacttg   5040
cggctggagc tgcccaagac tactcaaccc gaataaacta catgagcgcg ggaccccaca   5100
tgatatcccg ggtcaacgga atccgcgccc accgaaaccg aattctcctc gaacaggcgg   5160
ctattaccac cacacctcgt aataacctta atccccgtag ttggcccgct gccctggtgt   5220
accaggaaag tcccgctccc accactgtgg tacttcccag agacgcccag gccgaagttc   5280
agatgactaa ctcaggggcg cagcttgcgg gcggctttcg tcacagggtg cggtcgcccg   5340
ggcgttttag ggcggagtaa cttgcatgta ttgggaattg tagttttttt aaaatgggaa   5400
gtgacgtatc gtgggaaaac ggaagtgaag atttgaggaa gttgtgggtt ttttggcttt   5460
cgtttctggg cgtaggttcg cgtgcggttt tctgggtgtt ttttgtggac tttaaccgtt   5520
acgtcatttt ttagtcctat atatactcgc tctgtacttg gccctttttta cactgtgact   5580
gattgagctg gtgccgtgtc gagtggtgtt ttttaatagg tttttttact ggtaaggctg   5640
actgttatgg ctgccgctgt ggaagcgctg tatgttgttc tggagcggga gggtgctatt   5700
ttgcctaggc aggagggttt ttcaggtgtt tatgtgtttt tctctcctat taattttgtt   5760
atacctccta tgggggctgt aatgttgtct ctacgcctgc gggtatgtat tcccccgggc   5820
tatttcggtc gctttttagc actgaccgat gttaaccaac ctgatgtgtt taccgagtct   5880
tacattatga ctccggacat gaccgaggaa ctgtcggtgg tgctttttaa tcacggtgac   5940
cagtttttt acggtcacgc cggcatggcc gtagtccgtc ttatgcttat aagggttgtt   6000
tttcctgttg taagacaggc ttctaatgtt taaatgtttt tttttttgtt attttatttt   6060
gtgtttaatg caggaacccg cagacatgtt tgagagaaaa atggtgtctt tttctgtggt   6120
ggttccggaa cttacctgcc tttatctgca tgagcatgac tacgatgtgc ttgctttttt   6180
gcgcgaggct ttgcctgatt ttttgagcag caccttgcat tttatatcgc cgcccatgca   6240
acaagcttac ataggggcta cgctggttag catagctccg agtatgcgtg tcataatcag   6300
tgtgggttct tttgtcatgg ttcctggcgg ggaagtggcc gcgctggtcc gtgcagacct   6360
gcacgattat gttcagctgg ccctgcgaag ggacctacgg gatcgcggta tttttgttaa   6420
tgttccgctt ttgaatctta tacaggtctg tgaggaacct gaatttttgc aatcatgatt   6480
cgctgcttga ggctgaaggt ggagggcgct ctggagcaga tttttacaat ggccggactt   6540
```

aatattcggg atttgcttag agacatattg ataaggtggc gagatgaaaa ttatttgggc 6600
atggttgaag gtgctggaat gtttatagag gagattcacc ctgaagggtt tagcctttac 6660
gtccacttgg acgtgagggc agtttgcctt ttggaagcca ttgtgcaaca tcttacaaat 6720
gccattatct gttctttggc tgtagagttt gaccacgcca ccggagggga gcgcgttcac 6780
ttaatagatc ttcattttga ggttttggat aatcttttgg aataaaaaaa aaaaaacatg 6840
gttcttccag ctcttcccgc tcctcccgtg tgtgactcgc agaacgaatg tgtaggttgg 6900
ctgggtgtgg cttattctgc ggtggtggat gttatcaggg cagcggcgca tgaaggagtt 6960
tacatagaac ccgaagccag ggggcgcctg gatgctttga gagagtggat atactacaac 7020
tactacacag agcgagctaa gcgacgagac cggagacgca gatctgtttg tcacgcccgc 7080
acctggtttt gcttcaggaa atatgactac gtccggcgtt ccatttggca tgacactacg 7140
accaacacga tctcggttgt ctcggcgcac tccgtacagt agggatcgcc tacctccttt 7200
tgagacagag acccgcgcta ccatactgga ggatcatccg ctgctgcccg aatgtaacac 7260
tttgacaatg cacaacgtga gttacgtgcg aggtcttccc tgcagtgtgg gatttacgct 7320
gattcaggaa tgggttgttc cctgggatat ggttctgacg cgggaggagc ttgtaatcct 7380
gaggaagtgt atgcacgtgt gcctgtgttg tgccaacatt gatatcatga cgagcatgat 7440
gatccatggt tacgagtcct gggctctcca ctgtcattgt tccagtcccg gttccctgca 7500
gtgcatagcc ggcgggcagg ttttggccag ctggtttagg atggtggtgg atggcgccat 7560
gtttaatcag aggtttatat ggtaccggga ggtggtgaat tacaacatgc caaaagaggt 7620
aatgtttatg tccagcgtgt ttatgagggg tcgccactta atctacctgc gcttgtggta 7680
tgatggccac gtgggttctg tggtccccgc catgagcttt ggatacagcg ccttgcactg 7740
tgggattttg aacaatattg tggtgctgtg ctgcagttac tgtgctgatt taagtgagat 7800
cagggtgcgc tgctgtgccc ggaggacaag gcgtctcatg ctgcgggcgg tgcgaatcat 7860
cgctgaggag accactgcca tgttgtattc ctgcaggacg gagcggcggc ggcagcagtt 7920
tattcgcgcg ctgctgcagc accaccgccc tatcctgatg cacgattatg actctacccc 7980
catgtaggcg tggacttccc cttcgccgcc cgttgagcaa ccgcaagttg gacagcagcc 8040
tgtggctcag cagctggaca gcgacatgaa cttaagcgag ctgcccgggg agtttattaa 8100
tatcactgat gagcgtttgg ctcgacagga aaccgtgtgg aatataacac ctaagaatat 8160
gtctgttacc catgatatga tgctttttaa ggccagccgg ggagaaagga ctgtgtactc 8220
tgtgtgttgg gagggaggtg gcaggttgaa tactagggtt ctgtgagttt gattaaggta 8280
cggtgatcaa tataagctat gtggtggtgg ggctatacta ctgaatgaaa aatgacttga 8340
aattttctgc aattgaaaaa taaacacgtt gaaacataac atgcaacagg ttcacgattc 8400
tttattcctg ggcaatgtag gagaaggtgt aagagttggt agcaaaagtt tcagtggtgt 8460
attttccact ttcccaggac catgtaaaag acatagagta agtgcttacc tcgctagttt 8520
ctgtggattc actagaatcg atgtcgacgt ttaaaccata tgatcagctc actcaaaggc 8580
ggtaatacgg ttatccacag aatcagggga taacgcagga aagaacatgt gagcaaaagg 8640
ccagcaaaag gccaggaacc gtaaaaaggc cgcgttgctg gcgtttttcc ataggctccg 8700
cccccctgac gagcatcaca aaaatcgacg ctcaagtcag aggtggcgaa acccgacagg 8760
actataaaga taccaggcgt ttccccctgg aagctccctc gtgcgctctc ctgttccgac 8820
cctgccgctt accggatacc tgtccgcctt tctcccttcg ggaagcgtgg cgctttctca 8880

-continued

```
tagctcacgc tgtaggtatc tcagttcggt gtaggtcgtt cgctccaagc tgggctgtgt   8940
gcacgaaccc cccgttcagc ccgaccgctg cgccttatcc ggtaactatc gtcttgagtc   9000
caacccggta agacacgact tatcgccact ggcagcagcc actggtaaca ggattagcag   9060
agcgaggtat gtaggcggtg ctacagagtt cttgaagtgg tggcctaact acggctacac   9120
tagaagaaca gtatttggta tctgcgctct gctgaagcca gttaccttcg gaaaaagagt   9180
tggtagctct tgatccggca aacaaaccac cgctggtagc ggtggttttt ttgtttgcaa   9240
gcagcagatt acgcgcagaa aaaaaggatc tcaagaagat cctttgatct tttctacggg   9300
gtctgacgct cagtggaacg aaaactcacg ttaagggatt ttggtcatga gattatcaaa   9360
aaggatcttc acctagatcc ttttaaatta aaaatgaagt tttaaatcaa tctaaagtat   9420
atatgagtaa acttggtctg acagttacca atgcttaatc agtgaggcac ctatctcagc   9480
gatctgtcta tttcgttcat ccatagttgc ctgactcccc gtcgtgtaga taactacgat   9540
acgggagggc ttaccatctg gccccagtgc tgcaatgata ccgcgagacc cacgctcacc   9600
ggctccagat ttatcagcaa taaaccagcc agccggaagg gccgagcgca gaagtggtcc   9660
tgcaacttta tccgcctcca tccagtctat taattgttgc cgggaagcta gagtaagtag   9720
ttcgccagtt aatagtttgc gcaacgttgt tgccattgct acaggcatcg tggtgtcacg   9780
ctcgtcgttt ggtatggctt cattcagctc cggttcccaa cgatcaaggc gagttacatg   9840
atcccccatg ttgtgcaaaa aagcggttag ctccttcggt cctccgatcg ttgtcagaag   9900
taagttggcc gcagtgttat cactcatggt tatggcagca ctgcataatt ctcttactgt   9960
catgccatcc gtaagatgct tttctgtgac tggtgagtac tcaaccaagt cattctgaga  10020
atagtgtatg cggcgaccga gttgctcttg cccggcgtca atacgggata ataccgcgcc  10080
acatagcaga actttaaaag tgctcatcat tggaaaacgt tcttcggggc gaaaactctc  10140
aaggatctta ccgctgttga gatccagttc gatgtaaccc actcgtgcac ccaactgatc  10200
ttcagcatct tttactttca ccagcgtttc tgggtgagca aaaacaggaa ggcaaaatgc  10260
cgcaaaaaag ggaataaggg cgacacggaa atgttgaata ctcatactct tcctttttca  10320
atattattga agcatttatc agggttattg tctcatgagc ggatacatat ttgaatgtat  10380
ttagaaaaat aaacaaatag gggttccgcg cacatttccc cgaaaagtgc cacctaaatt  10440
gtaagcgtta atattttgtt aaaattcgcg ttaaattttt gttaaatcag ctcatttttt  10500
aaccaatagg ccgaaatcgg caaaatccct tataaatcaa aagaatagac cgagataggg  10560
ttgagtgttg ttccagtttg gaacaagagt ccactattaa agaacgtgga ctccaacgtc  10620
aaagggcgaa aaaccgtcta tcagggcgat ggcccactac gtgaaccatc accctaatca  10680
agttttttgg ggtcgaggtg ccgtaaagca ctaaatcgga accctaaagg gagcccccga  10740
tttagagctt gacggggaaa gccggcgaac gtggcgagaa aggaagggaa gaaagcgaaa  10800
ggagcgggcg ctagggcgct ggcaagtgta gcggtcacgc tgcgcgtaac caccacaccc  10860
gccgcgctta atgcgccgct acagggcgcg atggatcc                         10898
```

<210> SEQ ID NO 36
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 36

-continued

```
ggacgaccgg gguucgaacc ccggauccgg ccgucc                              36


<210> SEQ ID NO 37
<211> LENGTH: 68
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(3)
<223> OTHER INFORMATION: /note="This region may or may not be present"
<220> FEATURE:
<221> NAME/KEY: source
<223> OTHER INFORMATION: /note="See specification as filed for detailed
      description of substitutions and preferred embodiments"

<400> SEQUENCE: 37

agcgggcacu cuuccguggu cugguggaua aauucgcaag gguaucaugg cggacgaccg     60

ggguucga                                                              68


<210> SEQ ID NO 38
<211> LENGTH: 95
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (91)..(95)
<223> OTHER INFORMATION: /note="This region may encompass 0-5
      nucleotides"

<400> SEQUENCE: 38

cccggauccg gccguccgcc gugauccaug cgguuaccgc ccgcgugucg aacccaggug     60

ugcgacguca gacaacgggg gagcgcuccu uuuuu                                95


<210> SEQ ID NO 39
<211> LENGTH: 13
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(11)
<223> OTHER INFORMATION: a, c, u, g, unknown or other

<400> SEQUENCE: 39

wwnnnnnnnn nwg                                                        13
```

STABLE CELL LINES FOR INDUCIBLE PRODUCTION OF rAAV VIRIONS

1. CROSS-REFERENCE TO RELATED APPLICATIONS

This application claims the benefit of and priority to U.S. Provisional Application Nos. 63/058,887, filed Jul. 30, 2020; 63/058,894, filed Jul. 30, 2020; 63/058,900, filed Jul. 30, 2020; 63/156,230, filed Mar. 3, 2021; 63/156,207, filed Mar. 3, 2021, 63/156,239; filed Mar. 3, 2021; and 63/216,615, filed Jun. 30, 2021. The content of each of the above-referenced applications is incorporated by reference in its entirety.

2. INCORPORATION BY REFERENCE OF SEQUENCE LISTING PROVIDED AS A TEXT FILE

A Sequence Listing is provided herewith in a text file, SHPE-001_STX-018US_SeqList_ST25, created on Dec. 7, 2021, and having a size of 296,000 bytes. The contents of the text file are incorporated herein by reference in its entirety.

3. BACKGROUND

Recombinant adeno-associated virus (rAAV) is the preferred vehicle for in vivo gene delivery. AAV has no known disease associations, infects dividing and non-dividing cells, rarely if ever integrates into the mammalian cell genome, and can persist essentially for the lifetime of infected cells as a transcriptionally active nuclear episome. The FDA has recently approved several rAAV gene therapy products and many other rAAV-based gene therapy and gene editing products are in development.

The most widely used method for producing rAAV virions is based on the helper-virus-free transient transfection of multiple plasmids, typically a triple transfection, into adherent cell lines. Although there is ongoing investment to increase production capacity, current AAV manufacturing processes are inefficient and expensive. In addition, they result in variable product quality, with low levels of encapsidation of a payload, such as a therapeutic payload.

There is, therefore, a need for improved methods for producing rAAV products. Any such solution must address the toxicity to the host production cell due to constitutive expression of AAV Rep protein and the toxicity to the host production cell due to constitutive expression of adenoviral helper protein.

4. SUMMARY

Disclosed herein are stable mammalian cell lines, wherein the cells are capable of conditionally producing recombinant AAV (rAAV) virions within which are packaged an expressible payload.

Further provided herein is a stable mammalian cell line, wherein the cells are capable of conditionally producing recombinant AAV (rAAV) virions within which are packaged an expressible payload; and wherein a population of virions produced by the stable cell are more homogenous than a population of virions produced by an otherwise comparable cell producing rAAV virions upon transient transfection.

Further provided herein is a stable mammalian cell line, wherein the cells are capable of conditionally producing recombinant AAV (rAAV) virions within which are packaged an expressible payload; and production of virions is inducible upon addition of a triggering agent.

Further provided herein is a stable mammalian cell line, wherein the cells are capable of conditionally producing recombinant AAV (rAAV) virions within which are packaged an expressible payload; and production of virions is not conditioned on the presence of a plasmid within the cell.

In some aspects, a composition comprising one or more nucleic acids which together comprises: (i) a first recombinant nucleic acid sequence encoding an AAV Rep protein and an AAV Cap protein; and (ii) a second recombinant nucleic acid sequence encoding one or more adenoviral helper proteins, wherein when the one or more nucleic acids are integrated into the nuclear genome of a mammalian cell the AAV Rep protein, the AAV Cap protein, and/or the one or more adenoviral helper proteins are conditionally expressible and thereby conditionally produce recombinant AAV (rAAV) virions. In some embodiments, the conditional expression of the AAV Rep protein, the AAV Cap protein, and/or the one or more adenoviral helper proteins is controlled by one or more excisable elements present in the one or more nucleic acids. In some embodiments, the one or more excisable elements comprise one or more introns and/or one or more exons. In some embodiments, the first recombinant nucleic acid sequence encodes: a) a first part of the AAV Rep protein coding sequence; b) the second part of the AAV Rep protein coding sequence; c) an excisable element between the first part of the AAV Rep protein coding sequence and the second part of the AAV Rep protein coding sequence; and d) the AAV Cap protein coding sequence. In some embodiments, the excisable element comprises: a) a first spacer segment comprising a first intron, b) a second spacer segment comprising a coding sequence of a detectable marker; and c) a third spacer segment comprising a second intron, and wherein the first spacer segment and the third spacer segment are capable of being excised by endogenous cellular machinery of a mammalian cell. In some embodiments, the excisable element comprises from 5' to 3': a) a 5' splice site; b) a first spacer segment comprising a first intron; c) a second spacer segment comprising: i) a first lox sequence; ii) a 3' splice site; iii) an exon; iv) a stop signaling sequence; and v) a second lox sequence; and d) a third spacer segment comprising a second intron. In some embodiments, the detectable marker is a luminescent marker, a radiolabel or a fluorescent marker, optionally a fluorescent marker which is GFP, EGFP, RFP, CFP, BFP, YFP, or mCherry. In some embodiments, a) the first spacer segment comprises a nucleic acid sequence having at least 80% identity to SEQ ID NO: 1; and/or b) the second spacer segment comprises a nucleic acid sequence having at least 80% identity to SEQ ID NO: 2; and/or c) the third spacer segment comprises a nucleic acid sequence having at least 80% identity to SEQ ID NO: 3. In some embodiments, the second spacer segment is capable of being excised by a Cre polypeptide. In some embodiments, the expression of the AAV Rep protein and/or the AAV Cap protein is driven by native promoters. In some embodiments, wherein: a) the native promoters P5 and/or P19 drive the expression of the AAV Rep protein; and/or b) the native promoter P40 drives the expression of the AAV Cap protein. In some embodiments, the second recombinant nucleic acid sequence encodes: a) one or more adenoviral helper proteins; b) a conditionally self-excising element; and c) an inducible promoter; wherein, once integrated into the nuclear genome of a mammalian cell, the expression of the one or more adenoviral helper protein coding sequences is under the control of the conditionally self-excising element and the inducible promoter. In some embodiments, the one or more adenoviral helper proteins comprise E2A and E4. In some embodiments, the self-excising element comprises a sequence which encodes a polypeptide, preferably a recombinase polypeptide, more preferably a Cre polypeptide. In some embodiments, the polypeptide encoded by the self-excising element is conditionally expressible and is expressed only in the presence of a triggering agent. In some embodiments, the triggering agent is a hormone, preferably tamoxifen. In some embodiments, the inducible promoter is a Tet inducible promoter. In some embodiments, the second recombinant nucleic acid sequence further comprises a sequence that encodes a Tet responsive activator protein, preferably Tet-on-3G. In some embodiments, the expression of Tet-On 3G activator protein is driven by an E1 alpha promoter. In some embodiments, the second recombinant nucleic acid sequence comprises a sequence with at least 80% homology, at least 90% homology, at least 95% homology, at least 99% homology, or a sequence identical to SEQ ID NO: 11 or SEQ ID NO: 12. In some embodiments, the one or more nucleic acids further comprises a nucleic acid sequence encoding a VA RNA sequence. In some embodiments, the expression of VA RNA is constitutive. In some embodiments, the expression of VA RNA is inducible. In some embodiments, the VA RNA sequence comprises one or more mutations in the VA RNA internal promoter, preferably G16A and G60A. In some embodiments, the expression of VA RNA is driven by a E1 alpha promoter or a U6 promoter. In some embodiments, the expression of VA RNA is driven by a U6 promoter, and wherein the U6 promoter comprises: a) a first part of a U6 promoter sequence, b) a stuffer sequence, and c) a second part of a U6 promoter sequence, and wherein the stuffer sequence is capable of being excised by a Cre polypeptide. In some embodiments, a serotype of the AAV Cap protein is selected from the group consisting of AAV1, AAV2, AAV3, AAV4, AAV5, AAV6, AAV7, AAV8, AAV9, AAV 10, AAV11, AAV 12, AAV13, AAV 14, AAV 15 and AAV 16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, AAV.HSC16 and AAVhu68. In some embodiments, the serotype is an AAV5 and the Cap protein that comprises one or more mutations or insertions. In some embodiments, the one or more recombinant nucleic acids further encode a third recombinant nucleic acid sequence encoding a payload, optionally wherein the payload is: (a) a polynucleotide payload, such as a guide RNA for RNA editing, a guide RNA for Cas protein-directed DNA editing, a tRNA suppressor, or a gene for replacement gene therapy; or (b) a protein such as a therapeutic antibody or a vaccine immunogen. In some embodiments, the one or more recombinant nucleic acids comprise one or more mammalian cell selection elements. In some embodiments, one or more of the mammalian cell selection elements encodes an antibiotic resistance gene, optionally a blasticidin resistance gene. In some embodiments, one or more of the mammalian cell selection elements is an auxotrophic selection element which encodes an active protein, preferably wherein the protein is DHFR. In some embodiments, one or more of the mammalian cell selection elements is a first auxotrophic selection element which encodes an inactive protein that requires expression of a second inactive protein from a second auxotrophic selection coding sequence for activity In some embodiments, the first auxotrophic selection coding sequence encodes for DHFR Z-Cter (SEQ ID NO: 5) activity, and/or wherein the second auxotrophic selection coding sequence encodes for DHFR Z-Nter (SEQ ID NO: 4). In some embodiments, a) the first recombinant nucleic acid comprises a mammalian cell selection element which encodes an antibiotic resistance gene, preferably a blasticidin resistance gene; and b) i. the second recombinant nucleic acid comprises a first auxotrophic selection element which encodes an inactive protein that requires expression of a second inactive protein from a second auxotrophic selection coding sequence for activity; and ii. the third recombinant nucleic acid comprises the second auxotrophic selection element which encodes the inactive protein that requires expression of the first inactive protein from the first auxotrophic selection coding sequence for activity; and wherein in (i) or (ii) the first auxotrophic selection coding sequence encodes for DHFR Z-Cter (SEQ ID NO: 5), and the second auxotrophic selection coding sequence encodes for DHFR Z-Nter (SEQ ID NO: 4) or wherein the first auxotrophic selection coding sequence encodes for DHFR Z-Nter (SEQ ID NO: 4), and the second auxotrophic selection coding sequence encodes for DHFR Z-Cter (SEQ ID NO: 5).

In some aspects, disclosed herein is a mammalian cell wherein the nuclear genome of the cell comprises a plurality of integrated recombinant nucleic acid constructs which together encode for a recombinant adeno-associated virus (rAAV) virions, wherein the rAAV virions can be conditionally expressed from the cell. In some embodiments, the plurality of integrated recombinant nucleic acid constructs comprise the one or more recombinant nucleic acids of any one of previous embodiment, wherein the AAV Rep protein, the AAV Cap protein and/or the adenoviral helper proteins can be conditionally expressed from the cell. In some embodiments, the cell line expresses adenoviral helper proteins E1A and E1B. In some embodiments, the plurality of integrated recombinant nucleic acid constructs comprise: (i) a first integrated polynucleotide construct comprising: a) a first part of an AAV Rep protein coding sequence; b) a second part of an AAV Rep protein coding sequence; c) an excisable element between the first part of the AAV Rep protein coding sequence and the second part of the AAV Rep protein coding sequence, wherein the excisable element comprises: i) a first spacer segment comprising a first intron; ii) a second spacer segment comprising a coding sequence of a detectable marker, wherein the second spacer segment is capable of being excised by a Cre polypeptide; and iii) a third spacer segment comprising a second intron; and d) an AAV Cap protein coding sequence; wherein the AAV Rep protein and the AAV Cap protein is driven by the native promoters P5, P19, and P40; (ii) a second integrated polynucleotide construct comprising a) a conditionally expressible VA RNA coding sequence which comprises a mutation in the VA RNA internal promoter, wherein the expression of VA RNA is driven by a U6 promoter, optionally wherein the VA RNA sequence comprises G16A and G60A mutations; b) one or more adenoviral helper protein coding sequences, wherein the adenoviral helper proteins are E2A and E4; c) a conditionally self-excising element which encodes a Cre polypeptide which translocates to the nucleus and self-excises only in the presence of a triggering agent which is tamoxifen, and d) an inducible promoter which is a Tet inducible promoter, and wherein the expression of the one or more adenoviral helper protein coding sequences is under the control of the conditionally self-excising element and the inducible promoter; and (iii) a third integrated polynucleotide construct comprising encodes for the payload, wherein the payload is a polynucleotide payload.

In some aspects, a method of producing a population of rAAV virions comprises: (a) culturing the cell of any one of aspects 36-39 in conditions which allow for the expression of the rAAV virions; and (b) isolating the rAAV virions from the cell culture.

In some embodiments, the prepurification rAAV viral genome (VG) to viral particle (VG:VP) ratio of greater than 0.5. In some embodiments, the population of rAAV virions produced by the cell has: (a) a ratio of viral genomes to transduction units of about 500 to 1 to 1 to 1; and/or (b) a ratio of vector genomes to infectious unit of 100:1.

In some aspects, a method of preparing the cell of any one of the previous embodiments comprises: i) providing a mammalian cell and the one or more nucleic acids of any one of the previous embodiments; and ii) integrating the one or more nucleic acids of any one of the previous embodiments into the nuclear genome of the mammalian cell.

In some aspects, a population of rAAV virions produced by the method of any one of the previous embodiments. In some embodiments, the infectivity of the virions is at least 50% at an MOI of 10000.

In some aspects, a pharmaceutical composition comprising a population of rAAV virions according to any one of the previous embodiments, for use as a medicament, optionally for use in treating a monogenic disorder. In some embodiments, the population of rAAV virions according to any one of the previous embodiments or the pharmaceutical composition according to any one of the previous embodiments, for use as a medicament, optionally for use in treating a monogenic disorder. In some embodiments, the population of rAAV virions or the pharmaceutical composition for use according to any one of the previous embodiments, wherein the rAAV virions are administered at a dosage of 4×1014 or lower.

Also provided herein are cells comprising: a) a first polynucleotide construct coding for an AAV Rep protein and an AAV Cap protein; b) a second polynucleotide construct coding for one or more adenoviral helper proteins; wherein when the one or more nucleic acids are integrated into the nuclear genome of a mammalian cell the AAV Rep protein, the AAV Cap protein, and/or the one or more adenoviral helper proteins are conditionally expressible and thereby conditionally produce recombinant AAV (rAAV) virions.

In some embodiments, the second polynucleotide construct comprises a sequence coding for: a) one or more helper proteins; b) a self-excising element upstream of the one or more helper proteins; and c) an inducible promoter upstream of the self-excising element. In some embodiments, the self-excising element is operably linked to the inducible promoter. In some embodiments, expression of the self-excising element is driven by the inducible promoter.

In some embodiments, the inducible promoter is a tetracycline-responsive promoter element (TRE). In some embodiments, the TRE comprises Tet operator (tetO) sequence concatemers fused to a minimal promoter. In some embodiments, the minimal promoter is a human cytomegalovirus promoter. In some embodiments, the inducible promoter comprises a sequence having at least 70%, 80%, 90%, 95%, 99%, or 100% sequence identity to SEQ ID NO: 22. In some embodiments, transcription is activated from the inducible promoter upon binding of an activator. In some embodiments, the activator binds to the inducible promoter in the presence of a first triggering agent. In some embodiments, the second polynucleotide construct further comprises a sequence coding for an activator. In some embodiments, the activator is operably linked to a constitutive promoter. In some embodiments, the constitutive promoter is E1 alpha promoter or human cytomegalovirus promoter. In some embodiments, the E1 alpha promoter comprises at least one mutation. In some embodiments, the constitutive promoter comprises a sequence having at least 70%, 80%, 90%, 95%, 99%, or 100% sequence identity with SEQ ID NO: 20. In some embodiments, the activator is reverse tetracycline-controlled transactivator (rTA) comprising a Tet Repressor binding protein (TetR) fused to a VP16 transactivation domain. In some embodiments, the rTA comprises four mutations in the tetR DNA binding moiety. In some embodiments, the rTA comprises a sequence having at least 70%, 80%, 90%, 95%, 99%, or 100% sequence identity to SEQ ID NO: 21.

In some embodiments, the inducible promoter is a cumate operator sequence. In some embodiments, the cumate operator sequence is downstream of a constitutive promoter. In some embodiments, the constitutive promoter is a human cytomegalovirus promoter. In some embodiments, the inducible promoter is bound by a cymR repressor in the absence of a first triggering agent. In some embodiments, the inducible promoter is activated in the presence of a first triggering agent. In some embodiments, the first triggering agent binds to the cymR repressor. In some embodiments, the second polynucleotide construct further comprises a cymR repressor. In some embodiments, the cymR repressor is operably linked to a constitutive promoter. In some embodiments, the constitutive promoter is E1alpha promoter. In some embodiments, the E1 alpha promoter comprises at least one mutation. In some embodiments, the constitutive promoter comprises a sequence having at least 70%, 80%, 90%, 95%, 99%, or 100% sequence identity with SEQ ID NO: 20. In some embodiments, the first triggering agent is a cumate.

In some embodiments, the sequence coding for the self-excising element comprises a poly A sequence. In some embodiments, the self-excising element is a recombinase. In some embodiments, the recombinase is fused to a ligand binding domain. In some embodiments, the recombinase is Cre polypeptide or flippase polypeptide. In some embodiments, the Cre polypeptide is fused to a ligand binding domain. In some embodiments, the ligand binding domain is a hormone receptor. In some embodiments, the recombinase is a Cre-ERT2 polypeptide. In some embodiments, the self-excising element translocates to the nucleus in the presence of a second triggering agent. In some embodiments, the second triggering agent is an estrogen receptor ligand. In some embodiments, the second triggering agent is a selective estrogen receptor modulator (SERM). In some embodiments, the second triggering agent is tamoxifen. In some embodiments, the recombinase is flanked by recombination sites. In some embodiments, the recombination sites are lox sites or flippase recognition target (FRT) sites. In some embodiments, the lox sites are loxP sites.

In some embodiments, the one or more adenoviral helper proteins comprise E2A and E4. In some embodiments, the E2A is FLAG-tagged E2A. In some embodiments, the sequence coding for E2A and the sequence coding for E4 are separated by an internal ribosome entry site (IRES) or by P2A.

In some embodiments, the second polynucleotide construct further comprises a sequence coding for a selectable marker. In some embodiments, the selectable marker is an antibiotic resistance protein. In some embodiments, the selectable marker is a split intein linked to an N-terminus of the antibiotic resistance protein or split intein linked to a C-terminus of the antibiotic resistance protein. In some embodiments, the antibiotic resistance protein is for puromycin resistance or blasticidin resistance.

In some embodiments, the second polynucleotide construct further comprises a sequence coding for VA RNA. In some embodiments, the sequence coding for VA RNA is a transcriptionally dead sequence. In some embodiments, the sequence coding for VA RNA comprises at least two mutations in the internal promoter. In some embodiments, expression of VA RNA is driven by a U6 promoter. In some embodiments, the second polynucleotide construct further comprises upstream of the sequence coding for VA RNA gene sequence, from 5' to 3': a) a first part of a U6 promoter sequence; b) a first recombination site; c) a stuffer sequence; d) a second recombination site; and e) a second part of a U6 promoter sequence. In some embodiments, the stuffer sequence is excisable by the recombinase. In some embodiments, the stuffer sequence comprises a sequence encoding a gene. In some embodiments, the stuffer sequence comprises a promoter. In some embodiments, the promoter is a constitutive promoter. In some embodiments, the promoter is a CMV promoter.

In some embodiments, the first polynucleotide construct comprises: a) a sequence of a first part of a Rep gene; b) a sequence of a second part of the Rep gene; c) a sequence of a Cap gene; and d) an excisable element positioned between the first part of the sequence of Rep gene and the second part of the sequence of the Rep gene.

In some embodiments, the excisable element comprises a stop signaling sequence. In some embodiments, the excisable element comprises a rabbit beta globin intron. In some embodiments, the excisable element comprises an exon. In some embodiments, the excisable element comprises an intron and an exon. In some embodiments, the excisable element comprises an intron.

In some embodiments, two splice sites are positioned between the sequence of the first part of the Rep gene and the sequence of the second part of the Rep gene. In some embodiments, the two splice sites are a 5' splice site and a 3' splice site. In some embodiments, the 5' splice site is a rabbit beta globin 5' splice site. In some embodiments, the 3' splice site is a rabbit beta globin 3' splice site. In some embodiments, three splice sites are positioned between the sequence of the first part of the Rep gene and the sequence of the second part of the Rep gene. In some embodiments, the three splice sites are a 5' splice site, a first 3' splice site, and a second 3' splice site. In some embodiments, a first 3' splice site is a duplicate of the second 3' splice site. In some embodiments, the first 3' splice site is a rabbit beta globin 3' splice site. In some embodiments, the second 3' splice site is a rabbit beta globin 3' splice site.

In some embodiments, the excisable element comprises a recombination site. In some embodiments, the recombination site is a lox site or FRT site. In some embodiments, the lox site is a loxP site.

In some embodiments, the excisable element comprises from 5' to 3': a) the 5' splice site; b) a first recombination site; c) the first 3' splice site; d) a stop signaling sequence; e) a second recombination site; and f) the second 3' splice site.

In some embodiments, the excisable element comprises from 5' to 3': a) the 5' splice site; b) a first spacer segment; c) a second spacer segment comprising: i) a first recombination site; ii) the first 3' splice site; iv) a stop signaling sequence; and v) a second recombination site; and d) a third spacer segment comprising the second 3' splice site. In some embodiments, the first spacer sequence comprises an intron. In some embodiments, the first spacer segment comprises a sequence having at least 70%, 80%, 90%, 95%, 99%, or 100% sequence identity to SEQ ID NO: 1. In some embodiments, the second spacer segment comprises a sequence having at least 70%, 80%, 90%, 95%, 99%, or 100% sequence identity to SEQ ID NO: 2. In some embodiments, the third spacer segment comprises a sequence having at least 70%, 80%, 90%, 95%, 99%, or 100% sequence identity to SEQ ID NO: 3. In some embodiments, the third spacer segment comprises an intron. In some embodiments, the first spacer segment and the third spacer segment are capable of being excised by endogenous cellular machinery. In some embodiments, the second spacer segment comprises an exon. In some embodiments, the second spacer segment further comprises a polyA sequence. In some embodiments, the polyA sequence is 3' of the exon. In some embodiments, the polyA sequence comprises a rabbit beta globin (RBG) polyA sequence.

In some embodiments, the second spacer segment comprises from 5' to 3': a) a first recombination site; b) the first 3' splice site; c) an exon; d) a stop signaling sequence; and e) a second recombination site. In some embodiments, the first recombination site is a first lox sequence and the second recombination site is a second lox sequence. In some embodiments, the first lox sequence is a first loxP sequence and a second lox sequence is a second loxP sequence. In some embodiments, the first recombination site is a first FRT site and the second recombination site is a second FRT site. In some embodiments, the stop signaling sequence is a termination codon of the exon or a polyA sequence. In some embodiments, the polyA sequence comprises a rabbit beta globin (RBG) polyA sequence. In some embodiments, the exon encodes a detectable marker or a selectable marker. In some embodiments, the detectable marker comprises a luminescent marker or a fluorescent marker. In some embodiments, the fluorescent marker is GFP, EGFP, RFP, CFP, BFP, YFP, or mCherry.

In some embodiments, the second spacer segment is excisable by a recombinase. In some embodiments, the recombinase is a Cre polypeptide or a Flippase polypeptide. In some embodiments, the Cre polypeptide is fused to a ligand binding domain. In some embodiments, the ligand binding domain is a hormone receptor. In some embodiments, the recombinase is a Cre-ERT2 polypeptide.

In some embodiments, the Rep gene codes for Rep polypeptides. In some embodiments, the Cap gene codes for Cap polypeptides. In some embodiments, transcription of the Rep gene and the Cap gene are driven by native promoters. In some embodiments, the native promoters comprise P5, P19, and P40.

In some embodiments, the Rep polypeptides are wildtype Rep polypeptides. In some embodiments, the Rep polypeptides comprise Rep78, Rep68, Rep52, and Rep40. In some embodiments, a truncated replication associated protein comprising a polypeptide expressed from the sequence of first part of a Rep gene and the exon is capable of being expressed in the absence of the recombinase.

In some embodiments, the Cap polypeptides are wildtype Cap polypeptides. In some embodiments, the Cap polypeptides are AAV capsid proteins. In some embodiments, the AAV capsid proteins comprise VP1, VP2, and VP3. In some embodiments, a serotype of the AAV capsid proteins is selected from the group consisting of AAV1, AAV2, AAV3, AAV4, AAV5, AAV6, AAV7, AAV8, AAV9, AAV 10, AAV11, AAV 12, AAV13, AAV 14, AAV 15 and AAV 16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, AAV.HSC16, and AAVhu68.

In some embodiments, the first polynucleotide construct further comprises a sequence coding for a selectable marker. In some embodiments, the selectable marker is a mammalian cell selection element. In some embodiments, the selectable marker is an auxotrophic selection element. In some embodiments, the auxotrophic selection element codes for an active protein. In some embodiments, the active protein is DHFR. In some embodiments, the selectable marker is an antibiotic resistance protein. In some embodiments, the selectable marker is a split intein linked to an N-terminus of the antibiotic resistance protein or split intein linked to a C-terminus of the antibiotic resistance protein. In some embodiments, the selectable marker is a leucine zipper linked to an N-terminus of the antibiotic resistance protein or leucine zipper linked to a C-terminus of the antibiotic resistance protein. In some embodiments, the antibiotic resistance protein is for puromycin resistance or blasticidin resistance.

In some embodiments, the first polynucleotide construct comprises a sequence having at least 70%, 80%, 90%, 95%, 99%, or 100% sequence identity to any one of SEQ ID NO: 1-SEQ ID NO: 3, SEQ ID 6-SEQ ID NO: 8, or SEQ ID NO: 32. In some embodiments, the second polynucleotide construct has at least 70%, 80%, 90%, 95%, 99%, or 100% sequence identity to any one of SEQ ID NO: 9-SEQ ID NO: 19, SEQ ID 23-SEQ ID NO: 32, or SEQ ID NO: 35. In some embodiments, the first polynucleotide construct and the second polynucleotide construct are stably integrated in the cell's genome.

In some embodiments, the cell further comprises a payload construct, wherein the payload construct is a polynucleotide coding for a payload. In some embodiments, the payload construct comprises a sequence having at least 70%, 80%, 90%, 95%, 99%, or 100% sequence identity to SEQ ID NO: 33. In some embodiments, the payload construct comprises a sequence of a payload flanked by ITR sequences. In some embodiments, expression of the sequence of the payload is driven by a constitutive promoter. In some embodiments, the constitutive promoter and sequence of the payload are flanked by ITR sequences.

In some embodiments, the sequence of the payload comprises a polynucleotide sequence coding for a gene. In some embodiments, the gene codes for a selectable marker or detectable marker. In some embodiments, the gene codes for a therapeutic polypeptide or transgene.

In some embodiments, the sequence of the payload comprises a polynucleotide sequence coding for a therapeutic polynucleotide. In some embodiments, the therapeutic polynucleotide is a tRNA suppressor or a guide RNA. In some embodiments, the guide RNA is a polyribonucleotide capable of binding to a protein. In some embodiments, the protein is nuclease. In some embodiments, the protein is a Cas protein, an ADAR protein, or an ADAT protein. In some embodiments, the Cas protein is catalytically inactive Cas protein. In some embodiments, the payload construct is stably integrated into the genome of the cell.

In some embodiments, a plurality of the payload construct are stably integrated into the genome of the cell. In some embodiments, the plurality of the payload constructs are separately stably integrated into the genome of the cell. In some embodiments, the payload construct further comprises a sequence coding for a selectable marker or detectable marker outside of the ITR sequences. In some embodiments, the payload construct is integrated into the genome of the cell.

Also provided herein are methods of producing a stable cell line comprising expanding a cell described above.

Also provided herein are methods of producing a plurality of rAAV virion comprising culturing a cell described above in the presence of a first triggering agent and a second triggering agent. In some embodiments, the first triggering agent is doxycycline and the second triggering agent is tamoxifen. In some embodiments, the plurality of rAAV virion have an encapsidation ratio of no less than 0.5, 0.6, 0.7, 0.8, 0.9, 0.95, 0.97, or 0.99 prior to purification. In some embodiments, the plurality of rAAV virion have a F:E ratio of no less than 0.5, 0.6, 0.7, 0.8, 0.9, 0.95, 0.97, or 0.99 prior to purification. In some embodiments, the plurality of rAAV virion have a concentration of greater than $1\times10^{11}$ or no less than $5\times10^{11}$, $1\times10^{12}$, $5\times10^{12}$, $1\times10^{13}$ or $1\times10^{14}$ viral genomes per milliliter prior to purification. In some embodiments, the plurality of rAAV virion have an infectivity of no less than 50%, 60%, 70%, 80%, 90%, 95%, or 99% at an MOI of $1\times10^{5}$ vg/target cell or less. In some embodiments, the culturing is in a bioreactor.

Also provided herein are pharmaceutical compositions comprising the rAAV virion produced by the cell or the method described above and a pharmaceutically acceptable carrier. Also provided herein are methods of treating a condition or disorder, the method comprising administering a therapeutically effective amount of the pharmaceutical composition to a patient in need thereof.

5. BRIEF DESCRIPTION OF THE DRAWINGS

FIG. 1 depicts the pre-triggered state of an exemplary cell in which a plurality of synthetic nucleic acid constructs have been separately integrated into the nuclear genome. This exemplary cell gives rise to a stable cell line capable of conditionally producing recombinant AAV (rAAV) virions that package a payload (e.g., a therapeutic polynucleotide). The brackets in construct 3 indicate the position of the flanking ITRs.

FIGS. 2A-2C depict an exemplary embodiment of construct 2 from FIG. 1 in greater detail. This construct permits conditional expression of Cre. In the pre-triggered state (top of FIG. 2A) the integrated nucleic acid construct has a Cre coding sequence and adenoviral E2A and E4 helper protein coding sequences collectively under the control of an inducible promoter that becomes active upon the addition of a triggering agent. Other coding elements (activator and a gene that permits mammalian selection (mammalian selection)) are under control of a constitutive promoter ("CMV promoter"). The Cre coding element is positioned between LoxP sites and is additionally fused to estrogen response elements ("ER2"), which allows for control over the localization of Cre in response to estrogen agonists, such as tamoxifen. Upon addition of a triggering agent, Cre is expressed (bottom of FIG. 2A), and upon addition of Tamoxifen, Cre translocates to the nucleus. As shown in FIG. 2B, following translation and translocation of the Cre protein into the cell nucleus, the Cre protein effects excision of its own coding sequence, leaving the integrated construct shown at the bottom of FIG. 2B. Shown in FIG. 2C is an optional insert in construct 2. The optional insert includes a Cre inducible U6 promoter that drives the expression of transcriptionally dead mutants of VA RNA1 (VA RNA). Specifically, the U6 promoter is split into two parts separated by a Lox flanked stuffer sequence. The U6 promoter is inactive because of the presence of the stuffer sequence. Cre mediated excision of the stuffer sequence activates the U6 promoter, which then drives the expression of VA RNA.

FIGS. 3A-3B are schematics depicting details of an exemplary embodiment of construct 1. This construct is designed to permit expression of AAV Rep and Cap proteins from their endogenous promoters after a triggering event. FIG. 3A shows the pre-triggered state of the integrated nucleic acid construct. An intervening spacer (excisable spacer) interrupts the Rep coding sequence. The excisable spacer comprises a first spacer segment, a second spacer segment which is excisable (second "excisable" spacer segment), and a third spacer segment. The second "excisable" spacer segment comprises EGFP flanked by LoxP sites and an upstream 3' splice site (3'SS). A pre-triggered transcript is shown at the bottom of the figure. This pre-triggered transcript encodes the 5' portion of AAV rep fused to a fluorescent marker protein, EGFP. The pre-triggered transcript contains a single intron flanked by 5' splice site (5'SS) and 3' splice site (3'SS). FIG. 3B shows the conversion of the pre-triggered construct (top schematics) to a post-triggered state (bottom schematics) upon exposure to Cre in the cell nucleus. Cre excises the second "excisable" spacer segment, which includes the EGFP marker coding sequence and the upstream 3' splice site (3' SS). When the second "excisable" spacer segment is excised by Cre, the construct allows for expression of functional Rep and Cap transcripts from their respective endogenous promoters.

FIG. 4 depicts an exemplary embodiment of construct 3. Construct 3 comprises a sequence that encodes a payload (payload polynucleotide). The payload polynucleotide is under control of a constitutive promoter. The brackets indicate the position of the flanking ITRs. As indicated, in various nonlimiting embodiments, the payload is a transgene encoding a protein of interest, a homology element for homology-directed repair (e.g., HDR homology region), or a guide RNA. Also shown is a coding sequence coding for a protein that permits selection in mammalian cells (mammalian selection).

FIG. 5A depicts an exemplary embodiment of a split auxotrophic selection system that permits stable retention of two integrated nucleic acid constructs under a single selective pressure. One construct encodes the N-terminal fragment of mammalian dihydrofolate reductase (DHFR) fused to a leucine zipper peptide ("Nter-DHFR"). This N-terminal fragment is enzymatically nonfunctional. The other construct encodes the C-terminal fragment of DHFR fused to a leucine zipper peptide ("Cter-DHFR"). This C-terminal fragment is enzymatically nonfunctional. When both fragments are concurrently expressed in the cell, a functional DHFR enzyme complex is formed through association of the leucine zipper peptides. Both constructs can be stably retained in the genome of a DHFR null cell by growth in a medium lacking hypoxanthine and thymidine (-HT selection).

FIG. 5B shows an exemplary deployment of this split auxotrophic selection design in the multi-construct system of FIG. 1 in its pre-triggered state. In this example, the split auxotrophic selection elements are deployed in constructs 1 and 3. A separate exemplary antibiotic selection approach, blasticidin resistance, is deployed in construct 2. This results in the ability to stably maintain all three constructs in the mammalian cell line by culturing in medium having a single antibiotic, blasticidin, and lacking both thymidine and hypoxanthine.

FIG. 6 depicts the post-triggered state of all 3 constructs following the addition of tamoxifen and a triggering agent. In the presence of the triggering agent, adenoviral E2A and E4 helper proteins are expressed. AAV rep and cap coding sequences are expressed under control of endogenous promoters. The payload is expressed under control of a constitutive promoter. rAAV virions encapsidating the payload are therefore produced. The three integrated constructs are stably maintained in the nuclear genome with a single antibiotic (Blasticidin) and auxotrophic selection (media lacking both thymidine and hypoxanthine).

FIGS. 7A-7B are light and fluorescence microscopic images. Light microscope images are presented in the left column. Green fluorescence images are presented in the middle column. Red fluorescence images are presented in the right column. Following addition of different amounts of Cre vesicles containing Cre protein and a red fluorescence marker protein, cells were either mock-transfected ("Mock"), transfected with a plasmid having construct 1 ("AAV2 CODE"), or transfected with a control AAV2 plasmid capable of expression Rep and Cap proteins ("AAV2"). Without addition of Cre (FIG. 7A), only the cells transfected with a plasmid having Construct 1 show intense green fluorescence, indicating expression of the Rep-EGFP fusion protein (see bottom of FIG. 3A). FIG. 7B shows decreased EGFP fluorescence in the presence of increasing amounts of Cre, indicating recombination and subsequent removal of EGFP cassette from construct 1.

FIGS. 8A-8B are blots and graphs showing Rep production from post-triggered plasmid construct 1. FIG. 8A shows Western blots illustrating that Cre-mediated excision of the excisable spacer segment induces Rep protein production from post-triggered plasmid construct 1. In addition, the presence of the rabbit beta globin intron does not interfere with Rep protein expression level. FIG. 8B shows a schematic of a Rep/Cap polynucleotide construct, which is cloned into a piggybac vector with a Blasticidin resistance gene (SEQ ID NO: 8). The excisable element interrupting the Rep gene was inserted downstream of the p19 promoter. The GFP levels confirm successful integration of the Rep/Cap construct in cells from STXC0068 cell line (bottom FACS plot) compared to cells from the parental cell line (top FACS plot). Graphs of the cell density (top graph) and viability (bottom graph) data of the STXC0068 cell line illustrate that there were no negative effects from the integrated AAV sequences. The left blot shows the production of Rep proteins and the right blot shows total protein, for the parental cell line, the parental cell line after the addition of Cre, the STXC0068 cell line, and the STXC0068 cell line after the addition of Cre.

FIG. 9A presents a schematic of the PKR pathway interactions.

Figure 22:
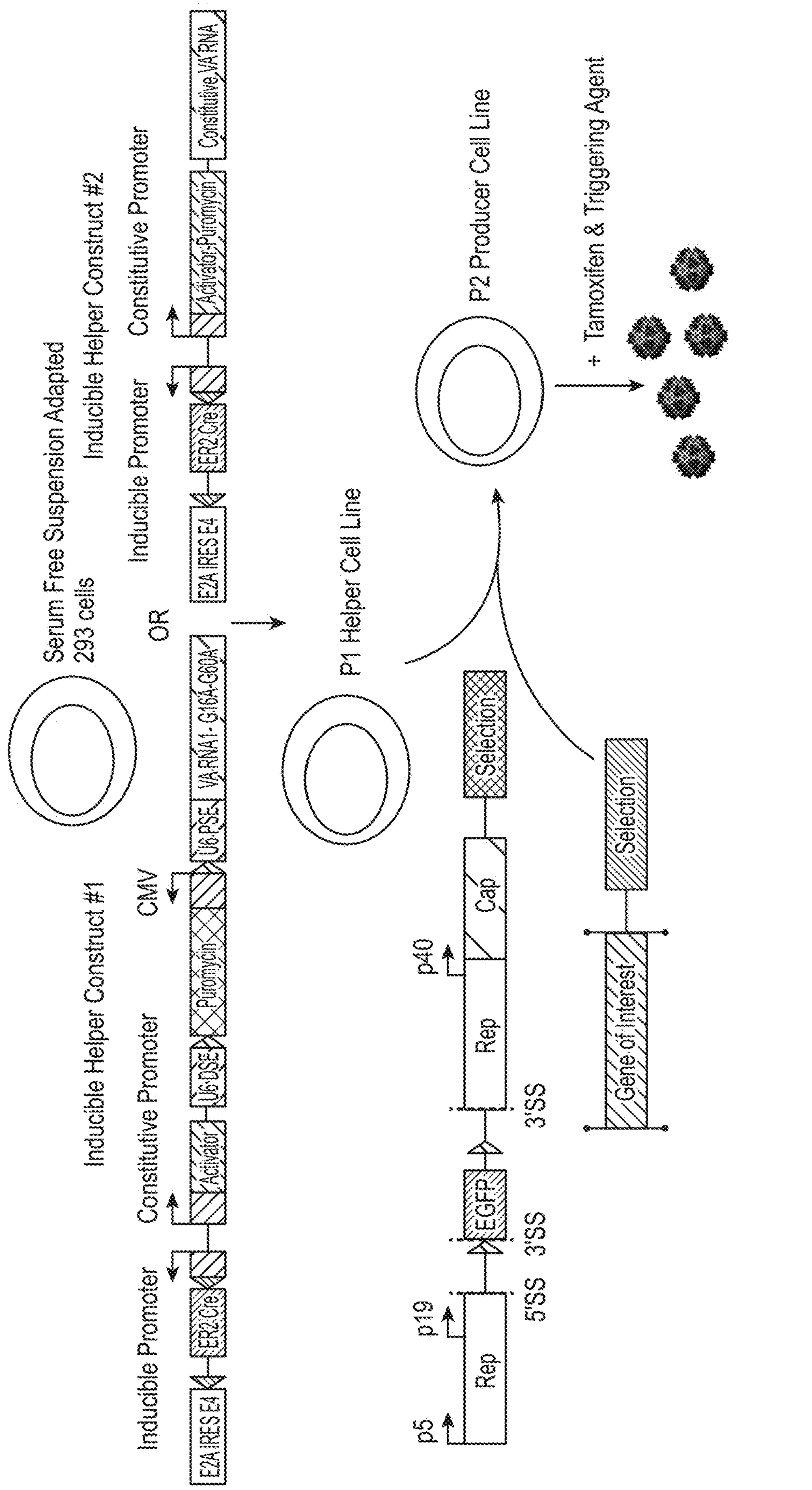

FIG. 22 is a schematic showing the production of an exemplary stable cell line (P2 Producer Cell Line) containing a Rep/Cap construct, an inducible helper construct, and a construct with payload construct and the packaging of the payload (Gene of Interest) into virions. The P1 Helper Cell Line is produced from integration of either inducible helper construct #1 or inducible construct #2 into the Serum Free Suspension Adapted 293 cells.

Figure 23:
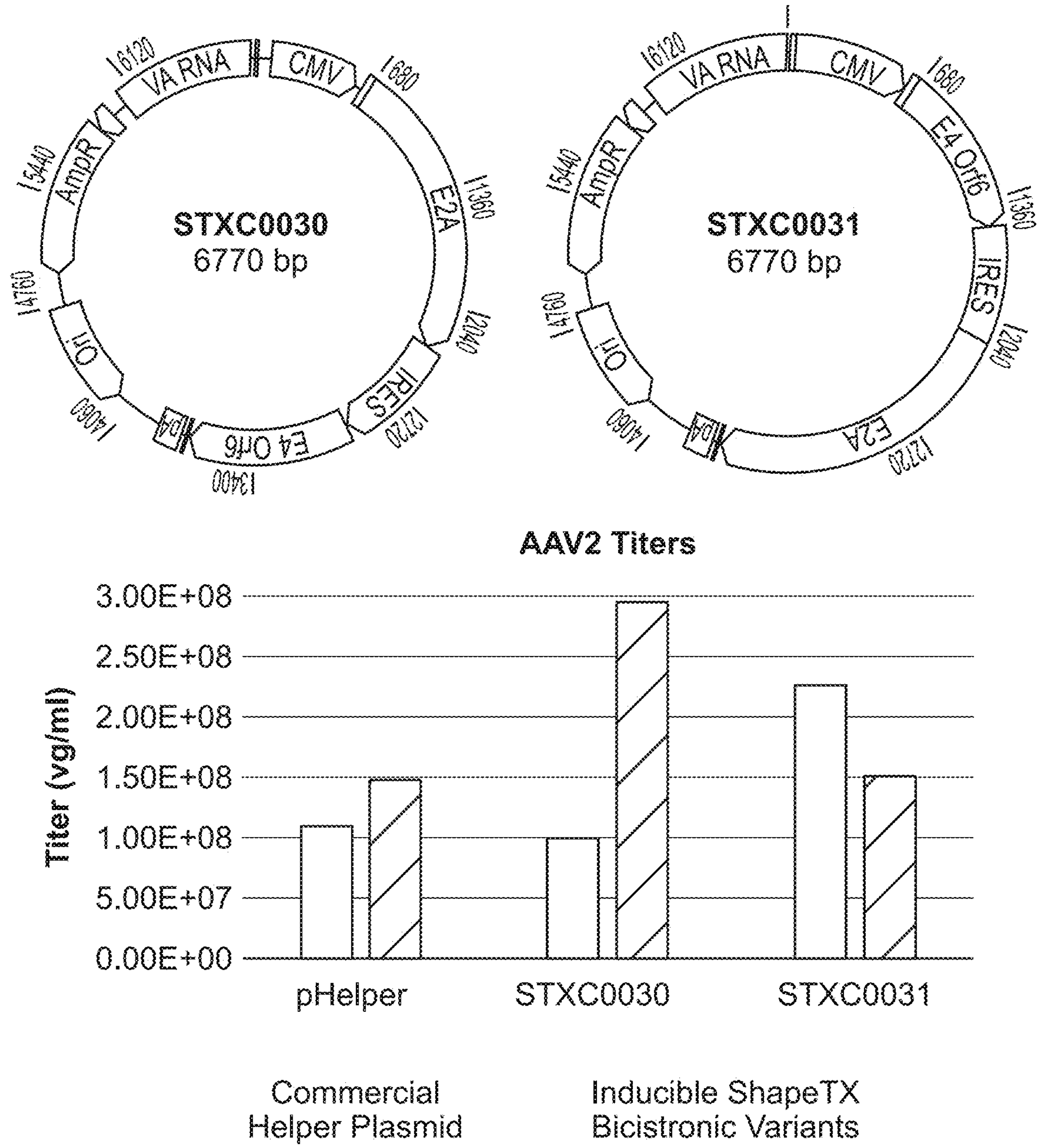

FIG. 23 shows plasmid maps and a graph showing Rep production using inducible bicistronic constructs in a transient transfection system.

Figure 24:
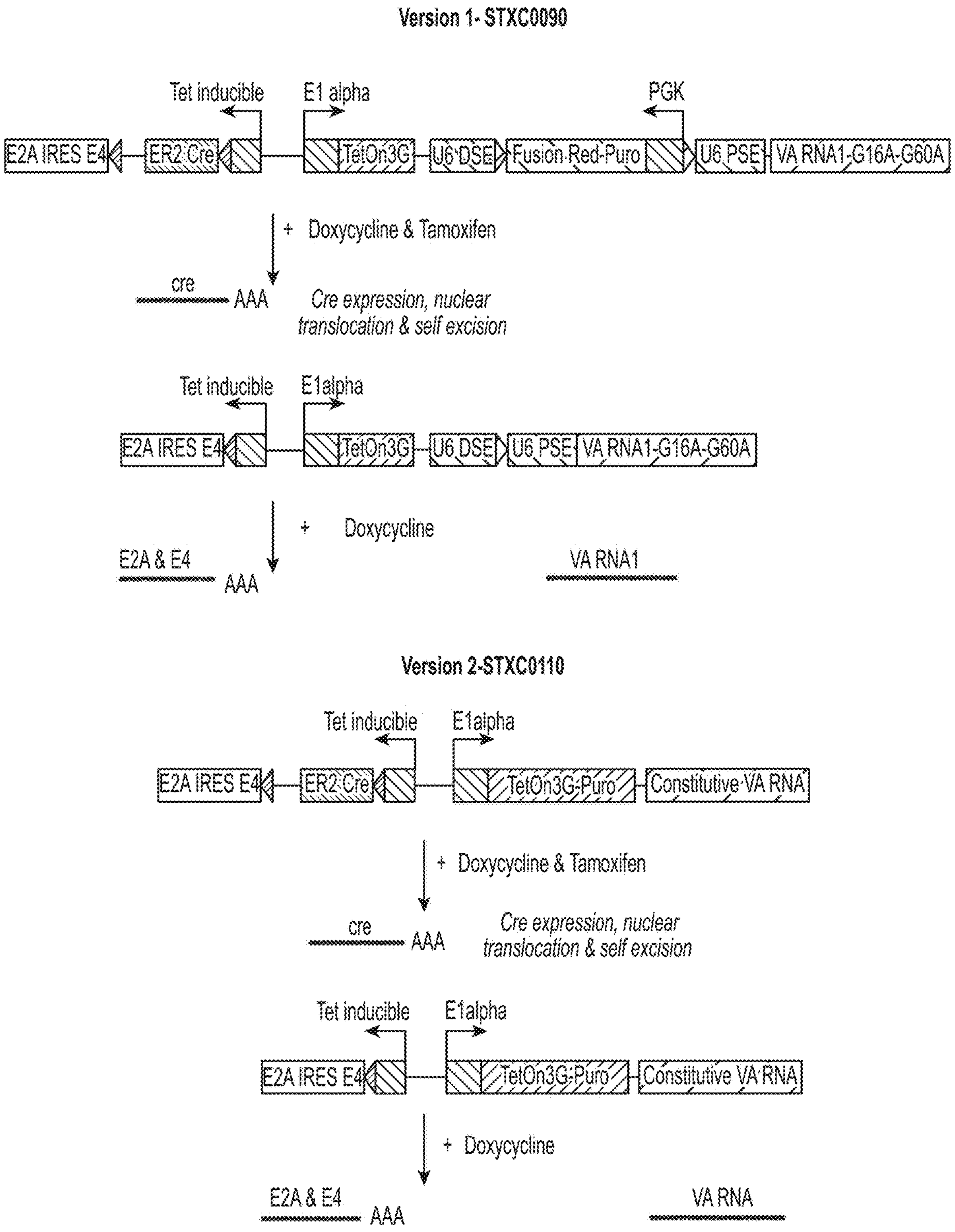

FIG. 24 shows schematics of STXC0090 and STXC0110 constructs illustrating helper and Cre induction using the TetOn system.

Figure 25:
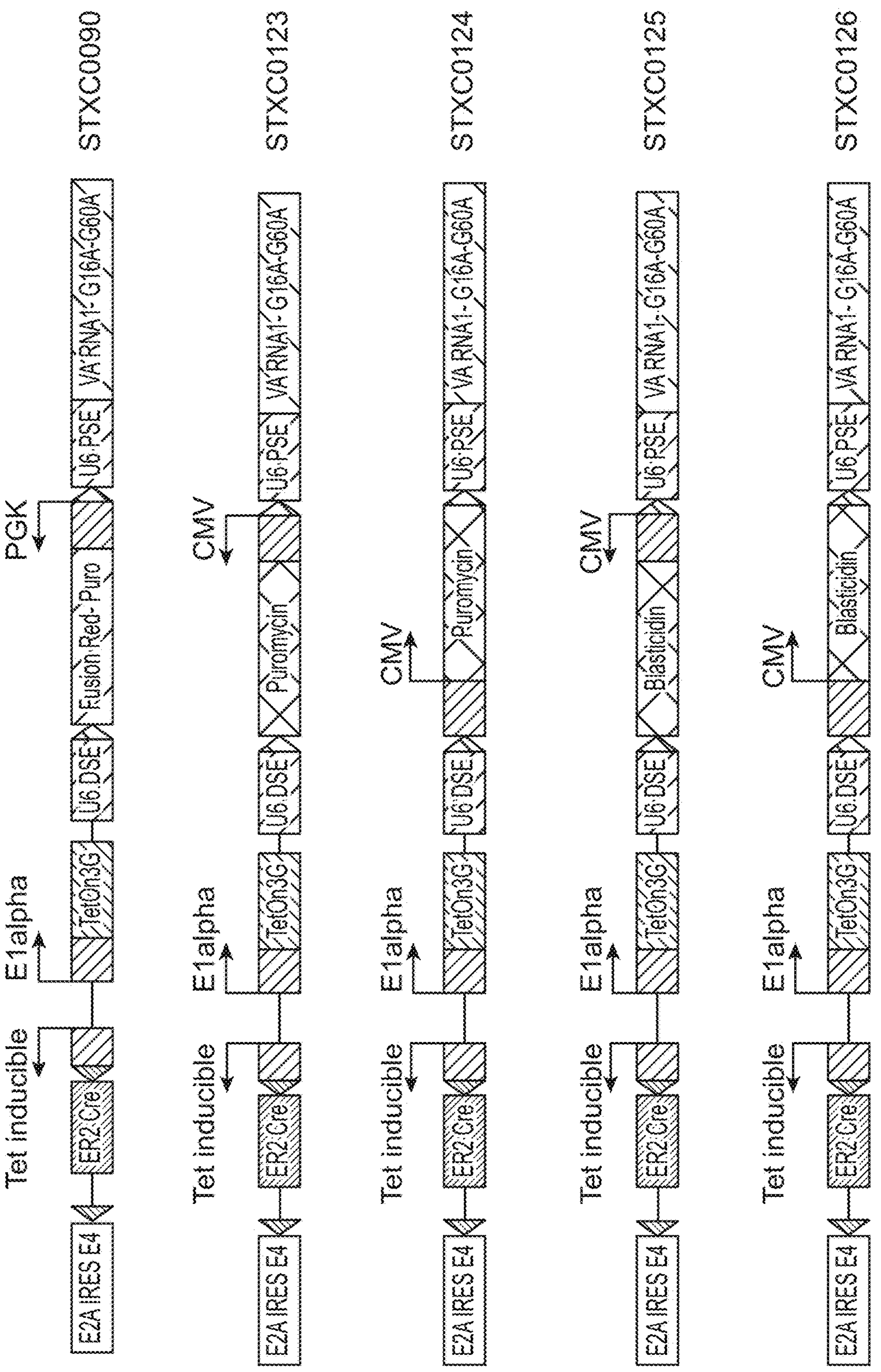

FIG. 25 shows schematics of VA RNA mutant constructs and various promoter and selection options.

Figure 26:
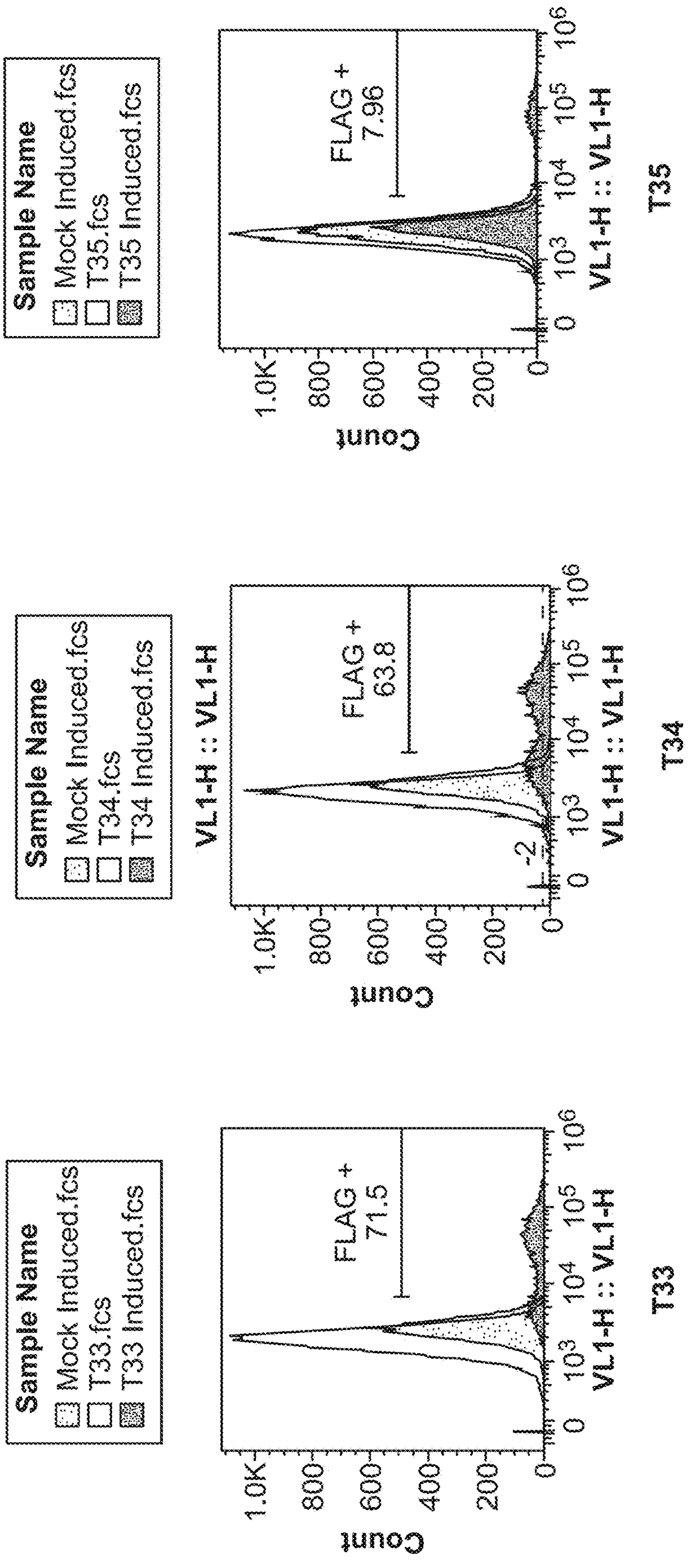

FIG. 26 shows intracellular staining for expression of FLAG-tagged E2A from cells with stable integration of STXC-0123 (T33, left plot), STXC-0124 (T34, middle plot), or STXC-0125 (T35, right plot) helper constructs, and after either mock induction, no induction, or induction of Cre.

Figure 27:
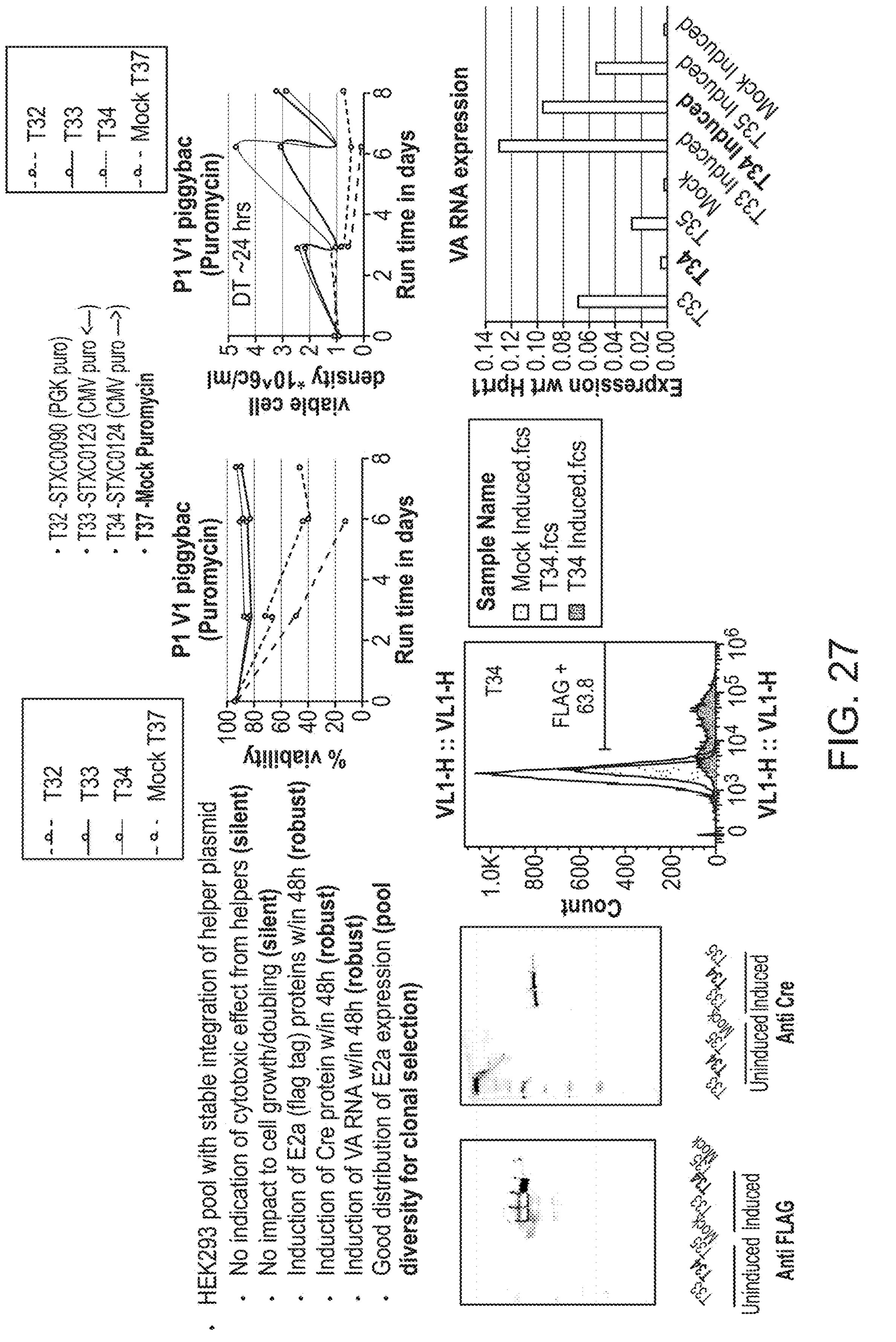

FIG. 27 shows an overview of HEK293 cells with the stably integrated helper plasmid showing no cytotoxic effects and induction of Cre, production of VA RNA and good distribution of E2A expression.

Figure 28:
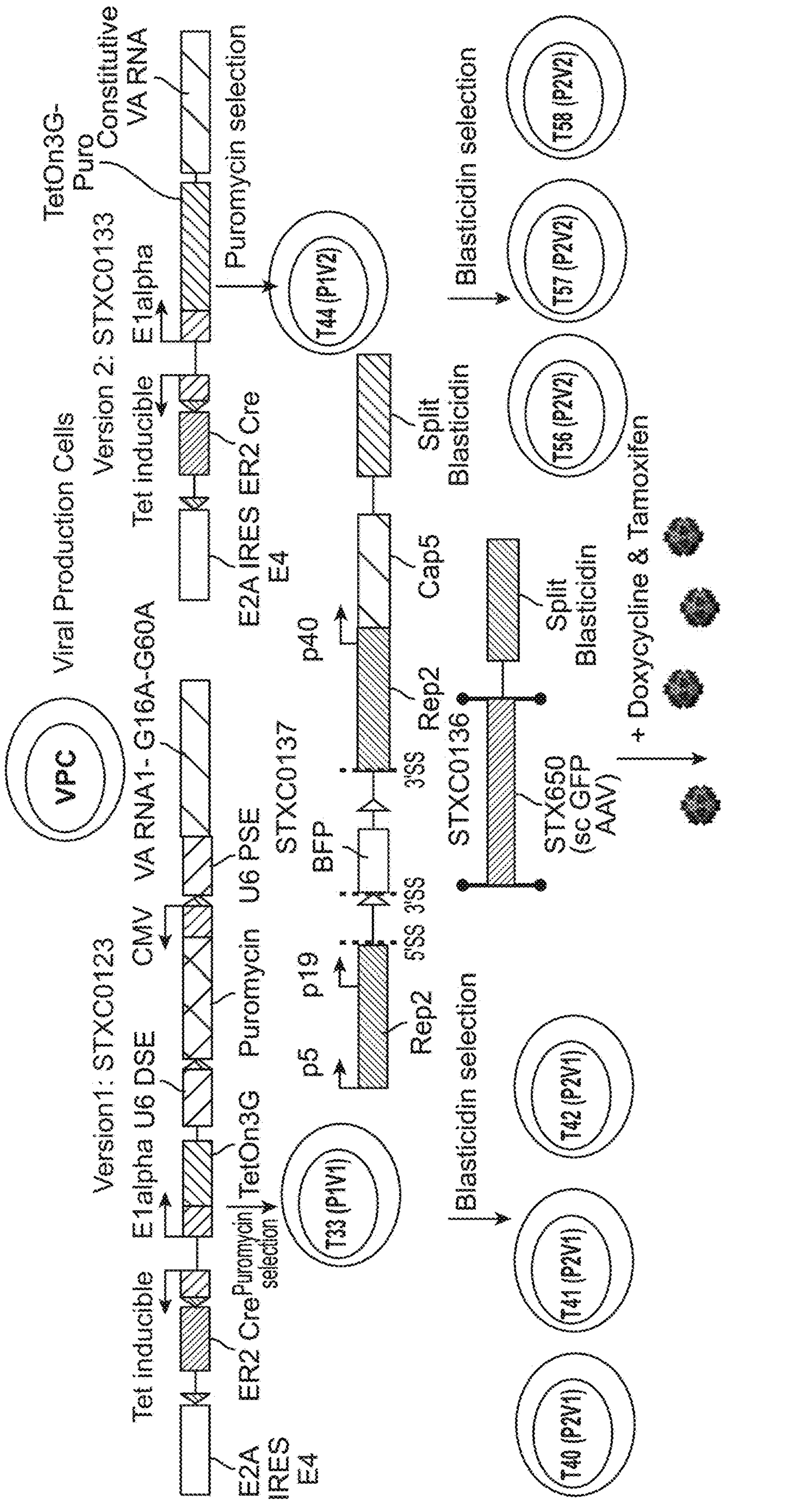

FIG. 28 shows work flows for producing stable cell line pools. The schematic and work flow on the left illustrates integration of STXC0123 to produce the T33 pool, in which STXC0137 and STXC0136 are then integrated, to produce three stable cell line pools (T40, T41, and T42). The schematic and work flow on the right illustrates integration of STXC0133 to produce the T44 pool, in which STXC0137 and STXC0136 are then integrated, to produce three stable cell line pools (T56, T57, and T58). The stable cell line pools are then treated with doxycycline and tamoxifen to produce virions encapsidating STXC650.

Figure 29:
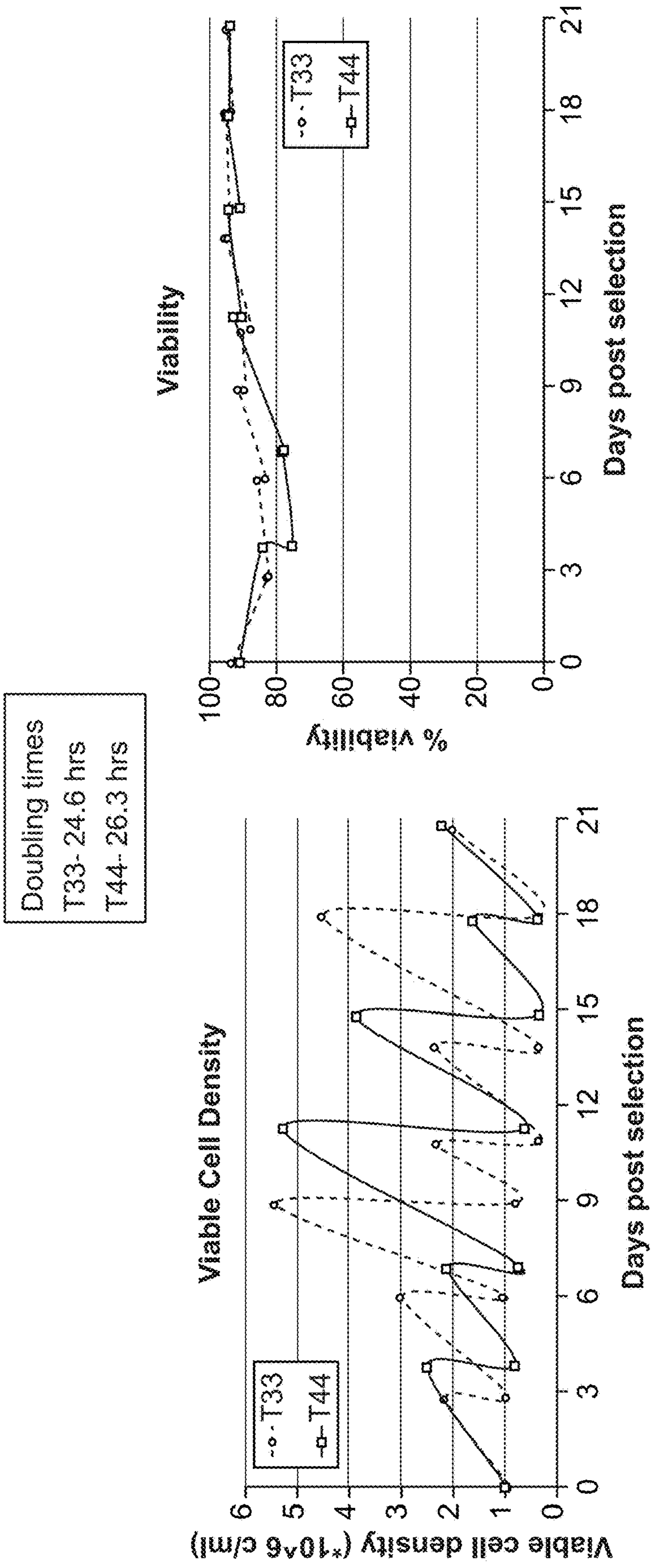

FIG. 29 shows graphs of the viable cell density (left graph) and viability (right graph) for the T33 pool and T44 pool (FIG. 28), and illustrate that there were no negative effects from the integrated plasmid constructs.

Figure 30:
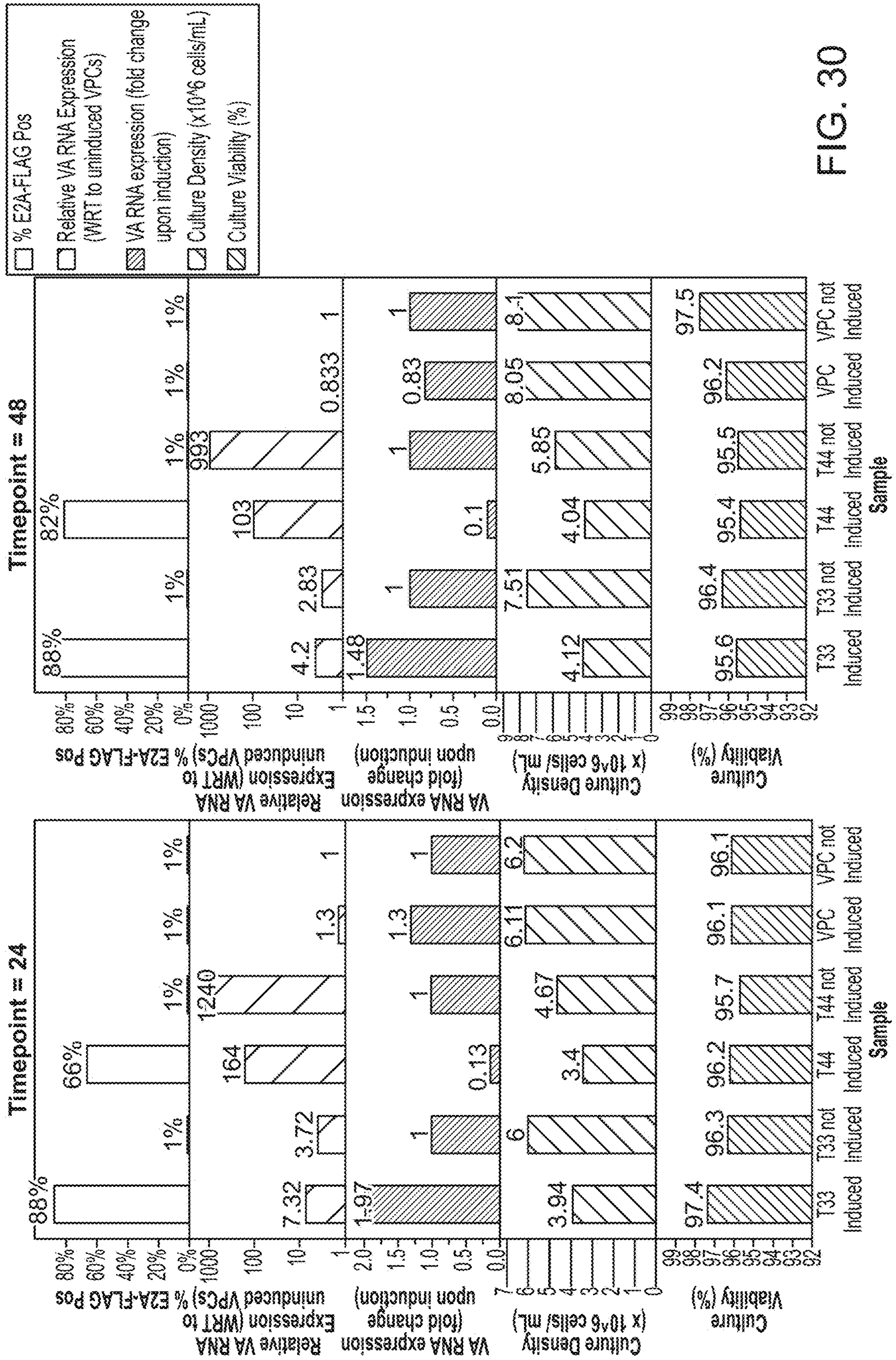

FIG. 30 shows graphs for E2A expression, VA RNA expression, culture density and culture viability for the T33 pool stable cell line, the T44 stable cell line, and the parental cell line (VPC) either not induced or after induction. The left graph is at 24 hours post induction and the right graph is at 48 hours post induction.

Figure 31:
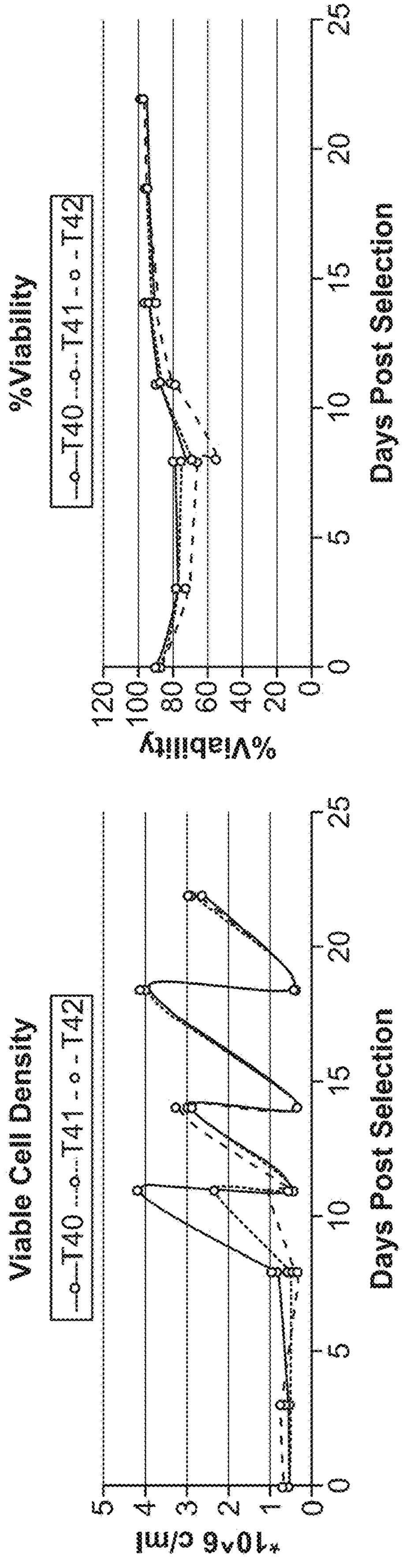

FIG. 31 shows graphs of the viable cell density (left graph) and viability (right graph) for the T40, T41, and T42 cell line pools illustrated in FIG. 28.

Figure 32:
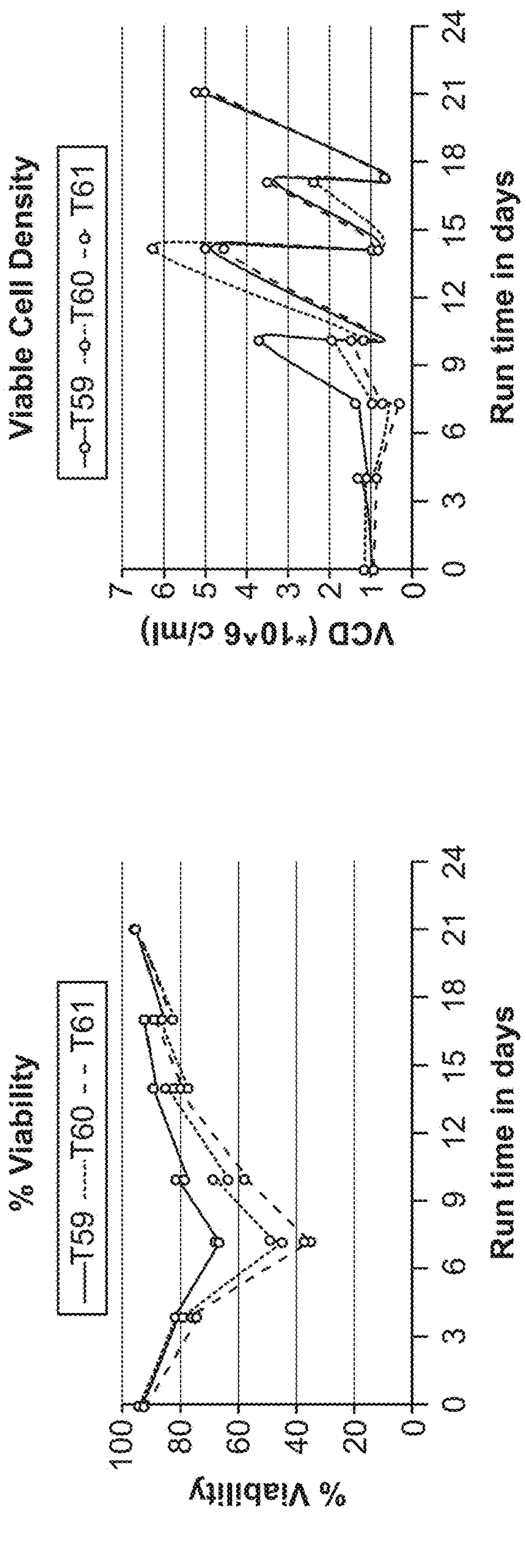

FIG. 32 shows graphs of the viable cell density (right graph) and viability (left graph) for the T59, T60, and T61 cell line pools, which were produced the same way as the T56, T57, and T58 cell line pools illustrated in FIG. 28.

Figure 33:
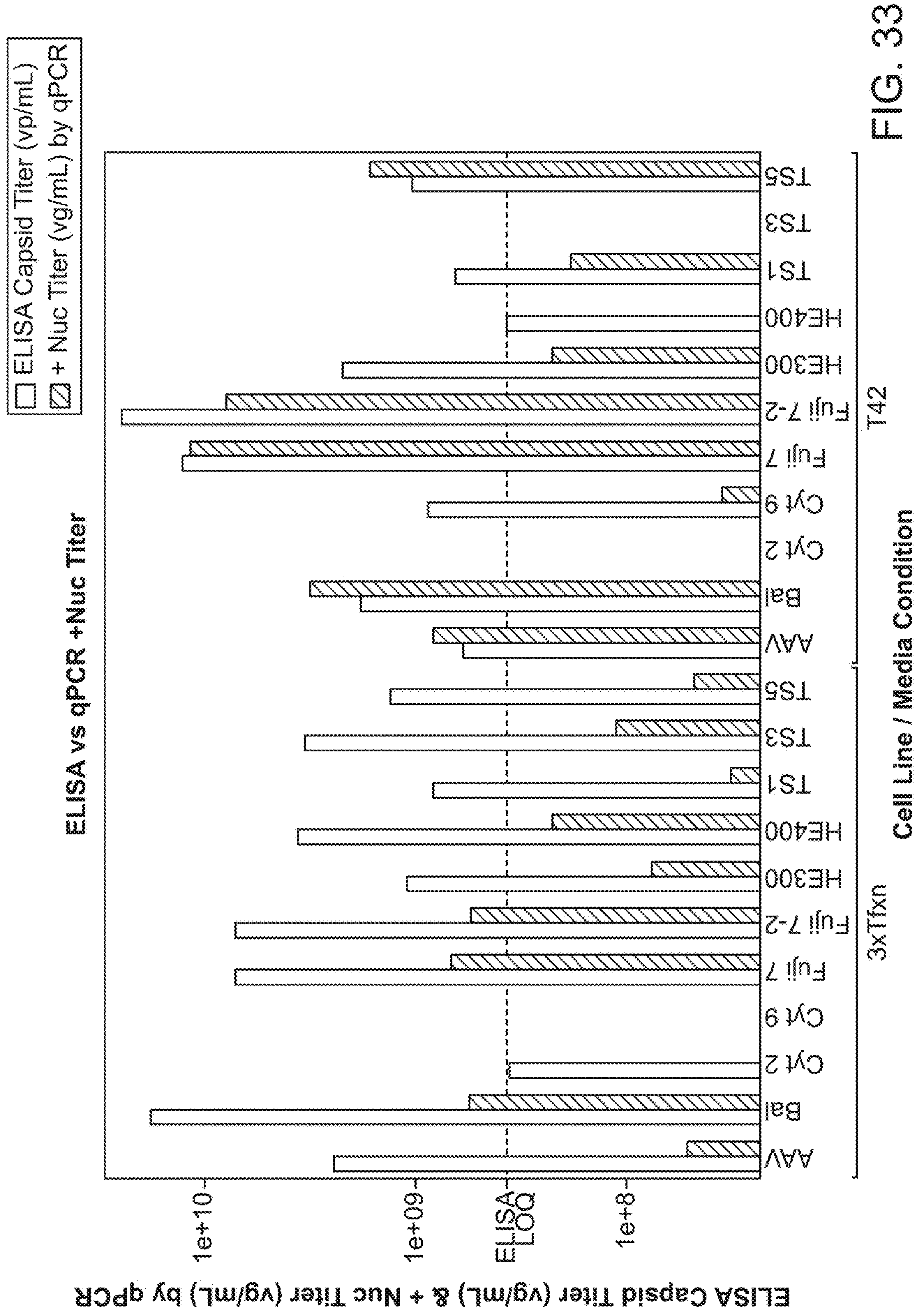

FIG. 33 shows a graph of capsid production from the T42 pool stable cell line after induction compared to cells produced by transient triple transfection (3×Tfxn) in various cell medias (AAV, Bal, Cyt 2, Cyt9, Fuji 7, Fuji 7-2, HE300, TS1, TS3, or TS5). The left bar for each media type indicates total capsid titer and the right bar for each media type indicates the titer of capsids encapsidating a viral genome (e.g., the payload construct).

Figure 34:
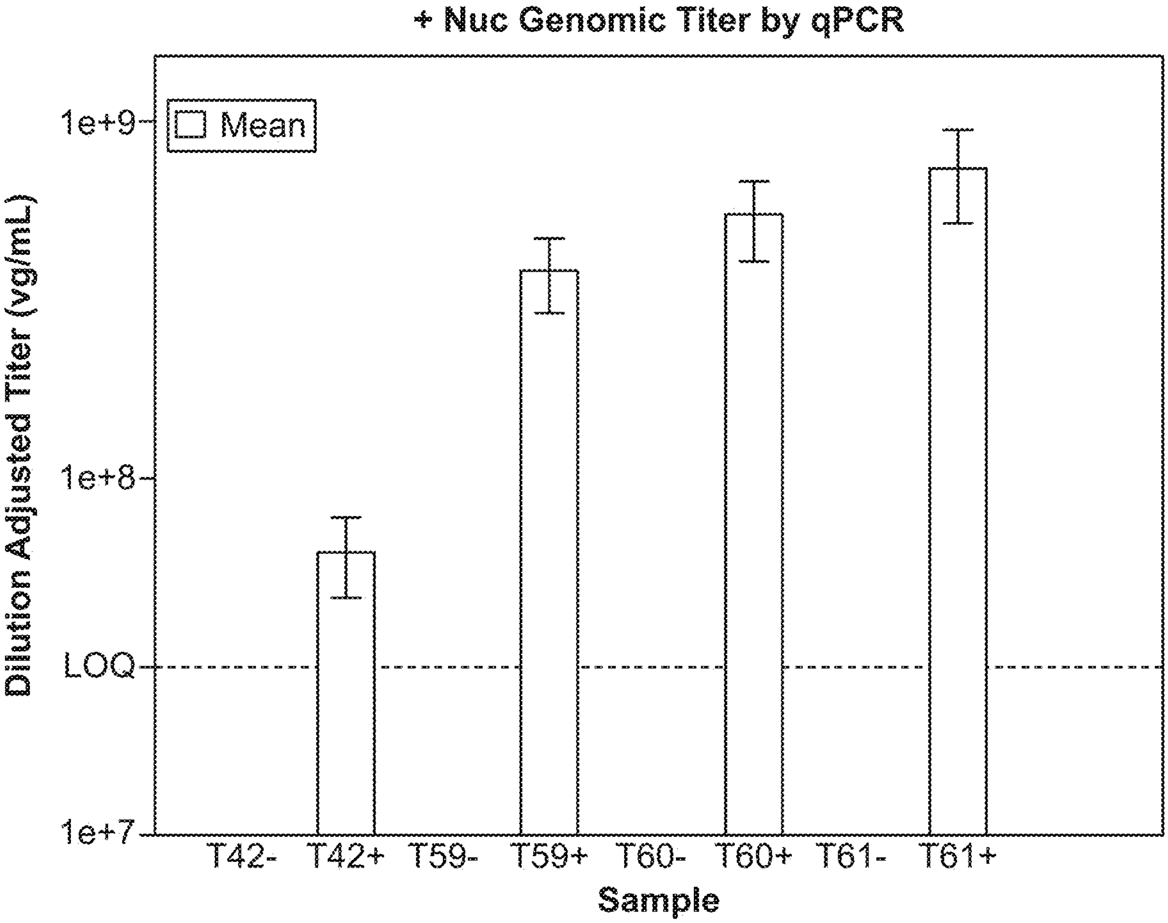

FIG. 34 shows the titer of capsids encapsidating a viral genome (e.g., the payload construct) for the T42 stable cell line pool, T59 stable cell line pool, T60 stable cell line pool, and T61 stable cell line pool either with (+) or without (−) induction in HE300 media.

Figure 35:
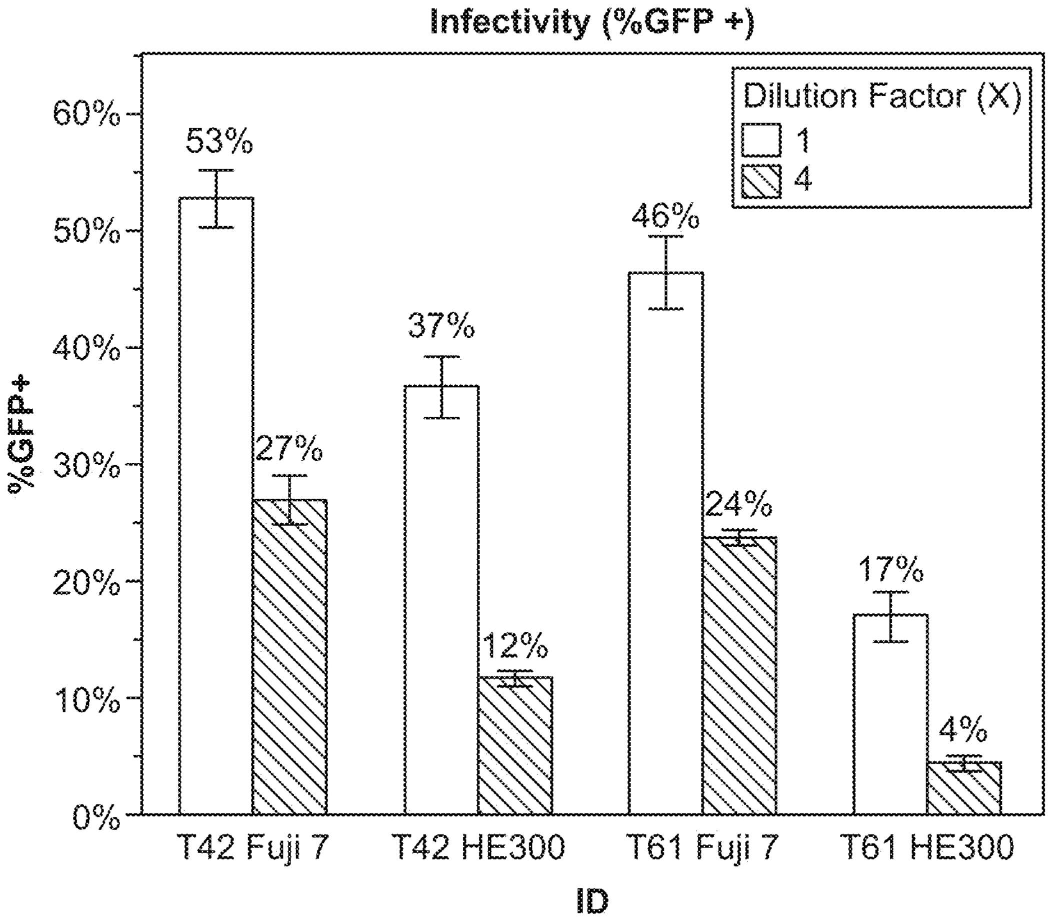

FIG. 35 shows infectivity as indicated by the percentage of GFP+ cells after infecting target cells (CHO Pro-5 cells) with capsids from the T42 pool stable cell line compared to the T61 pool stable cell line in various media. The left bar for each cell line type/media is for a dilution factor of 1 and the right bar for each cell line type/media is for a dilution factor of 4.

Figure 36:
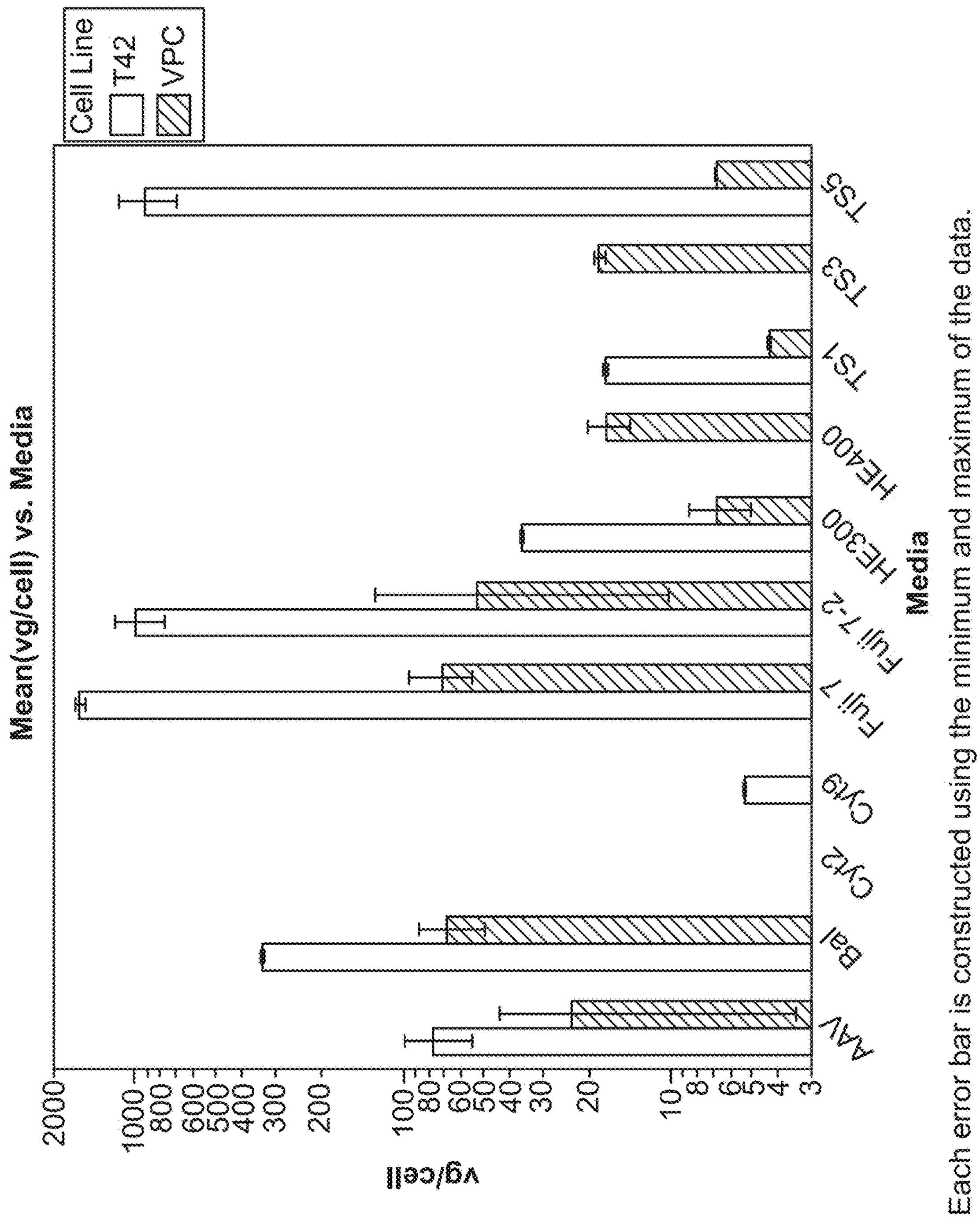

FIG. 36 shows a graph of the titer of capsids encapsidating a viral genome (e.g., the payload construct) per cell from the T42 pool stable cell line after induction compared the titer of capsids encapsidating a viral genome (e.g., the payload construct) to per cell from the triple transfected parental cells (VPC) in various cell medias. The left bar for each media type indicates titer of capsids encapsidating a viral genome produced per cell from the T42 pool stable cell line and the right bar for each media type indicates titer of capsids encapsidating a viral genome produced per cell from the triple transfected parental cell line (VPC).

Figure 37:
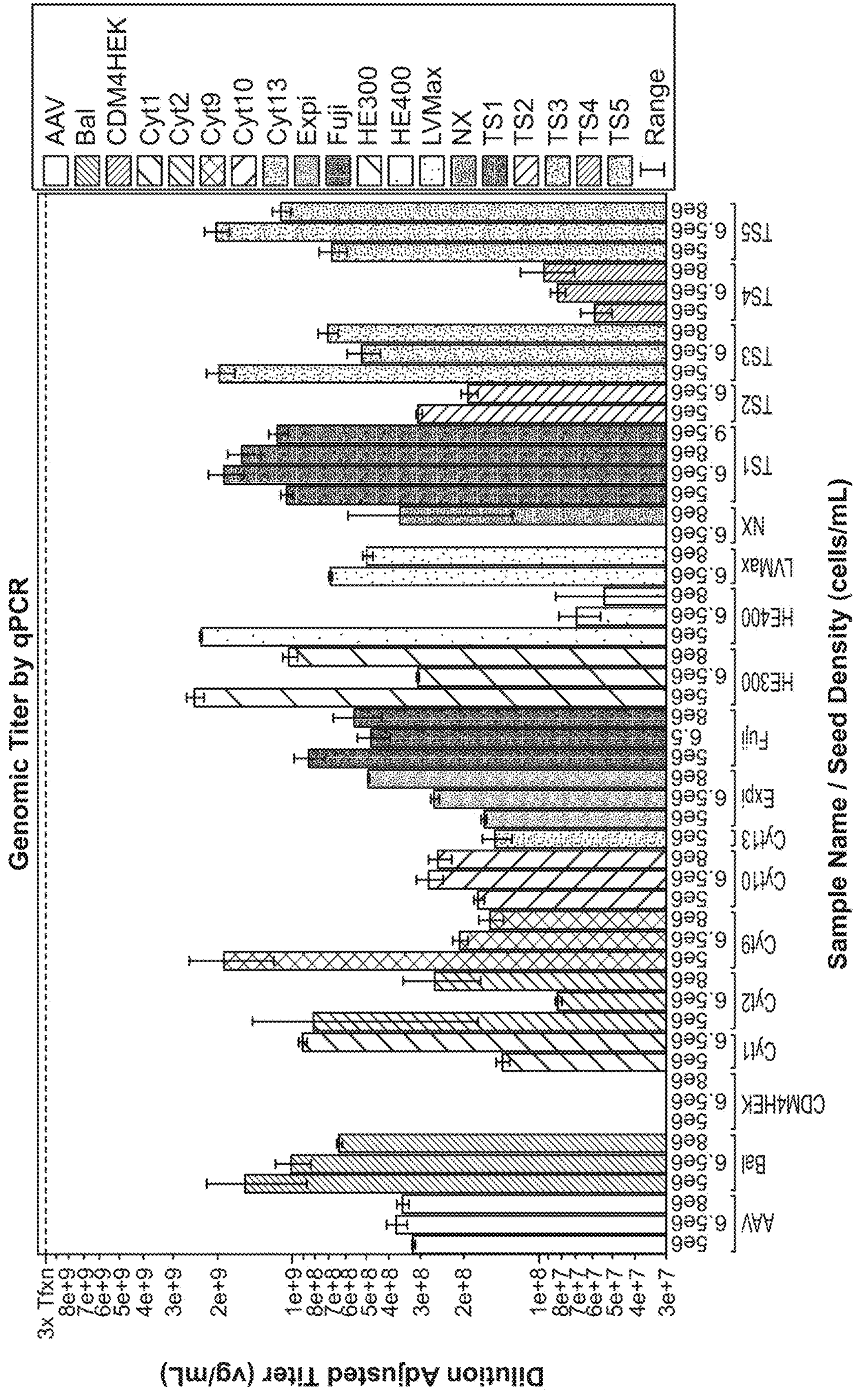

FIG. 37 shows a graph of the dilution adjusted titer of capsids encapsidating a viral genome (e.g., the payload construct) from the T42 pool stable cell line after induction at different seed densities in various cell medias. The 3×Tfxn dashed line indicates the dilution adjusted titer of capsids encapsidating a viral genome (e.g., the payload construct) produced by cells after transient triple transfection (3×Tfxn).

Figure 38:
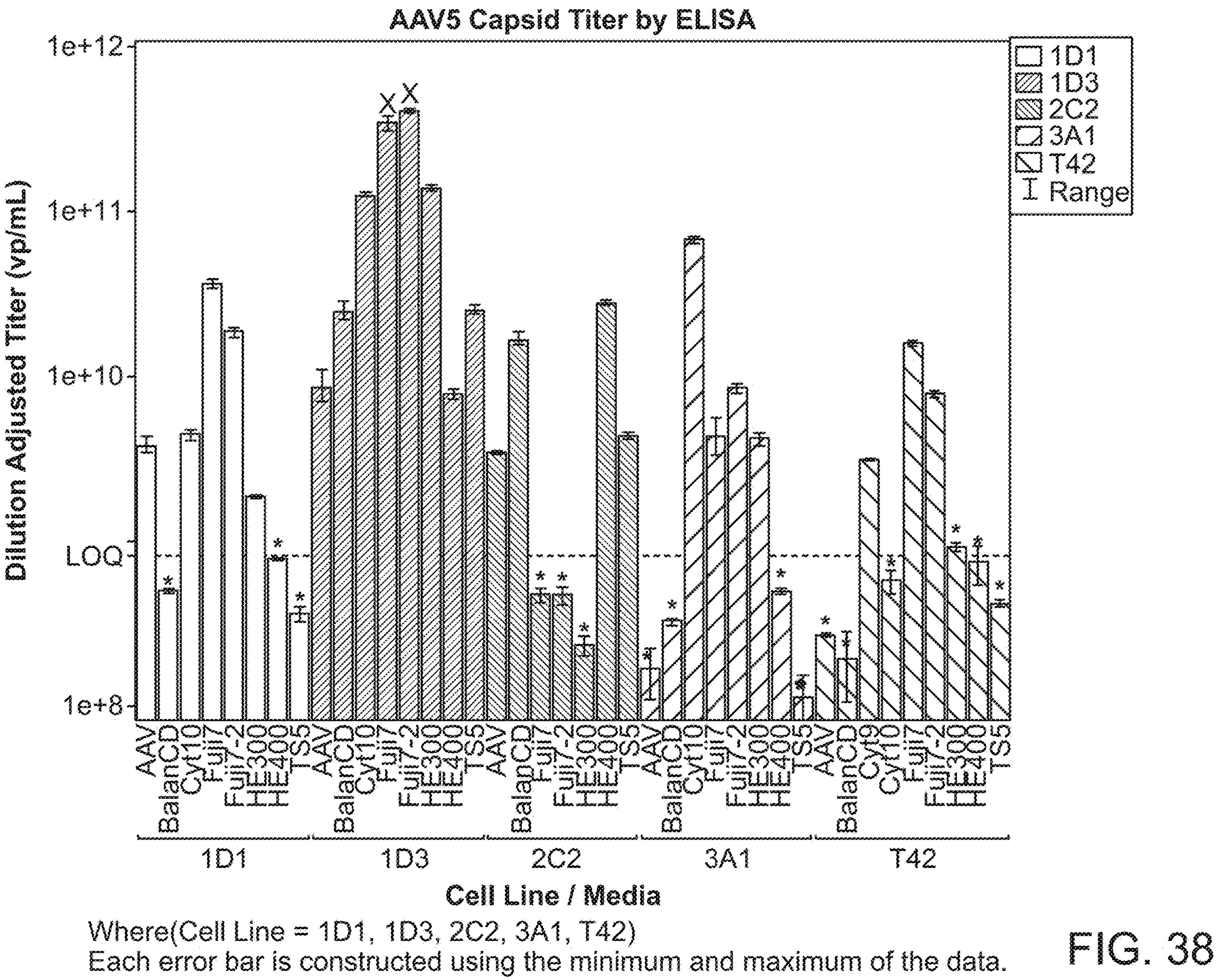

FIG. 38 shows a graph of total capsids in different cell media with mini pool clones selected from the T42 pool stable cell line compared to the T42 pool stable cell line after induction in different cell media.

Figure 39:
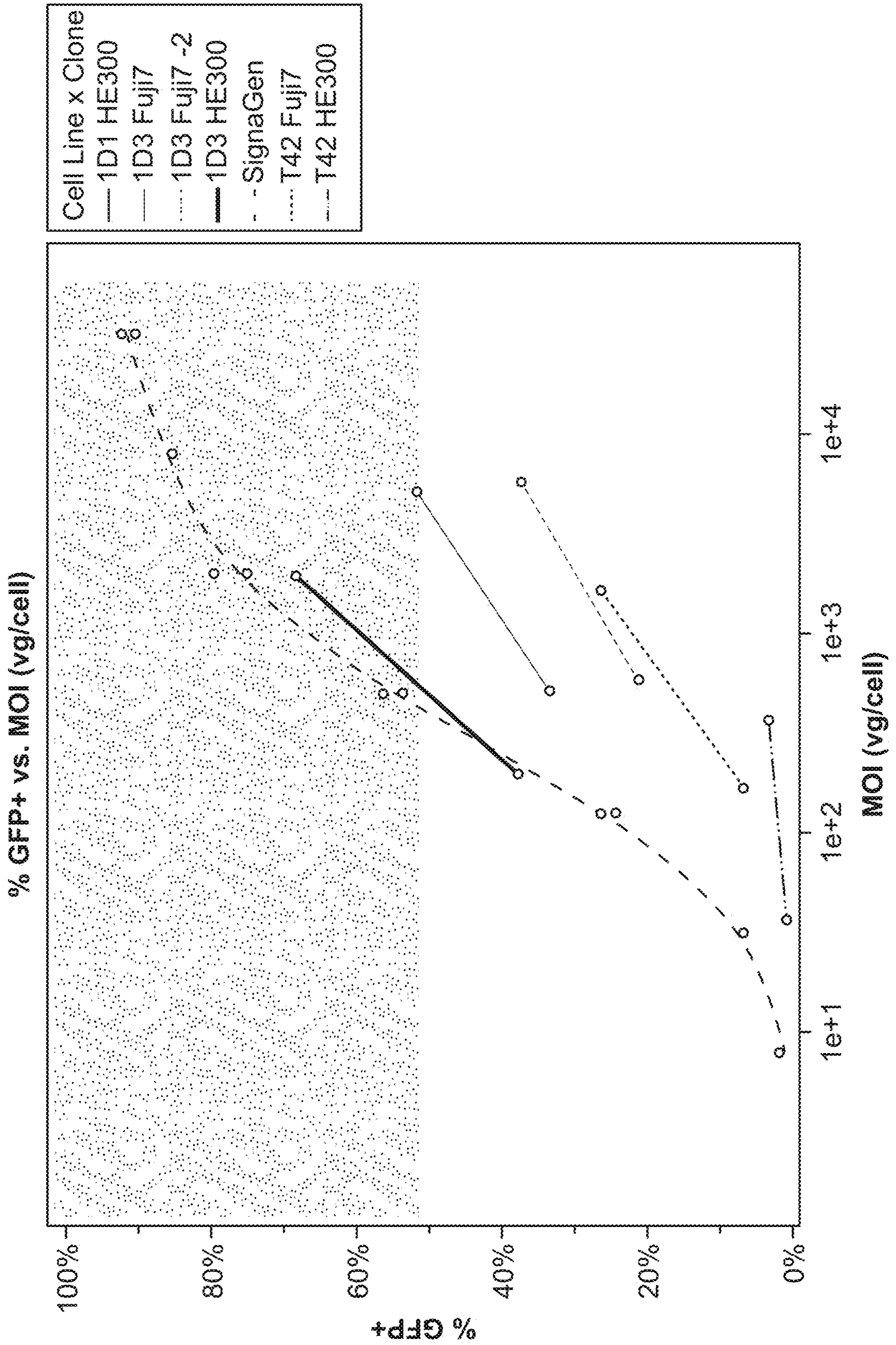

FIG. 39 shows infectivity as indicated by the percentage of GFP+ cells (encapsidated payload) after infecting target cells (CHO Pro-5 cells) with capsids versus multiplicity of infection (vg/cell) for mini pool clones selected from the T42 pool stable cell line in various cell media from FIG. 38. (Control is a purified capsid produced by cells after transient transfection).

Figure 40:
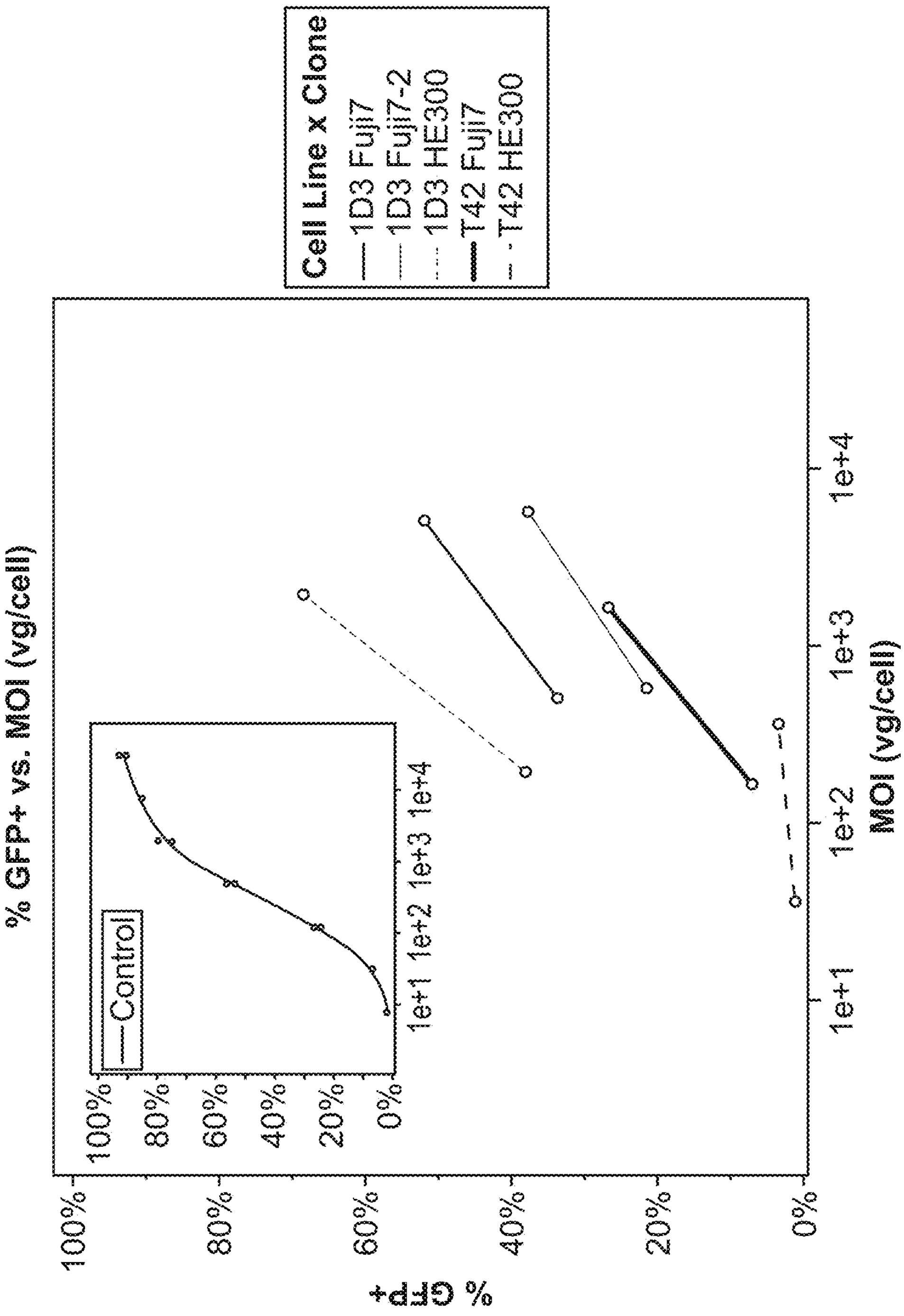

FIG. 40 shows infectivity as indicated by the percentage of GFP+ cells (encapsidated payload) after infecting target cells (CHO Pro-5 cells) with capsids versus multiplicity of infection (vg/cell) for mini pool clones selected from the T42 pool stable cell line in various cell media from FIG. 38. The inset control shows infectivity as indicated by the percentage of GFP+ cells (encapsidated payload) after infecting target cells (CHO Pro-5 cells) with capsids versus multiplicity of infection (vg/cell) for a purified capsid produced by cells after transient transfection.

6. DETAILED DESCRIPTION

To solve the problems presented by transient transfection approaches to rAAV production while addressing the toxicity of AAV Rep protein when constitutively expressed, disclosed herein are polynucleotide constructs and cell lines stably integrated with said polynucleotide constructs (referred to herein as "stable cell lines") that enable conditional (also referred to herein as "inducible") production of recombinant AAV (rAAV) virions. In some embodiments, the compositions and methods of use thereof as disclosed herein provide rAAV virions that encapsidate a desired expressible payload, such as an expressible therapeutic payload. Further provided herein is a stable mammalian cell line, wherein the cells are capable of conditionally producing recombinant AAV (rAAV) virions within which are packaged an expressible payload; and wherein a population of virions produced by the stable cell are more homogenous than a population of virions produced by an otherwise comparable cell producing rAAV virions upon transient transfection.

Further provided herein is a stable mammalian cell line, wherein the cells are capable of conditionally producing recombinant AAV (rAAV) virions within which are packaged an expressible payload; and production of virions is inducible upon addition of a triggering agent.

Further provided herein is a stable mammalian cell line, wherein the cells are capable of conditionally producing recombinant AAV (rAAV) virions within which are packaged an expressible payload; and production of virions is not conditioned on the presence of a plasmid within the cell.

6.1. DEFINITIONS

Unless defined otherwise, all technical and scientific terms used herein have the meaning commonly understood by one of ordinary skill in the art to which the invention pertains.

"Recombinant", as applied to an AAV virion, means that the rAAV virion (synonymously, rAAV virus particle) is the product of one or more procedures that result in an AAV particle construct that is distinct from an AAV virion in nature.

In some aspects, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. A host cell may be used as a recipient of an AAV helper construct, an AAV minigene plasmid, an accessory function vector, or other transfer DNA associated with the production of recombinant AAVs. The term includes the progeny of the original cell which has been transfected. Thus, a "host cell" may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation. A "host cell" as used herein may refer to any mammalian cell which is capable of functioning as an adenovirus packaging cell, i.e., expresses any adenovirus proteins essential to the production of AAV, such as HEK 293 cells and their derivatives (HEK293T cells, HEK293F cells), HeLa, A549, Vero, CHO cells or CHO-derived cells, and other packaging cells.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

The term "cell culture," refers to cells grown adherent or in suspension, bioreactors, roller bottles, hyperstacks, microspheres, macrospheres, flasks and the like, as well as the components of the supernatant or suspension itself, including but not limited to rAAV particles, cells, cell debris, cellular contaminants, colloidal particles, biomolecules, host cell proteins, nucleic acids, and lipids, and flocculants. Large scale approaches, such as bioreactors, including suspension cultures and adherent cells growing attached to microcarriers or macrocarriers in stirred bioreactors, are also encompassed by the term "cell culture." Cell culture procedures for both large and small-scale production of proteins are encompassed by the present disclosure.

As used herein, the term "intermediate cell line" refers to a cell line that contains the AAV rep and cap components integrated into the host cell genome or a cell line that contains the adenoviral helper functions integrated into the host cell genome.

As used herein, the term "packaging cell line" refers to a cell line that contains the AAV rep and cap components and the adenoviral helper functions integrated into the host cell genome. A payload construct must be added to the packaging cell line to generate rAAV virions.

As used herein, the term "production cell line" refers to a cell line that contains the AAV rep and cap components, the adenoviral helper functions, and a payload construct. The rep and cap components and the adenoviral helper functions are integrated into the host cell genome. The payload construct can be stably integrated into the host cell genome or transiently transfected. rAAV virions can be generated from the production cell line upon the introduction of one or more triggering agents in the absence of any plasmid or transfection agent.

As used herein, the term "downstream purification" refers to the process of separating rAAV virions from cellular and other impurities. Downstream purification processes include chromatography-based purification processes, such as ion exchange (IEX) chromatography and affinity chromatography.

The term "prepurification yield" refers to the rAAV yield prior to the downstream purification processes. The term "postpurification yield" refers to the rAAV yield after the downstream purification processes. rAAV yield can be measured as viral genome (vg)/L.

The encapsidation ratio of a population of rAAV virions can be measured as the ratio of rAAV viral particle (VP) to viral genome (VG). The rAAV viral particle includes empty capsids, partially full capsids (e.g., comprising a partial viral genome), and full capsids (e.g., comprising a full viral genome).

The F:E ratio of a population of rAAV virions can be measured as the ratio of rAAV full capsids to empty capsids. The rAAV full capsid particle includes partially full capsids (e.g., comprising a partial viral genome) and full capsids (e.g., comprising a full viral genome). The empty capsids lack a viral genome.

The potency or infectivity of a population of rAAV virions can be measured as the percentage of target cells infected by the rAAV virions at a multiplicity of infection (MOI; viral genomes/target cell). Exemplary MOI values are 1×101, 1×102, 2×103, 5×104, or 1×105 vg/target cell. An MOI can be a value chosen from the range of $1\times10^1$ to $1\times10^5$ vg/target cell.

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. The use of the term "vector" throughout this specification refers to either plasmid or viral vectors, which permit the desired components to be transferred to the host cell via transfection or infection. For example, an adeno-associated viral (AAV) vector is a plasmid comprising a recombinant AAV genome. In some embodiments, useful vectors are contemplated to be those vectors in which the nucleic acid segment to be transcribed is positioned under the transcriptional control of a promoter.

The phrases "operatively positioned," "operatively linked," "under control" or "under transcriptional control" means that the promoter is in the correct location and orientation in relation to the nucleic acid to control RNA polymerase initiation and expression of the gene.

The term "expression vector or construct" or "synthetic construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product or functional RNA (e.g., guide RNA) from a transcribed gene.

The term "auxotrophic" or "auxotrophic selection marker" as used herein refers to the usage of a medium lacking a supplement, such as a medium lacking an essential nutrient such as the purine precursors hypoxanthine and thymidine (HT), or the like, for selection of a functional enzyme which allows for growth in the medium lacking the essential nutrient, e.g. a functional dihydrofolate reductase or the like.

The term cytostatic as used herein refers to a cellular component or agent/element or condition that inhibits cell growth. Cytostasis is the inhibition of cell growth and multiplication.

The term cytotoxic as used herein refers to quality of being toxic to cells. For instance, cells exposed to a cytotoxic agent or condition may undergo necrosis, in which they lose membrane integrity and die rapidly as a result of cell lysis. Cells exposed to a cytotoxic agent can also stop actively growing and dividing (a decrease in cell viability), or the cells can activate a genetic program of controlled cell death (apoptosis).

As used herein, a "monoclonal cell line" or "monoclonality" is used to describe cells produced from a single ancestral cell by repeated cellular replication. Thus, "monoclonal cells" can be said to form a single clone.

The terms "tetracycline" is used generically herein to refer to all antibiotics that are structurally and functionally related to tetracycline, including tetracycline, doxycycline, demeclocycline, minocycline, sarecycline, oxytetracycline, omadacycline, or eravacycline.

The terms "constitutive" or "constitutive expression" are used interchangeably herein. They refer to genes that are transcribed in an ongoing manner. In some embodiments, the terms refer to the expression of a therapeutic payload or a nucleic acid sequence that is not conditioned on addition of an expression triggering agent to the cell culture medium.

The term "expressible therapeutic polynucleotide or "expressible polynucleotide encoding a payload" or "payload polynucleotide" or "payload" refers to a polynucleotide that is encoded in an AAV genome vector ("AAV genome vector") flanked by AAV inverted terminal repeats (ITRs). A payload disclosed herein may be a therapeutic payload. A payload may include any one or combination of the following: a transgene, a tRNA suppressor, a guide RNA, or any other target binding/modifying oligonucleotide or derivative thereof, or payloads may include immunogens for vaccines, and elements for any gene editing machinery (DNA or RNA editing). Payloads can also include those that deliver a transgene encoding antibody chains or fragments that are amenable to viral vector-mediated expression (also referred to as "vectored or vectorized antibody" for gene delivery). See, e.g. Curr Opin HIV AIDS. 2015 May; 10(3): 190-197, describing vectored antibody gene delivery for the prevention or treatment of HIV infection. See also, U.S. Pat. No. 10,780,182, which describes AAV delivery of trastuzumab (Herceptin) for treatment of HER2+ brain metastases. A payload disclosed herein may not be a therapeutic payload (e.g., a coding for a detectable marker such as GFP).

In particular, in some instances the payload polynucleotide refers to a polynucleotide that can be a homology element for homology-directed repair, or a guide RNA to be delivered for a variety of purposes. In some embodiments, the transgene refers to a nucleic acid sequence coded for expression of guide RNA for ADAR editing or ADAT editing. In some embodiments, the transgene refers to a transgene packaged for gene therapy. In some embodiments, the transgene refers to synthetic constructs packaged for vaccines.

6.2. SYSTEM OVERVIEW

The stable mammalian cell line relies on stable integration and maintenance of a plurality of synthetic nucleic acid constructs within the nuclear genome of the cell. One of these constructs permits inducible expression of a hormone-activated excising element. The excising element can be a recombinase. The recombinase can be a site-specific recombinase. The site-specific recombinase can be a Cre polypeptide or a flippase. Triggering of Cre expression leads to genomic rearrangements, which in turn lead to expression of adenovirus helper proteins, expression of AAV Rep and Cap proteins, and production of rAAV, optionally, encapsidating a therapeutic payload (e.g., transgene, a tRNA suppressor, a guide RNA, or other oligonucleotide).

Figure 1:
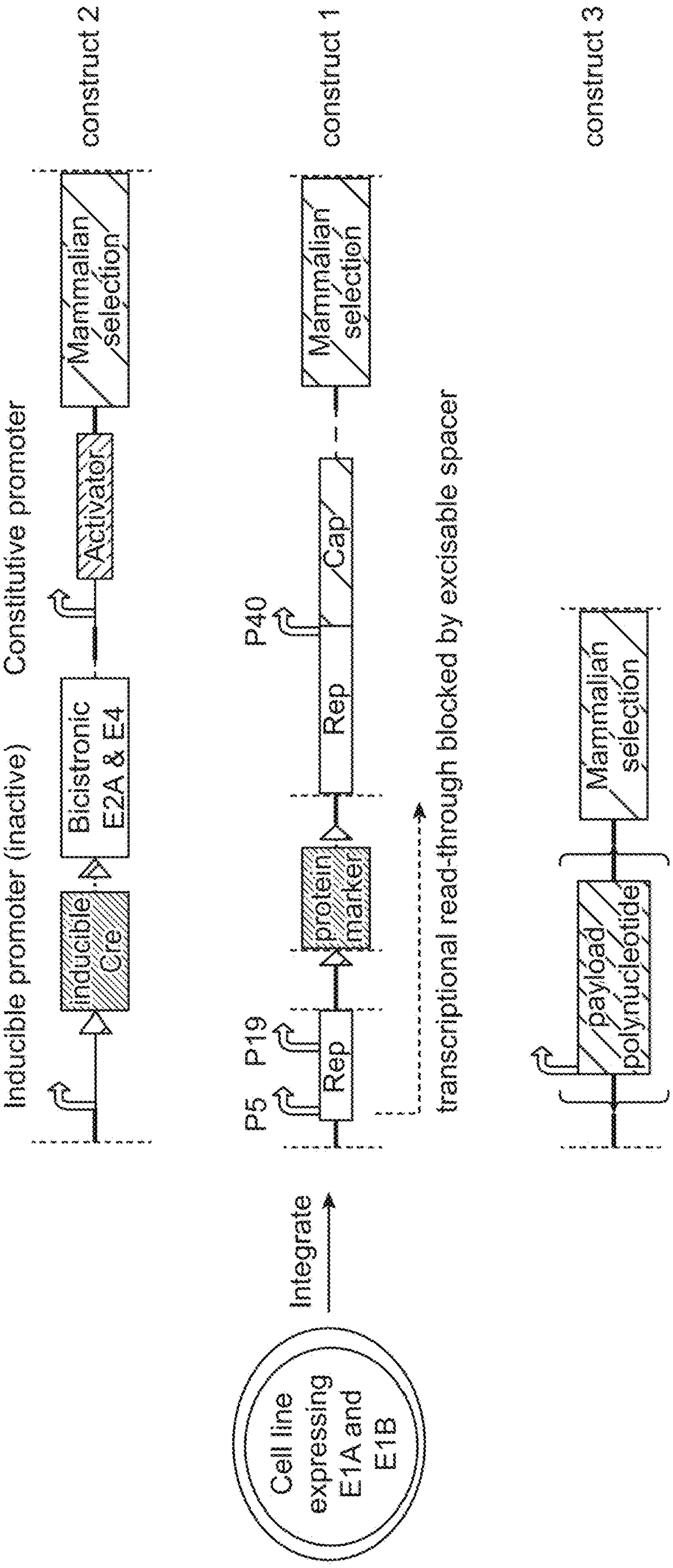

FIG. 1 depicts the pre-triggered state of an exemplary embodiment. In the embodiment shown, three synthetic nucleic acid constructs are separately integrated into the nuclear genome of a cell line that expresses adenovirus E1A and E1B, such as HEK 293 cells. In the pre-triggered state, transcriptional read-through of rep on construct 1 is blocked by an intervening spacer. The payload polynucleotide on construct 3 is flanked by AAV ITRs, represented by the brackets.

Figure 2A:
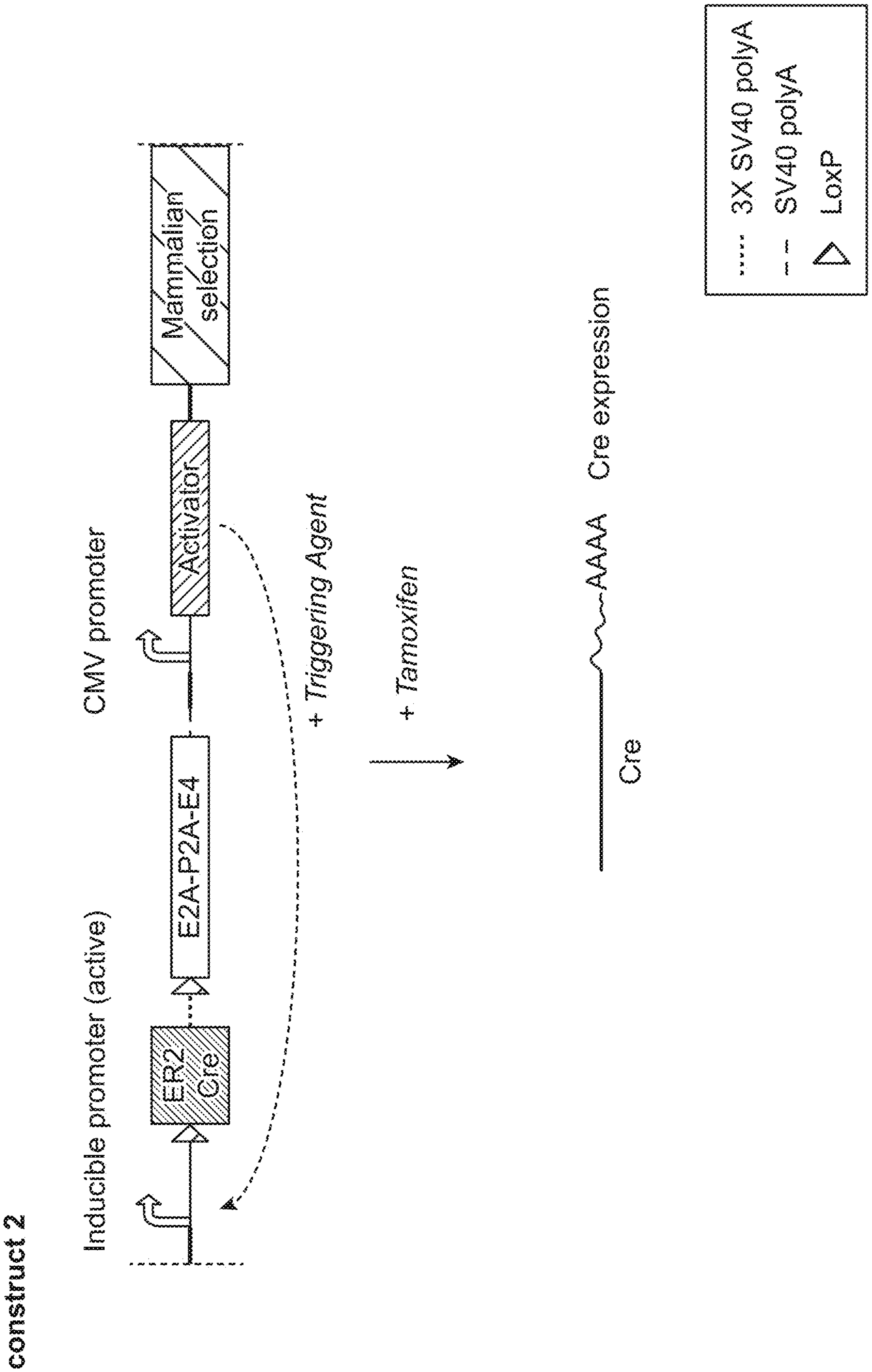
Figure 2B:
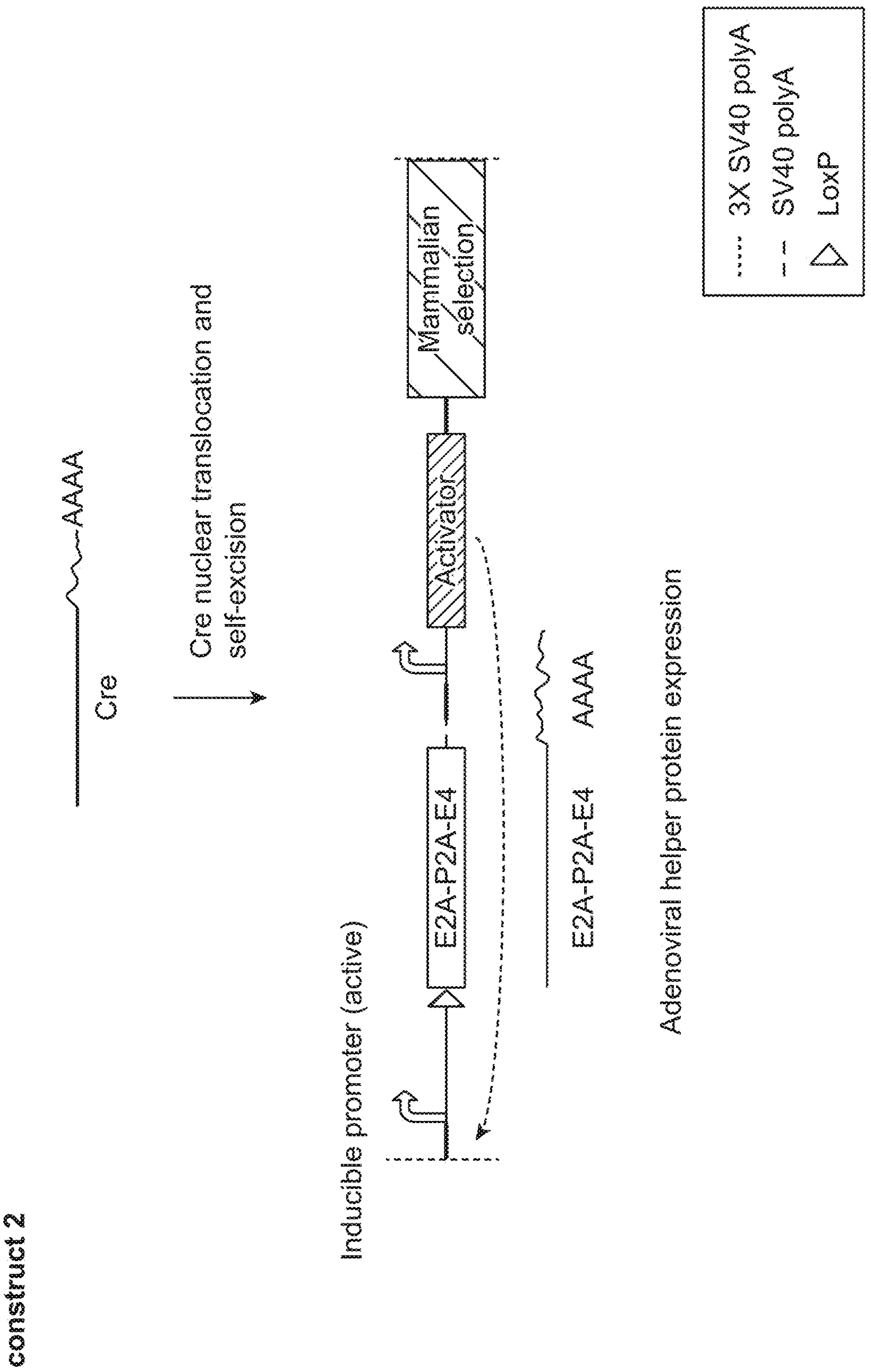
Figure 2C:
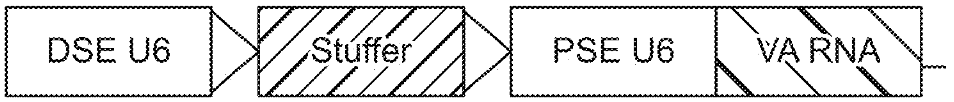

An exemplary construct 2 is shown in greater detail in FIGS. 2A-2C. This construct permits conditional expression of Cre. In some embodiments, the construct 2 comprises a P2A sequence positioned between an E2A sequence and an E4 sequence. In some embodiments, the construct 2 comprises an internal ribosomal entry site (IRES) sequence positioned between an E2A sequence and an E4 sequence. In some embodiments, the inducible promoter system of construct 2 is a Tet On inducible promoter system. In some embodiments, the inducible promoter system of construct 2 is a Tet Off inducible promoter system. In some embodiments, the inducible promoter system of construct 2 is a cumate inducible promoter system.

In the pre-triggered state (top of FIG. 2A), the Cre coding sequence is under the control of an inducible promoter. For example, the inducible promoter is a Tet-inducible promoter. In the absence of a triggering agent, inducible promoter is not active. For example, a triggering agent for Tet-inducible promoter is a tetracycline. In the absence of a tetracycline, such as doxycycline ("Dox"), Tet activator protein (TetOn3G) cannot bind and activate the basal Tet On promoter. In addition, the localization of Cre is under control of estrogen response elements ("ER2") that require binding of an estrogen agonist or selective modulator, such as tamoxifen, for the translocation from the cytoplasm to the nucleus. This approach limits pre-triggering Cre expression with consequent promiscuous recombination events and toxicity. The ER2 Cre element also comprises a strong 3' polyadenylation signal, which prevents basal expression of the downstream adenoviral helper genes, E2A and E4. In some embodiments, the Cre is split into two fragments, that can be fused in the presence of a chemical agent, such as rapamycin. In some embodiments, the Cre is a light inducible Cre.

When the triggering agent (e.g., Dox) and tamoxifen are added to the culture medium, TetOn3G binds the Tet responsive basal promoter and estrogen response elements are activated, triggering Cre expression (bottom of FIG. 2A). Following translation and then translocation of the Cre protein into the cell nucleus, Cre excises its own coding sequence from construct 2, leaving the integrated construct shown at the bottom of FIG. 2B. Elimination of the upstream poly-adenylation site allows expression of E2A and E4 helper proteins, maintained by the presence of doxycycline. Similarly, for the optional additional insert shown in FIG. 2C, VA-RNA is expressed by Cre mediated excision of the stuffer sequence, which activates the U6 promoter which then drives the expression of VA RNA.

Figure 3A:
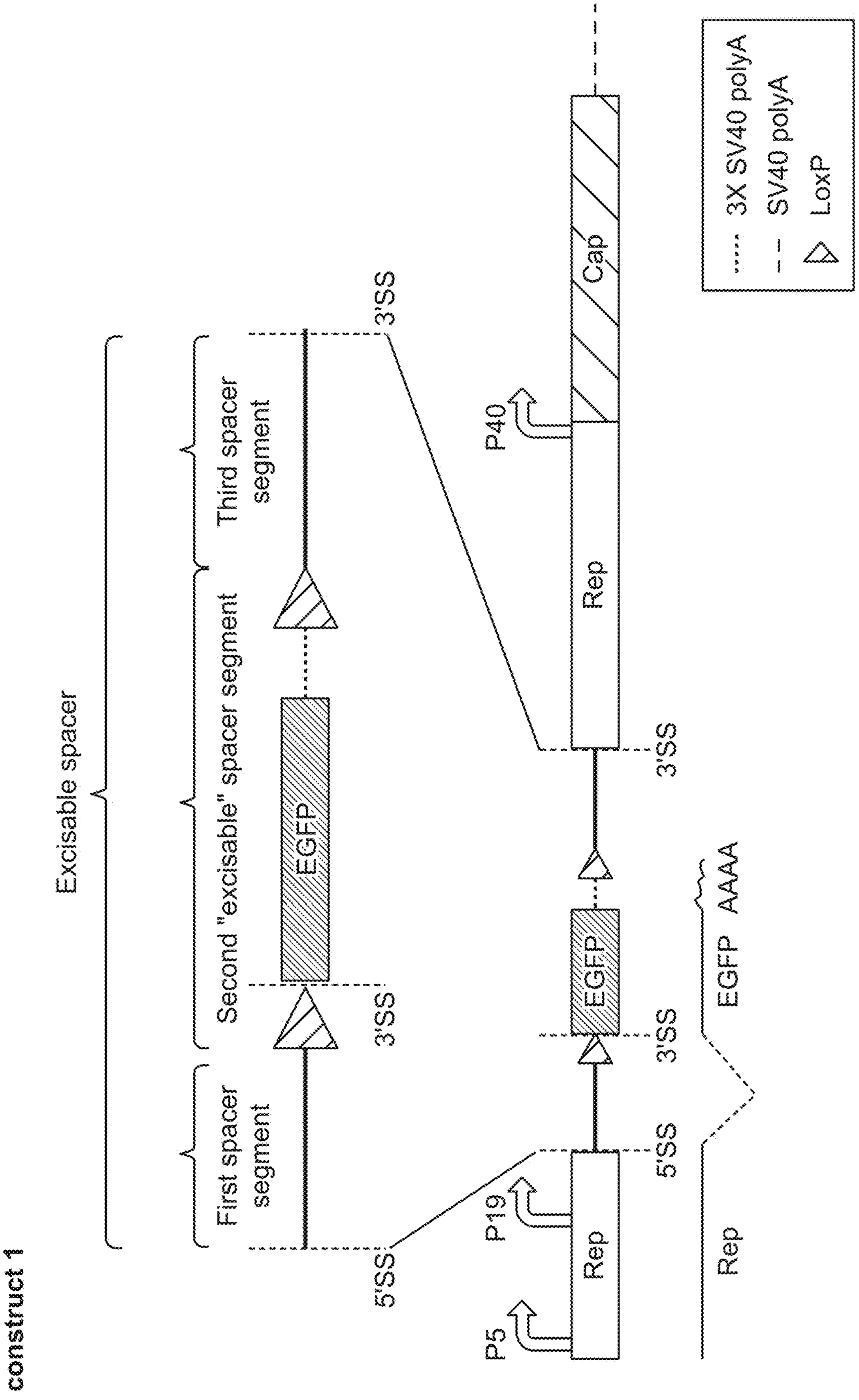
Figure 3B:
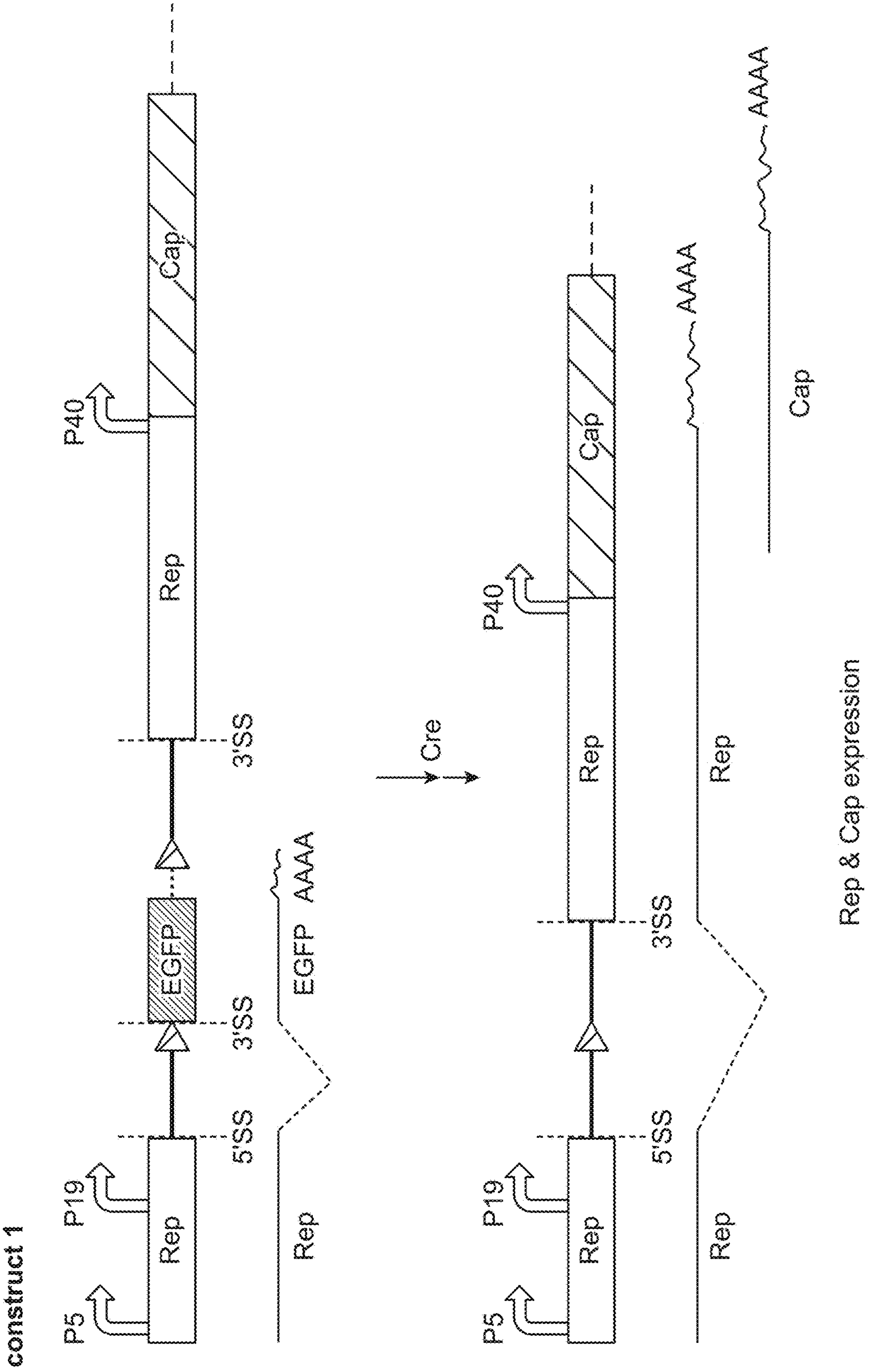

FIGS. 3A-3B schematically depict details of an exemplary embodiment of construct 1. This construct is designed to prevent expression of AAV Rep prior to a triggering event, yet permit expression of AAV Rep and Cap proteins from their endogenous promoters after a triggering event.

FIG. 3A shows the pre-triggered state of integrated nucleic acid construct 1. An excisable spacer interrupts the rep coding sequence, blocking transcriptional read-through of the full-length rep coding sequence. A pre-triggered transcript is shown at the bottom of the figure. This pre-triggered transcript encodes the 5' portion of AAV Rep fused to a fluorescent marker protein, EGFP. The transcript contains a single intron flanked by 5' and 3' splice sites. Routine splicing produces a transcript that encodes a fusion protein that includes the N-terminal portion of rep fused to an enhanced green fluorescent protein (EGFP). The fusion protein lacks the toxicity of full-length Rep protein, and presence of pre-triggered construct 1 in the cell genome can be detected by EGFP fluorescence for quality control. In some embodiments, the EGFP fluorescence is used to select for cells that have integrated nucleic acid construct 1, which then form a stable cell pool. A stable cell pool with the integrated nucleic acid construct 1 can therefore be produced from selecting for cells expressing EGFP.

As shown at the top of FIG. 3A, the excisable spacer comprises a first spacer segment, a second spacer segment, and a third spacer segment. FIG. 3B shows the conversion of the pre-triggered construct (above) to a post-triggered state (below) upon exposure to Cre within the cell nucleus. Cre excises the second spacer segment, which includes the EGFP marker coding sequence and the upstream 3' splice site. As rearranged, the construct now allows expression of functional Rep and Cap transcripts from their respective endogenous promoters, as shown at the bottom of FIG. 3B. Loss of EGFP expression indicates successful Cre-mediated genomic recombination.

Figure 4:
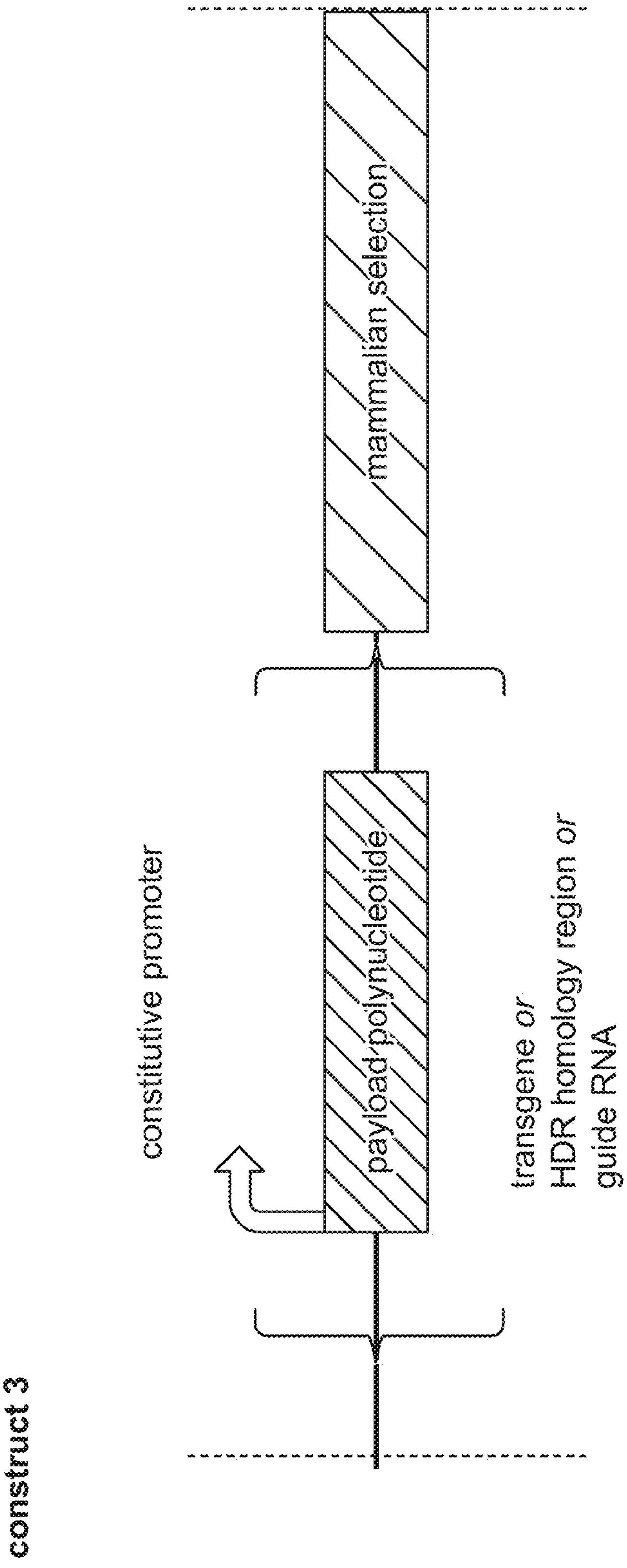

FIG. 4 depicts an exemplary embodiment of construct 3, which is an exemplary payload construct. Construct 3 comprises a sequence that encodes a payload. This sequence element is under control of a constitutive promoter. The payload can be any payload for which rAAV is an appropriate vehicle, including a transgene encoding a protein of interest, a homology element for homology-directed repair, or a guide RNA. The payload is flanked by AAV ITRs, represented by the brackets.

Figure 6:
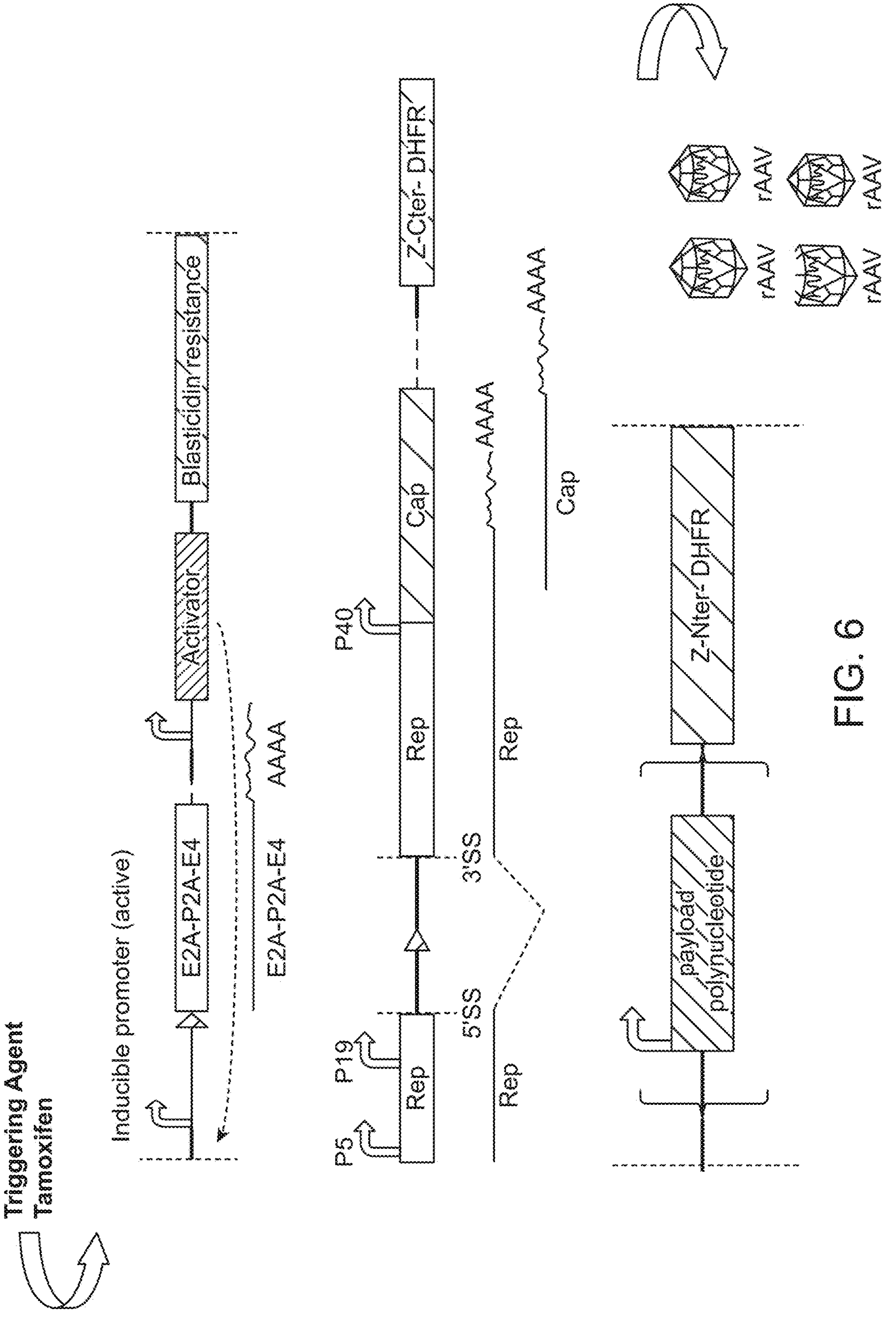

FIG. 6 depicts the post-triggered state of all 3 constructs following the addition of tamoxifen and doxycycline to the cell medium. Adenoviral E2A and E4 helper proteins are expressed from integrated construct 2 under control of the inducible promoter (e.g., a Tet-On promoter activated in the presence of Dox). AAV rep and cap coding sequences are expressed from construct 1 under control of endogenous promoters. The payload is expressed under control of a constitutive promoter. rAAV virions that encapsidate the payload are therefore produced.

This approach provides numerous benefits over current AAV systems for delivery of payloads.

Maintaining constructs stably in the cellular genome requires selective pressure. To reduce the number of selective agents (and in particular, antibiotics) required to stably maintain three integrated constructs within the cell line genome, we have designed an approach that stably maintains all 3 constructs in the nuclear genome with a single antibiotic selection, plus a single auxotrophic selection.

Figure 5A:
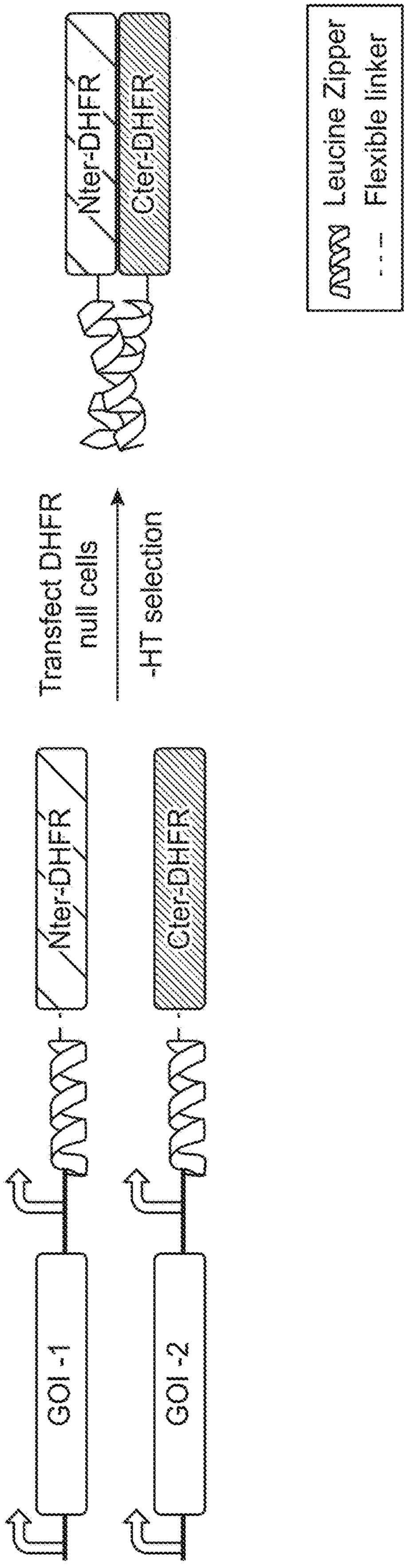

FIG. 5A depicts a split auxotrophic selection system that permits stable retention of two integrated nucleic acid constructs under a single selective pressure. One construct encodes the N-terminal fragment of mammalian dihydrofolate reductase (DHFR) fused to a leucine zipper peptide ("Nter-DHFR"). This N-terminal fragment is enzymatically nonfunctional. The other construct encodes the C-terminal fragment of DHFR fused to a leucine zipper peptide ("Cter-DHFR"). This C-terminal fragment is enzymatically non-functional. When both fragments are concurrently expressed in the cell, a functional DHFR enzyme complex is formed through association of the leucine zipper peptides. Both constructs can be stably retained in the genome of a DHFR null cell by growth in a medium lacking hypoxanthine and thymidine.

Figure 5B:
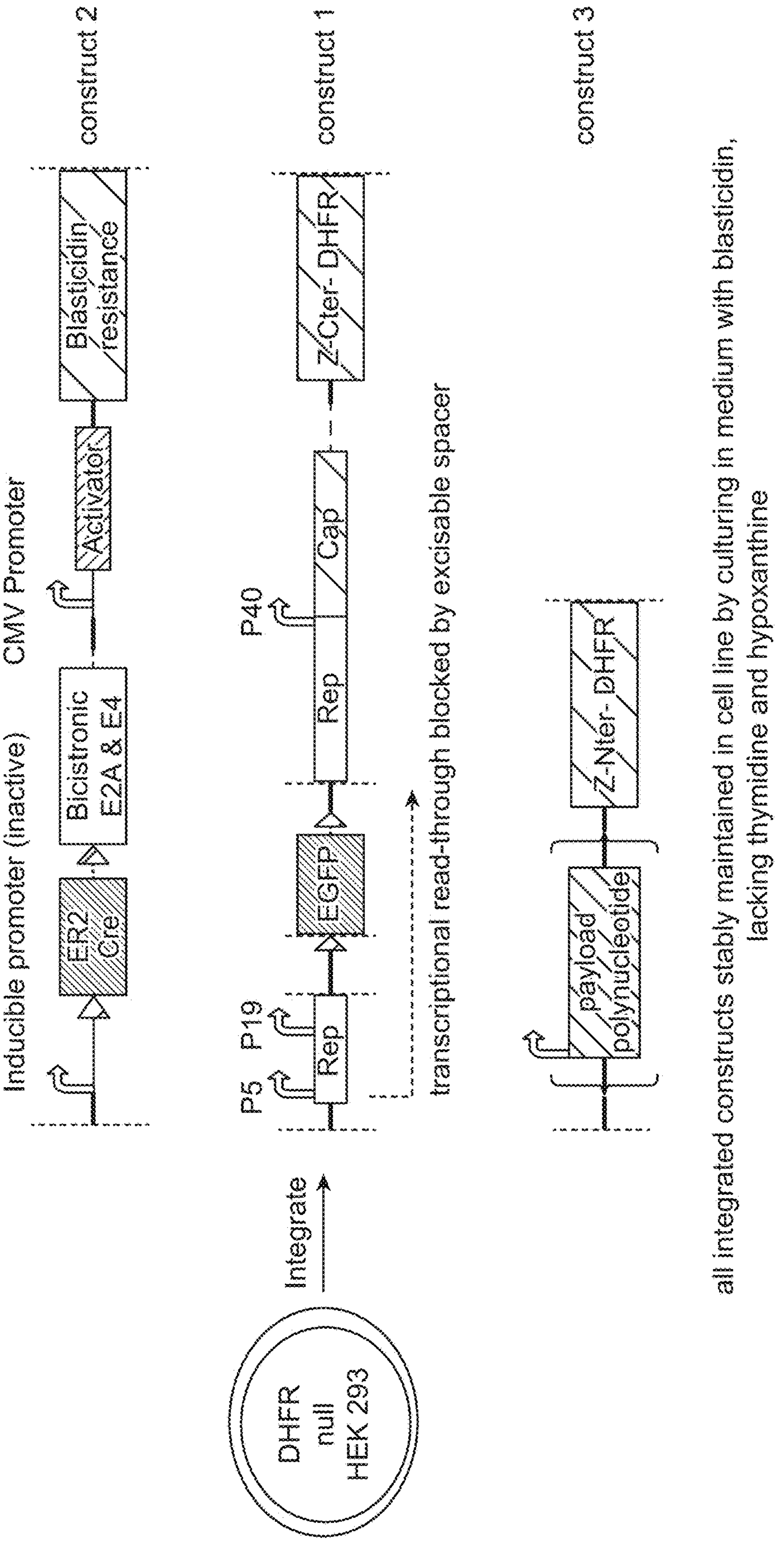

FIG. 5B shows an exemplary deployment of this split auxotrophic selection design in the multi-construct system of FIG. 1 in its pre-triggered state. In this example, the split auxotrophic selection elements are deployed on constructs 1 and 3. A separate exemplary antibiotic selection approach, blasticidin resistance, is deployed on construct 2. This results in the ability to stably maintain all three constructs in the mammalian cell line using a single antibiotic, culturing in medium with blasticidin, lacking thymidine and hypoxanthine.

Following triggering and Cre-mediated genomic rearrangement, the selection elements remain unchanged, allowing continued maintenance of the three post-triggering integrated constructs using a single antibiotic in medium lacking hypoxanthine and thymidine.

Viral proteins needed for AAV virion formation are inhibited by host cell mechanisms. Inhibition of these host cell mechanisms to maximize AAV viral titers in the stable cell lines described herein include, but are not limited to: knocking out PKR (PKR KO) (pathway is responsible for inhibition of viral proteins) in the starting cell line (P0), introducing a mutant EIF2alpha (in the PKR pathway) in the starting cell line (P0), and/or manipulating or modulating virus-associated (VA) RNAs (VA RNAs, an inhibitor of PKR). Virus-associated (VA) RNAs from adenovirus act as small-interference RNAs and are transcribed from the vector genome. These VA RNAs can trigger the innate immune response. Moreover, VA RNAs are processed to functional viral miRNAs and disturb the expression of numerous cellular genes. Therefore, VA-deleted adenoviral vector production constructs (AdVs) lacking VA RNA genes, or having modified VA RNA, would be advantageous. However, VA-deleted AdVs do not produce commercially sufficient quantities of AAV titers (e.g. resulting in fewer and poor-quality virions). Conversely, overexpressing VA RNA also results in a low titer of AAV production that would not be commercially feasible for scale-up. Thus, developing conditional VA RNA constructs, and combining any of those optimized constructs with the conditional helper constructs described herein, will provide commercially relevant, high-quality virions from the AAV production systems as described herein. All three of these strategies can be done in any combination.

VA RNA is also an inhibitor of PKR, which is involved in a pathway responsible for inhibiting AAV viral protein synthesis. In particular, PKR phosphorylates EIF2alpha, which results in inhibition of viral protein synthesis. FIG. 4A shows a schematic of VA RNA inhibition of PKR and the PKR pathway is shown below at left. The structure of VA RNA, which is a double stranded RNA (dsRNA) is shown in FIG. 4B.

While the limited interactions between VA RNA, PKR, and EIF2alpha are understood, PKR is a major kinase that may self-phosphorylate and EIF2alpha may be phosphorylated by other kinases. As such, three strategies (PKR KO, EIF2alpha mutation, manipulation of VA RNA) are being developed for use in any combination in the AAV production systems described herein.

Thus, an option for overcoming the general antiviral effects of mammalian cell production of AAV virions is to modify expression of VA RNA. Therefore, VA-deleted adenoviral vector production constructs (AdVs) lacking VA RNA genes, or having modified VA RNA, have been designed and are described herein in FIG. 2C and FIGS. 4-15. It is noted that VA-deleted AdVs do not produce commercially sufficient quantities of AAV titers (e.g. resulting in fewer and poor-quality virions). Conversely, overexpressing VA RNA also results in a low titer of AAV virion production that would not be commercially feasible for scale-up. Thus, developing conditional VA RNA constructs, and combining any of those optimized constructs with the conditional helper constructs described herein, will provide commercially relevant, high-quality virions from the AAV production systems as described herein. FIG. 2C and FIGS. 4-15 illustrate various modified and inducible mutant VA RNA constructs and their effects on virion production. These various approaches provide numerous benefits over current systems for AAV production.

6.3. CONDITIONAL EXPRESSION

In a first aspect, the stable cell lines are provided. In some embodiments, the stable cell lines are mammalian stable cell lines. The cells are capable of conditionally producing recombinant AAV (rAAV) virions. In some embodiments, the cells are capable of conditionally producing rAAV virions. In some embodiments, said rAAV virions package an expressible payload. In some embodiments, said rAAV virions package a sequence encoding a payload. In preferred embodiments, production of virions is not conditioned on the presence of an episome or independent plasmid within the cell.

In some embodiments, expression of AAV Rep is conditional. In some embodiments, expression of AAV Rep and Cap proteins is conditional. In certain embodiments, expression of AAV Rep and Cap proteins is conditioned on addition of at least a first expression triggering agent to the cell culture medium. In certain embodiments, expression of AAV Rep and Cap proteins is conditioned on addition of a first expression triggering agent and a second expression triggering agent to the cell culture medium.

In a system with a triggering agent, doxycycline is a suitable agent. In certain embodiments, a Tet inducible promoter can be utilized that is under the control of doxycycline. Alternatively, a cumate inducible promoter system can be utilized in which the cumate inducible promoter is under the control of cumate.

In a system with a triggering agent, doxycycline is a suitable agent. In certain embodiments, doxycycline is used to the control a Tet inducible promoter. Alternatively, a cumate inducible promoter system can be utilized instead of a Tet inducible promoter, which is under the control of cumate.

Any suitable inducible excising agent (e.g., recombinase) can be utilized. An excising agent can be a recombinase. An excising agent can be a site-specific recombinase. An excising agent can target a recombination site. Examples of suitable inducible excising agents include Cre and a flippase. The Cre element can be hormone activated Cre, or light inducible Cre. A recombination site can be a lox site. A lox site can be a loxP site. A recombination site can be an FRT site.

The Flippase recombinase system is based on Flp-FRT recombination, a site-directed recombination technology used to manipulate DNA under controlled conditions in vivo. It is analogous to Cre-lox recombination but involves the recombination of sequences between short flippase recognition target (FRT) sites by the recombinase flippase (Flp) derived from the 2μ plasmid of baker's yeast *Saccharomyces cerevisiae*. The Flp protein, much like Cre, is a tyrosine family site-specific recombinase.

In typical embodiments, the cells do not express cytotoxic levels of Rep protein prior to addition of both the first expression and second triggering agents to the cell culture medium. In certain embodiments, the cells do not express cytostatic levels of Rep protein prior to addition of both the first and second expression triggering agents to the cell culture medium. In certain embodiments, the average concentration of Rep protein within the cells is less than the amount prior to addition of both of the first and second expression triggering agents to the cell culture medium. In some embodiments, expression of Rep and Cap proteins becomes constitutive after addition of all of the at least first expression triggering agents to the cell culture medium.

In some embodiments, expression of at least one adenoviral helper protein is conditional.

In certain embodiments, expression of the at least one adenoviral helper protein is conditioned on addition of at least a third expression triggering agent to the cell culture medium. In particular embodiments, the third expression triggering agent is the same as the first expression triggering agent. In certain embodiments, expression of adenoviral helper proteins is conditioned on addition of a third expression triggering agent and a fourth expression triggering agent to the cell culture medium. In particular embodiments, the fourth expression triggering agent is the same as the second expression triggering agent. In particular embodiments, the third expression triggering agent is the same as the first expression triggering agent and the fourth expression triggering agent is the same as the second expression triggering agent.

In some embodiments, continued expression of adenoviral helper proteins following triggering of expression by contact of the cell with the at least third expression triggering agent requires the presence of only the third expression triggering agent in the cell culture medium. In certain embodiments, the third triggering agent is the same as the first triggering agent.

In some embodiments, expression of at least one adenoviral helper RNA is conditional. In certain embodiments, the adenoviral helper proteins comprise Ad E2A. In certain embodiments, the adenoviral helper proteins comprise Ad E4. In some embodiments, the adenoviral helper protein is tagged. A tag can be a protein tag. A protein tag can be a FLAG tag. In some embodiments, E2A is FLAG-tagged. In some embodiments, E4 is FLAG-tagged.

In particular embodiments, the adenoviral helper RNA is a VA RNA. In particular embodiments, the adenoviral helper RNA is an inducible VA RNA construct. In some embodiments, the VA RNA is a mutant VA RNA. In some embodiments, the VA RNA is a transcriptionally dead VA RNA. In some embodiments, the VA RNA is under the control of a U6 promoter.

In some embodiments, the third expression triggering agent is a tetracycline. In certain embodiments, the tetracycline is doxycycline ("Dox"). In some embodiments, the fourth expression triggering agent is an estrogen receptor ligand. In certain embodiments, the estrogen receptor ligand is a selective estrogen receptor modulator (SERM). In particular embodiments, the estrogen receptor ligand is tamoxifen.

In some embodiments of the stable cell line, expression of the payload is conditioned on addition of at least a fifth expression triggering agent to the cell culture medium. In some embodiments, expression of the payload is not conditioned on addition of an expression triggering agent to the cell culture medium.

In some embodiments, expression of Rep and Cap proteins, adenoviral helper proteins, and the payload becomes constitutive after addition of only one expression triggering agent to the cell culture medium. In certain embodiments, expression of Rep and Cap proteins and the adenoviral helper proteins becomes constitutive after addition of only one expression triggering agent to the cell culture medium.

In certain embodiments, the one expression triggering agent is the first expression triggering agent. In certain embodiments, the first expression triggering agent is a tetracycline. In particular embodiments, the first expression triggering agent is doxycycline.

6.4. SYNTHETIC NUCLEIC ACID CONSTRUCTS

In typical embodiments, the nuclear genome of the cell of the stable cell line comprises a plurality of integrated synthetic nucleic acid constructs. Typically, each of the plurality of synthetic nucleic acid constructs is separately integrated into the nuclear genome of the cell. In some embodiments, only a single non-auxotrophic selection is required to maintain all of the plurality of synthetic nucleic acid constructs stably within the nuclear genome of the cells. In some embodiments, antibiotic resistance is required to maintain the plurality of synthetic constructs stably within the nuclear genomes of the cells. In some embodiments, both a non-auxotrophic selection and antibiotic resistance is required to maintain the plurality of synthetic constructs stably within the nuclear genomes of the cells. I In some embodiments, the nuclear genome of the cell comprises two integrated synthetic constructs.

In some embodiments, the nuclear genome of the cell comprises three integrated synthetic constructs. In particular embodiments, the first integrated synthetic construct comprises conditionally expressible AAV Rep and Cap coding sequences; the second integrated synthetic construct comprises a conditionally expressible Cre coding sequence and conditionally expressible adenoviral helper protein coding sequences; and the third integrated synthetic construct comprises expressible coding sequences for the payload.

6.4.1. Construct 1 (AAV Rep/Cap Construct)

Disclosed herein are polynucleotide constructs encoding for a Rep and Cap polypeptide. Provided herein is a first polynucleotide construct, which encodes for Rep and Cap and comprises spacer or excisable elements. This first polynucleotide construct is also referred to as a Rep/Cap construct, and/or "AAV Rep/Cap Construct."

These polynucleotide constructs are designed to be stably integrated into a cell line and only be triggered to produce AAV Rep and Cap polypeptides in the presence of an excising element. In some embodiments, the first integrated synthetic construct comprises conditionally expressible AAV Rep and Cap coding sequences.

The Rep sequence can encode Rep from any desired AAV serotype. In some embodiments, the encoded Rep protein is drawn from the same serotype as the Cap protein. In some embodiments, the encoded Rep protein is drawn from a different serotype from the Cap protein. In particular embodiments, the encoded Rep protein includes, but is not limited to, a Rep protein from AAV serotypes AAV-1, AAV-2, AAV-3, AAV-4, AAV-5, AAV-6, AAV-7, AAV-8, AAV-9, AAV-10 and AAV-11, or chimeric combinations thereof.

The nucleotide sequences of the genomes of the AAV serotypes are known. For example, the complete genome of AAV-1 is provided in GenBank Accession No. NC_002077; the complete genome of AAV-2 is provided in GenBank Accession No. NC_001401 and Srivastava et al., J. Virol, 45: 555-564 (1983); the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively (see also U.S. Pat. Nos. 7,282,199 and 7,790,449 relating to AAV-8); the AAV-9 genome is provided in Gao et al. Virol, 78: 6381-6388 (2004); the AAV-10 genome is provided in Mol Ther, 13(1): 67-76 (2006); and the AAV-11 genome is provided in Virology, 330(2): 375-383 (2004).

In the exemplary embodiments illustrated in FIG. 3A, prior to the cell being contacted with the first expression triggering agent, the Rep coding sequence is interrupted by an intervening spacer.

In certain embodiments, the intervening spacer segment comprises, from 5' to 3', a first spacer segment, a second spacer segment, and a third spacer segment.

In particular embodiments, the first spacer segment comprises a 5' splice site (5'SS) 5' to the first spacer element. In some embodiments, the first spacer segment comprises a nucleic acid sequence having at least 80% identity to SEQ ID NO: 1.

In some embodiments, the second spacer segment comprises a polynucleotide encoding a detectable protein marker flanked by lox sites. In certain embodiments, the detectable protein marker is a fluorescent protein. In particular embodiments, the fluorescent protein is a green fluorescent protein (GFP). In specific embodiments, the GFP is EGFP. In particular embodiments, the fluorescent protein is a blue fluorescent protein (BFP). Screening for the fluorescent marker can be used to confirm integration of the construct into the cell genome, and can subsequently be used to confirm excision of the intervening spacer segment. In some embodiments, the second spacer segment further comprises a polyA sequence. In certain embodiments, the poly A sequence comprises a rabbit beta globin (RBG) polyA. In some embodiments, the second spacer segment further comprises a first 3' splice site (3'SS) between the first lox site and the polynucleotide encoding the protein marker.

In some embodiments, the second spacer segment comprises a nucleic acid sequence having at least 80% identity to SEQ ID NO: 2.

In some embodiments, the third spacer segment further comprises a second 3' splice site (3'SS). In particular embodiments, the second 3' splice site is positioned 3' to the second lox site.

In some embodiments, the third spacer segment comprises a nucleic acid sequence having at least 80% identity to SEQ ID NO: 3.

In various embodiments, the Rep coding sequence is operatively linked to an endogenous P5 promoter. In various embodiments, the Rep coding sequence is operatively linked to an endogenous P19 promoter. In some embodiments, the intervening spacer is inserted into the Rep coding sequence at a position downstream of the P19 promoter.

In some embodiments, the Rep coding sequence is 5' to the Cap coding sequence. In certain embodiments, the Cap coding sequence is operatively linked to an endogenous P40 promoter.

In various embodiments, the Cap protein is selected from the capsid of an avian AAV, bovine AAV, canine AAV, equine AAV, primate AAV, non-primate AAV, and ovine AAV, and modifications, derivatives, or pseudotypes thereof.

In some embodiments, the capsid is a capsid selected from AAV1, AAV2, AAV3, AAV4, AAV5, AAV6, AAV7, AAV8, AAV9, AAV 10, AAV11, AAV 12, AAV13, AAV 14, AAV 15 and AAV 16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, AAV.HSC16 or AAVhu68 (described in WO2020/033842, incorporated herein by reference in its entirety). The hu68 capsid is described in WO 2018/160582, incorporated herein by reference in its entirety.

In some embodiments, the capsid is a derivative, modification, or pseudotype of AAV1, AAV2, AAV3, AAV4, AAV5, AAV6, AAV7, AAV8, AAV9, AAV 10, AAV11, AAV 12, AAV 13, AAV 14, AAV 15 and AAV 16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, AAV.HSC16 or AAVhu68.

In some embodiments, capsid protein is a chimera of capsid proteins from two or more serotype selected from AAV1, AAV2, rAAV3, AAV4, AAV5, AAV6, AAV7, AAV8, AAV9, AAV 10, AAV11, AAV 12, AAV13, AAV 14, AAV 15 and AAV 16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, and AAV.HSC16 (described in WO2020/033842, incorporated herein by reference in its entirety). In certain embodiments, the capsid is an rh32.33 capsid, described in U.S. Pat. No. 8,999,678, incorporated herein by reference in its entirety.

In particular embodiments, the capsid is an AAV1 capsid. In particular embodiments, the capsid is an AAV5 capsid. In particular embodiments, the capsid is an AAV9 capsid.

In various embodiments, the first integrated construct further comprises a first mammalian cell selection element.

Figure 8A:
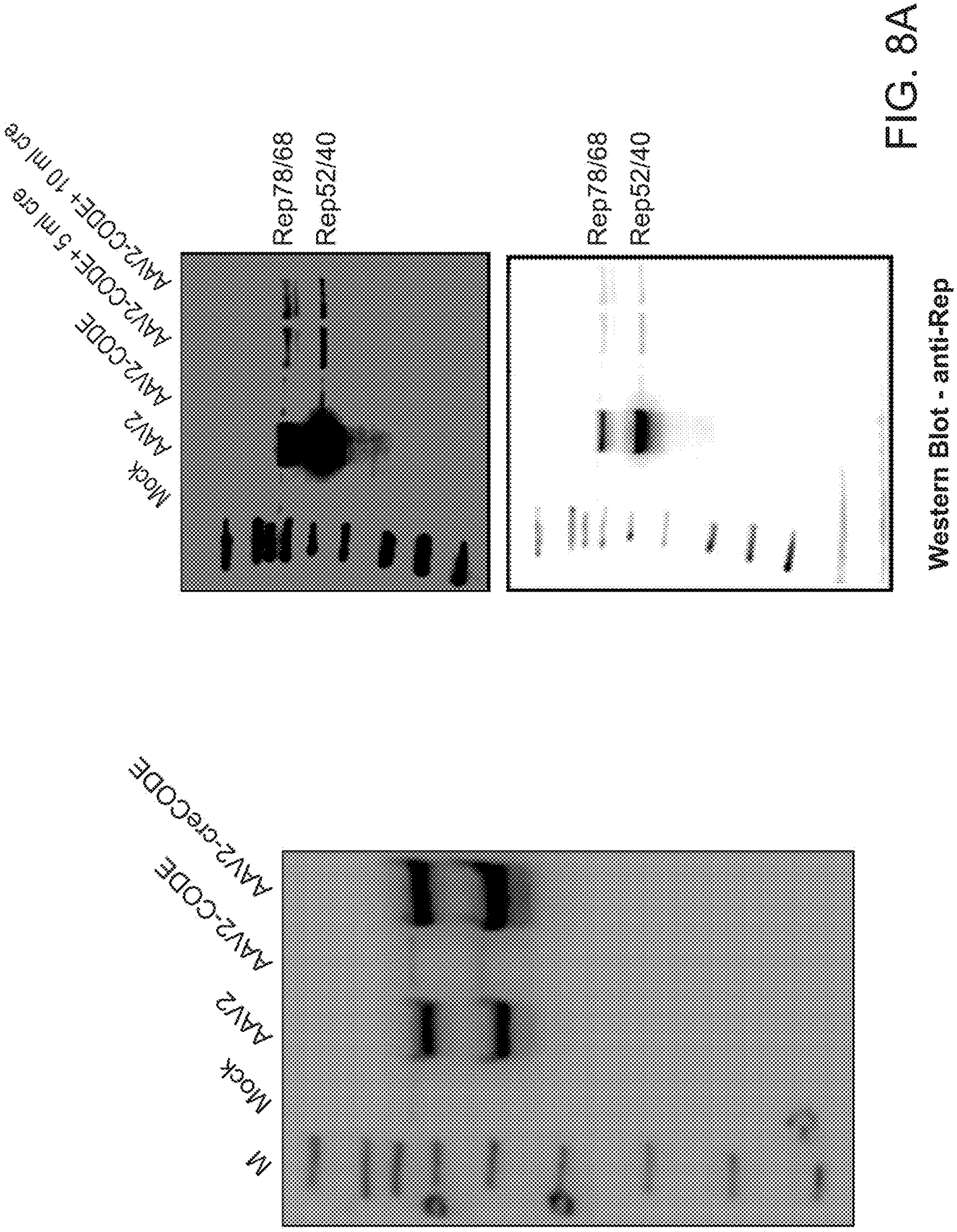
Figure 8B:
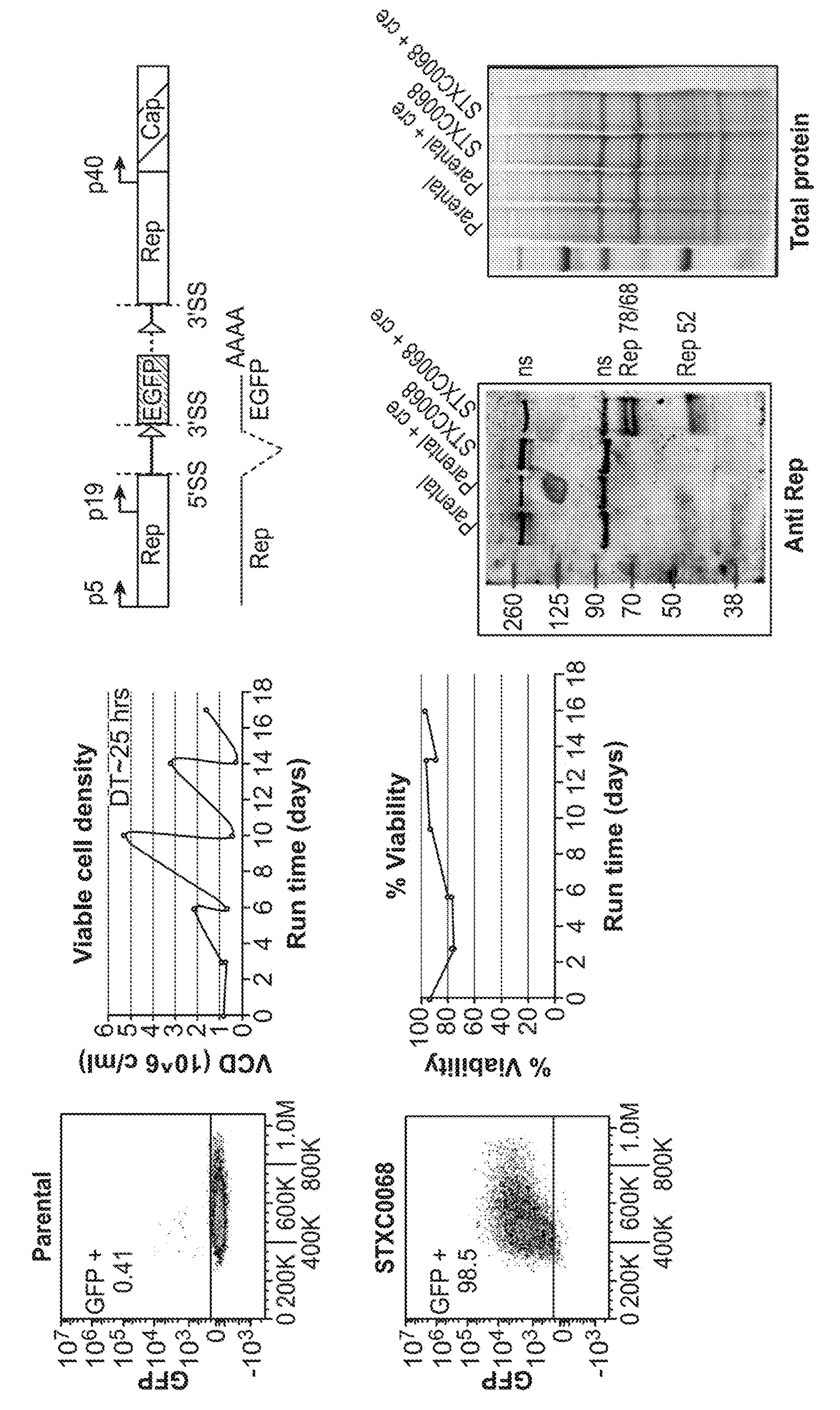

In some embodiments, the inducible Rep and Cap construct is as shown in FIG. 8B. In some embodiments, the inducible polynucleotide construct encoding for Rep and Cap encodes for a first part of a Rep polypeptide, a second part of a Rep polypeptide, a Cap polypeptide, and an excisable element. The excisable element may be positioned between the first part of the Rep polypeptide and the second part of the Rep polypeptide. The excisable element may, thus, interrupt the sequence encoding for the Rep polypeptide at any point along the sequence encoding for Rep. Without excision of the excisable element, Rep is minimally expressed or not expressed at all. In some embodiments, the Rep polypeptide is a wildtype Rep polypeptide. In other embodiments, the Rep polypeptide is a mutant Rep polypeptide. In some embodiments, the Cap polypeptide is a wildtype Cap polypeptide. In other embodiments, the Cap polypeptide is a mutant Cap polypeptide. In some embodiments, the excisable element comprises an intron, an exon, or an intron and an exon. In particular embodiments, the excisable element from 5' to 3' comprises a 5' splice site; a first spacer segment comprising a first intron; a second spacer segment comprising: a first lox sequence, a 3' splice site, an exon, a stop signaling sequence, a second lox sequence; and a third spacer segment comprising a second intron. The first spacer segment and the third spacer segment may be excised by endogenous cellular machinery.

In some embodiments, the second spacer segment in the excisable element is excised by Cre. Cre may be provided as any form of exogenous Cre, such as Cre gesicles. Cre may also be encoded for by a second polynucleotide construct. In some embodiments, a construct encoding for adenoviral helper proteins also encodes for Cre. In some embodiments, the second polynucleotide construct is also inducible, for example, as described below in Section 4.3.2.

In some embodiments, expression of the Rep and Cap are driven by native promoters, including P5, P19, P40, or any combination thereof. In some embodiments the exon of the excisable element may be any detectable marker. For example, detectable markers contemplated herein include luminescent markers, fluorescent markers, or radiolabels. Fluorescent markers include, but are not limited to, EGFP, GFP, BFP, RFP, or any combination thereof.

In some embodiments, the Rep/Cap construct is a polynucleotide construct comprising: a) a sequence of a first part of a Rep gene; b) sequence of a second part of the Rep gene; c) a sequence of a Cap gene; and d) an excisable element positioned between the first part of the sequence of Rep gene and the second part of the sequence of the Rep gene. In some embodiments, the excisable element comprises a stop signaling sequence. In some embodiments, the excisable element comprises a rabbit beta globin intron. In some embodiments, the excisable element comprises an exon. In some embodiments, the excisable element comprises an intron and an exon. In some embodiments, the excisable element comprises an intron. In some embodiments, two splice sites are positioned between the sequence of the first part of the Rep gene and the sequence of the second part of the Rep gene. In some embodiments, the two splice sites are a 5' splice site and a 3' splice site. In some embodiments, the 5' splice site is a rabbit beta globin 5' splice site. In some embodiments, the 3' splice site is a rabbit beta globin 3' splice site. In some embodiments, three splice sites are positioned between the sequence of the first part of the Rep gene and the sequence of the second part of the Rep gene. In some embodiments, the three splice sites are a 5' splice site, a first 3' splice site, and a second 3' splice site. In some embodiments, a first 3' splice site is a duplicate of the second 3' splice site. In some embodiments, the first 3' splice site is a rabbit beta globin 3' splice site. In some embodiments, the second 3' splice site is a rabbit beta globin 3' splice site. In some embodiments, the excisable element comprises a recombination site. In some embodiments, the recombination site is a lox site or FRT site. In some embodiments, the lox site is a loxP site. In some embodiments, the excisable element comprises from 5' to 3': a) the 5' splice site; b) a first recombination site; c) the first 3' splice site; d) a stop signaling sequence; e) a second recombination site; and f) the second 3' splice site. In some embodiments, the excisable element comprises from 5' to 3': a) the 5' splice site; b) a first spacer segment; c) a second spacer segment comprising: i) a first recombination site; ii) the first 3' splice site; iv) a stop signaling sequence; and v) a second recombination site; and d) a third spacer segment comprising the second 3' splice site. In some embodiments, the first spacer sequence comprises an intron. In some embodiments, the first spacer segment comprises a sequence having at least 70%, 80%, 90%, 95%, 99%, or 100% sequence identity to SEQ ID NO: 1. In some embodiments, the second spacer segment comprises a sequence having at least 70%, 80%, 90%, 95%, 99%, or 100% sequence identity to SEQ ID NO: 2. In some embodiments, the third spacer segment comprises a sequence having at least 70%, 80%, 90%, 95%, 99%, or 100% sequence identity to SEQ ID NO: 3. In some embodiments, the third spacer segment comprises an intron. In some embodiments, the first spacer segment and the third spacer segment are capable of being excised by endogenous cellular machinery. In some embodiments, the second spacer segment comprises an exon. In some embodiments, the second spacer segment further comprises a polyA sequence. In some embodiments, the polyA sequence is 3' of the exon. In some embodiments, the polyA sequence comprises a rabbit beta globin (RBG) polyA sequence. The polynucleotide construct of any one of claims, wherein the second spacer segment comprises from 5' to 3': a) a first recombination site; b) the first 3' splice site; c) an exon; d) a stop signaling sequence; and e) a second recombination site. In some embodiments, the first recombination site is a first lox sequence and the second recombination site is a second lox sequence. In some embodiments, the first lox sequence is a first loxP sequence and a second lox sequence is a second loxP sequence. In some embodiments, the first recombination site is a first FRT site and the second recombination site is a second FRT site. In some embodiments, the stop signaling sequence is a termination codon of the exon or a polyA sequence. In some embodiments, the polyA sequence comprises a rabbit beta globin (RBG) polyA sequence. In some embodiments, the exon encodes a detectable marker or a selectable marker. In some embodiments, the detectable marker comprises a luminescent marker or a fluorescent marker. In some embodiments, the fluorescent marker is GFP, EGFP, RFP, CFP, BFP, YFP, or mCherry. In some embodiments, the second spacer segment is excisable by a recombinase. In some embodiments, the recombinase is a site-specific recombinase. The polynucleotide construct of any one of claims, wherein the recombinase is a Cre polypeptide or a Flippase polypeptide. The polynucleotide construct of any one claims X, wherein the Cre polypeptide is fused to a ligand binding domain. In some embodiments, the ligand binding domain is a hormone receptor. In some embodiments, the hormone receptor is an estrogen receptor. In some embodiments, the estrogen receptor comprises a point mutation. In some embodiments, the estrogen receptor is ERT2. The polynucleotide construct of any one claims X, wherein the recombinase is a Cre-ERT2 polypeptide. The polynucleotide construct of claim 9, wherein the recombinase is encoded by a second polynucleotide construct or exogenously provided. In some embodiments, the Rep gene codes for Rep polypeptides. In some embodiments, the Cap gene codes for Cap polypeptides. In some embodiments, transcription of the Rep gene and the Cap gene are driven by native promoters. In some embodiments, the native promoters comprise P5, P19, and P40. In some embodiments, the Rep polypeptides are wildtype Rep polypeptides. In some embodiments, the Rep polypeptides comprise Rep78, Rep68, Rep52, and Rep40. In some embodiments, a truncated replication associated protein comprising a polypeptide expressed from the sequence of first part of a Rep gene and the exon is capable of being expressed in the absence of the recombinase. In some embodiments, the Cap polypeptides are wildtype Cap polypeptides. In some embodiments, the Cap polypeptides are AAV capsid proteins. In some embodiments, the AAV capsid proteins comprise VP1, VP2, and VP3. In some embodiments, a serotype of the AAV capsid proteins is selected from the group consisting of AAV1, AAV2, AAV3, AAV4, AAV5, AAV6, AAV7, AAV8, AAV9, AAV 10, AAV11, AAV 12, AAV13, AAV 14, AAV 15 and AAV 16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, AAV.HSC16, and AAVhu68.

In some embodiments, the Rep/Cap construct further comprises a sequence coding for a selectable marker. In some embodiments, the selectable marker is a mammalian cell selection element. In some embodiments, the selectable marker is an auxotrophic selection element. In some embodiments, the auxotrophic selection element codes for an active protein. In some embodiments, the active protein is DHFR. In some embodiments, the auxotrophic selection coding sequence encodes an inactive protein that requires expression of a second auxotrophic selection coding sequence for activity. In some embodiments, the second auxotrophic selection coding sequence encodes for DHFR Z-Cter or DHFR Z-Nter. In some embodiments, the inactive protein comprises a DHFR Z-Nter or DHFR Z-Cter In some embodiments, the selectable marker is DHFR Z-Nter or DHFR Z-Cter. The polynucleotide construct of any one of claims 2-6, wherein the DHFR Z-Nter comprises a sequence having at least 70%, 80%, 90%, 95%, 99%, or 100% sequence identity to SEQ ID NO: 4. The polynucleotide construct of any one of claims 2-6, wherein the DHFR Z-Cter comprises a sequence having at least 70%, 80%, 90%, 95%, 99%, or 100% sequence identity to SEQ ID NO: 5. In some embodiments, the selectable marker is an antibiotic resistance protein. In some embodiments, the selectable marker is a split intein linked to an N-terminus of the antibiotic resistance protein or split intein linked to a C-terminus of the antibiotic resistance protein. In some embodiments, the selectable marker is a leucine zipper linked to an N-terminus of the antibiotic resistance protein or leucine zipper linked to a C-terminus of the antibiotic resistance protein. the antibiotic resistance protein is for puromycin resistance or blasticidin resistance.

In some embodiments, the Rep/Cap construct is in a vector. In some embodiments, the Rep/Cap construct is in a plasmid. In some embodiments, the Rep/Cap construct is in a bacterial artificial chromosome or yeast artificial chromosome. In some embodiments, the Rep/Cap construct is a synthetic nucleic acid construct. In some embodiments, the Rep/Cap construct comprises a sequence having at least 70%, 80%, 90%, 95%, 99%, or 100% sequence identity to any one of SEQ ID NO: 1-SEQ ID NO: 3, SEQ ID 6-SEQ ID NO: 8, or SEQ ID NO: 32. In some embodiments, the Rep/Cap construct has at least 70%, 80%, 90%, 95%, 99%, or 100% sequence identity to any one of SEQ ID NO: 1-SEQ ID NO: 3, SEQ ID 6-SEQ ID NO: 8, or SEQ ID NO: 32.

In some embodiments, the Rep/Cap construct further comprises a sequence coding for VA RNA. In some embodiments, the sequence coding for VA RNA is a transcriptionally dead sequence. In some embodiments, the sequence coding for VA RNA comprises at least two mutations in the internal promoter. In some embodiments, expression of VA RNA is driven by a U6 promoter. The polynucleotide construct of any one of claims X, comprising upstream of the sequence coding for VA RNA gene sequence, from 5' to 3': a) a first part of a U6 promoter sequence; b) a first recombination site; c) a stuffer sequence; d) a second recombination site; e) a second part of a U6 promoter sequence. In some embodiments, the stuffer sequence is excisable by the recombinase. In some embodiments, the stuffer sequence comprises a sequence encoding a gene. In some embodiments, the stuffer sequence comprises a promoter. In some embodiments, the promoter is a constitutive promoter. In some embodiments, the promoter is a CMV promoter.

A major advantage of the inducible polynucleotide constructs disclosed herein encoding for Rep and Cap include that upon stable integration into a mammalian cell line, expression of Rep and Cap is inducible even in the absence of a transfection agent or a plasmid. In some embodiments, the stable cell line populations disclosed herein are homogeneous. For example, at least 70%, at least 80%, at least 90%, at least 95%, or 100% of the stable cell population comprises the stably integrated polynucleotide construct encoding for Rep and Cap proteins.

6.4.2. Construct 2 (Adenoviral Helper Construct (Provides E2A/E4))

Provided herein is a second polynucleotide construct, which encodes for one or more adenoviral helper proteins. This second polynucleotide construct is also referred to as an inducible helper construct (e.g., Adenoviral Helper Construct (provides E2A/E4)). In certain embodiments, the adenoviral helper construct provides inducible production of E2A/E4. In some embodiments, an adenoviral helper protein further comprises a protein tag. A protein tag can be a FLAG tag. In some embodiments, E2A is a FLAG tagged E2A. In some embodiments, E4 is a FLAG tagged E4. A protein tag, such as a FLAG tag, can be used to screen for or to confirm integration the second polynucleotide construct and expression of the adenoviral helper protein from the second polynucleotide construct in a cell after induction.

In some embodiments, the second integrated synthetic construct comprises conditionally expressible Cre recombinase and conditionally expressible adenovirus helper proteins. In the exemplary embodiments illustrated in FIG. 2A, prior to the cell being contacted with at least a third expression triggering agent, the second integrated construct comprises, from 5' to 3': an inducible promoter, a Cre coding sequence, a first polyA sequence, adenoviral helper protein coding sequences, a second polyA sequence, a constitutive promoter, a coding sequence for a protein that is responsive to the first expression triggering agent, and a second mammalian cell selection element.

In typical embodiments, the Cre coding sequence is operatively linked to the inducible promoter. In various embodiments, the inducible promoter comprises an element responsive to the third expression triggering agent. In certain embodiments, the inducible promoter comprises a plurality of tetracycline (Tet) operator elements capable of binding to a Tet responsive activator protein in the presence of a tetracycline. In some embodiments, the plurality of tetracycline (Tet) operator elements form a Tetracycline Responsive element (TRE). In some embodiments, the TRE comprises seven repeats of a 19 base pair operator sequence. In further embodiments, the TRE comprises seven repeats of a 19 base pair operator sequence upstream of a minimal CMV promoter sequence.

In some embodiments, the second construct further comprises an element responsive to a fourth expression triggering agent. In certain embodiments, the fourth expression triggering agent-responsive element comprises a plurality of hormone-response elements. In particular embodiments, the hormone-response elements are estrogen responsive elements (EREs). In various embodiments, the third expression triggering element is the same as the first expression triggering element, and the fourth expression triggering element is the same as the second expression triggering element.

In some embodiments, the Cre coding sequence is flanked by a first lox site and a second lox site.

In some embodiments, the inducible promoter comprises a plurality of Tet operator elements capable of binding to a Tet responsive activator protein in the presence of a third expression triggering agent. In particular embodiments, the third expression triggering agent is the same as the first expression triggering agent.

In some embodiments, the first polyA sequence is positioned between the Cre coding sequence and adenoviral helper protein coding sequences that encode one or both of adenovirus E2A and E4. The strong 3' polyadenylation signal positioned upstream (5' to) the coding sequences for the adenovirus helper proteins prevents basal expression of the downstream adenoviral helper genes, E2A and E4.

In some embodiments, the further segment shown in FIG. 2C provides for inducible production of VA-RNA from construct 2.

In this embodiment, the further segment includes a Cre-inducible U6 promoter. The U6 promoter is split into 2 parts separated by a Lox flanked stuffer sequence. The U6 promoter is inactive because of the presence of the stuffer sequence. Cre mediated excision of the stuffer activates the U6 promoter. The U6 promoter drives the expression of transcriptionally dead mutants of VA RNA1 (a preferred embodiment is a double point mutant G16A-G60A). Other embodiments provide for alternative sources of VA-RNA.

In various embodiments, the coding sequence for the first expression triggering agent-responsive protein is operatively linked to a CMV promoter. In some embodiments, the coding sequence for the first expression triggering agent-responsive protein comprises a coding sequence for the Tet responsive activator protein. In particular embodiments, the Tet responsive activator protein is Tet-on-3G activator protein.

In various embodiments, the second mammalian cell selection element confers antibiotic resistance. In particular embodiments, the antibiotic resistance conferring element is a blasticidin resistance gene.

In some embodiments, the inducible helper polynucleotide construct is as shown at left or at right in FIG. 25. Multiple inducible helper polynucleotide constructs are contemplated herein. In some embodiments, said inducible helper polynucleotide constructs encode for one or more adenoviral helper proteins, such as VA RNA, E2A, E4, or any combination thereof. In some embodiments, the present disclosure provides for an inducible polynucleotide construct encoding for a mutated VA RNA gene sequence. In some embodiments, the mutations to VA RNA render its internal promoters inactive. For example, as shown in FIG. 25 (at left), the inducible helper polynucleotide construct may comprise from 5' to 3' a first part of a U6 promoter sequence, a first lox sequence, a stuffer sequence, a second lox sequence, and a second part of a U6 promoter sequence. The stuffer sequence may be any polynucleotide sequence and is excised by Cre. Cre may be exogenously provided, such as in the form of Cre gesicles. Cre may also be encoded for in the same inducible helper polynucleotide construct and expression of Cre may be conditioned on the presence of at least two triggering agents, such as doxycycline and tamoxifen. Cre may be a hormone activated Cre.

In other embodiments, instead of a mutated VA RNA gene sequence, the inducible helper constructs may comprise a constitutively expressed VA RNA that is not mutated, for example, as shown in FIG. 25 (at right).

In some embodiments, the inducible helper polynucleotide construct also encodes for one or more helper proteins, a self-excising element upstream of the one or more helper proteins, and an inducible promoter upstream of the self-excising element. Expression of the self-excising element may be driven by a Tet-On-3G system. For example, the construct may comprise a Tet-On 3G gene sequence, wherein expression is driven by an E1alpha promoter. The E1alpha promoter may be a mutated E1alpha promoter. The mutated E1alpha promoter can have a sequence of: ggatctgcgatcgctccggtgcccgtcagtgggcagagcgcacatcgcccacagtccccgagaagttggggggaggggtcggcaattgaacgggtgcctagagaaggtggcgcggggtaaactgggaaagtgatgtcgtgtactggctccgcctttttcccgagggtgggggagaaccgtatgtaagtgcagtagtcgccgtgaacgttctttttcgcaacgggtttgccgccagaacacagctgaagcttcgaggggctcgcatctctccttcacgcgcccgccgccctacctgaggccgccatccacgccggttgagtcgcgttctgccgcctcccgcctgtggtgcctcctgaactgcgtccgccgtctaggtaagtttaaagctcaggtcgagaccgggcctttgtccggcgctcccttggagcctacctagactcagccggctctccacgctttgcctgaccctgcttgctcaactctacgtctttgtttcgttttctgttctgcgccgttacagatccaagctgtgaccggcgcctac (SEQ ID NO: 20).

In the presence of a first triggering agent, such as doxycycline, Tet-On-3G is able to bind the Tet inducible promoter. Upon this binding event, the Tet inducible promoter drives expression of the self-excising element. In some embodiments, the self-excising element is a hormone activated Cre. In the presence of a second triggering agent, such as tamoxifen, and upon expression of Cre, Cre self-excises itself leading to expression of downstream adenoviral helper proteins. Thus, mammalian cell lines stably integrated with the inducible helper constructs disclosed herein only express adenoviral helper proteins in the presence of at least two triggering agents (e.g., doxycycline and tamoxifen).

In some embodiments, an inducible helper construct is a polynucleotide construct coding for: a) one or more helper proteins; b) a self-excising element upstream of the one or more helper proteins; and c) an inducible promoter upstream of the self-excising element. In some embodiments, the self-excising element is operably linked to the inducible promoter. In some embodiments, expression of the self-excising element is driven by the inducible promoter.

In some embodiments, the inducible promoter is a tetracycline-responsive promoter element (TRE). In some embodiments, the TRE comprises Tet operator (tetO) sequence concatemers fused to a minimal promoter. In some embodiments, the minimal promoter is a human cytomegalovirus promoter. In some embodiments, the inducible promoter comprises a sequence having at least 70%, 80%, 90%, 95%, 99%, or 100% sequence identity to SEQ ID NO: 22. In some embodiments, transcription is activated from the inducible promoter upon binding of an activator. In some embodiments, the activator binds to the inducible promoter in the presence of a first triggering agent. In some embodiments, further comprising an activator. In some embodiments, the activator is operably linked to a constitutive promoter. In some embodiments, the constitutive promoter is E1alpha promoter or human cytomegalovirus promoter. In some embodiments, the E1 alpha promoter comprises at least one mutation. In some embodiments, the constitutive promoter comprises a sequence having at least 70%, 80%, 90%, 95%, 99%, or 100% sequence identity with SEQ ID NO: 20. In some embodiments, the activator is reverse tetracycline-controlled transactivator (rTA) comprising a Tet Repressor binding protein (TetR) fused to a VP16 transactivation domain. In some embodiments, the rTA comprises four mutations in the tetR DNA binding moiety. In some embodiments, the rTA comprises a sequence having at least 70%, 80%, 90%, 95%, 99%, or 100% sequence identity to SEQ ID NO: 21.

In some embodiments, the inducible promoter is bound by a repressor in the absence of a first triggering agent. In some embodiments, the inducible promoter is activated in the presence of a first triggering agent. In some embodiments, the first triggering agent binds to the repressor. In some embodiments, the repressor is a tetracycline-controlled transactivator. In some embodiments, further comprising the repressor. In some embodiments, the repressor is operably linked to a constitutive promoter. In some embodiments, further comprising a tetracycline-controlled transactivator. In some embodiments, the tetracycline-controlled transactivator is operably linked to a constitutive promoter. In some embodiments, the constitutive promoter is E1alpha promoter. In some embodiments, the E1 alpha promoter comprises at least one mutation. In some embodiments, the constitutive promoter comprises a sequence having at least 70%, 80%, 90%, 95%, 99%, or 100% sequence identity with SEQ ID NO: 20. In some embodiments, the tetracycline-controlled transactivator is unbound in the presence of a first triggering agent. In some embodiments, the tetracycline-controlled transactivator does not bind to the inducible promoter in the presence of a first triggering agent. In some embodiments, the constitutive promoter is E1alpha promoter. In some embodiments, the E1 alpha promoter comprises at least one mutation. In some embodiments, the constitutive promoter comprises a sequence having at least 70%, 80%, 90%, 95%, 99%, or 100% sequence identity with SEQ ID NO: 20. In some embodiments, transcription is activated from the inducible promoter upon binding of the first triggering agent to the repressor. In some embodiments, the repressor binds to the first triggering agent. In some embodiments, the first triggering agent is a tetracycline. In some embodiments, the tetracycline is doxycycline.

In some embodiments, wherein the inducible promoter is a cumate operator sequence. In some embodiments, the cumate operator sequence is downstream of a constitutive promoter. In some embodiments, the constitutive promoter is a human cytomegalovirus promoter. In some embodiments, wherein the inducible promoter is bound by a cymR repressor in the absence of a first triggering agent. In some embodiments, the inducible promoter is activated in the presence of a first triggering agent. In some embodiments, the first triggering agent binds to the cymR repressor. The polynucleotide construct of any one of claims X, further comprising a cymR repressor. In some embodiments, the cymR repressor is operably linked to a constitutive promoter. In some embodiments, the constitutive promoter is E1alpha promoter. In some embodiments, the E1 alpha promoter comprises at least one mutation. In some embodiments, the constitutive promoter comprises a sequence having at least 70%, 80%, 90%, 95%, 99%, or 100% sequence identity with SEQ ID NO: 20. In some embodiments, the first triggering agent is a cumate.

In some embodiments, a sequence coding for the self-excising element comprises a poly A sequence. In some embodiments, the self-excising element is a recombinase. In some embodiments, the recombinase is a site-specific recombinase. In some embodiments, the recombinase is fused to a ligand binding domain. In some embodiments, the recombinase is Cre polypeptide or flippase polypeptide. In some embodiments, the Cre polypeptide is fused to a ligand binding domain. In some embodiments, the ligand binding domain is a hormone receptor. In some embodiments, the hormone receptor is an estrogen receptor. In some embodiments, the estrogen receptor comprises a point mutation. In some embodiments, the estrogen receptor is ERT2. In some embodiments, the recombinase is a Cre-ERT2 polypeptide. In some embodiments, the self-excising element translocates to the nucleus in the presence of a second triggering agent. In some embodiments, the second triggering agent is an estrogen receptor ligand. In some embodiments, the second triggering agent is a selective estrogen receptor modulator (SERM). In some embodiments, the second triggering agent is tamoxifen. In some embodiments, the recombinase is flanked by recombination sites In some embodiments, the recombination sites are lox sites or flippase recognition target (FRT) sites. In some embodiments, the lox sites are loxP sites.

In some embodiments, the one or more adenoviral helper proteins comprise E2A and E4. In some embodiments, the one or more adenoviral helper proteins further comprises a protein tag. In some embodiments, the protein tag is a FLAG-tag. In some embodiments, the E2A is FLAG-tagged E2A. In some embodiments, the sequence coding for E2 and the sequence coding for E4 are separated by an internal ribosome entry site (IRES) or by P2A.

In some embodiments, the inducible helper construct further comprising a sequence coding for a selectable marker. In some embodiments, the selectable marker is an antibiotic resistance protein. In some embodiments, the selectable marker is a split intein linked to an N-terminus of the antibiotic resistance protein or split intein linked to a C-terminus of the antibiotic resistance protein. In some embodiments, the selectable marker is a leucine zipper linked to an N-terminus of the antibiotic resistance protein or leucine zipper linked to a C-terminus of the antibiotic resistance protein. In some embodiments, the antibiotic resistance protein is for puromycin resistance or blasticidin resistance.

In some embodiments, an inducible helper construct further comprises a sequence coding for VA RNA. In some embodiments, the sequence coding for VA RNA is a transcriptionally dead sequence. In some embodiments, the sequence coding for VA RNA comprises at least two mutations in the internal promoter. In some embodiments, expression of VA RNA is driven by a U6 promoter. The polynucleotide construct of any one of claims X, comprising upstream of the sequence coding for VA RNA gene sequence, from 5' to 3': a) a first part of a U6 promoter sequence; b) a first recombination site; c) a stuffer sequence; d) a second recombination site; e) a second part of a U6 promoter sequence. In some embodiments, the stuffer sequence is excisable by the recombinase. In some embodiments, the stuffer sequence comprises a sequence encoding a gene. In some embodiments, the stuffer sequence comprises a promoter. In some embodiments, the promoter is a constitutive promoter. In some embodiments, the promoter is a CMV promoter.

In some embodiments, the gene encodes a detectable marker or a selectable marker. In some embodiments, the selectable marker is an antibiotic resistance protein. In some embodiments, the selectable marker is a split intein linked to an N-terminus of the antibiotic resistance protein or split intein linked to a C-terminus of the antibiotic resistance protein. In some embodiments, the selectable marker is a leucine zipper linked to an N-terminus of the antibiotic resistance protein or leucine zipper linked to a C-terminus of the antibiotic resistance protein. In some embodiments, the selectable marker is a mammalian cell selection element. In some embodiments, the selectable marker is an auxotrophic selection element. In some embodiments, the auxotrophic selection element codes for an active protein. In some embodiments, the active protein is DHFR. In some embodiments, the auxotrophic selection coding sequence encodes an inactive protein that requires expression of a second auxotrophic selection coding sequence for activity. In some embodiments, the second auxotrophic selection coding sequence encodes for DHFR Z-Cter or DHFR Z-Nter. In some embodiments, the inactive protein comprises a DHFR Z-Nter or DHFR Z-Cter In some embodiments, the selectable marker is DHFR Z-Nter or DHFR Z-Cter. In some embodiments, the DHFR Z-Nter comprises a sequence having at least 70%, 80%, 90%, 95%, 99%, or 100% sequence identity to SEQ ID NO: 4. In some embodiments, wherein the DHFR Z-Cter comprises a sequence having at least 70%, 80%, 90%, 95%, 99%, or 100% sequence identity to SEQ ID NO: 5. In some embodiments, the antibiotic resistance protein is for puromycin resistance or blasticidin resistance. In some embodiments, the detectable marker comprises a luminescent marker or a fluorescent marker. In some embodiments, the fluorescent marker is GFP, EGFP, RFP, CFP, BFP, YFP, or mCherry. In some embodiments, the first recombination site is a first lox sequence and the second recombination site is a second lox sequence. In some embodiments, the first lox sequence is a first loxP site and the second lox sequence is a second loxP site. In some embodiments, the first recombination site is a first FRT site and the second recombination site is a second FRT site.

In some embodiments, an inducible helper construct is in a vector. In some embodiments, an inducible helper construct is in a plasmid. In some embodiments, an inducible helper construct is in a bacterial artificial chromosome or yeast artificial chromosome. In some embodiments, an inducible helper construct is a synthetic nucleic acid construct. In some embodiments, an inducible helper construct comprises a sequence having at least 70%, 80%, 90%, 95%, 99%, or 100% sequence identity to any one of SEQ ID NO: 9-SEQ ID NO: 19, SEQ ID 23-SEQ ID NO: 32, or SEQ ID NO: 35. In some embodiments, an inducible helper construct has at least 70%, 80%, 90%, 95%, 99%, or 100% sequence identity to any one of SEQ ID NO: 9-SEQ ID NO: 19, SEQ ID 23-SEQ ID NO: 32, or SEQ ID NO: 35.

In some embodiments, an inducible helper construct comprises a polynucleotide construct coding for a VA RNA, wherein a sequence coding for the VA RNA comprises at least two mutations in an internal promoter. In some embodiments, a separate polynucleotide construct codes for a VA RNA, wherein a sequence coding for the VA RNA comprises at least two mutations in an internal promoter. In some embodiments, the sequence coding for the VA RNA comprises a sequence coding for a transcriptionally dead VA RNA. In some embodiments, the sequence coding for the VA RNA comprises a deletion of from about 5-10 nucleotides in the promoter region. In some embodiments, the sequence coding for the VA RNA comprises at least one mutation. In some embodiments, the at least one mutation is in the A Box promoter region. In some embodiments, the at least one mutation is in the B Box promoter region. In some embodiments, the at least one mutation is G16A and G60A. In some embodiments, expression of the VA RNA is driven by a U6 promoter. The polynucleotide construct of any one of claims X, comprising upstream of the VA RNA gene sequence, from 5' to 3': a) a first part of a U6 promoter sequence; b) a first recombination site; c) a stuffer sequence; d) a second recombination site; e) a second part of a U6 promoter sequence. In some embodiments, the stuffer sequence is excisable by a recombinase. In some embodiments, the stuffer sequence comprises a sequence encoding a gene. In some embodiments, the stuffer sequence comprises a promoter. In some embodiments, the promoter is a constitutive promoter. In some embodiments, the promoter is a CMV promoter. In some embodiments, the gene encodes a detectable marker or a selectable marker. In some embodiments, the selectable marker is a mammalian cell selection element. In some embodiments, the selectable marker is an auxotrophic selection element. In some embodiments, the auxotrophic selection element codes for an active protein. In some embodiments, the active protein is DHFR. In some embodiments, the auxotrophic selection coding sequence encodes an inactive protein that requires expression of a second auxotrophic selection coding sequence for activity. In some embodiments, the second auxotrophic selection coding sequence encodes for DHFR Z-Cter or DHFR Z-Nter. In some embodiments, the inactive protein comprises a DHFR Z-Nter or DHFR Z-Cter In some embodiments, the selectable marker is DHFR Z-Nter or DHFR Z-Cter. In some embodiments, wherein the DHFR Z-Nter comprises a sequence having at least 70%, 80%, 90%, 95%, 99%, or 100% sequence identity to SEQ ID NO: 4. In some embodiments, the DHFR Z-Cter comprises a sequence having at least 70%, 80%, 90%, 95%, 99%, or 100% sequence identity to SEQ ID NO: 5. In some embodiments, the selectable marker is an antibiotic resistance protein. In some embodiments, the selectable marker is a split intein linked to an N-terminus of the antibiotic resistance protein or split intein linked to a C-terminus of the antibiotic resistance protein. In some embodiments, the selectable marker is a leucine zipper linked to an N-terminus of the antibiotic resistance protein or leucine zipper linked to a C-terminus of the antibiotic resistance protein. In some embodiments, the antibiotic resistance protein is for puromycin resistance or blasticidin resistance. In some embodiments, the detectable marker comprises a luminescent marker or a fluorescent marker. In some embodiments, the fluorescent marker is GFP, EGFP, RFP, CFP, BFP, YFP, or mCherry. In some embodiments, an inducible helper construct comprises a polynucleotide construct coding for a VA RNA or the VA RNA construct further comprising a sequence coding for a recombinase. In some embodiments, the recombinase is exogenously provided. In some embodiments, the recombinase is a site-specific recombinase. In some embodiments, the recombinase is a Cre polypeptide or a Flippase polypeptide. In some embodiments, the Cre polypeptide is fused to a ligand binding domain. In some embodiments, the ligand binding domain is a hormone receptor. In some embodiments, the hormone receptor is an estrogen receptor. In some embodiments, the estrogen receptor comprises a point mutation. In some embodiments, the estrogen receptor is ERT2. In some embodiments, the recombinase is a Cre-ERT2 polypeptide. In some embodiments, the first recombination site is a first lox sequence and the second recombination site is a second lox sequence. In some embodiments, the first lox sequence is a first loxP site and the second lox sequence is a second loxP site. In some embodiments, the first recombination site is a first FRT site and the second recombination site is a second FRT site. In some embodiments, the construct comprising the VA RNA as described herein further comprises a sequence coding for a selectable marker. In some embodiments, the selectable marker is an antibiotic resistance protein. In some embodiments, the selectable marker is a split intein linked to an N-terminus of the antibiotic resistance protein or split intein linked to a C-terminus of the antibiotic resistance protein. In some embodiments, the selectable marker is a leucine zipper linked to an N-terminus of the antibiotic resistance protein or leucine zipper linked to a C-terminus of the antibiotic resistance protein. In some embodiments, the antibiotic resistance protein is for puromycin resistance or blasticidin resistance. In some embodiments, an inducible helper construct comprises a polynucleotide construct coding for a VA RNA or the VA RNA construct is in a vector. In some embodiments, an inducible helper construct comprises a polynucleotide construct coding for a VA RNA or the VA RNA construct is in a plasmid. In some embodiments, an inducible helper construct comprises a polynucleotide construct coding for a VA RNA or the VA RNA construct is in a bacterial artificial chromosome or yeast artificial chromosome. In some embodiments, an inducible helper construct comprises a polynucleotide construct coding for a VA RNA or the VA RNA construct is a synthetic nucleic acid construct. In some embodiments, an inducible helper construct comprises a sequence having at least 70%, 80%, 90%, 95%, 99%, or 100% sequence identity to any one of SEQ ID NO: 13-SEQ ID NO: 19 or SEQ ID 23-SEQ ID NO: 2. In some embodiments, an inducible helper construct has at least 70%, 80%, 90%, 95%, 99%, or 100% sequence identity to any one of SEQ ID NO: 13-SEQ ID NO: 19 or SEQ ID 23-SEQ ID NO: 2. In some embodiments, a VA RNA construct comprises a sequence having at least 70%, 80%, 90%, 95%, 99%, or 100% sequence identity to any one of SEQ ID NO: 13-SEQ ID NO: 19 or SEQ ID 23-SEQ ID NO: 2. In some embodiments, a VA RNA construct has a sequence having at least 70%, 80%, 90%, 95%, 99%, or 100% sequence identity to any one of SEQ ID NO: 13-SEQ ID NO: 19 or SEQ ID 23-SEQ ID NO: 2.

6.4.3. Construct 3 (Polynucleotide Encoding a Payload)

In some embodiments, the third integrated synthetic construct comprises the coding sequence for an expressible payload and a third mammalian cell selection element. In the exemplary embodiments shown in FIG. 4, the expressible payload is under the control of a constitutive promoter. This construct can be referred to as construct 3 or payload construct, interchangeably.

In some embodiments, the expressible payload encodes a guide RNA. In certain embodiments, the guide RNA directs RNA editing. In some embodiments, the guide RNA directs CAS-mediated DNA editing. In some embodiments, the third integrated synthetic construct comprises a sequence encoding for any of the expressible payloads disclosed herein. For example, said sequence can encode for any therapeutic. For example, the therapeutic may be a transgene, a guide RNA, an antisense RNA, an oligonucleotide, an mRNA, a miRNA, a shRNA, a tRNA suppressor, a CRISPR-Cas protein, any gene editing enzyme, or any combination thereof. In some embodiments, the third integrated synthetic construct comprises sequences encoding for more than one of the expressible payloads disclosed herein.

In some embodiments, the expressible payload encodes a protein. In certain embodiments, the expressible payload is an enzyme, useful for replacement gene therapy. In some embodiments, the protein is a therapeutic antibody. In some embodiments, the protein is a vaccine immunogen. In particular embodiments, the vaccine immunogen is a viral protein.

In some embodiments, the expressible payload is a homology construct for homologous recombination.

In various embodiments, the third mammalian cell selection element is an auxotrophic selection element.

In some embodiments, the payload construct comprises a sequence having at least 70%, 80%, 90%, 95%, 99%, or 100% sequence identity to SEQ ID NO: 33. In some embodiments, the payload construct comprises a sequence having at least 70%, 80%, 90%, 95%, 99%, or 100% sequence identity to SEQ ID NO: 33, wherein SEQ ID NO: 34 in SEQ ID NO: 33 is replaced with a sequence of the payload of interest. In some embodiments, the payload construct comprises a sequence of a payload flanked by ITR sequences. In some embodiments, expression of the sequence of the payload is driven by a constitutive promoter. In some embodiments, the constitutive promoter and sequence of the payload are flanked by ITR sequences. In some embodiments, the sequence of the payload comprises a polynucleotide sequence coding for a gene. In some embodiments, the gene codes for a selectable marker or detectable marker. In some embodiments, the gene codes for a therapeutic polypeptide or transgene. In some embodiments, the sequence of the payload comprises a polynucleotide sequence coding for a therapeutic polynucleotide. In some embodiments, the therapeutic polynucleotide is a tRNA suppressor or a guide RNA. In some embodiments, the guide RNA is a polyribonucleotide capable of binding to a protein. In some embodiments, the protein is nuclease. In some embodiments, the protein is a Cas protein, an ADAR protein, or an ADAT protein. In some embodiments, the Cas protein is catalytically inactive Cas protein. In some embodiments, the payload construct is stably integrated into the genome of the cell. In some embodiments, a plurality of the payload construct are stably integrated into the genome of the cell. In some embodiments, the plurality of the payload constructs are separately stably integrated into the genome of the cell. In some embodiments, the payload construct further comprises a sequence coding for a selectable marker or detectable marker outside of the ITR sequences. In some embodiments, the selectable marker is a mammalian cell selection element. In some embodiments, the selectable marker is an auxotrophic selection element. In some embodiments, the auxotrophic selection element codes for an active protein. In some embodiments, the active protein is DHFR. In some embodiments, the auxotrophic selection coding sequence encodes an inactive protein that requires expression of a second auxotrophic selection coding sequence for activity. In some embodiments, the second auxotrophic selection coding sequence encodes for DHFR Z-Cter or DHFR Z-Nter. In some embodiments, the inactive protein comprises a DHFR Z-Nter or DHFR Z-Cter In some embodiments, the selectable marker is DHFR Z-Nter or DHFR Z-Cter. The polynucleotide construct of any one of claims 2-6, wherein the DHFR Z-Nter comprises a sequence having at least 70%, 80%, 90%, 95%, 99%, or 100% sequence identity to SEQ ID NO: 4. The polynucleotide construct of any one of claims 2-6, wherein the DHFR Z-Cter comprises a sequence having at least 70%, 80%, 90%, 95%, 99%, or 100% sequence identity to SEQ ID NO: 5. In some embodiments, the selectable marker is an antibiotic resistance protein. In some embodiments, the selectable marker outside of the ITR sequences is a split intein linked to an N-terminus of the antibiotic resistance protein or split intein linked to a C-terminus of the antibiotic resistance protein. In some embodiments, the selectable marker outside of the ITR sequences is a leucine zipper linked to an N-terminus of the antibiotic resistance protein or leucine zipper linked to a C-terminus of the antibiotic resistance protein. In some embodiments, the antibiotic resistance protein is for puromycin resistance or blasticidin resistance.

6.4.4. Host Production Cell

The plurality of synthetic nucleic acid constructs are integrated into the genome of a production host cell. In some embodiments, the production cell is an insect cell. In some embodiments, the production cell is a mammalian cell.

In typical embodiments, the production host cell is a mammalian cell line that expresses adenovirus E1A and E1B. In particular embodiments, the cell is a human embryonic kidney (HEK) 293 cell line or derivatives thereof (HEK293T cells, HEK293F cells), a human HeLa cell line that expresses E1A and E1B, a Chinese hamster ovary (CHO) cell line that expresses E1A and E1B, or a Vero cell that expresses adenovirus E1A and E1B. In particular embodiments, the host cell is a HEK293 cell line.

In certain embodiments, the host cell is DHFR null. In specific embodiments, the host cell is a DHFR null HEK293 cell.

In some embodiments, the HEK293 cell expresses AAV E1A and E1B. In the presence of doxycycline and tamoxifen, the ER2 Cre is excised from the first integrated synthetic construct, thereby permitting expression of AAV E2A and E4. The self-excised ER2 Cre recombines by virtue of the lox sites flanking the EGFP cassette in the second integrated synthetic construct, thereby removing the EGFP segment from the second spacer element in the integrated second synthetic construct. As such, any cells comprising only the second integrated synthetic construct will be EGFP signal positive whereas cells comprising both the first and second integrated synthetic constructs will be EGFP signal negative, following the addition of the triggering agents. Absence of EGFP signal indicates successful transfection of both the first and second integrated synthetic constructs in a cell. This is further ensured by antibiotic resistance selection, e.g., blasticidin resistance.

Additionally, removal of the EGFP cassette provides for the functional expression of Rep and Cap proteins, which can be linked to a first DHFR selection element, e.g., Z-Cter DHFR. The Z-Cter DHFR is capable of associating with a second DHFR selection element, e.g., Z-Nter DHFR, present in the third integrated synthetic construct to form an active molecule that allows the cell to survive in a selection medium, e.g., HT lacking media selection.

In some embodiments, the third integrated synthetic construct comprises a payload. The payload can be a guide RNA (FIGS. 4 and 5B), an HDR homology region, or a gene of interest.

In sum, a preferred embodiment of this system requires only one antibiotic resistance marker, and two split auxotrophic constructs for selection of all three plasmids, each being transformed just once into the DHFR knockout strain-producing a master cell line for virion production which can be stored and then utilized for scaled-up production without further transformations. This approach provides inducible control over expression of the Rep/Cap products avoiding the toxicity typically associated with Rep/Cap production and also avoids selection with multiple antibiotics, which is not preferred for therapeutic products. Both overexpression of Rep/Cap and selection with multiple antibiotics can be toxic and result in diminished virion yield. The transformed cells can be frozen for storage and thawed for subsequent applications.

6.4.5. Payloads

Disclosed herein are payloads that may be encoded for by polynucleotide construct 3, which encodes for a payload. This third polynucleotide is referred to herein as a "payload construct" or "therapeutic payload." Thus, disclosed herein are stable mammalian cell lines that encapsidate a payload. The payload may be an expressible payload. The polynucleotide may encode for any therapeutic. For example, the therapeutic may be a transgene, a guide RNA, an antisense RNA, an oligonucleotide, an mRNA, a miRNA, a shRNA, a tRNA suppressor, a CRISPR-Cas protein, any gene editing enzyme, or any combination thereof. In some embodiments, the stable mammalian cell lines disclosed herein can conditionally produce rAAV virions that encapsidate more than one payload. Any combination of payloads disclosed herein is contemplated.

6.4.6. Split Auxotrophic Selection

Maintaining constructs stably in the cellular genome requires selective pressure.

Typically, each integrated nucleic acid construct comprises a mammalian cell selection element. In some embodiments, the stable cell line comprises three integrated nucleic acid constructs, wherein the first nucleic acid construct comprises a first mammalian cell selection element, the second nucleic acid construct comprises a second mammalian cell selection element, and the third nucleic acid construct comprises a third mammalian cell selection element.

FIG. 5A depicts an exemplary split auxotrophic selection system that permits stable retention of two integrated nucleic acid constructs under a single selective pressure. One construct encodes the N-terminal fragment of mammalian dihydrofolate reductase (DHFR) fused to a leucine zipper peptide ("Nter-DHFR"). This N-terminal fragment is enzymatically nonfunctional. The other construct encodes the C-terminal fragment of DHFR fused to a leucine zipper peptide ("Cter-DHFR"). This C-terminal fragment is enzymatically nonfunctional. When both fragments are concurrently expressed in the cell, a functional DHFR enzyme complex is formed through association of the leucine zipper peptides. Both constructs can be stably retained in the genome of a DHFR null cell by growth in a medium lacking hypoxanthine and thymidine.

FIG. 5B shows an exemplary deployment of this split auxotrophic selection design in the multi-construct system of FIG. 1 in its pre-triggered state. In this embodiment, the split auxotrophic selection elements are deployed on constructs 1 and 3. A separate exemplary antibiotic selection element, blasticidin resistance, is deployed on construct 2. This results in the ability to stably maintain all three constructs in the mammalian cell line using a single antibiotic, culturing in medium with blasticidin, lacking thymidine and hypoxanthine. In some embodiments, the construct 2 further comprising a sequence coding for VA RNA as described herein. In some embodiments, the VA RNA is a mutated VA RNA. In some embodiments, the VA RNA is transcriptionally dead VA RNA. In some embodiments, the VA RNA is under the control of a U6 promoter. In some embodiments, the U6 promoter is a conditionally active. In some embodiments, the U6 promoter comprises an interrupting sequence that is capable of being floxed upon addition a triggering agent (e.g., the triggering agent induces the expression of a recombinase as described herein).

In some embodiments, the first nucleic acid construct comprises a first mammalian cell selection element, and the first mammalian cell selection element is a first auxotrophic selection element. In certain embodiments, the first auxotrophic selection element encodes an active protein. In particular embodiments, the first auxotrophic selection element is DHFR. In some embodiments, the first auxotrophic selection coding sequence encodes an inactive protein that requires expression of a second auxotrophic selection coding sequence for activity. In certain embodiments, the first auxotrophic selection element encodes Z-Cter-DHFK (SEQ ID NO: 5).

In various embodiments, the second nucleic acid construct comprises a second mammalian cell selection element, and the second mammalian cell selection element encodes antibiotic resistance. In particular embodiments, the antibiotic resistance gene is a blasticidin resistance gene.

In various embodiments, the third nucleic acid construct comprises a third mammalian cell selection element. In some embodiments, the third mammalian cell selection element is a second auxotrophic selection element. In certain embodiments, the second auxotrophic selection element encodes an active protein. In particular embodiments, the second auxotrophic selection element is DHFR. In some embodiments, the second auxotrophic selection coding sequence encodes an inactive protein that requires expression of a first auxotrophic selection coding sequence for activity. In certain embodiments, the second auxotrophic selection element encodes Z-Nter-DHFR (SEQ ID NO:4).

In various embodiments, the stable mammalian cell line can be propagated in growth media lacking hypoxanthine and thymidine.

6.4.7. Complete System in Detail

The first integrated synthetic construct comprises an intervening spacer sequence inserted into the coding sequence of AAV2 Rep protein. The intervening spacer sequence comprises an enhanced green fluorescent protein (EGFP) and a rabbit beta globin (RBG) polyadenylation (polyA) signal, flanked by two lox sites, are inserted into an RBG intron. The RBG intron includes the 5' splice site (5'SS) and the 3' splice site (3'SS) (as shown in FIGS. 3A-3B). The RBG intron is inserted downstream of the Rep endogenous P5 and P19 promoters and interrupt the Rep coding sequence. This design blocks the expression of Rep proteins generated by both P5 and P19 promoters. The EGFP serves as a visual indicator of successful integration and to monitor Cre mediated excision, and could be replaced by any suitable marker. For instance, loss of EGFP expression indicates successful Cre-mediated genomic recombination (See, FIG. 3B). Current approaches rely on inserting the EGFP and the polyA within an intron without duplication of 3' splice site (3'SS). If there is readthrough after polyA, the 5'SS can combine with the native 3'SS, thus removing the entire RBG intron and as a result, commencing Rep expression. By contrast, the design as described herein includes an additional 3' SS upstream of the EGFP, which solves the problem of undesired Rep expression. The present design provides that if there is readthrough, the construct allows splicing of 5'SS to the upstream 3'SS. Without being bound to any theories, the additional 3'SS which is nearest to the 5'SS is preferred since it is the same 3'SS as the downstream one and the two 3'SS are of equal strength. As such, all Rep proteins will be produced fused to the EGFP protein and then terminate. In an event where the Rep proteins do not terminate after EGFP, they will continue to produce codons coded by the rest of the RBG intro, thereby making a non-functional Rep protein. This approach prevents overexpression of Rep proteins which may have inhibitory effects on adenovirus and cell growth, thereby reducing toxicity of the recombinant AAV (rAAV) construct.

As described herein, expression of functional Rep protein is induced only in the presence of a first expression triggering agent, e.g., the addition of doxycycline which results in the production of Cre. In the presence of Cre, the intervening spacer is excised thereby resuming intact coding sequencing of the Rep protein. This approach provides controlled and inducible Rep expression.

This is driven by the second integrated synthetic construct, which comprises an estrogen inducible Cre (ER2 Cre) gene and adenoviral helper genes, E2A and E4orf6 (E4) (See, FIGS. 1, 2A-2B, 3A-3B, and 6).

In certain embodiments, the third integrated synthetic construct ("construct three") comprises a polynucleotide flanked by AAV inverted terminal repeats (ITRs, shown by brackets in FIG. 1, FIG. 4, FIG. 5B, and FIG. 6). In certain embodiments, the third integrated construct further comprises a component of a split auxotrophic selection, as described above in Section 4.4.5. In particular embodiments, the component of the split auxotrophic selection comprises a first enzymatically nonfunctional dihydrofolate reductase (DHFR) fragment fused to a leucine zipper. Binding with a second DHFR fragment also fused to a leucine zipper produces an active complex, and allows selection for cells expressing both the first and the third integrated synthetic constructs. The construct three polynucleotide can comprise any payload including at least a guide RNA, a gene of interest, a transgene, an HDR homology region, a minigene or a therapeutic polynucleotide. This approach requires only a single auxotrophic selection agent, and a single antibiotic selection agent to be present in the cell culture medium to maintain all of the plurality of synthetic nucleic acid constructs stably within the nuclear genome of the cells. This approach also avoids multiple antibiotic resistance selection, which may be undesirable for downstream applications, e.g., gene therapy.

In one aspect, provided herein is a stable mammalian cell line, wherein the cells are capable of conditionally producing recombinant AAV (rAAV) virions within which are packaged an expressible payload; and production of virions is not conditioned on the presence of an episome within the cell.

In various embodiments, expression of AAV rep and cap proteins is conditional. In some embodiments, expression of AAV rep and cap proteins is conditioned on addition of at least a first expression triggering agent to the cell culture medium. In some embodiments, expression of AAV Rep and Cap proteins is conditioned on addition of a first expression triggering agent and a second expression triggering agent to the cell culture medium.

In some embodiments, the cells do not express cytotoxic levels of Rep protein prior to addition of the at least a first expression triggering agent to the cell culture medium. In some embodiments, the cells do not express cytostatic levels of Rep protein prior to addition of the at least first expression triggering agent to the cell culture medium.

In some embodiments, the average concentration of Rep protein within the cells is less than between 1-99%, 10-90%, 20-80%, 30-70%, 40-60% prior to addition of the at least first expression triggering agent to the cell culture medium. In some embodiments, the average concentration of Rep protein within the cells is less than about 1%, 5%, 10%, 15%, 20%, 25%, 30%, 35%, 40%, 45%, 50%, 55%, 60%, 65%, 70%, 75%, 80%, 85%, 90%, 95%, or 99% prior to addition of the at least first expression triggering agent to the cell culture medium.

In various embodiments, expression of Rep and Cap proteins becomes constitutive after addition of the at least first expression triggering agent to the cell culture medium. The stable cell lines include those wherein expression of adenoviral helper proteins is conditional. In some embodiments, expression of adenoviral helper proteins is conditioned on addition of at least a first expression triggering agent to the cell culture medium. In some embodiments, expression of adenoviral helper proteins is conditioned on addition of a first expression triggering agent and a second expression triggering agent to the cell culture medium. In some embodiments, continued expression of adenoviral helper proteins following triggering of expression requires presence of only the first expression triggering agent in the cell culture medium.

In some embodiments, the adenoviral helper proteins include E2A and E4.

In some embodiments, the first expression triggering agent is a tetracycline. In some embodiments, the tetracycline is doxycycline.

In some embodiments, the second expression triggering agent is an estrogen receptor ligand. In some embodiments, the estrogen receptor ligand is a selective estrogen receptor modulator (SERM). In some embodiments, the estrogen receptor ligand is tamoxifen.

In some embodiments, expression of the payload is not conditioned on addition of an expression triggering agent to the cell culture medium.

In various embodiments, the nuclear genome of the cell comprises a plurality of integrated synthetic nucleic acid constructs. In some embodiments, the nuclear genome of the cell comprises two integrated synthetic constructs. In some embodiments, the nuclear genome of the cell comprises three integrated synthetic constructs. In some embodiments, each of the plurality of synthetic nucleic acid constructs is separately integrated into the nuclear genome of the cell.

In some embodiments, only a single non-auxotrophic selection agent is required to be present in the cell culture medium to maintain all of the plurality of synthetic nucleic acid constructs stably within the nuclear genome of the cells.

In some embodiments, the first integrated synthetic construct comprises conditionally expressible AAV Rep and Cap coding sequences; the second integrated synthetic construct comprises a conditionally expressible Cre coding sequence and conditionally expressible adenoviral helper protein coding sequences; and the third integrated synthetic construct comprises expressible coding sequences for the payload.

In some embodiments, the first integrated construct comprises a Rep coding sequence interrupted by an intervening spacer. In some embodiments, the intervening spacer comprises, from 5' to 3', a first spacer, a second spacer and a third spacer. In some embodiments, the intervening spacer comprises nucleic acid sequences of a rabbit beta globin (RBG) intron and a rabbit beta globin (RBG) poly A. In some embodiments, the first spacer comprises a nucleic acid sequence of at least 80% identity to SEQ ID NO: 1. In some embodiments, the first spacer comprises a 5' splice site (5'SS) 5' to the first spacer. In some embodiments, the second spacer comprises a nucleic acid sequence of at least 80% identity to SEQ ID NO: 2. In some embodiments, the second spacer comprises, from 5' to 3' a first lox site, an enhanced green fluorescent protein (EGFP), the RBG polyA sequence, and a second lox site. In some embodiments, the second spacer further comprises a first 3' splice site (3'SS) flanked by the first lox site and the EGFP. In some embodiments, the third spacer comprises a nucleic acid sequence of at least 80% identity to SEQ ID NO: 3. In some embodiments, the third spacer further comprises a second 3' splice site (3'SS) 3' to the third spacer.

In some embodiments, the Rep coding sequence comprises a polynucleotide sequence operatively linked to an endogenous P5 promoter. In some embodiments, the Rep coding sequence comprises a polynucleotide sequence operatively linked to an endogenous P19 promoter. In some embodiments, the intervening spacer is inserted into the Rep coding sequence at a position downstream of the P19 promoter. In some embodiments, the intervening spacer is inserted into the Rep coding sequence at a position in frame with the protein produced from activation of the P5 promoter and the P19 promoter. In some embodiments, wherein the Rep coding sequence is 5' to the Cap coding sequence. In some embodiments, the Cap coding sequence is operatively linked to an endogenous P40 promoter.

In some embodiments, the second integrated construct comprises, from 5' to 3', a Cre coding sequence and a first polyA sequence, adenoviral helper protein coding sequences and a second polyA sequence, a first expression triggering agent responsive element, and an antibiotic selection element. In some embodiments, the Cre coding sequence is flanked by a first lox site and a second lox site. In some embodiments, the Cre coding sequence is operatively linked to an inducible promoter. In some embodiments, the inducible promoter comprises a plurality of tetracycline (Tet) operator elements capable of binding to a Tet responsive activator protein in the presence of a first expression triggering agent. In some embodiments, the inducible promoter comprises a plurality of Tet operator elements capable of binding to a Tet responsive activator protein in the presence of a first expression triggering agent and a second expression triggering agent responsive element. In some embodiments, the adenoviral helper protein coding sequences comprise E2A and E4 sequences. In some embodiments, the first expression triggering agent responsive element is operatively linked to a CMV promoter. In some embodiments, the first expression triggering agent responsive element comprises the Tet responsive activator protein (Tet-on-3G). In some embodiments, the antibiotic selection element is blasticidin resistance.

In some embodiments, the third integrated synthetic construct comprises a coding sequence for the expressible payload and a first element of an auxotrophic selection agent and the first integrated synthetic construct comprises coding sequences for a second element of the auxotrophic selection agent. In some embodiments, the first element of a auxotrophic selection agent comprises a first dihydrofolate reductase (DHFR) selectable marker (SEQ ID NO: 4). In some embodiments, the first DHFR comprises a leucine zipper (Nter). In some embodiments, the second element of the auxotrophic selection agent comprises a second DHFR (SEQ ID NO: 5). In some embodiments, the second DHFR comprises a leucine zipper (Cter). In some embodiments, the DHFR selection comprises the ability to grow in media lacking hypoxantine-thymidine.

In some embodiments, the mammalian cell line is selected from the group consisting of a human embryonic kidney (HEK) 293 cell line, a human HeLa cell line, and a Chinese hamster ovary (CHO) cell line. In some embodiments, the mammalian cell line is a HEK293 cell line. In some embodiments, the mammalian cell line expresses adenovirus helper functions E1A and E1B.

A. The Stable Mammalian Cell or Cell Line

As described herein, the stable mammalian cell or cell line can be a human derived cell or cell line such as a human embryonic kidney (HEK) 293 cell line or a human HeLa cell line, or a mammalian cell or cell line such as Chinese hamster ovary (CHO) cell line. In some embodiments, the mammalian cell line is a HEK293 cell line. In some embodiments, the mammalian cell line expresses adenovirus helper functions E1A and E1B.

B. The First Integrated Synthetic Construct

Shown are exemplary designs of the first integrated synthetic construct (FIGS. 1, 3B and 6).

As described in FIGS. 3A-3B, the first integrated synthetic construct comprises a Rep coding sequence 5' of a Cap coding sequence. The Rep coding sequence is interrupted by an intervening spacer. In some embodiments, the first integrated synthetic construct further comprises a selection element such as an auxotrophic selection marker (FIG. 5B). In some embodiments, the selection element is a partial or a second element of the non-auxotrophic selection marker. The intervening spacer comprises a rabbit beta globin (RBG) intron, which is modified by duplicating the RBG 3' splice site (3'SS) upstream to an enhanced green fluorescent protein (EGFP) cassette within the intron. The EGFP cassette is cloned immediately downstream of this duplicated splice site followed by a rabbit beta globin polyadenylation signal. This entire modification (3'SS, EGFP and polyA) is flanked by two lox sites so that the module can be removed upon Cre expression. The modified rabbit beta globin intron (the intervening spacer sequence) is inserted into the coding sequence of AAV2 Rep protein. The point of insertion is downstream of P19 promoter, away from any known regulatory elements. It is also in frame with the proteins produced from P5 and P19 protein so that EGFP expression can be visualized. Cap genes from any AAV serotype are cloned downstream of the AAV2 Rep cassette. The Cap genes are driven by their endogenous P40 promoter. In the absence of Cre, the 5' splice site (5'SS) gets spliced to the upstream of 3'SS, so the EGFP becomes the terminal exon and transcription terminates at the beta globin polyadenylation signal. Thus, the expression of all Rep proteins either from the P5 or P19 promoter is prematurely terminated. Since expression of the P40 promoter is dependent on the presence of the Rep proteins, the P40 promoter is silent and there is no expression of Cap proteins. Upon Cre expression from a second integrated synthetic construct, the entire second spacer element (except for the left lox site is excised from the beta globin intron. The 5'SS now splices with the native 3'SS site and expression of all Rep proteins commences. Rep expression activates the P40 proteins and Cap proteins are therefore also expressed.

C. The Second Integrated Synthetic Construct

Shown are exemplary designs of the second integrated synthetic construct (FIGS. 2A-2C).

As shown in FIG. 2A, the second integrated synthetic construct comprising, from 5' to 3', a Cre coding sequence and a first polyA sequence, adenoviral helper protein coding sequences and a second polyA sequence, a first expression triggering agent responsive element, and an antibiotic selection element. The Cre coding sequence is flanked by a first lox site and a second lox site, and is operatively linked to an inducible promoter. The inducible promoter comprises a plurality of tetracycline (Tet) operator elements capable of binding to a Tet responsive activator protein in the presence of a first expression triggering agent, e.g., doxycycline or tetracycline. In some embodiments, the inducible promoter comprises a plurality of tetracycline (Tet) operator elements capable of binding to a Tet responsive activator protein in the presence of a first expression triggering agent and a second expression triggering agent responsive element, e.g., tamoxifen. The first expression triggering element may comprise a Tet responsive activator protein (Tet-on-3G) and is operatively linked to a CMV promoter. The antibiotic selection element can be blasticidin resistance (FIG. 5B). The optional insert shown in FIG. 2C provides for inducible production of VA-RNA, which are short non-coding transcripts essential for Adenovirus replication. In this construct, an alternative insert to construct 2, includes a Cre inducible U6 promoter that drives the expression of transcriptionally dead mutants of VA RNA1 (a preferred embodiment is a double point mutant G16A-G60A). The U6 promoter is split into 2 parts separated by a Lox flanked stuffer sequence. The U6 promoter is inactive because of the presence of the stuffer sequence. Cre mediated excision of the stuffer activates the U6 promoter which then drives the expression of VA RNA. Other embodiments may provide for alternative sources of VA-RNA.

In some embodiments, the Cre coding sequencing is an estrogen inducible Cre that has a strong polyadenylation signal (stop signal) at its 3' end. Following this is a bicistronic E2A, E4orf6 cassette. The plasmid also has a constitutive promoter (CMV) which drives the expression of the Tet responsive activator protein (Tet-on 3G).

In the off state when doxycycline (Dox) is absent, the Tet-on 3G cannot bind to the Tet operator elements in the Tet-regulatable promoter so the promoter is not active. Estrogen responsive Cre is used instead of simple Cre to counteract the basal or leaky expression of the Tet-regulatable promoter. In the off state if there is leaky expression of Cre gene, the expressed Cre protein will be held inactive in the cytoplasm. The strong polyadenylation signal, 3' of the cre gene will prevent basal expression of adenoviral helper genes, E2A and E4. To induce expression, doxycycline and tamoxifen are added to the cell culture (FIG. 6). Doxycycline will bind to the Tet-on 3G protein and this will promote binding of the Tet-on 3G to the tet operator elements in the Tet-regulatable promoter. This will trigger the activation of the promoter. ER2 Cre will be expressed at high levels and tamoxifen will bring the Cre to the nucleus.

D. The Third Integrated Synthetic Construct

Shown are exemplary designs of the third integrated synthetic construct (FIGS. 1, 4, 5B and 6). As described in FIGS. 4 and 6, the third integrated synthetic construct comprises coding sequences for an expressible payload, and/or a guide RNA, and a first element of a non-auxotrophic selection agent capable of binding to a partial or a second element of the non-auxotrophic selection agent in the first integrated synthetic construct. In some embodiments, the first element of a non-auxotrophic selection agent comprises a first dihydrofolate reductase (DHFR) selectable marker (SEQ ID NO: 4). The first DHFR may comprise a leucine zipper (Nter). In some embodiments, the second element of the non-auxotrophic selection agent comprises a second DHFR (SEQ ID NO: 5). The second DHFR may comprise a leucine zipper (Cter). In some embodiments, the DHFR selection comprises hypoxantine-thymidine selection. In some embodiments, re-association of the first and second DHFR selection markers allows for selection of a mammalian cell expression both the first integrated synthetic construct and the third integrated synthetic construct.

In some embodiments, a cell comprises two constructs (any combination of Rep/Cap construct, inducible helper construct, and the payload construct). In some embodiments, a cell comprises the Rep/Cap construct and the inducible helper construct. In some embodiments, the cell, the inducible helper construct comprises a VA RNA construct as described herein. In some embodiments, cell further comprises the VA RNA construct.

In some embodiments, a cell comprises all three constructs (Rep/Cap construct, inducible helper construct, and the payload construct). In some embodiments, the cell, the inducible helper construct comprises a VA RNA construct as described herein. In some embodiments, cell further comprises the VA RNA construct. In some embodiments, this cell is capable of producing an rAAV virion upon addition of at least one triggering agent. In some embodiments, the rAAV virion comprising the capsid protein and the payload nucleic acid sequence have an infectivity of no less than 50%, 60%, 70%, 80%, 90%, 95%, or 99% at an MOI of $1\times10^5$ vg/target cell or less. In some embodiments, the rAAV virions have an increased infectivity compared rAAV virions produced by an otherwise comparable the population of cells capable of producing rAAV virions upon transient transfection at the same MOI. In some embodiments, the rAAV virions have at least 1%, 5%, 10%, 15%, 20%, 30%, 40%, or 50% greater infectivity compared rAAV virions produced by an otherwise comparable the population of cells capable of producing rAAV virions upon transient transfection at the same MOI. In some embodiments, the rAAV virions have at least 50%, 60%, 70%, 80%, 90%, 95%, 97%, 98%, 99%, or 100% infectivity as compared to AAV virions produced by a cell having wildtype AAV at the same MOI. In some embodiments, the rAAV virions have at least 50%, 60%, 70%, 80%, 90%, 95%, 97%, 98%, 99%, or 100% infectivity as compared to AAV virions at the same MOI. In some embodiments, the AAV virions are wildtype AAV virions produced by a cell having wildtype AAV. In some embodiments, the MOI is $1\times10^1$, $1\times10^2$, $2\times10^3$, $5\times10^4$, or $1\times10^5$ vg/target cell. In some embodiments, the MOI is selected from a range of $1\times10^1$ to $1\times10^5$ vg/target cell. In some embodiments, the cell is conditionally capable of producing rAAV virions having a payload encapsidation ratio of no less than 0.5, 0.6, 0.7, 0.8, 0.9, 0.95, 0.97, or 0.99. In some embodiments, the rAAV virions have a payload encapsidation ratio of no less than 0.5, 0.6, 0.7, 0.8, 0.9, 0.95, 0.97, or 0.99 prior to purification. In some embodiments, the rAAV virions have a concentration of greater than $1\times10^{11}$ or no less than $5\times10^{11}$, $1\times10^{12}$, $5\times10^{12}$, $1\times10^{13}$ or $1\times10^{14}$ viral genomes per milliliter prior to purification. In some embodiments, the cell is capable of producing rAAV virions comprising the payload nucleic acid sequence at a titer of greater than $1\times10^{11}$ or no less than $5\times10^{11}$, $1\times10^{12}$, $5\times10^{12}$, $1\times10^{13}$ or $1\times10^{14}$ viral genomes per milliliter. In some embodiments, the cell is capable of producing rAAV virions comprising the payload nucleic acid sequence at a concentration of greater than $1\times10^{11}$ or no less than $5\times10^{11}$, $1\times10^{12}$, $5\times10^{12}$, $1\times10^{13}$ or $1\times10^{14}$ viral genomes per milliliter prior to purification. In some embodiments, this cell is expanded to produce a population of cells. In some embodiments, the population of cells produces a stable cell line as described herein. In some embodiments, this cell is passaged at least three times. In some embodiments, this cell can be passaged up to 60 times. In some embodiments, this cell can be passage more than 60 times. In some embodiments, the cell maintains the ability to be conditionally induced after each passage.

6.5. CELL COMPRISING A CONSTRUCT

In some embodiments, a cell comprise one construct (Rep/Cap construct, inducible helper construct, and the payload construct). In some embodiments, the one construct is stably integrated into the genome of the cell. In some embodiments, a plurality of the one construct is stably integrated into the genome of the cell. In some embodiments, a cell comprises two constructs (any combination of Rep/Cap construct, inducible helper construct, and the payload construct). In some embodiments, the two constructs are stably integrated into the genome of the cell. In some embodiments, the two constructs are separately stably integrated into the genome of the cell. In some embodiments, a plurality of the two constructs are stably integrated into the genome of the cell. In some embodiments, a plurality of the two constructs are separately stably integrated into the genome of the cell. In some embodiments, a cell comprises the Rep/Cap construct and the inducible helper construct. In some embodiments, the cell, the inducible helper construct comprises a VA RNA construct as described herein. In some embodiments, cell further comprises the VA RNA construct as described herein. In some embodiments, the VA RNA construct is stably integrated into the genome of the cell.

In some embodiments, a cell comprises all three constructs (Rep/Cap construct, inducible helper construct, and the payload construct). In some embodiments, the three constructs are stably integrated into the genome of the cell. In some embodiments, the three constructs are separately stably integrated into the genome of the cell. In some embodiments, a plurality of the three constructs are stably integrated into the genome of the cell. In some embodiments, a plurality of the three constructs are separately stably integrated into the genome of the cell. In some embodiments, the cell, the inducible helper construct comprises a VA RNA construct as described herein. In some embodiments, cell further comprises the VA RNA construct.

In some embodiments, a VA RNA construct is a polynucleotide construct coding for a VA RNA, wherein a sequence coding for the VA RNA comprises at least two mutations in an internal promoter. In some embodiments, the sequence coding for the VA RNA comprises a sequence coding for a transcriptionally dead VA RNA. In some embodiments, the sequence coding for the VA RNA comprises a deletion of from about 5-10 nucleotides in the promoter region. In some embodiments, the sequence coding for the VA RNA comprises at least one mutation. In some embodiments, the at least one mutation is in the A Box promoter region. In some embodiments, the at least one mutation is in the B Box promoter region. In some embodiments, the at least one mutation is G16A and G60A. In some embodiments, expression of the VA RNA is driven by a U6 promoter. The polynucleotide construct of any one of claims X, comprising upstream of the VA RNA gene sequence, from 5' to 3': a) a first part of a U6 promoter sequence; b) a first recombination site; c) a stuffer sequence; d) a second recombination site; e) a second part of a U6 promoter sequence. In some embodiments, the stuffer sequence is excisable by a recombinase. In some embodiments, the stuffer sequence comprises a sequence encoding a gene. In some embodiments, the stuffer sequence comprises a promoter. In some embodiments, the promoter is a constitutive promoter. In some embodiments, the promoter is a CMV promoter. In some embodiments, the gene encodes a detectable marker or a selectable marker. In some embodiments, the selectable marker is a mammalian cell selection element. In some embodiments, the selectable marker is an auxotrophic selection element. In some embodiments, the auxotrophic selection element codes for an active protein. In some embodiments, the active protein is DHFR. In some embodiments, the auxotrophic selection coding sequence encodes an inactive protein that requires expression of a second auxotrophic selection coding sequence for activity. In some embodiments, the second auxotrophic selection coding sequence encodes for DHFR Z-Cter or DHFR Z-Nter. In some embodiments, the inactive protein comprises a DHFR Z-Nter or DHFR Z-Cter In some embodiments, the selectable marker is DHFR Z-Nter or DHFR Z-Cter. In some embodiments, the DHFR Z-Nter comprises a sequence having at least 70%, 80%, 90%, 95%, 99%, or 100% sequence identity to SEQ ID NO: 4. In some embodiments, the DHFR Z-Cter comprises a sequence having at least 70%, 80%, 90%, 95%, 99%, or 100% sequence identity to SEQ ID NO: 5. In some embodiments, the selectable marker is an antibiotic resistance protein. In some embodiments, the selectable marker is a split intein linked to an N-terminus of the antibiotic resistance protein or split intein linked to a C-terminus of the antibiotic resistance protein. In some embodiments, the selectable marker is a leucine zipper linked to an N-terminus of the antibiotic resistance protein or leucine zipper linked to a C-terminus of the antibiotic resistance protein. In some embodiments, the antibiotic resistance protein is for puromycin resistance or blasticidin resistance. In some embodiments, the detectable marker comprises a luminescent marker or a fluorescent marker. In some embodiments, the fluorescent marker is GFP, EGFP, RFP, CFP, BFP, YFP, or mCherry. In some embodiments, the VA RNA construct further comprising a sequence coding for a recombinase. In some embodiments, the recombinase is exogenously provided. In some embodiments, the recombinase is a site-specific recombinase. The polynucleotide construct of any one of claims, wherein the recombinase is a Cre polypeptide or a Flippase polypeptide. In some embodiments, the Cre polypeptide is fused to a ligand binding domain. In some embodiments, the ligand binding domain is a hormone receptor. In some embodiments, the hormone receptor is an estrogen receptor. In some embodiments, the estrogen receptor comprises a point mutation. In some embodiments, the estrogen receptor is ERT2. The polynucleotide construct of any one claims X, wherein the recombinase is a Cre-ERT2 polypeptide. In some embodiments, the first recombination site is a first lox sequence and the second recombination site is a second lox sequence. In some embodiments, the first lox sequence is a first loxP site and the second lox sequence is a second loxP site. In some embodiments, the first recombination site is a first FRT site and the second recombination site is a second FRT site. The polynucleotide construct of any one of claims X, further comprising a sequence coding for a selectable marker. In some embodiments, the selectable marker is an antibiotic resistance protein. In some embodiments, the selectable marker is a split intein linked to an N-terminus of the antibiotic resistance protein or split intein linked to a C-terminus of the antibiotic resistance protein. In some embodiments, the selectable marker is a leucine zipper linked to an N-terminus of the antibiotic resistance protein or leucine zipper linked to a C-terminus of the antibiotic resistance protein. In some embodiments, the antibiotic resistance protein is for puromycin resistance or blasticidin resistance.

In some embodiments, the VA RNA construct comprises a sequence having at least 70%, 80%, 90%, 95%, 99%, or 100% sequence identity to any one of SEQ ID NO: 13-SEQ ID NO: 19 or SEQ ID 23-SEQ ID NO: 2. In some embodiments, VA RNA construct has at least 70%, 80%, 90%, 95%, 99%, or 100% sequence identity to any one of SEQ ID NO: 13-SEQ ID NO: 19 or SEQ ID 23-SEQ ID NO: 26.

In some embodiments, the cell is a mammalian cell or insect cell. In some embodiments, the cell is a HEK293 cell, HeLa cell, CHO cell, or SF9 cell. In some embodiments, the cell expresses E1A protein and E1B protein. In some embodiments, the cell further comprising a payload construct. In some embodiments, the payload construct comprises a sequence having at least 70%, 80%, 90%, 95%, 99%, or 100% sequence identity to SEQ ID NO: 33. In some embodiments, the payload construct comprises a sequence of a payload flanked by ITR sequences. In some embodiments, expression of the sequence of the payload is driven by a constitutive promoter. In some embodiments, the constitutive promoter and sequence of the payload are flanked by ITR sequences. In some embodiments, the sequence of the payload comprises a polynucleotide sequence coding for a gene. In some embodiments, the gene codes for a selectable marker or detectable marker. In some embodiments, the gene codes for a therapeutic polypeptide or transgene. In some embodiments, the sequence of the payload comprises a polynucleotide sequence coding for a therapeutic polynucleotide. In some embodiments, the therapeutic polynucleotide is a tRNA suppressor or a guide RNA. In some embodiments, the guide RNA is a polyribonucleotide capable of binding to a protein. In some embodiments, the protein is nuclease. In some embodiments, the protein is a Cas protein, an ADAR protein, or an ADAT protein. In some embodiments, the Cas protein is catalytically inactive Cas protein. In some embodiments, the payload construct is stably integrated into the genome of the cell. In some embodiments, a plurality of the payload construct are stably integrated into the genome of the cell. In some embodiments, the plurality of the payload constructs are separately stably integrated into the genome of the cell. In some embodiments, the payload construct further comprises a sequence coding for a selectable marker or detectable marker outside of the ITR sequences. In some embodiments, the selectable marker is a mammalian cell selection element. In some embodiments, the selectable marker is an auxotrophic selection element. In some embodiments, the auxotrophic selection element codes for an active protein. In some embodiments, the active protein is DHFR. In some embodiments, the auxotrophic selection coding sequence encodes an inactive protein that requires expression of a second auxotrophic selection coding sequence for activity. In some embodiments, the second auxotrophic selection coding sequence encodes for DHFR Z-Cter or DHFR Z-Nter. In some embodiments, the inactive protein comprises a DHFR Z-Nter or DHFR Z-Cter In some embodiments, the selectable marker is DHFR Z-Nter or DHFR Z-Cter. The polynucleotide construct of any one of claims 2-6, wherein the DHFR Z-Nter comprises a sequence having at least 70%, 80%, 90%, 95%, 99%, or 100% sequence identity to SEQ ID NO: 4. The polynucleotide construct of any one of claims 2-6, wherein the DHFR Z-Cter comprises a sequence having at least 70%, 80%, 90%, 95%, 99%, or 100% sequence identity to SEQ ID NO: 5. In some embodiments, the selectable marker is an antibiotic resistance protein. In some embodiments, the selectable marker outside of the ITR sequences is a split intein linked to an N-terminus of the antibiotic resistance protein or split intein linked to a C-terminus of the antibiotic resistance protein. In some embodiments, the selectable marker outside of the ITR sequences is a leucine zipper linked to an N-terminus of the antibiotic resistance protein or leucine zipper linked to a C-terminus of the antibiotic resistance protein. In some embodiments, the antibiotic resistance protein is for puromycin resistance or blasticidin resistance. In some embodiments, the payload construct is in a plasmid. In some embodiments, the payload construct is in a bacterial artificial chromosome or yeast artificial chromosome. In some embodiments, the payload construct is stably integrated into the genome of the cell. In some embodiments, the payload construct is a synthetic nucleic acid construct. In some embodiments, the cell is capable of producing an rAAV virion that encapsidates the sequence of the payload. In some embodiments, the cell is capable of producing an rAAV virion upon addition of at least one triggering agent.

In some embodiments, this cell is capable of producing an rAAV virion upon addition of at least one triggering agent. In some embodiments, the rAAV virion comprising the capsid protein and the payload nucleic acid sequence have an infectivity of no less than 50%, 60%, 70%, 80%, 90%, 95%, or 99% at an MOI of $1\times10^5$ vg/target cell or less. In some embodiments, the rAAV virions have an increased infectivity compared rAAV virions produced by an otherwise comparable the population of cells capable of producing rAAV virions upon transient transfection at the same MOI. In some embodiments, the rAAV virions have at least 1%, 5%, 10%, 15%, 20%, 30%, 40%, or 50% greater infectivity compared rAAV virions produced by an otherwise comparable the population of cells capable of producing rAAV virions upon transient transfection at the same MOI. In some embodiments, the rAAV virions have at least 50%, 60%, 70%, 80%, 90%, 95%, 97%, 98%, 99%, or 100% infectivity as compared to AAV virions produced by a cell having wildtype AAV at the same MOI. In some embodiments, the rAAV virions have at least 50%, 60%, 70%, 80%, 90%, 95%, 97%, 98%, 99%, or 100% infectivity as compared to AAV virions at the same MOI. In some embodiments, the AAV virions are wildtype AAV virions produced by a cell having wildtype AAV. In some embodiments, the MOI is $1\times10^1$, $1\times10^2$, $2\times10^3$, $5\times10^4$, or $1\times10^5$ vg/target cell. In some embodiments, the MOI is selected from a range of $1\times10^1$ to $1\times10^5$ vg/target cell. In some embodiments, the cell is conditionally capable of producing rAAV virions having a F:E ratio of no less than 0.5, 0.6, 0.7, 0.8, 0.9, 0.95, 0.97, or 0.99. In some embodiments, the rAAV virions have a F:E ratio of no less than 0.5, 0.6, 0.7, 0.8, 0.9, 0.95, 0.97, or 0.99 prior to purification. In some embodiments, the cell is conditionally capable of producing rAAV virions having a encapsidation ratio of no less than 0.5, 0.6, 0.7, 0.8, 0.9, 0.95, 0.97, or 0.99. In some embodiments, the rAAV virions have a payload encapsidation ratio of no less than 0.5, 0.6, 0.7, 0.8, 0.9, 0.95, 0.97, or 0.99 prior to purification. In some embodiments, the rAAV virions have a concentration of greater than $1\times10^{11}$ or no less than $5\times10^{11}$, $1\times10^{12}$, $5\times10^{12}$, $1\times10^{13}$ or $1\times10^{14}$ viral genomes per milliliter prior to purification. In some embodiments, the cell is capable of producing rAAV virions comprising the payload nucleic acid sequence at a titer of greater than $1\times10^{11}$ or no less than $5\times10^{11}$, $1\times10^{12}$, $5\times10^{12}$, $1\times10^{13}$ or $1\times10^{14}$ viral genomes per milliliter. In some embodiments, the cell is capable of producing rAAV virions comprising the payload nucleic acid sequence at a concentration of greater than $1\times10^{11}$ or no less than $5\times10^{11}$, $1\times10^{12}$, $5\times10^{12}$, $1\times10^{13}$ or $1\times10^{14}$ viral genomes per milliliter prior to purification. In some embodiments, this cell is expanded to produce a population of cells. In some embodiments, the population of cells produces a stable cell line as described herein. In some embodiments, this cell is passaged at least three times. In some embodiments, this cell can be passaged up to 60 times. In some embodiments, this cell can be passage more than 60 times. In some embodiments, the cell maintains the ability to be conditionally induced after each passage.

6.6. POPULATION OF CELLS COMPRISING A CONSTRUCT

In some embodiments, a population of cells comprise one construct (Rep/Cap construct, inducible helper construct, and the payload construct). In some embodiments, the one construct is stably integrated into the genomes of the cells. In some embodiments, a plurality of the one construct is stably integrated into the genomes of the cells. In some embodiments, a population of cells comprises two constructs (any combination of Rep/Cap construct, inducible helper construct, and the payload construct). In some embodiments, the two constructs are stably integrated into the genomes of the cells. In some embodiments, the two constructs are separately stably integrated into the genomes of the cells. In some embodiments, a plurality of the two constructs are stably integrated into the genome of the cell. In some embodiments, a plurality of the two constructs are separately stably integrated into the genomes of the cells. In some embodiments, a cell comprises the Rep/Cap construct and the inducible helper construct. In some embodiments, the cell, the inducible helper construct comprises a VA RNA construct as described herein. In some embodiments, cell further comprises the VA RNA construct as described herein. In some embodiments, the VA RNA construct is stably integrated into the genomes of the cells.

In some embodiments, a population of cells comprises all three constructs (Rep/Cap construct, inducible helper construct, and the payload construct). In some embodiments, the three constructs are stably integrated into the genomes of the cells. In some embodiments, the three constructs are separately stably integrated into the genomes of the cells. In some embodiments, a plurality of the three constructs are stably integrated into the genomes of the cells. In some embodiments, a plurality of the three constructs are separately stably integrated into the genomes of the cells. In some embodiments, the inducible helper construct comprises a VA RNA construct as described herein. In some embodiments, a population of cells further comprises the VA RNA construct separately integrated into the genomes of the cells.

A population of cells capable of producing rAAV virions having a encapsidation ratio of no less than 0.5, 0.6, 0.7, 0.8, 0.9, 0.95, 0.97, or 0.99. In some embodiments, the population of cells are a population of mammalian cells or a population of insect cells. In some embodiments, the population of cells are a population of HEK293 cells, HeLa cells, CHO cells, or SF9 cells. In some embodiments, the cell expresses E1A protein and E1B protein. In some embodiments, the population of cells further comprises a payload construct. In some embodiments, the payload construct comprises a sequence of a payload flanked by ITR sequences. In some embodiments, expression of the payload is driven by a constitutive promoter. In some embodiments, the constitutive promoter and sequence of the payload are flanked by ITR sequences. In some embodiments, the payload comprises a polynucleotide sequence encoding a gene. In some embodiments, the gene codes for a selectable marker or detectable marker. In some embodiments, the gene codes for a therapeutic polypeptide or transgene. In some embodiments, the payload comprises a polynucleotide sequence coding for a therapeutic polynucleotide. In some embodiments, the therapeutic polynucleotide is a tRNA suppressor or a guide RNA. In some embodiments, the guide RNA is a polyribonucleotide capable of binding to a protein. In some embodiments, the protein is nuclease. In some embodiments, the protein is a Cas protein, an ADAR protein, or an ADAT protein. In some embodiments, the Cas protein is catalytically inactive Cas protein. In some embodiments, the payload construct is stably integrated into the genome of the cell. In some embodiments, the payload construct further comprises a sequence coding for a selectable marker or detectable marker outside of the ITR sequences. In some embodiments, the selectable marker is an antibiotic resistance protein. In some embodiments, the selectable marker outside of the ITR sequences is a split intein linked to an N-terminus of the antibiotic resistance protein or split intein linked to a C-terminus of the antibiotic resistance protein. In some embodiments, the selectable marker outside of the ITR sequences is a leucine zipper linked to an N-terminus of the antibiotic resistance protein or leucine zipper linked to a C-terminus of the antibiotic resistance protein. In some embodiments, the antibiotic resistance protein is for puromycin resistance or blasticidin resistance. In some embodiments, the payload construct is in a plasmid. In some embodiments, the payload construct is in a bacterial artificial chromosome or yeast artificial chromosome. In some embodiments, the payload construct is stably integrated into the genomes of the population of cells. A population of cells produced by expanding a cell of any one of claims X. In some embodiments, expanding comprises passaging the cell at least three times. In some embodiments, a cell of the population of cells is capable of conditionally producing recombinant AAV (rAAV) virions upon addition of at least two triggering agents. In some embodiments, the cell is capable of conditionally producing rAAV virions upon addition of at least two triggering agents. In some embodiments, the at least two triggering agents comprise doxycycline and tamoxifen. In some embodiments, the at least two triggering agents induce the expression and translocation of an excising element to the nucleus. In some embodiments, a cell of the population of cells is capable of conditionally producing rAAV virions upon addition of an excising element. In some embodiments, the excising element is a recombinase. In some embodiments, the excising element is a site-specific recombinase. In some embodiments, the excising element is a Cre polypeptide or a flippase polypeptide. In some embodiments, the excising element is hormone regulated. In some embodiments, the population of cells are conditionally capable of producing rAAV virions within which are packaged an expressible polynucleotide encoding a payload; and wherein a population of virions produced by the population of cells are more homogenous than a population of virions produced by an otherwise comparable the population of cells capable of producing rAAV virions upon transient transfection. In some embodiments, the population of virions produced by the population of cells has a ratio of viral genomes to transduction units of about 500:1 to 1:1. In some embodiments, the population of virions produced by the population of cells has a ratio of vector genomes to infectious unit of 100:1. In some embodiments, production of virions is inducible upon addition of a triggering agent. In some embodiments, production of virions is inducible upon addition of at least two triggering agents. In some embodiments, the population of cells is conditionally capable of producing rAAV virions having a payload encapsidation ratio of no less than 0.5, 0.6, 0.7, 0.8, 0.9, 0.95, 0.97, or 0.99. In some embodiments, the rAAV virions have a payload encapsidation ratio of no less than 0.5, 0.6, 0.7, 0.8, 0.9, 0.95, 0.97, or 0.99 prior to purification. In some embodiments, the population of cells are capable of reaching a viable cell density of no less than $1\times10^6$, $2\times10^6$, $5\times10^6$, or $1\times10^7$ cells per milliliter. In some embodiments, the rAAV virions have a concentration of greater than $1\times10^{11}$ or no less than $5\times10^{11}$, $1\times10^{12}$, $5\times10^{12}$, $1\times10^{13}$ or $1\times10^{14}$ viral genomes per milliliter prior to purification. In some embodiments, the population of cells is capable of producing rAAV virions comprising the payload nucleic acid sequence at a titer of greater than $1\times10^{11}$ or no less than $5\times10^{11}$, $1\times10^{12}$, $5\times10^{12}$, $1\times10^{13}$ or $1\times10^{14}$ viral genomes per milliliter. In some embodiments, the population of cells is capable of producing rAAV virions comprising the payload nucleic acid sequence at a concentration of greater than $1\times10^{11}$ or no less than $5\times10^{11}$, $1\times10^{12}$, $5\times10^{12}$, $1\times10^{13}$ or $1\times10^{14}$ viral genomes per milliliter prior to purification. In some embodiments, the rAAV virions comprising the capsid protein and the payload nucleic acid sequence have an infectivity of no less than 50%, 60%, 70%, 80%, 90%, 95%, or 99% at an MOI of $1\times10^5$ vg/target cell or less. In some embodiments, the rAAV virions have an increased infectivity compared rAAV virions produced by an otherwise comparable the population of cells capable of producing rAAV virions upon transient transfection at the same MOI. In some embodiments, the rAAV virions have at least 1%, 5%, 10%, 15%, 20%, 30%, 40%, or 50% greater infectivity compared rAAV virions produced by an otherwise comparable the population of cells capable of producing rAAV virions upon transient transfection at the same MOI. In some embodiments, the rAAV virions have at least 50%, 60%, 70%, 80%, 90%, 95%, 97%, 98%, 99%, or 100% infectivity as compared AAV virions AAV at the same MOI. In some embodiments, the AAV virions are wildtype AAV virions produced by a cell having wildtype AAV. In some embodiments, the MOI is $1\times10^1$, $1\times10^2$, $2\times10^3$, $5\times10^4$, or $1\times10^5$ vg/target cell. In some embodiments, the MOI is selected from a range of $1\times10^1$ to $1\times10^5$ vg/target cell. In some embodiments, the cell is conditionally capable of producing rAAV virions having a F:E ratio of no less than 0.5, 0.6, 0.7, 0.8, 0.9, 0.95, 0.97, or 0.99. In some embodiments, the rAAV virions have a F:E ratio of no less than 0.5, 0.6, 0.7, 0.8, 0.9, 0.95, 0.97, or 0.99 prior to purification. In some embodiments, the cells are cryopreserved. In some embodiments, the cells are comprised within a vial, flask, syringe, or other suitable cell-storage container. In some embodiments, production of rAAV virions is inducible in the absence of a plasmid. In some embodiments, expression of AAV Rep and Cap proteins is inducible in the absence of a plasmid. In some embodiments, expression of the at least one or more helper proteins is inducible in the absence of a plasmid. In some embodiments, production of rAAV virions is inducible in the absence of a transfection agent. In some embodiments, expression of AAV Rep and Cap proteins is inducible in the absence of a transfection agent. In some embodiments, expression of the at least one or more helper proteins is inducible in the absence of a transfection agent. A second population of cell produced by expanding the population of cells of any one of the preceding embodiments. The second population of cells, wherein expanding the population of cells comprises passaging the population of cells at least three times. In some embodiments expanding the population of cells comprises passaging the population of cells from 3 to 60 times. In some embodiments, expanding the population of cells comprises passaging the population of cells at least 4, 5, 6, 7, 8, 9, 10, 15, 20, 25, 30, 35, 40, 45, 50, 55, or 60 times.

In some embodiments, an rAAV virion produced by the methods described herein have increased infectivity compared to a comparable rAAV virion produced by transient transfection methods.

6.7. STABLE CELL LINE

In some embodiments, a stable cell line is produced from the cell as described herein. In some embodiments, a stable cell line is produced from the population of cells as described herein. In some embodiments, the stable cell line is derived from a single cell and is monclonal. The stable cell line can be a mammalian stable cell line. The stable cell line can be produced by expanding or passaging a cell as described herein.

In some embodiments, a stable cell line comprises the population of cells as disclosed herein. In some embodiments, the population of cells are derived from a single cell. In some embodiments, at least 70%, 80%, 90%, 95%, 99%, or 100% of the cells of the stable cell line are the population of cells as disclosed herein. A stable cell line derived from a cell as disclosed herein. A stable cell line expanded from a cell as disclosed herein. In some embodiments, the stable cell line is a mammalian stable cell line. In some embodiments, expression of one or more helper proteins is inducible in the absence of a plasmid. In some embodiments, expression of one or more helper proteins is inducible in the absence of a transfection agent. In some embodiments, expression of AAV Rep and Cap proteins is inducible in the absence of a plasmid. In some embodiments, expression of AAV Rep and Cap proteins is inducible in the absence of a transfection agent. In some embodiments, production of rAAV virions is inducible in the absence of a plasmid. In some embodiments, production of rAAV virions is inducible in the absence of a transfection agent. In some embodiments, the stable cell line is capable of producing rAAV virions comprising the payload nucleic acid sequence at a concentration of greater than $1\times10^{11}$ or no less than $5\times10^{11}$, $1\times10^{12}$, $5\times10^{12}$, $1\times10^{13}$ or $1\times10^{14}$ viral genomes per milliliter. In some embodiments, the stable cell line is capable of producing rAAV virions comprising the payload nucleic acid sequence at a concentration of greater than $1\times10^{11}$ or no less than $5\times10^{11}$, $1\times10^{12}$, $5\times10^{12}$, $1\times10^{13}$ or $1\times10^{14}$ viral genomes per milliliter prior to purification. In some embodiments, the stable cell line is conditionally capable of producing rAAV virions having a encapsidation ratio of no less than 0.5, 0.6, 0.7, 0.8, 0.9, 0.95, 0.97, or 0.99. In some embodiments, the rAAV virions have a encapsidation ratio of no less than 0.5, 0.6, 0.7, 0.8, 0.9, 0.95, 0.97, or 0.99 prior to purification. In some embodiments, the rAAV virions comprising the capsid protein and the payload nucleic acid sequence have an infectivity of no less than 50%, 60%, 70%, 80%, 90%, 95%, or 99%. at an MOI of $1\times10^{5}$ vg/target cell or less. In some embodiments, the rAAV virions have an increased infectivity compared rAAV virions produced by an otherwise comparable the population of cells capable of producing rAAV virions upon transient transfection at the same MOI. In some embodiments, the rAAV virions have at least 1%, 5%, 10%, 15%, 20%, 30%, 40%, or 50% greater infectivity compared rAAV virions produced by an otherwise comparable the population of cells capable of producing rAAV virions upon transient transfection at the same MOI. In some embodiments, the rAAV virions have at least 50%, 60%, 70%, 80%, 90%, 95%, 97%, 98%, 99%, or 100% infectivity as compared to AAV virions produced by a cell having wildtype AAV at the same MOI. In some embodiments, the rAAV virions have at least 50%, 60%, 70%, 80%, 90%, 95%, 97%, 98%, 99%, or 100% infectivity as compared to AAV virions at the same MOI. In some embodiments, the AAV virions are wildtype AAV virions produced by a cell having wildtype AAV. In some embodiments, the MOI is $1\times10^{1}$, $1\times10^{2}$, $2\times10^{3}$, $5\times10^{4}$, or $1\times10^{5}$ vg/target cell. In some embodiments, the MOI is selected from a range of $1\times10^{1}$ to $1\times10^{5}$ vg/target cell. In some embodiments, the stable cell line is conditionally capable of producing rAAV virions having a F:E ratio of no less than 0.5, 0.6, 0.7, 0.8, 0.9, 0.95, 0.97, or 0.99. In some embodiments, the rAAV virions have a F:E ratio of no less than 0.5, 0.6, 0.7, 0.8, 0.9, 0.95, 0.97, or 0.99 prior to purification. In some embodiments, at least one cell of the stable cell line is cryopreserved. In some embodiments, at least one cell of the stable cell line is in a vial, flask, syringe, or other suitable cell-storage container.

In some embodiments, a method of producing a stable cell line comprises contacting a cell to the Rep/Cap construct as described herein, and expanding the cell to produce the stable cell line. In some embodiments, a method of producing a stable cell line comprises contacting a cell to the inducible helper construct as described herein, and expanding the cell to produce the stable cell line. In some embodiments, a method of producing a stable cell line comprises contacting a cell to the Rep/Cap construct, contacting the cell to the inducible helper construct as described herein, and expanding the cell to produce the stable cell line. In some embodiments, a method of producing a stable cell line comprises contacting a cell to the Rep/Cap construct, contacting the cell to inducible helper construct as described herein, contacting the cell to the payload construct, and expanding the cell to produce the stable cell line.

6.8. CELL CULTURES AND BIOREACTORS

In some embodiments, a cell, population of cells, or stable cell line as disclosed herein is in a cell culture. In some embodiments, a cell culture composition comprising: a) suspension-adapted cells, b) serum-free cell culture media, and c) recombinant AAV (rAAV) virions, wherein the cell culture composition is free of herpes simplex virus, baculovirus, and adenovirus, and wherein the cell culture composition is free of plasmid and transfection agent. In some embodiments, the cell culture composition is free of polyethylenimine (PEI). In some embodiments, the suspension-adapted cells are suspension-adapted mammalian cells. In some embodiments, the suspension-adapted cells are suspension-adapted HEK293 cells or derivatives thereof. In some embodiments, the suspension-adapted mammalian cells are cells from the stable cell line of as disclosed herein, the population of cells as disclosed herein, or comprise a cell as disclosed herein. In some embodiments, the cell culture composition has a prepurification rAAV concentration of no less than $1\times10^{14}$, $2\times10^{14}$, $3\times10^{14}$, $4\times10^{14}$, $5\times10^{14}$, $6\times10^{14}$, $7\times10^{14}$, $8\times10^{14}$, $9\times10^{14}$, $1\times10^{15}$, or $5\times10^{15}$ viral genome (vg)/L. In some embodiments, the cell culture composition has a prepurification rAAV encapsidation ratio of no less than 0.5, 0.6, 0.7, 0.8, 0.9, 0.95, 0.97, or 0.99.

In some embodiments, rAAV virion from the stable cells as disclosed herein is produced in a bioreactor. In some embodiments, a bioreactor comprises the stable cell line as disclosed herein. In some embodiments, a bioreactor comprising the population of cells of as disclosed herein. In some embodiments, a bioreactor comprising the cell as disclosed herein. In some embodiments, a bioreactor contains the cell culture as disclosed herein. In some embodiments, the bioreactor is a 1 L bioreactor. In some embodiments, the 1 L bioreactor has a total rAAV yield of greater than $1\times10^{14}$ viral genome (vg). In some embodiments, the bioreactor is a 5 L bioreactor. In some embodiments, the 5 L bioreactor has a total rAAV yield of greater than $5\times10^{14}$ viral genome (vg). In some embodiments, the bioreactor is a 50 L bioreactor. In some embodiments, the 50 L bioreactor has a total rAAV yield of greater than $5\times10^{15}$ viral genome (vg). In some embodiments, the bioreactor is a 100 L bioreactor. In some embodiments, the 100 L bioreactor has a total rAAV yield of greater than $1\times10^{16}$ viral genome (vg). In some embodiments, the bioreactor is a 500 L bioreactor. In some embodiments, the 500 L bioreactor has a total rAAV yield of greater than $5\times10^{16}$ viral genome (vg). In some embodiments, the bioreactor is a 2000 L bioreactor. In some embodiments, the 2000 L bioreactor has a total rAAV yield of greater than $2\times10^{17}$ viral genome (vg). In some embodiments, a bioreactor comprises a plurality of rAAV virions having a concentration of greater than $1\times10^{14}$, $2\times10^{14}$, $3\times10^{14}$, $4\times10^{14}$, $5\times10^{14}$, $6\times10^{14}$ $7\times10^{14}$, $8\times10^{14}$, $9\times10^{14}$, $1\times10^{15}$, or $5\times10^{15}$ viral genome (vg)/L. In some embodiments, a bioreactor comprises a plurality of rAAV virions having a prepurification concentration of greater than $1\times10^{14}$, $2\times10^{14}$, $3\times10^{14}$, $4\times10^{14}$, $5\times10^{14}$, $6\times10^{14}$ $7\times10^{14}$, $8\times10^{14}$, $9\times10^{14}$, $1\times10^{15}$, or $5\times10^{15}$ viral genome (vg)/L. In some embodiments, the bioreactor is a 1 L, 5 L, 50 L, 100 L, 500 L, or 2000 L bioreactor. In some embodiments, the bioreactor is a single use bioreactor.

6.9. COMPOSITIONS OF RAAV

In some embodiments, the cell, population of cells, or stable cell line as disclosed herein is induced (as disclosed herein, e.g., after administration of a first and a second triggering agent in a bioreactor) to produce a plurality of rAAV virons. In some embodiments, a composition comprises a plurality of rAAV virions encapsidating a viral genome, wherein the composition has a prepurification concentration of greater than $1\times10^{11}$ or no less than $5\times10^{11}$, $1\times10^{12}$, $5\times10^{12}$, $1\times10^{13}$ or $1\times10^{14}$ viral genomes per milliliter. In some embodiments, a composition comprises a plurality of rAAV virions encapsidating a viral genome, wherein the composition has a prepurification encapsidation ratio of no less than 0.5, 0.6, 0.7, 0.8, 0.9, 0.95, 0.97, or 0.99. In some embodiments, a composition comprises a plurality of rAAV virions encapsidating a viral genome, wherein the composition has a prepurification F:E ratio of no less than 0.5, 0.6, 0.7, 0.8, 0.9, 0.95, 0.97, or 0.99. In some embodiments, a composition comprises an rAAV virion encapsidating a viral genome, wherein the composition has an infectivity of no less than 50%, 60%, 70%, 80%, 90%, 95%, or 99% at an MOI of $1\times10^{5}$ vg/target cell or less. In some embodiments, the rAAV virion has an increased infectivity compared an rAAV virion produced by an otherwise comparable cell capable of producing rAAV virions upon transient transfection at the same MOI. In some embodiments, the rAAV virion has at least 1%, 5%, 10%, 15%, 20%, 30%, 40%, or 50% greater infectivity compared an rAAV virion produced by an otherwise comparable cell capable of producing rAAV virions upon transient transfection at the same MOI. In some embodiments, the rAAV virion has at least 50%, 60%, 70%, 80%, 90%, 95%, 97%, 98%, 99%, or 100% infectivity as compared an AAV virion produced by a cell having wildtype AAV at the same MOI. In some embodiments, the rAAV virion has at least 50%, 60%, 70%, 80%, 90%, 95%, 97%, 98%, 99%, or 100% infectivity as compared an AAV virion produced by a cell having wildtype AAV at the same MOI. In some embodiments, the compositions further comprises a plurality of the rAAV virion. In some embodiments, the plurality of rAAV virions have a prepurification concentration of greater than $1\times10^{11}$ or no less than $5\times10^{11}$, $1\times10^{12}$, $5\times10^{12}$, $1\times10^{13}$ or $1\times10^{14}$ viral genomes per milliliter. In some embodiments, the plurality of rAAV virions have a prepurification encapsidation ratio of no less than 0.5, 0.6, 0.7, 0.8, 0.9, 0.95, 0.97, or 0.99. In some embodiments, the plurality of rAAV virions have a prepurification F:E ratio of no less than 0.5, 0.6, 0.7, 0.8, 0.9, 0.95, 0.97, or 0.99. In some embodiments, the plurality of rAAV virions have an infectivity of no less than 50%, 60%, 70%, 80%, 90%, 95%, or 99%. In some embodiments, the plurality of rAAV virions have an increased infectivity compared a plurality of rAAV virions produced by an otherwise comparable the population of cells capable of producing rAAV virions upon transient transfection at the same MOI. In some embodiments, the plurality of rAAV virions have at least 1%, 5%, 10%, 15%, 20%, 30%, 40%, or 50% greater infectivity compared a plurality of rAAV virions produced by an otherwise comparable the population of cells capable of producing rAAV virions upon transient transfection at the same MOI. In some embodiments, the plurality of rAAV virions have at least 50%, 60%, 70%, 80%, 90%, 95%, 97%, 98%, 99%, or 100% infectivity as compared a plurality of AAV virions produced by a cell having wildtype AAV at the same MOI. In some embodiments, the MOI is $1\times10^{1}$, $1\times10^{2}$, $2\times10^{3}$, $5\times10^{4}$, or $1\times10^{5}$ vg/target cell. In some embodiments, the MOI is selected from a range of $1\times10^{1}$ to $1\times10^{5}$ vg/target cell. In some embodiments, the viral genome comprises a sequence coding for a payload. In some embodiments, expression of the sequence of the payload is driven by a constitutive promoter. In some embodiments, the sequence of the payload comprises a polynucleotide sequence coding for a gene. In some embodiments, the gene codes for a selectable marker or detectable marker. In some embodiments, the gene codes for a therapeutic polypeptide or transgene. In some embodiments, the sequence of the payload comprises a polynucleotide sequence coding for a therapeutic polynucleotide. In some embodiments, the therapeutic polynucleotide is a tRNA suppressor or a guide RNA. In some embodiments, the guide RNA is a polyribonucleotide capable of binding to a protein. In some embodiments, the protein is nuclease. In some embodiments, the protein is a Cas protein, an ADAR protein, or an ADAT protein. In some embodiments, the Cas protein is catalytically inactive Cas protein. In some embodiments, the rAAV virion comprises a Cap polypeptide. In some embodiments, the Cap polypeptide is an AAV capsid protein. In some embodiments, the AAV capsid protein is VP1, VP2, or VP3. In some embodiments, a serotype of the AAV capsid protein is selected from the group consisting of AAV1, AAV2, AAV3, AAV4, AAV5, AAV6, AAV7, AAV8, AAV9, AAV 10, AAV11, AAV 12, AAV13, AAV 14, AAV 15 and AAV 16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, AAV.HSC16, and AAVhu68.

In some embodiments, rAAV virions as disclosed herein are in a first composition and a second composition. In some embodiments, the first composition and the second composition have an encapsidation ratio that varies by no more than 20%, 10%, 5%, 4%, 3%, 2%, or 1%. In some embodiments, the first composition and the second composition have an F:E ratio that varies by no more than 20%, 10%, 5%, 4%, 3%, 2%, or 1%. In some embodiments, the first composition and the second composition have a concentration of viral genomes per milliliter that varies by no more than 20%, 10%, 5%, 4%, 3%, 2%, or 1%. In some embodiments, the first composition and the second composition have an infectivity that varies by no more than 20%, 10%, 5%, 4%, 3%, 2%, or 1%. In some embodiments, the first composition is a first dose and the second composition is a second dose. In some embodiments, the first composition is produced at least 1, 2, 3, 4, 5, 6, or 7 days before the second composition is produced. In some embodiments, a plurality of rAAV virions of the first composition is produced at least 1, 2, 3, 4, 5, 6, or 7 days before a plurality of rAAV virions of the second composition is produced. In some embodiments, the first composition is produced at least 1, 2, 3, 4, 5, 6, 7, 8, 9, 10, 11, or 12 months before the second composition is produced. In some embodiments, a plurality of rAAV virions of the first composition is produced at least 1, 2, 3, 4, 5, 6, 7, 8, 9, 10, 11, or 12 months before the second composition is produced. In some embodiments, the first composition is produced at least 1, 2, 3, 4, 5, 6, 7, 8, 9, 10, 11, or 12 years before the second composition is produced. In some embodiments, a plurality of rAAV virions of the first composition is produced at least 1, 2, 3, 4, 5, 6, 7, 8, 9, 10, 11, or 12 years before the second composition is produced. In some embodiments, the first composition is produced from a plurality of virions from a first bioreactor and the second composition is produced from a plurality of virions from a second bioreactor. In some embodiments, a third composition or more compositions are produced from the rAAV as disclosed herein. In some embodiments, the first composition, the second composition, and the third composition have an encapsidation ratio that varies by no more than 20%, 10%, 5%, 4%, 3%, 2%, or 1%. In some embodiments, the first composition, the second composition, and the third composition have an F:E ratio that varies by no more than 20%, 10%, 5%, 4%, 3%, 2%, or 1%. In some embodiments, the first composition, the second composition, and the third composition have a concentration of viral genomes per milliliter that varies by no more than 20%, 10%, 5%, 4%, 3%, 2%, or 1%. In some embodiments, the first composition, the second composition, and the third composition have an infectivity that varies by no more than 20%, 10%, 5%, 4%, 3%, 2%, or 1%. In some embodiments, the third composition is a third dose. In some embodiments, the third composition is produced at least 1, 2, 3, 4, 5, 6, or 7 days after the second composition is produced. In some embodiments, a plurality of rAAV virions of the third composition is produced at least 1, 2, 3, 4, 5, 6, or 7 days after a plurality of rAAV virions of the second composition is produced. In some embodiments, the third composition is produced at least 1, 2, 3, 4, 5, 6, 7, 8, 9, 10, 11, or 12 months after the second composition is produced. In some embodiments, a plurality of rAAV virions of the third composition is produced at least 1, 2, 3, 4, 5, 6, 7, 8, 9, 10, 11, or 12 months after the second composition is produced. In some embodiments, the third composition is produced at least 1, 2, 3, 4, 5, 6, 7, 8, 9, 10, 11, or 12 years after the second composition is produced. In some embodiments, a plurality of rAAV virions of the third composition is produced at least 1, 2, 3, 4, 5, 6, 7, 8, 9, 10, 11, or 12 years after the second composition is produced. In some embodiments, the third composition is produced from a plurality of virions from a third bioreactor.

6.10. PHARMACEUTICAL COMPOSITIONS

In some embodiments, a pharmaceutical composition comprises the plurality of rAAV virions of claims as disclosed herein and a pharmaceutically acceptable carrier. In some embodiment, a plurality of pharmaceutical doses each independently comprise the plurality of rAAV virions of claims as disclosed herein and a pharmaceutically acceptable carrier. In some embodiments, the encapsidation ratio has a difference of not more than 20%, 10%, 5%, 4%, 3%, 2%, or 1% between a first dose and a second dose of a plurality of pharmaceutical doses. In some embodiments, the F:E ratio has a difference of not more than 20%, 10%, 5%, 4%, 3%, 2%, or 1% between a first dose and a second dose of a plurality of pharmaceutical doses. In some embodiments, the concentration of viral genomes has a difference of not more than 20%, 10%, 5%, 4%, 3%, 2%, or 1% between a first dose and a second dose of a plurality of pharmaceutical doses. In some embodiments, the concentration of vector genomes has a difference of not more than 20%, 10%, 5%, 4%, 3%, 2%, or 1% between a first dose and a second dose of a plurality of pharmaceutical doses. In some embodiments, the rAAV virion infectivity has a difference of not more than 20%, 10%, 5%, 4%, 3%, 2%, or 1% between a first dose and a second dose of a plurality of pharmaceutical doses.

6.11. METHOD OF PRODUCING RAAV

In another aspect, methods of producing rAAV from stable cell lines is provided. The method comprises adding the at least first and at least second expression triggering agents to the medium within which the stable mammalian cell lines described above are being cultured.

In particular embodiments, the first expression triggering agent is a tetracycline. In specific embodiments, the first expression triggering agent is Dox. In particular embodiments, the second expression triggering agent is an estrogen agonist or selective estrogen receptor modulator. In specific embodiments, the second expression triggering agent is tamoxifen.

In some embodiments, the method further comprises a later step of culturing the stable mammalian cell line only in the presence of the first expression triggering agent.

In some embodiments, the method further comprises purifying rAAV from culture medium. In some embodiments, the purifying comprises performing chromatographic purification. In some embodiments, the chromatographic purification comprises using a positively charged anion exchange resin, using a negatively charged anion exchange resin, using cation exchange chromatography, using affinity chromatography, using size exclusion chromatography, or a combination thereof. In some embodiments, the chromatographic purification comprises using column chromatographic fractionation.

In some embodiments, rAAV is produced in a bioreactor as described herein.

In some embodiments, a method of inducing the cell as described herein, the population of cells as described herein, or the stable cell line as described herein comprises administering a first triggering agent to the cell, population of cells, or the stable cell line, thereby inducing expression of the Rep polypeptides, Cap polypeptides, and one or more adenoviral helper proteins, in the cell, population of cells, or stable cell line. In some embodiments, the first triggering agent binds to an activator or a repressor. In some embodiments, activation of an inducible promoter is induced. In some embodiments, the activated inducible promoter transcribes a recombinase. In some embodiments, the first triggering agent is tetracycline or cumate. In some embodiments, the tetracycline is doxycycline. The methods described herein further comprise culturing the cell, population of cells, or the stable cell line with a second triggering agent. In some embodiments, the second triggering agent is an estrogen receptor ligand. In some embodiments, the second triggering agent is a selective estrogen receptor modulator (SERM). In some embodiments, the second triggering agent is tamoxifen. In some embodiments, the second triggering agent binds to the recombinase. In some embodiments, the second triggering agent induces the recombinase to translocate to a nucleus of the cell, of a cell of the population of cells, of a cell of the stable cell lines.

In some embodiments, a method of producing rAAV virion comprises administering a first triggering agent to the cell, population of cells, or the stable cell line, administering a second triggering agent to the cell, population of cells, or stable cell line, thereby producing the rAAV virion in the cell, population of cells, or stable cell line. In some embodiments, the first triggering agent binds to an activator or a repressor. In some embodiments, activation of an inducible promoter is induced. In some embodiments, the activated inducible promoter transcribes a recombinase. In some embodiments, the first triggering agent is tetracycline or cumate. In some embodiments, the tetracycline is doxycycline. The method of any one of claims X, further comprising culturing the cell, population of cells, or the stable cell line with a second triggering agent. In some embodiments, the second triggering agent is an estrogen receptor ligand. In some embodiments, the second triggering agent is a selective estrogen receptor modulator (SERM). In some embodiments, the second triggering agent is tamoxifen. In some embodiments, the second triggering agent binds to the recombinase. In some embodiments, the second triggering agent induces the recombinase to translocate to a nucleus of the cell, of a cell of the population of cells, of a cell of the stable cell lines. In some embodiments, the recombinase cuts at recombinase sites. In some embodiments, the at least one adenoviral help proteins, the Rep polypeptides, and the Cap polypeptides are expressed. In some embodiments, the Rep polypeptides and the Cap polypeptides assemble into an rAAV virion. In some embodiments, the rAAV virion encapsidates a sequence of a payload. In some embodiments, the cell, population of cells, or stable cell line do not express cytotoxic levels of Rep polypeptides prior to administration of both the first triggering agent and the second triggering agent. In some embodiments, the cell, population of cells, or stable cell line do not express cytotoxic levels of Cap polypeptides prior to administration of both the first triggering agent and the second triggering agent. In some embodiments, the cell, population of cells, or stable cell line do not express cytostatic levels of Rep polypeptides prior to administration of both the first triggering agent and the second triggering agent. In some embodiments, the average concentration of Rep polypeptides within the cell, population of cells, or stable cell line is less than the amount prior to administration of both of the first triggering agent and second triggering agent. In some embodiments, expression of Rep polypeptides and Cap polypeptides becomes constitutive after administration of both the first triggering agent and the second triggering agent. The method of any one of claims X, further comprising performing at least a portion of the method in a bioreactor. In some embodiments, the bioreactor is not less than 20 L, 30, L, 40 L, 50 L, 100 L, 250 L, 300 L, or 500 L.

In some embodiments, the method further comprises producing the rAAV virions in a plurality of batches. In some embodiments, the method further comprises producing the rAAV virions having a difference in the encapsidation ratio of not more than 20%, 15%, 10%, 5%, 3%, 2%, or 1% between a first batch and a second batch. In some embodiments, the method further comprises producing the rAAV virions having a difference in the F:E ratio of not more than 20%, 15%, 10%, 5%, 3%, 2%, or 1% between a first batch and a second batch. In some embodiments, the method further comprises producing the rAAV virions having a difference in the concentration of viral genomes of not more than 20%, 15%, 10%, 5%, 3%, 2%, or 1% between a first batch and a second batch. In some embodiments, the method further comprises producing the rAAV virions having a difference in the concentration of vector genomes of not more than 20%, 15%, 10%, 5%, 3%, 2%, or 1% between a first batch and a second batch. In some embodiments, the method further comprises producing the rAAV virions having a difference in infectivity of not more than 20%, 15%, 10%, 5%, 3%, 2%, or 1% between a first batch and a second batch. In some embodiments, the method further comprises performing the method according to good manufacturing practice (GMP) standards. In some embodiments, the method further comprises performing the method in a GMP facility. In some embodiments, the method further comprises comprising culturing the cells in a culture medium and collecting a portion of the plurality of rAAV virions from the culture medium. In some embodiments, the method further comprises purifying at least some of the plurality of rAAV virions collected from the culture medium to obtain a purified rAAV population. In some embodiments, the purifying comprises performing chromatographic purification. In some embodiments, the chromatographic purification comprises using a positively charged anion exchange resin, using a negatively charged anion exchange resin, using cation exchange chromatography, using affinity chromatography, using size exclusion chromatography, or a combination thereof. In some embodiments, the chromatographic purification comprises using column chromatographic fractionation.

In some embodiments, an rAAV virion is made by the methods as disclosed herein. In some embodiments, a composition comprising a plurality of rAAV virions is made by the methods as disclosed herein. In some embodiments, the rAAV virion produced as disclosed herein has increased infectivity compared to an rAAV virion produced by comparable transient transfection methods.

6.12. METHODS OF TREATMENT

In another aspect, methods of treatment are provided. In various embodiments, the method comprises administering rAAV produced by the process described above to a patient in need thereof. In some embodiments, the administering is by intravenous administration, intramuscular administration, intrathecal administration, intracisternal administration, or administration via brain surgery.

In some embodiments, a method of treating a condition or disorder comprises administering a therapeutically effective amount of the pharmaceutical composition of as disclosed herein to a patient in need thereof. In some embodiments, the disorder is a monogenic disorder. In some embodiments, the treatment results in at least one undesirable side effect and wherein the undesirable side effect is reduced relative to administering a daily dose that deviates more than 50%, 40%, 30%, 30%, 15%, 10%, 5%, or 2% from an expected dose. In some embodiments, the administering is by injection. In some embodiments, the injection is an infusion. In some embodiments, the daily dose is administered to the patient once. In some embodiments, the daily dose is administered to the patient two or more times. In some embodiments, the treatment results in at least one undesirable side effect and wherein the undesirable side effect is reduced relative to administering a plurality of rAAV virions produced from a triple transfection method.

In some embodiments, the methods reduce the immunogenicity of a dose of rAAV having a predetermined number of viral genomes (VG) as compared to the same rAAV VG dose prepared by transient triple transfection. In some embodiments, the immunogenicity is measured by the titer or concentration of neutralizing antibodies in a subject. In some embodiments, a concentration of rAAV virion neutralizing antibody in the blood serum of the patient is reduced relative to a concentration of rAAV virion neutralizing antibody in the blood serum of a patient after administering a plurality of rAAV virions produced from a triple transfection method. In some embodiments, the concentration of rAAV virion neutralizing antibodies is measured by an ELISA assay.

In some embodiments, the methods reduce the number or intensity of adverse effects caused by administering a dose of rAAV having a predetermined number of viral genomes (VG) as compared to the same rAAV VG dose prepared by transient triple transfection. In some embodiments, the methods reduce the number of adverse effects. In some embodiments, the predetermined number of VG in a dose is no greater than $3\times10^{14}$ vg/kg. In some embodiments, the predetermined number of VG in a dose is no greater than $1\times10^{14}$ vg/kg. In some embodiments, the predetermined number of VG in a dose is no greater than $5\times10^{13}$ vg/kg. In some embodiments, the methods reduce the intensity of adverse effects. In some embodiments, the methods reduce both the number and the intensity of adverse events.

In some embodiments, a method of administering a dose of rAAV virions having a predetermined number of viral genomes (VG) to a subject with reduced number or intensity of adverse effects as compared to administration of the same rAAV VG dose prepared by transient triple transfection comprises: administering a dose of rAAV produced in the cell as disclosed herein, the population of cells disclosed herein, or the stable cells as disclosed herein. In some embodiments, the adverse effect is selected from the group consisting of: liver dysfunction, liver inflammation, gastrointestinal infection, vomiting, bacterial infection, sepsis, increases in troponin levels, decreases in red blood cell counts, decreases in platelet counts, activation of the complement immune system response, acute kidney injury, cardio-pulmonary insufficiency, and death. In some embodiments, the adverse effect is an increase in serum levels of one or more proinflammatory cytokines. In some embodiments, the adverse effect is an increase in serum levels of one or more of interferon gamma (IFNγ), interleukin 1β (IL-1β), and interleukin 6 (IL-6).

In another aspects, a method of repeatedly administering a dose of rAAV to a subject in need thereof are provided. In some embodiments, the method comprises administering a first dose of rAAV produced by the cell lines and the processes described above, and then administering at least a second dose of rAAV produced by the cell lines and the processes described above. In some embodiments, the method comprises administering a first dose and a second dose of rAAV produced by the cell lines and the processes described above. In some embodiments, the method comprises administering a first dose, a second dose, and a third dose of rAAV produced by the cell lines and the processes described above. In some embodiments, the method comprises administering more than three doses of rAAV produced by the cell lines and the processes described above. In some embodiments, the first dose of rAAV and the at lease second dose of rAAV are administered through the same route of administration. In some embodiments, the first dose of rAAV and the at least second dose of rAAV are administered through different routes of administration. In some embodiments, the route of administration is intravenous administration, intramuscular administration, intrathecal administration, intracisternal administration, or administration via brain surgery.

In some embodiments, a method of treating a condition or disorder comprises administering a first therapeutically effective amount of the pharmaceutical composition of as disclosed herein having a predetermined number of viral genomes to a patient in need thereof and a second therapeutically effective amount of the pharmaceutical composition as disclosed herein having the predetermined number of viral genomes to the patient in need thereof. In some embodiments, the first therapeutically effective amount and the second therapeutically effective amount vary by no more than 1%, 5%, 10%, or 15%.

6.13. KITS

In another aspect, components or embodiments described herein for the system are provided in a kit. For example, any of the plasmids, as well as the mammalian cells, related buffers, media, triggering agents, or other components related to cell culture and virion production can be provided, with optional components frozen and packaged as a kit, alone or along with separate containers of any of the other agents and optional instructions for use. In some embodiments, the kit may comprise culture vessels, vials, tubes, or the like.

The methods for producing and packaging recombinant vectors in desired AAV capsids to produce the rAAVs are not meant to be limiting and other suitable methods will be apparent to the skilled artisan.

6.14. ASPECTS OF THE INVENTION

The below items disclose various aspects of the invention. Each of the aspects described below can be combined with other aspects and embodiments disclosed elsewhere herein, including the claims, where the combinations are clearly compatible. For example, described herein are three exemplary constructs, referred to as "construct 1", "construct 2" and "construct 3". The disclosure provided herein describes these constructs in specific and general detail.

In the following aspects, the first recombinant nucleic acid sequence encoding an AAV Rep protein and an AAV Cap protein corresponds to the specific and general disclosures of "construct 1" provided herein. It is intended that any aspects described below relating to the first recombinant nucleic acid may be combined with any of the specific and general disclosures of "construct 1" provided herein where the combinations are clearly compatible.

In the following aspects, the second recombinant nucleic acid sequence encoding one or more adenoviral helper proteins corresponds to the specific and general disclosures of "construct 2" provided herein. It is intended that any aspects described below relating to the second recombinant nucleic acid may be combined with any of the specific and general disclosures of "construct 2" provided herein where the combinations are clearly compatible.

In the following aspects, the third recombinant nucleic acid sequence encoding a payload corresponds to the specific and general disclosures of "construct 3" provided herein. It is intended that any aspects described below relating to the third recombinant nucleic acid may be combined with any of the specific and general disclosures of "construct 3" provided herein where the combinations are clearly compatible.

It is intended that any aspects and disclosures provided herein relating to the first, second and third recombinant nucleic acids, and relating to the specific and general disclosures of constructs 1, 2 and 3 may be combined together where the combinations are clearly compatible.

1. A composition comprising one or more nucleic acids which together comprise:
   (i) a first recombinant nucleic acid sequence encoding an AAV Rep protein and an AAV Cap protein; and
   (ii) a second recombinant nucleic acid sequence encoding one or more adenoviral helper proteins,
   wherein when the one or more nucleic acids are integrated into the nuclear genome of a mammalian cell the AAV Rep protein, the AAV Cap protein, and/or the one or more adenoviral helper proteins are conditionally expressible and thereby conditionally produce recombinant AAV (rAAV) virions.
2. The composition of aspect 1, wherein the conditional expression of the AAV Rep protein, the AAV Cap protein, and/or the one or more adenoviral helper proteins is controlled by one or more excisable elements present in the one or more nucleic acids.
3. The composition of aspect 2, wherein the one or more excisable elements comprise one or more introns and/or one or more exons.
4. The composition of any one of the preceding aspects, wherein the first recombinant nucleic acid sequence encodes:
   a) a first part of the AAV Rep protein coding sequence;
   b) the second part of the AAV Rep protein coding sequence;
   c) an excisable element between the first part of the AAV Rep protein coding sequence and the second part of the AAV Rep protein coding sequence; and
   d) the AAV Cap protein coding sequence.
5. The composition of any one of aspects 2-4, wherein the excisable element comprises:
   a) a first spacer segment comprising a first intron,
   b) a second spacer segment comprising a coding sequence of a detectable marker; and
   c) a third spacer segment comprising a second intron, and wherein the first spacer segment and the third spacer segment are capable of being excised by endogenous cellular machinery of a mammalian cell.
6. The composition of aspect 5, wherein the excisable element comprises from 5' to 3':
   a) a 5' splice site;
   b) a first spacer segment comprising a first intron;
   c) a second spacer segment comprising:
      i) a first lox sequence;
      ii) a 3' splice site;
      iii) an exon;
      iv) a stop signaling sequence; and
      v) a second lox sequence; and
   d) a third spacer segment comprising a second intron.
7. The composition of aspect 5 or aspect 6, wherein the detectable marker is a luminescent marker, a radiolabel or a fluorescent marker, optionally a fluorescent marker which is GFP, EGFP, RFP, CFP, BFP, YFP, or mCherry.
8. The composition of any one of aspects 5-7, wherein:
   a) the first spacer segment comprises a nucleic acid sequence having at least 80% identity to SEQ ID NO: 1; and/or
   b) the second spacer segment comprises a nucleic acid sequence having at least 80% identity to SEQ ID NO: 2; and/or
   c) the third spacer segment comprises a nucleic acid sequence having at least 80% identity to SEQ ID NO: 3.
9. The composition of any one of aspects 5-8, wherein the second spacer segment is capable of being excised by a Cre polypeptide.
10. The composition of any one of the preceding aspects, wherein the expression of the AAV Rep protein and/or the AAV Cap protein is driven by native promoters.
11. The composition of aspect 10, wherein:
   a) the native promoters P5 and/or P19 drive the expression of the AAV Rep protein; and/or
   b) the native promoter P40 drives the expression of the AAV Cap protein.
12. The composition of any one of the preceding aspects, wherein the second recombinant nucleic acid sequence encodes:
   a) one or more adenoviral helper proteins;
   b) a conditionally self-excising element; and
   c) an inducible promoter;

wherein, once integrated into the nuclear genome of a mammalian cell, the expression of the one or more adenoviral helper protein coding sequences is under the control of the conditionally self-excising element and the inducible promoter.

13. The composition of aspect 12, wherein the one or more adenoviral helper proteins comprise E2A and E4.
14. The composition of aspect 12 or aspect 13, wherein the self-excising element comprises a sequence which encodes a polypeptide, preferably a recombinase polypeptide, more preferably a Cre polypeptide.
15. The composition of aspect 14, wherein the polypeptide encoded by the self-excising element is conditionally expressible and is expressed only in the presence of a triggering agent.
16. The composition of aspect 15, wherein the triggering agent is a hormone, preferably tamoxifen.
17. The composition of any one of aspects 9-16, wherein the inducible promoter is a Tet inducible promoter.
18. The composition of any one of aspects 12-17, wherein the second recombinant nucleic acid sequence further comprises a sequence that encodes a Tet responsive activator protein, preferably Tet-on-3G.
19. The composition of aspect 18, wherein the expression of Tet-On 3G activator protein is driven by an E1 alpha promoter.
20. The composition of any one of aspects 12-19, wherein the second recombinant nucleic acid sequence comprises a sequence with at least 80% homology, at least 90% homology, at least 95% homology, at least 99% homology, or a sequence identical to SEQ ID NO: 11 or SEQ ID NO: 12.

21. The composition of any one of the preceding aspects, wherein the one or more nucleic acids further comprises a nucleic acid sequence encoding a VA RNA sequence.

22. The composition of aspect 21, wherein the expression of VA RNA is constitutive.

23. The composition of aspect 21, wherein the expression of VA RNA is inducible.

24. The composition of aspect 23, wherein the VA RNA sequence comprises one or more mutations in the VA RNA internal promoter, preferably G16A and G60A.

25. The composition of any one of aspects 21 to 24, wherein the expression of VA RNA is driven by a E1 alpha promoter or a U6 promoter.

26. The composition of aspect 25, wherein the expression of VA RNA is driven by a U6 promoter, and wherein the U6 promoter comprises:

a) a first part of a U6 promoter sequence, b) a stuffer sequence, and c) a second part of a U6 promoter sequence, and wherein the stuffer sequence is capable of being excised by a Cre polypeptide.

27. The composition of any one of the preceding aspects, wherein a serotype of the AAV Cap protein is selected from the group consisting of AAV1, AAV2, AAV3, AAV4, AAV5, AAV6, AAV7, AAV8, AAV9, AAV 10, AAV11, AAV 12, AAV13, AAV 14, AAV 15 and AAV 16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, AAV.HSC16 and AAVhu68.

28. The composition of aspect 27, wherein the serotype is an AAV5 and the Cap protein that comprises one or more mutations or insertions.

29. The composition of any one of the preceding aspects, wherein the one or more recombinant nucleic acids further encode a third recombinant nucleic acid sequence encoding a payload, optionally wherein the payload is:

(a) a polynucleotide payload, such as a guide RNA for RNA editing, a guide RNA for Cas protein-directed DNA editing, a tRNA suppressor, or a gene for replacement gene therapy; or (b) a protein such as a therapeutic antibody or a vaccine immunogen.

30. The composition of any one of the preceding aspects, wherein the one or more recombinant nucleic acids comprise one or more mammalian cell selection elements.

31. The composition of aspect 30, wherein one or more of the mammalian cell selection elements encodes an antibiotic resistance gene, optionally a blasticidin resistance gene.

32. The composition of aspect 30 or aspect 31, wherein one or more of the mammalian cell selection elements is an auxotrophic selection element which encodes an active protein, preferably wherein the protein is DHFR.

33. The composition of aspect 30 or aspect 31, wherein one or more of the mammalian cell selection elements is a first auxotrophic selection element which encodes an inactive protein that requires expression of a second inactive protein from a second auxotrophic selection coding sequence for activity.

34. The composition of aspect 33, wherein the first auxotrophic selection coding sequence encodes for DHFR Z-Cter (SEQ ID NO: 5) activity, and/or wherein the second auxotrophic selection coding sequence encodes for DHFR Z-Nter (SEQ ID NO: 4).

35. The composition of any one of aspects 1-30, wherein:

a) the first recombinant nucleic acid comprises a mammalian cell selection element which encodes an antibiotic resistance gene, preferably a blasticidin resistance gene; and b)

i. the second recombinant nucleic acid comprises a first auxotrophic selection element which encodes an inactive protein that requires expression of a second inactive protein from a second auxotrophic selection coding sequence for activity; and ii. the third recombinant nucleic acid comprises the second auxotrophic selection element which encodes the inactive protein that requires expression of the first inactive protein from the first auxotrophic selection coding sequence for activity; and wherein in (i) or (ii) the first auxotrophic selection coding sequence encodes for DHFR Z-Cter (SEQ ID NO: 5), and the second auxotrophic selection coding sequence encodes for DHFR Z-Nter (SEQ ID NO: 4) or wherein the first auxotrophic selection coding sequence encodes for DHFR Z-Nter (SEQ ID NO: 4), and the second auxotrophic selection coding sequence encodes for DHFR Z-Cter (SEQ ID NO: 5).

36. A mammalian cell wherein the nuclear genome of the cell comprises a plurality of integrated recombinant nucleic acid constructs which together encode for a recombinant adeno-associated virus (rAAV) virions, wherein the rAAV virions can be conditionally expressed from the cell.

37. The mammalian cell of aspect 36, wherein the plurality of integrated recombinant nucleic acid constructs comprise the one or more recombinant nucleic acids of any one of aspects 1-35, wherein the AAV Rep protein, the AAV Cap protein and/or the adenoviral helper proteins can be conditionally expressed from the cell.

38. The mammalian cell of aspect 36 or aspect 37, wherein the cell line expresses adenoviral helper proteins E1A and E1B.

39. A mammalian cell of any one of aspects 36-38, wherein the plurality of integrated recombinant nucleic acid constructs comprise:

(i) a first integrated polynucleotide construct comprising:

a) a first part of an AAV Rep protein coding sequence;

b) a second part of an AAV Rep protein coding sequence;

c) an excisable element between the first part of the AAV Rep protein coding sequence and the second part of the AAV Rep protein coding sequence, wherein the excisable element comprises:

i) a first spacer segment comprising a first intron;

ii) a second spacer segment comprising a coding sequence of a detectable marker, wherein the second spacer segment is capable of being excised by a Cre polypeptide; and iii) a third spacer segment comprising a second intron; and d) an AAV Cap protein coding sequence;

wherein the AAV Rep protein and the AAV Cap protein is driven by the native promoters P5, P19, and P40;

(ii) a second integrated polynucleotide construct comprising a) a conditionally expressible VA RNA coding sequence which comprises a mutation in the VA RNA internal promoter, wherein the expression of VA RNA is driven by a U6 promoter, optionally wherein the VA RNA sequence comprises G16A and G60A mutations;

b) one or more adenoviral helper protein coding sequences, wherein the adenoviral helper proteins are E2A and E4;

c) a conditionally self-excising element which encodes a Cre polypeptide which translocates to the nucleus and self-excises only in the presence of a triggering agent which is tamoxifen, and c) an inducible promoter which is a Tet inducible promoter, and wherein the expression of the one or more adenoviral helper protein coding sequences is under the control of the conditionally self-excising element and the inducible promoter; and (iii) a third integrated polynucleotide construct comprising encodes for the payload, wherein the payload is a polynucleotide payload.

40. A method of producing a population of rAAV virions comprising:

(a) culturing the cell of any one of aspects 36-39 in conditions which allow for the expression of the rAAV virions; and (b) isolating the rAAV virions from the cell culture.

41. The method of aspect 40, wherein the prepurification rAAV viral genome (VG) to viral particle (VG:VP) ratio of greater than 0.5.

42. The method of aspect 40 or aspect 41, wherein the population of rAAV virions produced by the cell has:

(a) a ratio of viral genomes to transduction units of about 500 to 1 to 1 to 1; and/or (b) a ratio of vector genomes to infectious unit of 100:1.

43. A method of preparing the cell of any one of aspects 36-39 comprising:

i) providing a mammalian cell and the one or more nucleic acids of any one of aspects 1-35; and ii) integrating the one or more nucleic acids of any one of aspects 1-35 into the nuclear genome of the mammalian cell.

44. A population of rAAV virions produced by the method of any one of aspects 40-42.

45. The population of rAAV virions of aspect 44, wherein the infectivity of the virions is at least 50% at an MOI of 10000.

46. A pharmaceutical composition comprising a population of rAAV virions according to aspect 44 or aspect 45, for use as a medicament, optionally for use in treating a monogenic disorder.

47. The population of rAAV virions according to aspect 44 or aspect 45 or the pharmaceutical composition according to aspect 46, for use as a medicament, optionally for use in treating a monogenic disorder.

48. The population of rAAV virions or the pharmaceutical composition for use according to aspect 47, wherein the rAAV virions are administered at a dosage of $4\times10^{14}$ or lower.

6.15. NUMBERED EMBODIMENTS #1

[1] A polynucleotide construct coding for:

a) a first part of a Rep polypeptide;

b) a second part of a Rep polypeptide;

c) a Cap polypeptide; and d) an excisable element positioned between the first part of the Rep polypeptide and the second part of the Rep polypeptide.

[2] The polynucleotide construct of embodiment 1, wherein the Rep polypeptide is a wildtype Rep polypeptide.

[3] The polynucleotide construct of any one of embodiments 1-2, wherein the Cap polypeptide is a wildtype Cap polypeptide.

[4] The polynucleotide construct of any one of embodiments 1-3, wherein the excisable element comprises an intron.

[5] The polynucleotide construct of any one of embodiments 1-4, wherein the excisable element comprises an exon.

[6] The polynucleotide construct of any one of embodiments 1-5, wherein the excisable element comprises an intron and an exon.

[7] The polynucleotide construct of any one of embodiments 1-6, wherein the excisable element comprises from 5' to 3':

a) a 5' splice site;

b) a first spacer segment comprising a first intron;

c) a second spacer segment comprising:

i) a first lox sequence;

ii) a 3' splice site;

iii) an exon;

iv) a stop signaling sequence; and v) a second lox sequence; and d) a third spacer segment comprising a second intron.

wherein the first spacer segment and the third spacer segment are capable of being excised by endogenous cellular machinery.

[8] The polynucleotide construct of embodiment 7, wherein the first and second lox sequences are loxP sequences.

[9] The polynucleotide construct of embodiment 7, wherein the second spacer segment is excisable by a Cre polypeptide.

[10] The polynucleotide construct of embodiment 9, wherein the Cre polypeptide is encoded by a second polynucleotide construct.

[11] The polynucleotide construct of any one of embodiments 1-10, wherein expression of the Rep polypeptide and the Cap polypeptide are driven by native promoters.

[12] The polynucleotide construct of embodiment 11, wherein the native promoters comprise P5, P19, and P40. [13] The polynucleotide construct of any one of embodiments 7-12, wherein the exon encodes a detectable marker.

[14] The polynucleotide construct of embodiment 13, wherein the detectable marker comprises a luminescent marker, a fluorescent marker, or radiolabel.

[15] The polynucleotide construct of embodiment 14, wherein the fluorescent marker is GFP, EGFP, RFP, CFP, BFP, YFP, or mCherry.

[16] A stable mammalian cell line, wherein cells of the cell line are suitable for conditional production of rAAV virions and wherein expression of a Rep polypeptide and a Cap polypeptide is inducible in the absence of a transfection agent.

[17] A stable mammalian cell line, wherein cells of the cell line are suitable for conditional production of rAAV virions and wherein expression of a Rep polypeptide and aCap polypeptide is inducible in the absence of a plasmid.

[18] The stable mammalian cell line of any one of embodiments 16-17, wherein the cells comprise the polynucleotide construct of any one of embodiments 1-15 stably integrated into the cell's nuclear genome.

[19] The stable mammalian cell line of embodiment 18, wherein the cell line is monoclonal.

[20] The stable mammalian cell line of any one of embodiments 16-19, wherein cells of the cell line are capable of conditionally producing recombinant AAV (rAAV) virions upon addition of an excising element.

[21] A stable mammalian cell line, wherein a cell of the cell line comprises a stably integrated polynucleotide construct of any one of embodiments 1-14 and wherein the cell is capable of conditionally producing recombinant AAV (rAAV) virions upon addition of an excising element.

[22] The stable mammalian cell line of embodiment 21, wherein the excising element is a Cre polypeptide or a flippase.

[23] The stable mammalian cell line of embodiment 22, wherein the Cre polypeptide is encoded by a second polynucleotide construct.

[24] The stable mammalian cell line of any one of embodiments 21-23, wherein localization of the excising element is hormone regulated.

[25] The stable mammalian cell line of any one of embodiments 16-24, wherein the cell is capable of conditionally producing rAAV virions upon addition of at least two triggering agents.

[26] The stable mammalian cell line of embodiment 25, wherein the at least two triggering agents comprise doxycycline and tamoxifen.

[27] A polynucleotide construct coding for a mutated VA RNA, wherein the mutated VA RNA gene sequence comprises at least two mutations in an internal promoter.

[28] The polynucleotide construct of embodiment 27, wherein expression of VA RNA is driven by a U6 promoter.

[29] The polynucleotide construct of any one of embodiments 27-28, comprising upstream of the mutated VA RNA gene sequence, from 5' to 3':

a) a first part of a U6 promoter sequence;
b) a first lox sequence;
c) a stuffer sequence;
d) a second lox sequence;
e) a second part of a U6 promoter sequence.

[30] The polynucleotide construct of embodiment 29, wherein the stuffer sequence is excisable by a Cre polypeptide.

[31] The polynucleotide construct of embodiment 30, wherein the Cre polypeptide is exogenously provided.

[32] The polynucleotide construct of embodiment 30, wherein the Cre polypeptide is encoded by the polynucleotide construct.

[33] The polynucleotide construct of embodiment 30, wherein the stuffer sequence is positioned between the first part of the U6 promoter sequence and the second part of the U6 promoter sequence.

[34] A polynucleotide construct coding for:

a) one or more helper proteins;
b) a self-excising element upstream of the one or more helper proteins; and
c) an inducible promoter upstream of the self-excising element.

[35] The polynucleotide construct of embodiment 34, wherein expression of the self-excising element is driven by a Tet-On-3G system.

[36] The polynucleotide construct of any one of embodiments 34-35, wherein the polynucleotide construct further comprises a sequence that encodes a Tet responsive activator protein (Tet-on-3G).

[37] The polynucleotide construct of embodiment 36, wherein expression of Tet-On 3G activator protein is driven by an E1alpha promoter.

[38] The polynucleotide construct of embodiment 37, wherein, in the presence of a first triggering agent, Tet-On 3G activator protein binds to the inducible promoter.

[39] The polynucleotide construct of embodiment 38, wherein the inducible promoter is a Tet inducible promoter.

[40] The polynucleotide construct of any one of embodiments 34-39, wherein the self-excising element is a sequence encoding a Cre polypeptide.

[41] The polynucleotide construct of any one of embodiments 34-40, wherein expression of the self-excising element is hormone regulated.

[42] The polynucleotide construct of embodiment 41, wherein the self-excising element is expressed and self-excises only in the presence of a hormone.

[43] The polynucleotide construct of embodiment 42, wherein the hormone is tamoxifen.

[44] The polynucleotide construct of any one of embodiments 34-43, wherein the one or more adenoviral helper proteins comprise E2 and E4.

[45] The polynucleotide construct of any one of embodiments 34-44, wherein the polynucleotide construct further encodes a VA RNA.

[46] The polynucleotide construct of embodiment 45, wherein expression of VA RNA is driven by a E1 alpha promoter.

[47] The polynucleotide construct of any one of embodiments 45-46, wherein the VA RNA is the mutated VA RNA of any one of embodiments 27-33.

[48] The polynucleotide construct of embodiment 37 or 46, wherein the E1 alpha promoter comprises at least one mutation.

[49] A stable mammalian cell line, wherein cells of the cell line are suitable for conditional production of rAAV virions and wherein expression of one or more helper proteins is inducible in the absence of a transfection agent.

[50] A stable mammalian cell line, wherein cells of the cell line are suitable for conditional production of rAAV virions and wherein expression of one or more helper proteins is inducible in the absence of a plasmid.

[51] A stable mammalian cell line, wherein at least 70%, at least 80%, at least 90%, at least 95%, or 100% of the cells comprise the polynucleotide construct of any one of embodiments 27-48 stably integrated into the cell's nuclear genome.

[52] The stable mammalian cell line of any one of embodiments 49-51, wherein cells of the cell line comprise the polynucleotide construct of any one of embodiments 27-48 stably integrated into the cell's nuclear genome.

[53] The stable mammalian cell line of any one of embodiments 49-52, wherein a cell of the cell line is capable of conditionally producing recombinant AAV (rAAV) virions upon addition of at least two triggering agents.

[54] A stable mammalian cell line, wherein a cell of the cell line comprises a stably integrated polynucleotide construct of any one of embodiments 27-48, and wherein the cell is capable of conditionally producing recombinant AAV (rAAV) virions upon addition of at least two triggering agents.

[55] The stable mammalian cell line of any one of embodiments 53-54, wherein the at least two triggering agents comprise doxycycline and tamoxifen.

[56] A stable mammalian cell line, wherein:

the cells are capable of conditionally producing recombinant AAV (rAAV) virions within which are packaged an expressible polynucleotide encoding a payload; and wherein a population of virions produced by the stable cell are more homogenous than a population of virions produced by an otherwise comparable mammalian cell producing rAAV virions upon transient transfection.

[57] The stable mammalian cell line of embodiment 56, wherein the population of virions produced by the stable cell has a ratio of viral genomes to transduction units of about 500:1 to 1:1.

[58] The stable mammalian cell line of embodiment 57, wherein the population of virions produced by the stable cell has a ratio of vector genomes to infectious unit of 100:1.

[59] The stable mammalian cell line of any one of embodiments 56-58, wherein production of virions is inducible upon addition of a triggering agent.

[60] The stable mammalian cell line of any one of embodiments 56-58, wherein production of virions is inducible upon addition of at least two triggering agents.

[61] The stable mammalian cell line of any one of embodiments 56-60, wherein a cell of the cell line comprises a stably integrated polynucleotide construct of any one of embodiments 1-15, 27-33, and 34-48.

[62] A stable mammalian cell line, wherein:

the cells are capable of conditionally producing recombinant AAV (rAAV) virions within which are packaged an expressible polynucleotide encoding a payload; and production of virions is inducible upon addition of a triggering agent.

[63] A stable mammalian cell line, wherein:

the cells are capable of conditionally producing recombinant AAV (rAAV) virions within which are packaged an expressible polynucleotide encoding a payload; and production of virions is not conditioned on the presence of a plasmid within the cell.

[64] The stable cell line of any of the previous embodiments, wherein expression of AAV Rep and Cap proteins is conditional.

[65] The stable cell line of any of the previous embodiments, wherein expression of AAV Rep and Cap proteins is conditioned on addition of at least a first expression triggering agent to the cell culture medium.

[66] The stable cell line of embodiment 65, wherein expression of AAV Rep and Cap proteins is conditioned on addition of a first expression triggering agent and a second expression triggering agent to the cell culture medium.

[67] The stable cell line of embodiment 66, wherein the cells do not express cytotoxic levels of Rep protein prior to addition of both the first expression and second triggering agents to the cell culture medium.

[68] The stable cell line of embodiment 67, wherein the cells do not express cytostatic levels of Rep protein prior to addition of both the first and second expression triggering agents to the cell culture medium.

[69] The stable cell line of embodiment 67 or 68, wherein the average concentration of Rep protein within the cells is less than the amount prior to addition of both of the first and second expression triggering agents to the cell culture medium.

[70] The stable cell line of any one of embodiments 65-69, wherein expression of Rep and Cap proteins becomes constitutive after addition of all of the at least first expression triggering agents to the cell culture medium.

[71] The stable cell line of any of embodiments 65-70, wherein expression of adenoviral helper proteins is conditional.

[72] The stable cell line of embodiment 71, wherein expression of adenoviral helper proteins is conditioned on addition of at least a third expression triggering agent to the cell culture medium.

[73] The stable cell line of embodiment 72, wherein the third expression triggering agent is the same as the first expression triggering agent.

[74] The stable cell line of embodiment 72 or 73, wherein expression of adenoviral helper proteins is conditioned on addition of a third expression triggering agent and a fourth expression triggering agent to the cell culture medium.

[75] The stable cell line of embodiment 74, wherein the fourth is the same as the second expression triggering agent.

[76] The stable cell line of embodiment 72 or 74, wherein the third expression triggering agent is the same as the first expression triggering agent and the fourth expression triggering agent is the same as the second expression triggering agent.

[77] The stable cell line of embodiment 76, wherein continued expression of adenoviral helper proteins following triggering of expression by contact of the cell with the at least third expression triggering agent requires the presence of only the third expression triggering agent in the cell culture medium.

[78] The stable cell line of embodiment 77, wherein the third triggering agent is the same as the first triggering agent.

[79] The stable cell line of any one of embodiments 71-78, wherein the adenoviral helper proteins include E2A and E4.

[80] The stable cell line of any one of embodiments 65-75, wherein the first expression triggering agent is a tetracycline.

[81] The stable cell line of embodiment 80, wherein the tetracycline is doxycycline.

[82] The stable cell line of any one of embodiments 74-76, wherein the fourth expression triggering agent is an estrogen receptor ligand.

[83] The stable cell line of embodiment 82, wherein the estrogen receptor ligand is a selective estrogen receptor modulator (SERM).

[84] The stable cell line of embodiment 83, wherein the estrogen receptor ligand is tamoxifen.

[85] The stable cell line of any of the previous embodiments, wherein expression of the therapeutic polynucleotide is conditioned on addition of at least a fifth expression triggering agent to the cell culture medium.

[86] The stable cell line of any one of embodiments 62-84, wherein expression of the therapeutic polynucleotide is not conditioned on addition of an expression triggering agent to the cell culture medium.

[87] The stable cell line of any of embodiments 62-86, wherein expression of Rep and Cap proteins, adenoviral helper proteins, and the expressible polynucleotide encoding a payload becomes constitutive after addition of only one expression triggering agent to the cell culture medium.

[88] The stable cell line of any of embodiments 62-87, wherein expression of Rep and Cap proteins and the adenoviral helper proteins becomes constitutive after addition of only one expression triggering agent to the cell culture medium.

[89] The stable cell line of embodiment 87 or 88, wherein the one expression triggering agent is the first expression triggering agent.

[90] The stable cell line of embodiment 89, wherein the first expression triggering agent is a tetracycline.

[91] The stable cell line of embodiment 90, wherein the first expression triggering agent is doxycycline.

[92] The stable cell line of any one of embodiments 62-91, wherein the nuclear genome of the cell comprises a plurality of integrated synthetic nucleic acid constructs.

[93] 93. The stable cell line of embodiment 92, wherein the nuclear genome of the cell comprises at least two integrated synthetic constructs.

[94] The stable cell line of embodiment 93, wherein the nuclear genome of the cell comprises at least three integrated synthetic constructs.

[95] The stable cell line of any one of embodiments 92-94, wherein each of the plurality of synthetic nucleic acid constructs is separately integrated into the nuclear genome of the cell.

[96] The stable cell line of any one of embodiments 92-94, wherein only a single non-auxotrophic selection is required to maintain all of the plurality of synthetic nucleic acid constructs stably within the nuclear genome of the cells.

[97] The stable mammalian cell line of any one of embodiments 92-96, wherein:

the first integrated synthetic construct comprises conditionally expressible AAV Rep and Cap coding sequences;

the second integrated synthetic construct comprises a conditionally expressible Cre coding sequence and conditionally expressible adenoviral helper protein coding sequences; and the third integrated synthetic construct comprises expressible coding sequences for the expressible polynucleotide encoding a payload.

[98] The stable mammalian cell line of embodiment 97, wherein, prior to the cell being contacted with the first expression triggering agent, the Rep coding sequence of the first integrated construct is interrupted by an intervening spacer.

[99] The stable mammalian cell line of embodiment 98, wherein the intervening spacer comprises, from 5' to 3', a first spacer segment, a second spacer segment, and a third spacer segment.

[100] The stable mammalian cell line of embodiment 99, wherein the first spacer segment comprises a 5' splice site (5'SS) 5' to the first spacer element.

[101] The stable mammalian cell line of any one of embodiments 99-100, wherein the first spacer segment has a nucleic acid sequence having at least 80% identity to SEQ ID NO: 1.

[102] The stable mammalian cell line of embodiments 99-101, wherein the second spacer segment comprises a polynucleotide encoding a detectable protein marker flanked by lox sites.

[103] The stable mammalian cell line of embodiment 102, wherein the detectable protein marker is a fluorescent protein.

[104] The stable mammalian cell line of embodiment 103, wherein the fluorescent protein is a GFP.

[105] The stable mammalian cell line of embodiment 104, wherein the GFP is eGFP.

[106] The stable mammalian cell line of embodiment 99, wherein the second spacer segment further comprises a polyA sequence.

[107] The stable mammalian cell line of embodiment 106, wherein the polyA sequence comprises a rabbit beta globin (RBG) polyA.

[108] The stable mammalian cell line of embodiment 99, wherein the second spacer segment further comprises a first 3' splice site (3'SS) between the first lox site and the polynucleotide encoding the protein marker.

[109] The stable mammalian cell line of any one of embodiments 98-101, wherein the second spacer segment comprises a nucleic acid sequence having at least 80% identity to SEQ ID NO: 2.

[110] The stable mammalian cell line of embodiment 99, wherein the third spacer segment further comprises a second 3' splice site (3'SS).

[111] The stable mammalian cell line of embodiment 110, wherein the second 3' splice site is positioned 3' to the second lox site.

[112] The stable mammalian cell line of any one of embodiments 98-111, wherein the third spacer segment comprises a nucleic acid sequence having at least 80% identity to SEQ ID NO: 3.

[113] The stable mammalian cell line of any one of embodiments 98-112, wherein the Rep coding sequence is operatively linked to an endogenous P5 promoter.

[114] The stable mammalian cell line of any one of embodiments 98-113, wherein the Rep coding sequence is operatively linked to an endogenous P19 promoter.

[115] The stable mammalian cell line of any one of embodiments 98-114, wherein the intervening spacer is inserted into the Rep coding sequence at a position downstream of the P19 promoter.

[116] The stable mammalian cell line of any one of embodiments 98-115, wherein the Rep coding sequence is 5' to the Cap coding sequence.

[117] The stable mammalian cell line of embodiment 116, wherein the Cap coding sequence is operatively linked to an endogenous P40 promoter.

[118] The stable mammalian cell line of any one of embodiments 98-117, wherein the first integrated construct further comprises a first mammalian cell selection element.

[119] The stable mammalian cell line of embodiment 118, wherein the first mammalian cell selection element is an auxotrophic selection element.

[120] The stable mammalian cell line of embodiment 119, wherein the auxotrophic selection element encodes an active protein.

[121] The stable mammalian cell line of embodiment 120, wherein the active protein is DHFR.

[122] The stable mammalian cell line of any one of embodiments 119-121, wherein the auxotrophic selection coding sequence encodes an inactive protein that requires expression of a second auxotrophic selection coding sequence for activity.

[123] The stable mammalian cell line of embodiment 122, wherein the second auxotrophic selection coding sequence codes for DHFR Z-Cter (SEQ ID NO: 5).

[124] The stable mammalian cell line of any one of embodiments 97-123, wherein, prior to the cell being contacted with the first expression triggering agent, the second integrated construct comprises, from 5' to 3', an inducible promoter, a Cre coding sequence, a first polyA sequence, adenoviral helper protein coding sequences, a second polyA sequence, a constitutive promoter, a coding sequence for a protein that is responsive to the first expression triggering agent, and a second mammalian cell selection element.

[125] The stable mammalian cell line of embodiment 124, wherein the Cre coding sequence is operatively linked to the inducible promoter.

[126] The stable mammalian cell line of embodiment 125, wherein the inducible promoter comprises an element responsive to the third expression triggering agent.

[127] The stable mammalian cell line of embodiment 125, wherein the inducible promoter comprises a plurality of tetracycline (Tet) operator elements capable of binding to a Tet responsive activator protein in the presence of a tetracycline.

[128] The stable mammalian cell line of any one of embodiments 124-127, further comprises an element responsive to the fourth expression triggering agent.

[129] The stable mammalian cell line of embodiment 128, wherein the fourth expression triggering agent-responsive element comprises a plurality of hormone-response elements.

[130] The stable mammalian cell line of embodiment 129, wherein the hormone-response elements are estrogen responsive elements (EREs).

[131] The stable mammalian cell line of any one of embodiments 124-130, wherein the third expression triggering element is the same as the first expression triggering element, and the fourth expression triggering element is the same as the second expression triggering element.

[132] The stable mammalian cell line of embodiment 124, wherein the Cre coding sequence is flanked by a first lox site and a second lox site.

[133] The stable mammalian cell line of embodiment 124, wherein the inducible promoter comprises a plurality of Tet operator elements capable of binding to a Tet responsive activator protein in the presence of a first expression triggering agent.

[134] The stable mammalian cell line of any one of embodiments 124-133, wherein the adenoviral helper protein coding sequences encode E2A and E4.

[135] The stable mammalian cell line of any one of embodiments 124-133, wherein the coding sequence for the first expression triggering agent-responsive protein is operatively linked to a CMV promoter.

[136] The stable mammalian cell line of any one of embodiments 124-135, wherein the coding sequence for the first expression triggering agent-responsive protein comprises a coding sequence for the Tet responsive activator protein (Tet-on-3G).

[137] The stable mammalian cell line of any one of embodiments 124-136, wherein the second mammalian cell selection element confers antibiotic resistance.

[138] The stable mammalian cell line of embodiment 137, wherein the antibiotic resistance conferring element is a blasticidin resistance gene.

[139] The stable mammalian cell line of any one of embodiments 98-138, wherein the third integrated synthetic construct comprises coding sequence for the expressible polynucleotide payload, and a third mammalian cell selection element.

[140] The stable mammalian cell line of embodiment 139, wherein the expressible polynucleotide payload encodes a guide RNA for RNA editing.

[141] The stable mammalian cell line of embodiment 139, wherein the expressible polynucleotide payload encodes a guide RNA for Cas protein-directed DNA editing.

[142] The stable mammalian cell line of embodiment 139, wherein the expressible polynucleotide payload encodes a protein.

[143] The stable mammalian cell line of embodiment 139, wherein the expressible polynucleotide payload comprises a gene for replacement gene therapy.

[144] The stable mammalian cell line of embodiment 139, wherein the expressible polynucleotide payload comprises a homology construct for homologous recombination.

[145] The stable mammalian cell line of embodiment 139, wherein the expressible polynucleoide payload encodes a therapeutic antibody.

[146] The stable mammalian cell line of embodiment 139, wherein the expressible payload polynucleotide encodes a vaccine immunogen.

[147] The stable mammalian cell line of any one of embodiments 139-146, wherein the third mammalian cell selection element is an auxotrophic selection element.

[148] The stable mammalian cell line of embodiment 147, wherein the auxotrophic selection element encodes an active protein.

[149] The stable mammalian cell line of embodiment 148, wherein the active protein is DHFR.

[150] The stable mammalian cell line of any one of embodiments 147-149, wherein the auxotrophic selection coding sequence encodes an inactive protein that requires expression of a second auxotrophic selection coding sequence for activity.

[151] The stable mammalian cell line of embodiment 150, wherein the second auxotrophic selection coding sequence codes for DHFR Z-Nter (SEQ ID NO: 4).

[152] The stable mammalian cell line of embodiment 123 or 151, wherein DHFR selection comprises cell growth in media lacking hypoxanthine-thymidine.

[153] The stable mammalian cell line of any one of the proceeding embodiments, wherein the mammalian cell line expresses adenovirus helper proteins E1A and E1B and is a human embryonic kidney (HEK) 293 cell line, a human HeLa cell line, or a Chinese hamster ovary (CHO) cell line.

[154] The stable mammalian cell line of any one of the proceeding embodiments, wherein the mammalian cell line is a HEK293 cell line.

[155] The stable mammalian cell line of any one of the proceeding embodiments, wherein the mammalian cell line expresses adenovirus helper proteins E1A and E1B.

[156] A method of producing rAAV, comprising adding all of the at least first and at least second expression triggering agents to the stable mammalian cell line of any one of embodiments 62-155, in culture.

[157] The method of embodiment 156, further comprising a later step of culturing the stable mammalian cell line only in the presence of the first expression triggering agent.

[158] The method of embodiment 157, further comprising purifying rAAV from culture medium.

[159] An rAAV product made by the process of embodiments 156-158.

[160] A method of treating a condition or disorder, comprising administering a therapeutically effective amount of the rAAV product according to embodiment 159 to a patient in need thereof.

[161] A method of treating a monogenic disorder, comprising administering a therapeutically effective amount of the rAAV product according to embodiment 159 to a patient having a monogenic disorder, wherein expression of the rAAV payload improves the symptoms of the disorder.

[162] The stable cell line of any one of embodiments 27-48, 54-55, and 71, further comprising an inducible VA RNA.

[163] The stable cell line of embodiment 162, wherein the VA RNA is encoded by a construct comprising at least one mutation in a promoter operatively linked to the VA RNA encoding sequence.

[164] 164. The stable cell line of embodiment 163, wherein the at least one mutation is in the A Box promoter region.

[165] 165. The stable cell line of embodiment 163, wherein the at least one mutation is in the B Box promoter region.

[166] 166. The stable cell line of embodiment 164, further comprising at least one mutation in B Box promoter region.

[167] 167. The stable cell line of embodiment 163, wherein the VA RNA is encoded by a construct comprising a deletion of from about 5-10 nucleotides in the promoter region.

[168] 168. The stable cell line of any of embodiments 162-167, wherein the inducible adenoviral RNA is operably linked to a U6 promoter segment.

[169] 169. The stable cell line of embodiment 168, wherein the U6 promoter segment comprises a stuffer or filler sequence that is flanked by a first lox site and a second lox site.

6.16. NUMBERED EMBODIMENTS #2

[1] A packaging cell line, comprising:
- a first integrated polynucleotide construct and
- a second integrated polynucleotide construct, wherein
- the first integrated polynucleotide construct comprises conditionally expressible AAV Rep protein and AAV Cap protein coding sequences;
- the second integrated polynucleotide construct comprises one or more conditionally expressible adenoviral helper protein coding sequences, and optionally a conditionally expressible VA RNA coding sequence; and
- the expression of Rep protein, Cap protein, and the one or more adenoviral helper proteins is inducible in the absence of a plasmid.

[2] The packaging cell line of embodiment 1, wherein the expression of Rep protein, Cap protein, and adenoviral helper proteins is inducible in the absence of a transfection agent.

[3] The packaging cell line of embodiment 1 or 2, wherein the first integrated polynucleotide construct comprises
- a) a first part of an AAV Rep protein coding sequence,
- b) a second part of an AAV Rep protein coding sequence
- c) an excisable element between the first part of the AAV Rep protein coding sequence and the second part of the AAV Rep protein coding sequence, and
- d) an AAV Cap protein coding sequence.

[4] The packaging cell line of embodiment 3, wherein the excisable element comprises
- a) a first spacer segment comprising a first intron,
- b) a second spacer segment comprising a coding sequence of a detectable marker, and
- c) a third spacer segment comprising a second intron, and wherein the first spacer segment and the third spacer segment are capable of being excised by endogenous cellular machinery.

[5] The packaging cell line of embodiment 4, wherein the detectable marker is a fluorescent marker or a luminescent marker.

[6] The packaging cell line of embodiment 4 or 5, wherein the second spacer segment is capable of being excised by a Cre polypeptide.

[7] The packaging cell line of any of the preceding embodiments, wherein the expression of the AAV Rep protein and the AAV Cap protein is driven by native promoters.

[8] The packaging cell line of embodiment 7, wherein the native promoters comprise P5, P19, and P40.

[9] The packaging cell line of any of the preceding embodiments, wherein the second integrated polynucleotide construct comprises
- a) one or more adenoviral helper protein coding sequences,
- b) a conditionally self-excising element, and
- c) an inducible promoter, and wherein the expression of the one or more adenoviral helper protein coding sequences is under the control of the conditionally self-excising element and the inducible promoter.

[10] The packaging cell line of embodiment 9, wherein the one or more adenoviral helper proteins comprise E2A and E4, and optionally, wherein E2A comprises FLAG tag.

[11] The packaging cell line of embodiment 9 or 10, wherein the self-excising element encodes a Cre polypeptide.

[12] The packaging cell line of any one of embodiments 9 to 11, wherein the polypeptide encoded by the self-excising element translocates to nucleus and self-excises only in the presence of a triggering agent.

[13] The packaging cell line of embodiment 12, wherein the triggering agent is tamoxifen.

[14] The packaging cell line of any one of embodiments 9 to 13, wherein the inducible promoter is a Tet inducible promoter.

[15] The packaging cell line of any one of embodiments 9 to 14, wherein the second integrated polynucleotide construct further comprises a sequence that encodes a Tet responsive activator protein (Tet-on-3G).

[16] The packaging cell line of embodiment 15, wherein the expression of Tet-On 3G activator protein is driven by an E1alpha promoter.

[17] The packaging cell line of any of the preceding embodiments, wherein the second integrated polynucleotide construct further comprises a segment encoding a VA RNA sequence.

[18] The packaging cell line of embodiment 17, wherein the expression of VA RNA is constitutive.

[19] The packaging cell line of embodiment 17, wherein the expression of VA RNA is inducible.

[20] The packaging cell line of embodiment 19, wherein the VA RNA sequence comprises a mutation in the VA RNA internal promoter.

[21] The packaging cell line of embodiment 20, wherein the VA RNA sequence comprises G16A and G60A mutations.

[22] The packaging cell line of any one of embodiment 19 to 21, wherein the expression of VA RNA is driven by a U6 promoter.

[23] The packaging cell line of embodiment 22, wherein the U6 promoter comprises a) a first part of a U6 promoter sequence, b) a stuffer sequence, and c) a second part of a U6 promoter sequence, and wherein the stuffer sequence is capable of being excised by a Cre polypeptide.

[24] The packaging cell line of any of the preceding embodiments, wherein the cell line expresses adenoviral helper proteins E1A and E1B.

[25] The packaging cell line of any of the preceding embodiments, wherein the AAV Cap protein is a capsid selected from the group consisting of AAV1, AAV2, AAV3, AAV4, AAV5, AAV6, AAV7, AAV8, AAV9, AAV 10, AAV11, AAV 12, AAV13, AAV 14, AAV 15 and AAV 16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, AAV.HSC16 and AAVhu68.

[26] The packaging cell line of embodiment 25, wherein the AAV Cap protein is an AAV5 capsid protein that comprises one or more mutations or insertions.

[27] A method of producing recombinant AAV (rAAV) virions, the method comprising:

transfecting the packaging cell line of any of the preceding embodiments with a polynucleotide construct that comprises a packageable coding sequence for a payload, and inducing the expression of Rep protein, Cap protein, one or more adenoviral helper proteins, and optionally VA RNA, whereby the packageable coding sequence for a payload is encapsidated in an AAV capsid.

[28] The method of embodiment 27, further comprising the subsequent step of purifying the rAAV virions from cell culture media and/or cell lysate.

[29] A production cell line, comprising:

the packaging cell line of any one of embodiments 1 to 26 and a polynucleotide construct comprising a packageable coding sequence for a payload.

[30] A production cell line, comprising:

a first integrated polynucleotide construct, a second integrated polynucleotide construct, and a third integrated polynucleotide construct, wherein the first integrated polynucleotide construct comprises conditionally expressible AAV Rep protein and AAV Cap protein coding sequences;

the second integrated polynucleotide construct comprises one or more conditionally expressible adenoviral helper protein coding sequences, and optionally a conditionally expressible VA RNA coding sequence;

the third integrated polynucleotide construct comprises a packageable coding sequence for a payload; and the production of recombinant AAV (rAAV) virions containing the coding sequence for the payload is inducible in the absence of a plasmid.

[31] The production cell line of embodiment 30, wherein the production of rAAV virions containing the coding sequence for the payload is inducible in the absence of a transfection agent.

[32] The production cell line of embodiment 30 or 31, wherein the first integrated polynucleotide construct comprises a) a first part of an AAV Rep protein coding sequence, b) a second part of an AAV Rep protein coding sequence, c) an excisable element between the first part of the AAV Rep protein coding sequence and the second part of the AAV Rep protein coding sequence, and d) an AAV Cap protein coding sequence.

[33] The production cell line of embodiment 32, wherein the excisable element comprises a) a first spacer segment comprising a first intron, b) a second spacer segment comprising a coding sequence of a detectable marker, and c) a third spacer segment comprising a second intron, and wherein the first spacer segment and the third spacer segment are capable of being excised by endogenous cellular machinery.

[34] The production cell line of embodiment 33, wherein the detectable marker is a fluorescent marker or a luminescent marker.

[35] The production cell line of embodiment 33 or 34, wherein the second spacer segment is capable of being excised by a Cre polypeptide.

[36] The production cell line of any one of embodiments 30 to 35, wherein the expression of the AAV Rep protein and the AAV Cap protein is driven by native promoters.

[37] The production cell line of embodiment 36, wherein the native promoters comprise P5, P19, and P40.

[38] The production cell line of any one of embodiments 30 to 37, wherein the second integrated polynucleotide construct comprises a) one or more adenoviral helper protein coding sequences, b) a conditionally self-excising element, and c) an inducible promoter, and wherein the expression of the one or more adenoviral helper protein coding sequences is under the control of the conditionally self-excising element and the inducible promoter.

[39] The production cell line of embodiment 38, wherein the one or more adenoviral helper proteins comprise E2A and E4.

[40] The production cell line of embodiment 38 or 39, wherein the self-excising element encode a Cre polypeptide.

[41] The production cell line of any one of embodiments 38 to 40, wherein the polypeptide encoded by the self-excising element translocates to nucleus and self-excises only in the presence of a triggering agent.

[42] The production cell line of embodiment 41, wherein the triggering agent is tamoxifen.

[43] The production cell line of any one of embodiments 38 to 42, wherein the inducible promoter is a Tet inducible promoter.

[44] The production cell line of any one of embodiments 38 to 43, wherein the second integrated polynucleotide construct further comprises a sequence that encodes a Tet responsive activator protein (Tet-on-3G).

[45] The production cell line of embodiment 44, wherein the expression of Tet-On 3G activator protein is driven by an E1alpha promoter.

[46] The production cell line of any one of embodiments 30 to 45, wherein the second integrated polynucleotide construct further comprises a segment encoding a VA RNA sequence.

[47] The production cell line of embodiment 46, wherein the expression of VA RNA is constitutive.

[48] The production cell line of embodiment 46, wherein the expression of VA RNA is inducible.

[49] The production cell line of embodiment 48, wherein the VA RNA sequence comprises a mutation in the VA RNA internal promoter.

[50] The production cell line of embodiment 49, wherein the VA RNA sequence comprises G16A and G60A mutations.

[51] The production cell line of any one of embodiments 48 to 50, wherein the expression of VA RNA is driven by a U6 promoter.

[52] The production cell line of embodiment 51, wherein the U6 promoter comprises a) a first part of a U6 promoter sequence, b) a stuffer sequence, and c) a second part of a U6 promoter sequence, and wherein the stuffer sequence is capable of being excised by a Cre polypeptide.

[53] The production cell line of any one of embodiments 30 to 52, wherein the cell line expresses adenoviral helper proteins E1A and E1B.

[54] The production cell line of any one of embodiments 30 to 53, wherein a serotype of the AAV Cap protein is the serotype selected from the group consisting of AAV1, AAV2, AAV3, AAV4, AAV5, AAV6, AAV7, AAV8, AAV9, AAV 10, AAV11, AAV 12, AAV13, AAV 14, AAV 15 and AAV 16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, AAV.HSC16 and AAVhu68.

[55] The production cell line of embodiment 54, wherein the AAV Cap protein comprises a VP1 capsid protein that comprises one or more mutations or insertions, and optionally, wherein the serotype is AAV5 or AAV9.

[56] A method of producing recombinant AAV (rAAV) virions, the method comprising:

culturing the production cell line of any one of embodiments 29 to 55, and inducing the expression of Rep protein, Cap protein, one or more adenoviral helper proteins, and optionally VA RNA.

[57] The method of embodiment 56, further comprising the subsequent step of purifying the rAAV virions from cell culture media or cell lysate.

[58] A production cell line for producing recombinant AAV (rAAV) virions, wherein the production of rAAV virions is inducible in the absence of a plasmid, and wherein following induction, the production cell line is capable of producing a prepurification rAAV yield of no less than $1\times10^{14}$ viral genome (vg)/L.

[59] The production cell line of embodiment 58, wherein the production of rAAV virions is inducible in the absence of a transfection agent.

[60] The production cell line of embodiment 58 or 59, wherein the production of rAAV virions is inducible in the absence of herpes simplex virus, baculovirus, and adenovirus.

[61] The production cell line of any one of embodiments 58 to 60, wherein following induction, the production cell line is capable of producing a prepurification rAAV full capsid to empty capsid ratio of no less than 0.5.

[62] The production cell line of any one of embodiments 58 to 61, wherein following induction, culturing, and downstream processing, the production cell line is capable of producing a postpurification rAAV yield of no less than $1\times10^{14}$ viral genome (vg)/L without ultracentrifugation.

[63] The production cell line of any one of embodiments 58 to 62, wherein following induction, culturing, and downstream processing, the production cell line is capable of producing a postpurification rAAV full capsid to empty capsid ratio of no less than 0.5 without ultracentrifugation.

[64] The production cell line of any one of embodiments 58 to 63, wherein following induction, the production cell line is capable of producing rAAV virions that are more homogenous than a population of rAAV virions produced by an otherwise comparable cell line following transient triple transfection.

[65] A production cell line for producing recombinant AAV (rAAV) virions, wherein the production of rAAV virions is inducible in the absence of a plasmid, and wherein following induction, the production cell line is capable of producing rAAV virions having a prepurification rAAV full capsid to empty capsid ratio of no less than 0.5.

[66] The production cell line of embodiment [65], wherein the production cell line is capable of producing rAAV virions that, following purification and administration to a subject, induce a lower titer of neutralizing antibodies per administered rAAV viral genome compared to a population of rAAV virions that have the same capsid and rAAV viral genome and are produced by an otherwise comparable cell line following transient triple transfection and that are administered by the same route of administration to a comparable subject.

[67] The production cell line of embodiment [65] or [66], wherein the production cell line is capable of producing rAAV virions that, following purification and administration to a subject, induce fewer and/or lower intensity adverse effects per administered rAAV viral genome compared to a population of rAAV virions that have the same capsid and rAAV viral genome and are produced by an otherwise comparable cell line following transient triple transfection and that are administered by the same route of administration to a comparable subject.

[68] The production cell line of embodiment [67], wherein the adverse effect is selected from the group consisting of: liver dysfunction, liver inflammation, gastrointestinal infection, vomiting, bacterial infection, sepsis, increases in troponin levels, decreases in red blood cell counts, decreases in platelet counts, activation of the complement immune system response, acute kidney injury, cardio-pulmonary insufficiency, and death.

[69] The production cell line of embodiment [67], wherein the adverse effect is an increase in serum levels of one or more of interferon gamma (IFNγ), interleukin 1β (IL-1β), and interleukin 6 (IL-6).

[70] The production cell line of any one of embodiments [65] to [69], wherein the production cell line is capable of producing rAAV virions that have an effective dose of less than $1\times10^{14}$ viral particles (vp)/kg.

[71] The production cell line of any one of embodiments [65] to [70], wherein the production cell line is capable of producing rAAV virions that can be administered to a patient more than once.

[72] The production cell line of any one of embodiments [65] to [71], wherein the production cell line is capable of producing rAAV virions that have a reduced prepurification quality variability compared to a population of rAAV virions produced by an otherwise comparable cell line following transient triple transfection.

[73] The production cell line of any one of embodiments [65] to [71], wherein the production cell line is capable of producing rAAV virions that have a reduced postpurification quality variability compared to a population of rAAV virions produced by an otherwise comparable cell line following transient triple transfection.

[74] The production cell line of embodiment [72] or [73], wherein the purification quality variability is selected from: viral genome to viral particle ratio variability, yield variability, potency variability, purity variability, DNA content variability, and capsid variability.

[75] A production cell line for producing recombinant AAV (rAAV) virions, wherein the production of rAAV virions is inducible in the absence of a plasmid, and wherein following induction, the production cell line is capable of producing rAAV virions that have an increased batch consistency of rAAV having a predetermined number of viral genomes (VG) compared to a population of rAAV virions that have the same capsid and VG and are produced by an otherwise comparable cell line following transient triple transfection.

[76] The production cell line of embodiment [75], wherein the batch consistency is measured by a variation in the number of viral particles (VP) between batches of rAAV having a predetermined number of viral genomes (VG) from different batches.

[77] The production cell line of embodiment [75] or [76], wherein the batch consistency is increased by 2-fold compared to a population of rAAV virions that have the same capsid and VG and are produced by an otherwise comparable cell line following transient triple transfection.

[78] The production cell line of embodiment [77], wherein the batch consistency is increased by 5-fold compared to a population of rAAV virions that have the same capsid and VG and are produced by an otherwise comparable cell line following transient triple transfection.

[79] The production cell line of embodiment [78], wherein the batch consistency is increased by 10-fold compared to a population of rAAV virions that have the same capsid and VG and are produced by an otherwise comparable cell line following transient triple transfection.

[80] The production cell line of any one of embodiments [75] to [79], wherein the number of viral particles (VP) between batches of rAAV having a predetermined number of viral genomes (VG) varies by no more than 20%.

[81] The production cell line of embodiment [80], wherein the number of viral particles (VP) between batches of rAAV having a predetermined number of viral genomes (VG) varies by no more than 10%.

[82] The production cell line of embodiment [81], wherein the number of viral particles (VP) between batches of rAAV having a predetermined number of viral genomes (VG) varies by no more than 5%.

[83] A cell culture composition comprising:

a) suspension-adapted mammalian cells, b) serum-free cell culture media, and c) recombinant AAV (rAAV) virions, wherein the cell culture composition is free of herpes simplex virus, baculovirus, and adenovirus, and wherein the cell culture composition is free of plasmid and transfection agent.

[84] The cell culture composition of embodiment 83, wherein the cell culture composition is free of polyethylenimine (PEI).

[85] The cell culture composition of embodiment 83 or 84, wherein the suspension-adapted mammalian cells are suspension-adapted HEK293 cells or derivatives thereof.

[86] The cell culture composition of any one of embodiments 83 to 85, wherein the suspension-adapted mammalian cells are cells of the packaging cell line of any one of embodiments 1 to 26 or cells of the production cell line of any one of embodiments 29 to 55.

[87] The cell culture composition of any one of embodiments 83 to 86, wherein the cell culture composition has a prepurification rAAV concentration of greater than $1\times10^{14}$ viral genome (vg)/L.

[88] The cell culture composition of any one of embodiments 83 to 87, wherein the cell culture composition has a prepurification rAAV viral particle to viral genome (VG) ratio of no less than 0.5.

[89] A bioreactor containing the cell culture composition of any one of embodiments 59 to 88.

[90] The bioreactor of embodiment 89, wherein the bioreactor is a 1 L bioreactor.

[91] The bioreactor of embodiment 90, wherein the bioreactor has a total rAAV yield of greater than $1\times10^{14}$ viral genome (vg).

[92] The bioreactor of embodiment 89, wherein the bioreactor is a 5 L bioreactor.

[93] The bioreactor of embodiment 92, wherein the bioreactor has a total rAAV yield of greater than $5\times10^{14}$ viral genome (vg).

[94] The bioreactor of embodiment 89, wherein the bioreactor is a SOL bioreactor.

[95] The bioreactor of embodiment 94, wherein the bioreactor has a total rAAV yield of greater than $5\times10^{15}$ viral genome (vg).

[96] The bioreactor of embodiment 89, wherein the bioreactor is a 100 L bioreactor.

[97] The bioreactor of embodiment 96, wherein the bioreactor has a total rAAV yield of greater than $1\times10^{16}$ viral genome (vg).

[98] The bioreactor of embodiment 89, wherein the bioreactor is a 500 L bioreactor.

[99] The bioreactor of embodiment 98, wherein the bioreactor has a total rAAV yield of greater than $5\times10^{16}$ viral genome (vg).

[100] The bioreactor of embodiment 89, wherein the bioreactor is a 2000 L bioreactor.

[101] The bioreactor of embodiment 100, wherein the bioreactor has a total rAAV yield of greater than $2\times10^{17}$ viral genome (vg).

[102] The bioreactor of any one of embodiments 89 to 101, wherein the bioreactor is a single use bioreactor.

[103] A method of producing recombinant AAV (rAAV) virions using a bioreactor, the method comprising:
- culturing the packaging cell line of any one of embodiments 1 to 26 in the bioreactor,
- transfecting the packaging cell line with a polynucleotide construct that comprises a packageable coding sequence for a payload, and
- inducing the expression of Rep protein, Cap protein, one or more adenoviral helper proteins, and optionally VA RNA.

[104] A method of producing recombinant AAV (rAAV) virions using a bioreactor, the method comprising:
- culturing the production cell line of any one of embodiments 29 to 55 in the bioreactor, and
- inducing the expression of Rep protein, Cap protein, one or more adenoviral helper proteins, and optionally VA RNA.

[105] The method of embodiment 103 or 104, further comprising the subsequent step of purifying the rAAV virions from the cell culture composition.

[106] A pharmaceutical composition, comprising:
- cGMP grade rAAV virions produced by the packaging cell line, the production cell line, the cell culture composition, the bioreactor, or the method of any of the preceding embodiments, and
- a pharmaceutically acceptable carrier.

[107] The pharmaceutical composition of embodiment 106, wherein the pharmaceutical composition is free of plasmid and transfection agent.

[108] The pharmaceutical composition of embodiment 106 or 107, wherein the pharmaceutical composition is free of herpes simplex virus, baculovirus, and adenovirus.

[109] The pharmaceutical composition of any one of embodiments 106 to 108, wherein the pharmaceutical composition is free of herpes simplex virus, baculovirus, and adenovirus DNA.

[110] The pharmaceutical composition of any one of embodiments 106 to 109, wherein the pharmaceutical composition has a postpurification rAAV concentration of at least $1\times10^{11}$ viral genome (vg)/mL.

[111] The pharmaceutical composition of any one of embodiments 106 to 110, wherein the pharmaceutical composition has a postpurification rAAV viral particle to viral genome (VG) ratio of no less than 0.8.

[112] A pharmaceutical unit dose comprising the pharmaceutical composition of any one of embodiments 106 to 111.

[113] The pharmaceutical unit dose of embodiment 112, wherein the number of viral particles between doses of rAAV having a predetermined number of viral genomes varies by no more than 20%.

[114] The pharmaceutical unit dose of embodiment [113], wherein the number of viral particles between doses of rAAV having a predetermined number of viral genomes varies by no more than 10%.

[115] The pharmaceutical unit dose of embodiment [114], wherein the number of viral particles between doses of rAAV having a predetermined number of viral genomes varies by no more than 5%.

[116] A pharmaceutical unit dose comprising: at least $1\times10^{11}$ rAAV viral genome at a postpurification rAAV full capsid to empty capsid ratio of no less than 0.8 in 2 mL.

[117] A method for reducing the immunogenicity of a dose of rAAV having a predetermined number of viral genomes (VG) as compared to the same rAAV VG dose prepared by transient triple transfection, the method comprising:
- producing the rAAV in the packaging cell line of any one of embodiments 1 to 26, the production cell line of any one of embodiments 29 to 55 and 58 to 74, or the cell culture composition of any one of embodiments 83 to 88, or the bioreactor of any one of embodiments 89 to 94, or using the production method of any one of embodiments 27, 28, 56, 57, and 103 to 105.

[118] A method for reducing the number or intensity of adverse effects caused by administering a dose of rAAV having a predetermined number of viral genomes (VG) as compared to the same rAAV VG dose prepared by transient triple transfection, the method comprising:
- producing the rAAV in the packaging cell line of any one of embodiments 1 to 26, the production cell line of any one of embodiments 29 to 55 and 58 to 74, or the cell culture composition of any one of embodiments 83 to 88, or the bioreactor of any one of embodiments 89 to 94, or using the production method of any one of embodiments 27, 28, 56, 57, and 103 to 105.

[119] The method of embodiment [118], wherein the adverse effect is selected from the group consisting of: liver dysfunction, liver inflammation, gastrointestinal infection, vomiting, bacterial infection, sepsis, increases in troponin levels, decreases in red blood cell counts, decreases in platelet counts, activation of the complement immune system response, acute kidney injury, cardio-pulmonary insufficiency, and death.

[120] The method of embodiment [118], wherein the adverse effect is an increase in serum levels of one or more of interferon gamma (IFNγ), interleukin 1β (IL-1β), and interleukin 6 (IL-6).

[121] A method of administering a dose of rAAV having a predetermined number of viral genomes (VG) to a subject with reduced production of neutralizing antibodies by the subject as compared to production of neutralizing antibodies after administration of the same rAAV VG dose prepared by transient triple transfection, the method comprising:

administering a first dose of rAAV produced in the packaging cell line of any one of embodiments 1 to 26, the production cell line of any one of embodiments 29 to 55 and 58 to 74, or the cell culture composition of any one of embodiments 83 to 88, or the bioreactor of any one of embodiments 89 to 94, or using the production method of any one of embodiments 27, 28, 56, 57, and 103 to 105.

[122] The method of embodiment [121], further comprising:

administering at least a second dose of rAAV produced in the packaging cell line of any one of embodiments 1 to 26, the production cell line of any one of embodiments 29 to 55 and 58 to 74, or the cell culture composition of any one of embodiments 83 to 88, or the bioreactor of any one of embodiments 89 to 94, or using the production method of any one of embodiments 27, 28, 56, 57, and 103 to 105.

[123] A method of administering a dose of rAAV having a predetermined number of viral genomes (VG) to a subject with reduced number or intensity of adverse effects as compared to administration of the same rAAV VG dose prepared by transient triple transfection, the method comprising:

administering a dose of rAAV produced in the packaging cell line of any one of embodiments 1 to 26, the production cell line of any one of embodiments 29 to 55 and 58 to 74, or the cell culture composition of any one of embodiments 83 to 88, or the bioreactor of any one of embodiments 89 to 94, or using the production method of any one of embodiments 27, 28, 56, 57, and 103 to 105.

[124] The method of embodiment [123], wherein the adverse effect is selected from the group consisting of: liver dysfunction, liver inflammation, gastrointestinal infection, vomiting, bacterial infection, sepsis, increases in troponin levels, decreases in red blood cell counts, decreases in platelet counts, activation of the complement immune system response, acute kidney injury, cardio-pulmonary insufficiency, and death.

[125] The method of embodiment [123], wherein the adverse effect is an increase in serum levels of one or more of interferon gamma (IFNγ), interleukin 1β (IL-1β), and interleukin 6 (IL-6).

[126] A method for repeatedly administering a dose of rAAV to a subject in need thereof, the method comprising:

administering a first dose of rAAV by a first route of administration, wherein the rAAV are produced in the packaging cell line of any one of embodiments 1 to 26, the production cell line of any one of embodiments 29 to 55 and 58 to 74, or the culture composition of any one of embodiments 83 to 88, or the bioreactor of any one of embodiments 89 to 94, or using the production method of any one of embodiments 27, 28, 56, 57, and 103 to 105, and then administering at least a second dose of rAAV by either the first route of administration or a second route of administration, wherein the rAAV are produced in the packaging cell line of any one of embodiments 1 to 26, the production cell line of any one of embodiments 29 to 55 and 58 to 74, or the cell culture composition of any one of embodiments 83 to 88, or the bioreactor of any one of embodiments 89 to 94, or using the production method of any one of embodiments 27, 28, 56, 57, and 103 to 105, wherein the therapeutic effect of the payload varies by less than 10%, 20%, 30%, 40%, or 50% after administering the first dose compared to after administering at least the second dose.

[127] The method of embodiment 126, wherein the therapeutic effect of the payload varies by less than 10%, 20%, 30%, 40%, or 50% after administering the first dose compared to after administering at least the second dose.

[128] A method for producing a plurality of rAAV batches having a number of viral genomes (VG) as compared to the same rAAV VG batches prepared by transient triple transfection, the method comprising:

producing the plurality of rAAV batches in the packaging cell line of any one of embodiments 1 to 26, the production cell line of any one of embodiments 29 to 55 and 58 to 74, or the cell culture composition of any one of embodiments 83 to 88, or the bioreactor of any one of embodiments 89 to 94, or using the production method of any one of embodiments 27, 28, 56, 57, and 103 to 105.

[129] The method of embodiment 128, wherein the number of viral genomes (VG) between the plurality of rAAV batches varies by no more than 50%, 40%, 30%, 20%, 10%, or 5%.

[130] The method of embodiment 128 or embodiment 129, wherein the number of viral particles between the plurality of rAAV batches varies by no more than 50%, 40%, 30%, 20%, 10%, or 5%.

[131] The method of embodiment any one of embodiments 128 to 130, wherein the number of viral particles (VP) or the number of viral genomes is from the plurality of batches prepurification.

[132] A method for increasing the batch consistency of a first rAAV batch and a second rAAV batch having a predetermined number of viral genomes (VG), the method comprising:

producing a first rAAV batch in the packaging cell line of any one of embodiments 1 to 26, the production cell line of any one of embodiments 29 to 55 and 58 to 74, or the cell culture composition of any one of embodiments 83 to 88, or the bioreactor of any one of embodiments 89 to 94, or using the production method of any one of embodiments 27, 28, 56, 57, and 103 to 105; and producing a second rAAV batch in the packaging cell line of any one of embodiments 1 to 26, the production cell line of any one of embodiments 29 to 55 and 58 to 74, or the cell culture composition of any one of embodiments 83 to 88, or the bioreactor of any one of embodiments 89 to 94, or using the production method of any one of embodiments 27, 28, 56, 57, and 103 to 105;

wherein a number of viral particles (VP) in the first rAAV batch has the predetermined number of viral genomes (VG) that varies by no more than 50%, 40%, 30%, or 20% compared to a number of viral particles (VP) and a number of viral genomes in the second batch rAAV batch.

[133] A method for increasing the batch consistency of a first rAAV batch and a second rAAV batch, the method comprising:

producing a first rAAV batch in the packaging cell line of any one of embodiments 1 to 26, the production cell line of any one of embodiments 29 to 55 and 58 to 74, or the cell culture composition of any one of embodiments 83 to 88, or the bioreactor of any one of embodiments 89 to 94, or using the production method of any one of embodiments 27, 28, 56, 57, and 103 to 105; and producing a second rAAV batch in the packaging cell line of any one of embodiments 1 to 26, the production cell line of any one of embodiments 29 to 55 and 58 to 74, or the cell culture composition of any one of embodiments 83 to 88, or the bioreactor of any one of embodiments 89 to 94, or using the production method of any one of embodiments 27, 28, 56, 57, and 103 to 105;

wherein the second rAAV batch has a number of viral genomes that varies by no more than 50%, 40%, 30%, 20%, 10%, or 5% compared to the number of viral genomes in the first rAAV batch.

[134] The method of embodiment 133, wherein the second rAAV batch has a number of viral genomes that varies by no more than 50%, 40%, 30%, 20%, 10%, or 5% prepurification compared to the number of viral genomes in the first rAAV batch.

[135] The method of embodiment 133 or 134, wherein the second rAAV batch has a number of viral particles that varies by no more than 50%, 40%, 30%, 20%, 10%, or 5% compared to the number of viral particles in the first rAAV batch.

[136] The method of any one of embodiments 133 to 135, wherein the second rAAV batch has a number of viral particles that varies by no more than 50%, 40%, 30%, 20%, 10%, or 5% prepurification compared to the number of viral particles in the first rAAV batch.

[137] The method of any one of embodiments 133 to 136, wherein the first rAAV batch and the second rAAV batch are produced from monoclonal cells.

[138] The method of any one of embodiments 133 to 137, wherein the first rAAV batch and the second rAAV batch are produced from cells from different monoclonal cell lines.

[139] The method of any one of embodiments 128 to 138, further comprising the subsequent step of purifying the rAAV virions from cell culture media and/or cell lysate.

[140] A product of rAAV made by the method of any one of embodiments 27, 28, 56, 57, and 103 to 105.

6.17. NUMBERED EMBODIMENTS #3

[1] A polynucleotide construct coding for:

a) one or more helper proteins;

b) a self-excising element upstream of the one or more helper proteins; and c) an inducible promoter upstream of the self-excising element.

[2] The polynucleotide construct of embodiment 1, wherein the self-excising element is operably linked to the inducible promoter.

[3] The polynucleotide construct of embodiment 2, wherein expression of the self-excising element is driven by the inducible promoter.

[4] The polynucleotide construct of any one of embodiments 2-3, wherein the inducible promoter is a tetracycline-responsive promoter element (TRE).

[5] The polynucleotide construct of embodiment 4, wherein the TRE comprises Tet operator (tetO) sequence concatemers fused to a minimal promoter.

[6] The polynucleotide construct of embodiment 5, wherein the minimal promoter is a human cytomegalovirus promoter.

[7] The polynucleotide construct of any one of embodiments 2-6, wherein the inducible promoter comprises a sequence having at least 70%, 80%, 90%, 95%, 99%, or 100% sequence identity to SEQ ID NO: 22.

[8] The polynucleotide construct of any one of embodiments 2-7, wherein transcription is activated from the inducible promoter upon binding of an activator.

[9] The polynucleotide construct of embodiment 8, wherein the activator binds to the inducible promoter in the presence of a first triggering agent.

[10] The polynucleotide construct of any one of embodiments 8-9, further comprising an activator.

[11] The polynucleotide construct of any one of embodiments 8-10, wherein the activator is operably linked to a constitutive promoter.

[12] The polynucleotide construct of embodiment 11, wherein the constitutive promoter is E1alpha promoter or human cytomegalovirus promoter.

[13] The polynucleotide construct of embodiment 12, wherein the E1 alpha promoter comprises at least one mutation.

[14] The polynucleotide construct of any one of embodiments 11-13, wherein the constitutive promoter comprises a sequence having at least 70%, 80%, 90%, 95%, 99%, or 100% sequence identity with SEQ ID NO: 20.

[15] The polynucleotide construct of any one of embodiments 8-14, wherein the activator is reverse tetracycline-controlled transactivator (rTA) comprising a Tet Repressor binding protein (TetR) fused to a VP16 transactivation domain.

[16] The polynucleotide construct of embodiment 15, wherein the rTA comprises four mutations in the tetR DNA binding moiety.

[17] The polynucleotide construct of any one of embodiments 15-16, wherein the rTA comprises a sequence having at least 70%, 80%, 90%, 95%, 99%, or 100% sequence identity to SEQ ID NO: 21.

[18] The polynucleotide construct of any one of embodiments 2-7, wherein the inducible promoter is bound by a repressor in the absence of a first triggering agent.

[19] The polynucleotide construct of any one of embodiments 2-19, wherein the inducible promoter is activated in the presence of a first triggering agent.

[20] The polynucleotide construct of any one of embodiments 18-19, wherein the first triggering agent binds to the repressor.

[21] The polynucleotide construct of any one of embodiments 18-20, wherein the repressor is a tetracycline-controlled transactivator.

[22] The polynucleotide construct of any one of embodiments 18-21, further comprising the repressor.

[23] The polynucleotide construct of any one of embodiments 18-22, wherein the repressor is operably linked to a constitutive promoter.

[24] The polynucleotide construct of any one of embodiments 18-23, further comprising a tetracycline-controlled transactivator.

[25] The polynucleotide construct of any one of embodiments 18-24, wherein the tetracycline-controlled transactivator is operably linked to a constitutive promoter.

[26] The polynucleotide construct of any one of embodiments 18-25, wherein the constitutive promoter is E1alpha promoter.

[27] The polynucleotide construct of any one of embodiments 18-26, wherein the E1 alpha promoter comprises at least one mutation.

[28] The polynucleotide construct of embodiment 27, wherein the constitutive promoter comprises a sequence having at least 70%, 80%, 90%, 95%, 99%, or 100% sequence identity with SEQ ID NO: 20.

[29] The polynucleotide construct of any one of embodiments 21 or 24-28, wherein the tetracycline-controlled transactivator is unbound in the presence of a first triggering agent.

[30] The polynucleotide construct of any one of embodiments 21 or 24-29, wherein the tetracycline-controlled transactivator does not bind to the inducible promoter in the presence of a first triggering agent.

[31] The polynucleotide construct of any one of embodiments 18-30, wherein the constitutive promoter is E1alpha promoter.

[32] The polynucleotide construct of embodiment 31, wherein the E1 alpha promoter comprises at least one mutation.

[33] The polynucleotide construct of any one of embodiments 31-32, wherein the constitutive promoter comprises a sequence having at least 70%, 80%, 90%, 95%, 99%, or 100% sequence identity with SEQ ID NO: 20.

[34] The polynucleotide construct of any one of embodiments 18-33, wherein transcription is activated from the inducible promoter upon binding of the first triggering agent to the repressor.

[35] The polynucleotide construct of any one of embodiments 18-34, wherein the repressor binds to the first triggering agent.

[36] The polynucleotide construct of any one of embodiments 18-35, wherein the first triggering agent is a tetracycline.

[37] The polynucleotide construct of embodiments 36, wherein the tetracycline is doxycycline.

[38] The polynucleotide construct of any one of embodiments 2-3, wherein the inducible promoter is a cumate operator sequence.

[39] The polynucleotide construct of embodiment 38, wherein the cumate operator sequence is downstream of a constitutive promoter.

[40] The polynucleotide construct of embodiment 39, wherein the constitutive promoter is a human cytomegalovirus promoter.

[41] The polynucleotide construct of any one of embodiments 38-40, wherein the inducible promoter is bound by a cymR repressor in the absence of a first triggering agent.

[42] The polynucleotide construct of any one of embodiments 38-41, wherein the inducible promoter is activated in the presence of a first triggering agent.

[43] The polynucleotide construct of embodiment 41, wherein the first triggering agent binds to the cymR repressor.

[44] The polynucleotide construct of any one of embodiments 41 or 43, further comprising a cymR repressor.

[45] The polynucleotide construct of any one of embodiments 41 or 43-44, wherein the cymR repressor is operably linked to a constitutive promoter.

[46] The polynucleotide construct of embodiment 45, wherein the constitutive promoter is E1alpha promoter.

[47] The polynucleotide construct of any one of embodiments 46, wherein the E1 alpha promoter comprises at least one mutation.

[48] The polynucleotide construct of any one of embodiments 46-47, wherein the constitutive promoter comprises a sequence having at least 70%, 80%, 90%, 95%, 99%, or 100% sequence identity with SEQ ID NO: 20.

[49] The polynucleotide construct of any one of embodiments 41-49, wherein the first triggering agent is a cumate.

[50] The polynucleotide construct of any one embodiments 1-49, wherein a sequence coding for the self-excising element comprises a poly A sequence.

[51] The polynucleotide construct of any one embodiments 1-50, wherein the self-excising element is a recombinase.

[52] The polynucleotide construct of embodiment 51, wherein the recombinase is a site-specific recombinase.

[53] The polynucleotide construct of embodiment 51, wherein the recombinase is fused to a ligand binding domain.

[54] The polynucleotide construct of embodiment 51, wherein the recombinase is Cre polypeptide or flippase polypeptide.

[55] The polynucleotide construct of embodiment 54, wherein the Cre polypeptide is fused to a ligand binding domain.

[56] The polynucleotide construct of embodiment 55, wherein the ligand binding domain is a hormone receptor.

[57] The polynucleotide construct of embodiment 56, wherein the hormone receptor is an estrogen receptor.

[58] The polynucleotide construct of embodiment 57, wherein the estrogen receptor comprises a point mutation.

[59] The polynucleotide construct of embodiment 58, wherein the estrogen receptor is ERT2.

[60] The polynucleotide construct of embodiment 51, wherein the recombinase is a Cre-ERT2 polypeptide.

[61] The polynucleotide construct of any one of embodiments 1-61, wherein the self-excising element translocates to the nucleus in the presence of a second triggering agent.

[62] The polynucleotide construct of embodiment 61, wherein the second triggering agent is an estrogen receptor ligand.

[63] The polynucleotide construct of any one of the preceding embodiments, wherein the second triggering agent is a selective estrogen receptor modulator (SERM).

[64] The polynucleotide construct of any one of the preceding embodiments, wherein the second triggering agent is tamoxifen.

[65] The polynucleotide construct of any one of the preceding embodiments, wherein the recombinase is flanked by recombination sites

[66] The polynucleotide construct of any one of the preceding embodiments, wherein the recombination sites are lox sites or flippase recognition target (FRT) sites.

[67] The polynucleotide construct of any one of the preceding embodiments, wherein the lox sites are loxP sites.

[68] The polynucleotide construct of any one of the preceding embodiments, wherein the one or more adenoviral helper proteins comprise E2A and E4.

[69] The polynucleotide construct of any one of the preceding embodiments, wherein the one or more adenoviral helper proteins further comprises a protein tag.

[70] The polynucleotide construct of any one of the preceding embodiments, wherein the protein tag is a FLAG-tag.

[71] The polynucleotide construct of any one of the preceding embodiments, wherein the E2A is FLAG-tagged E2A.

[72] The polynucleotide construct of any one of the preceding embodiments, wherein the sequence coding for E2 and the sequence coding for E4 are separated by an internal ribosome entry site (IRES) or by P2A.

[73] The polynucleotide construct of any one of the preceding embodiments, further comprising a sequence coding for a selectable marker.

[74] The polynucleotide construct of any one of the preceding embodiments, wherein the selectable marker is an antibiotic resistance protein.

[75] The polynucleotide construct of any one of the preceding embodiments, wherein the selectable marker is a split intein linked to an N-terminus of the antibiotic resistance protein or split intein linked to a C-terminus of the antibiotic resistance protein.

[76] The polynucleotide construct of any one of the preceding embodiments, wherein the selectable marker is a leucine zipper linked to an N-terminus of the antibiotic resistance protein or leucine zipper linked to a C-terminus of the antibiotic resistance protein.

[77] The polynucleotide construct of any one of the preceding embodiments, wherein the antibiotic resistance protein is for puromycin resistance or blasticidin resistance.

[78] The polynucleotide construct of any one of the preceding embodiments, further comprising a sequence coding for VA RNA.

[79] The polynucleotide construct of any one of the preceding embodiments, the sequence coding for VA RNA is a transcriptionally dead sequence.

[80] The polynucleotide construct of any one of the preceding embodiments, the sequence coding for VA RNA comprises at least two mutations in the internal promoter.

[81] The polynucleotide construct of any one of the preceding embodiments, wherein expression of VA RNA is driven by a U6 promoter.

[82] The polynucleotide construct of any one of the preceding embodiments, comprising upstream of the sequence coding for VA RNA gene sequence, from 5' to 3':

a) a first part of a U6 promoter sequence;
b) a first recombination site;
c) a stuffer sequence;
d) a second recombination site;
e) a second part of a U6 promoter sequence.

[83] The polynucleotide construct of any one of the preceding embodiments, wherein the stuffer sequence is excisable by the recombinase.

[84] The polynucleotide construct of any one of the preceding embodiments, wherein the stuffer sequence comprises a sequence encoding a gene.

[85] The polynucleotide construct of any one of the preceding embodiments, wherein the stuffer sequence comprises a promoter.

[86] The polynucleotide construct of any one of the preceding embodiments, wherein the promoter is a constitutive promoter.

[87] The polynucleotide construct of any one of the preceding embodiments, wherein the promoter is a CMV promoter.

[88] The polynucleotide construct of any one of the preceding embodiments, wherein the gene encodes a detectable marker or a selectable marker.

[89] The polynucleotide construct of any one of the preceding embodiments, wherein the selectable marker is an antibiotic resistance protein.

[90] The polynucleotide construct of any one of the preceding embodiments, wherein the selectable marker is a split intein linked to an N-terminus of the antibiotic resistance protein or split intein linked to a C-terminus of the antibiotic resistance protein.

[91] The polynucleotide construct of any one of the preceding embodiments, wherein the selectable marker is a leucine zipper linked to an N-terminus of the antibiotic resistance protein or leucine zipper linked to a C-terminus of the antibiotic resistance protein.

[92] The polynucleotide construct of any one of the preceding embodiments, wherein the selectable marker is a mammalian cell selection element.

[93] The polynucleotide construct of any one of the preceding embodiments, wherein the selectable marker is an auxotrophic selection element.

[94] The polynucleotide construct of any one of the preceding embodiments, wherein the auxotrophic selection element codes for an active protein.

[95] The polynucleotide construct of any one of the preceding embodiments, wherein the active protein is DHFR.

[96] The polynucleotide construct of any one of the preceding embodiments, wherein the auxotrophic selection coding sequence encodes an inactive protein that requires expression of a second auxotrophic selection coding sequence for activity.

[97] The polynucleotide construct of any one of the preceding embodiments, wherein the second auxotrophic selection coding sequence encodes for DHFR Z-Cter or DHFR Z-Nter.

[98] The polynucleotide construct of any one of the preceding embodiments, wherein the inactive protein comprises a DHFR Z-Nter or DHFR Z-Cter

[99] The polynucleotide construct of any one of the preceding embodiments, wherein the selectable marker is DHFR Z-Nter or DHFR Z-Cter.

[100] The polynucleotide construct of any one of the preceding embodiments, wherein the DHFR Z-Nter comprises a sequence having at least 70%, 80%, 90%, 95%, 99%, or 100% sequence identity to SEQ ID NO: 4.

[101] The polynucleotide construct of any one of the preceding embodiments wherein the DHFR Z-Cter comprises a sequence having at least 70%, 80%, 90%, 95%, 99%, or 100% sequence identity to SEQ ID NO: 5.

[102] The polynucleotide construct of any one of the preceding embodiments, wherein the antibiotic resistance protein is for puromycin resistance or blasticidin resistance.

[103] The polynucleotide construct of any one of the preceding embodiments, wherein the detectable marker comprises a luminescent marker or a fluorescent marker.

[104] The polynucleotide construct of any one of the preceding embodiments, wherein the fluorescent marker is GFP, EGFP, RFP, CFP, BFP, YFP, or mCherry.

[105] The polynucleotide construct of any one of the preceding embodiments, wherein the first recombination site is a first lox sequence and the second recombination site is a second lox sequence.

[106] The polynucleotide construct of any one of the preceding embodiments, wherein the first lox sequence is a first loxP site and the second lox sequence is a second loxP site.

[107] The polynucleotide construct of any one of the preceding embodiments, wherein the first recombination site is a first FRT site and the second recombination site is a second FRT site.

[108] The polynucleotide construct of any one of embodiments 1-107 in a vector.

[109] The polynucleotide construct of any one of embodiments 1-107 in a plasmid.

[110] The polynucleotide construct of any one of embodiments 1-107 in a bacterial artificial chromosome or yeast artificial chromosome.

[111] The polynucleotide construct of any one of embodiments 1-110, wherein the polynucleotide construct is a synthetic nucleic acid construct.

[112] The polynucleotide construct of any one of embodiments 1-111 comprising a sequence having at least 70%, 80%, 90%, 95%, 99%, or 100% sequence identity to any one of SEQ ID NO: 9-SEQ ID NO: 19, SEQ ID 23-SEQ ID NO: 32, or SEQ ID NO: 35.

[113] A cell comprising the polynucleotide construct of any one of embodiments 1-112.

[114] The cell of embodiment 113, wherein the polynucleotide is stably integrated into the genome of the cell.

[115] The cell of any one of embodiments 113-114, wherein the cell is a mammalian cell or insect cell.

[116] The cell of any one of embodiments 113-114, wherein the cell is a HEK293 cell, HeLa cell, CHO cell, or SF9 cell.

[117] The cell of any one of embodiments 113-116, wherein the cell expresses E1A protein and E1B protein.

[118] The cell of any one of embodiments 113-117, wherein the cell is DHFR null.

[119] A polynucleotide construct comprising:

a) a sequence of a first part of a Rep gene;

b) a sequence of a second part of the Rep gene;

c) a sequence of a Cap gene; and d) an excisable element positioned between the first part of the sequence of Rep gene and the second part of the sequence of the Rep gene.

[120] The polynucleotide construct of any one of the preceding embodiments, wherein the excisable element comprises a stop signaling sequence.

[121] The polynucleotide construct of any one of the preceding embodiments, wherein the excisable element comprises a rabbit beta globin intron.

[122] The polynucleotide construct of any one of the preceding embodiments, wherein the excisable element comprises an exon.

[123] The polynucleotide construct of any one of the preceding embodiments, wherein the excisable element comprises an intron and an exon.

[124] The polynucleotide construct of any one of the preceding embodiments, wherein the excisable element comprises an intron.

[125] The polynucleotide construct of any one of the preceding embodiments, wherein two splice sites are positioned between the sequence of the first part of the Rep gene and the sequence of the second part of the Rep gene.

[126] The polynucleotide construct of any one of the preceding embodiments, wherein the two splice sites are a 5' splice site and a 3' splice site.

[127] The polynucleotide construct of any one of the preceding embodiments, wherein the 5' splice site is a rabbit beta globin 5' splice site.

[128] The polynucleotide construct of any one of the preceding embodiments, wherein the 3' splice site is a rabbit beta globin 3' splice site.

[129] The polynucleotide construct of any one of the preceding embodiments, wherein three splice sites are positioned between the sequence of the first part of the Rep gene and the sequence of the second part of the Rep gene.

[130] The polynucleotide construct of any one of the preceding embodiments, wherein the three splice sites are a 5' splice site, a first 3' splice site, and a second 3' splice site.

[131] The polynucleotide construct of any one of the preceding embodiments, wherein a first 3' splice site is a duplicate of the second 3' splice site.

[132] The polynucleotide construct of any one of the preceding embodiments, wherein the first 3' splice site is a rabbit beta globin 3' splice site.

[133] The polynucleotide construct of any one of the preceding embodiments, wherein the second 3' splice site is a rabbit beta globin 3' splice site.

[134] The polynucleotide construct of any one of the preceding embodiments, wherein the excisable element comprises a recombination site.

[135] The polynucleotide construct of any one of the preceding embodiments, wherein the recombination site is a lox site or FRT site.

[136] The polynucleotide construct of any one of the preceding embodiments, wherein the lox site is a loxP site.

[137] The polynucleotide construct of any one of the preceding embodiments, wherein the excisable element comprises from 5' to 3':

a) the 5' splice site;

b) a first recombination site;

c) the first 3' splice site;

d) a stop signaling sequence;

e) a second recombination site; and f) the second 3' splice site.

[138] The polynucleotide construct of any one of the preceding embodiments, wherein the excisable element comprises from 5' to 3':

a) the 5' splice site;

b) a first spacer segment;

c) a second spacer segment comprising:

i) a first recombination site;

ii) the first 3' splice site;

iv) a stop signaling sequence; and v) a second recombination site; and d) a third spacer segment comprising the second 3' splice site.

[139] The polynucleotide construct of any one of the preceding embodiments, wherein the first spacer sequence comprises an intron.

[140] The polynucleotide construct of any one of the preceding embodiments, wherein the first spacer segment comprises a sequence having at least 70%, 80%, 90%, 95%, 99%, or 100% sequence identity to SEQ ID NO: 1.

[141] The polynucleotide construct of any one of the preceding embodiments, wherein the second spacer segment comprises a sequence having at least 70%, 80%, 90%, 95%, 99%, or 100% sequence identity to SEQ ID NO: 2.

[142] The polynucleotide construct of any one of the preceding embodiments, wherein the third spacer segment comprises a sequence having at least 70%, 80%, 90%, 95%, 99%, or 100% sequence identity to SEQ ID NO: 3.

[143] The polynucleotide construct of any one of the preceding embodiments, wherein the third spacer segment comprises an intron.

[144] The polynucleotide construct of any one of the preceding embodiments, wherein the first spacer segment and the third spacer segment are capable of being excised by endogenous cellular machinery.

[145] The polynucleotide construct of any one of the preceding embodiments, wherein the second spacer segment comprises an exon.

[146] The polynucleotide construct of any one of the preceding embodiments, wherein the second spacer segment further comprises a polyA sequence.

[147] The polynucleotide construct of any one of the preceding embodiments, wherein the polyA sequence is 3' of the exon.

[148] The polynucleotide construct of any one of the preceding embodiments, wherein the polyA sequence comprises a rabbit beta globin (RBG) polyA sequence.

[149] The polynucleotide construct of any one of embodiments, wherein the second spacer segment comprises from 5' to 3':

a) a first recombination site;
b) the first 3' splice site;
c) an exon;
d) a stop signaling sequence; and
e) a second recombination site.

[150] The polynucleotide construct of any one of the preceding embodiments, wherein the first recombination site is a first lox sequence and the second recombination site is a second lox sequence.

[151] The polynucleotide construct of any one of the preceding embodiments, wherein the first lox sequence is a first loxP sequence and a second lox sequence is a second loxP sequence.

[152] The polynucleotide construct of any one of the preceding embodiments, wherein the first recombination site is a first FRT site and the second recombination site is a second FRT site.

[153] The polynucleotide construct of any one of the preceding embodiments, wherein the stop signaling sequence is a termination codon of the exon or a polyA sequence.

[154] The polynucleotide construct of any one of the preceding embodiments, wherein the polyA sequence comprises a rabbit beta globin (RBG) polyA sequence.

[155] The polynucleotide construct of any one of the preceding embodiments, wherein the exon encodes a detectable marker or a selectable marker.

[156] The polynucleotide construct of any one of the preceding embodiments, wherein the detectable marker comprises a luminescent marker or a fluorescent marker.

[157] The polynucleotide construct of any one of the preceding embodiments, wherein the fluorescent marker is GFP, EGFP, RFP, CFP, BFP, YFP, or mCherry.

[158] The polynucleotide construct of any one of the preceding embodiments, wherein the second spacer segment is excisable by a recombinase.

[159] The polynucleotide construct of any one of the preceding embodiments, wherein the recombinase is a site-specific recombinase.

[160] The polynucleotide construct of any one of embodiments, wherein the recombinase is a Cre polypeptide or a Flippase polypeptide.

[161] The polynucleotide construct of any one the preceding embodiments, wherein the Cre polypeptide is fused to a ligand binding domain.

[162] The polynucleotide construct of any one of the preceding embodiments, wherein the ligand binding domain is a hormone receptor.

[163] The polynucleotide construct of any one of the preceding embodiments, wherein the hormone receptor is an estrogen receptor.

[164] The polynucleotide construct of any one of the preceding embodiments, wherein the estrogen receptor comprises a point mutation.

[165] The polynucleotide construct of any one of the preceding embodiments, wherein the estrogen receptor is ERT2.

[166] The polynucleotide construct of any one the preceding embodiments, wherein the recombinase is a Cre-ERT2 polypeptide.

[167] The polynucleotide construct of the preceding embodiments, wherein the recombinase is encoded by a second polynucleotide construct or exogenously provided.

[168] The polynucleotide construct of any one of the preceding embodiments, wherein the Rep gene codes for Rep polypeptides.

[169] The polynucleotide construct of any one of the preceding embodiments, wherein the Cap gene codes for Cap polypeptides.

[170] The polynucleotide construct of any one of the preceding embodiments, wherein transcription of the Rep gene and the Cap gene are driven by native promoters.

[171] The polynucleotide construct of any one of the preceding embodiments, wherein the native promoters comprise P5, P19, and P40.

[172] The polynucleotide construct of any one of the preceding embodiments, wherein the Rep polypeptides are wildtype Rep polypeptides.

[173] The polynucleotide construct of any one of the preceding embodiments, wherein the Rep polypeptides comprise Rep78, Rep68, Rep52, and Rep40.

[174] The polynucleotide construct of any one of the preceding embodiments, wherein a truncated replication associated protein comprising a polypeptide expressed from the sequence of first part of a Rep gene and the exon is capable of being expressed in the absence of the recombinase.

[175] The polynucleotide construct of any one of the preceding embodiments, wherein the Cap polypeptides are wildtype Cap polypeptides.

[176] The polynucleotide construct of any one of the preceding embodiments, wherein the Cap polypeptides are AAV capsid proteins.

[177] The polynucleotide construct of any one of the preceding embodiments, wherein the AAV capsid proteins comprise VP1, VP2, and VP3.

[178] The polynucleotide construct of any one of the preceding embodiments, wherein a serotype of the AAV capsid proteins is selected from the group consisting of AAV1, AAV2, AAV3, AAV4, AAV5, AAV6, AAV7, AAV8, AAV9, AAV 10, AAV11, AAV 12, AAV13, AAV 14, AAV 15 and AAV 16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, AAV.HSC16, and AAVhu68.

[179] The polynucleotide construct of any one of the preceding embodiments, further comprising a sequence coding for a selectable marker.

[180] The polynucleotide construct of any one of the preceding embodiments, wherein the selectable marker is a mammalian cell selection element.

[181] The polynucleotide construct of any one of the preceding embodiments, wherein the selectable marker is an auxotrophic selection element.

[182] The polynucleotide construct of any one of the preceding embodiments, wherein the auxotrophic selection element codes for an active protein.

[183] The polynucleotide construct of any one of the preceding embodiments, wherein the active protein is DHFR.

[184] The polynucleotide construct of any one of the preceding embodiments, wherein the auxotrophic selection coding sequence encodes an inactive protein that requires expression of a second auxotrophic selection coding sequence for activity.

[185] The polynucleotide construct of any one of the preceding embodiments, wherein the second auxotrophic selection coding sequence encodes for DHFR Z-Cter or DHFR Z-Nter.

[186] The polynucleotide construct of any one of the preceding embodiments, wherein the inactive protein comprises a DHFR Z-Nter or DHFR Z-Cter

[187] The polynucleotide construct of any one of the preceding embodiments, wherein the selectable marker is DHFR Z-Nter or DHFR Z-Cter.

[188] The polynucleotide construct of any one of embodiments 185-187, wherein the DHFR Z-Nter comprises a sequence having at least 70%, 80%, 90%, 95%, 99%, or 100% sequence identity to SEQ ID NO: 4.

[189] The polynucleotide construct of any one of embodiments 185-188, wherein the DHFR Z-Cter comprises a sequence having at least 70%, 80%, 90%, 95%, 99%, or 100% sequence identity to SEQ ID NO: 5.

[190] The polynucleotide construct of any one of the preceding embodiments, wherein the selectable marker is an antibiotic resistance protein.

[191] The polynucleotide construct of any one of the preceding embodiments, wherein the selectable marker is a split intein linked to an N-terminus of the antibiotic resistance protein or split intein linked to a C-terminus of the antibiotic resistance protein.

[192] The polynucleotide construct of any one of the preceding embodiments, wherein the selectable marker is a leucine zipper linked to an N-terminus of the antibiotic resistance protein or leucine zipper linked to a C-terminus of the antibiotic resistance protein.

[193] The polynucleotide construct of any one of the preceding embodiments, wherein the antibiotic resistance protein is for puromycin resistance or blasticidin resistance.

[194] The polynucleotide construct of any one of embodiments 119-193 further comprising the polynucleotide construct of any one of embodiments 1-112.

[195] The polynucleotide construct of any one of embodiments 119-194 in a vector.

[196] The polynucleotide construct of any one of embodiments 119-194 in a plasmid.

[197] The polynucleotide construct of any one of embodiments 119-194 in a bacterial artificial chromosome or yeast artificial chromosome.

[198] The polynucleotide construct of any one of embodiments 119-197, wherein the polynucleotide construct is a synthetic nucleic acid construct.

[199] The polynucleotide construct of any one of embodiments 119-198 comprising a sequence having at least 70%, 80%, 90%, 95%, 99%, or 100% sequence identity to any one of SEQ ID NO: 1-SEQ ID NO: 3, SEQ ID 6-SEQ ID NO: 8, or SEQ ID NO: 32.

[200] The polynucleotide construct of any one of embodiments 119-199, further comprising a sequence coding for VA RNA.

[201] The polynucleotide construct of embodiment 200, the sequence coding for VA RNA is a transcriptionally dead sequence.

[202] The polynucleotide construct of any one of the preceding embodiments, the sequence coding for VA RNA comprises at least two mutations in the internal promoter.

[203] The polynucleotide construct of any one of the preceding embodiments, wherein expression of VA RNA is driven by a U6 promoter.

[204] The polynucleotide construct of any one of the preceding embodiments, comprising upstream of the sequence coding for VA RNA gene sequence, from 5' to 3':

a) a first part of a U6 promoter sequence;

b) a first recombination site;

c) a stuffer sequence;

d) a second recombination site;

e) a second part of a U6 promoter sequence.

[205] The polynucleotide construct of any one of the preceding embodiments, wherein the stuffer sequence is excisable by the recombinase.

[206] The polynucleotide construct of any one of the preceding embodiments, wherein the stuffer sequence comprises a sequence encoding a gene.

[207] The polynucleotide construct of any one of the preceding embodiments, wherein the stuffer sequence comprises a promoter.

[208] The polynucleotide construct of any one of the preceding embodiments, wherein the promoter is a constitutive promoter.

[209] The polynucleotide construct of any one of the preceding embodiments, wherein the promoter is a CMV promoter.

[210] A cell comprising the polynucleotide construct of any one of embodiments 119-209.

[211] The cell of embodiment 210, wherein the polynucleotide is stably integrated into the genome of the cell.

[212] The cell of any one of embodiments 210-211, wherein the cell is a mammalian cell or insect cell.

[213] The cell of any one of embodiments 210-211, wherein the cell is a HEK293 cell, HeLa cell, CHO cell, or SF9 cell.

[214] The cell of any one of embodiments 210-213, wherein the cell expresses E1A protein and E1B protein.

[215] The cell of any one of embodiments 210-214, wherein the cell is DHFR null.

[216] A polynucleotide construct coding for a VA RNA, wherein a sequence coding for the VA RNA comprises at least two mutations in an internal promoter.

[217] The polynucleotide construct of any one of the preceding embodiments, wherein the sequence coding for the VA RNA comprises a sequence coding for a transcriptionally dead VA RNA.

[218] The polynucleotide construct of any one of the preceding embodiments, wherein the sequence coding for the VA RNA comprises a deletion of from about 5-10 nucleotides in the promoter region.

[219] The polynucleotide construct of any one of the preceding embodiments, wherein the sequence coding for the VA RNA comprises at least one mutation.

[220] The polynucleotide construct of any one of the preceding embodiments, wherein the at least one mutation is in the A Box promoter region.

[221] The polynucleotide construct of any one of the preceding embodiments, wherein the at least one mutation is in the B Box promoter region.

[222] The polynucleotide construct of any one of the preceding embodiments, wherein the at least one mutation is G16A and G60A.

[223] The polynucleotide construct of any one of the preceding embodiments, wherein expression of the VA RNA is driven by a U6 promoter.

[224] The polynucleotide construct of any one of the preceding embodiments, comprising upstream of the VA RNA gene sequence, from 5' to 3':

a) a first part of a U6 promoter sequence;

b) a first recombination site;

c) a stuffer sequence;

d) a second recombination site;

e) a second part of a U6 promoter sequence.

[225] The polynucleotide construct of any one of the preceding embodiments, wherein the stuffer sequence is excisable by a recombinase.

[226] The polynucleotide construct of any one of the preceding embodiments, wherein the stuffer sequence comprises a sequence encoding a gene.

[227] The polynucleotide construct of any one of the preceding embodiments, wherein the stuffer sequence comprises a promoter.

[228] The polynucleotide construct of any one of the preceding embodiments, wherein the promoter is a constitutive promoter.

[229] The polynucleotide construct of any one of the preceding embodiments, wherein the promoter is a CMV promoter.

[230] The polynucleotide construct of any one of the preceding embodiments, wherein the gene encodes a detectable marker or a selectable marker.

[231] The polynucleotide construct of any one of the preceding embodiments, wherein the selectable marker is a mammalian cell selection element.

[232] The polynucleotide construct of any one of the preceding embodiments, wherein the selectable marker is an auxotrophic selection element.

[233] The polynucleotide construct of any one of the preceding embodiments, wherein the auxotrophic selection element codes for an active protein.

[234] The polynucleotide construct of any one of the preceding embodiments, wherein the active protein is DHFR.

[235] The polynucleotide construct of any one of the preceding embodiments, wherein the auxotrophic selection coding sequence encodes an inactive protein that requires expression of a second auxotrophic selection coding sequence for activity.

[236] The polynucleotide construct of any one of the preceding embodiments, wherein the second auxotrophic selection coding sequence encodes for DHFR Z-Cter or DHFR Z-Nter.

[237] The polynucleotide construct of embodiment 236, wherein the inactive protein comprises a DHFR Z-Nter or DHFR Z-Cter

[238] The polynucleotide construct of any one of embodiments 236-237, wherein the selectable marker is DHFR Z-Nter or DHFR Z-Cter.

[239] The polynucleotide construct of any one of embodiments 236-238, wherein the DHFR Z-Nter comprises a sequence having at least 70%, 80%, 90%, 95%, 99%, or 100% sequence identity to SEQ ID NO: 4.

[240] The polynucleotide construct of any one of embodiments 236-239, wherein the DHFR Z-Cter comprises a sequence having at least 70%, 80%, 90%, 95%, 99%, or 100% sequence identity to SEQ ID NO: 5.

[241] The polynucleotide construct of any one of the preceding embodiments, wherein the selectable marker is an antibiotic resistance protein.

[242] The polynucleotide construct of any one of the preceding embodiments, wherein the selectable marker is a split intein linked to an N-terminus of the antibiotic resistance protein or split intein linked to a C-terminus of the antibiotic resistance protein.

[243] The polynucleotide construct of any one of the preceding embodiments, wherein the selectable marker is a leucine zipper linked to an N-terminus of the antibiotic resistance protein or leucine zipper linked to a C-terminus of the antibiotic resistance protein.

[244] The polynucleotide construct of any one of the preceding embodiments, wherein the antibiotic resistance protein is for puromycin resistance or blasticidin resistance.

[245] The polynucleotide construct of any one of the preceding embodiments, wherein the detectable marker comprises a luminescent marker or a fluorescent marker.

[246] The polynucleotide construct of any one of the preceding embodiments, wherein the fluorescent marker is GFP, EGFP, RFP, CFP, BFP, YFP, or mCherry.

[247] The polynucleotide construct of any one of the preceding embodiments, further comprising a sequence coding for a recombinase.

[248] The polynucleotide construct of any one of the preceding embodiments, wherein the recombinase is exogenously provided.

[249] The polynucleotide construct of any one of the preceding embodiments, wherein the recombinase is a site-specific recombinase.

[250] The polynucleotide construct of any one of the preceding embodiments, wherein the recombinase is a Cre polypeptide or a Flippase polypeptide.

[251] The polynucleotide construct of any one the preceding embodiments, wherein the Cre polypeptide is fused to a ligand binding domain.

[252] The polynucleotide construct of any one of the preceding embodiments, wherein the ligand binding domain is a hormone receptor.

[253] The polynucleotide construct of any one of the preceding embodiments, wherein the hormone receptor is an estrogen receptor.

[254] The polynucleotide construct of any one of the preceding embodiments, wherein the estrogen receptor comprises a point mutation.

[255] The polynucleotide construct of any one of the preceding embodiments, wherein the estrogen receptor is ERT2.

[256] The polynucleotide construct of any one the preceding embodiments, wherein the recombinase is a Cre-ERT2 polypeptide.

[257] The polynucleotide construct of any one of the preceding embodiments, wherein the first recombination site is a first lox sequence and the second recombination site is a second lox sequence.

[258] The polynucleotide construct of any one of the preceding embodiments, wherein the first lox sequence is a first loxP site and the second lox sequence is a second loxP site.

[259] The polynucleotide construct of any one of the preceding embodiments, wherein the first recombination site is a first FRT site and the second recombination site is a second FRT site.

[260] The polynucleotide construct of any one of the preceding embodiments, further comprising a sequence coding for a selectable marker.

[261] The polynucleotide construct of any one of the preceding embodiments, wherein the selectable marker is an antibiotic resistance protein.

[262] The polynucleotide construct of any one of the preceding embodiments, wherein the selectable marker is a split intein linked to an N-terminus of the antibiotic resistance protein or split intein linked to a C-terminus of the antibiotic resistance protein.

[263] The polynucleotide construct of any one of the preceding embodiments, wherein the selectable marker is a leucine zipper linked to an N-terminus of the antibiotic resistance protein or leucine zipper linked to a C-terminus of the antibiotic resistance protein.

[264] The polynucleotide construct of any one of the preceding embodiments, wherein the antibiotic resistance protein is for puromycin resistance or blasticidin resistance.

[265] The polynucleotide construct of any one of embodiments 216-264 further comprising a sequence of the polynucleotide construct of any one of embodiments 1-112.

[266] The polynucleotide construct of any one of embodiments 216-265 further comprising a sequence of the polynucleotide sequence of any one of embodiments 119-209.

[267] The polynucleotide construct of any one of embodiments 216-266 in a vector.

[268] The polynucleotide construct of any one of embodiments 216-266 in a plasmid.

[269] The polynucleotide construct of any one of embodiments 216-266 in a bacterial artificial chromosome or yeast artificial chromosome.

[270] The polynucleotide construct of any one of embodiments 216-269, wherein the polynucleotide construct is a synthetic nucleic acid construct.

[271] The polynucleotide construct of any one of embodiments 216-270 comprising a sequence having at least 70%, 80%, 90%, 95%, 99%, or 100% sequence identity to any one of SEQ ID NO: 13-SEQ ID NO: 19 or SEQ ID 23-SEQ ID NO: 26.

[272] A cell comprising the polynucleotide construct of any one of embodiments 216-271.

[273] The cell of embodiment 272, wherein the polynucleotide construct is stably integrated into the genome of the cell.

[274] The cell of any one of embodiments 272-273, wherein the cell is a mammalian cell or insect cell.

[275] The cell of any one of embodiments 272-273, wherein the cell is a HEK293 cell, HeLa cell, CHO cell, or SF9 cell.

[276] The cell of any one of embodiments 272-275, wherein the cell expresses E1A protein and E1B protein.

[277] The cell of any one of embodiments 272-276, wherein the cell is DHFR null.

[278] A cell comprising the polynucleotide construct of any one of embodiments 1-112 and the polynucleotide construct of any one of embodiments 119-209.

[279] A cell comprising the polynucleotide construct of any one of embodiments 1-112 and the polynucleotide construct of any one of embodiments 216-271.

[280] A cell comprising the polynucleotide construct of any one of embodiments Z and the polynucleotide construct of any one of embodiments 119-209.

[281] A cell comprising the polynucleotide construct of any one of embodiments 1-112, the polynucleotide sequence of any one of embodiments 119-209, and the polynucleotide construct of any one of embodiments 216-271.

[282] The cell of any one of embodiments 278-281, wherein the polynucleotide construct of any one of embodiments 1-112 is stably integrated into the genome of the cell.

[283] The cell of any one of embodiments 278-282, wherein the polynucleotide construct of any one of embodiments 119-209 is stably integrated into the genome of the cell.

[284] The cell of any one of embodiments 278-283, wherein the polynucleotide construct of any one of embodiments 216-271 is stably integrated into the genome of the cell.

[285] The cell of any one of embodiments 278-284, wherein the polynucleotide construct of any one of embodiments 1-112 and the polynucleotide construct of any one of embodiments 119-209 are separately stably integrated into the genome of the cell.

[286] The cell of any one of embodiments 278-285, wherein the polynucleotide construct of any one of embodiments 1-112 and the polynucleotide construct of any one of embodiments 216-271 are separately stably integrated into the genome of the cell.

[287] The cell of any one of embodiments 278-286, wherein the polynucleotide construct of any one of embodiments 216-271 and the polynucleotide construct of any one of embodiments 119-209 are separately stably integrated into the genome of the cell.

[288] The cell of any one of embodiments 278-287, wherein a plurality of the polynucleotide construct of any one of embodiments 1-112 are stably integrated into the genome of the cell.

[289] The cell of any one of embodiments 278-288, wherein a plurality of the polynucleotide construct of any one of embodiments 119-209 are stably integrated into the genome of the cell.

[290] The cell of any one of embodiments 278-289, wherein a plurality of the polynucleotide construct of any one of embodiments 216-271 are stably integrated into the genome of the cell.

[291] The cell of any one of embodiments 278-290, wherein a plurality of the polynucleotide construct of any one of embodiments 1-112 and a plurality of the polynucleotide construct of any one of embodiments 119-209 are stably integrated into the genome of the cell.

[292] The cell of any one of embodiments 278-291, wherein a plurality of the polynucleotide construct of any one of embodiments 1-112, a plurality of the polynucleotide construct of any one of embodiments 119-209, and a plurality of the polynucleotide construct of any one of embodiments 216-271 are stably integrated into the genome of the cell.

[293] The cell of any one of embodiments 278-292, wherein a plurality of the polynucleotide construct of any one of embodiments 1-112 are separately stably integrated into the genome of the cell.

[294] The cell of any one of embodiments 278-293, wherein a plurality of the polynucleotide construct of any one of embodiments 119-209 are separately stably integrated into the genome of the cell.

[295] The cell of any one of embodiments 278-294, wherein a plurality of the polynucleotide construct of any one of embodiments 216-271 are separately stably integrated into the genome of the cell.

[296] The cell of any one of embodiments 278-295, wherein a plurality of the polynucleotide construct of any one of embodiments 1-112 and a plurality of the polynucleotide construct of any one of embodiments 119-209 are separately stably integrated into the genome of the cell.

[297] The cell of any one of embodiments 278-296, wherein a plurality of the polynucleotide construct of any one of embodiments 1-112, a plurality of the polynucleotide construct of any one of embodiments 119-209, and a plurality of the polynucleotide construct of any one of embodiments 216-271 are separately stably integrated into the genome of the cell.

[298] The cell of any one of embodiments 278-297, wherein only a single non-auxotrophic selection is required to maintain a stable integration of the polynucleotide construct of any one of embodiments 1-112 and the polynucleotide construct of 119-209 in the genome of the cell.

[299] The cell of any one of embodiments 278-298, wherein only a single non-auxotrophic selection is required to maintain a stable integration of the polynucleotide construct of any one of embodiments 1-112 and the polynucleotide construct of 216-271 in the genome of the cell.

[300] The cell of any one of embodiments 278-299, wherein only a single non-auxotrophic selection is required to maintain a stable integration of the polynucleotide construct of any one of embodiments 216-271 and the polynucleotide construct of 119-209 in the genome of the cell.

[301] The cell of any one of embodiments 278-300, wherein the cell is a mammalian cell or insect cell.

[302] The cell of any one of embodiments 278-301, wherein the cell is a HEK293 cell, HeLa cell, CHO cell, or SF9 cell.

[303] The cell of any one of embodiments 278-302, wherein the cell expresses E1A protein and E1B protein.

[304] The cell of any one of embodiments 278-303, further comprising a payload construct.

[305] The cell of embodiment 304, wherein the payload construct comprises a sequence having at least 70%, 80%, 90%, 95%, 99%, or 100% sequence identity to SEQ ID NO: 33.

[306] The cell of any one of embodiments 304-305, wherein the payload construct comprises a sequence of a payload flanked by ITR sequences.

[307] The cell of any one of the preceding embodiments, wherein expression of the sequence of the payload is driven by a constitutive promoter.

[308] The cell of any one of the preceding embodiments, wherein the constitutive promoter and sequence of the payload are flanked by ITR sequences.

[309] The cell of any one of the preceding embodiments, wherein the sequence of the payload comprises a polynucleotide sequence coding for a gene.

[310] The cell of any one of the preceding embodiments, wherein the gene codes for a selectable marker or detectable marker.

[311] The cell of any one of the preceding embodiments, wherein the gene codes for a therapeutic polypeptide or transgene.

[312] The cell of any one of the preceding embodiments, wherein the sequence of the payload comprises a polynucleotide sequence coding for a therapeutic polynucleotide.

[313] The cell of any one of the preceding embodiments, wherein the therapeutic polynucleotide is a tRNA suppressor or a guide RNA.

[314] The cell of any one of the preceding embodiments, wherein the guide RNA is a polyribonucleotide capable of binding to a protein.

[315] The cell of any one of the preceding embodiments, wherein the protein is nuclease.

[316] The cell of any one of the preceding embodiments, wherein the protein is a Cas protein, an ADAR protein, or an ADAT protein.

[317] The cell of any one of the preceding embodiments, wherein the Cas protein is catalytically inactive Cas protein.

[318] The cell of any one of the preceding embodiments, wherein the payload construct is stably integrated into the genome of the cell.

[319] The cell of any one of the preceding embodiments, wherein a plurality of the payload construct are stably integrated into the genome of the cell.

[320] The cell of any one of the preceding embodiments, wherein the plurality of the payload constructs are separately stably integrated into the genome of the cell.

[321] The cell of any one of the preceding embodiments, wherein the payload construct further comprises a sequence coding for a selectable marker or detectable marker outside of the ITR sequences.

[322] The polynucleotide construct of any one of the preceding embodiments, wherein the selectable marker is a mammalian cell selection element.

[323] The polynucleotide construct of any one of the preceding embodiments, wherein the selectable marker is an auxotrophic selection element.

[324] The polynucleotide construct of any one of the preceding embodiments, wherein the auxotrophic selection element codes for an active protein.

[325] The polynucleotide construct of any one of the preceding embodiments, wherein the active protein is DHFR.

[326] The polynucleotide construct of any one of the preceding embodiments, wherein the auxotrophic selection coding sequence encodes an inactive protein that requires expression of a second auxotrophic selection coding sequence for activity.

[327] The polynucleotide construct of any one of the preceding embodiments, wherein the second auxotrophic selection coding sequence encodes for DHFR Z-Cter or DHFR Z-Nter.

[328] The polynucleotide construct of embodiment 327, wherein the inactive protein comprises a DHFR Z-Nter or DHFR Z-Cter

[329] The polynucleotide construct of any one of embodiments 327-328, wherein the selectable marker is DHFR Z-Nter or DHFR Z-Cter.

[330] The polynucleotide construct of any one of embodiments 327-329, wherein the DHFR Z-Nter comprises a sequence having at least 70%, 80%, 90%, 95%, 99%, or 100% sequence identity to SEQ ID NO: 4.

[331] The polynucleotide construct of any one of embodiments 327-330, wherein the DHFR Z-Cter comprises a sequence having at least 70%, 80%, 90%, 95%, 99%, or 100% sequence identity to SEQ ID NO: 5.

[332] The cell of any one of the preceding embodiments, wherein the selectable marker is an antibiotic resistance protein.

[333] The cell of any one of the preceding embodiments, wherein the selectable marker outside of the ITR sequences is a split intein linked to an N-terminus of the antibiotic resistance protein or split intein linked to a C-terminus of the antibiotic resistance protein.

[334] The cell of any one of the preceding embodiments, wherein the selectable marker outside of the ITR sequences is a leucine zipper linked to an N-terminus of the antibiotic resistance protein or leucine zipper linked to a C-terminus of the antibiotic resistance protein.

[335] The cell of any one of the preceding embodiments, wherein the antibiotic resistance protein is for puromycin resistance or blasticidin resistance.

[336] The cell of any one of the preceding embodiments, wherein only a single non-auxotrophic selection is required to maintain a stable integration of the polynucleotide construct of any one of embodiments 1-112, the polynucleotide construct of 119-209, and the payload construct of any one of the preceding embodiments in the genome of the cell.

[337] The cell of any one of the preceding embodiments, wherein only a single non-auxotrophic selection is required to maintain a stable integration of the polynucleotide construct of any one of embodiments 1-112, the polynucleotide construct of any one of embodiments 216-271, and the payload construct of any one of the preceding embodiments in the genome of the cell.

[338] The cell of any one of the preceding embodiments, wherein only a single non-auxotrophic selection is required to maintain a stable integration of the polynucleotide construct of any one of embodiments 216-271, the polynucleotide construct of 119-209, and the payload construct of any one of the preceding embodiments in the genome of the cell.

[339] The cell of any one of the preceding embodiments, wherein the payload construct is in a plasmid.

[340] The cell of any one of the preceding embodiments, wherein the payload construct is in a bacterial artificial chromosome or yeast artificial chromosome.

[341] The cell of any one of the preceding embodiments, wherein the payload construct is stably integrated into the genome of the cell.

[342] The cell of any one of the preceding embodiments, wherein the payload construct is a synthetic nucleic acid construct.

[343] The cell of any one of the preceding embodiments, wherein the cell is capable of producing an rAAV virion that encapsidates the sequence of the payload.

[344] The cell of any one of the preceding embodiments, wherein the cell is capable of producing an rAAV virion upon addition of at least one triggering agent.

[345] The cell of any one of the preceding embodiments, wherein the rAAV virion comprising the capsid protein and the payload nucleic acid sequence have an infectivity of no less than 50%, 60%, 70%, 80%, 90%, 95%, or 99% at an MOI of $1\times10^5$ vg/target cell or less.

[346] The cell of any one of the preceding embodiments, wherein the rAAV virions have an increased infectivity compared rAAV virions produced by an otherwise comparable the population of cells capable of producing rAAV virions upon transient transfection at the same MOI.

[347] The cell of any one of the preceding embodiments, wherein the rAAV virions have at least 1%, 5%, 10%, 15%, 20%, 30%, 40%, or 50% greater infectivity compared rAAV virions produced by an otherwise comparable the population of cells capable of producing rAAV virions upon transient transfection at the same MOI.

[348] The cell of any one of the preceding embodiments, wherein the rAAV virions have at least 50%, 60%, 70%, 80%, 90%, 95%, 97%, 98%, 99%, or 100% infectivity as compared to AAV virions produced by a cell having wildtype AAV at the same MOI.

[349] The cell of any one of the preceding embodiments, wherein the rAAV virions have at least 50%, 60%, 70%, 80%, 90%, 95%, 97%, 98%, 99%, or 100% infectivity as compared to AAV virions at the same MOI.

[350] The cell of any one of the preceding embodiments, wherein the AAV virions are wildtype AAV virions produced by a cell having wildtype AAV.

[351] The cell of any one of the preceding embodiments, wherein the MOI is $1\times10^1$, $1\times10^2$, $2\times10^3$, $5\times10^4$, or $1\times10^5$ vg/target cell.

[352] The cell of any one of the preceding embodiments, wherein the MOI is selected from a range of $1\times10^1$ to $1\times10^5$ vg/target cell.

[353] The cell of any one of the preceding embodiments, wherein the cell is conditionally capable of producing rAAV virions having an encapsidation ratio of no less than 0.5, 0.6, 0.7, 0.8, 0.9, 0.95, 0.97, or 0.99.

[354] The cell of any one of the preceding embodiments, wherein the rAAV virions have an encapsidation ratio of no less than 0.5, 0.6, 0.7, 0.8, 0.9, 0.95, 0.97, or 0.99 prior to purification.

[355] The cell of any one of the preceding embodiments, wherein the rAAV virions have a concentration of greater than $1\times10^{11}$ or no less than $5\times10^{11}$, $1\times10^{12}$, $5\times10^{12}$, $1\times10^{13}$ or $1\times10^{14}$ viral genomes per milliliter prior to purification.

[356] The cell of any one of the preceding embodiments, wherein the cell is capable of producing rAAV virions comprising the payload nucleic acid sequence at a titer of greater than $1\times10^{11}$ or no less than $5\times10^{11}$, $1\times10^{12}$, $5\times10^{12}$, $1\times10^{13}$ or $1\times10^{14}$ viral genomes per milliliter.

[357] The cell of any one of the preceding embodiments, wherein the cell is capable of producing rAAV virions comprising the payload nucleic acid sequence at a concentration of greater than $1\times10^{11}$ or no less than $5\times10^{11}$, $1\times10^{12}$, $5\times10^{12}$, $1\times10^{13}$ or $1\times10^{14}$ viral genomes per milliliter prior to purification.

[358] A population of cells capable of producing rAAV virions having an encapsidation ratio of no less than 0.5, 0.6, 0.7, 0.8, 0.9, 0.95, 0.97, or 0.99.

[359] A population of cells comprising the polynucleotide construct of any one of embodiments 1-112 and the polynucleotide construct of any one of embodiments 119-209.

[360] A population of cells comprising the polynucleotide construct of any one of embodiments 1-112 and the polynucleotide construct of any one of embodiments 216-271.

[361] A population of cells comprising the polynucleotide construct of any one of embodiments 216-271 and the polynucleotide construct of any one of embodiments 119-209.

[362] A population of cells comprising the polynucleotide construct of any one of embodiments 1-112, the polynucleotide sequence of any one of embodiments 119-209, and the polynucleotide construct of any one of embodiments 216-271.

[363] The population of cells of any one of the preceding embodiments, wherein the polynucleotide construct of any one of embodiments 1-112 is stably integrated into the genome of the population of cells.

[364] The population of cells of any one of the preceding embodiments, wherein the polynucleotide construct of any one of embodiments 119-209 is stably integrated into the genome of the cell.

[365] The population of cells of any one of the preceding embodiments, wherein the polynucleotide construct of any one of embodiments 216-271 is stably integrated into the genome of the cell.

[366] The population of cells of any one of the preceding embodiments, wherein the payload construct of any one of preceding embodiments is stably integrated into the genome of the population of cells.

[367] The population of cells of any one of the preceding embodiments, wherein the population of cells are a plurality of a cell of any one the preceding embodiments.

[368] The population of cells of any one of the preceding embodiments, wherein the population of cells are a population of mammalian cells or a population of insect cells.

[369] The population of cells of any one of the preceding embodiments, wherein the population of cells are a population of HEK293 cells, HeLa cells, CHO cells, or SF9 cells.

[370] The population of cells of any one of the preceding embodiments, wherein the cell expresses E1A protein and E1B protein.

[371] The population of cells of any one of the preceding embodiments, further comprising a payload construct.

[372] The population of cells of any one of the preceding embodiments, wherein the payload construct comprises a sequence of a payload flanked by ITR sequences.

[373] The population of cells of any one of the preceding embodiments, wherein expression of the payload is driven by a constitutive promoter.

[374] The population of cells of any one of the preceding embodiments, wherein the constitutive promoter and sequence of the payload are flanked by ITR sequences.

[375] The population of cells of any one of the preceding embodiments, wherein the payload comprises a polynucleotide sequence encoding a gene.

[376] The population of cells of any one of the preceding embodiments, wherein the gene codes for a selectable marker or detectable marker.

[377] The population of cells of any one of the preceding embodiments, wherein the gene codes for a therapeutic polypeptide or transgene.

[378] The population of cells of any one of the preceding embodiments, wherein the payload comprises a polynucleotide sequence coding for a therapeutic polynucleotide.

[379] The population of cells of any one of the preceding embodiments, wherein the therapeutic polynucleotide is a tRNA suppressor or a guide RNA.

[380] The population of cells of any one of the preceding embodiments, wherein the guide RNA is a polyribonucleotide capable of binding to a protein.

[381] The population of cells of any one of the preceding embodiments, wherein the protein is nuclease.

[382] The population of cells of any one of the preceding embodiments, wherein the protein is a Cas protein, an ADAR protein, or an ADAT protein.

[383] The population of cells of any one of the preceding embodiments, wherein the Cas protein is catalytically inactive Cas protein.

[384] The population of cells of any one of the preceding embodiments, wherein the payload construct is stably integrated into the genome of the cell.

[385] The population of cells of any one of the preceding embodiments, wherein the payload construct further comprises a sequence coding for a selectable marker or detectable marker outside of the ITR sequences.

[386] The population of cells of any one of the preceding embodiments, wherein the selectable marker is an antibiotic resistance protein.

[387] The population of cells of any one of the preceding embodiments, wherein the selectable marker outside of the ITR sequences is a split intein linked to an N-terminus of the antibiotic resistance protein or split intein linked to a C-terminus of the antibiotic resistance protein.

[388] The population of cells of any one of the preceding embodiments, wherein the selectable marker outside of the ITR sequences is a leucine zipper linked to an N-terminus of the antibiotic resistance protein or leucine zipper linked to a C-terminus of the antibiotic resistance protein.

[389] The population of cells of any one of the preceding embodiments, wherein the antibiotic resistance protein is for puromycin resistance or blasticidin resistance.

[390] The population of cells of any one of the preceding embodiments, wherein the payload construct is in a plasmid.

[391] The population of cells of any one of the preceding embodiments, wherein the payload construct is in a bacterial artificial chromosome or yeast artificial chromosome.

[392] The population of cells of any one of the preceding embodiments, wherein the payload construct is stably integrated into the genomes of the population of cells.

[393] A population of cells produced by expanding a cell of any one of the preceding embodiments.

[394] The population of cells of any one of the preceding embodiments, wherein expanding comprises passaging the cell at least three times.

[395] The population of cells of any one the preceding embodiments, wherein a cell of the population of cells is capable of conditionally producing recombinant AAV (rAAV) virions upon addition of at least two triggering agents.

[396] The population of cells of any one the preceding embodiments, wherein the cell is capable of conditionally producing rAAV virions upon addition of at least two triggering agents.

[397] The population of cells of any one the preceding embodiments, wherein the at least two triggering agents comprise doxycycline and tamoxifen.

[398] The population of cells of any one the preceding embodiments, wherein the at least two triggering agents induce the expression and translocation of an excising element to the nucleus.

[399] The population of cells of any one the preceding embodiments, wherein a cell of the population of cells is capable of conditionally producing rAAV virions upon addition of an excising element.

[400] The population of cells of any one the preceding embodiments, wherein the excising element is a recombinase.

[401] The population of cells of any one the preceding embodiments, wherein the excising element is a site-specific recombinase.

[402] The population of cells of any one the preceding embodiments, wherein the excising element is a Cre polypeptide or a flippase polypeptide.

[403] The population of cells of any one of the preceding embodiments, wherein the excising element is hormone regulated.

[404] The population of cells of any one of the preceding embodiments, wherein the population of cells are conditionally capable of producing rAAV virions within which are packaged an expressible polynucleotide encoding a payload; and wherein a population of virions produced by the population of cells are more homogenous than a population of virions produced by an otherwise comparable the population of cells capable of producing rAAV virions upon transient transfection.

[405] The population of cells of any one of the preceding embodiments, wherein the population of virions produced by the population of cells has a ratio of viral genomes to transduction units of about 500:1 to 1:1.

[406] The population of cells of any one of the preceding embodiments, wherein the population of virions produced by the population of cells has a ratio of vector genomes to infectious unit of 100:1.

[407] The population of cells of any one of the preceding embodiments, wherein production of virions is inducible upon addition of a triggering agent.

[408] The population of cells of any one of the preceding embodiments, wherein production of virions is inducible upon addition of at least two triggering agents.

[409] The population of cells of any one the preceding embodiments, wherein the population of cells is conditionally capable of producing rAAV virions having an encapsidation ratio of no less than 0.5, 0.6, 0.7, 0.8, 0.9, 0.95, 0.97, or 0.99.

[410] The population of cells of any one the preceding embodiments, wherein the rAAV virions have an encapsidation ratio of no less than 0.5, 0.6, 0.7, 0.8, 0.9, 0.95, 0.97, or 0.99 prior to purification.

[411] The population of cells of any one the preceding embodiments, wherein the population of cells are capable of reaching a viable cell density of no less than $1\times10^6$, $2\times10^6$, $5\times10^6$, or $1\times10^7$ cells per milliliter.

[412] The population of cells of any one the preceding embodiments, wherein the rAAV virions have a concentration of greater than $1\times10^{11}$ or no less than $5\times10^{11}$, $1\times10^{12}$, $5\times10^{12}$, $1\times10^{13}$ or $1\times10^{14}$ viral genomes per milliliter prior to purification.

[413] The population of cells of any one the preceding embodiments, wherein the population of cells is capable of producing rAAV virions comprising the payload nucleic acid sequence at a titer of greater than $1\times10^{11}$ or no less than $5\times10^{11}$, $1\times10^{12}$, $5\times10^{12}$, $1\times10^{13}$ or $1\times10^{14}$ viral genomes per milliliter.

[414] The population of cells of any one the preceding embodiments, wherein the population of cells is capable of producing rAAV virions comprising the payload nucleic acid sequence at a concentration of greater than $1\times10^{11}$ or no less than $5\times10^{11}$, $1\times10^{12}$, $5\times10^{12}$, $1\times10^{13}$ or $1\times10^{14}$ viral genomes per milliliter prior to purification.

[415] The population of cells of any one the preceding embodiments, wherein the rAAV virions comprising the capsid protein and the payload nucleic acid sequence have an infectivity of no less than 50%, 60%, 70%, 80%, 90%, 95%, or 99% at an MOI of $1\times10^5$ vg/target cell or less.

[416] The population of cells of any one the preceding embodiments, wherein the rAAV virions have an increased infectivity compared rAAV virions produced by an otherwise comparable the population of cells capable of producing rAAV virions upon transient transfection at the same MOI.

[417] The population of cells of any one the preceding embodiments, wherein the rAAV virions have at least 1%, 5%, 10%, 15%, 20%, 30%, 40%, or 50% greater infectivity compared rAAV virions produced by an otherwise comparable the population of cells capable of producing rAAV virions upon transient transfection at the same MOI.

[418] The population of cells of any one the preceding embodiments, wherein the rAAV virions have at least 50%, 60%, 70%, 80%, 90%, 95%, 97%, 98%, 99%, or 100% infectivity as compared AAV virions AAV at the same MOI.

[419] The population of cells of any one of the preceding embodiments, wherein the AAV virions are wildtype AAV virions produced by a cell having wildtype AAV.

[420] The population of cells of any one the preceding embodiments, wherein the MOI is $1\times10^1$, $1\times10^2$, $2\times10^3$, $5\times10^4$, or $1\times10^5$ vg/target cell.

[421] The population of cells of any one the preceding embodiments, wherein the MOI is selected from a range of $1\times10^1$ to $1\times10^5$ vg/target cell.

[422] The population of cells of any one the preceding embodiments, wherein the cells are cryopreserved.

[423] The population of cells of any one the preceding embodiments, wherein the cells are comprised within a vial, flask, syringe, or other suitable cell-storage container.

[424] The population of cells of any one the preceding embodiments, wherein production of rAAV virions is inducible in the absence of a plasmid.

[425] The population of cells of any one the preceding embodiments, wherein expression of AAV Rep and Cap proteins is inducible in the absence of a plasmid.

[426] The population of cells of any one the preceding embodiments, wherein expression of the at least one or more helper proteins is inducible in the absence of a plasmid.

[427] The population of cells of any one the preceding embodiments, wherein production of rAAV virions is inducible in the absence of a transfection agent.

[428] The population of cells of any one the preceding embodiments, wherein expression of AAV Rep and Cap proteins is inducible in the absence of a transfection agent.

[429] The population of cells of any one the preceding embodiments, wherein expression of the at least one or more helper proteins is inducible in the absence of a transfection agent.

[430] A second population of cell produced by expanding the population of cells of any one of the preceding embodiments.

[431] The second population of cells of embodiment 430, wherein expanding the population of cells comprises passaging the population of cells at least three times.

[432] The second population of cells of embodiment 430, wherein expanding the population of cells comprises passaging the population of cells from 3 to 60 times.

[433] The second population of cells of embodiment 430, wherein expanding the population of cells comprises passaging the population of cells at least 4, 5, 6, 7, 8, 9, 10, 15, 20, 25, 30, 35, 40, 45, 50, 55, or 60 times.

[434] A stable cell line comprising the population of cells of any one of the preceding embodiments.

[435] The stable cell line of embodiment 434, wherein the population of cells are derived from a single cell.

[436] A stable cell line comprising the population of cells of any one of the preceding embodiments.

[437] The stable cell line of any one of the preceding embodiments, wherein the population of cells are derived from a single cell.

[438] The stable cell line of any one of the preceding embodiments, wherein the single cell is the of any one of the preceding embodiments.

[439] The stable cell line of any one of the preceding embodiments, wherein at least 70%, 80%, 90%, 95%, 99%, or 100% of the cells of the stable cell line are the population of cells of any one of the preceding embodiments.

[440] A stable cell line derived from the cell of any one of the preceding embodiments.

[441] A stable cell line expanded from the cell of any one of the preceding embodiments.

[442] The stable cell line of any one of the preceding embodiments, wherein the stable cell line is a mammalian stable cell line.

[443] The stable cell line of any one of the preceding embodiments, wherein expression of one or more helper proteins is inducible in the absence of a plasmid.

[444] The stable cell line of any one of the preceding embodiments, wherein expression of one or more helper proteins is inducible in the absence of a transfection agent.

[445] The stable cell line of any one of the preceding embodiments, wherein expression of AAV Rep and Cap proteins is inducible in the absence of a plasmid.

[446] The stable cell line of any one of the preceding embodiments, wherein expression of AAV Rep and Cap proteins is inducible in the absence of a transfection agent.

[447] The stable cell line of any one of the preceding embodiments, wherein production of rAAV virions is inducible in the absence of a plasmid.

[448] The stable cell line of any one of the preceding embodiments, wherein production of rAAV virions is inducible in the absence of a transfection agent.

[449] The stable cell line of any one of the preceding embodiments, wherein the stable cell line is capable of producing rAAV virions comprising the payload nucleic acid sequence at a concentration of greater than $1\times10^{11}$ or no less than $5\times10^{11}$, $1\times10^{12}$, $5\times10^{12}$, $1\times10^{13}$ or $1\times10^{14}$ viral genomes per milliliter.

[450] The stable cell line of any one of the preceding embodiments, wherein the stable cell line is capable of producing rAAV virions comprising the payload nucleic acid sequence at a concentration of greater than $1\times10^{11}$ or no less than $5\times10^{11}$, $1\times10^{12}$, $5\times10^{12}$, $1\times10^{13}$ or $1\times10^{14}$ viral genomes per milliliter prior to purification.

[451] The stable cell line of any one of the preceding embodiments, wherein the stable cell line is conditionally capable of producing rAAV virions having an encapsidation ratio of no less than 0.5, 0.6, 0.7, 0.8, 0.9, 0.95, 0.97, or 0.99.

[452] The stable cell line of any one of the preceding embodiments, wherein the rAAV virions have an encapsidation ratio of no less than 0.5, 0.6, 0.7, 0.8, 0.9, 0.95, 0.97, or 0.99 prior to purification.

[453] The stable cell line of any one of the preceding embodiments, wherein the rAAV virions comprising the capsid protein and the payload nucleic acid sequence have an infectivity of no less than 50%, 60%, 70%, 80%, 90%, 95%, or 99%. at an MOI of $1\times10^{5}$ vg/target cell or less

[454] The stable cell line of any one of the preceding embodiments, wherein the rAAV virions have an increased infectivity compared rAAV virions produced by an otherwise comparable the population of cells capable of producing rAAV virions upon transient transfection at the same MOI.

[455] The stable cell line of any one of the preceding embodiments, wherein the rAAV virions have at least 1%, 5%, 10%, 15%, 20%, 30%, 40%, or 50% greater infectivity compared rAAV virions produced by an otherwise comparable the population of cells capable of producing rAAV virions upon transient transfection at the same MOI.

[456] The stable cell line of any one of the preceding embodiments, wherein the rAAV virions have at least 50%, 60%, 70%, 80%, 90%, 95%, 97%, 98%, 99%, or 100% infectivity as compared to AAV virions produced by a cell having wildtype AAV at the same MOI.

[457] The stable cell line of any one of the preceding embodiments, wherein the rAAV virions have at least 50%, 60%, 70%, 80%, 90%, 95%, 97%, 98%, 99%, or 100% infectivity as compared to AAV virions at the same MOI.

[458] The stable cell line of any one of the preceding embodiments, wherein the AAV virions are wildtype AAV virions produced by a cell having wildtype AAV.

[459] The stable cell line of any one of the preceding embodiments, wherein the MOI is $1\times10^1$, $1\times10^2$, $2\times10^3$, $5\times10^4$, or $1\times10^5$ vg/target cell.

[460] The stable cell line of any one of the preceding embodiments, wherein the MOI is selected from a range of $1\times10^1$ to $1\times10^5$ vg/target cell.

[461] The stable cell line of any one of the preceding embodiments, wherein at least one cell of the stable cell line is cryopreserved.

[462] The stable cell line of any one of the preceding embodiments, wherein at least one cell of the stable cell line is in a vial, flask, syringe, or other suitable cell-storage container.

[463] A cell culture composition comprising:

a) suspension-adapted cells, b) serum-free cell culture media, and c) recombinant AAV (rAAV) virions, wherein the cell culture composition is free of herpes simplex virus, baculovirus, and adenovirus, and wherein the cell culture composition is free of plasmid and transfection agent.

[464] The cell culture composition of any one of the preceding embodiments, wherein the cell culture composition is free of polyethylenimine (PEI).

[465] The cell culture composition of any one of the preceding embodiments, wherein the suspension-adapted cells are suspension-adapted mammalian cells.

[466] The cell culture composition of any one of the preceding embodiments, wherein the suspension-adapted cells are suspension-adapted HEK293 cells or derivatives thereof.

[467] The cell culture composition of any one of the preceding embodiments, wherein the suspension-adapted mammalian cells are cells from the stable cell line of any one of the preceding embodiments, the population of cells of any one of the preceding embodiments, or comprise a cell of any one of the preceding embodiments.

[468] The cell culture composition of any one of the preceding embodiments, wherein the cell culture composition has a prepurification rAAV concentration of no less than $1\times10^{14}$ $2\times10^{14}$, $3\times10^{14}$, $4\times10^{14}$, $5\times10^{14}$, $6\times10^{14}$, $7\times10^{14}$, $8\times10^{14}$, $9\times10^{14}$, $1\times10^{15}$, or $5\times10^{15}$ viral genome (vg)/L.

[469] The cell culture composition of any one of the preceding embodiments, wherein the cell culture composition has a prepurification rAAV encapsidation ratio of no less than 0.5, 0.6, 0.7, 0.8, 0.9, 0.95, 0.97, or 0.99.

[470] A bioreactor comprising the stable cell line of any one of the preceding embodiments.

[471] A bioreactor comprising the population of cells of any one of the preceding embodiments.

[472] A bioreactor comprising the cell of any one of the preceding embodiments.

[473] A bioreactor containing the cell culture of any one of the preceding embodiments.

[474] The bioreactor of any one of the preceding embodiments, wherein the bioreactor is a 1 L bioreactor.

[475] The bioreactor of any one of the preceding embodiments, wherein the bioreactor is a 1 L bioreactor.

[476] The bioreactor of any one of the preceding embodiments, wherein the bioreactor has a total rAAV yield of greater than $1\times10^{14}$ viral genome (vg).

[477] The bioreactor of any one of the preceding embodiments, wherein the bioreactor is a 5 L bioreactor.

[478] The bioreactor of any one of the preceding embodiments, wherein the bioreactor has a total rAAV yield of greater than $5\times10^{14}$ viral genome (vg).

[479] The bioreactor of any one of the preceding embodiments, wherein the bioreactor is a 50 L bioreactor.

[480] The bioreactor of any one of the preceding embodiments, wherein the bioreactor has a total rAAV yield of greater than $5\times10^{15}$ viral genome (vg).

[481] The bioreactor of any one of the preceding embodiments, wherein the bioreactor is a 100 L bioreactor.

[482] The bioreactor of any one of the preceding embodiments, wherein the bioreactor has a total rAAV yield of greater than $1\times10^{16}$ viral genome (vg).

[483] The bioreactor of any one of the preceding embodiments, wherein the bioreactor is a 500 L bioreactor.

[484] The bioreactor of any one of the preceding embodiments, wherein the bioreactor has a total rAAV yield of greater than $5\times10^{16}$ viral genome (vg).

[485] The bioreactor of any one of the preceding embodiments, wherein the bioreactor is a 2000 L bioreactor.

[486] The bioreactor of any one of the preceding embodiments, wherein the bioreactor has a total rAAV yield of greater than $2\times10^{17}$ viral genome (vg).

[487] A bioreactor comprising a plurality of rAAV virions having a concentration of greater than $1\times10^{14}$, $2\times10^{14}$, $3\times10^{14}$, $4\times10^{14}$, $5\times10^{14}$, $6\times10^{14}$, $7\times10^{14}$, $8\times10^{14}$, $9\times10^{14}$, $1\times10^{15}$, or $5\times10^{15}$ viral genome (vg)/L.

[488] A bioreactor comprising a plurality of rAAV virions having a prepurification concentration of greater than $1\times10^{14}$, $2\times10^{14}$, $3\times10^{14}$, $4\times10^{14}$, $5\times10^{14}$, $6\times10^{14}$, $7\times10^{14}$ $8\times10^{14}$, $9\times10^{14}$, $1\times10^{15}$, or $5\times10^{15}$ viral genome (vg)/L.

[489] The bioreactor of any one of the preceding embodiments, wherein the bioreactor is a 1 L, 5 L, 50 L, 100 L, 500 L, or 2000 L bioreactor.

[490] The bioreactor of any one of the preceding embodiments, wherein the bioreactor is a single use bioreactor.

[491] A composition comprising a plurality of rAAV virions encapsidating a viral genome, wherein the composition has a prepurification concentration of greater than $1\times10^{11}$ or no less than $5\times10^{11}$, $1\times10^{12}$, $5\times10^{12}$, $1\times10^{13}$ or $1\times10^{14}$ viral genomes per milliliter.

[492] A composition comprising a plurality of rAAV virions encapsidating a viral genome, wherein the composition has a prepurification encapsidation ratio of no less than 0.5, 0.6, 0.7, 0.8, 0.9, 0.95, 0.97, or 0.99.

[493] A composition comprising an rAAV virion encapsidating a viral genome, wherein the composition has an infectivity of no less than 50%, 60%, 70%, 80%, 90%, 95%, or 99% at an MOI of $1\times10^5$ vg/target cell or less.

[494] The composition of any one of the preceding embodiments, wherein the rAAV virion has an increased infectivity compared an rAAV virion produced by an otherwise comparable cell capable of producing rAAV virions upon transient transfection at the same MOI.

[495] The composition of any one of the preceding embodiments, wherein the rAAV virion has at least 1%, 5%, 10%, 15%, 20%, 30%, 40%, or 50% greater infectivity compared an rAAV virion produced by an otherwise comparable cell capable of producing rAAV virions upon transient transfection at the same MOI.

[496] The composition of any one of the preceding embodiments, wherein the rAAV virion has at least 50%, 60%, 70%, 80%, 90%, 95%, 97%, 98%, 99%, or 100% infectivity as compared an AAV virion produced by a cell having wildtype AAV at the same MOI.

[497] The composition of any one of the preceding embodiments, wherein the rAAV virion has at least 50%, 60%, 70%, 80%, 90%, 95%, 97%, 98%, 99%, or 100% infectivity as compared an AAV virion produced by a cell having wildtype AAV at the same MOI.

[498] The composition of embodiment, further comprising a plurality of the rAAV virion.

[499] The composition of any one of the preceding embodiments, wherein the plurality of rAAV virions having a prepurification concentration of greater than $1\times10^{11}$ or no less than $5\times10^{11}$, $1\times10^{12}$, $5\times10^{12}$, $1\times10^{13}$ or $1\times10^{14}$ viral genomes per milliliter.

[500] The composition of any one of the preceding embodiments, wherein the plurality of rAAV virions having a prepurification encapsidation ratio of no less than 0.5, 0.6, 0.7, 0.8, 0.9, 0.95, 0.97, or 0.99.

[501] The composition of any one of the preceding embodiments, wherein the plurality of rAAV virions have an infectivity of no less than 50%, 60%, 70%, 80%, 90%, 95%, or 99%.

[502] The composition of any one of the preceding embodiments, wherein the plurality of rAAV virions have an increased infectivity compared a plurality of rAAV virions produced by an otherwise comparable the population of cells capable of producing rAAV virions upon transient transfection at the same MOI.

[503] The composition of any one of the preceding embodiments, wherein the plurality of rAAV virions have at least 1%, 5%, 10%, 15%, 20%, 30%, 40%, or 50% greater infectivity compared a plurality of rAAV virions produced by an otherwise comparable the population of cells capable of producing rAAV virions upon transient transfection at the same MOI.

[504] The composition of any one of the preceding embodiments, wherein the plurality of rAAV virions have at least 50%, 60%, 70%, 80%, 90%, 95%, 97%, 98%, 99%, or 100% infectivity as compared a plurality of AAV virions produced by a cell having wildtype AAV at the same MOI.

[505] The composition of any one of the preceding embodiments, wherein the MOI is $1\times10^{1}$, $1\times10^{2}$, $2\times10^{3}$, $5\times10^{4}$, or $1\times10^{5}$ vg/target cell.

[506] The composition of any one of the preceding embodiments, wherein the MOI is selected from a range of $1\times10^{1}$ to $1\times10^{5}$ vg/target cell.

[507] The composition of any one of the preceding embodiments, wherein the viral genome comprises a sequence coding for a payload.

[508] The cell of any one of the preceding embodiments, wherein expression of the sequence of the payload is driven by a constitutive promoter.

[509] The cell of any one of the preceding embodiments, wherein the sequence of the payload comprises a polynucleotide sequence coding for a gene.

[510] The cell of any one of the preceding embodiments, wherein the gene codes for a selectable marker or detectable marker.

[511] The cell of any one of the preceding embodiments, wherein the gene codes for a therapeutic polypeptide or transgene.

[512] The cell of any one of the preceding embodiments, wherein the sequence of the payload comprises a polynucleotide sequence coding for a therapeutic polynucleotide.

[513] The cell of any one of the preceding embodiments, wherein the therapeutic polynucleotide is a tRNA suppressor or a guide RNA.

[514] The cell of any one of the preceding embodiments, wherein the guide RNA is a polyribonucleotide capable of binding to a protein.

[515] The cell of any one of the preceding embodiments, wherein the protein is nuclease.

[516] The cell of any one of the preceding embodiments, wherein the protein is a Cas protein, an ADAR protein, or an ADAT protein.

[517] The cell of any one of the preceding embodiments, wherein the Cas protein is catalytically inactive Cas protein.

[518] The composition of any one of the preceding embodiments, wherein the rAAV virion comprises a Cap polypeptide.

[519] The composition of any one of the preceding embodiments, wherein the Cap polypeptide is an AAV capsid protein.

[520] The composition of any one of the preceding embodiments, wherein the AAV capsid protein is VP1, VP2, or VP3.

[521] The composition of any one of the preceding embodiments, wherein a serotype of the AAV capsid protein is selected from the group consisting of AAV1, AAV2, AAV3, AAV4, AAV5, AAV6, AAV7, AAV8, AAV9, AAV 10, AAV11, AAV 12, AAV13, AAV 14, AAV 15 and AAV 16, AAV.rh8, AAV.rh10, AAV.rh20, AAV.rh39, AAV.Rh74, AAV.RHM4-1, AAV.hu37, AAV.Anc80, AAV.Anc80L65, AAV.7m8, AAV.PHP.B, AAV2.5, AAV2tYF, AAV3B, AAV.LK03, AAV.HSC1, AAV.HSC2, AAV.HSC3, AAV.HSC4, AAV.HSC5, AAV.HSC6, AAV.HSC7, AAV.HSC8, AAV.HSC9, AAV.HSC10, AAV.HSC11, AAV.HSC12, AAV.HSC13, AAV.HSC14, AAV.HSC15, AAV.HSC16, and AAVhu68.

[522] A first composition and a second composition, wherein the first composition comprises the composition of any one of the preceding embodiments and the second composition comprises the composition of any one of the preceding embodiments.

[523] The first composition and the second composition of any one of the preceding embodiments, wherein the first composition and the second composition have an encapsidation ratio that varies by no more than 20%, 10%, 5%, 4%, 3%, 2%, or 1%.

[524] The first composition and the second composition of any one of the preceding embodiments, wherein the first composition and the second composition have a concentration of viral genomes per milliliter that varies by no more than 20%, 10%, 5%, 4%, 3%, 2%, or 1%.

[525] The first composition and the second composition of any one of the preceding embodiments, wherein the first composition and the second composition have an infectivity that varies by no more than 20%, 10%, 5%, 4%, 3%, 2%, or 1%.

[526] The first composition and the second composition of any one of the preceding embodiments, wherein the first composition is a first dose and the second composition is a second dose.

[527] The first composition and the second composition of any one of the preceding embodiments, wherein the first composition is produced at least 1, 2, 3, 4, 5, 6, or 7 days before the second composition is produced.

[528] The first composition and the second composition of any one of the preceding embodiments, wherein a plurality of rAAV virions of the first composition is produced at least 1, 2, 3, 4, 5, 6, or 7 days before a plurality of rAAV virions of the second composition is produced.

[529] The first composition and the second composition of any one of the preceding embodiments, wherein the first composition is produced at least 1, 2, 3, 4, 5, 6, 7, 8, 9, 10, 11, or 12 months before the second composition is produced.

[530] The first composition and the second composition of any one of the preceding embodiments, wherein a plurality of rAAV virions of the first composition is produced at least 1, 2, 3, 4, 5, 6, 7, 8, 9, 10, 11, or 12 months before the second composition is produced.

[531] The first composition and the second composition of any one of the preceding embodiments, wherein the first composition is produced at least 1, 2, 3, 4, 5, 6, 7, 8, 9, 10, 11, or 12 years before the second composition is produced.

[532] The first composition and the second composition of any one of the preceding embodiments, wherein a plurality of rAAV virions of the first composition is produced at least 1, 2, 3, 4, 5, 6, 7, 8, 9, 10, 11, or 12 years before the second composition is produced.

[533] The first composition and the second composition of any one of the preceding embodiments, wherein the first composition is produced from a plurality of virions from a first bioreactor and the second composition is produced from a plurality of virions from a second bioreactor.

[534] The first composition and the second composition of any one of the preceding embodiments, further comprising a third composition.

[535] The first composition and the second composition of any one of the preceding embodiments, wherein the first composition, the second composition, and the third composition have an encapsidation ratio that varies by no more than 20%, 10%, 5%, 4%, 3%, 2%, or 1%.

[536] The first composition and the second composition of any one of the preceding embodiments, wherein the first composition, the second composition, and the third composition have a concentration of viral genomes per milliliter that varies by no more than 20%, 10%, 5%, 4%, 3%, 2%, or 1%.

[537] The first composition and the second composition of any one of the preceding embodiments, wherein the first composition, the second composition, and the third composition have an infectivity that varies by no more than 20%, 10%, 5%, 4%, 3%, 2%, or 1%.

[538] The first composition and the second composition of any one of the preceding embodiments, wherein the third composition is a third dose.

[539] The first composition and the second composition of any one of the preceding embodiments, wherein the third composition is produced at least 1, 2, 3, 4, 5, 6, or 7 days after the second composition is produced.

[540] The first composition and the second composition of any one of the preceding embodiments, wherein a plurality of rAAV virions of the third composition is produced at least 1, 2, 3, 4, 5, 6, or 7 days after a plurality of rAAV virions of the second composition is produced.

[541] The first composition and the second composition of any one of the preceding embodiments, wherein the third composition is produced at least 1, 2, 3, 4, 5, 6, 7, 8, 9, 10, 11, or 12 months after the second composition is produced.

[542] The first composition and the second composition of any one of the preceding embodiments, wherein a plurality of rAAV virions of the third composition is produced at least 1, 2, 3, 4, 5, 6, 7, 8, 9, 10, 11, or 12 months after the second composition is produced.

[543] The first composition and the second composition of any one of the preceding embodiments, wherein the third composition is produced at least 1, 2, 3, 4, 5, 6, 7, 8, 9, 10, 11, or 12 years after the second composition is produced.

[544] The first composition and the second composition of any one of the preceding embodiments, wherein a plurality of rAAV virions of the third composition is produced at least 1, 2, 3, 4, 5, 6, 7, 8, 9, 10, 11, or 12 years after the second composition is produced.

[545] The first composition and the second composition of any one of the preceding embodiments, wherein the third composition is produced from a plurality of virions from a third bioreactor.

[546] A pharmaceutical composition comprising the plurality of rAAV virions of any one of the preceding embodiments and a pharmaceutically acceptable carrier.

[547] A plurality of pharmaceutical doses, wherein each dose independently comprises a pharmaceutical composition of embodiment 546.

[548] The plurality of pharmaceutical doses of embodiment 547, wherein the encapsidation ratio has a difference of not more than 20%, 10%, 5%, 4%, 3%, 2%, or 1% between a first dose and a second dose.

[549] The plurality of pharmaceutical doses of any one of the preceding embodiments, wherein the concentration of viral genomes has a difference of not more than 20%, 10%, 5%, 4%, 3%, 2%, or 1% between a first dose and a second dose.

[550] The plurality of pharmaceutical doses of any one of the preceding embodiments, wherein the concentration of vector genomes has a difference of not more than 20%, 10%, 5%, 4%, 3%, 2%, or 1% between a first dose and a second dose.

[551] The plurality of pharmaceutical doses of any one of the preceding embodiments, wherein the rAAV virion infectivity has a difference of not more than 20%, 10%, 5%, 4%, 3%, 2%, or 1% between a first dose and a second dose.

[552] A method of generating a stable cell line, the method comprising:

contacting a cell to the polynucleotide construct of any one of embodiments 1-112, wherein the polynucleotide construct of any one embodiments 1-112 stably integrates into the genome of the cell; and passaging the cell to generate the stable cell line.

[553] A method of generating a stable cell line, the method comprising:

contacting a cell to the polynucleotide construct of any one of embodiments 1-112, wherein the polynucleotide construct of any one embodiments 1-112 stably integrates into the genome of the cell;

contacting the cell to the polynucleotide construct of any one of embodiments 119-209, wherein the polynucleotide construct of any one of embodiments 119-209 stably integrates into the genome of the cell; and passaging the cell to generate the stable cell line.

[554] A method of generating a stable cell line, the method comprising:

contacting a cell to the polynucleotide construct of any one of embodiments 1-112, wherein the polynucleotide construct of any one embodiments 1-112 stably integrates into the genome of the cell;

contacting the cell to the polynucleotide construct of any one of embodiments 119-209, wherein the polynucleotide construct of any one of embodiments 119-209 stably integrates into the genome of the cell; and passaging the cell to generate the stable cell line.

[555] A method of generating a stable cell line, the method comprising:

contacting a cell to the polynucleotide construct of any one of embodiments 119-209, wherein the polynucleotide construct of any one embodiments 119-209 stably integrates into the genome of the cell;

contacting the cell to the polynucleotide construct of any one of embodiments 216-271, wherein the polynucleotide construct of any one of embodiments Z stably integrates into the genome of the cell; and passaging the cell to generate the stable cell line.

[556] A method of generating a stable cell line, the method comprising:

contacting a cell to a plurality of the polynucleotide construct of any one of embodiments 1-112, wherein the plurality of polynucleotide construct of any one embodiments 1-112 stably integrates into the genome of the cell;

contacting the cell to a plurality of the polynucleotide construct of any one of embodiments 119-209, wherein the plurality of the polynucleotide construct of any one of embodiments 119-209 stably integrates into the genome of the cell; and passaging the cell to generate the stable cell line.

[557] A method of generating a stable cell line, the method comprising:

contacting a cell to a plurality of the polynucleotide construct of any one of embodiments 1-112, wherein the plurality of polynucleotide construct of any one embodiments 1-112 stably integrates into the genome of the cell;

contacting the cell to a plurality of the polynucleotide construct of any one of embodiments 216-271, wherein the plurality of the polynucleotide construct of any one of embodiments 216-271 stably integrates into the genome of the cell; and passaging the cell to generate the stable cell line.

[558] A method of generating a stable cell line, the method comprising:

contacting a cell to a plurality of the polynucleotide construct of any one of embodiments 216-271 wherein the plurality of polynucleotide construct of any one embodiments 216-271 stably integrates into the genome of the cell;

contacting the cell to a plurality of the polynucleotide construct of any one of embodiments 119-209, wherein the plurality of the polynucleotide construct of any one of embodiments 119-209 stably integrates into the genome of the cell; and passaging the cell to generate the stable cell line.

[559] A method of generating a stable cell line, the method comprising:

contacting a cell to a plurality of the polynucleotide construct of any one of embodiments 1-112, wherein the plurality of polynucleotide construct of any one embodiments 1-112 stably integrates into the genome of the cell;

contacting the cell to a plurality of the polynucleotide construct of any one of embodiments 119-209, wherein the plurality of the polynucleotide construct of any one of embodiments 119-209 stably integrates into the genome of the cell;

contacting the cell to a plurality of the polynucleotide construct of any one of embodiments 216-271, wherein the plurality of the polynucleotide construct of any one of embodiments 216-271 stably integrates into the genome of the cell; and passaging the cell to generate the stable cell line.

[560] A method of generating a stable cell line, the method comprising:

contacting a cell to a plurality of the polynucleotide construct of any one of embodiments 216-271 wherein the plurality of polynucleotide construct of any one embodiments 216-271 stably integrates into the genome of the cell;

contacting the cell to a plurality of the polynucleotide construct of any one of embodiments 1-112, wherein the plurality of the polynucleotide construct of any one of embodiments 1-112 stably integrates into the genome of the cell;

contacting the cell to a plurality of the polynucleotide construct of any one of embodiments 119-209, wherein the plurality of the polynucleotide construct of any one of embodiments 119-209 stably integrates into the genome of the cell; and passaging the cell to generate the stable cell line.

[561] The method of any one of the preceding embodiments, wherein the polynucleotide construct of any one embodiments 1-112 and the polynucleotide construct of any one embodiments 119-209 separately integrate into the genome of the cell.

[562] The method of any one of the preceding embodiments, wherein the plurality of the polynucleotide construct of any one embodiments 1-112 and the plurality of the polynucleotide construct of any one embodiments 119-209 separately integrate into the genome of the cell.

[563] The method of any one of the preceding embodiments, wherein the polynucleotide construct of any one embodiments 216-271 and the polynucleotide construct of any one embodiments 119-209 separately integrate into the genome of the cell.

[564] The method of any one of the preceding embodiments, wherein the plurality of the polynucleotide construct of any one embodiments 216-271 and the plurality of the polynucleotide construct of any one embodiments 119-209 separately integrate into the genome of the cell.

[565] The method of any one of the preceding embodiments, wherein the polynucleotide construct of any one embodiments 1-112 and the polynucleotide construct of any one embodiments 216-271 separately integrate into the genome of the cell.

[566] The method of any one of the preceding embodiments, wherein the plurality of the polynucleotide construct of any one embodiments 1-112 and the plurality of the polynucleotide construct of any one embodiments 216-271 separately integrate into the genome of the cell.

[567] The method of any one of the preceding embodiments, wherein the polynucleotide construct of any one embodiments 1-112, the polynucleotide construct of any of embodiments 216-271, and the polynucleotide construct of any one embodiments 119-209 separately integrate into the genome of the cell.

[568] The method of any one of the preceding embodiments, wherein the plurality of the polynucleotide construct of any one embodiments 1-112, the plurality of any one of embodiments 216-271, and the plurality of the polynucleotide construct of any one embodiments 119-209 separately integrate into the genome of the cell.

[569] The method of any one of the preceding embodiments, further comprising contacting the cell to a payload construct.

[570] The method of any one of the preceding embodiments, wherein the payload construct stably integrates into the genome of the cell.

[571] The method of any one of the preceding embodiments, wherein the polynucleotide construct of any one embodiments 1-112 and the payload construct separately integrate into the cell.

[572] The method of any one of the preceding embodiments, wherein the polynucleotide construct of any one embodiments 119-209 and the payload construct separately integrate into the cell.

[573] The method of any one of the preceding embodiments, wherein the polynucleotide construct of any one embodiments 216-271 and the payload construct separately integrate into the cell.

[574] The method of any one of the preceding embodiments, wherein the polynucleotide construct of any one embodiments 1-112, the polynucleotide construct of any one embodiments 119-209, and the payload construct separately integrate into the cell.

[575] The method of any one of the preceding embodiments, wherein the polynucleotide construct of any one embodiments 1-112, the polynucleotide construct of any one embodiments 216-271, and the payload construct separately integrate into the cell.

[576] The method of any one of the preceding embodiments, wherein the polynucleotide construct of any one embodiments 216-271, the polynucleotide construct of any one embodiments 119-209, and the payload construct separately integrate into the cell.

[577] The method of any one of the preceding embodiments, wherein the polynucleotide construct of any one of embodiments 1-112, the polynucleotide construct of any one embodiments 216-271, the polynucleotide construct of any one embodiments 119-209, and the payload construct separately integrate into the cell.

[578] The method of any one of the preceding embodiments, further comprising contacting the cell to a plurality of a payload construct.

[579] The method of any one of the preceding embodiments, wherein the plurality of the payload construct stably integrates into the genome of the cell.

[580] The method of any one of the preceding embodiments, wherein the plurality of the polynucleotide construct of any one embodiments 1-112 and the plurality of the payload construct separately integrate into the cell.

[581] The method of any one of the preceding embodiments, wherein the plurality of the polynucleotide construct of any one embodiments 119-209 and the plurality of the payload construct separately integrate into the cell.

[582] The method of any one of the preceding embodiments, wherein the plurality of the polynucleotide construct of any one embodiments 216-271 and the plurality of the payload construct separately integrate into the cell.

[583] The method of any one of the preceding embodiments, wherein the plurality of the polynucleotide construct of any one embodiments 1-112, the plurality of the polynucleotide construct of any one embodiments 119-209, and the plurality of the payload construct separately integrate into the cell.

[584] The method of any one of the preceding embodiments, wherein the plurality of the polynucleotide construct of any one embodiments 1-112, the plurality of the polynucleotide construct of any one embodiments 216-271, and the plurality of the payload construct separately integrate into the cell.

[585] The method of any one of the preceding embodiments, wherein the plurality of the polynucleotide construct of any one embodiments 216-271, the plurality of the polynucleotide construct of any one embodiments 119-209, and the plurality of the payload construct separately integrate into the cell.

[586] The method of any one of the preceding embodiments, wherein the plurality of the polynucleotide construct of any one of embodiments 1-112, the plurality of the polynucleotide construct of any one embodiments 216-271, the plurality of the polynucleotide construct of any one embodiments 119-209, and the plurality of the payload construct of any one of the preceding embodiments separately integrate into the cell.

[587] The method of any one of the preceding embodiments, wherein the passaging is in a cell media comprising a selective pressure.

[588] The method of any one of the preceding embodiments, wherein the passaging is in a cell media comprising at least two selective pressures.

[589] The method of any one of the preceding embodiments, wherein the selective pressure is an antibiotic.

[590] The method of any one of the preceding embodiments, wherein the antibiotic is blasticidin or puromycin.

[591] The method of any one of the preceding embodiments, wherein the passaging is in a cell media comprising at least two antibiotics.

[592] The method of any one of the preceding embodiments, wherein the selection pressure is a lack of a nutrient.

[593] The method of any one the preceding embodiments, wherein the lack of a nutrient is a lack of hypoxanthine and a lack of thymidine.

[594] The method of any one of the preceding embodiments, wherein the stable cell line is capable of reaching a viable cell density of no less than $1\times10^6$, $2\times10^6$, $5\times10^6$, or $1\times10^7$ cells per milliliter.

[595] A method of generating a stable cell, the method comprising:

contacting a cell to the polynucleotide construct of any one of embodiments 1-112, wherein the polynucleotide construct of any one embodiments 1-112 stably integrates into the genome of the cell

[596] A method of generating a stable cell, the method comprising:
contacting a cell to the polynucleotide construct of any one of embodiments 1-112, wherein the polynucleotide construct of any one embodiments 1-112 stably integrates into the genome of the cell; and
contacting the cell to the polynucleotide construct of any one of embodiments 119-209, wherein the polynucleotide construct of any one of embodiments 119-209 stably integrates into the genome of the cell.

[597] A method of generating a stable cell, the method comprising:
contacting a cell to the polynucleotide construct of any one of embodiments 1-112, wherein the polynucleotide construct of any one embodiments 1-112 stably integrates into the genome of the cell; and
contacting the cell to the polynucleotide construct of any one of embodiments 216-271, wherein the polynucleotide construct of any one of embodiments 216-271 stably integrates into the genome of the cell.

[598] A method of generating a stable cell, the method comprising:
contacting a cell to the polynucleotide construct of any one of embodiments 119-209, wherein the polynucleotide construct of any one embodiments 119-209 stably integrates into the genome of the cell; and
contacting the cell to the polynucleotide construct of any one of embodiments 216-271, wherein the polynucleotide construct of any one of embodiments 216-271 stably integrates into the genome of the cell.

[599] A method of generating a stable cell, the method comprising:
contacting a cell to a plurality of the polynucleotide construct of any one of embodiments 1-112, wherein the plurality of polynucleotide construct of any one embodiments 1-112 stably integrates into the genome of the cell; and
contacting the cell to a plurality of the polynucleotide construct of any one of embodiments 119-209, wherein the plurality of the polynucleotide construct of any one of embodiments 119-209 stably integrates into the genome of the cell.

[600] A method of generating a stable cell, the method comprising:
contacting a cell to a plurality of the polynucleotide construct of any one of embodiments 1-112, wherein the plurality of polynucleotide construct of any one embodiments 1-112 stably integrates into the genome of the cell; and
contacting the cell to a plurality of the polynucleotide construct of any one of embodiments 216-271, wherein the plurality of the polynucleotide construct of any one of embodiments 216-271 stably integrates into the genome of the cell.

[601] A method of generating a stable cell, the method comprising:
contacting a cell to a plurality of the polynucleotide construct of any one of embodiments 216-271 wherein the plurality of polynucleotide construct of any one embodiments 216-271 stably integrates into the genome of the cell; and
contacting the cell to a plurality of the polynucleotide construct of any one of embodiments 119-209, wherein the plurality of the polynucleotide construct of any one of embodiments 119-209 stably integrates into the genome of the cell.

[602] A method of generating a stable cell, the method comprising:
contacting a cell to a plurality of the polynucleotide construct of any one of embodiments 1-112, wherein the plurality of polynucleotide construct of any one embodiments 1-112 stably integrates into the genome of the cell;
contacting the cell to a plurality of the polynucleotide construct of any one of embodiments 119-209, wherein the plurality of the polynucleotide construct of any one of embodiments 119-209 stably integrates into the genome of the cell; and
contacting the cell to a plurality of the polynucleotide construct of any one of embodiments 216-271, wherein the plurality of the polynucleotide construct of any one of embodiments 216-271 stably integrates into the genome of the cell.

[603] A method of generating a stable cell, the method comprising:
contacting a cell to a plurality of the polynucleotide construct of any one of embodiments 216-271 wherein the plurality of polynucleotide construct of any one embodiments 216-271 stably integrates into the genome of the cell;
contacting the cell to a plurality of the polynucleotide construct of any one of embodiments 1-112, wherein the plurality of the polynucleotide construct of any one of embodiments 1-112 stably integrates into the genome of the cell; and
contacting the cell to a plurality of the polynucleotide construct of any one of embodiments 119-209, wherein the plurality of the polynucleotide construct of any one of embodiments 119-209 stably integrates into the genome of the cell.

[604] A method of generating a population of stable cells, the method comprising:
contacting a cell to the polynucleotide construct of any one of embodiments 1-112, wherein the polynucleotide construct of any one embodiments 1-112 stably integrates into the genome of the cell; and
passaging the cell to generate the population of stable cells.

[605] A method of generating a population of stable cells, the method comprising:
contacting a cell to the polynucleotide construct of any one of embodiments 1-112, wherein the polynucleotide construct of any one embodiments 1-112 stably integrates into the genome of the cell;
contacting the cell to the polynucleotide construct of any one of embodiments 119-209, wherein the polynucleotide construct of any one of embodiments 119-209 stably integrates into the genome of the cell; and
passaging the cell to generate the population of stable cells.

[606] A method of generating a population of stable cells, the method comprising:
contacting a cell to the polynucleotide construct of any one of embodiments 1-112, wherein the polynucleotide construct of any one embodiments 1-112 stably integrates into the genome of the cell;
contacting the cell to the polynucleotide construct of any one of embodiments 216-271, wherein the polynucleotide construct of any one of embodiments 216-271 stably integrates into the genome of the cell; and passaging the cell to generate the population of stable cells.

[607] A method of generating a population of stable cells, the method comprising:

contacting a cell to the polynucleotide construct of any one of embodiments 119-209, wherein the polynucleotide construct of any one embodiments 119-209 stably integrates into the genome of the cell;

contacting the cell to the polynucleotide construct of any one of embodiments 216-271, wherein the polynucleotide construct of any one of embodiments 216-271 stably integrates into the genome of the cell; and passaging the cell to generate the population of stable cells.

[608] A method of generating a population of stable cells, the method comprising:

contacting a cell to a plurality of the polynucleotide construct of any one of embodiments 1-112, wherein the plurality of polynucleotide construct of any one embodiments 1-112 stably integrates into the genome of the cell;

contacting the cell to a plurality of the polynucleotide construct of any one of embodiments 119-209, wherein the plurality of the polynucleotide construct of any one of embodiments 119-209 stably integrates into the genome of the cell; and passaging the cell to generate the population of stable cells.

[609] A method of generating a population of stable cells, the method comprising:

contacting a cell to a plurality of the polynucleotide construct of any one of embodiments 1-112, wherein the plurality of polynucleotide construct of any one embodiments 1-112 stably integrates into the genome of the cell;

contacting the cell to a plurality of the polynucleotide construct of any one of embodiments 216-271, wherein the plurality of the polynucleotide construct of any one of embodiments 216-271 stably integrates into the genome of the cell; and passaging the cell to generate the population of stable cells.

[610] A method of generating a population of stable cells, the method comprising:

contacting a cell to a plurality of the polynucleotide construct of any one of embodiments 216-271 wherein the plurality of polynucleotide construct of any one embodiments 216-271 stably integrates into the genome of the cell;

contacting the cell to a plurality of the polynucleotide construct of any one of embodiments 119-209, wherein the plurality of the polynucleotide construct of any one of embodiments 119-209 stably integrates into the genome of the cell; and passaging the cell to generate the population of stable cells.

[611] A method of generating a population of stable cells, the method comprising:

contacting a cell to a plurality of the polynucleotide construct of any one of embodiments 1-112, wherein the plurality of polynucleotide construct of any one embodiments 1-112 stably integrates into the genome of the cell;

contacting the cell to a plurality of the polynucleotide construct of any one of embodiments 119-209, wherein the plurality of the polynucleotide construct of any one of embodiments 119-209 stably integrates into the genome of the cell;

contacting the cell to a plurality of the polynucleotide construct of any one of embodiments 216-271, wherein the plurality of the polynucleotide construct of any one of embodiments 216-271 stably integrates into the genome of the cell; and passaging the cell to generate the population of stable cells.

[612] A method of generating a population of stable cells, the method comprising:

contacting a cell to a plurality of the polynucleotide construct of any one of embodiments 216-271 wherein the plurality of polynucleotide construct of any one embodiments 216-271 stably integrates into the genome of the cell;

contacting the cell to a plurality of the polynucleotide construct of any one of embodiments 1-112, wherein the plurality of the polynucleotide construct of any one of embodiments 1-112 stably integrates into the genome of the cell;

contacting the cell to a plurality of the polynucleotide construct of any one of embodiments 119-209, wherein the plurality of the polynucleotide construct of any one of embodiments 119-209 stably integrates into the genome of the cell; and passaging the cell to generate the population of stable cells.

[613] The method of any one of the preceding embodiments, wherein the population of stable cells is capable of reaching a viable cell density of no less than $1\times10^6$, $2\times10^6$, $5\times10^6$, or $1\times10^7$ cells per milliliter.

[614] A method of generating a stable cell line, the method comprising:

contacting a cell to the polynucleotide construct of any one of embodiments 1-112, wherein the polynucleotide construct of any one embodiments 1-112 stably integrates into the genome of the cell; and passaging the cell to generate the stable cell line.

[615] A method of generating a stable cell line, the method comprising:

contacting a cell to the polynucleotide construct of any one of embodiments 1-112, wherein the polynucleotide construct of any one embodiments 1-112 stably integrates into the genome of the cell;

contacting the cell to the polynucleotide construct of any one of embodiments 119-209, wherein the polynucleotide construct of any one of embodiments 119-209 stably integrates into the genome of the cell; and passaging the cell to generate the stable cell line.

[616] A method of generating a stable cell line, the method comprising:

contacting a cell to the polynucleotide construct of any one of embodiments 1-112, wherein the polynucleotide construct of any one embodiments 1-112 stably integrates into the genome of the cell;

contacting the cell to the polynucleotide construct of any one of embodiments 216-271, wherein the polynucleotide construct of any one of embodiments 216-271 stably integrates into the genome of the cell; and passaging the cell to generate the stable cell line.

[617] A method of generating a stable cell line, the method comprising:

contacting a cell to the polynucleotide construct of any one of embodiments 119-209, wherein the polynucleotide construct of any one embodiments 119-209 stably integrates into the genome of the cell;

contacting the cell to the polynucleotide construct of any one of embodiments 216-271, wherein the polynucleotide construct of any one of embodiments 216-271 stably integrates into the genome of the cell; and passaging the cell to generate the stable cell line.

[618] A method of generating a stable cell line, the method comprising:

contacting a cell to a plurality of the polynucleotide construct of any one of embodiments 1-112, wherein the plurality of polynucleotide construct of any one embodiments 1-112 stably integrates into the genome of the cell;

contacting the cell to a plurality of the polynucleotide construct of any one of embodiments 119-209, wherein the plurality of the polynucleotide construct of any one of embodiments 119-209 stably integrates into the genome of the cell; and passaging the cell to generate the stable cell line.

[619] A method of generating a stable cell line, the method comprising:

contacting a cell to a plurality of the polynucleotide construct of any one of embodiments 1-112, wherein the plurality of polynucleotide construct of any one embodiments 1-112 stably integrates into the genome of the cell;

contacting the cell to a plurality of the polynucleotide construct of any one of embodiments 216-271, wherein the plurality of the polynucleotide construct of any one of embodiments 216-271 stably integrates into the genome of the cell; and passaging the cell to generate the stable cell line.

[620] A method of generating a stable cell line, the method comprising:

contacting a cell to a plurality of the polynucleotide construct of any one of embodiments 216-271 wherein the plurality of polynucleotide construct of any one embodiments 216-271 stably integrates into the genome of the cell;

contacting the cell to a plurality of the polynucleotide construct of any one of embodiments 119-209, wherein the plurality of the polynucleotide construct of any one of embodiments 119-209 stably integrates into the genome of the cell; and passaging the cell to generate the stable cell line.

[621] A method of generating a stable cell line, the method comprising:

contacting a cell to a plurality of the polynucleotide construct of any one of embodiments 1-112, wherein the plurality of polynucleotide construct of any one embodiments 1-112 stably integrates into the genome of the cell;

contacting the cell to a plurality of the polynucleotide construct of any one of embodiments 119-209, wherein the plurality of the polynucleotide construct of any one of embodiments 119-209 stably integrates into the genome of the cell;

contacting the cell to a plurality of the polynucleotide construct of any one of embodiments 216-271, wherein the plurality of the polynucleotide construct of any one of embodiments 216-271 stably integrates into the genome of the cell; and passaging the cell to generate the stable cell line.

[622] A method of generating a stable cell line, the method comprising:

contacting a cell to a plurality of the polynucleotide construct of any one of embodiments 216-271 wherein the plurality of polynucleotide construct of any one embodiments 216-271 stably integrates into the genome of the cell;

contacting the cell to a plurality of the polynucleotide construct of any one of embodiments 1-112, wherein the plurality of the polynucleotide construct of any one of embodiments 1-112 stably integrates into the genome of the cell;

contacting the cell to a plurality of the polynucleotide construct of any one of embodiments 119-209, wherein the plurality of the polynucleotide construct of any one of embodiments 119-209 stably integrates into the genome of the cell; and passaging the cell to generate the stable cell line.

[623] The method of any one of the preceding embodiments, wherein the polynucleotide construct of any one embodiments 1-112 and the polynucleotide construct of any one embodiments 119-209 separately integrate into the genome of the cell.

[624] The method of any one of the preceding embodiments, wherein the plurality of the polynucleotide construct of any one embodiments 1-112 and the plurality of the polynucleotide construct of any one embodiments 119-209 separately integrate into the genome of the cell.

[625] The method of any one of the preceding embodiments, wherein the polynucleotide construct of any one embodiments 216-271 and the polynucleotide construct of any one embodiments 119-209 separately integrate into the genome of the cell.

[626] The method of any one of the preceding embodiments, wherein the plurality of the polynucleotide construct of any one embodiments 216-271 and the plurality of the polynucleotide construct of any one embodiments 119-209 separately integrate into the genome of the cell.

[627] The method of any one of the preceding embodiments, wherein the polynucleotide construct of any one embodiments 1-112 and the polynucleotide construct of any one embodiments 216-271 separately integrate into the genome of the cell.

[628] The method of any one of the preceding embodiments, wherein the plurality of the polynucleotide construct of any one embodiments 1-112 and the plurality of the polynucleotide construct of any one embodiments 216-271 separately integrate into the genome of the cell.

[629] The method of any one of the preceding embodiments, wherein the polynucleotide construct of any one embodiments 1-112, the polynucleotide construct of any of embodiments 216-271, and the polynucleotide construct of any one embodiments 119-209 separately integrate into the genome of the cell.

[630] The method of any one of the preceding embodiments, wherein the plurality of the polynucleotide construct of any one embodiments 1-112, the plurality of any one of embodiments 216-271, and the plurality of the polynucleotide construct of any one embodiments Y separately integrate into the genome of the cell.

[631] The method of any one of the preceding embodiments, further comprising contacting the cell to a payload construct.

[632] The method of any one of the preceding embodiments, wherein the payload construct stably integrates into the genome of the cell.

[633] The method of any one of the preceding embodiments, wherein the polynucleotide construct of any one embodiments 1-112 and the payload construct separately integrate into the cell.

[634] The method of any one of the preceding embodiments, wherein the polynucleotide construct of any one embodiments 119-209 and the payload construct separately integrate into the cell.

[635] The method of any one of the preceding embodiments, wherein the polynucleotide construct of any one embodiments 216-271 and the payload construct separately integrate into the cell.

[636] The method of any one of the preceding embodiments, wherein the polynucleotide construct of any one embodiments 1-112, the polynucleotide construct of any one embodiments 119-209, and the payload construct separately integrate into the cell.

[637] The method of any one of the preceding embodiments, wherein the polynucleotide construct of any one embodiments 1-112, the polynucleotide construct of any one embodiments 216-271, and the payload construct separately integrate into the cell.

[638] The method of any one of the preceding embodiments, wherein the polynucleotide construct of any one embodiments 216-271, the polynucleotide construct of any one embodiments 119-209, and the payload construct separately integrate into the cell.

[639] The method of any one of the preceding embodiments, wherein the polynucleotide construct of any one of embodiments 1-112, the polynucleotide construct of any one embodiments 216-271, the polynucleotide construct of any one embodiments 119-209, and the payload construct separately integrate into the cell.

[640] The method of any one of the preceding embodiments, further comprising contacting the cell to a plurality of a payload construct.

[641] The method of any one of the preceding embodiments, wherein the plurality of the payload construct stably integrates into the genome of the cell.

[642] The method of any one of the preceding embodiments, wherein the plurality of the polynucleotide construct of any one embodiments 1-112 and the plurality of the payload construct separately integrate into the cell.

[643] The method of any one of the preceding embodiments, wherein the plurality of the polynucleotide construct of any one embodiments 119-209 and the plurality of the payload construct separately integrate into the cell.

[644] The method of any one of the preceding embodiments, wherein the plurality of the polynucleotide construct of any one embodiments 216-271 and the plurality of the payload construct separately integrate into the cell.

[645] The method of any one of the preceding embodiments, wherein the plurality of the polynucleotide construct of any one embodiments 1-112, the plurality of the polynucleotide construct of any one embodiments 119-209, and the plurality of the payload construct separately integrate into the cell.

[646] The method of any one of the preceding embodiments, wherein the plurality of the polynucleotide construct of any one embodiments 1-112, the plurality of the polynucleotide construct of any one embodiments 216-271, and the plurality of the payload construct separately integrate into the cell.

[647] The method of any one of the preceding embodiments, wherein the plurality of the polynucleotide construct of any one embodiments 216-271, the plurality of the polynucleotide construct of any one embodiments 119-209, and the plurality of the payload construct separately integrate into the cell.

[648] The method of any one of the preceding embodiments, wherein the plurality of the polynucleotide construct of any one of embodiments 1-112, the plurality of the polynucleotide construct of any one embodiments 216-271, the plurality of the polynucleotide construct of any one embodiments 119-209, and the plurality of the payload construct separately integrate into the cell.

[649] The cell of any one of the preceding embodiments, wherein the payload construct comprises a sequence of a payload flanked by ITR sequences.

[650] The cell of any one of the preceding embodiments, wherein expression of the sequence of the payload is driven by a constitutive promoter.

[651] The cell of any one of the preceding embodiments, wherein the constitutive promoter and sequence of the payload are flanked by ITR sequences.

[652] The cell of any one of the preceding embodiments, wherein the sequence of the payload comprises a polynucleotide sequence coding for a gene.

[653] The cell of any one of the preceding embodiments, wherein the gene codes for a selectable marker or detectable marker.

[654] The cell of any one of the preceding embodiments, wherein the gene codes for a therapeutic polypeptide or transgene.

[655] The cell of any one of the preceding embodiments, wherein the sequence of the payload comprises a polynucleotide sequence coding for a therapeutic polynucleotide.

[656] The cell of any one of the preceding embodiments, wherein the therapeutic polynucleotide is a tRNA suppressor or a guide RNA.

[657] The cell of any one of the preceding embodiments, wherein the guide RNA is a polyribonucleotide capable of binding to a protein.

[658] The cell of any one of the preceding embodiments, wherein the protein is nuclease.

[659] The cell of any one of the preceding embodiments, wherein the protein is a Cas protein, an ADAR protein, or an ADAT protein.

[660] The cell of any one of the preceding embodiments, wherein the Cas protein is catalytically inactive Cas protein.

[661] The method of any one of the preceding embodiments, wherein the passaging is in a cell media comprising a selective pressure.

[662] The method of any one of the preceding embodiments, wherein the passaging is in a cell media comprising at least two selective pressures.

[663] The method of any one of the preceding embodiments, wherein the selective pressure is an antibiotic.

[664] The method of any one of the preceding embodiments, wherein the antibiotic is blasticidin or puromycin.

[665] The method of any one of the preceding embodiments, wherein the passaging is in a cell media comprising at least two antibiotics.

[666] The method of any one of the preceding embodiments, wherein the selection pressure is a lack of a nutrient.

[667] The method of any one the preceding embodiments, wherein the lack of a nutrient is a lack of hypoxanthine and a lack of thymidine.

[668] The method of any one of the preceding embodiments, wherein the stable cell line is capable of reaching a viable cell density of no less than $1\times10^6$, $2\times10^6$, $5\times10^6$, or $1\times10^7$ cells per milliliter.

[669] method of inducing the cell of any one of the preceding embodiments, the population of cells of any one of embodiments, or the stable cell line of any one of embodiments, the method comprising administering a first triggering agent to the cell, population of cells, or the stable cell line, thereby inducing expression of the Rep polypeptides, Cap polypeptides, and one or more adenoviral helper proteins, in the cell, population of cells, or stable cell line.

[670] The method of any one of the preceding embodiments, wherein the first triggering agent binds to an activator or a repressor.

[671] The method of any one of the preceding embodiments, wherein activation of an inducible promoter is induced.

[672] The method of any one of the preceding embodiments, wherein the activated inducible promoter transcribes a recombinase.

[673] The method of any one of the preceding embodiments, wherein the first triggering agent is tetracycline or cumate.

[674] The method of any one of the preceding embodiments, wherein the tetracycline is doxycycline.

[675] The method of any one of the preceding embodiments, further comprising culturing the cell, population of cells, or the stable cell line with a second triggering agent.

[676] The method of any one of the preceding embodiments, wherein the second triggering agent is an estrogen receptor ligand.

[677] The method of any one of the preceding embodiments, wherein the second triggering agent is a selective estrogen receptor modulator (SERM).

[678] The method of any one of the preceding embodiments, wherein the second triggering agent is tamoxifen.

[679] The method of any one of the preceding embodiments, wherein the second triggering agent binds to the recombinase.

[680] The method of any one of the preceding embodiments, wherein the second triggering agent induces the recombinase to translocate to a nucleus of the cell, of a cell of the population of cells, of a cell of the stable cell lines.

[681] A method of producing rAAV virion, the method comprising administering a first triggering agent to the cell, population of cells, or the stable cell line, administering a second triggering agent to the cell, population of cells, or stable cell line, thereby producing the rAAV virion in the cell, population of cells, or stable cell line.

[682] The method of any one of the preceding embodiments, wherein the first triggering agent binds to an activator or a repressor.

[683] The method of any one of the preceding embodiments, wherein activation of an inducible promoter is induced.

[684] The method of any one of the preceding embodiments, wherein the activated inducible promoter transcribes a recombinase.

[685] The method of any one of the preceding embodiments, wherein the first triggering agent is tetracycline or cumate.

[686] The method of any one of the preceding embodiments, wherein the tetracycline is doxycycline.

[687] The method of any one of the preceding embodiments, further comprising culturing the cell, population of cells, or the stable cell line with a second triggering agent.

[688] The method of any one of the preceding embodiments, wherein the second triggering agent is an estrogen receptor ligand.

[689] The method of any one of the preceding embodiments, wherein the second triggering agent is a selective estrogen receptor modulator (SERM).

[690] The method of any one of the preceding embodiments, wherein the second triggering agent is tamoxifen.

[691] The method of any one of the preceding embodiments, wherein the second triggering agent binds to the recombinase.

[692] The method of any one of the preceding embodiments, wherein the second triggering agent induces the recombinase to translocate to a nucleus of the cell, of a cell of the population of cells, of a cell of the stable cell lines.

[693] The method of any one of the preceding embodiments, wherein the recombinase cuts at recombination sites.

[694] The method of any one of the preceding embodiments, wherein the at least one adenoviral help proteins, the Rep polypeptides, and the Cap polypeptides are expressed.

[695] The method of any one of the preceding embodiments, wherein the Rep polypeptides and the Cap polypeptides assemble into an rAAV virion.

[696] The method of any one of the preceding embodiments, wherein the rAAV virion encapsidates a sequence of a payload.

[697] The method of any one of the preceding embodiments, wherein the cell, population of cells, or stable cell line do not express cytotoxic levels of Rep polypeptides prior to administration of both the first triggering agent and the second triggering agent.

[698] The method of any one of the preceding embodiments, wherein the cell, population of cells, or stable cell line do not express cytotoxic levels of Cap polypeptides prior to administration of both the first triggering agent and the second triggering agent.

[699] The method of any one of the preceding embodiments, wherein the cell, population of cells, or stable cell line do not express cytostatic levels of Rep polypeptides prior to administration of both the first triggering agent and the second triggering agent.

[700] The method of any one of the preceding embodiments, wherein the average concentration of Rep polypeptides within the cell, population of cells, or stable cell line is less than the amount prior to administration of both of the first triggering agent and second triggering agent.

[701] The method of any one of the preceding embodiments, wherein expression of Rep polypeptides and Cap polypeptides becomes constitutive after administration of both the first triggering agent and the second triggering agent.

[702] The method of any one of the preceding embodiments, further comprising performing at least a portion of the method in a bioreactor.

[703] The method of any one of the preceding embodiments, wherein the bioreactor is not less than 20 L, 30, L, 40 L, 50 L, 100 L, 250 L, 300 L, or 500 L.

[704] The method of any one of the preceding embodiments, further comprising producing the rAAV virions in a plurality of batches.

[705] The method of any one of the preceding embodiments, further comprising producing the rAAV virions having a difference in the payload encapsidation ratio of not more than 20%, 15%, 10%, 5%, 3%, 2%, or 1% between a first batch and a second batch.

[706] The method of any one of the preceding embodiments, further comprising producing the rAAV virions having a difference in the concentration of viral genomes of not more than 20%, 15%, 10%, 5%, 3%, 2%, or 1% between a first batch and a second batch.

[707] The method of any one of the preceding embodiments, further comprising producing the rAAV virions having a difference in the concentration of vector genomes of not more than 20%, 15%, 10%, 5%, 3%, 2%, or 1% between a first batch and a second batch.

[708] The method of any one of the preceding embodiments, further comprising producing the rAAV virions having a difference in infectivity of not more than 20%, 15%, 10%, 5%, 3%, 2%, or 1% between a first batch and a second batch.

[709] The method of any one of the preceding embodiments, further comprising performing the method according to good manufacturing practice (GMP) standards.

[710] The method of any one of the preceding embodiments, further comprising performing the method in a GMP facility.

[711] The method of any one of the preceding embodiments, further comprising culturing the cells in a culture medium and collecting a portion of the plurality of rAAV virions from the culture medium.

[712] The method of any one of the preceding embodiments, further comprising purifying at least some of the plurality of rAAV virions collected from the culture medium to obtain a purified rAAV population.

[713] The method of any one of the preceding embodiments, wherein the purifying comprises performing chromatographic purification.

[714] The method of any one of the preceding embodiments, wherein the chromatographic purification comprises using a positively charged anion exchange resin, using a negatively charged anion exchange resin, using cation exchange chromatography, using affinity chromatography, using size exclusion chromatography, or a combination thereof.

[715] The method of any one of the preceding embodiments, wherein the chromatographic purification comprises using column chromatographic fractionation.

[716] method of treating a condition or disorder, the method comprising administering a therapeutically effective amount of the pharmaceutical composition of any one of the preceding embodiments to a patient in need thereof.

[717] The method of embodiment 716, wherein the disorder is a monogenic disorder.

[718] The method of any one of embodiments 716-717, wherein the treatment results in at least one undesirable side effect and wherein the undesirable side effect is reduced relative to administering a daily dose that deviates more than 50%, 40%, 30%, 30%, 15%, 10%, 5%, or 2% from an expected dose.

[719] The method of any one of embodiments 716-719, wherein the administering is by injection.

[720] The method of embodiment 719, wherein the injection is an infusion.

[721] The method of any one of embodiments 716-720, wherein the daily dose is administered to the patient once.

[722] The method of any one of embodiments 716-720, wherein the daily dose is administered to the patient two or more times.

[723] The method of any one of embodiments 716-722, wherein the treatment results in at least one undesirable side effect and wherein the undesirable side effect is reduced relative to administering a plurality of rAAV virions produced from a triple transfection method.

[724] The method of any one of embodiments 716-723, wherein a concentration of rAAV virion neutralizing antibody in the blood serum of the patient is reduced relative to a concentration of rAAV virion neutralizing antibody in the blood serum of a patient after administering a plurality of rAAV virions produced from a triple transfection method.

[725] The method of embodiment 724, wherein the concentration of rAAV virion neutralizing antibodies is measured by an ELISA assay.

[726] method of administering a dose of rAAV virions having a predetermined number of viral genomes (VG) to a subject with reduced number or intensity of adverse effects as compared to administration of the same rAAV VG dose prepared by transient triple transfection, the method comprising:

administering a dose of rAAV produced in the cell of any one of the preceding embodiments, the population of cells of any one of the preceding embodiments, or the stable cells of any one of the preceding embodiments.

[727] The method of embodiment 726, wherein the adverse effect is selected from the group consisting of: liver dysfunction, liver inflammation, gastrointestinal infection, vomiting, bacterial infection, sepsis, increases in troponin levels, decreases in red blood cell counts, decreases in platelet counts, activation of the complement immune system response, acute kidney injury, cardio-pulmonary insufficiency, and death.

[728] The method of any one of embodiments 726-727, wherein the adverse effect is an increase in serum levels of one or more of interferon gamma (IFNγ), interleukin 1β (IL-1β), and interleukin 6 (IL-6).

[729] method of treating a condition or disorder, the method comprising administering a first therapeutically effective amount of the pharmaceutical composition of any one of the preceding embodiments having a predetermined number of viral genomes to a patient in need thereof and a second therapeutically effective amount of the pharmaceutical composition of any one of the preceding embodiments having the predetermined number of viral genomes to the patient in need thereof.

[730] The method of embodiment 729, wherein the first therapeutically effective amount and the second therapeutically effective amount vary by no more than 1%, 5%, 10%, or 15%.

[731] n rAAV virion made by the methods of any one of the preceding embodiments.

[732] composition comprising a plurality of rAAV virions produced by the method of any one of the preceding embodiments.

[733] n rAAV virion made by the methods of any one of the preceding embodiments.

[734] composition comprising a plurality of rAAV virions produced by the method of any one of the preceding embodiments.

6.18. EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature.

6.18.1. Example 1—Mammalian Cell Line with Three Stably Integrated Plasmids

A stable mammalian cell line capable of inducible expression of rAAV encapsidating a payload is constructed by integrating three nucleic acid constructs into the nuclear genome of a cell line that expresses adenovirus E1A and E1B (FIGS. 1, 5B, and 6). As described in FIG. 6, the cell line is a DHFR null HEK293 cell line. Cells that successfully integrated all 3 constructs are selected and maintained by growth in media lacking hypoxanthine and thymidine, and in the presence of blasticidin. Successful integration of construct 1 with concurrent repression of Cre expression from construct 2 is determined by confirming fluorescence emission from EGFP prior to triggering.

6.18.2. Example 2—Cre-Inducible Expression of Rep/Cap Proteins

Experiments were performed to test performance of construct 1, as illustrated in FIG. 3A. The construct is designed so that Cre-mediated recombination excises the second spacer segment (FIG. 3B). Excision of the second spacer segment (i) abolishes EGFP expression (FIGS. 7A-7B), (ii) results in production of Rep transcripts from the endogenous P5 and P19 promoters, and (iii) facilitates production of Cap transcripts from an endogenous P40 promoter. The Cap genes are cloned downstream of the Rep gene and operatively linked to the endogenous P40 promoter. Thus, Rep protein expression facilitates Cap protein expression.

HEK293 cells were plated in 24 well plates. Plates were centrifuged for 30 min. at room temperature followed by incubation at 37° C. for 30 min. Media was replaced with growth media and cells were immediately transfected with either an AAV2 positive control plasmid (AAV2) or an AAV2 construct 1 plasmid (AAV CODE) using TransIT 293 reagent. Mock samples were not transfected. Different volumes of Cre gesicles were added to the wells. No Cre gesicles were added to wells imaged in FIG. 7A. No Cre gesicles, 5 μl of Cre gesicles, or 10 μl of Cre gesicles were added as indicated to the wells imaged in FIG. 7B. Cells were imaged 24 hours post transfection and then harvested for protein analysis.

Figure 7A:
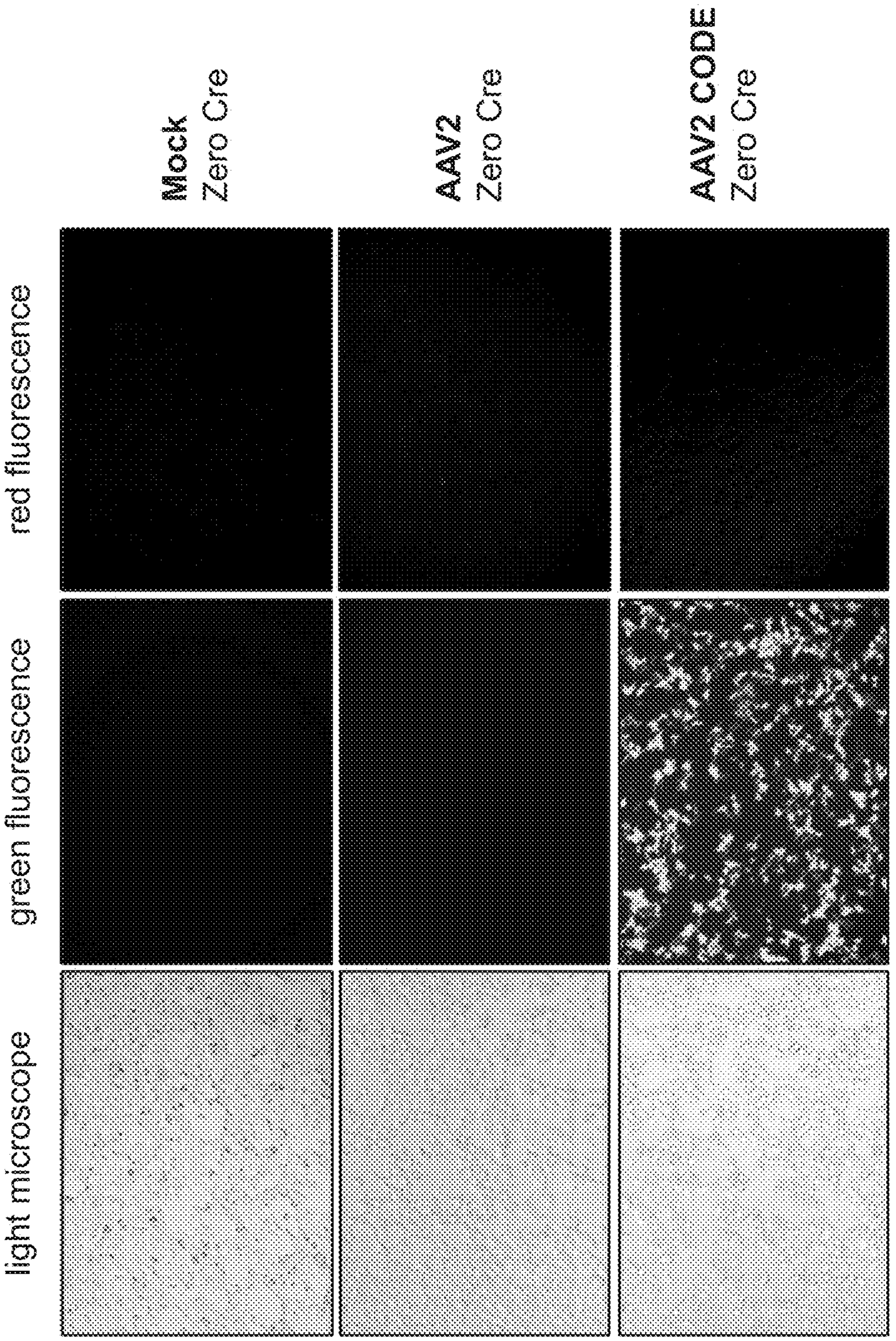
Figure 7B:
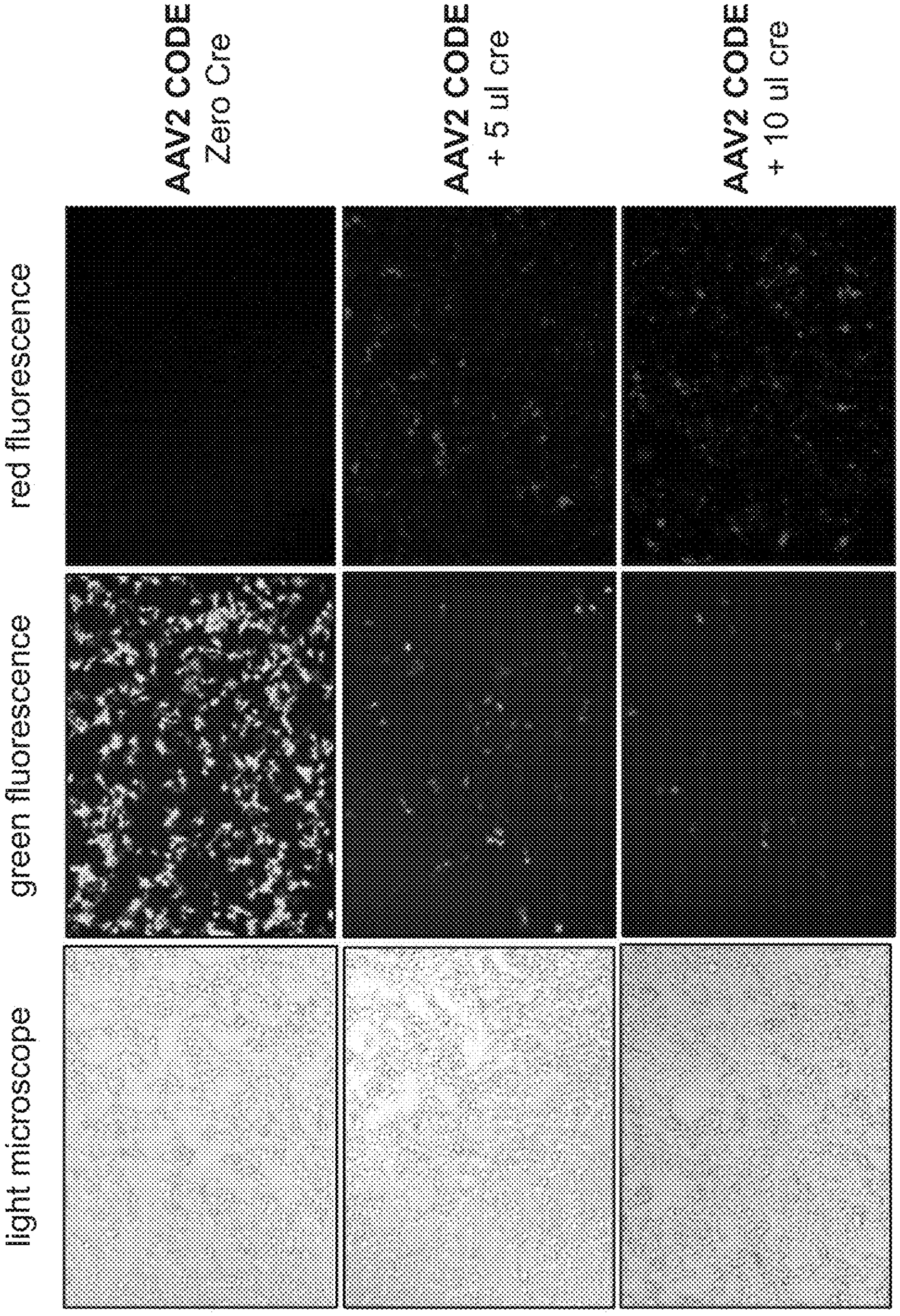

The results are shown in FIGS. 7A-7B, which are light microscope and fluorescence microscope images. Light microscope images are shown in the leftmost column. Green fluorescence microscopic images are shown in the middle column. Red fluorescence images are shown in the rightmost column.

As shown in FIG. 7A, without addition of Cre, cells transfected with construct 1 show intense EGFP fluorescence caused by expression of the Rep-EGFP fusion transcript, splicing of the intron, and translation (see FIG. 3A). FIG. 7B shows decreased GFP fluorescence upon Cre delivery. Cre is delivered by gesicles loaded with Cre protein and red fluorescent marker protein to track delivery into cells. Delivery of Cre affects recombination, with removal of the EGFP cassette from construct 1.

FIG. 8A shows Western blots illustrating that Cre-mediated excision of the excisable spacer segment induces Rep protein production from post-triggered plasmid construct 1. In addition, the presence of the rabbit beta globin intron does not interfere with Rep protein expression level. FIG. 8B shows GFP expression, viability and density graphs of the cells containing the Rep/Cap construct, and blots illustrating Rep production and total protein production.

6.18.3. Example 3—Exemplary Sequence and Construction of Construct 1 (the Rep/Cap Construct)

A plasmid encoding the AAV2 genome (pAV2) from the ATCC was utilized to amplify the AAV2 genome, minus the ITRs. This amplified construct was cloned into a pCR Blunt II Topo vector, forming the backbone for construct 1. The construct 1 intervening spacer and Rep/Cap coding sequences were assembled from gblocks and inserted at nucleotide position 1022 (with reference to WT AAV2). This cloning position is downstream from the P19 promoter, away from any known cis regulatory elements. The EGFP cassette in the second excisable spacer element is in frame with proteins produced by both the P5 and P19 transcripts. The details of pre-triggered construct 1 are shown in FIG. 3A, with an exemplary sequence provided in SEQ ID NO: 6, with the accompanying feature descriptions shown below.

6.18.4. Example 4—Modifying or Inhibiting Antiviral Responses

Viral proteins needed for AAV virion formation are inhibited by host cell mechanisms. Inhibition of these host cell mechanisms to maximize AAV viral titers in the stable cell lines described herein include, but are not limited to: knocking out PKR (PKR KO) (which is a pathway responsible for inhibition of viral proteins) in the starting cell line (P0), introducing a mutant EIF2alpha (in the PKR pathway) in the starting cell line (P0), and/or manipulating or modulating VA RNA (an inhibitor of PKR). As such, development of three strategies: manipulation of VA RNA, PKR KO, and EIF2alpha mutation, are being developed for use in any combination in the AAV production systems described herein. All three of these strategies can be done in any combination.

A. Modification of VA RNA for Optimized Expression

VA RNA Expression is being Analyzed in Four Ways:

1. Constitutive Expression of VA RNA (Traditional Approach) Utilized as a Control, No Manipulation of the VA RNA Promoter or Sequence.

2. Inducible VA RNA

Figure 9A:
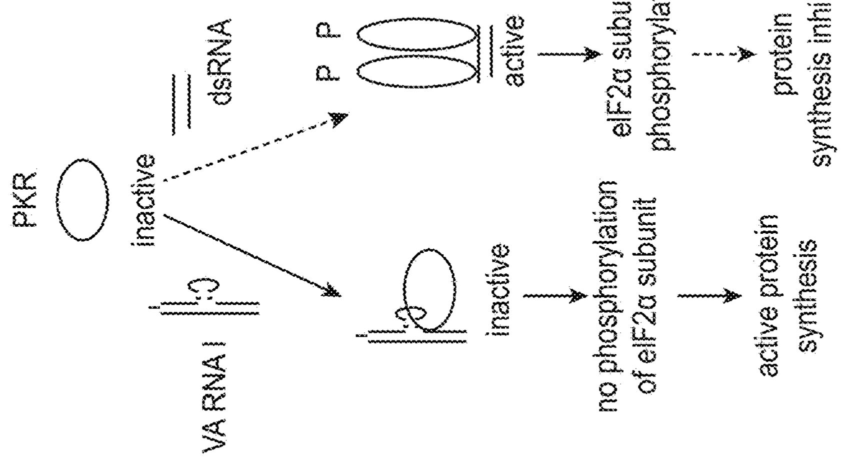
FIG. 9B shows a diagram VA RNA construct and the sequence of VA RNA1 that shows its double-stranded RNA (dsRNA) structure.
Figure 9B:
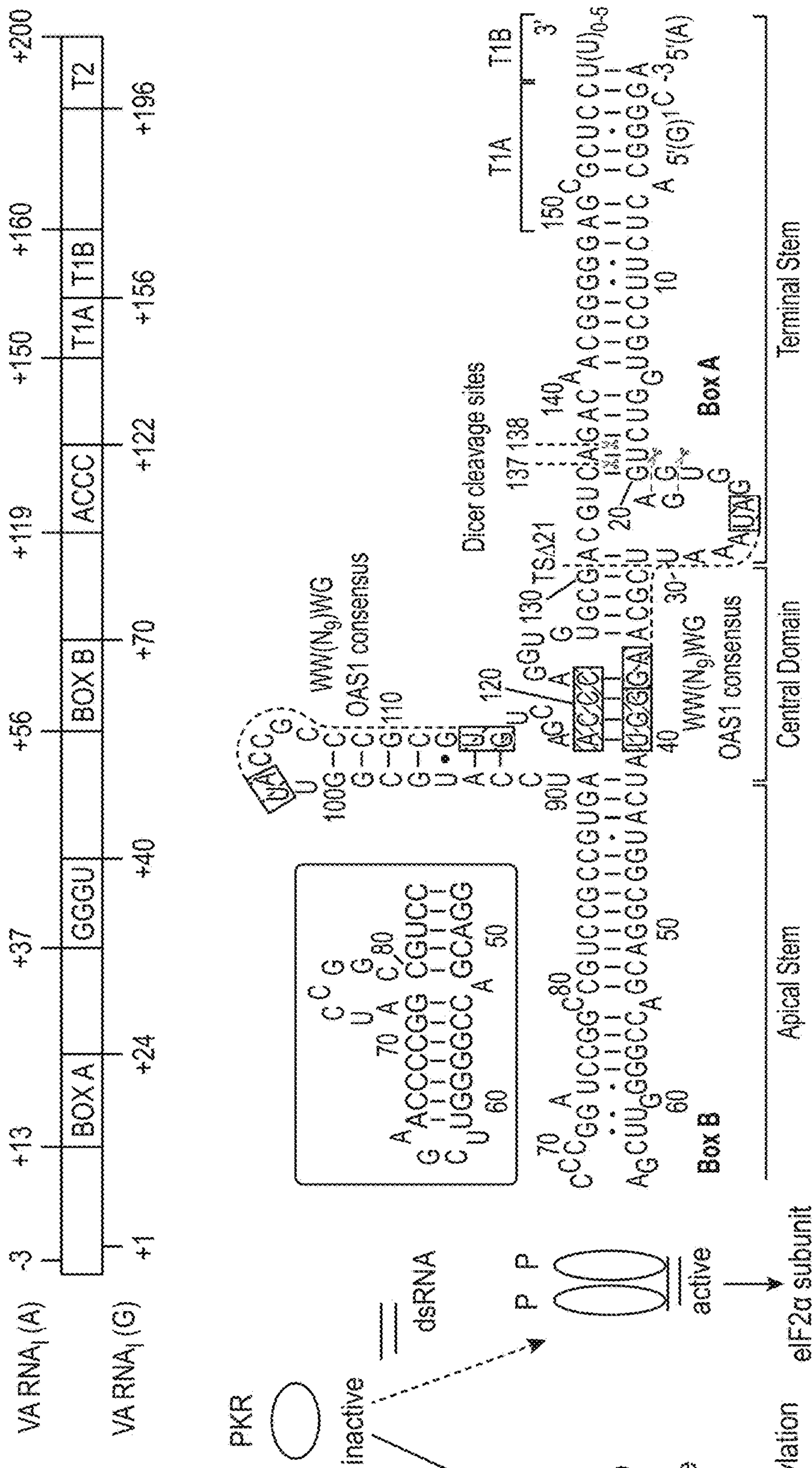

VA RNA naturally has internal constitutive promoters (A Box and B Box; see construct map in upper right hand of FIG. 9B). For experiments to create an inducible VA RNA construct, mutations are first introduced in the internal promoters to abolish their activity.

Figure 18:
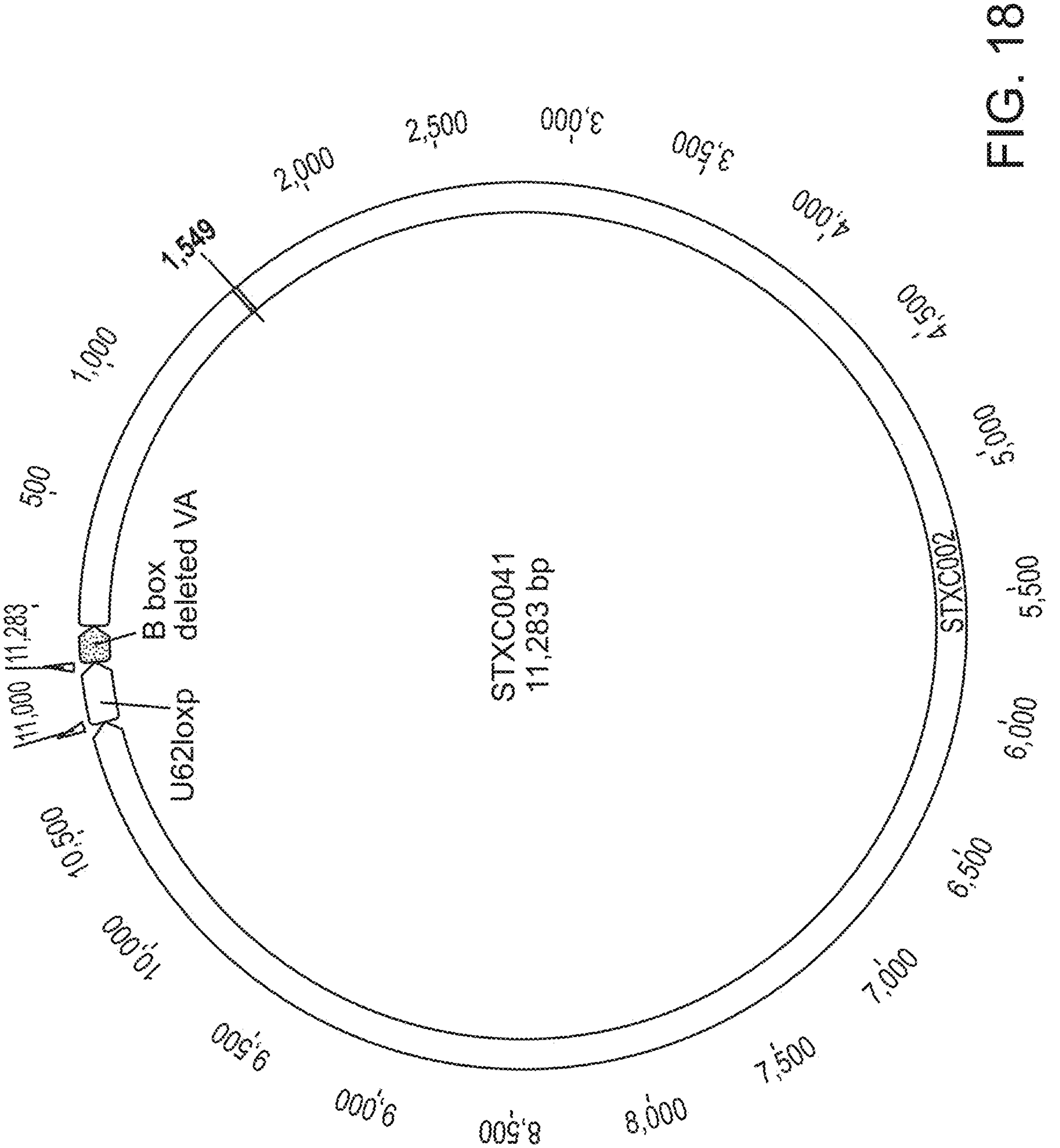
FIG. 18 shows a plasmid map of STX_C0041, which is made by modifying the STX_00033 helper construct containing VA RNA1 B1 mutant (a six nucleotide segment deleted from the B Box) to contain a U6 inducible promoter construct (as shown in FIG. 12A). The position of the new U6 promoter and Lox sites are shown.
Figure 19:
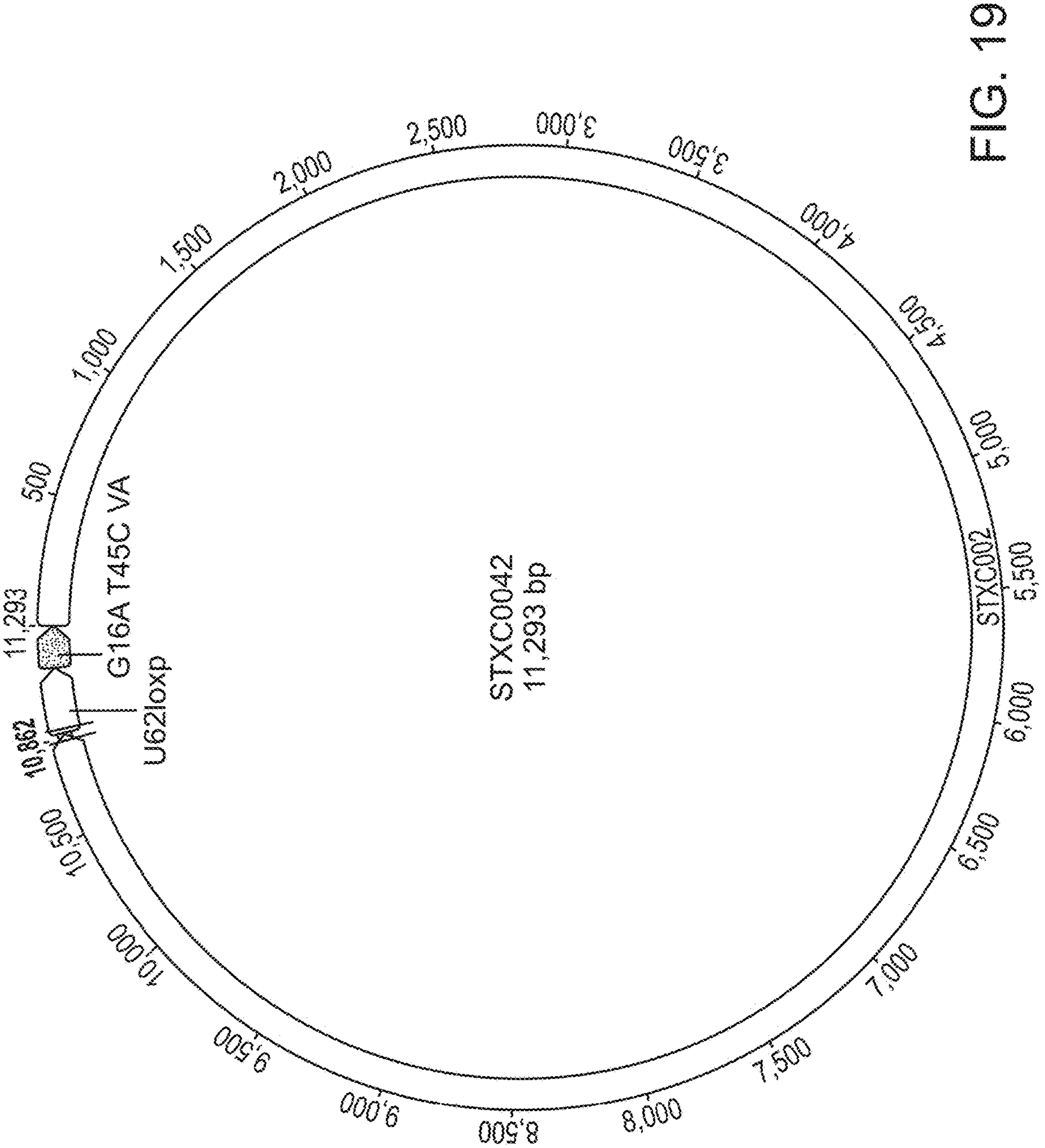
FIG. 19 shows a plasmid map of STX_C0042 which is made by modifying the STX_C0035 helper plasmid containing the VA RNA mutations G16A and T45C to contain a U6 inducible promoter construct (as shown in FIG. 12A). The position of the new U6 promoter and Lox sites are shown.
Figure 20:
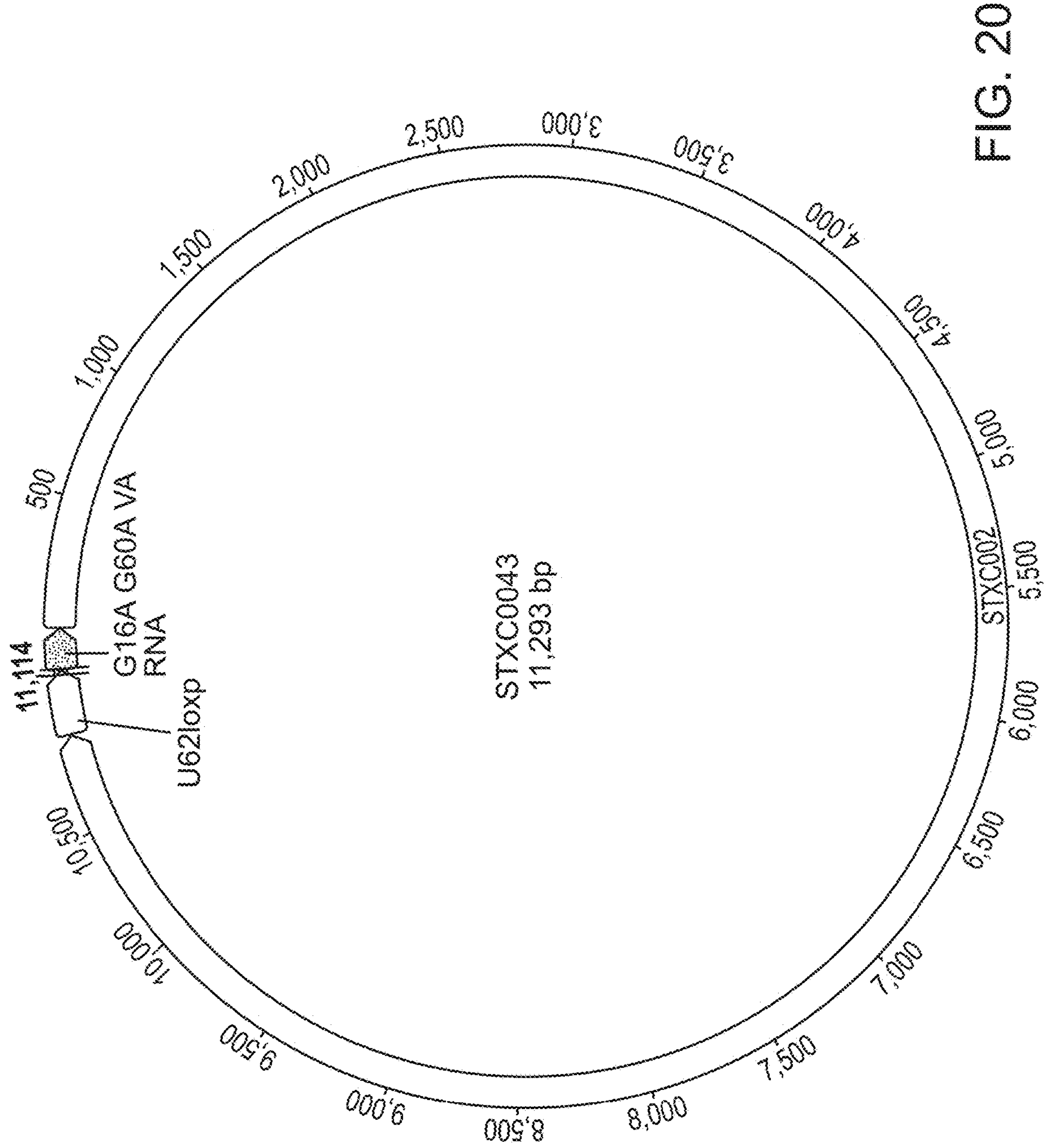
FIG. 20 shows a plasmid map of STX_C0043 which is made by modifying the STX_C0037 helper plasmid containing the VA RNA mutations G16A and G60A. The position of the new U6 promoter and Lox sites are shown.
Figure 21:
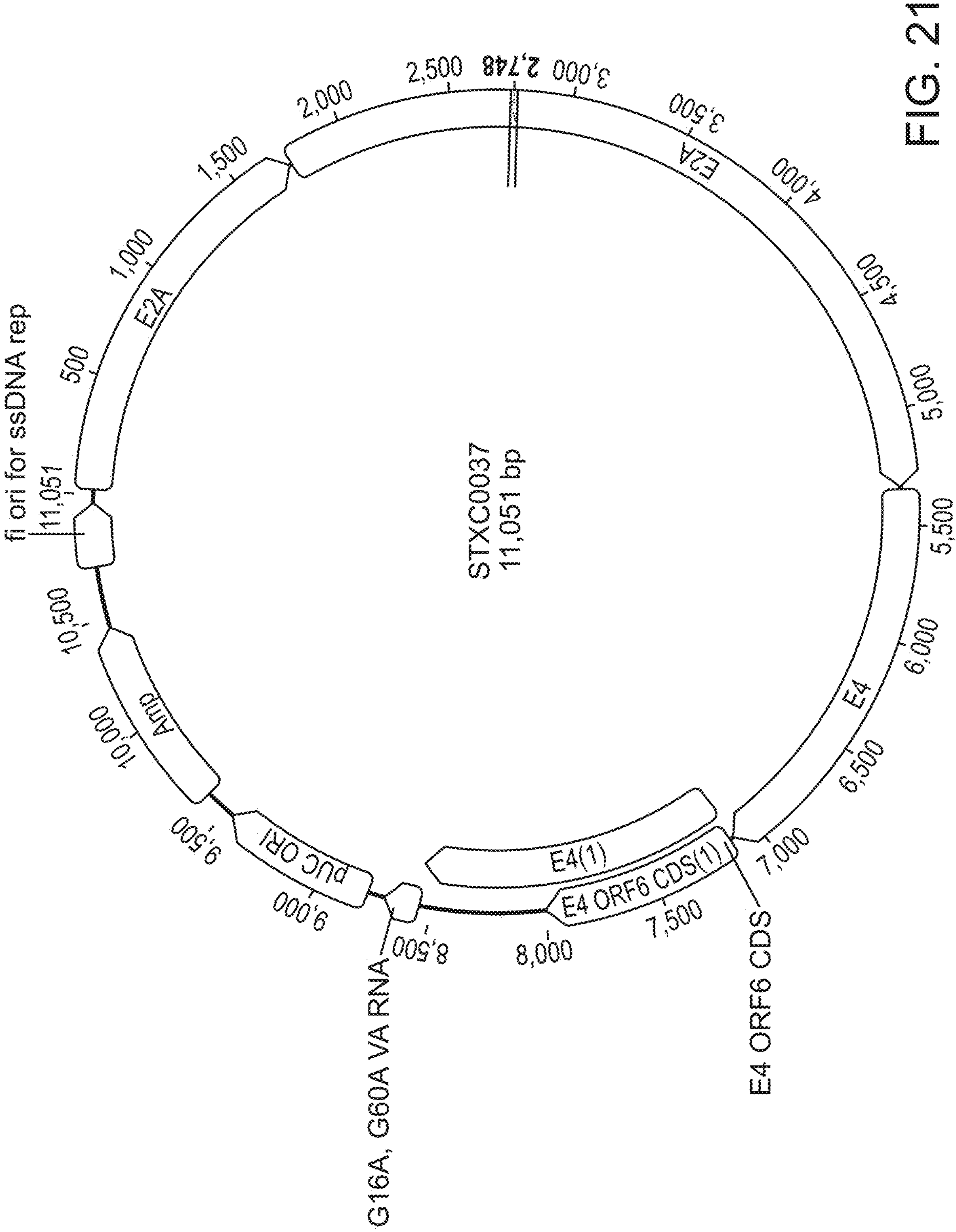
FIG. 21 shows a plasmid map of STX_C0037 containing the VA RNA mutations G16A and G60A.

An inducible U6 promoter system is used to drive expression of VA RNA, as shown in FIG. 2C and in FIGS. 18-20. An advantage to this strategy is that better cell viability and higher AAV titers is expected when using an inducible VA RNA system, in which there is an optimized amount of VA RNA in the production cell system since there may be some cell toxicity associated with constitutive expression of VA RNA.

3. No VA RNA+Compensatory/Analog Viral Proteins

A third option is being developed where VA RNA is eliminated altogether from the system, and another viral protein (e.g. IC34.5 from HSV; an analog of VA RNA) is tested to replace VA RNA function (inhibition of PKR) in order to determine whether the analog can compensate and/or improve ultimate AAV titers as compared to VA RNA in the production system.

4. No VA RNA

In the scenario that viral protein synthesis is unaffected and there is no real hit to AAV titer in helper constructs where VA RNA is excluded altogether, VA RNA is removed from the production cell system. This would only be feasible in cell lines that have been engineered to be optimal for AAV production (e.g., the LV max cells), See FIG. 13.

The following experiments have all been run via triple transfection. It is expected that the results from the triple transfection experiments can be applied, optimized, and tested in the stable cell line context (e.g., the constructs described herein).

B: Testing Alternative Viral Proteins to Compensate for VA RNA

Figures 10A, 10B:
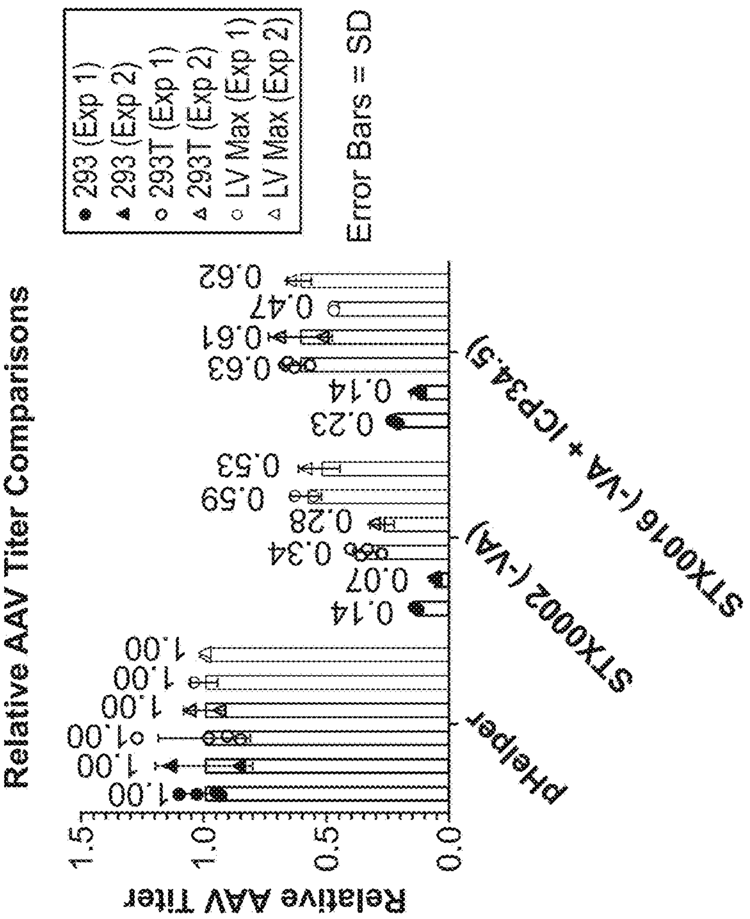
FIGS. 10A-10B depict the plasmid descriptions (FIG. 10A) and testing (FIG. 10B) of these plasmid constructs comprising VA RNA constructs including wildtype VA RNA (pHelper), VA RNA knockout (STXC002), and VA RNA knockout with a compensatory viral protein (infected cell protein 34.5 (ICP34.5); STXC0016) to evaluate the effect of VA RNA on AAV titers.

An experiment was run in which VA RNA was substituted with another viral protein (infected cell protein 34.5 (ICP34.5)) to see if AAV titers could be improved. As shown in FIG. 10A, three groups were tested:

pHelper (No Change to Helper Plasmid and VA RNA is Present)

This is the positive control for VA RNA, and for these experiments a triple transfection with the following plasmids was performed: the pHelper vector, along with STX295 (construct 3 in which the payload is a fluorescent marker flanked by AAV2 ITRs), and pRC2 (this is the Rep/Cap construct, Rep/ITRs from AAV2 and Cap from AAV2).

STXC0002 (VA RNA is Deleted)

This is the negative control for VA RNA and for these experiments, a triple transfection with the following plasmids was performed: the STXC0002 helper vector, along with plasmid STX295 (construct 3 in which the payload is a fluorescent marker flanked by AAV2 ITRs), and pRC2 (this is the Rep/Cap construct, Rep/ITRs from AAV2 and Cap from AAV2).

STXC0016 (VA RNA is Deleted and IC34.5 Added)

This is an experimental group and a triple transfection with the following plasmids was performed: the STXC0016 helper vector (VA RNA is deleted and IC34.5 added as encoded on the 0016 plasmid), STX295 (construct 3 in which the payload is a fluorescent marker flanked by AAV2 ITRs), and pRC2 (this is the Rep/Cap construct, Rep/ITRs from AAV2 and Cap from AAV2).

Results: Alternative Viral Proteins to Compensate for VA RNA

FIG. 10B shows the relative AAV titers from triple transfection with each of the three groups from FIG. 10A in 293 cells, 293T cells, and LV max cells. AAV titers were determined by qPCR. AAV titers were relatively abrogated after triple transfection with STXC0002 (VA RNA is deleted). In 293T cells, AAV titers were restored after triple transfection with STXC0016 (VA RNA is deleted and IC34.5 added). In LV max cells, AAV titer was similar between STXC0002 (VA RNA is deleted) and STXC0016 (VA RNA is deleted and IC34.5 added) (FIG. 10B). The results for wildtype VA RNA are shown for the pHelper construct, which serves as the positive control.

C. Testing Modified or Inducible VA RNA Constructs

Figures 11A, 11B:
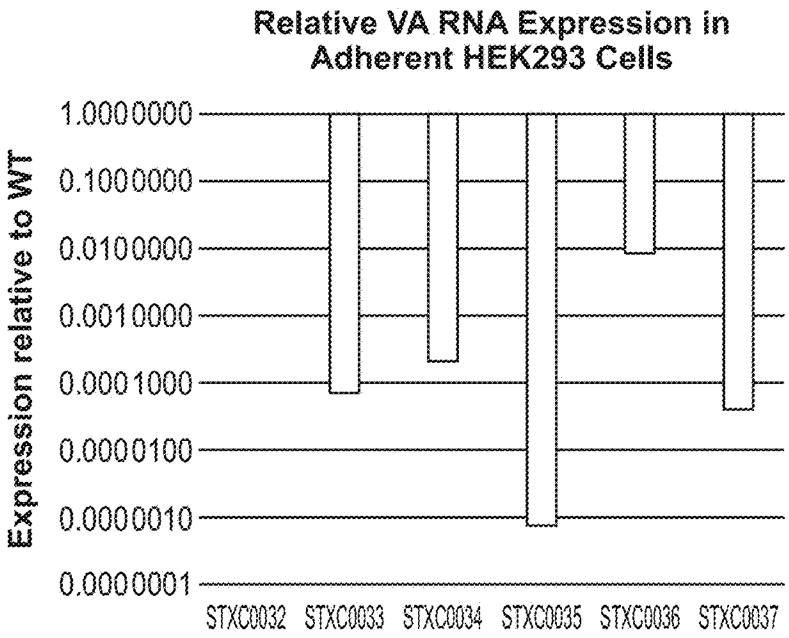
FIGS. 11A-11B depict the plasmid descriptions (FIG. 11A) and testing of these plasmids (FIG. 11B) comprising VA RNA promoter mutants for the relative VA RNA expression in adherent HEK293 cells.

To test modified VA RNA constructs, deletions or mutations were made to the internal promoters in VA-RNA, including deletions or mutations to the A box and the B box. FIG. 11A is a description of each plasmid tested and the corresponding deletions or mutations in VA-RNA. G16A is a mutation in the A box and G60A is a mutation in the B box promoter region. FIG. 11B shows expression of VA RNA relative to the positive control (STXC0032; which is the STXC0002 with WT VA added).

Figures 12A, 12B:
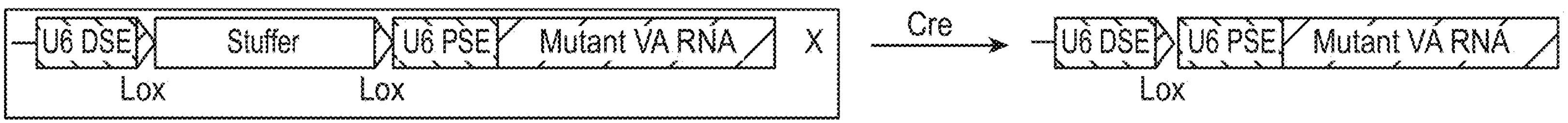
FIGS. 12A-12D depict the design of an inducible U6 promoter segment containing mutant VA RNA (FIG. 12A), the plasmid descriptions (FIG. 12B) for the control and test plasmids, and the relative VA RNA expression in LV max cells (FIGS. 12C & 12D), illustrating rescue of select mutants with an inducible promoter.

To test an inducible VA RNA system, constructs containing a Cre-inducible U6 promoter were made to drive expression of VA-RNA for each of the mutant VA-RNA constructs shown in FIG. 11A. FIG. 12A shows a schematic of the inducible U6 promoter (a similar schematic is shown in FIG. 2C). In this example, the U6 promoter is separated by a stuffer sequence (PGK-neo), which is flanked by Lox sites. Cre, when present, excises the stuffer sequence thereby mediating recombination and resulting in an inducible U6 promoter. STXC0033, STXC0035, and STXC0037 constructs from FIG. 11A, were modified to include the Cre-inducible U6 promoter, yielding STXC0041, STXC0042, and STXC0043, respectively (FIG. 12B).

Results: Inducible VA RNA Constructs

Figure 12C:
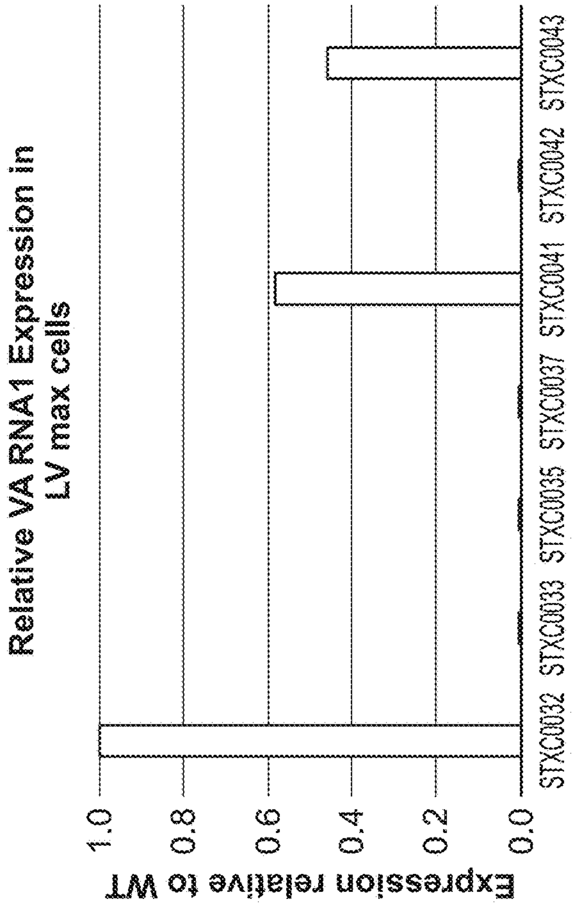
Figure 12D:
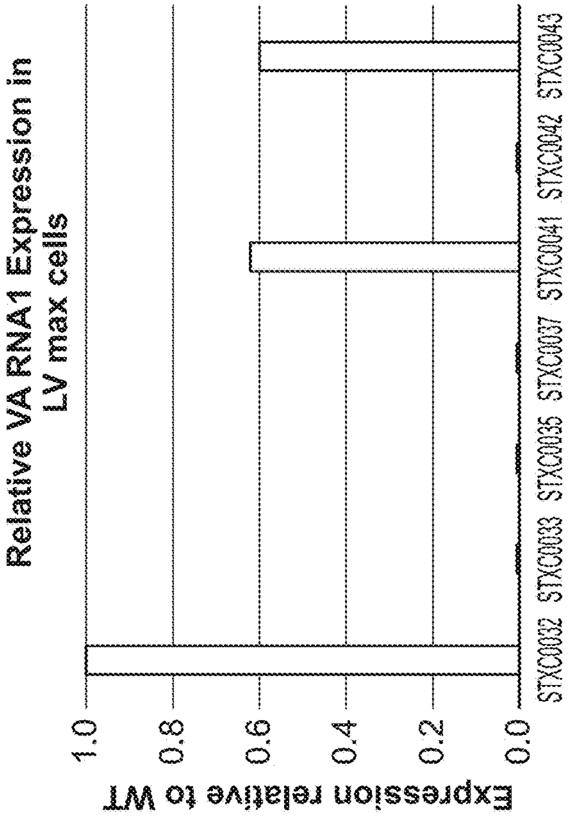

While STXC0041 and STXC0043 displayed similar levels of relative VA RNA expression, STXC0043 achieved these levels of VA RNA expression with less disruption to VA RNA (with just the two mutations: G16A and G60A) as compared to the STXC0041 plasmid (which has a 6 nucleotide deletion in the B box promoter region) (FIG. 12C-12D).

Figure 13A:
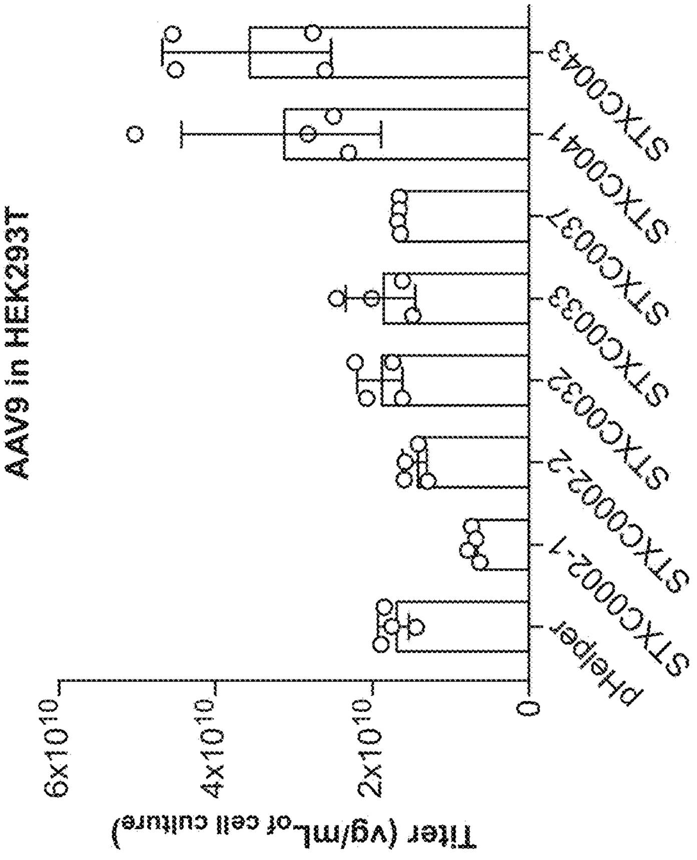
FIGS. 13A-13B are graphs showing titer results using the mutant and inducible VA RNA constructs from FIG. 12B in HEK293T cells (FIG. 13A) and LV Max cells (FIG. 13B).
Figure 13B:
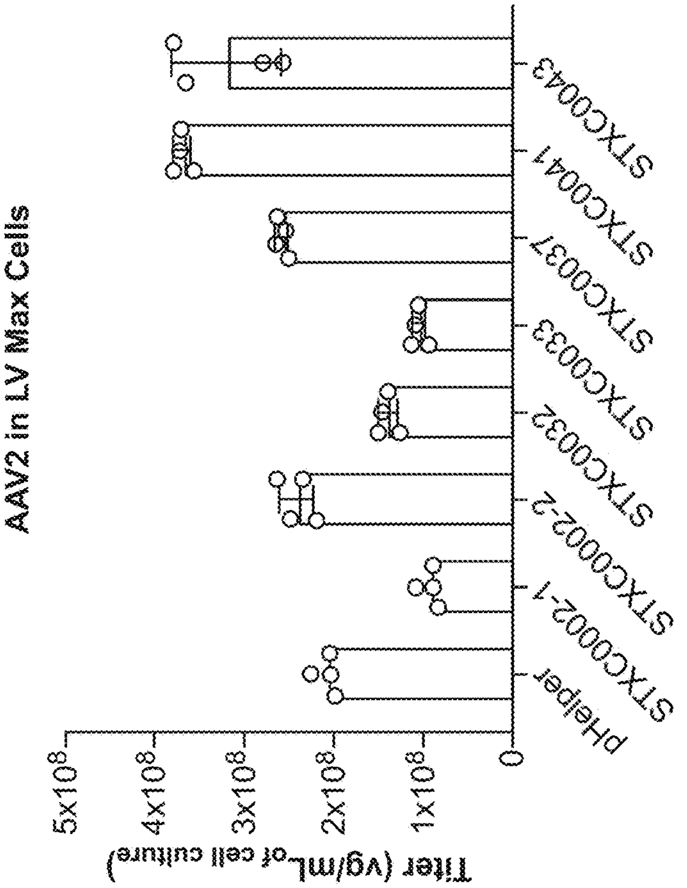
Figure 14:
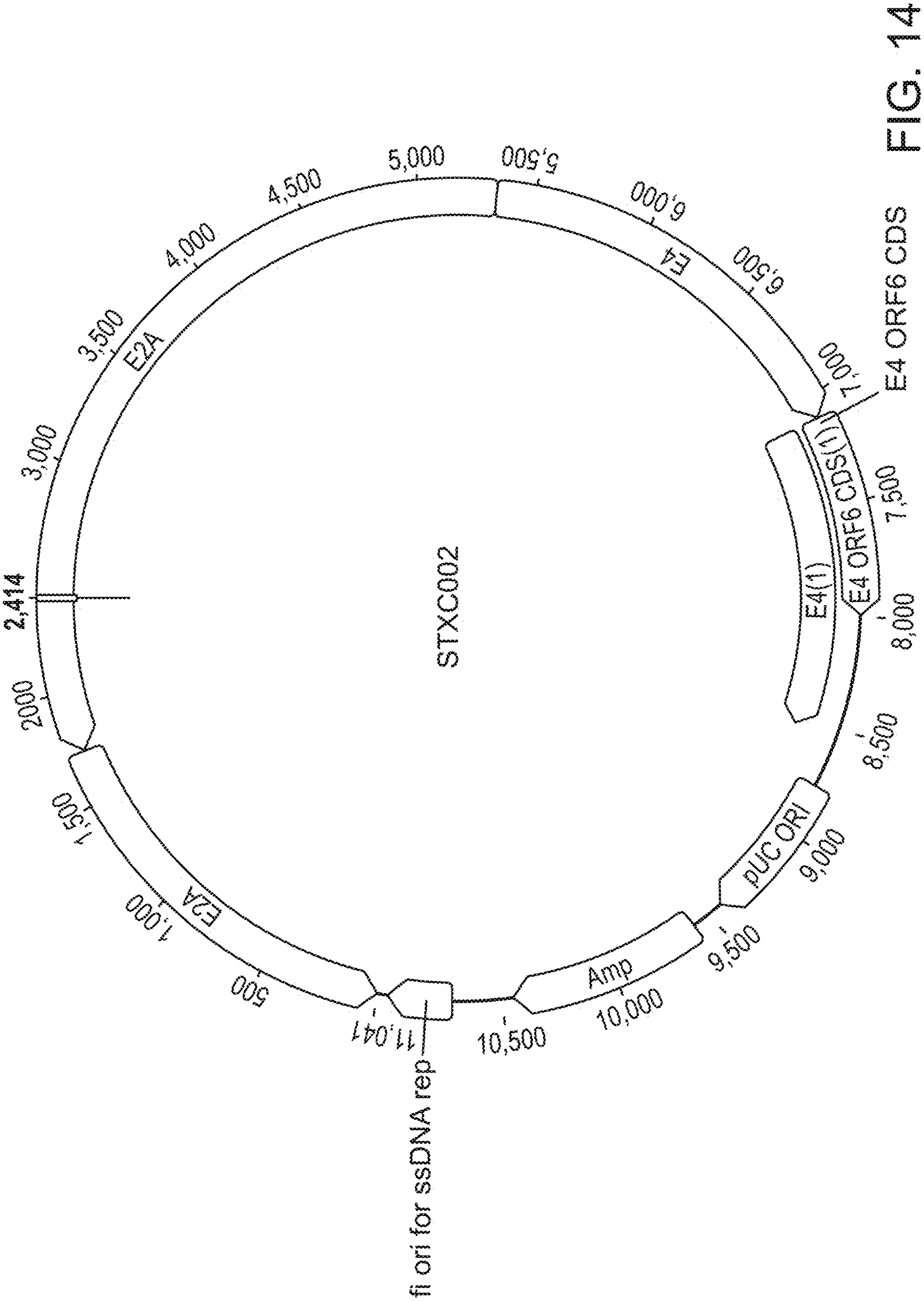
FIG. 14 shows a plasmid map of STX_C002, which is a helper plasmid without VA RNA expression (VA RNA is deleted).
Figure 15:
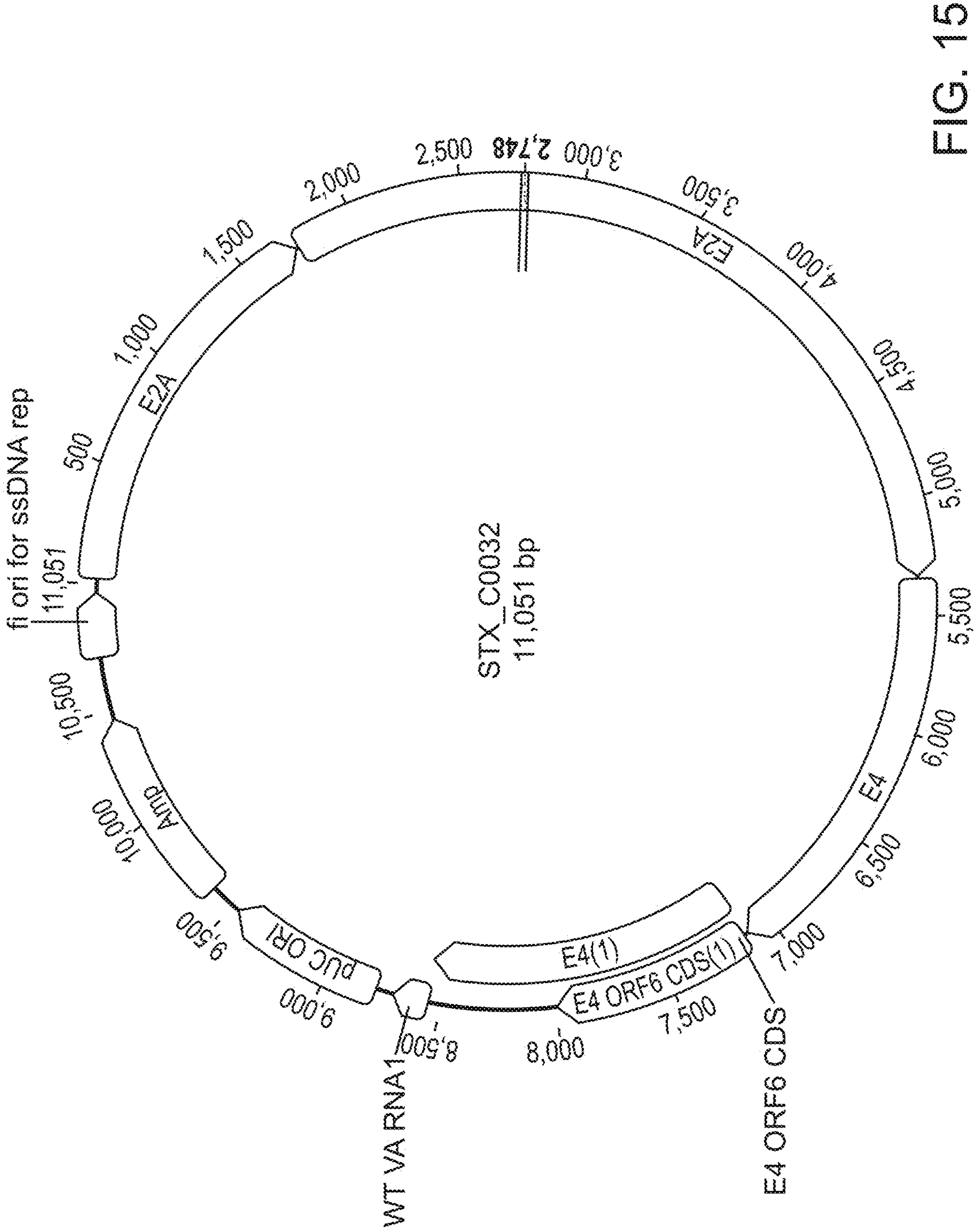
FIG. 15 shows a plasmid map of STX_C0032, which is a STX_C002helper plasmid backbone containing a WT VA RNA.
Figure 16:
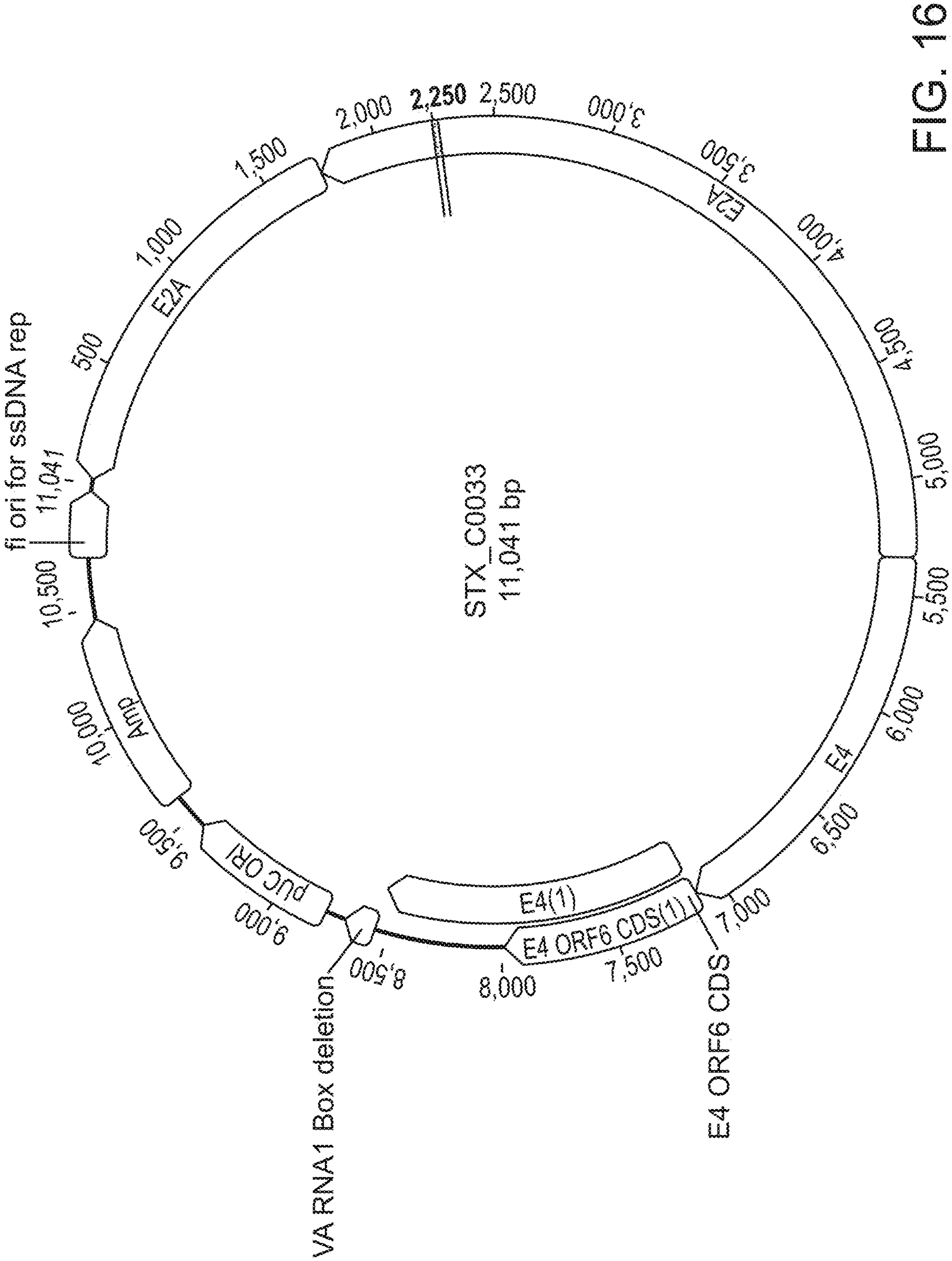
FIG. 16 shows a plasmid map of STX_C0033, which is a STX_C002 helper plasmid backbone containing a VA RNA1 B1 mutant (a six-nucleotide segment deleted from the B Box) with the VA RNA in reverse orientation.
Figure 17:
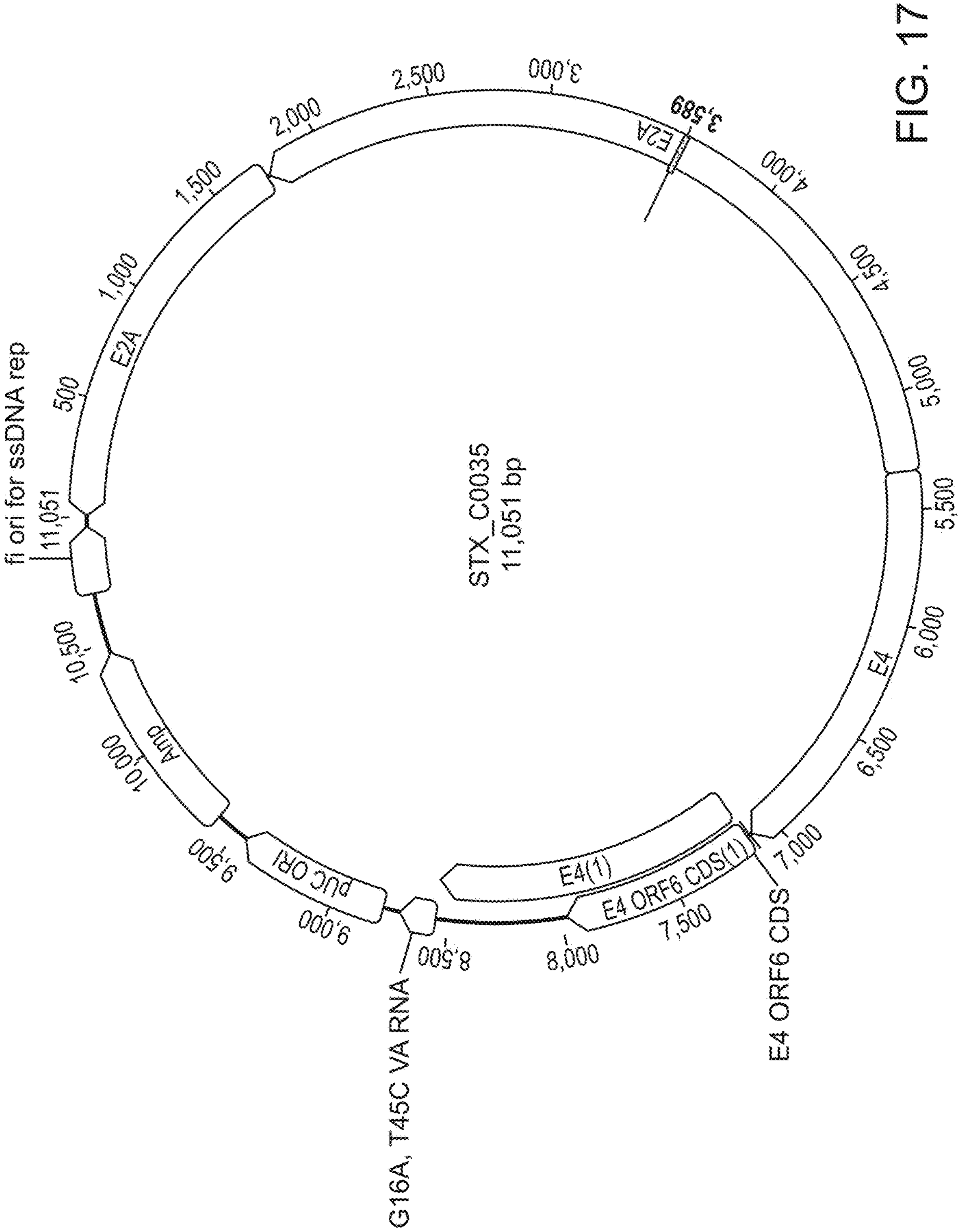
FIG. 17 shows a plasmid map of STX_C0036, which is a STX_C002 helper plasmid containing the VA RNA mutations G16A and T45C, with the VA RNA in reverse orientation).

FIGS. 13A-13B show results from a triple transfection experiment which was carried out for a subset of the plasmid constructs from FIG. 12B, using AAV9 in HEK293T cells (FIG. 13A) and AAV2 in LV Max cells (FIG. 13B). Triple transfections utilizing the STXC0041 and STXC0043 constructs displayed the highest levels of titers.

The tables below show sequences of various elements of the above constructs.

| Construct | Sequence of VA RNA |
|---|---|
| STXC0032<br>SEQ ID<br>NO: 13 | GGGCACTCTTCCGTGGTCTGGTGGATAAATTCGCAAGGGTATCA<br>TGGCGGACGACCGGGGTTCGAACCCCGGATCCGGCCGTCCGCCG<br>TGATCCATGCGGTTACCGCCCGCGTGTCGAACCCAGGTGTGCGA<br>CGTCAGACAACGGGGGAGCGCTCCTTTTT |
| STXC0033<br>SEQ ID<br>NO: 14 | GGGCACTCTTCCGTGGTCTGGTGGATAAATTCGCAAGGGTATCA<br>TGGCGGACGACCGGCCGGATCCGGCCGTCCGCCGTGATCCATGC<br>GGTTACCGCCCGCGTGTCGAACCCAGGTGTGCGACGTCAGACAA<br>CGGGGGAGCGCTCCTTTTT |
| STXC0035<br>SEQ ID<br>NO: 15 | GGGCACTCTTCCGTGATCTGGTGGATAAATTCGCAAGGGTATCA<br>TGGCGGACGACCGGGGTTCGAACCCCGGATCCGGCCGTCCGCCG<br>TGATCCATGCGGTTACCGCCCGCGTGTCGAACCCAGGTGTGCGA<br>CGTCAGACAACGGGGGAGCGCTCCTTTTT |
| STXC0037<br>SEQ ID<br>NO: 16 | GGGCACTCTTCCGTGATCTGGTGGATAAATTCGCAAGGGTATCA<br>TGGCGGACGACCGGGATTCGAACCCCGGATCCGGCCGTCCGCCG<br>TGATCCATGCGGTTACCGCCCGCGTGTCGAACCCAGGTGTGCGA<br>CGTCAGACAACGGGGGAGCGCTCCTTTTT |

| Construct | Sequence of 5' U6 DSE to 3' VA RNA |
|---|---|
| STXC0041<br>SEQ ID<br>NO: 17 | CGATGGAGGGCCTATTTCCCATGATTCCTTCATATTTGCATATAC<br>GATACAAGGCTGTTAGAGAGATAATTAGAATTAATTTGACTGTA<br>AACACAAAGATATTAGTACAAAATAATAACTTCGTATAATGTAT<br>GCTATACGAAGTTATTTTGCAGTTTTAAAATTATGTTTTAAAATG<br>GACTATCATATGCTTACCGTAACTTGAAAGTATTTCGATTTCTTG<br>GCTTTATATATCTTGTGGAAAGGACGAAACACCGGGCACTCTTC<br>CGTGGTCTGGTGGATAAATTCGCAAGGGTATCATGGCGGACGAC<br>CGGCCGGATCCGGCCGTCCGCCGTGATCCATGCGGTTACCGCCC<br>GCGTGTCGAACCCAGGTGTGCGACGTCAGACAACGGGG |
| STXC0042<br>SEQ ID<br>NO: 18 | CGATGGAGGGCCTATTTCCCATGATTCCTTCATATTTGCATATAC<br>GATACAAGGCTGTTAGAGAGATAATTAGAATTAATTTGACTGTA<br>AACACAAAGATATTAGTACAAAATAATAACTTCGTATAATGTAT<br>GCTATACGAAGTTATTTTGCAGTTTTAAAATTATGTTTTAAAATG<br>GACTATCATATGCTTACCGTAACTTGAAAGTATTTCGATTTCTTG<br>GCTTTATATATCTTGTGGAAAGGACGAAACACCGGGCACTCTTC<br>CGTGATCTGGTGGATAAATTCGCAAGGGTATCATGGCGGACGAC<br>CGGGGTTCGAACCCCGGATCCGGCCGTCCGCCGTGATCCATGCG<br>GTTACCGCCCGCGTGTCGAACCCAGGTGTGCGACGTCAGACAAC<br>GGGGGAGCGCTCCTTTTT |
| STXC0043<br>SEQ ID<br>NO: 19 | TTCACTAGAATCGATGGAGGGCCTATTTCCCATGATTCCTTCATA<br>TTTGCATATACGATACAAGGCTGTTAGAGAGATAATTAGAATTA<br>ATTTGACTGTAAACACAAAGATATTAGTACAAAATAATAACTTC<br>GTATAATGTATGCTATACGAAGTTATTTTGCAGTTTTAAAATTAT<br>GTTTTAAAATGGACTATCATATGCTTACCGTAACTTGAAAGTATT<br>TCGATTTCTTGGCTTTATATATCTTGTGGAAAGGACGAAACACC<br>GGGCACTCTTCCGTGATCTGGTGGATAAATTCGCAAGGGTATCA<br>TGGCGGACGACCGGGATTCGAACCCCGGATCCGGCCGTCCGCCG<br>TGATCCATGCGGTTACCGCCCGCGTGTCGAACCCAGGTGTGCGA<br>CGTCAGACAACGGGGGAGCGCTCCTTTTT |

6.18.5. Example 5—Rep/Cap Construct Integration into a Stable Cell Line

This example describes integration of construct one encoding Rep and Cap polypeptides (SEQ ID NO: 7) into a stable cell line and describes inducible expression of Rep and Cap polypeptides in said stable cell lines. An AAV2 genome without the ITRs and with the polynucleotide construct shown at the top right of FIG. 8B was cloned into a piggybac vector with a Blasticidin resistance gene (SEQ ID NO: 8). The excisable element interrupting Rep was inserted downstream of the p19 promoter, as shown in FIG. 8B.

Suspension HEK293 cells (viral production cells, VPCs; also referred to as the parental cells or parental VPC pool) were transfected using a PEI pro transfection reagent. The ratio of transposon to transposase ratio used was 2:1. Cells were allowed to recover in non-selective media for 72 hours and passaged into selective media (10 μg/ml Blasticidin). Cell growth and viability was monitored every 3 to 4 days using a Vicell cell counter. After full recovery, doubling time of the cell pool was around 25 hours, which is comparable to that of the parental VPC pool, indicating that there were no negative effects from the integrated AAV sequences (FIG. 8B, top graph).

Cells were analyzed by flow cytometry to quantify GFP expressing cells. As shown in FIG. 8B (on the left, the bottom FACS plot), almost all cells were GFP positive, thus, confirming successful integration of the rep/cap polynucleotide construct shown in FIG. 8B into the cells.

6.18.6. Example 6—Cre Mediated Induction of Rep Proteins

This example describes Cre mediated induction of Rep proteins in a stable cell line integrated with the Rep/Cap construct of FIG. 8B and described in Example 5. VPCs integrated with the AAV2 Rep/Cap construct of FIG. 8B were treated with Cre gesicles. Briefly 200,000 cells were treated with 5 μl of Cre gesicles in 10 μg/ml polybrene media. Cells were centrifuged at 25,000 rpm for 30 minutes and incubated for 2 hrs at 37° C. Parental cells were used as control. After the incubation, cells were resuspended in fresh media and incubated for an additional 24 hours. Rep expression was analyzed by Western blot using an anti-Rep antibody. Results shown in FIG. 8B demonstrates inducible expression of various Rep isoforms upon Cre treatment.

6.18.7. Example 7—Inducible Helper Constructs

This example describes inducible helper constructs of the present disclosure. Two versions of inducible helper constructs disclosed herein are shown in FIG. 24. A tetracycline/doxycycline ("Dox") inducible promoter (TRE3G) drives the expression of estrogen inducible cre (ER2 cre). The estrogen inducible cre has a strong polyadenylation signal (stop signal) at its 3' end. The cre gene and the polyadenylation signal are flanked by lox sites. Following this is a bicistronic E2A E4, orf6 cassette. The plasmid also has a constitutive promoter (mutant EF1a), which drives the expression of Tet-on 3G (Tet responsive activator protein). Mechanism of Action:

In the off state (in the absence of Dox), Tet-on 3G is unable to bind the Tet operator elements in the TRE3G promoter and, thus, the TRE3G promoter is not active. In an embodiment of the system, an estrogen responsive Cre is used instead of simple Cre to counteract any basal (or "leaky") expression of the TRE3G promoter. Thus, even if the system yields leaky expression of the Cre gene, the expressed Cre protein will be held inactive in the cytoplasm. The strong polyadenylation stop signal positioned 3' of the Cre gene will prevent basal expression of adenoviral helper genes (E2A and E4).

To induce expression, Dox and Tamoxifen are added to the cell culture. Dox binds to the Tet-on 3G protein and promotes binding of Tet-on 3G to the Tet operator elements in the TRE3G promoter. This triggers activation of the promoter. ER2 Cre is expressed at high levels and Tamoxifen brings Cre to the nucleus. Cre recombines the lox sites, causing excision of the Cre-polyadenylation cassette. This brings the bicistronic E2A and E4 cassette next to the Tet inducible promoter triggering their expression. Self-excision of Cre will limit the duration of Cre expression in the cells thus limiting Cre related toxicity and promiscuous recombination events.

A first version of an inducible helper construct is shown in FIG. 24, at left. The construct shown in FIG. 24 (at left) also has a mutant of VA RNA (G16A and G60A, which disable the internal PolIII promoter) driven by a U6 promoter. The proximal sequence element (PSE) and distal sequence element (DSE) of the U6 promoter are separated by a Lox sequence-flanked stuffer sequence (PGK driven Fusion Red-PuroR), thus, disabling the promoter. The promoter is reconstituted by Cre mediated excision of the stuffer sequence, resulting in VA RNA expression conditional upon Cre expression A second version of an inducible helper construct is shown in FIG. 24, at right. The construct shown in FIG. 24 (at right) has a constitutively expressed VA RNA element driven by its internal native promoters.

FIG. 25 shows multiple variations of the inducible helper construct shown in FIG. 24 (at left). Fusion Red-PuroR is replaced with PuromycinR and the PGK promoter is replaced with a CMV promoter in two different orientations. Suspension HEK293 cells (viral production cells, VPCs) were transfected with different variations of the inducible helper construct (shown in FIG. 25) encoded for in plasmids using a PEI pro transfection reagent. The ratio of transposon to transposase ratio used was 2:1. Cells were allowed to recover in non-selective media for 72 hrs and passaged into selective media (1.5 μg/ml Puromycin). Cell growth and viability was monitored every 3 to 4 days using a Vicell cell counter. Results are shown in the top graphs of FIG. 27. After full recovery, doubling time of the cell pools was around 23 hours which is comparable to that of parental VPCs, indicating no negative effects of integrated sequences.

6.18.8. Example 8—Helper Constructs Stably Integrated into Cell Lines

This example describes stable integration of inducible helper constructs of the present disclosure into cell lines. Pools were induced with 20 ng/ml Dox and 2 uM Tamoxifen and analyzed 48 hours post induction. Pools showed no basal expression and robust expression of E2A post induction by both western blot (FIG. 27) and intracellular staining as detected by anti-FLAG antibody. RNA samples were analyzed by RT QPCR using VA RNA specific primers and probes showing upregulation of VA RNA expression post-induction (FIG. 27). FIG. 27 shows an overview of HEK293 cells with the stably integrated helper plasmid showing no cytotoxic effects and induction of Cre, production of VA RNA and good distribution of E2a expression.

6.18.9. Example 9—Inducible Stable Cell Lines

This example describes production of inducible stable cell lines using the constructs of the present disclosure. Two versions of inducible helper constructs (Version 1: STXC0123 and Version 2: STXC0133) disclosed herein are shown in FIG. 28. In both inducible helper constructs, a tetracycline/doxycycline ("Dox") inducible promoter (TRE3G) drives the expression of estrogen inducible Cre (ER2 Cre). The estrogen inducible Cre has a strong polyadenylation signal (stop signal) at its 3' end. The Cre gene and the polyadenylation signal are flanked by lox sites. Following this is a bicistronic E2A E4, orf6 cassette. The plasmid also has a constitutive promoter (mutant EF1a), which drives the expression of Tet-on 3G (Tet responsive activator protein).

However, STXC0123 comprises a mutant of VA RNA (G16A and G60A, which disable the internal PolIII promoter) driven by a U6 promoter. The proximal sequence element (PSE) and distal sequence element (DSE) of the U6 promoter were separated by a Lox sequence-flanked stuffer sequence (CMV driven Puromycin resistance gene), thus, disabling the promoter. The promoter is reconstituted by Cre mediated excision of the stuffer sequence, resulting in VA RNA expression conditional upon Cre expression In contrast, STXC0133 comprises a TetOn-3G puromycin resistance gene cassette and a constitutively expressed VA RNA element driven by its internal native promoters.

Suspension HEK293 cells (viral production cells, VPCs) were transfected with STXC0123 or STXC0133 encoded for in plasmids using a transfection reagent. Cells were allowed to recover in non-selective media and passaged into media comprising Puromycin. For both versions, puromycin selection was used to ensure construct integration into the viral production cells (VPCs). STXC0123 produced the T33 (P1V1) cell line and STC0133 produced the T44 (P1V2) cell line. Viable cell density and viability was monitored every 3 days for T33 and T44. Results are shown in the graphs of FIG. 29. After full recovery, doubling time of the cell pools was around 24.6 hours for T33 and 26.3 hours for T44 hours, which is comparable to that of parental VPCs, indicating no negative effects of integrated sequences.

To confirm the stable integration and inducibility of T33 and T44 pools, cells from these pools were tested for E2A expression, VA RNA expression, culture density, and cell viability. Cells from the T33 pool and T44 pool were seeded at 1 million cells/mL, induced with 160 ng/ul Dox and 4 uM Tamoxifen, and analyzed at 24 hours and 48 hours post induction. Pools showed minimal basal expression and robust expression of E2A post induction at both 24 hours and 48 hours (top graphs in FIG. 30). RNA samples were analyzed by RT QPCR using VA RNA specific primers and probes showing VA RNA expression relative to uninduced VPCs at 24 hours and 48 hours post-induction (second graphs from top in FIG. 30) or showing VA RNA expression compared to uninduced T33 or T44 cells at 24 hours and 48 hours post-induction (third graphs from top in FIG. 30). Culture density (fourth graphs from top in FIG. 30) and cell viability (bottom graphs in FIG. 30) also tested at 24 hours and 48 hours post-induction.

Next, the Rep/Cap construct (STXC0137) and payload construct (STC0136) were transfected using a transfection reagent into the T33 (P1V1) cell line and the T44 (P1V2) cell line for integration. For both T33 and T44, the Rep/Cap construct was designed to permit constitutive expression of one half of a split blasticidin resistance gene and expression of AAV Rep and Cap proteins from their endogenous promoters after induction. The construct shown in FIG. 28 is pre-induction of the integrated nucleic acid construct. An intervening spacer interrupts the Rep coding sequence. The intervening spacer comprises a first spacer segment, a second spacer segment which is excisable (BFP flanked by Lox sites), and a third spacer segment. The transcript contains a single intron flanked by 5' and 3' splice sites.

The payload construct (STXC0136) comprises a sequence that encodes GFP flanked by ITRs (STX650 (sc GFP AAV)) and the other half of a split blasticidin resistance gene, both under control of a constitutive promoter.

After transfection, cells were allowed to recover in non-selective media and then were passaged into media comprising Blasticidin. For both versions, Blasticidin selection was used to ensure both constructs integrated into the T33 stable cell line and T44 stable cell line. The integration in T33 produced three stable cell lines: T40 (P2V1), T41 (P2V1), and T42 (P2V1). The integration in T44 produced three stable cell lines: T56 (P2V2), T57 (P2V2), and T58 (P2V2). Viable cell density and viability was monitored for T40, T41, and T42 (FIG. 31), and for T59, T60, and T62 (FIG. 32).

In the off state (in the absence of Dox), Tet-on 3G is unable to bind the Tet operator elements in the TRE3G promoter and, thus, the TRE3G promoter is not active. In the constructs of FIG. 28, an estrogen responsive Cre was used instead of simple Cre to counteract any basal (or "leaky") expression of the TRE3G promoter. Thus, even if the system yields leaky expression of the Cre gene, the expressed Cre protein will be held inactive in the cytoplasm. The strong polyadenylation stop signal positioned 3' of the Cre gene will prevent basal expression of adenoviral helper genes (E2A and E4).

To induce expression, Dox and Tamoxifen are added to the cell culture of the T40, T41, T42, T56, T57, and T58 stable cells lines. Dox bound to the Tet-on 3G protein and promoted binding of Tet-on 3G to the Tet operator elements in the TRE3G promoter. This triggered activation of the promoter. ER2 Cre was expressed at high levels and Tamoxifen brought Cre to the nucleus. Cre recombined the lox sites, causing excision of the Cre-polyadenylation cassette. This brings the bicistronic E2A and E4 cassette next to the Tet inducible promoter triggering their expression. Cre additionally excised the puromycin resistant gene cassette of STXC0123, reconstituting the U6 promoter and subsequently allowing expression of the mutant VA RNA1 G16A and G60A. Cre also excised the second spacer segment of STX0137, which includes the BFP marker coding sequence and the upstream 3' splice site. As rearranged, the STX0137 construct allowed expression of functional Rep and Cap transcripts from their respective endogenous promoters. Self-excision of Cre limited the duration of Cre expression in the cells thus limiting Cre related toxicity and promiscuous recombination events. Induction of the helper constructs and Rep/Cap constructs subsequently allowed capsid production and packaging of the STXC0136 in the produced capsids.

6.18.10. Example 10—Induction of Inducible Stable Cell Lines

This example describes induction of the inducible stable cell lines of the present disclosure. Cells from the T42 pool cell line (T42) and cells from triple transfection of VPCs (3×Tfxn) were induced in different cell medias. Capsid ELISA was performed to determine total capsid titer. Nuclease treatment and qPCR were performed to determine the titer of capsids encapsidating the viral genome (e.g., the payload construct). FIG. 33 shows a graph of capsid production in different cell media from the T42 pool stable cell line after induction compared to capsid production in cells after triple transfection. The left bar for each media type indicates total capsid titer and the right bar for each media type indicates the titer of capsids encapsidating a viral genome (e.g., the payload construct). The total capsid titer as shown by ELISA was higher for the T42 cells induced in Fuji 7, Fuji 7-2, and HE 300 media compared to the cells produced by triple transfection. The below Table 1 shows the total capsid titer and the titer of capsids encapsidating a viral genome of FIG. 33.

TABLE 1

Total capsid titer and the titer of capsids encapsidating a viral genome of T42 cells versus 3 × Tfxn cells after induction in different cell medias.

| Cell Line | Media | Total Capsid Titer (vp/mL) | Viral Genome Encapsidated Titer (vg/mL) |
|---|---|---|---|
| T42 | Fuji 7 | $1.29 \times 10^{10}$ | $1.16 \times 10^{10}$ |
| T42 | Fuji 7-2 | $2.48 \times 10^{10}$ | $7.92 \times 10^{9}$ |
| T42 | Bal | $1.81 \times 10^{9}$ | $3.18 \times 10^{9}$ |
| T42 | TS5 | $1.03 \times 10^{9}$ | $1.64 \times 10^{9}$ |
| T42 | AAV | $5.95 \times 10^{8}$ | $8.30 \times 10^{8}$ |
| T42 | HE300 | $2.24 \times 10^{9}$ | $2.26 \times 10^{8}$ |
| T42 | TS1 | $6.49 \times 10^{8}$ | $1.86 \times 10^{8}$ |
| T42 | Cyt9 | $8.69 \times 10^{8}$ | $3.52 \times 10^{7}$ |
| T42 | HE400 | $3.74 \times 10^{8}$ | |
| T42 | Cyt2 | | |
| T42 | TS3 | | |
| 3 × Tfxn | Fuji 7 | $7.21 \times 10^{9}$ | $6.83 \times 10^{8}$ |
| 3 × Tfxn | Fuji 7-2 | $1.79 \times 10^{10}$ | $5.59 \times 10^{8}$ |
| 3 × Tfxn | Bal | $7.18 \times 10^{9}$ | $5.45 \times 10^{8}$ |
| 3 × Tfxn | TS5 | $3.62 \times 10^{9}$ | $2.26 \times 10^{8}$ |
| 3 × Tfxn | AAV | $3.35 \times 10^{9}$ | $1.12 \times 10^{8}$ |
| 3 × Tfxn | HE300 | $1.09 \times 10^{9}$ | $7.63 \times 10^{7}$ |
| 3 × Tfxn | TS1 | $2.44 \times 10^{9}$ | $5.20 \times 10^{7}$ |
| 3 × Tfxn | Cyt9 | $1.31 \times 10^{9}$ | $4.77 \times 10^{7}$ |
| 3 × Tfxn | HE400 | $8.27 \times 10^{8}$ | $3.20 \times 10^{7}$ |
| 3 × Tfxn | Cyt2 | $3.60 \times 10^{8}$ | BLOQ |
| 3 × Tfxn | TS3 | BLOQ | BLOQ |

*BLOQ = below assay limit of quantitation

Cells from the T42 stable cell line pool, the T59 stable cell line pool, the T60 stable cell line pool, or the T61 stable cell line pool were either not induced (−) or induced (+) in HE300 media. Nuclease treatment and qPCR were performed to determine the titer of capsids encapsidating the viral genome (e.g., the payload construct) (FIG. 34).

Capsids from induction of the T42 pool stable cell line and capsids from induction of the T61 pool stable cell line were used to infect cells and determine infectivity. The percentage of GFP+ cells after infecting cells with capsids (payload was GFP) is shown in FIG. 35. The left bar for each cell line type/media is for a dilution factor of 1 and the right bar for each cell line type/media is for a dilution factor of 4.

The virus produced per cell (titer productivity) was also tested for the T42 pool stable cell line after induction compared to the triple transfected parental cells (VPC). Cultures of T42 stable cell line were induced at $3\times10^6$ cells/mL and harvested 96 hours post induction. Cultures of the parental cell line (VPCs) were triple transfected at $3\times10^6$ cells/mL and harvested 96 hours post transfection. Harvested cells underwent nuclease treatment (benzonase) and qPCR was performed to determine the titer of capsids encapsidating the viral genome (e.g., the payload construct). Titer productivity (vg/cell) on a per cell basis was calculated by dividing the total qPCR titer by the viable cell density at harvest. FIG. 36 shows a graph of capsids encapsidating a viral genome (e.g., the payload construct) in different cell media from the T42 pool stable cell line after induction compared to the triple transfected parental cells (VPC). The left bar for each media type indicates titer of capsids encapsidating a viral genome produced per cell by cells from the T42 pool stable cell line and the right bar for each media type indicates titer of capsids encapsidating a viral genome produced per cell by cells from the triple transfected parental cell line (VPC).

6.18.11. Example 11—Media Screen

This example describes induction of the inducible stable cell lines of the present disclosure in different cell media. Cells from the T42 pool cell line (T42) were tested in 18 different cell medias. Cells were seeded at $5\times10^6$ cells/mL, $6.5\times10^6$ cells/mL, $8\times10^6$ cells/mL, or $9.5\times10^6$ cells/mL. The cells were then induced with Tamoxifen and Dox. Cells were harvested at 70% viability. Harvested cells underwent nuclease treatment (benzonase) and qPCR was performed to determine the titer of capsids encapsidating the viral genome (e.g., the payload construct). The titer of capsids encapsidating a viral genome (e.g., the payload construct) in each cell media at each seed density after induction is shown in FIG. 37.

6.18.12. Example 12—Induction of Inducible Stable Cell Lines

This example describes induction of mini pool clones from the T42 pool cell line compared to the T42 pool cell line. Mini pool clones from the T42 pool cell lines were passaged for a minimum of three passages. Each mini pool clone was tested in eight different media. The mini pool clones or the T42 pool cell lines cells were induced at $5\times10^6$ cells/mL and then harvested 96 hours post induction with tamoxifen and doxycycline. Capsid ELISA was performed to determine total capsid titer for each mini pool clone and for the T42 pool stable cell line after induction for each of the cell medias as shown in FIG. 38. Infectivity of the capsids from select mini pool clones and for the T42 stable cell line after induction in various cell media was then tested. The percentage of GFP+ cells after infecting target cells (CHO Pro-5 cells) with capsids (payload was GFP) compared to the multiplicity of infection (MOI; vg/target cell) is shown in FIG. 39 and FIG. 40. Mini pool clone 1D3 in HE300 and and 1D3 in Fuji7 showed greater than 50% infectivity at MOIs of less than $1\times10^5$.

6.18.13. Example 13—Bioreactor Production

This example describes production of rAAV virions in a 50 L bioreactor from stable cells as disclosed herein versus from transiently transfected cells. Triple transient transfected cells, a current stable cell line (for example, a stable cell line expanded from a clone of the T42 stable cell line of Example 12), or a new stable cell line are cultured and are induced in a 50 L bioreactor. rAAV virion production from these 50 L bioreactors is shown Table 2. Lower bioreactor titer is produced from the triple transient transfected cells compared to from a current stable cell line or from a new stable cell line. Using standard purification processes, a 40% downstream yield is produced for the rAAV virion that is produced from the triple transient transfected cells and from a current stable cell line. An increase in yield to 60% is produced when higher quality rAAV virion (e.g., higher full capsid:empty capsid ratio) is produced from a new cell line and when the purification processes is improved for a new cell line. Therefore, a higher net process yield for rAAV virion is produced from a new clone from a new stable cell line and from a clone from a current stable cell line compared to from the triple transient transfected cells.

TABLE 2

| rAAV virion is produced from 50 L Bioreactor | | | | |
|---|---|---|---|---|
| Basis of Design Process | Bioreactor Scale (L) | Bioreactor Titer (vg/L) | Downstream Yield (%) | Net Process Yield (vg) |
| Triple Transient Transfection (Current Capability) | 50 | 1.00E+14 | 40% | 2.00E+15 |
| Current Stable Cell Line | 50 | 4.00E+14 | 40% | 8.00E+15 |
| New Stable Cell Line | 50 | 1.00E+15 | 60% | 3.00E+16 |

6.18.14. Example 14—rAAV Virion Dosing

This example describes dosing of rAAV virion for non-intravenous or intravenous administration to a patient. Table 3 shows multiplicity of infection (MOI), average dose, and yield for rAAV virion that is produced by triple transient transfect cells, current stable cell line (for example, a stable cell line expanded from a clone of the T42 stable cell line of Example 12), or a new stable cell line for either non-intravenous or intravenous administration to a patient. MOI is increased for the rAAV virion that is produced by a new stable cell line compared to by the current cell line or the triple transient transfected cells. Therefore, average dose is decreased for the rAAV virion that is produced by a new stable cell line compared to by the current cell line or the triple transient transfected cells.

TABLE 3

| | Non IV | IV |
|---|---|---|
| Triple Transient Transfection | | |
| MOI | 1:1000 | 1:1000 |
| Avg Dose (vg) | 1.00E+12 | 4.00E+15 |
| Yield (vg/L) | 4.00E+13 | 4.00E+13 |
| Current Stable Cell Line | | |
| MOI | 1:1000 | 1:1000 |
| Avg Dose (vg) | 1.00E+12 | 4.00E+15 |
| Yield (vg/L) | 1.60E+14 | 1.60E+14 |
| New Stable Cell Line | | |
| MOI | 1:200 | 1:200 |
| Avg Dose (vg) | 2.00E+11 | 8.00E+14 |
| Yield | 6.00E+14 | 6.00E+14 |

Table 4 shows the number of patient doses per batch of rAAV virion that is produced by triple transient transfect cells, a current stable cell line, or a new stable cell line in a 50 L bioreactor or a 500 L bioreactor for either non-intravenous or intravenous administration to a patient. Yield is increased for the rAAV virion that is produced by a current stable cell line or a new stable cell line compared to by the triple transient transfected cells (see Table 3). Therefore, the number of doses per batch is increased for the rAAV virion that is produced by a new stable cell line or the current cell line compared to by the triple transient transfected cells.

TABLE 4

| Scale | Non IV # Dose/Batch | IV # Dose/Batch |
|---|---|---|
| Triple Transient Transfection | | |
| 50 | 2000 | 0.5 |
| 500 | 20000 | 5 |
| Current Stable Cell Line | | |
| 50 | 8000 | 2 |
| 500 | 80000 | 20 |
| New Stable Cell Line | | |
| 50 | 150000 | 37.5 |
| 500 | 1500000 | 375 |

Exemplary Construct 1/Rep/Cap Features

| Name | type | location |
|---|---|---|
| Rep68 CDS2 | misc_feature | 4012 . . . 4036 |
| Rabbit beta globin | intronmisc_feature | 878 . . . 1230 |
| Rep40 CDS2 | misc_feature | 4012 . . . 4036 |
| 3'SS | misc_feature | 2760 . . . 2806 |
| VP1 | misc_feature | 3987 . . . 6194 |
| EGFP | misc_feature | 1312 . . . 2030 |
| VP3 | misc_feature | 4593 . . . 6194 |
| loxP | misc_feature | 1231 . . . 1264 |
| Rep52 | misc_feature | 848 . . . 877 |
| Rep40 CDS1 | misc_feature | 848 . . . 877 |
| Rep78 | misc_feature | 176 . . . 877 |
| Rep68 CDS1 | misc_feature | 176 . . . 877 |
| 5 prime terminus of | RNA1misc_feature | 142 . . . 151 |
| TATA box P5 | misc_feature | 110 . . . 115 |
| TATA box p19 | misc_feature | 698 . . . 705 |
| 5 prime terminus of | RNA2misc_feature | 728 . . . 737 |
| 5 prime terminus of | RNA3misc_feature | 3637 . . . 3644 |
| TATA box of P40 | misc_feature | 3606 . . . 3614 |
| polyA sequence | misc_feature | 6208 . . . 6213 |
| Rep52 | misc_feature | 2807 . . . 3970 |
| Rep40 CDS1 | misc_feature | 2807 . . . 3690 |
| Rep78 | misc_feature | 2807 . . . 3970 |
| Rep68 CDS1 | misc_feature | 2807 . . . 3690 |
| AAV 3'UTR | misc_feature | 6195 . . . 6318 |
| 3'SS | misc_feature | 1265 . . . 1311 |
| Rabbit beta globin | polyAmisc_feature | 2032 . . . 2552 |
| rabbit beta globin | intronmisc_feature | 2587 . . . 2806 |
| VP (CAP) proteins | misc_feature | 3987 . . . 6194 |
| pCRII Topo | misc_feature | 6319 . . . 9837 |
| M13-fwd | primer_bind | rev:6415 . . . 6432 |
| M13-rev | primer_bind | 9707 . . . 9727 |
| T7 | primer_bind | rev:6389 . . . 6416 |
| SP6 | primer_bind | 9733 . . . 9758 |
| ColE1 origin | rep_origin | 8657 . . . 9339 |
| LacO | misc_binding | 9679 . . . 9701 |
| LoxP | misc_recomb | rev:1231 . . . 1264 |
| LoxP | misc_recomb | rev:2553 . . . 2586 |
| Kan/neoR | CDS | 7223 . . . 8014 |

8. EQUIVALENTS AND INCORPORATION BY REFERENCE

All references cited herein are incorporated by reference to the same extent as if each individual publication, database entry (e.g. Genbank sequences or GeneID entries), patent application, or patent, was specifically and individually indicated to be incorporated by reference in its entirety, for all purposes. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

While the invention has been particularly shown and described with reference to a preferred embodiment and various alternate embodiments, it will be understood by persons skilled in the relevant art that various changes in form and details can be made therein without departing from the spirit and scope of the invention.

What is claimed is:

1. A method of generating a cell for inducibly producing recombinant AAV (rAAV) virions comprising a payload, the method comprising:

introducing into a cell a first polynucleotide construct comprising a first sequence, a second sequence and a third sequence, the first sequence comprising from 5' to 3': an inducible promoter operably linked to a sequence encoding an inducible recombinase; a self-excising element comprising a first recombination site, the sequence encoding the inducible recombinase, and a second recombination site, wherein the first recombination site and the second recombination site are oriented in the same direction; and a sequence encoding one or more AAV helper proteins, wherein the inducible promoter is not operably linked to the sequence encoding the one or more AAV helper proteins;

the second sequence comprising a first constitutive promoter operably linked to a sequence encoding an activator, wherein the cell constitutively expresses the activator and the activator is unable to activate the inducible promoter in absence of a first triggering agent, wherein in the presence of the first triggering agent, the activator activates the inducible promoter resulting in expression of the inducible recombinase, and the inducible recombinase is expressed and wherein in the presence of a second triggering agent, the inducible recombinase translocates to a nucleus of the cell and causes recombination between the first recombination site and the second recombination site resulting in excision of the self-excising element, thereby operably linking the inducible promoter to the sequence encoding the one or more AAV helper proteins and allowing expression of the one or more AAV helper proteins; and the third sequence comprising a second constitutive promoter operably linked to a sequence encoding a first selectable marker, wherein the cell constitutively expresses the first selectable marker, selecting for a cell expressing the first selectable marker;

introducing a second polynucleotide construct and a third polynucleotide construct into the cell expressing the first selectable marker, the second polynucleotide construct comprising:

from 5' to 3': one or more promoters operably linked to a first sequence comprising a first part of an AAV Rep coding sequence, a 5' splice site, a first intron, a third recombination site, a first 3' splice site, a coding sequence comprising a stop signaling sequence, a fourth recombination site, a second intron, a second 3' splice site, a second sequence comprising a second part of the AAV Rep coding sequence, wherein the third recombination site, the first 3' splice site, the coding sequence comprising the stop signaling sequence, and the fourth recombination site form an excisable element, wherein the third recombination site and the fourth recombination site are oriented in the same direction, and wherein the one or more promoters are not operably linked to the second sequence comprising the second part of the AAV Rep coding sequence; a third sequence comprising a sequence encoding AAV capsid proteins, wherein the second sequence comprises a promoter that is operably linked to the third sequence, wherein the third and fourth recombination sites are recombined by the inducible recombinase in the presence of the first triggering agent and the second triggering agent resulting in excision of the excisable element, and the first part of the AAV Rep coding sequence and the second part of the AAV Rep coding sequence are joined to form a complete AAV Rep coding sequence, allowing expression of AAV Rep proteins; and a third constitutive promoter operably linked to a sequence encoding a first portion of a second selectable marker, the third polynucleotide construct comprising a sequence encoding the payload and a fourth constitutive promoter operably linked to a second portion of the second selectable marker, wherein the sequence encoding the payload is flanked by AAV inverted terminal repeats (ITRs);

selecting for a cell expressing the first selectable marker and the second selectable marker, thereby generating the cell for inducibly producing recombinant AAV (rAAV) virions comprising the payload.

2. The method of claim 1, further comprising contacting the cell with the first triggering agent and the second triggering agent for inducibly producing recombinant AAV (rAAV) virions comprising the payload.

3. The method of claim 1, wherein the cell expresses adenovirus E1A protein and adenovirus E1B protein.

4. The method of claim 1, wherein the sequence coding for one or more AAV helper proteins comprises a bicistronic open reading frame encoding two AAV helper proteins.

5. The method of claim 4, wherein the two AAV helper proteins are E2a and E4.

6. The method of claim 4, wherein the bicistronic open reading frame comprises an internal ribosome entry site (IRES) or a peptide 2A (P2A) sequence.

7. The method of claim 1, wherein the inducible promoter in the first polynucleotide construct comprises a tetracycline-responsive promoter element (TRE).

8. The method of claim 7, wherein the TRE comprises Tet operator (tetO) sequence concatemers fused to a minimal promoter.

9. The method of claim 8, wherein the minimal promoter is a human cytomegalovirus promoter.

10. The method of claim 1, wherein the activator is a reverse tetracycline-controlled transactivator (rTA) comprising a Tet Repressor binding protein (TetR) fused to a VP16 transactivation domain, and the first triggering agent is tetracycline or doxycycline.

11. The method of claim 2, wherein the inducible recombinase is fused to an estrogen response element (ER) and translocates to the nucleus in the presence of the second triggering agent, wherein the second triggering agent is tamoxifen.

12. The method of claim 1, wherein the first polynucleotide construct further comprises an insert comprising:

a first part of a fifth constitutive promoter and a second part of a fifth constitutive promoter separated by a second excisable element comprising a fifth recombination site and a sixth recombination site flanking a stuffer sequence, wherein the fifth and sixth recombination sites are oriented in the same direction, and a VA-RNA coding sequence, wherein excision of the second excisable element by the inducible recombinase generates a functional complete fifth constitutive promoter operably linked to the VA-RNA coding sequence thereby allowing expression of the VA-RNA.

13. The method of claim 12, wherein the first part of the fifth constitutive promoter comprises a distal sequence element (DSE) of a U6 promoter, and the second part of the fifth constitutive promoter comprises a proximal sequence element (PSE) of a U6 promoter.

14. The method of claim 12, wherein the sequence coding for VA-RNA is a transcriptionally dead sequence.

15. The method of claim 14, wherein the sequence coding for VA RNA comprises at least two mutations in an internal promoter.

16. The method of claim 1, wherein the first selectable marker encoded by the first polynucleotide construct comprises a first antibiotic resistance protein or a first auxotrophic selection marker.

17. The method of claim 16, wherein the first selectable marker is a first antibiotic resistance protein, wherein the first antibiotic resistance protein is puromycin.

18. The method of claim 1, wherein transcription of the AAV Rep coding sequences and the sequence encoding one or more AAV capsid proteins are driven by native AAV promoters.

19. The method of claim 1, wherein transcription of the AAV Rep coding sequences is driven by P5 and P19 promoters and transcription of the sequence encoding one or more AAV capsid proteins is driven by P40 promoter.

20. The method of claim 1, wherein the AAV capsid proteins comprise VP1, VP2, and VP3.

21. The method of claim 1, wherein the first portion of the second selectable marker encoded by the second polynucleotide construct comprises a C-terminal fragment of a mammalian DHFR (Cter-DHFR) fused to a leucine zipper peptide, and the second portion of the second selectable marker encoded by the third polynucleotide construct comprises an N-terminal fragment of the mammalian DHFR (Nter-DHFR) fused to a leucine zipper peptide, or vice versa.

22. The method of claim 1, wherein the first portion of the second selectable marker encoded by the second polynucleotide construct comprises a split intein linked to an N-terminus of an antibiotic resistance protein and the second portion of the second selectable marker encoded by the third polynucleotide construct comprises a split intein linked to a C-terminus of the antibiotic resistance protein, or vice versa.

23. The method of claim 22, wherein the second selectable marker is blasticidin.

24. The method of claim 1, wherein the coding sequence comprising the stop signaling sequence of the second polynucleotide construct encodes for a protein marker.

25. The method of claim 1, wherein the 5' splice site is a rabbit beta globin 5' splice site.

26. The method of claim 1, wherein both of the first and second 3' splice sites are rabbit beta globin 3' splice sites.

27. The method of claim 1, wherein the first recombination site and second recombination site in the first polynucleotide construct and the third recombination site and fourth recombination site in the second polynucleotide construct are lox sites and the recombinase is a cre recombinase or wherein the first recombination site and the second recombination site in the first polynucleotide construct and the third recombination site and fourth recombination site in the second polynucleotide are flippase recognition target (FRT) sites and the recombinase is a flippase (Flp) recombinase.

28. The method of claim 1, wherein the sequence encoding the payload comprises a reporter gene, a therapeutic gene, or a transgene encoding a protein of interest.

29. The method of claim 1, wherein the sequence encoding the payload comprises a guide RNA or a homology region for homology-directed repair.

30. The method of claim 1, wherein the first polynucleotide construct, the second polynucleotide construct, the third polynucleotide construct, or all three are integrated into the nuclear genome of the cell.

31. The method of claim 1, wherein the cell is a HEK293 cell.

32. The method of claim 31, wherein the HEK293 cell is DHFR-deficient.

* * * * *